US012552813B2

(12) United States Patent
Zhang et al.

(10) Patent No.: US 12,552,813 B2
(45) Date of Patent: Feb. 17, 2026

(54) HETEROCYCLIC SUBSTITUTED PYRIMIDOPYRAN COMPOUND AND USE THEREOF

(71) Applicant: Medshine Discovery Inc., Jiangsu (CN)

(72) Inventors: Yang Zhang, Shanghai (CN); Wentao Wu, Shanghai (CN); Zhixiang Li, Shanghai (CN); Wenyuan Zhu, Shanghai (CN); Ping Yang, Shanghai (CN); Qiu Li, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 19/072,501

(22) Filed: Mar. 6, 2025

(65) Prior Publication Data

US 2025/0250288 A1 Aug. 7, 2025

Related U.S. Application Data

(63) Continuation of application No. 18/878,435, filed as application No. PCT/CN2023/101890 on Jun. 21, 2023.

(51) Int. Cl.

| | |
|---|---|
| ***C07D 519/00*** | (2006.01) |
| ***A61K 31/519*** | (2006.01) |
| ***A61K 31/5517*** | (2006.01) |
| ***A61P 35/00*** | (2006.01) |

(52) U.S. Cl.

CPC .......... *C07D 519/00* (2013.01); *A61K 31/519* (2013.01); *A61K 31/5517* (2013.01); *A61P 35/00* (2018.01)

(58) Field of Classification Search

CPC ..... C07D 519/00; A61P 35/00; A61K 31/519; A61K 31/5517

See application file for complete search history.

(56) References Cited

U.S. PATENT DOCUMENTS

| | | | | |
|---|---|---|---|---|
| 2016/0297774 A1 | 10/2016 | Li et al. | | |
| 2025/0109146 A1* | 4/2025 | Zhang | .................... | A61K 31/55 |

FOREIGN PATENT DOCUMENTS

| | | | |
|---|---|---|---|
| CN | 112390788 A | 2/2021 | |
| WO | 2021107160 A1 | 6/2021 | |
| WO | 2021180181 A1 | 9/2021 | |
| WO | 2021248090 A1 | 12/2021 | |
| WO | 2022081655 A1 | 4/2022 | |

OTHER PUBLICATIONS

U.S. Appl. No. 18/878,435, filed Jun. 21, 2023, Zhang, et al.*
International Search Report and Written Opinion received for PCT Application No. PCT/CN2023/101890, mailed on Sep. 21, 2023, 13 pages. (English translation submitted).

* cited by examiner

*Primary Examiner* — Erich A Leeser
(74) *Attorney, Agent, or Firm* — Mintz, Levin, Cohn, Ferris, Glovsky and Popeo, P.C.

(57) ABSTRACT

The present invention discloses a heterocyclic substituted pyrimidopyran compound and use thereof, and specifically discloses a compound represented by formula (VII) and a pharmaceutically acceptable salt thereof.

(VII)

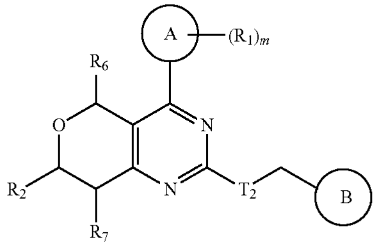

30 Claims, No Drawings

HETEROCYCLIC SUBSTITUTED PYRIMIDOPYRAN COMPOUND AND USE THEREOF

CROSS-REFERENCES TO RELATED APPLICATIONS

The present application is a continuation of U.S. patent application Ser. No. 18/878,435, filed Dec. 23, 2024, which is a 35 U.S.C. 371 national stage filing of International Patent Application No. PCT/CN2023/101890, filed Jun. 21, 2023, designating the United States, which claims the benefit of and priority to International Patent Application Chinese Application Nos. 202210731477.1, filed Jun. 24, 2022; CN202210743845.4, Filing Date: Jun. 27, 2022; CN202210969097.1, Filing Date: Aug. 12, 2022; CN202211494347.7, Filing Date: Nov. 25, 2022; CN202310010084.6, Filing Date: Jan. 4, 2023; CN202310082801.6, Filing Date: Feb. 3, 2023; and CN202310206933.5, Filing Date: Mar. 6, 2023, the entire contents of which are hereby expressly incorporated by reference herein.

FIELD OF THE INVENTION

The present invention relates to a heterocyclic substituted pyrimidopyran compound and use thereof, and specifically discloses a compound represented by formula (VII) and a pharmaceutically acceptable salt thereof.

BACKGROUND OF THE INVENTION

RAS oncogene mutations are the most common activation mutations in human cancers, occurring in about 30% of human tumors. The RAS gene family consists of three subtypes (KRAS, HRAS, and NRAS), of which 85% of RAS-driven cancers are caused by mutations in the KRAS subtype. KRAS is a murine Sarcoma viral oncogene and an important member of RAS protein. KRAS is like a molecular switch, which can control the pathway of cell growth under normal conditions; after mutation, the KRAS gene can independently transmit growth and proliferation signals to downstream pathways without depending on the upstream growth factor receptor signals, resulting in uncontrolled cell growth and tumor progression. At the same time, whether the KRAS gene has mutations is also an important indicator of tumor prognosis.

KRAS mutations are common in solid tumors, such as lung adenocarcinoma, ductal pancreatic cancer, and colorectal cancer. In KRAS mutant tumors, 80% of carcinogenic mutations occur on codon 12, and the most common mutations include p.G12D (41%), p.G12V (28%), and p.G12C (14%). There are about 166,000 new patients with KRAS single mutations (G12D and G12V mutations accounted for the highest), about 9,000 new patients with KRAS amplifications, and about 4,000 new patients with KRAS multiple mutations in USA, and the vast majority of patients currently lack effective targeted therapeutic drugs.

At present, small molecules directly targeting KRAS mutations are mainly concentrated in the $KRAS^{G12C}$ field. Among them, AMG510 of Amgen and MRTX849 of Mirati Therapeutics have been approved for marketing, and have shown good therapeutic effects on $KRAS^{G12C}$ mutant tumor patients. However, there is still no small molecules targeting pan-KRAS mutations entering the clinical research stage, and tumor patients with pan-KRAS mutations and KRAS amplifications have not benefited from precise medical treatment.

SUMMARY OF THE INVENTION

The present invention provides a compound represented by formula (VII) or a pharmaceutically acceptable salt thereof, (VII)

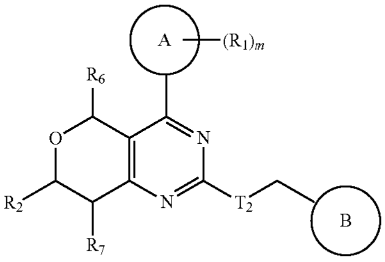

, where ring B is selected from

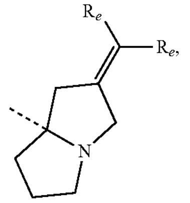

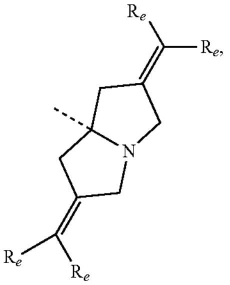

5-12-membered heterocyclic alkenyl, and 7-12-membered tricyclic heterocyclic alkyl, the

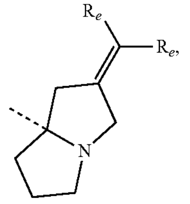

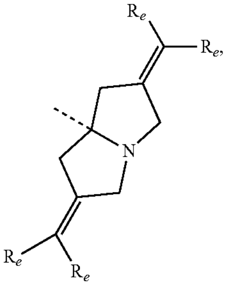

5-12-membered heterocyclic alkenyl, and 7-12-membered tricyclic heterocyclic alkyl being independently and optionally substituted with 1, 2, 3, 4, 5 or 6 $R_e$, respectively, and ring A is selected from

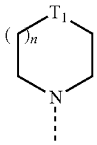

,

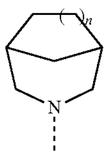

,

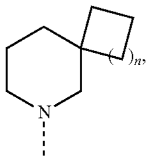

-continued

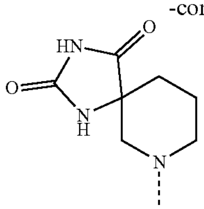, 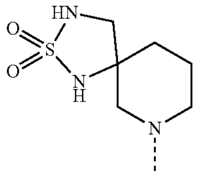,

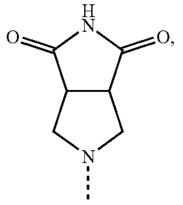 and 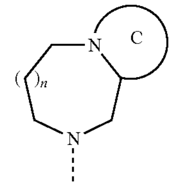;

or, ring B is selected from

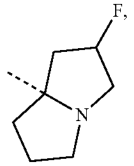

and ring A is selected from

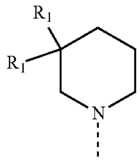, 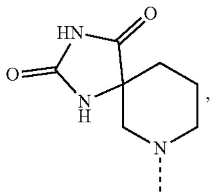,

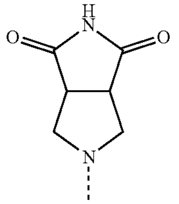 and 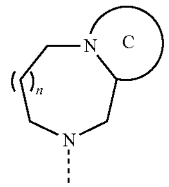;

ring C is selected from 5-6-membered nitrogen-containing heteroaryl;

each $R_1$ is independently selected from F, Cl, Br, I, OH, $NH_2$, CN, $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, —SH, —C(═O)—$NR_aR_b$, —C(═O)—$R_c$,

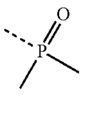, 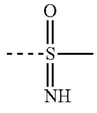, 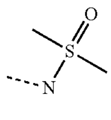, $C_{3-6}$ cycloalkyl, and 5-6-membered heteroaryl, the $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, $C_{3-6}$ cycloalkyl, and 5-6-membered heteroaryl being independently and optionally substituted with 1, 2, 3 or 4 R, respectively; or, $R_1$ on two adjacent atoms, together with the atoms to which they are attached, form a 5-6-membered heterocyclic alkenyl, the 5-6-membered heterocyclic alkenyl being independently and optionally substituted with 1, 2, 3, 4, or 5 R, respectively;

$R_2$ is selected from phenyl, naphthyl and 5-10-membered heteroaryl, the phenyl, naphthyl and 5-10-membered heteroaryl being independently and optionally substituted with 1, 2, 3, 4 or 5 $R_d$, respectively;

$R_6$ and $R_7$ are independently selected from H, $C_{1-3}$ alkyl, F, Cl, Br and I, respectively;

$T_1$ is selected from $CH_2$ and O;

$T_2$ is selected from O and S;

$R_a$ is selected from H and $C_{1-3}$ alkyl, the $C_{1-3}$ alkyl being independently and optionally substituted with 1, 2, 3, 4 or 5 $R_0$, respectively;

$R_b$ is selected from H and $C_{1-3}$ alkyl, the $C_{1-3}$ alkyl being independently and optionally substituted with 1, 2, 3, 4 or 5 $R_0$, respectively;

$R_c$ is selected from H, $C_{3-6}$ cycloalkyl, and 4-6-membered heterocyclic alkyl, the $C_{3-6}$ cycloalkyl and 4-6-membered heterocyclic alkyl being independently and optionally substituted with 1, 2, 3 or 4 R, respectively;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 $R_0$, respectively;

each $R_e$ is independently selected from H, F, Cl, Br, I, CN, $CH_3$, and $OCH_3$, respectively;

each R is independently selected from F, Cl, Br, I, and $C_{1-3}$ alkyl, respectively;

each $R_0$ is independently selected from D, F, Cl, Br and I, respectively;

m is selected from 0, 1, 2, 3, 4 and 5; and n is selected from 0, 1 and 2.

The present invention further provides a compound represented by formula (VII) or a pharmaceutically acceptable salt thereof, (VII)

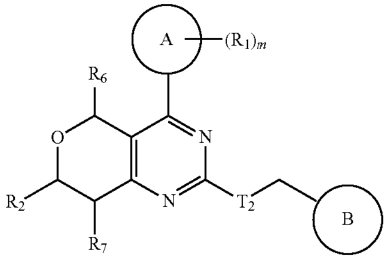, where ring A is selected from

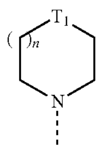, 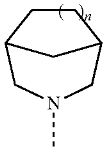, 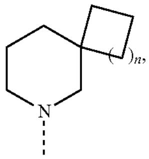,

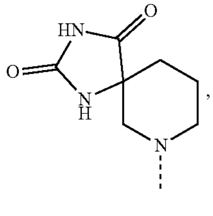, 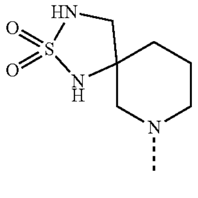,

-continued

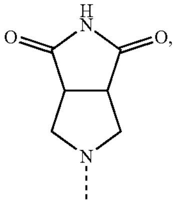

, and

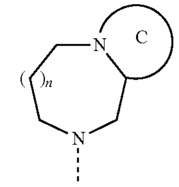

, ring B is selected from

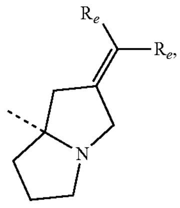

,

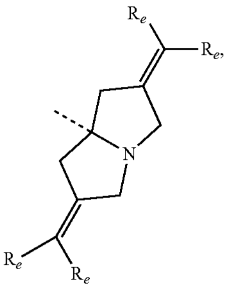

, 5-12-membered heterocyclic alkenyl, and 7-12-membered tricyclic heterocyclic alkyl, the

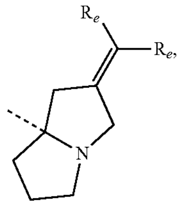

,

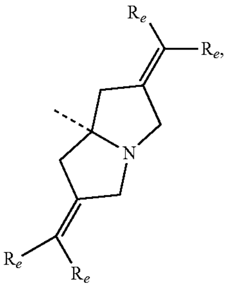

, 5-12-membered heterocyclic alkenyl, and 7-12-membered tricyclic heterocyclic alkyl being independently and optionally substituted with 1, 2, 3, 4, 5 or 6 $R_e$, respectively;

or, ring A is selected from

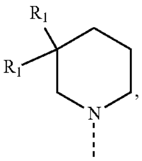

,

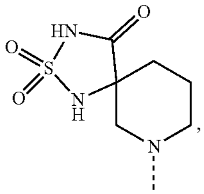

,

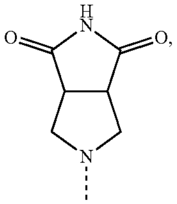

, and

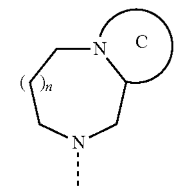

, and ring B is selected from

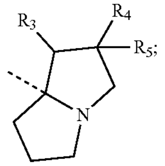

;

ring C is selected from 5-6-membered nitrogen-containing heteroaryl;

each $R_1$ is independently selected from halogen, OH, $NH_2$, CN, $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, —SH, —C(═O)—$NR_aR_b$, —C(═O)—$R_c$,

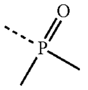

,

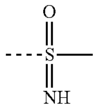

,

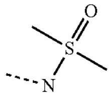

, $C_{3-6}$ cycloalkyl, and 5-6-membered heteroaryl, the $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, $C_{3-6}$ cycloalkyl, and 5-6-membered heteroaryl being independently and optionally substituted with 1, 2, 3 or 4 R, respectively;

or, $R_1$ on two adjacent atoms, together with the atoms to which they are attached, form a 5-6-membered heterocyclic alkenyl, the 5-6-membered heterocyclic alkenyl being independently and optionally substituted with 1, 2, 3, 4, or 5 R, respectively;

$R_2$ is selected from phenyl, naphthyl and 5-10-membered heteroaryl, the phenyl, naphthyl and 5-10-membered heteroaryl being independently and optionally substituted with 1, 2, 3, 4 or 5 $R_d$, respectively;

$R_3$ is selected from H;

$R_4$ is selected from F;

$R_5$ is selected from H;

$R_6$ and $R_7$ are independently selected from H, $C_{1-3}$ alkyl, and halogen, respectively;

$T_1$ is selected from CH and O;

$T_2$ is selected from O and S;

$R_a$ is selected from H and $C_{1-3}$ alkyl, the $C_{1-3}$ alkyl being independently and optionally substituted with 1, 2, 3, 4 or 5 halogen, respectively;

$R_b$ is selected from H and $C_{1-3}$ alkyl, the $C_{1-3}$ alkyl being independently and optionally substituted with 1, 2, 3, 4 or 5 halogen, respectively;

$R_c$ is selected from H, $C_{3-6}$ cycloalkyl, and 5-6-membered heterocyclic alkyl, the $C_{3-6}$cycloalkyl and 5-6-membered heterocyclic alkyl being independently and optionally substituted with 1, 2, 3 or 4 R, respectively;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively;

each $R_e$ is independently selected from H, F, Cl, Br, I, CN, $CH_3$, and $OCH_3$, respectively;

each R is independently selected from F, Cl, Br, I and $C_{1-3}$ alkyl, respectively;

m is selected from 0, 1, 2, 3, 4 and 5; and n is selected from 0, 1 and 2.

The present invention further provides a compound represented by formula (V) or a pharmaceutically acceptable salt thereof, (V)

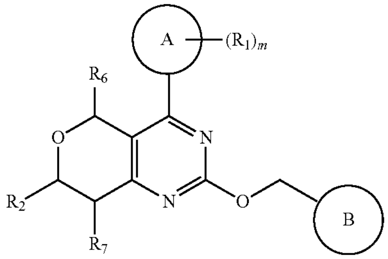, where ring A is selected from

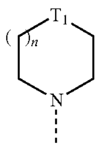, 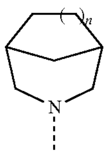, 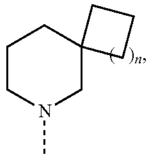

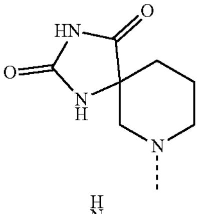, 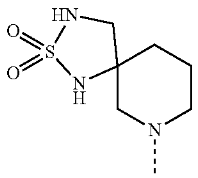,

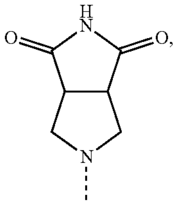 and 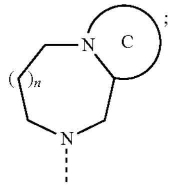;

ring B is selected from

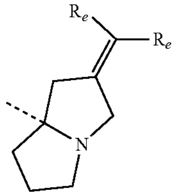 and 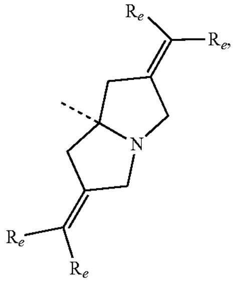, the

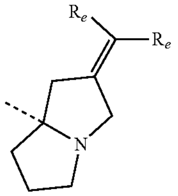 and 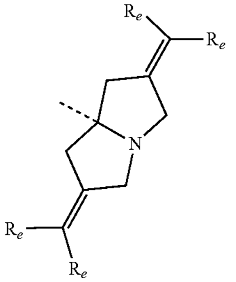

being independently and optionally substituted with 1, 2, 3, 4, 5 or 6 $R_e$, respectively;

or, ring B is selected from 5-12-membered heterocyclic alkenyl, and 7-12-membered tricyclic heterocyclic alkyl, the 5-12-membered heterocyclic alkenyl and 7-12-membered tricyclic heterocyclic alkyl being independently and optionally substituted with 1, 2, 3, 4, 5 or 6 $R_e$, respectively;

ring C is selected from 5-6-membered nitrogen-containing heteroaryl;

each $R_1$ is independently selected from halogen, OH, $NH_2$, CN, $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, —SH, —C(═O)—$NR_aR_b$, —C(═O)—$R_c$,

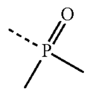, 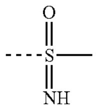, 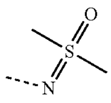, $C_{3-6}$ cycloalkyl, and 5-6-membered heteroaryl, the $C_{1-3}$ alkyl, $C_{1-4}$ alkoxy, $C_{2-4}$ alkenyl, $C_{2-4}$ alkynyl, —$C_{1-3}$ alkyl-O—$C_{1-3}$ alkyl, $C_{3-6}$ cycloalkyl, and 5-6-membered heteroaryl being independently and optionally substituted with 1, 2, 3 or 4 R, respectively;

or, $R_1$ on two adjacent atoms, together with the atoms to which they are attached, form a 5-6-membered heterocyclic alkenyl, the 5-6-membered heterocyclic alkenyl being independently and optionally substituted with 1, 2, 3, 4, or 5 R, respectively;

$R_2$ is selected from phenyl, naphthyl, and 5-10-membered heteroaryl, the phenyl, naphthyl, and 5-10-membered heteroaryl being independently and optionally substituted with 1, 2, 3, 4 or 5 $R_d$, respectively;

$R_6$ and $R_7$ are independently selected from H, $C_{1-3}$ alkyl, and halogen, respectively;

$T_1$ is selected from CH and O;

$R_a$ is selected from H and $C_{1-3}$ alkyl, the $C_{1-3}$ alkyl being independently and optionally substituted with 1, 2, 3, 4 or 5 halogen, respectively;

$R_b$ is selected from H and $C_{1-3}$ alkyl, the $C_{1-3}$ alkyl being independently and optionally substituted with 1, 2, 3, 4 or 5 halogen, respectively;

$R_c$ is selected from H, $C_{3-6}$ cycloalkyl, and 5-6-membered heterocyclic alkyl, the $C_{3-6}$cycloalkyl and 5-6-membered heterocyclic alkyl being independently and optionally substituted with 1, 2, 3 or 4 R, respectively;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively;

each $R_e$ is independently selected from H, F, Cl, Br, I, CN, $CH_3$, and $OCH_3$, respectively;

each R is independently selected from F, Cl, Br, I, and $C_{1-3}$ alkyl, respectively;

m is selected from 0, 1, 2, 3, 4 and 5; and n is selected from 0, 1 and 2.

The present invention further provides a compound represented by formula (IV) or a pharmaceutically acceptable salt thereof, (IV)

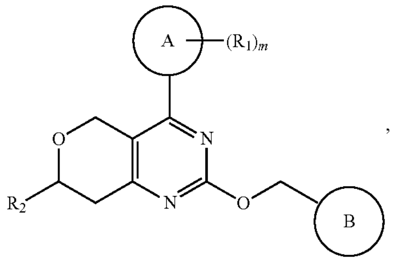

, where $R_1$ is selected from halogen, OH, $C_{1-3}$ alkyl, —C(═O)—$NR_aR_b$, —C(═O)—$R_c$, and 5-6-membered heteroaryl, the $C_{1-3}$ alkyl and 5-6-membered heteroaryl being independently and optionally substituted with 1, 2, 3 or 4 R, respectively;

$R_2$ is selected from phenyl, naphthyl, and 5-10-membered heteroaryl, the phenyl, naphthyl, and 5-10-membered heteroaryl being independently and optionally substituted with 1, 2, 3, 4 or 5 $R_d$, respectively;

ring A is selected from

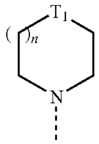
,
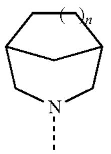
,
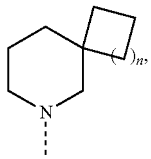

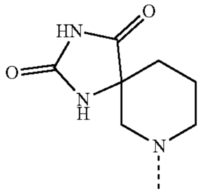
,
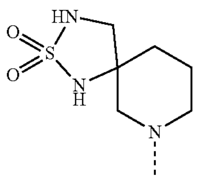
,

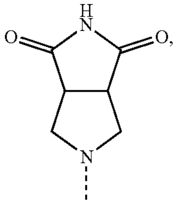
and
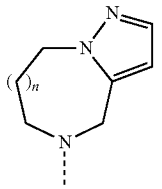
;

or, ring B is selected from

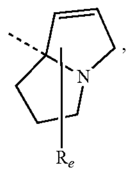
,
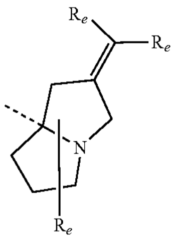
, and

-continued

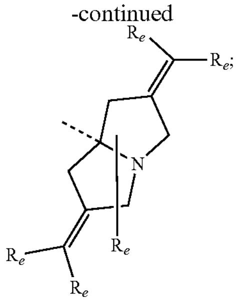

$T_1$ is selected from CH and O;

$R_a$ is selected from H and $C_{1-3}$ alkyl;

$R_b$ is selected from H and $C_{1-3}$ alkyl;

$R_c$ is selected from H, $C_{3-6}$cycloalkyl, and 5-6-membered heterocyclic alkyl;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively;

each $R_e$ is independently selected from H, F, Cl, Br, I, CN, $CH_3$, and $OCH_3$, respectively;

each R is independently selected from F, Cl, Br, I, and $C_{1-3}$ alkyl, respectively;

m is selected from 0, 1, 2 and 3; and n is selected from 0, 1 and 2.

In some embodiments of the present invention, of the compound or pharmaceutically acceptable salt thereof, the compound is selected from formula (V-1), (V-1)

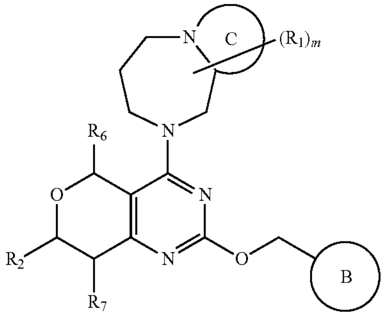

where $R_1$, $R_2$, $R_6$, $R_7$, Rings B, Rings C, and m are as defined herein.

In some embodiments of the present invention, of the compound or pharmaceutically acceptable salt thereof, the compound is selected from formula (V-1), (V-1)

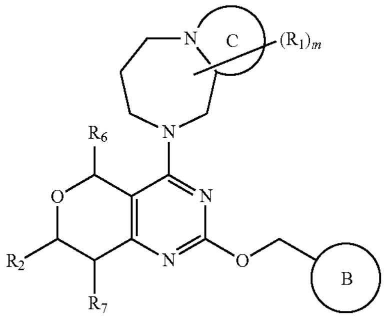

where $R_1$, $R_2$, ring B, ring C, and m are as defined herein.

In some embodiments of the present invention, of the compound or pharmaceutically acceptable salt thereof, the compound is selected from formula (IV-3), (IV-3)

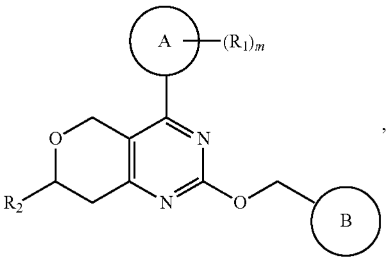

, where $R_1$ is selected from halogen, OH, $C_{1-3}$ alkyl, and 5-6-membered heteroaryl, the $C_{1-3}$ alkyl and 5-6-membered heteroaryl being independently and optionally substituted with 1, 2, 3 or 4 R, respectively;

R, $R_1$, $R_2$, ring A, ring B, and m are as defined herein.

In some embodiments of the present invention, of the compound or pharmaceutically acceptable salt thereof, the compound is selected from formula (IV-1), (IV-1)

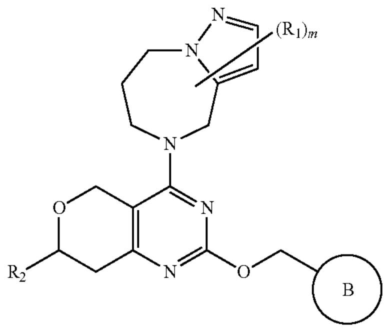

where $R_1$, $R_2$, ring B, and m are as defined herein.

In some embodiments of the present invention, of the compound or pharmaceutically acceptable salt thereof, the compound is selected from formula (P-1), (P-1)

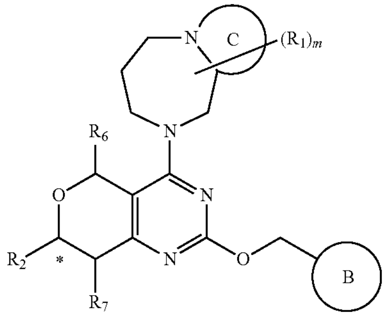

, where ring B is selected from

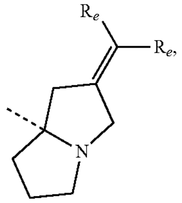

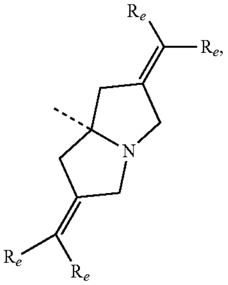

and 5-12-membered heterocyclic alkenyl, and

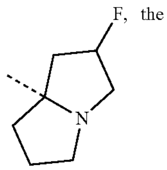

the

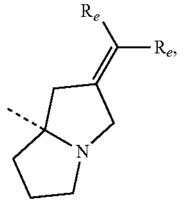

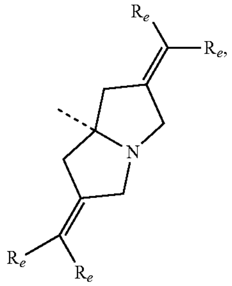

and 5-12-membered heterocyclic alkenyl being independently and optionally substituted with 1, 2, 3, 4, 5 or 6 $R_e$, respectively;

$R_1$, $R_2$, $R_6$, $R_7$, each $R_e$, ring C, and m are as defined herein; and the carbon atom with "*" is a chiral carbon atom, which exists in the form of (R) or (S) single enantiomer or enantiomerically enriched form.

In some embodiments of the present invention, of the compound or pharmaceutically acceptable salt thereof, the compound is selected from formula (P-2), (P-21)

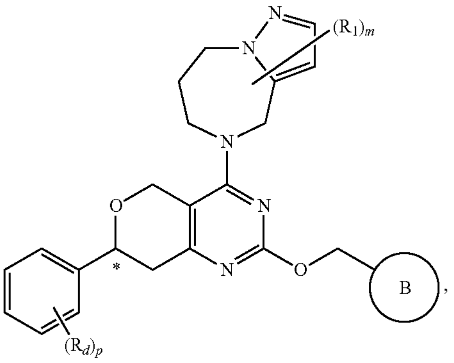

where ring B is selected from

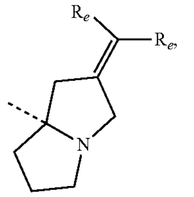

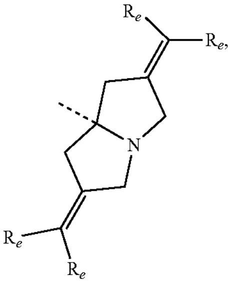

and

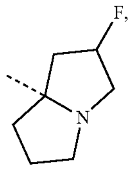

the

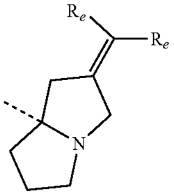

and

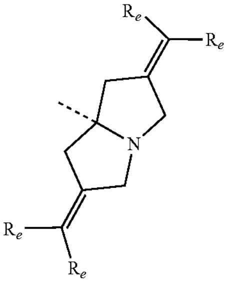

being independently and optionally substituted with 1, 2, 3, 4, 5 or 6 $R_e$, respectively;

p is selected from 1, 2, 3, 4, or 5;

$R_1$, each $R_e$, each $R_d$, and m are as defined herein; and the carbon atom with "*" is a chiral carbon atom, which exists in the form of (R) or (S) single enantiomer or enantiomerically enriched form.

In some embodiments of the present invention, of the compound or pharmaceutically acceptable salt thereof, the compound is selected from formulas (P-2-1), (P-2-2), and (P-2-3), (P-2-1)

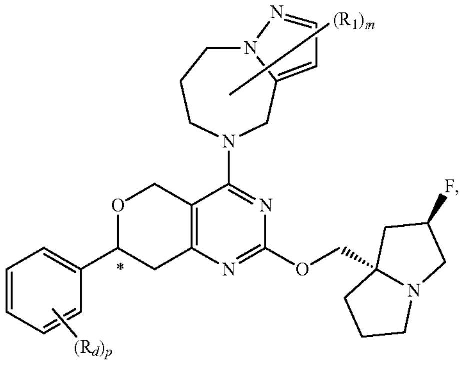

(P-2-2)

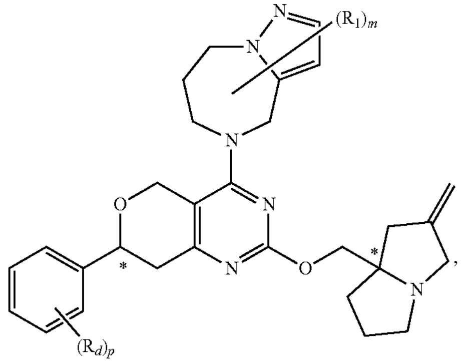

(P-2-3)

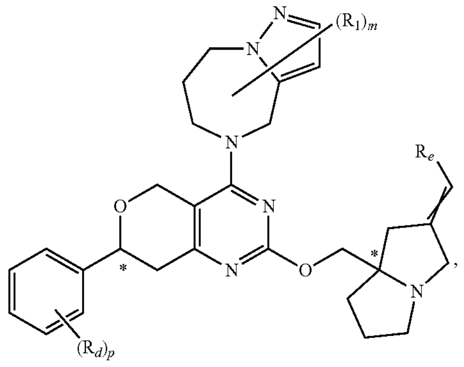

where p is selected from 1, 2, 3, 4, or 5;

$R_1$, $R_e$, each $R_d$, and m are as defined herein; and the carbon atom with "*" is a chiral carbon atom, which exists in the form of (R) or (S) single enantiomer or enantiomerically enriched form.

In some embodiments of the present invention, of the compound or pharmaceutically acceptable salt thereof, the compound is selected from formula (IV-2), (IV-2)

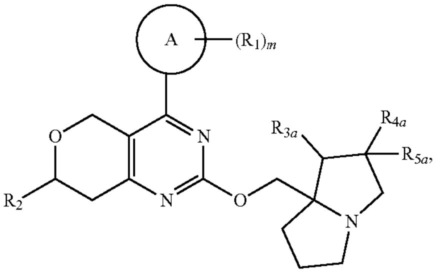

where ring A is selected from

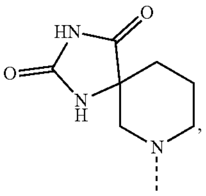

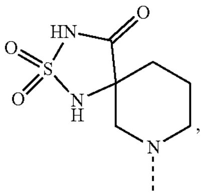

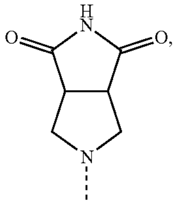

and

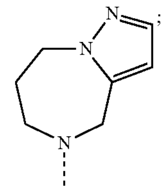

or, ring A is selected from;

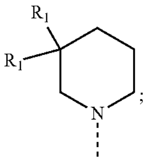

$R_1$ is selected from halogen, OH, $C_{1-3}$ alkyl, —C(═O)—$NR_aR_b$, and —C(═O)—$R_c$;

$R_2$ is selected from phenyl and naphthyl, the phenyl and naphthyl being independently and optionally substituted with 1, 2, 3, 4 or 5 $R_d$, respectively;

$R_{3a}$ and $R_{4a}$ are linked, so that the structural unit

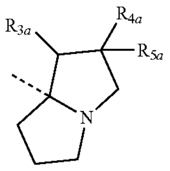

is selected from

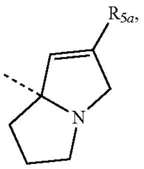

and $R_{5a}$ is selected from H;

or, $R_{4a}$ and $R_{5a}$ are concatenated to form

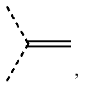

the

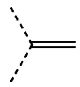

being optionally substituted with 1 or 2 $R_e$, and $R_{3a}$ being selected from H;

$R_a$ is selected from H and $C_{1-3}$ alkyl;

$R_b$ is selected from H and $C_{1-3}$ alkyl;

$R_c$ is selected from 5-6-membered heterocyclic alkyl;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively;

each $R_e$ is independently selected from H, F, Cl, Br, I, CN, $CH_3$, and $OCH_3$, respectively;

m is selected from 0, 1, 2 and 3.

In some embodiments of the present invention, of the compound or pharmaceutically acceptable salt thereof, the compound is selected from formula (I-1), (I-1)

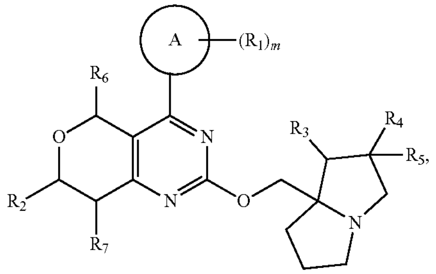

where ring A is selected from

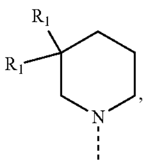

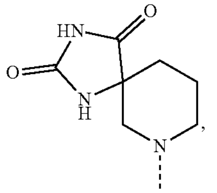

-continued

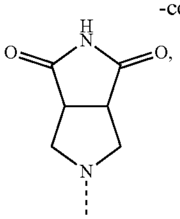 and 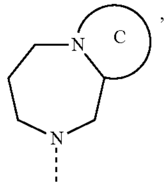, $R_1$, $R_2$, $R_3$, $R_4$, $R_5$, $R_6$, $R_7$, ring C, and m are as defined herein.

In some embodiments of the present invention, each R is independently selected from F, Cl, Br, I, $CH_3$, $CH_2CH_3$, and $CH_2CH_2CH_3$, and other variables are as defined herein.

In some embodiments of the present invention, the R is selected from F and $CH_3$, and other variables are as defined herein.

In some embodiments of the present invention, the $R_0$ is selected from D, and other variables are as defined herein.

In some embodiments of the present invention, the $R_a$ is selected from H, $CH_3$, $CD_3$, and $CH(CH_3)_2$, and other variables are as defined herein.

In some embodiments of the present invention, the $R_a$ is selected from H, $CH_3$, and $CH(CH_3)_2$, and other variables are as defined herein.

In some embodiments of the present invention, the $R_b$ is selected from H, $CH_3$, $CD_3$, and $CH(CH_3)_2$, and other variables are as defined herein.

In some embodiments of the present invention, the $R_b$ is selected from H, $CH_3$, and $CH(CH_3)_2$, and other variables are as defined herein.

In some embodiments of the present invention, the $R_c$ is selected from H, cyclopropyl, tetrahydropyrrolyl, and morpholinyl, and other variables are as defined herein.

In some embodiments of the present invention, the $R_c$ is selected from tetrahydropyrrolyl and morpholinyl, and other variables are as defined herein.

In some embodiments of the present invention, the $R_d$ is independently selected from H, F, Cl, Br, I, OH, $NH_2$, CN, $CH_3$, $CH_2F$, $CF_2H$, $CF_3$, $CH_2CH_3$, $CF_2CF_3$, —C≡CH, —C≡CF, —C≡CBr, —C≡$CCH_3$, and —C≡$CCF_3$, respectively, and other variables are as defined herein.

In some embodiments of the present invention, the $R_d$ is independently selected from F, Cl, $NH_2$, OH, $CH_3$, $CF_3$, $CH_2CH_3$, —C≡CH, and —C≡$CCH_3$, respectively, and other variables are as defined herein.

In some embodiments of the present invention, the $R_e$ is independently selected from H and F, respectively, and other variables are as defined herein.

In some embodiments of the present invention, the $T_1$ is selected from CH, and other variables are as defined herein.

In some embodiments of the present invention, the $T_1$ is selected from 0, and other variables are as defined herein.

In some embodiments of the present invention, the $T_2$ is selected from 0, and other variables are as defined herein.

In some embodiments of the present invention, the $R_1$ is independently selected from F, Cl, Br, I, OH, $NH_2$, CN,

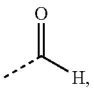 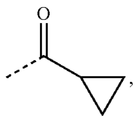, 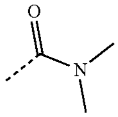, 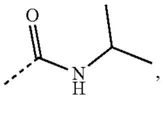,

-continued

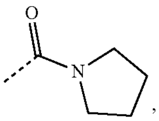, 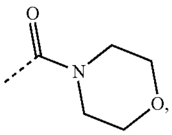

$CH_3$, $CH_2CH_3$, $CH_2CH_2CH_3$, —CH═$CH_2$, —$CH_2$—CH═$CH_2$,

, , $OCH_3$, $OCH_2CH_3$, $OCH_2CH_2CH_3$, —$CH_3OCH_3$, —$CH_3OCH_2CH_3$, —$CH_2CH_3OCH_3$, —$CH_2CH_2CH_3OCH_3$, —SH,

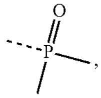, 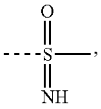, 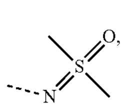

cyclopropyl, cyclobutyl, pyridyl, pyrimidinyl, thiophene, 1,2,4-oxadiazole, 1,2,5-oxadiazole, and 1,3,4-oxadiazole, the $CH_3$, $CH_2CH_3$, $CH_2CH_2CH_3$, —CH═$CH_2$, —$CH_2$—CH═$CH_2$,

, , cyclopropyl, cyclobutyl, pyridyl, pyrimidinyl, thiophene, 1,2,4-oxadiazole, 1,2,5-oxadiazole, and 1,3,4-oxadiazole being independently and optionally substituted with 1,2,3 or 4 R, respectively, and other variables are as defined herein.

In some embodiments of the present invention, the $R_1$ is selected from F, Cl, Br, I, OH,

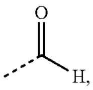 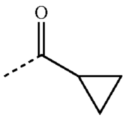, 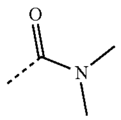, 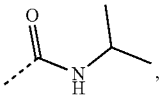,

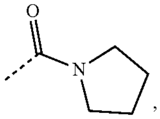, 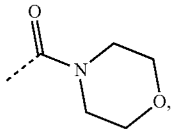

$CH_3$, $CH_2CH_3$, $CH_2CH_2CH_3$, pyridyl, pyrimidinyl, thiophene, 1,2,4-oxadiazole, 1,2,5-oxadiazole, and 1,3,4-oxadiazole, the $CH_3$, $CH_2CH_3$, $CH_2CH_2CH_3$, pyridinyl, pyrimidinyl, thiophene, 1,2,4-oxadiazole, 1,2,5-oxadiazole, and 1,3,4-oxadiazole are independently and optionally substituted with 1,2,3 or 4 R, respectively, and other variables are as defined herein.

In some embodiments of the present invention, the $R_1$ is independently selected from F, Cl, Br, OH, $NH_2$, CN, $CH_3$, $CH(CH_3)_2$,

, , cyclopropyl, $CF_3$,

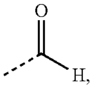, 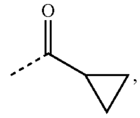, 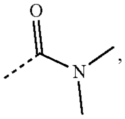, 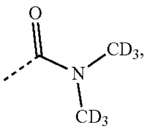, 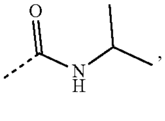, 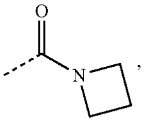, 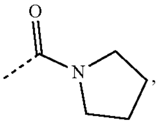, 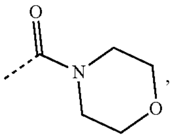, 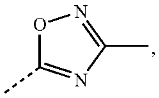, and 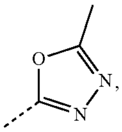, respectively, and other variables are as defined herein.

In some embodiments of the present invention, the $R_1$ is independently selected from F, Cl, OH, $NH_2$, CN, $CH_3$, $CH(CH_3)_2$,

, cyclopropyl, $CF_3$,

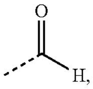, 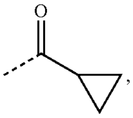, 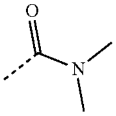, 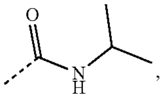, 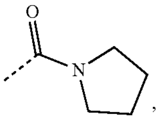, 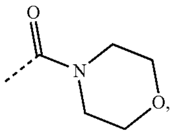, 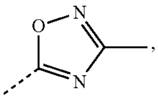, and 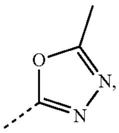, respectively, and other variables are as defined herein.

In some embodiments of the present invention, the $R_1$ is selected from F, Cl, OH, $CH_3$, $CF_3$,

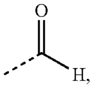, 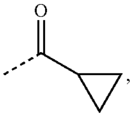, 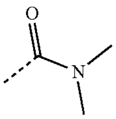, 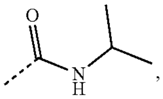,

-continued

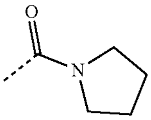, 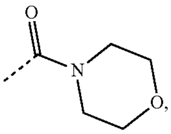, 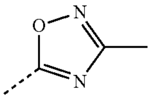, and 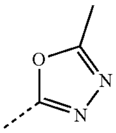

respectively, and other variables are as defined herein.

In some embodiments of the present invention, the $R_1$ is selected from F, Cl, OH, $CH_3$,

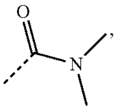, 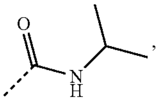, 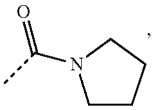, and 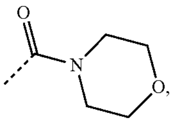, and, and other variables are as defined herein.

In some embodiments of the present invention, the $R_2$ is selected from phenyl, naphthyl, indolyl, pyridyl, pyrrolyl, benzopyrimidinyl, and quinolyl, the phenyl, naphthyl, indolyl, pyridyl, pyrrolyl, benzopyrimidinyl and quinolyl being independently and optionally substituted with 1, 2, 3, 4 or 5 $R_d$, respectively, and other variables are as defined herein.

In some embodiments of the present invention, the $R_2$ is selected from phenyl, naphthyl, and pyridyl, the phenyl, naphthyl, and pyridyl being independently and optionally substituted with 1, 2, 3, 4 or 5 $R_d$, respectively, and other variables are as defined herein.

In some embodiments of the present invention, the $R_2$ is selected from phenyl and naphthyl, the phenyl and naphthyl being independently and optionally substituted with 1, 2, 3, 4 or 5 $R_d$, respectively, and other variables are as defined herein.

In some embodiments of the present invention, the $R_2$ is selected from

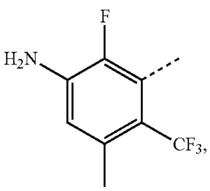, 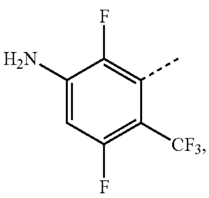, 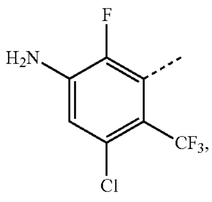, 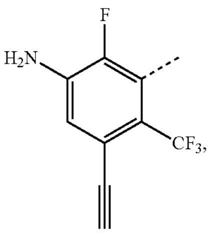,

-continued
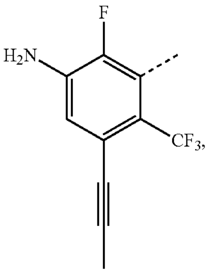
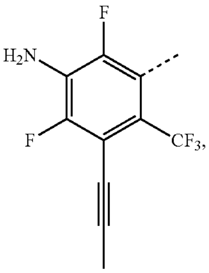
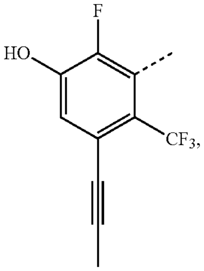
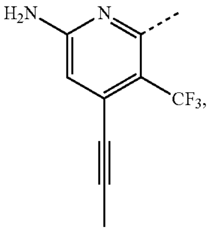
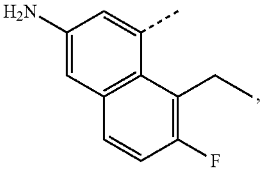
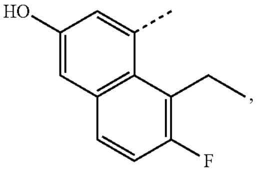
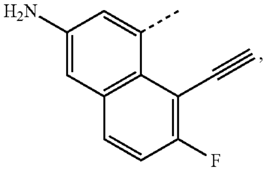
and
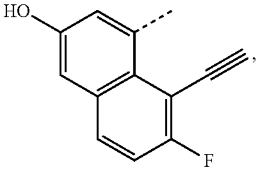
and other variables are as defined herein.
In some embodiments of the present invention, the $R_2$ is selected from
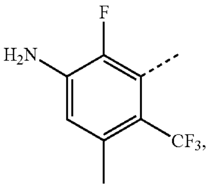
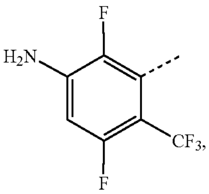
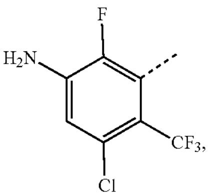
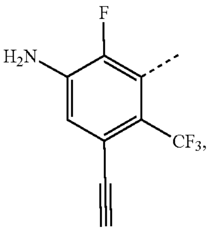
-continued
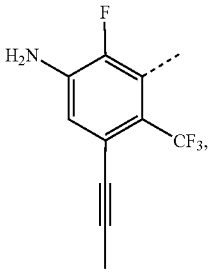
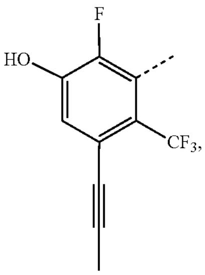
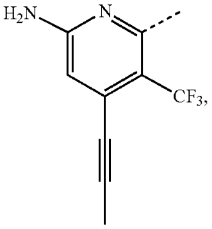
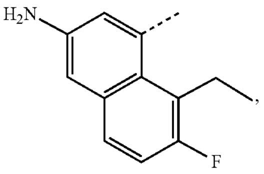
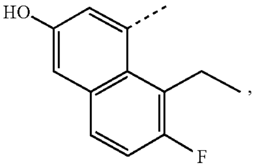
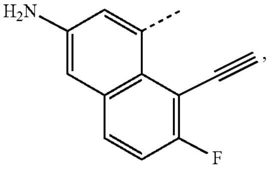
and
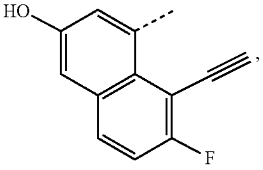
and other variables are as defined herein.
In some embodiments of the present invention, the 2 is selected from
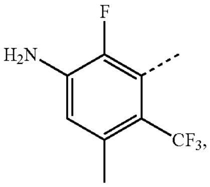
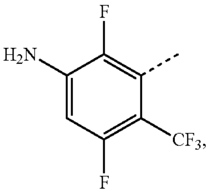
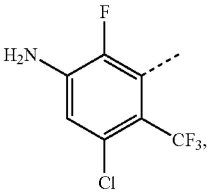
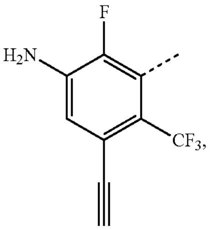

-continued

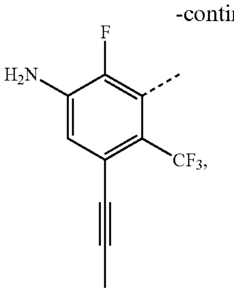 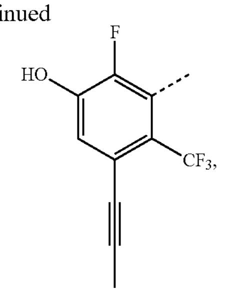

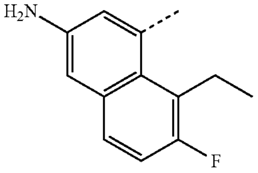, 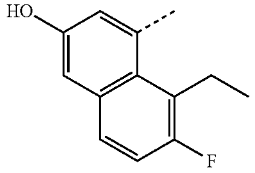,

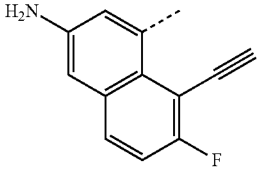, and

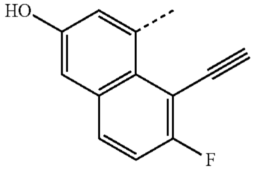, and other variables are as defined herein.

In some embodiments of the present invention, the ring C is selected from pyrrolyl, pyrazolyl, imidazolyl, oxazolyl, triazolyl, isoxazolyl, thiazolyl, pyridyl, pyrazinyl, and pyrimidinyl, and other variables are as defined herein.

In some embodiments of the present invention, the ring C is selected frompyrazolyl and imidazolyl, and other variables are as defined herein.

In some embodiments of the present invention, the ring A is selected from

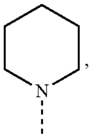, 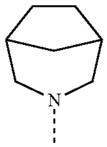, 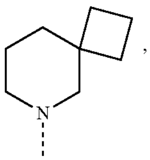,

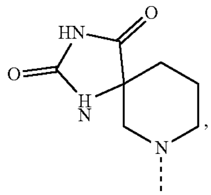, 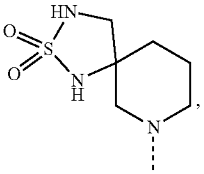,

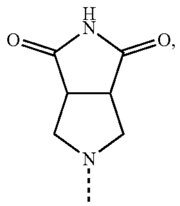 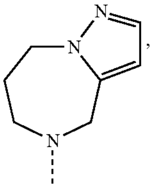, 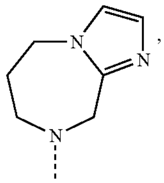,

-continued

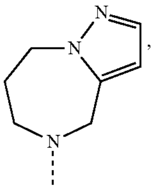, and 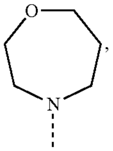, and other variables are as defined herein.

In some embodiments of the present invention, the ring A is selected from

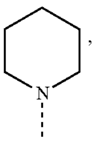, 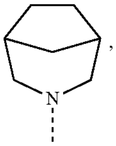, 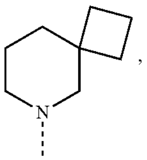,

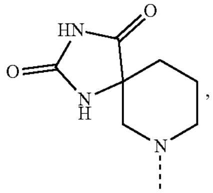, 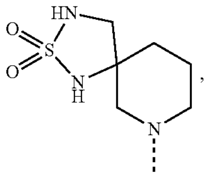,

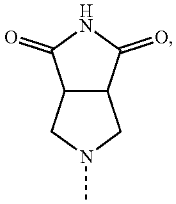 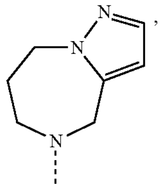, 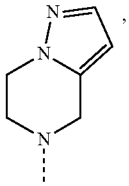, and

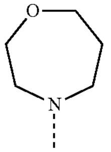

and other variables are as defined herein.

In some embodiments of the present invention, the ring A is selected from

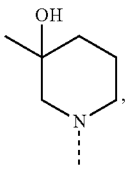, 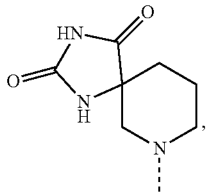, 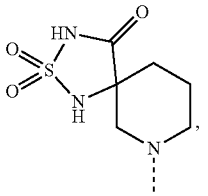,

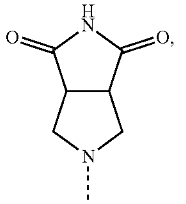 and 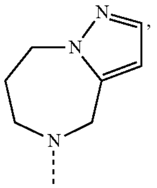, and other variables are as defined herein.

In some embodiments of the present invention, the ring A is selected from

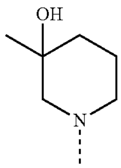,
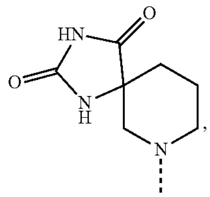,
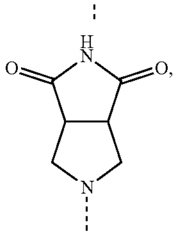, and
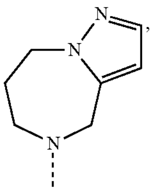, and other variables are as defined herein.

In some embodiments of the present invention, the ring B is selected from 8-9-membered heterocyclic alkenyl, and other variables are as defined herein.

In some embodiments of the present invention, the ring B is selected from

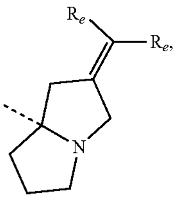
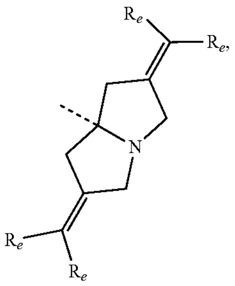

5-12-membered heterocyclic alkenyl, 7-12-membered tricyclic heterocyclic alkyl, and

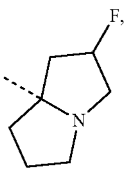, the
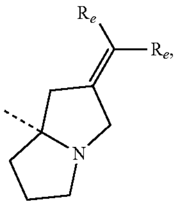
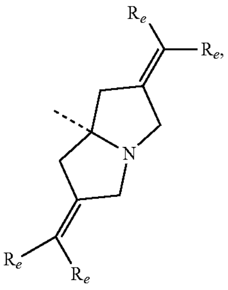

5-12-membered heterocyclic alkenyl, and 7-12-membered tricyclic heterocyclic alkyl being independently and optionally substituted with 1, 2, 3, 4, 5 or 6 $R_e$, respectively, and other variables are as defined herein.

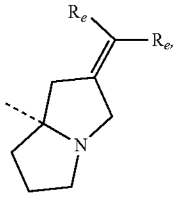
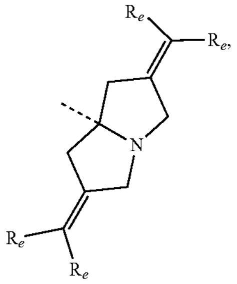

In some embodiments of the present invention, the ring B is selected from and 5-12-membered heterocyclic alkenyl, the

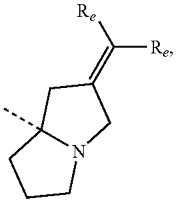
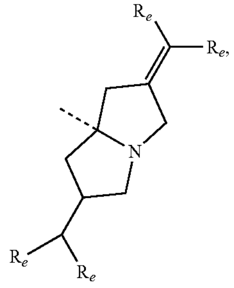

and 5-12-membered heterocyclic alkenyl are independently and optionally substituted with 1, 2, 3, 4, 5 or 6 $R_e$, respectively; or the ring B is selected from

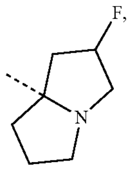

and other variables are as defined herein.

In some embodiments of the present invention, the ring B is selected from

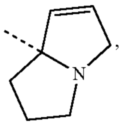,
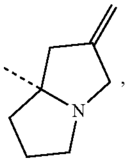,
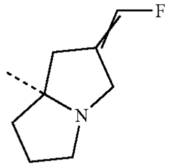,
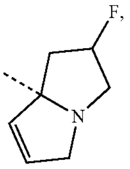,
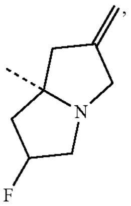, and
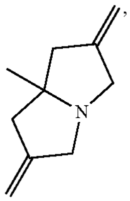, and other variables are as defined herein.

In some embodiments of the present invention, the ring B is selected from

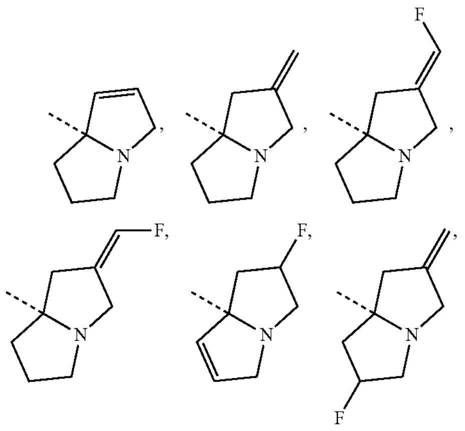

, and

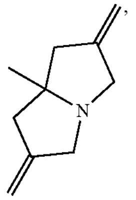

and other variables are as defined herein.

In some embodiments of the present invention, the structural unit

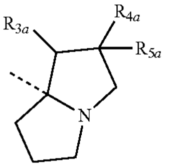

is selected from

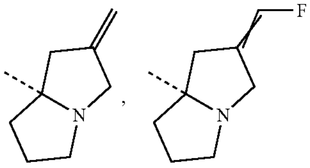

, and

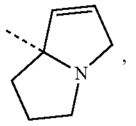

and other variables are as defined herein.

In some embodiments of the present invention, the structural unit

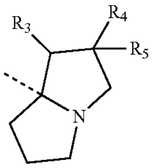

is selected from

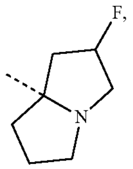

and other variables are as defined herein.

In some embodiments of the present invention, the structural unit

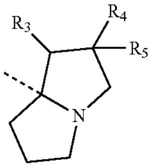

is selected from and other variables are as defined herein.

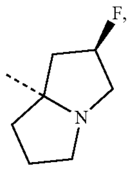

In some embodiments of the present invention, the ring A is selected from

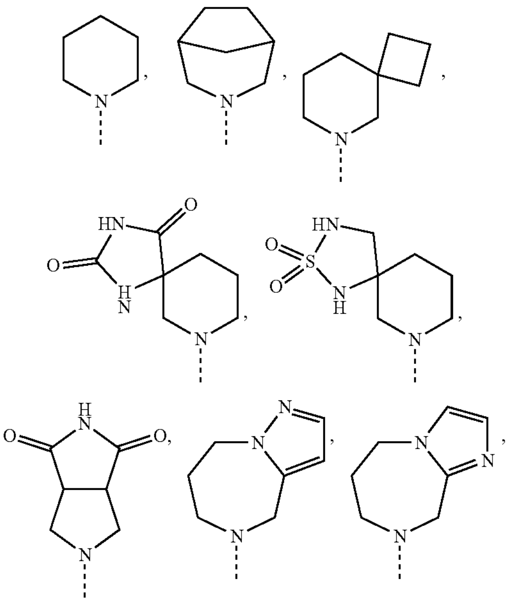

-continued

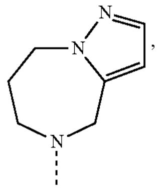

, and

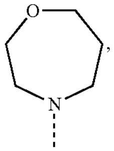

the ring B is selected from

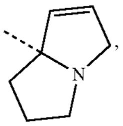
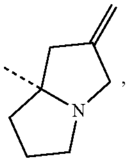
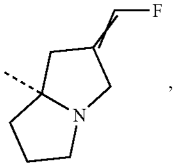
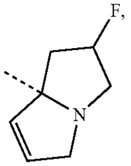
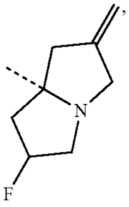

, and

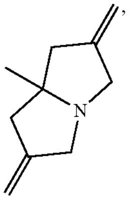

and other variables are as defined herein.

In some embodiments of the present invention, the ring A is selected from

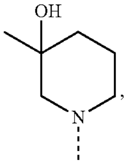
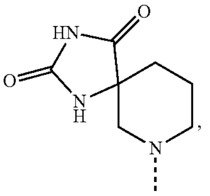
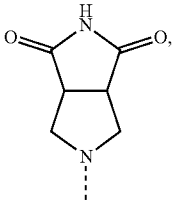

and

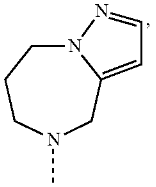

the ring B is selected from

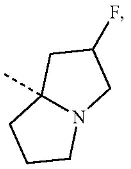

and other variables are as defined herein.

In some embodiments of the present invention, the $R_1$ on two adjacent atoms, together with the atoms to which they are attached, form a 5-6-membered heterocyclic alkenyl, the 5-6-membered heterocyclic alkenyl being independently and optionally substituted with 1, 2, 3, 4 or 5 R, respectively, so that the structural unit is

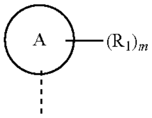

selected from

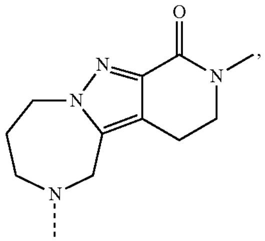

and other variables are as defined herein.

In some embodiments of the present invention, the structural unit

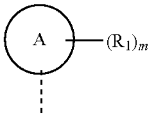

is selected from

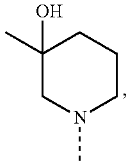
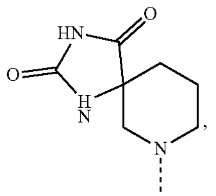
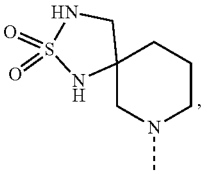
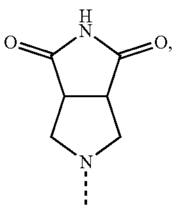
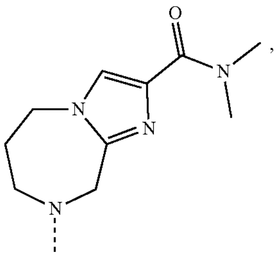

-continued
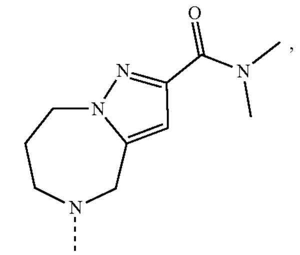
,
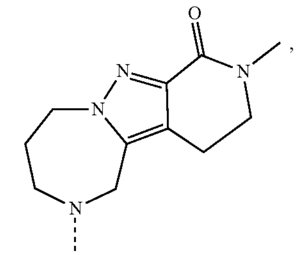
,
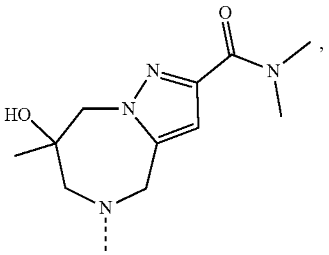
,
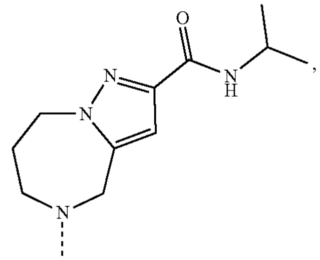
,
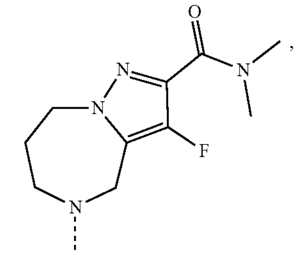
,
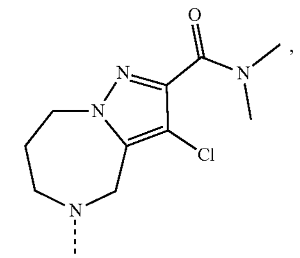
,
-continued
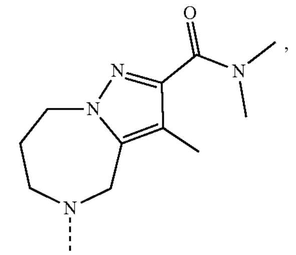
,
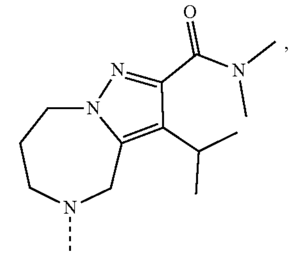
,
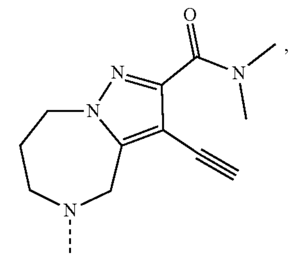
,
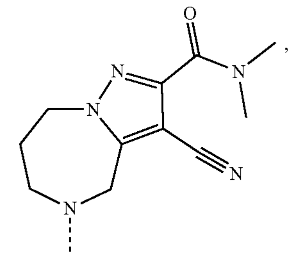
,
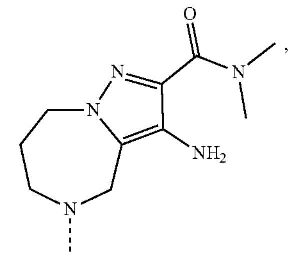
,
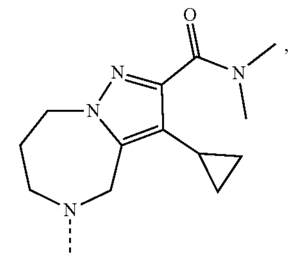
, -continued
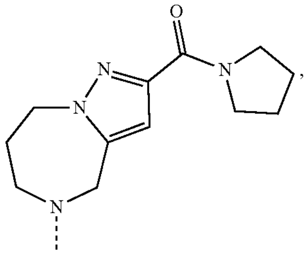
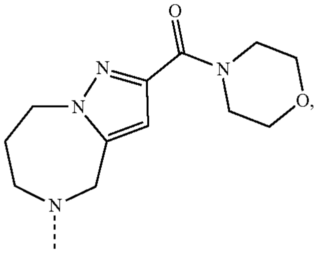
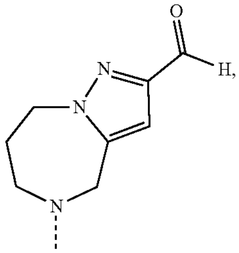
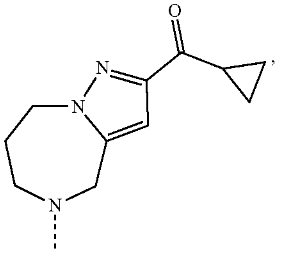
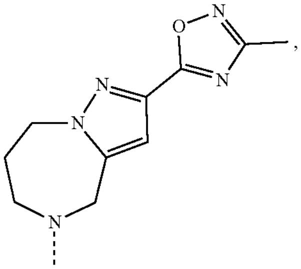
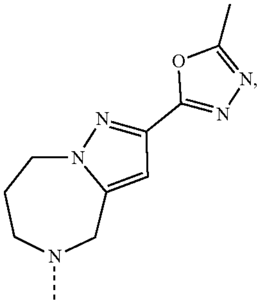
-continued
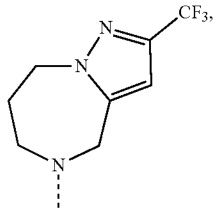
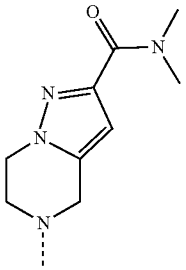
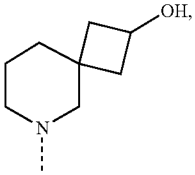
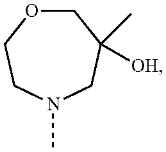 amd 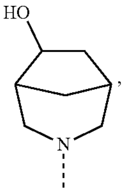
and other variables are as defined herein.
In some embodiments of the present invention, the structural unit
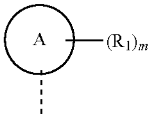
is selected from
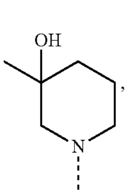
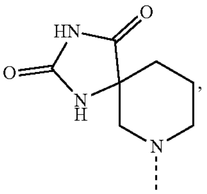
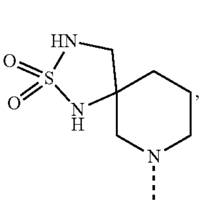
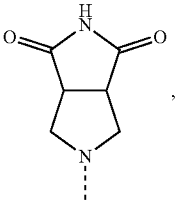

-continued
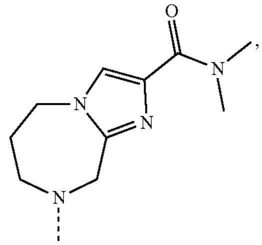
,
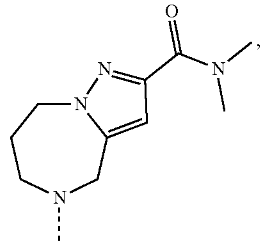
,
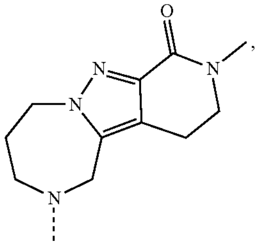
,
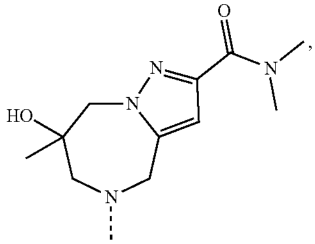
,
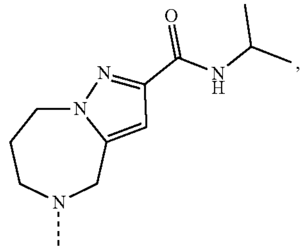
,
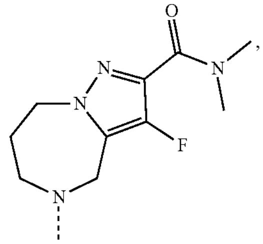
,
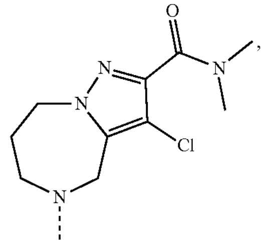
,
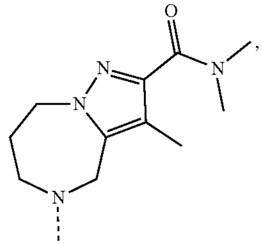
,
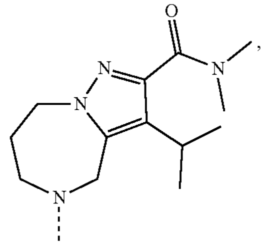
,
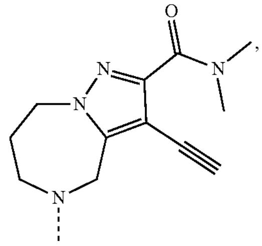
,
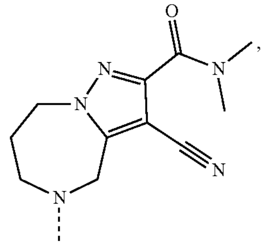
-continued
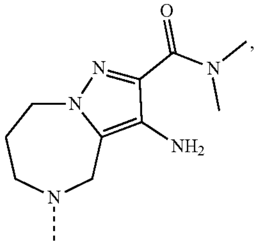
,
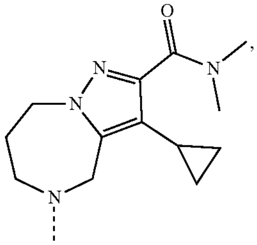
,
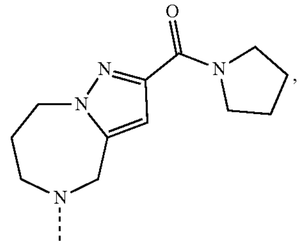
,
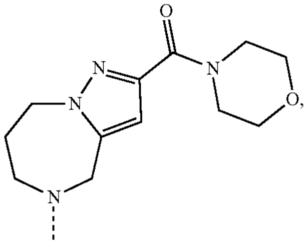
,
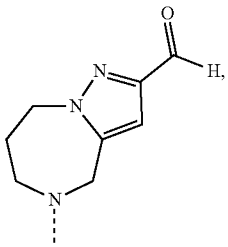
,
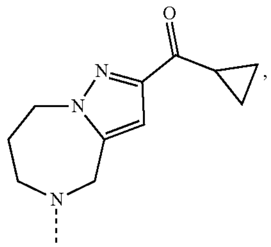
,
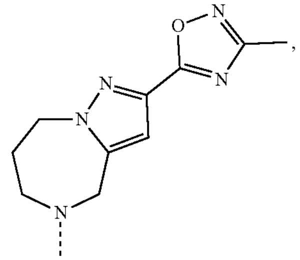
,
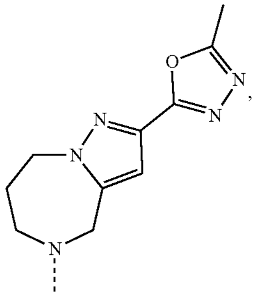
,
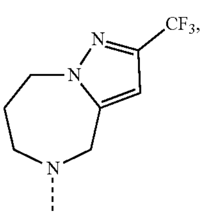
, -continued
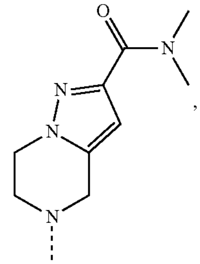,
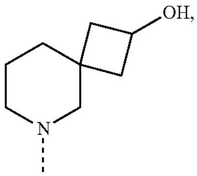
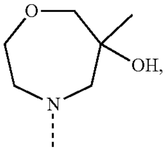
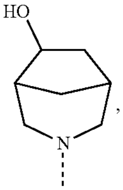,
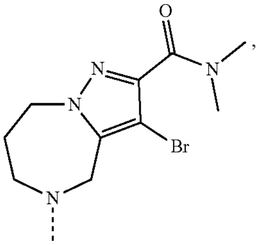
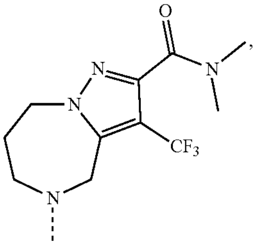
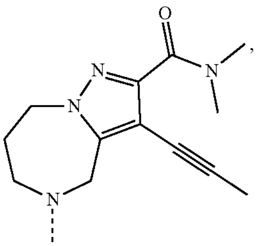
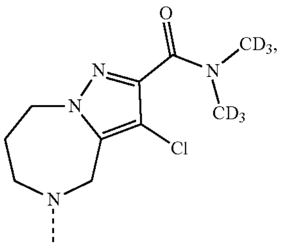
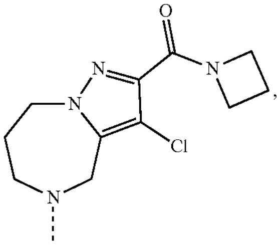, and
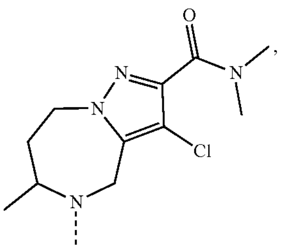
and other variables are as defined herein.
In some embodiments of the present invention, the structural unit
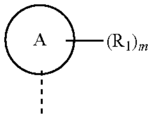
is selected from
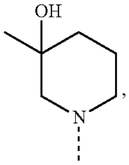,
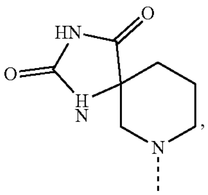,
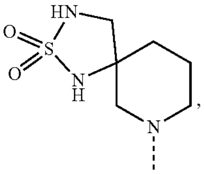,
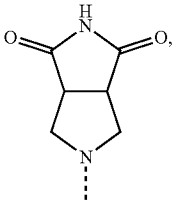
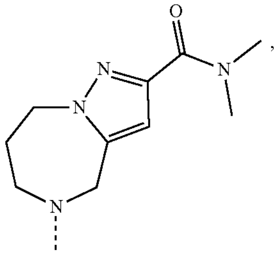
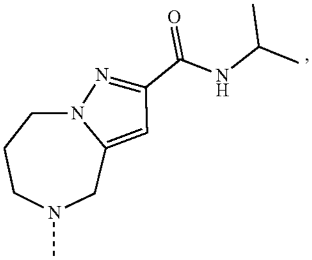
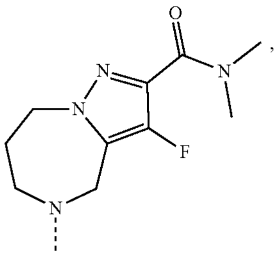
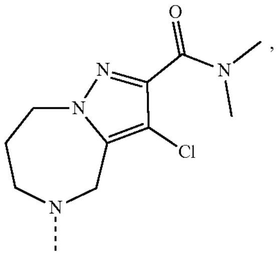

-continued
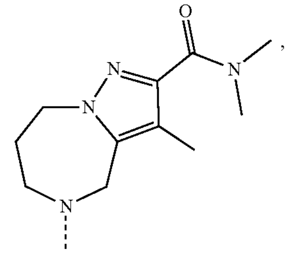
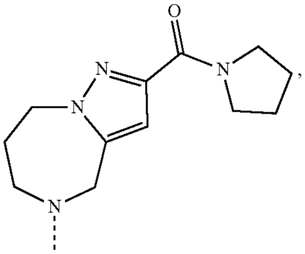
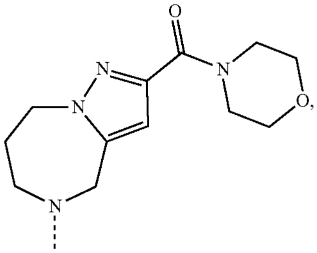
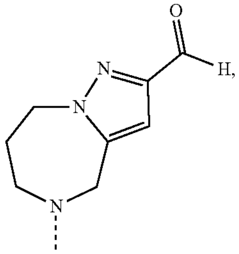
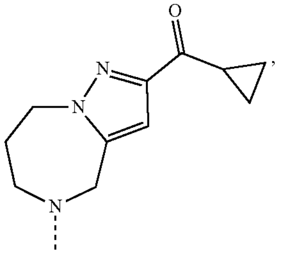
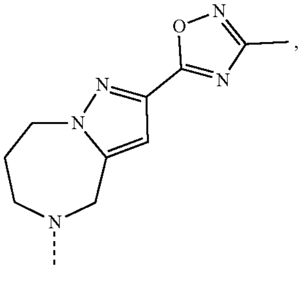
-continued
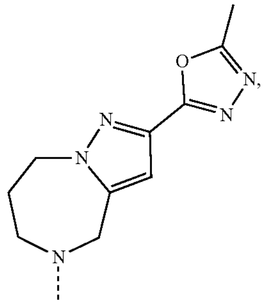
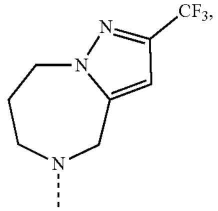
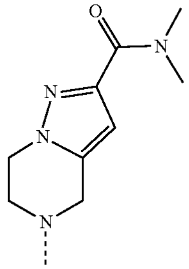
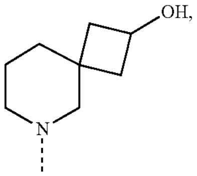
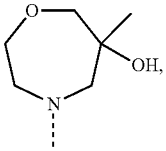 amd 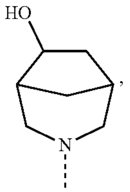
and other variables are as defined herein.
In some embodiments of the present invention, the structural unit
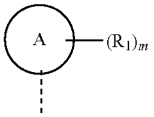
is selected from
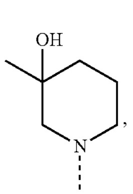
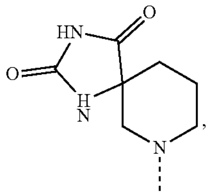

-continued
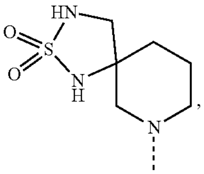
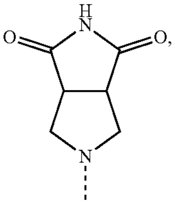
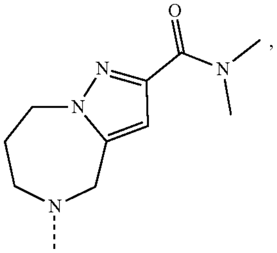
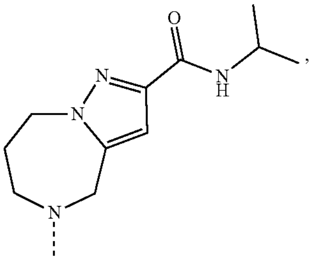
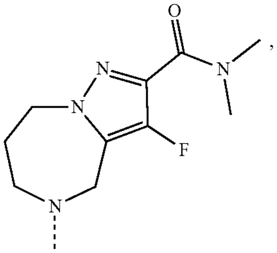
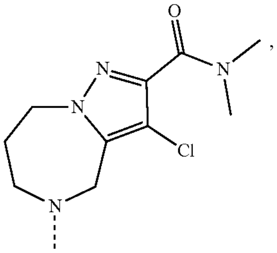
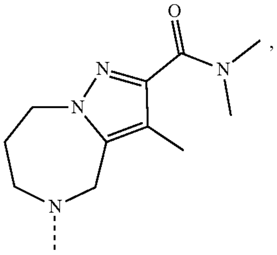
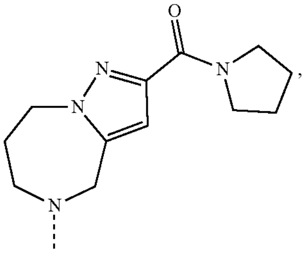 and
-continued
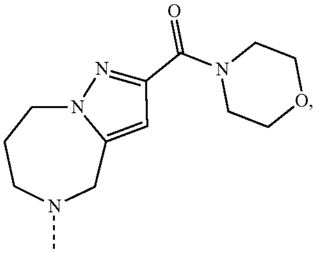
and other variables are as defined herein.
In some embodiments of the present invention, the structural unit
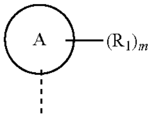
is selected from
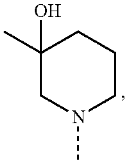
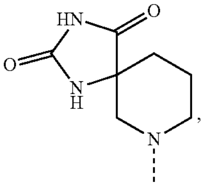
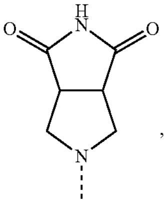
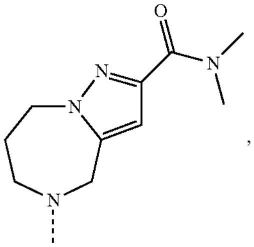
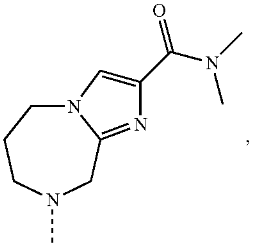
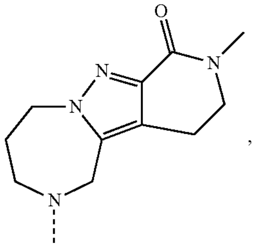
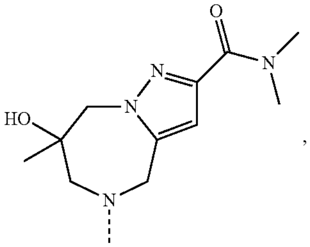
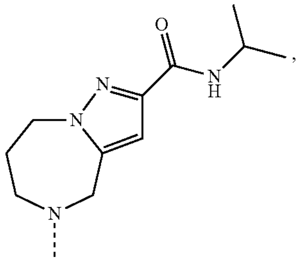
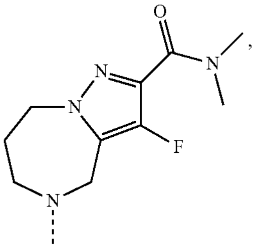

-continued
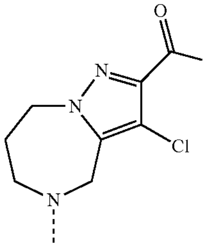
,
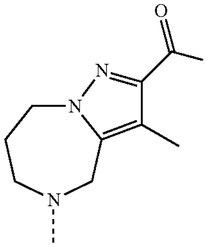
,
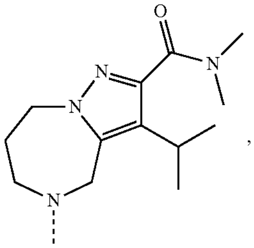
,
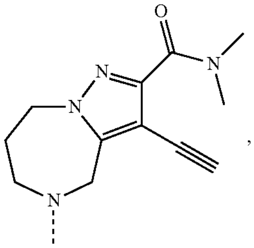
,
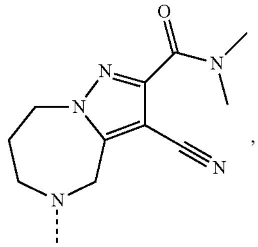
,
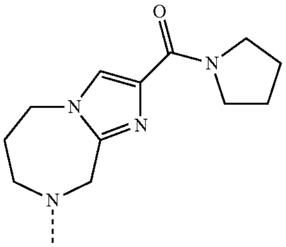
,
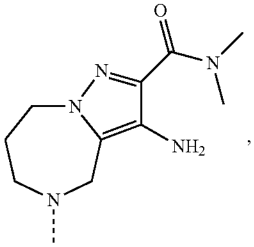
,
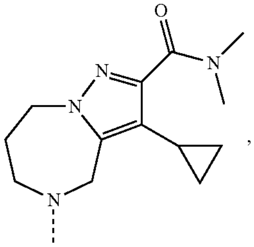
,
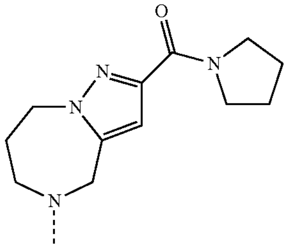
,
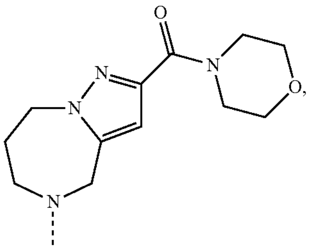
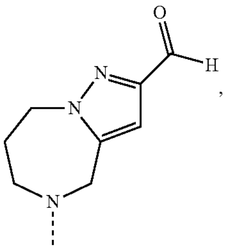
,
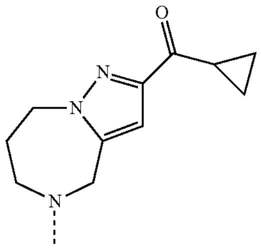
,
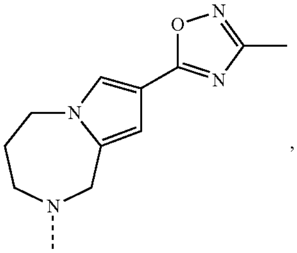
,
-continued
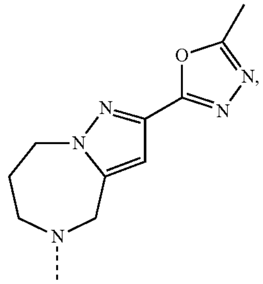
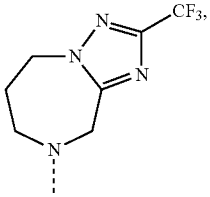
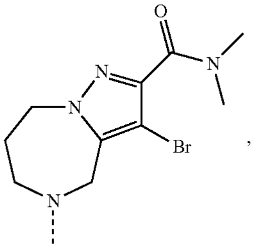
,
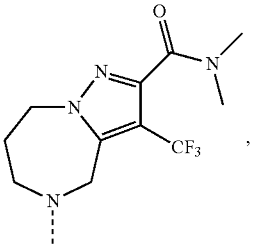
,
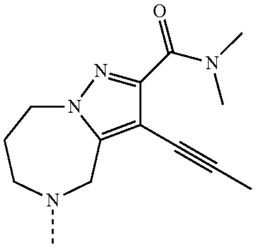
,
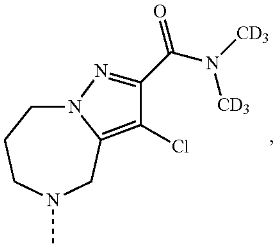
,
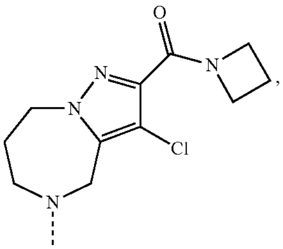
and
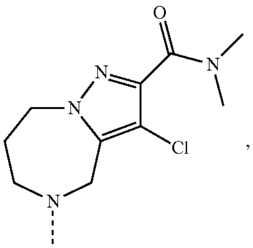
,
and other variables are as defined herein.
In some embodiments of the present invention, the structural unit
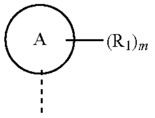

is selected from
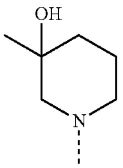,
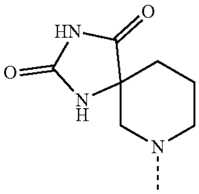,
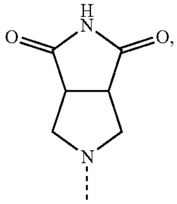
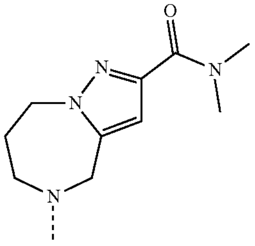,
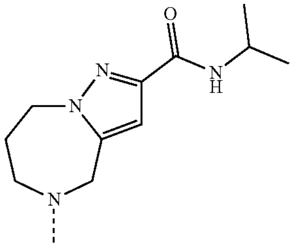,
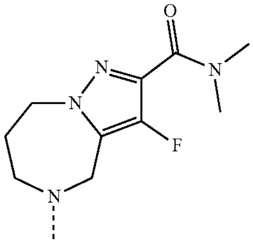,
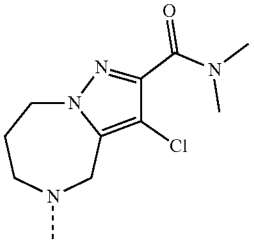,
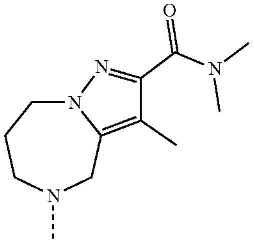,
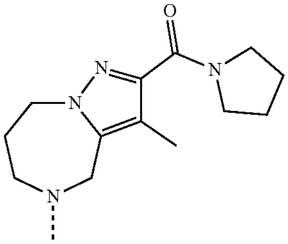, and
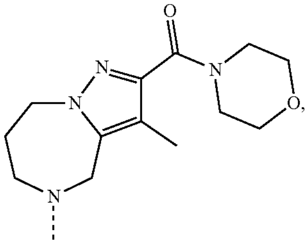
and other variables are as defined herein.
In some embodiments of the present invention, the ring B is selected from
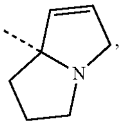,
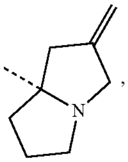,
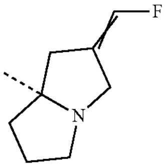,
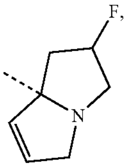
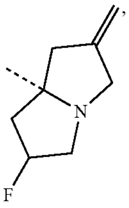, and
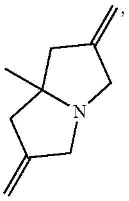,
the structural unit
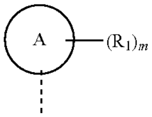
is selected from
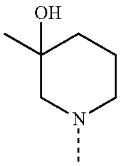,
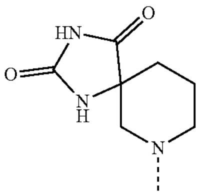,
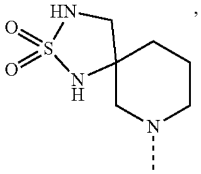,
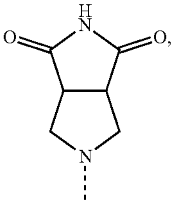
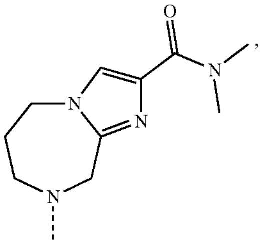
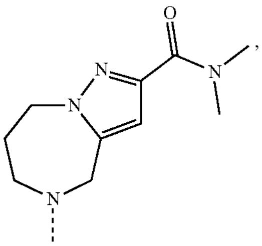

-continued
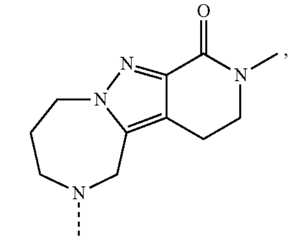
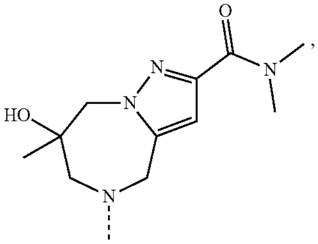
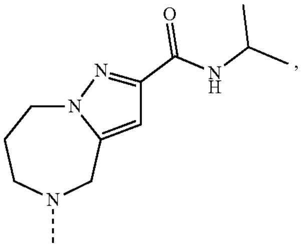
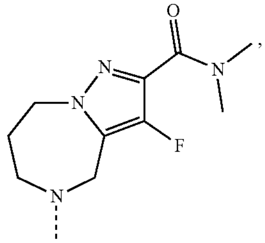
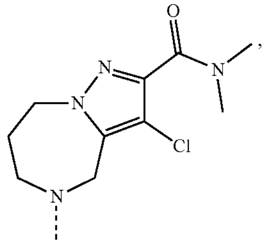
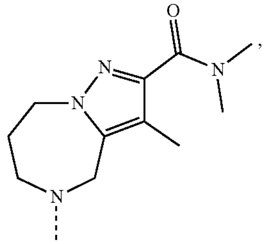
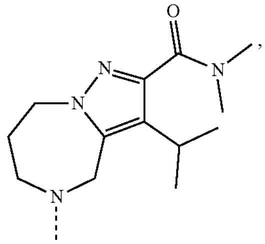
-continued
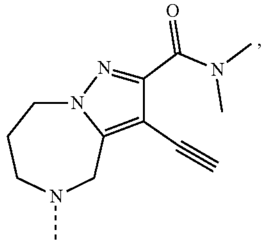
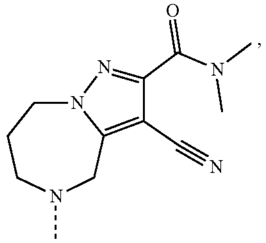
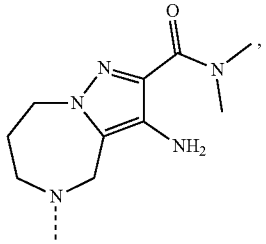
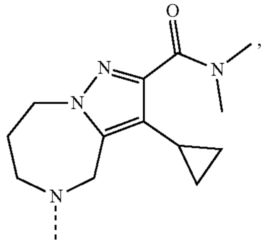
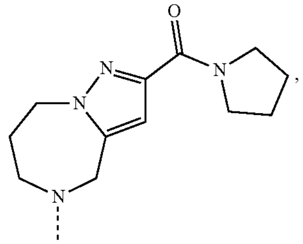
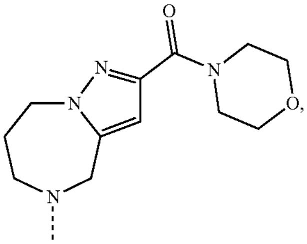
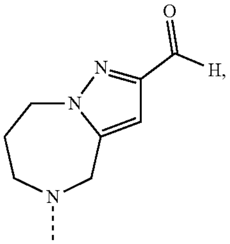
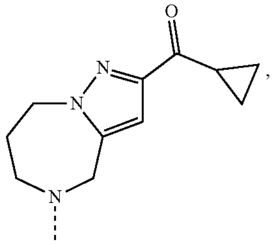

-continued
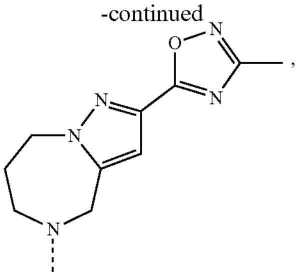,
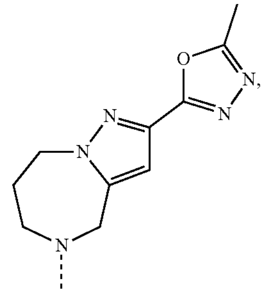,
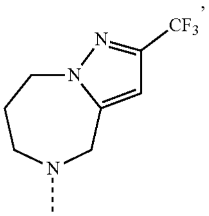,
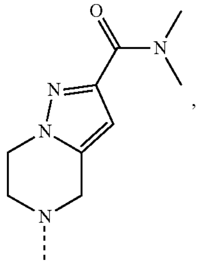,
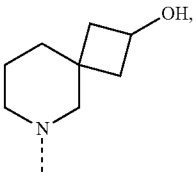
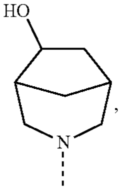,
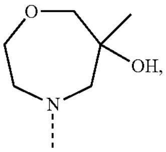
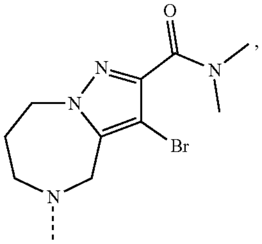,
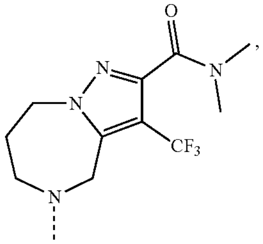,
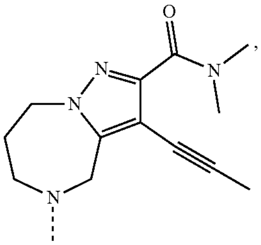,
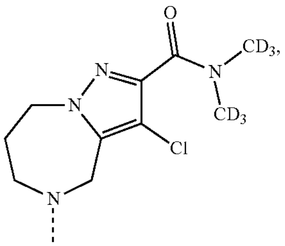
-continued
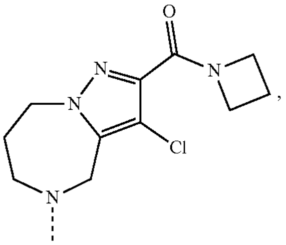, and
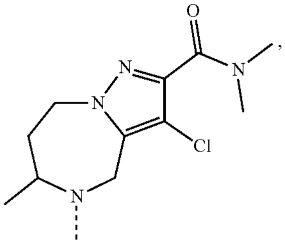,
and other variables are as defined herein.
N In some embodiments of the present invention, the ring B is selected from
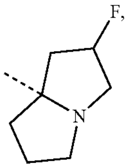
the structural unit
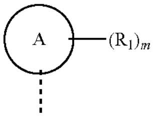
is selected from
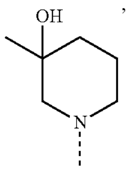,
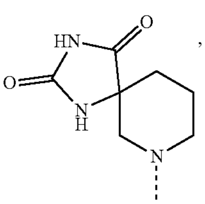,
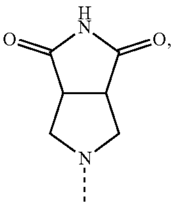
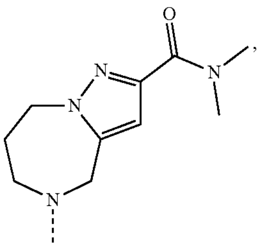,
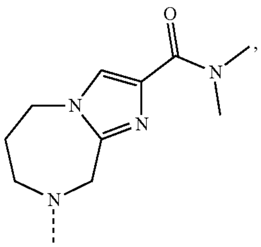

-continued
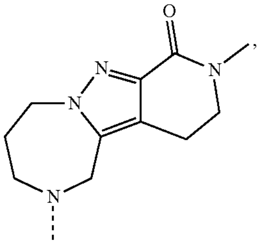
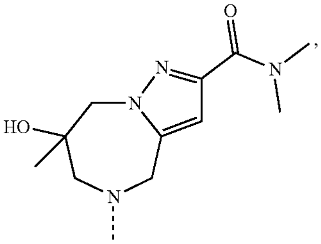
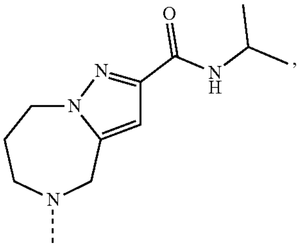
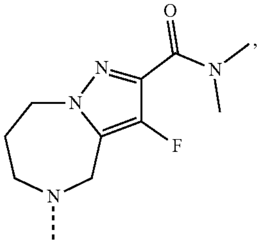
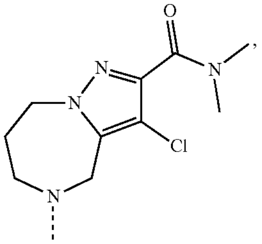
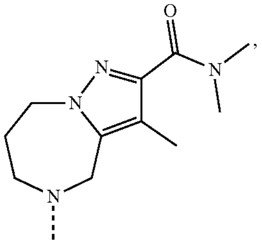
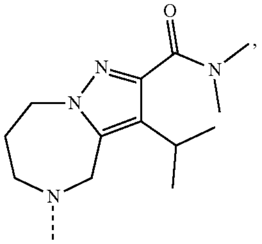
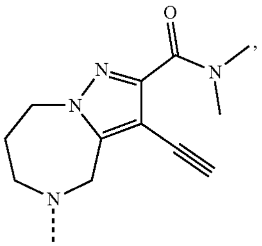
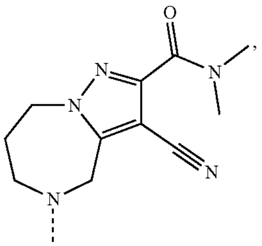
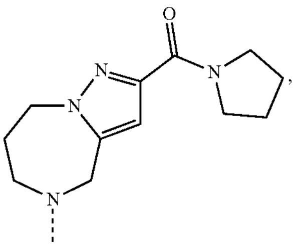
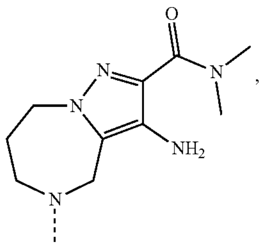
-continued
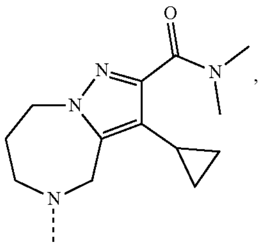
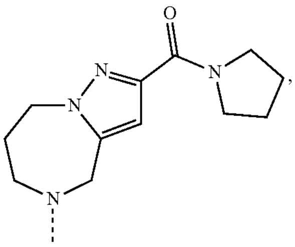
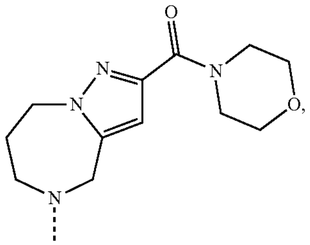
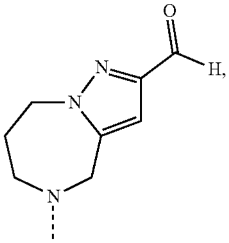
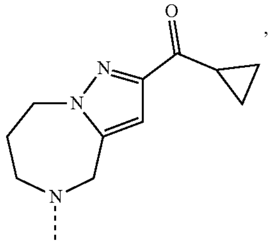
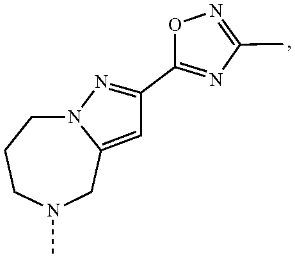
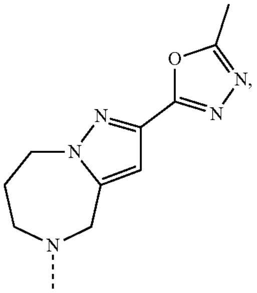
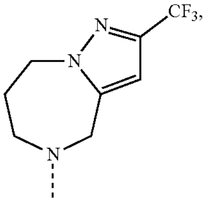
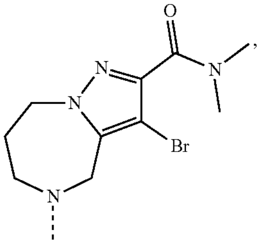
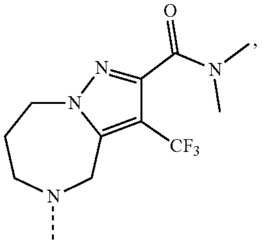
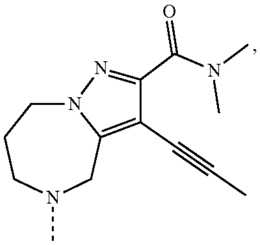
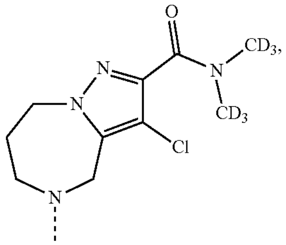

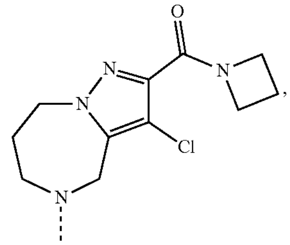
, and
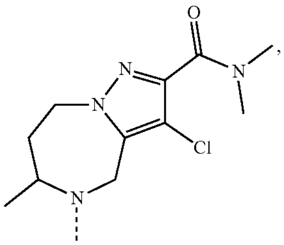
and other variables are as defined herein.
In some embodiments of the present invention, the structural unit
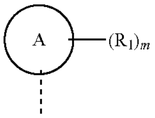
is selected from
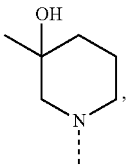
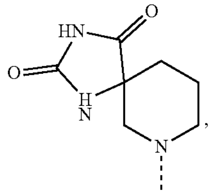
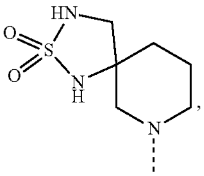
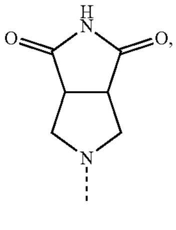
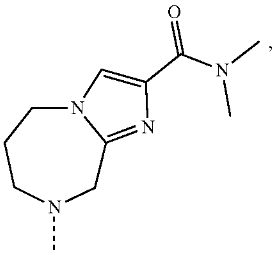
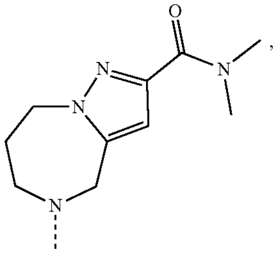
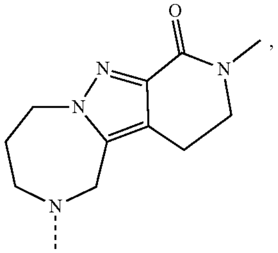
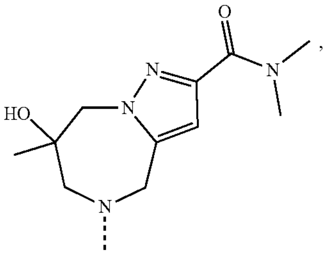
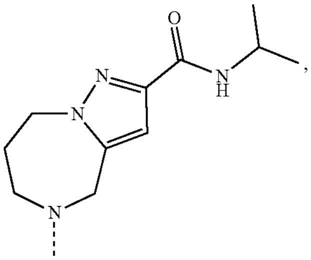
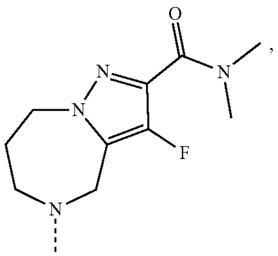
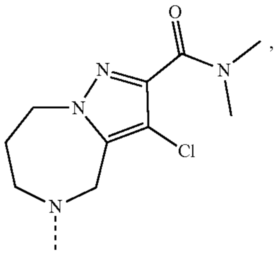

-continued
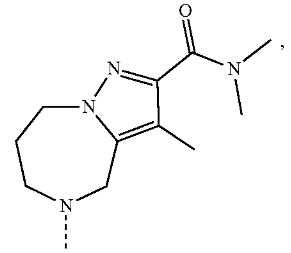
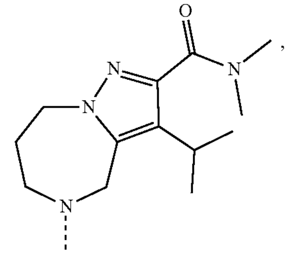
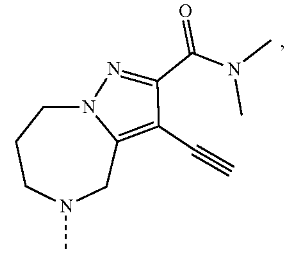
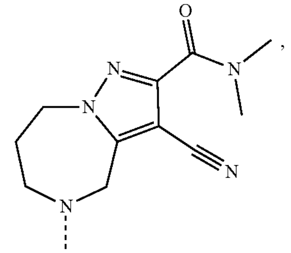
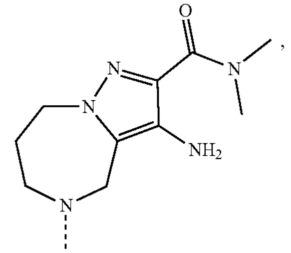
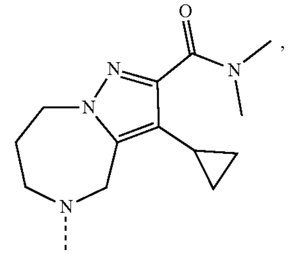
-continued
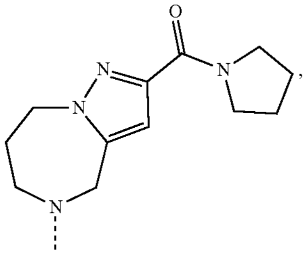
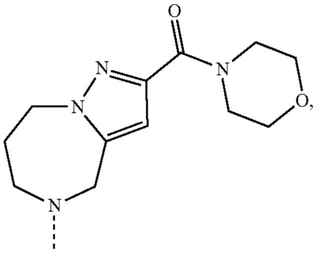
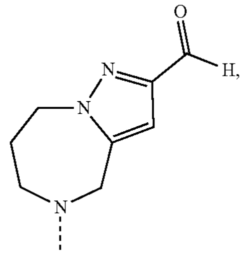
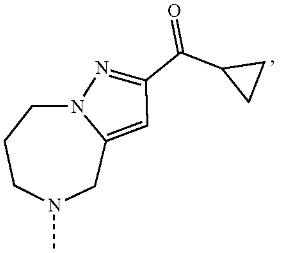
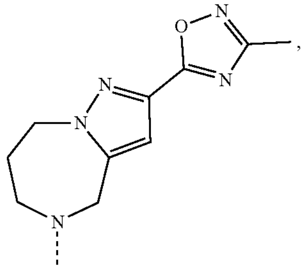
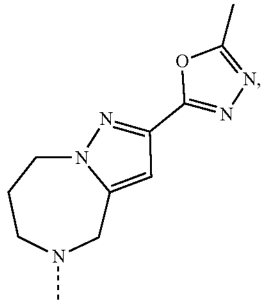

-continued
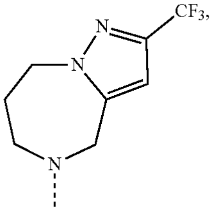
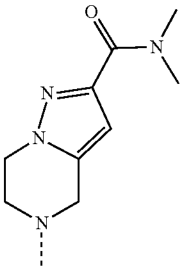
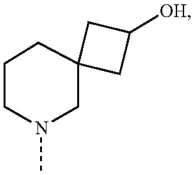
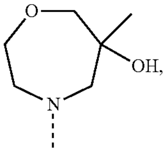 amd 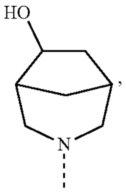
the ring B is selected from
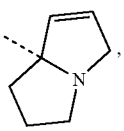 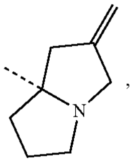 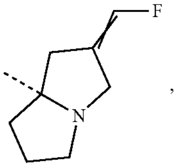 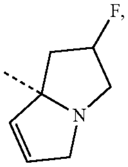 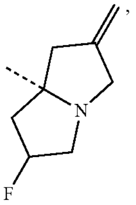 and 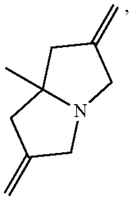
and other variables are as defined herein.
In some embodiments of the present invention, the structural unit
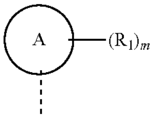
is selected from
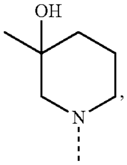 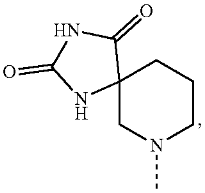 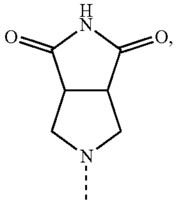
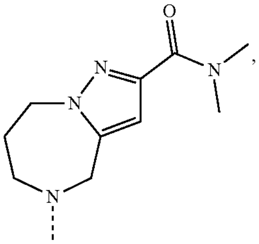 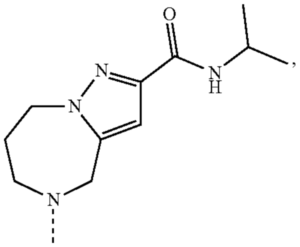
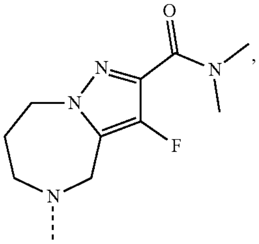 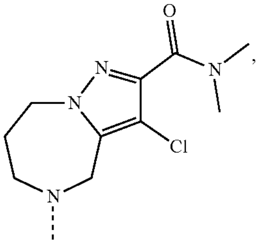
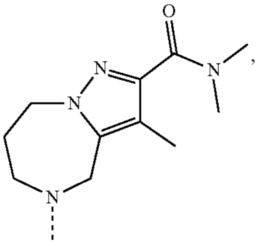
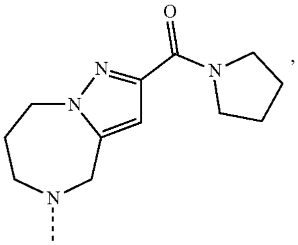 and
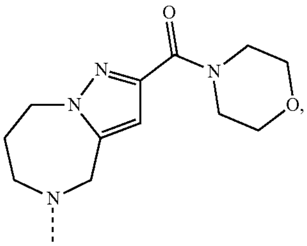

the ring B is selected from

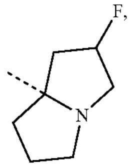

and other variables are as defined herein.

In some embodiments of the present invention, the $R_6$ is selected from H, and other variables are as defined herein.

In some embodiments of the present invention, the $R_7$ is selected from H, and other variables are as defined herein.

The present invention further provides a compound represented by formula (I) and a pharmaceutically acceptable salt thereof, where (I)

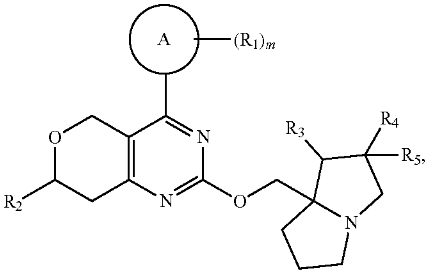

ring A is selected from

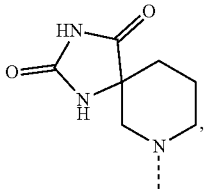

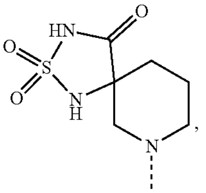

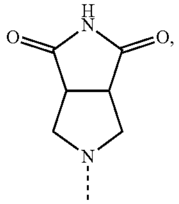

and

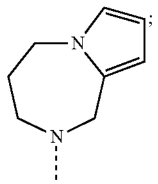

or, ring A is selected from

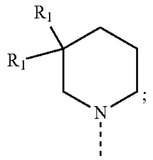

$R_1$ is selected from halogen, OH, $C_{1-3}$ alkyl, —C(═O)—$NR_aR_b$, and —C(═O)—$R_c$;

$R_2$ is selected from phenyl and naphthyl, the phenyl and naphthyl being independently and optionally substituted with 1, 2, 3, 4 or 5 $R_d$, respectively;

$R_3$ is selected from H, $R_4$ is selected from F, and $R_5$ is selected from H;

or, $R_3$ and $R_4$ are linked, so that the structural unit

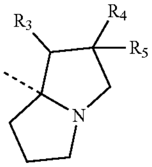

is selected from

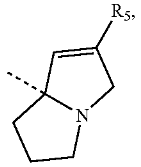

and $R_5$ is selected from H;

or, $R_4$ and $R_5$ are linked to form

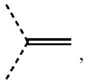

the

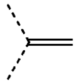

being optionally substituted with 1 or 2 $R_e$, and $R_3$ is selected from H;

$R_a$ is selected from H and $C_{1-3}$ alkyl;

$R_b$ is selected from H and $C_{1-3}$ alkyl;

$R_c$ is selected from 5-6-membered heterocyclic alkyl;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively;

each $R_e$ is independently selected from H, F, Cl, Br, I, CN, $CH_3$, and $OCH_3$, respectively;

m is selected from 0, 1, 2 and 3.

The present invention further provides a compound represented by formula (I) and a pharmaceutically acceptable salt thereof.

(I)

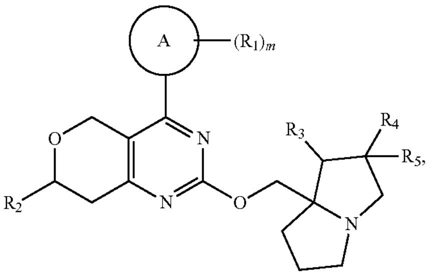

where ring A is selected from

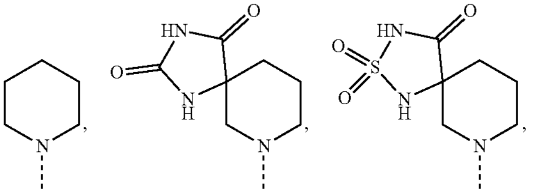

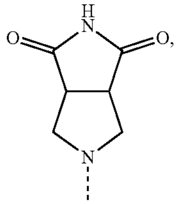

and

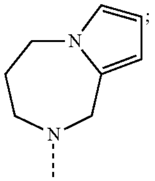

$R_1$ is selected from halogen, OH, $C_{1-3}$ alkyl, —C(=O)—$NR_aR_b$, and —C(=O)—$R_c$;

$R_2$ is selected from phenyl and naphthyl, the phenyl and naphthyl being independently and optionally substituted with 1, 2, 3, 4 or 5 $R_d$, respectively;

$R_3$ is selected from H, $R_4$ is selected from F, and $R_5$ is selected from H;

or, $R_3$ and $R_4$ are linked, so that the structural unit

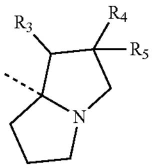

is selected from

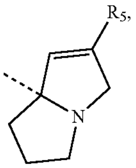

and $R_5$ is selected from H;

or, $R_4$ and $R_5$ are linked, so that the structural unit

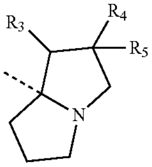

is selected from

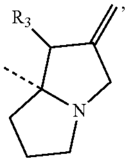

and $R_3$ is selected from H;

$R_a$ is selected from H and $C_{1-3}$ alkyl;

$R_b$ is selected from H and $C_{1-3}$ alkyl;

$R_c$ is selected from 5-6-membered heterocyclic alkyl;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively; and m is selected from 0, 1, 2 or 3.

The present invention further provides a compound represented by formula (I) and a pharmaceutically acceptable salt thereof.

(I)

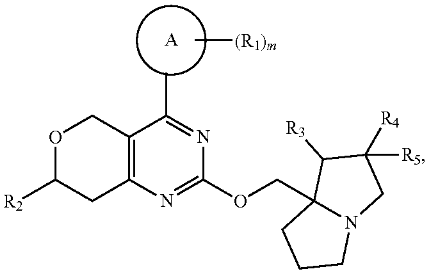

where ring A is selected from

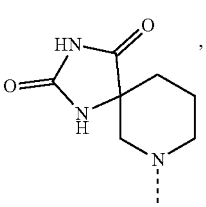

,

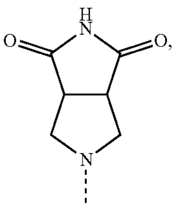

and

-continued

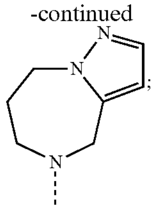

or, ring A is selected from

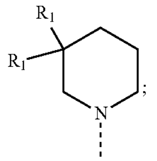

$R_1$ is selected from halogen, OH, $C_{1-3}$ alkyl, —C(═O)—$NR_aR_b$, and —C(═O)—$R_c$;

$R_2$ is selected from phenyl and naphthyl, the phenyl and naphthyl being independently and optionally substituted with 1, 2, 3, 4 or 5 $R_d$, respectively;

$R_3$ is selected from H, R 4 is selected from F, and $R_5$ is selected from H;

$R_a$ is selected from H and $C_{1-3}$ alkyl;

$R_b$ is selected from H and $C_{1-3}$ alkyl;

$R_c$ is selected from 5-6-membered heterocyclic alkyl;

each $R_d$ is independently selected from H, F, Cl, Br, I, OH, $NH_2$, CN, $C_{1-3}$ alkyl, and $C_{2-4}$ alkynyl, the $C_{1-3}$ alkyl and $C_{2-4}$ alkynyl being independently and optionally substituted with 1, 2, 3, 4 or 5 halogen, respectively; and m is selected from 0, 1, 2 and 3.

In some embodiments of the present invention, in the compound represented by formula (I) or pharmaceutically acceptable salt thereof, $R_a$ is selected from H, $CH_3$, and $CH(CH_3)_2$, and other variables are as defined herein.

In some embodiments of the present invention, in the compound represented by formula (I) or pharmaceutically acceptable salt thereof, $R_b$ is selected from H, $CH_3$, and $CH(CH_3)_2$, and other variables are as defined herein.

In some embodiments of the present invention, in the compound represented by formula (I) or pharmaceutically acceptable salt thereof, $R_c$ is selected from tetrahydropyrrolyl and morpholinyl, and other variables are as defined herein.

In some embodiments of the present invention, in the compound represented by formula (I) or pharmaceutically acceptable salt thereof, each $R_d$ is independently selected from H, F, Cl, Br, I, OH, $NH_2$, CN, $CH_3$, $CH_2F$, $CF_2H$, $CF_3$, $CH_2CH_3$, $CF_2CF_3$, —C≡CH, —C≡CF, —C≡CBr, —C≡$CCH_3$, and —C≡$CCF_3$, respectively, and other variables are as defined herein.

In some embodiments of the present invention, in the compound represented by formula (I) or pharmaceutically acceptable salt thereof, each $R_d$ is independently selected from F, Cl, $NH_2$, OH, $CH_3$, $CF_3$, $CH_2CH_3$, —C≡CH, and —C≡$CCH_3$, respectively, and other variables are as defined herein.

In some embodiments of the present invention, in the compound represented by formula (I) or pharmaceutically acceptable salt thereof, $R_1$ is selected from F, Cl, OH, $CH_3$,

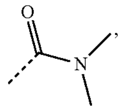
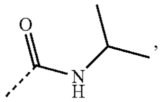
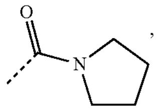
, and
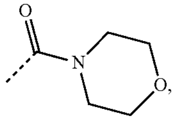

and other variables are as defined herein.

In some embodiments of the present invention, in the compound represented by formula (I) or pharmaceutically acceptable salt thereof, $R_2$ is selected from phenyl and naphthyl, the phenyl and naphthyl being independently and optionally substituted with 1, 2, 3, 4 or 5 $R_d$, respectively, and other variables are as defined herein.

In some embodiments of the present invention, in the compound represented by formula (I) or pharmaceutically acceptable salt thereof, $R_2$ is selected from

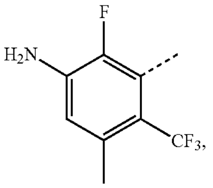
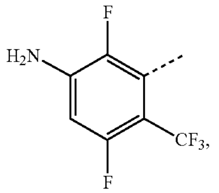
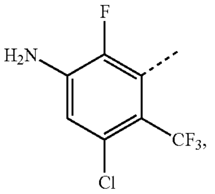
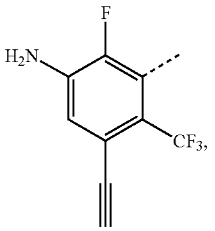
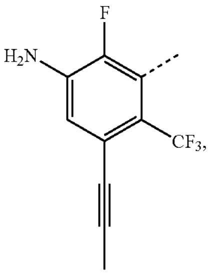
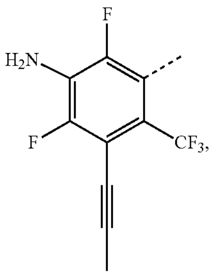
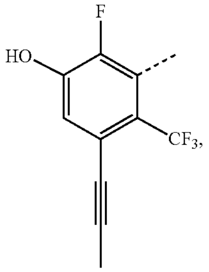
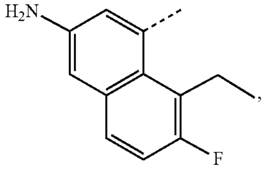

-continued

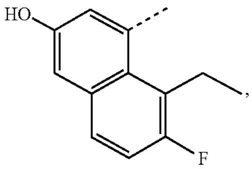,

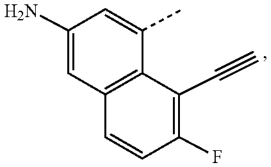, and

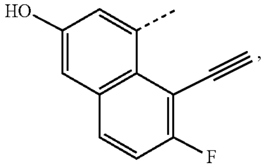, and other variables are as defined herein.

In some embodiments of the present invention, in the compound represented by formula (I) or pharmaceutically acceptable salt thereof, $R_2$ is selected from

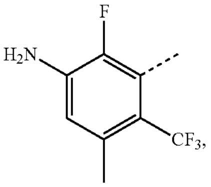

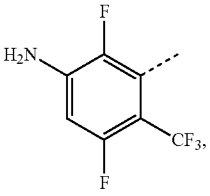

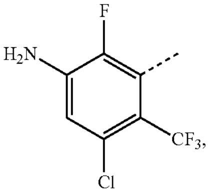

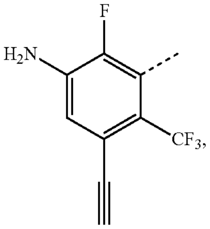

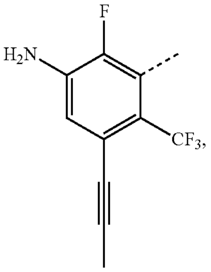

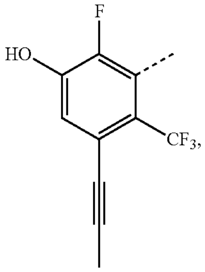

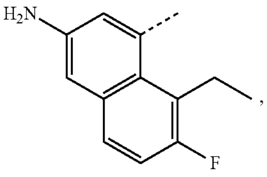,

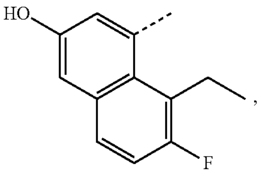,

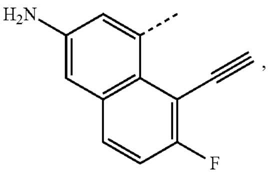, and

-continued

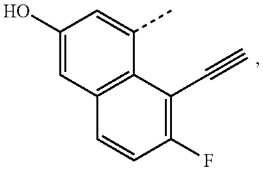, and other variables are as defined herein.

In some embodiments of the present invention, in the compound represented by formula (I) or pharmaceutically acceptable salt thereof, ring A is selected from

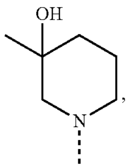,

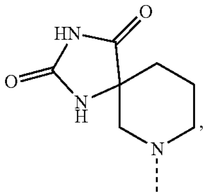,

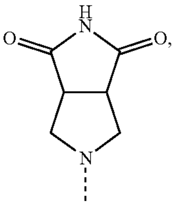, and

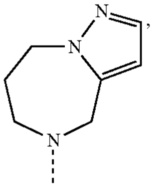, and other variables are as defined herein.

In some embodiments of the present invention, in the compound represented by formula (I) or pharmaceutically acceptable salt thereof, a structural unit

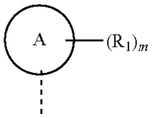

is selected from

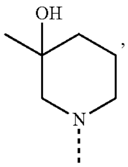,

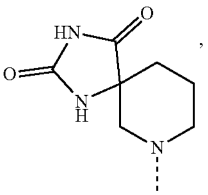,

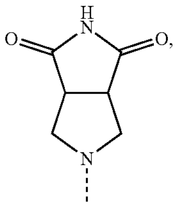,

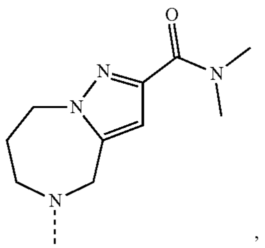,

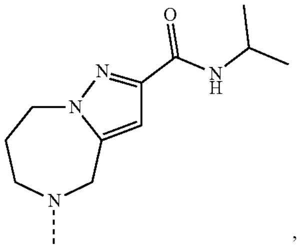,

-continued

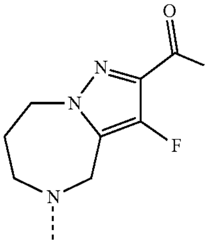
,
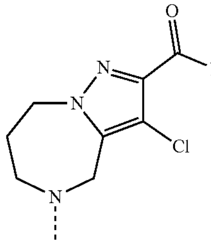
,
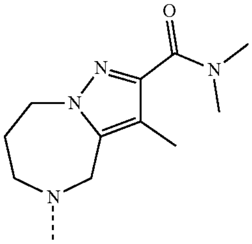
,
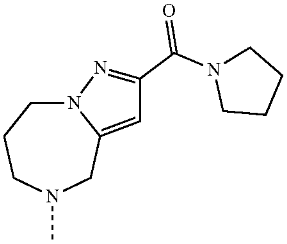
, and
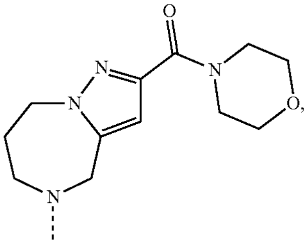

and other variables are as defined herein.

In some embodiments of the present invention, in the compound represented by formula (I) or pharmaceutically acceptable salt thereof, a structural unit

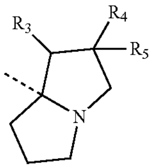

is selected from

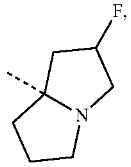

and other variables are as defined herein.

In some embodiments of the present invention, in the compound represented by formula (I) or pharmaceutically acceptable salt thereof, a structural unit

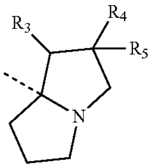

is selected from

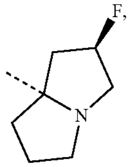

and other variables are as defined herein.

In some embodiments of the present invention, in the compound represented by formula (I) or pharmaceutically acceptable salt thereof, a structural unit

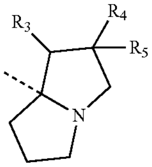

is selected from

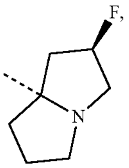
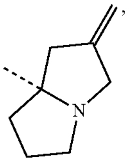
, and
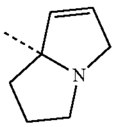
, and other variables are as defined herein.

In some embodiments of the present invention, in the compound represented by formula (I) or pharmaceutically acceptable salt thereof, a structural unit

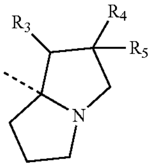

is selected from

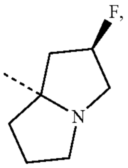
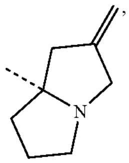
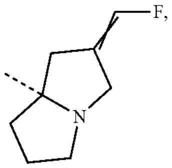
and

-continued

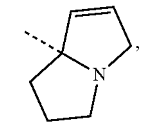

and other variables are as defined herein.

In some embodiments of the present invention, in the compound represented by formula (I) or pharmaceutically acceptable salt thereof, a structural unit

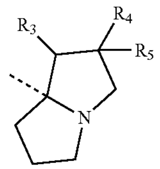

is selected from

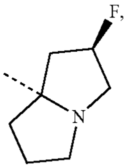

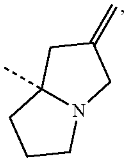

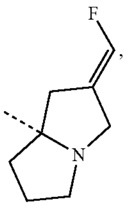

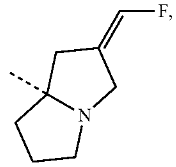

and

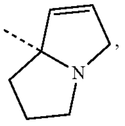

and other variables are as defined herein.

There are also some embodiments of the present invention that can be obtained by arbitrarily combining the above variables.

The present invention provides the following compounds or pharmaceutically acceptable salts:

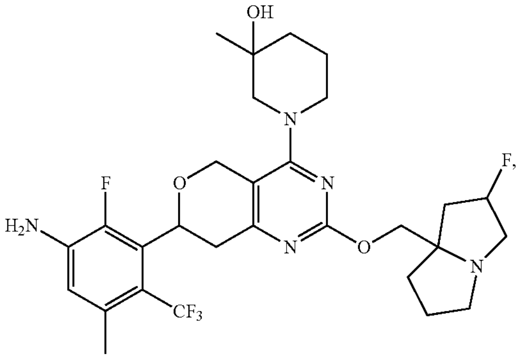

-continued

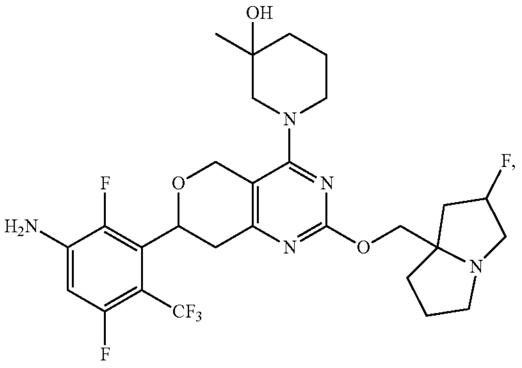

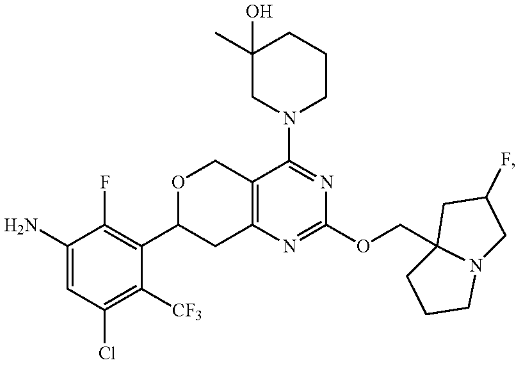

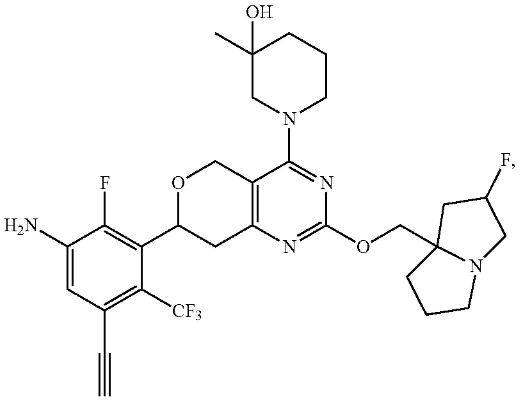

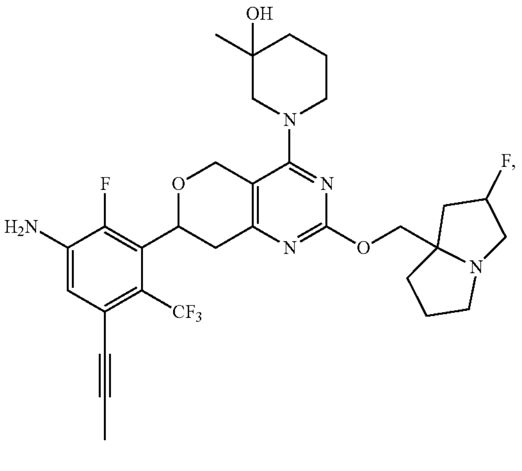

-continued
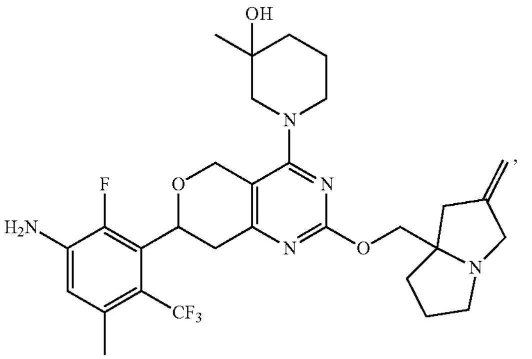
,
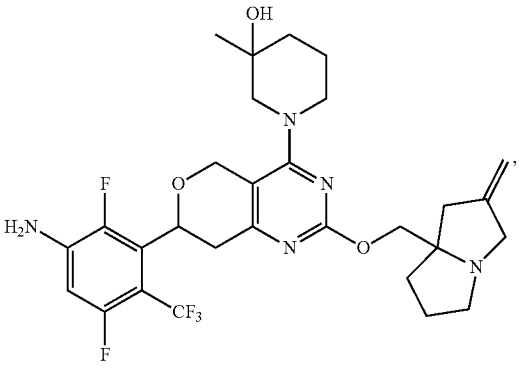
,
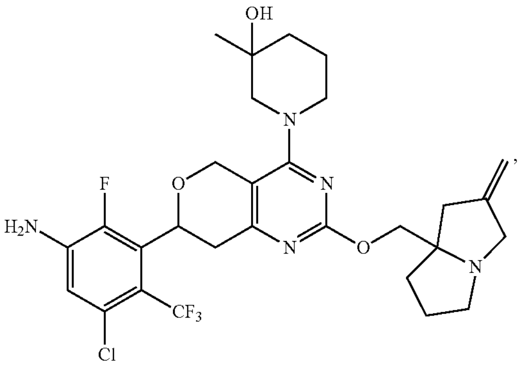
,
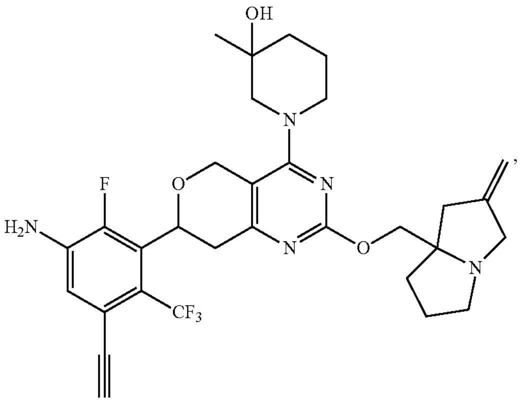
,
-continued
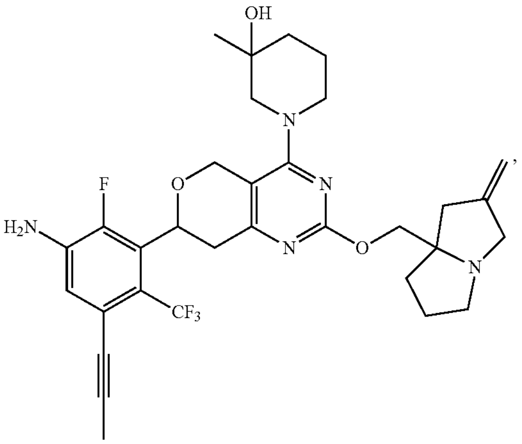
,
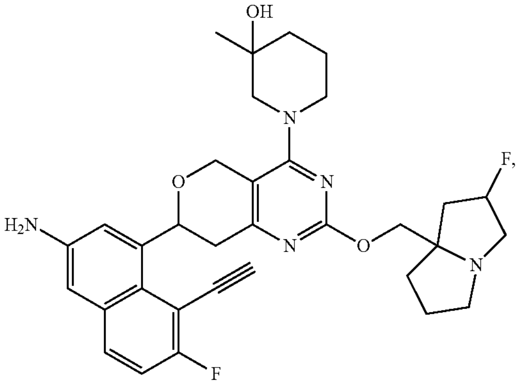
,
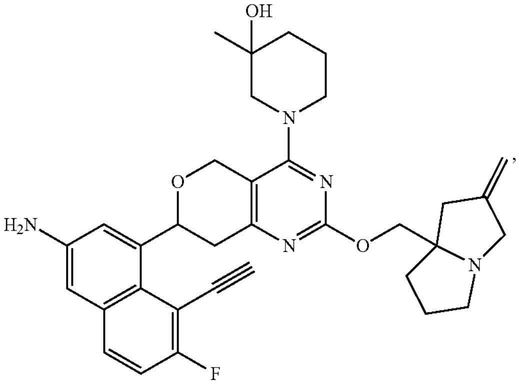
,
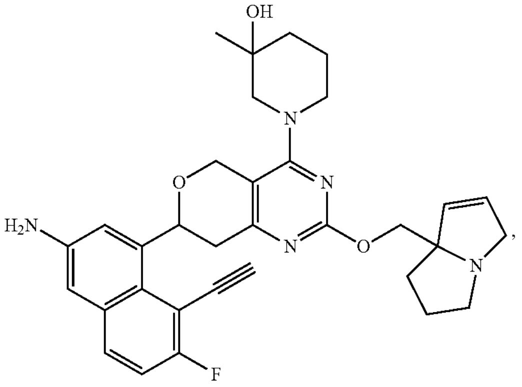
, -continued
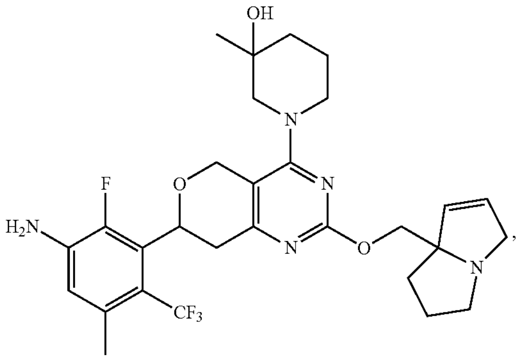
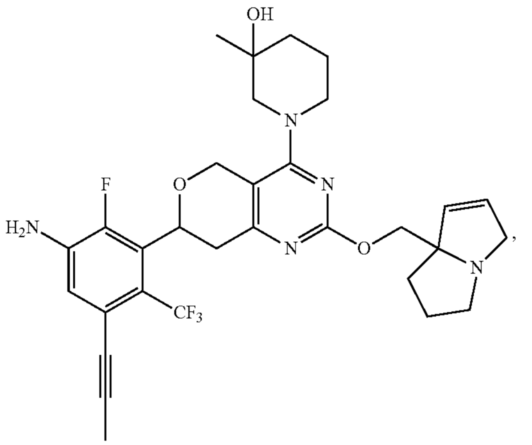
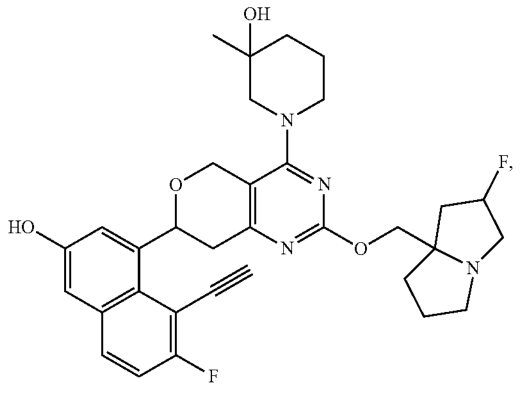
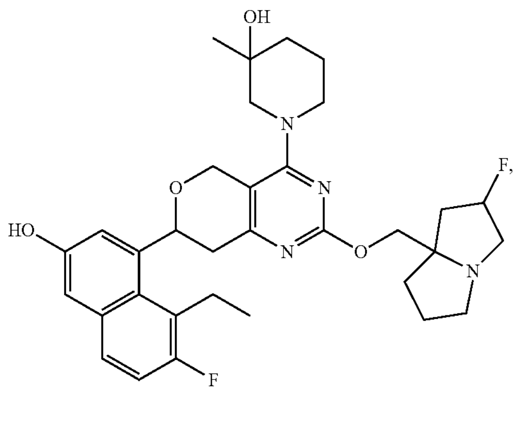
-continued
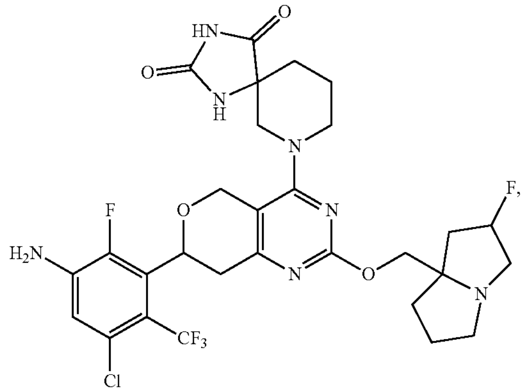
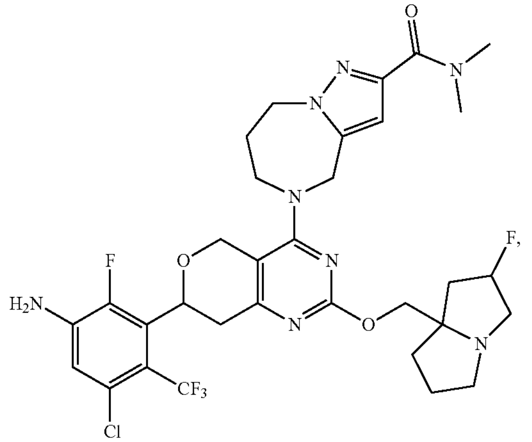
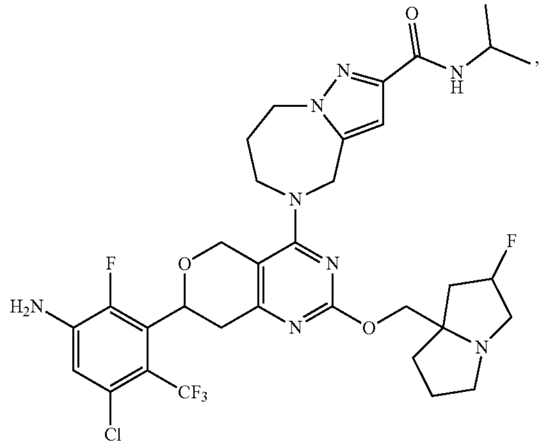
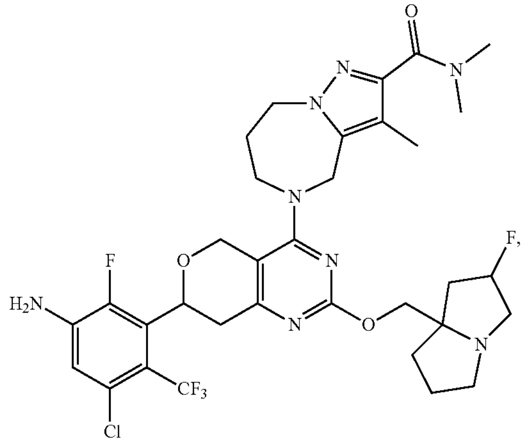

-continued
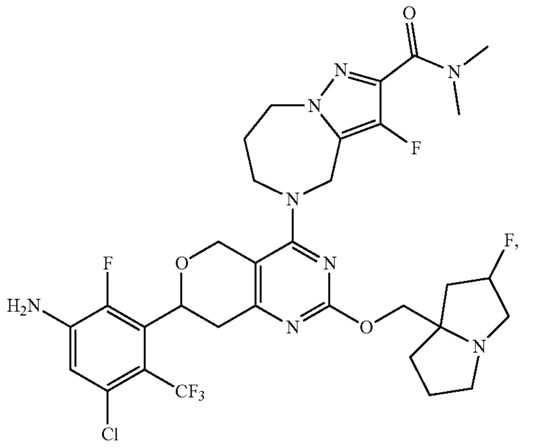
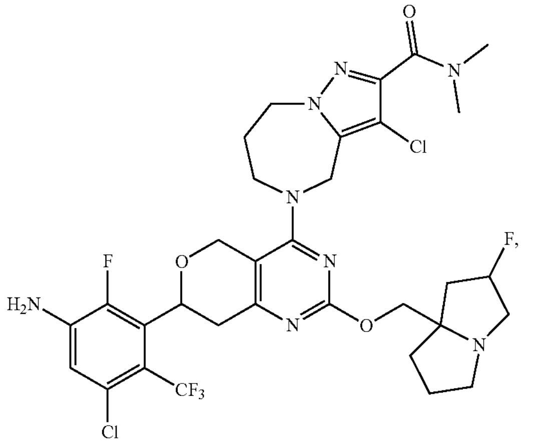
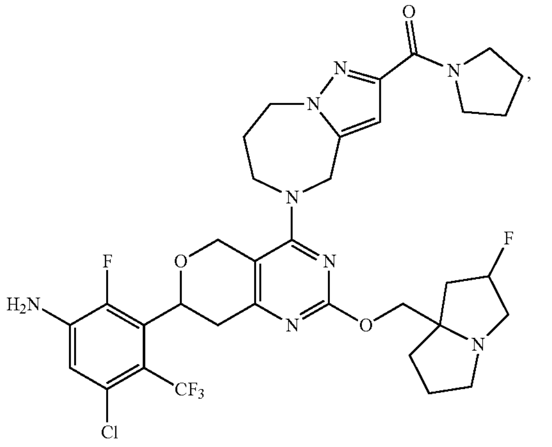
-continued
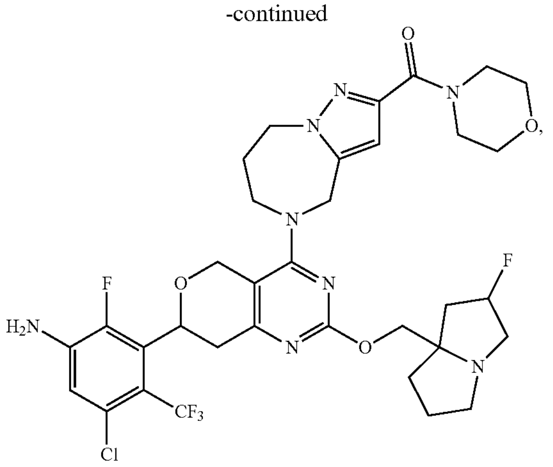
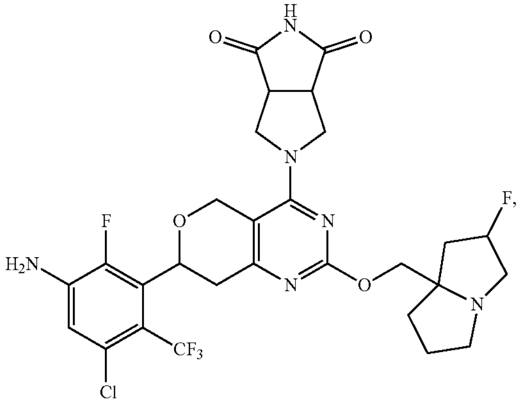
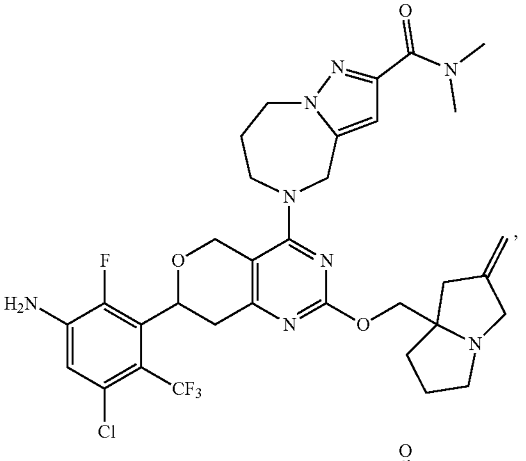
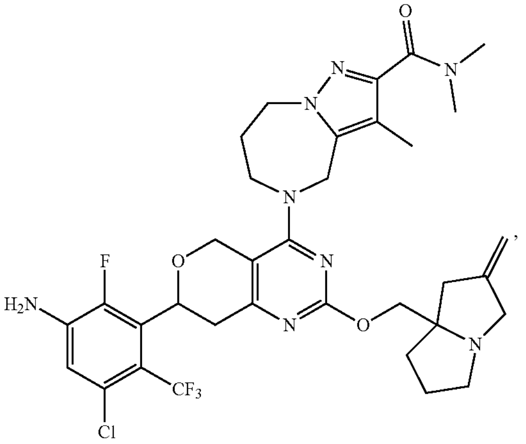

-continued
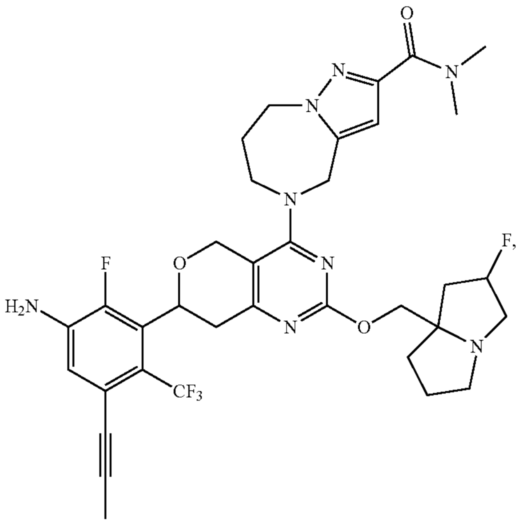
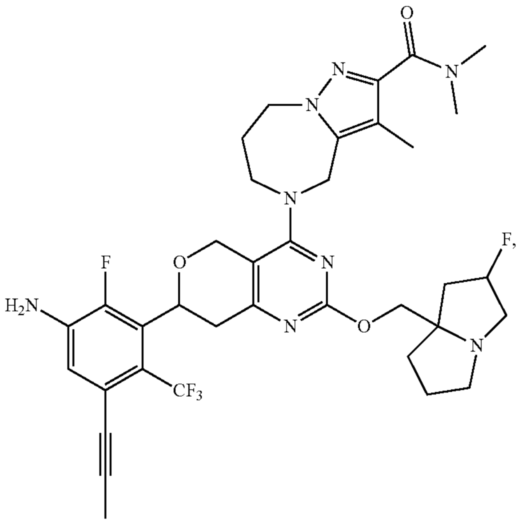
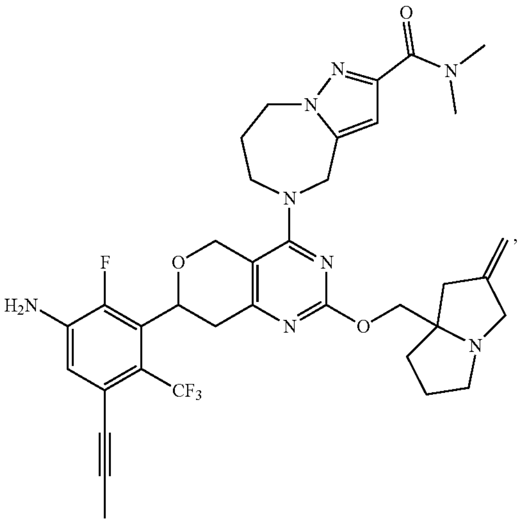
-continued
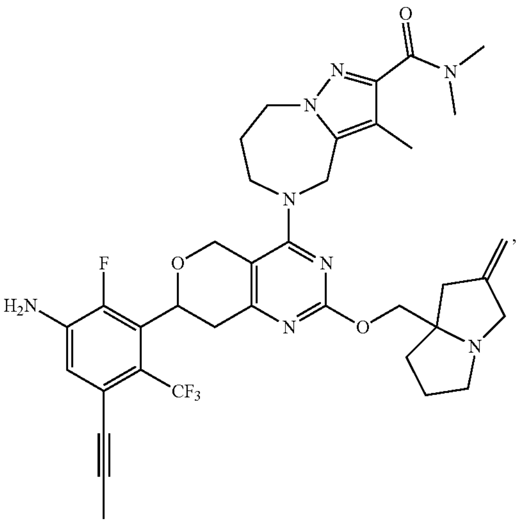
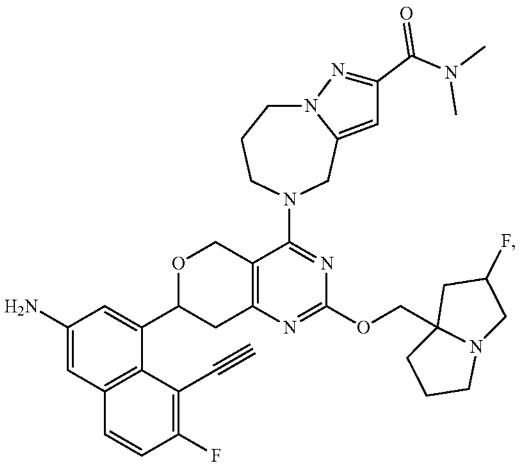
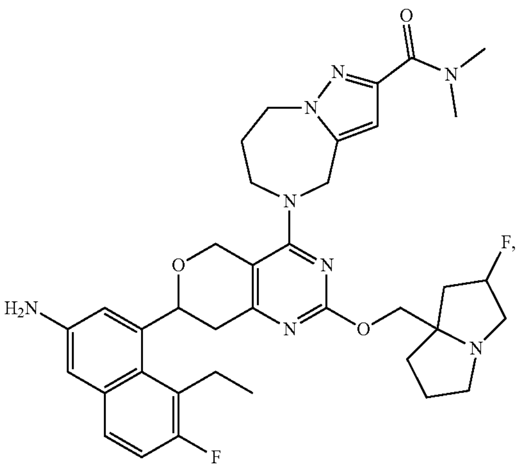

-continued
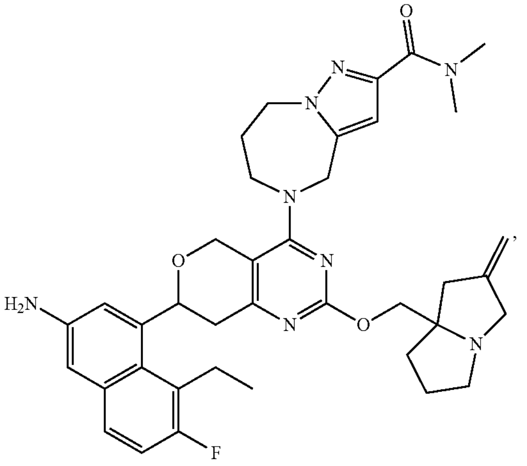
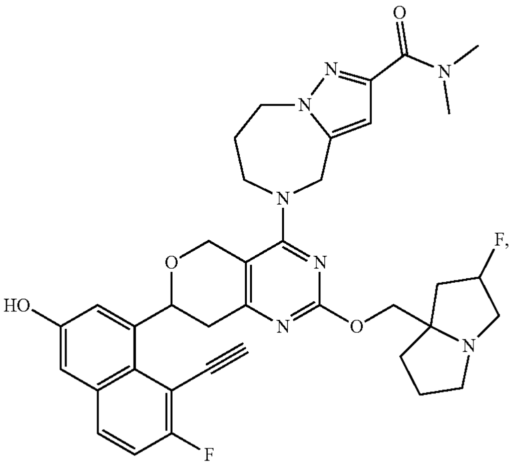
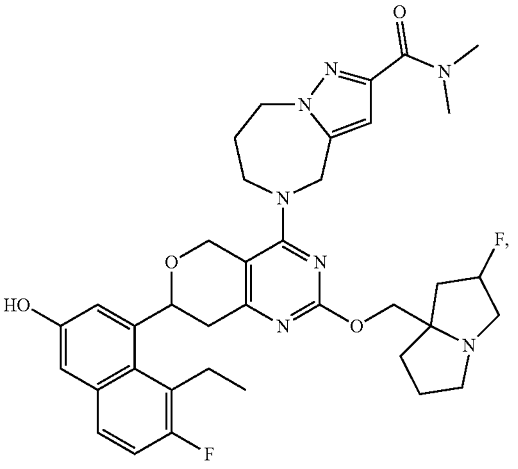
-continued
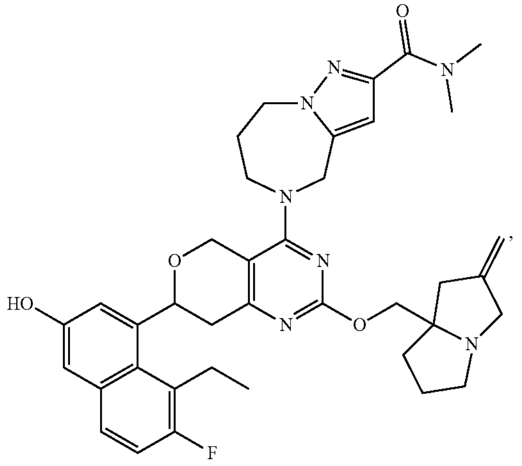
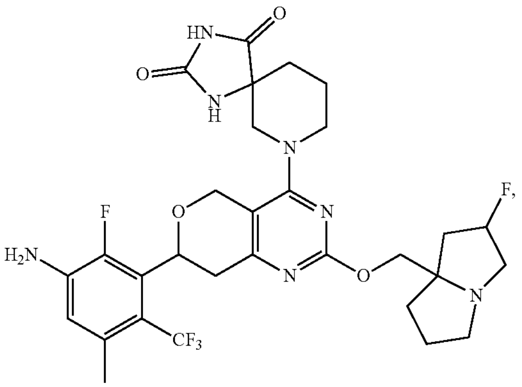
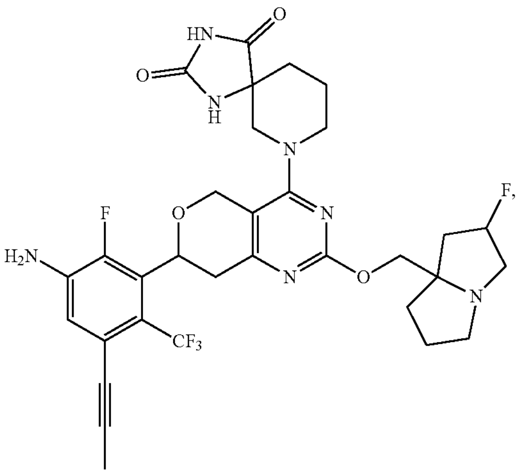

-continued
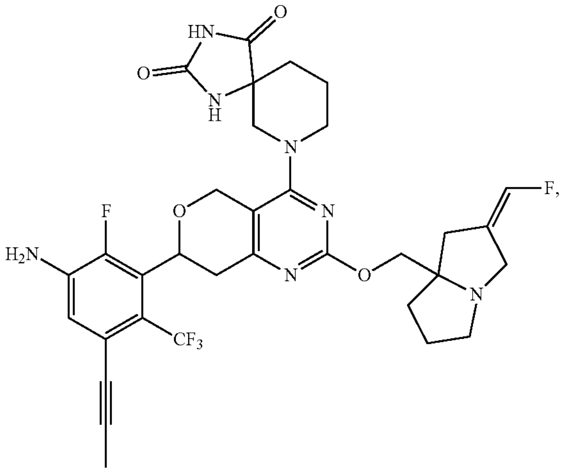
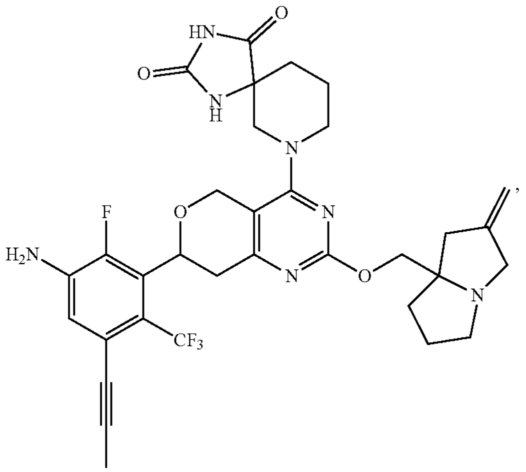
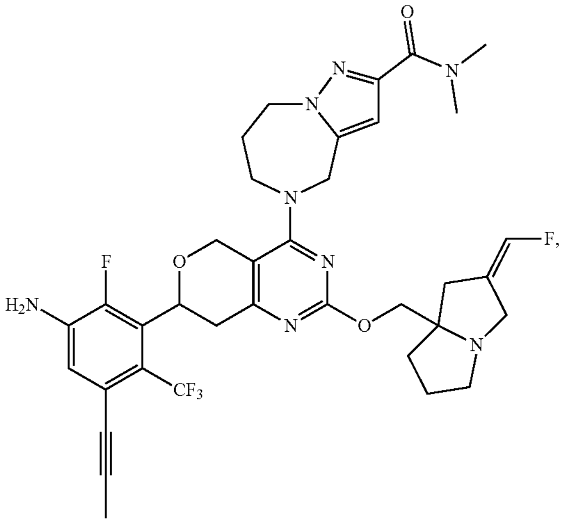
-continued
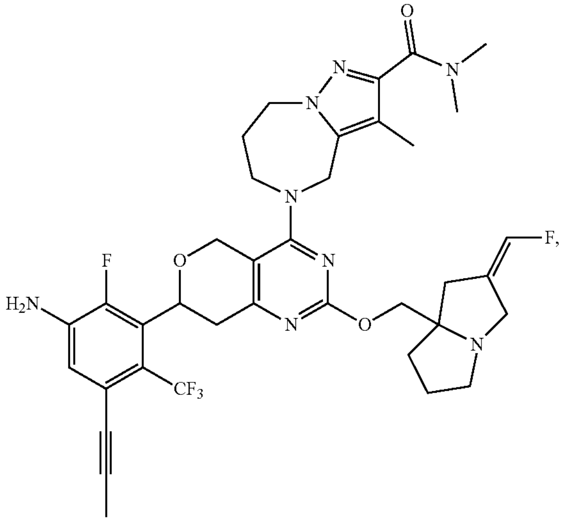
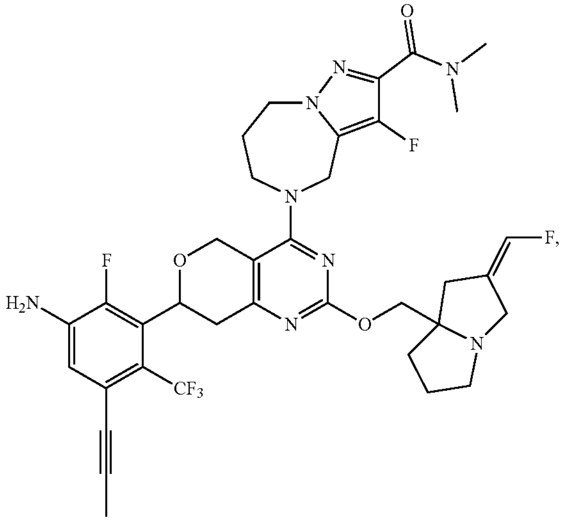
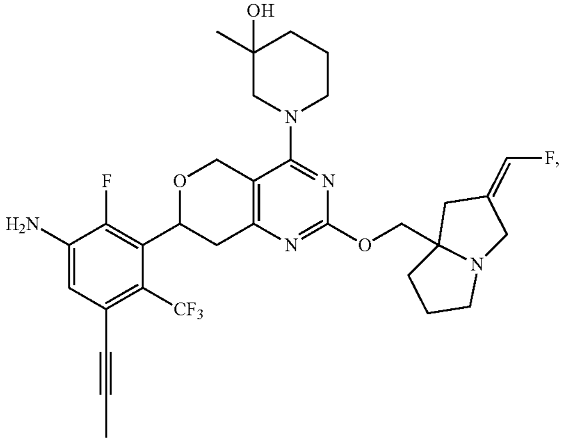

-continued
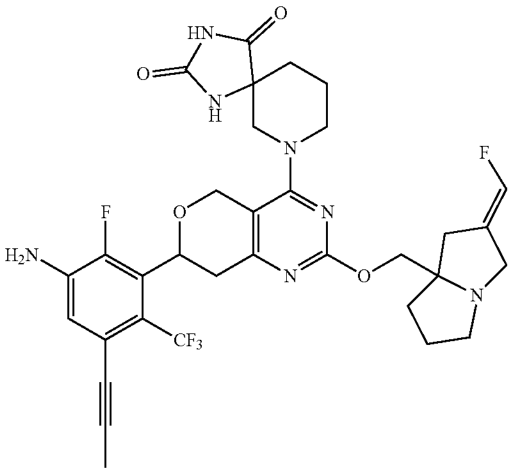
,
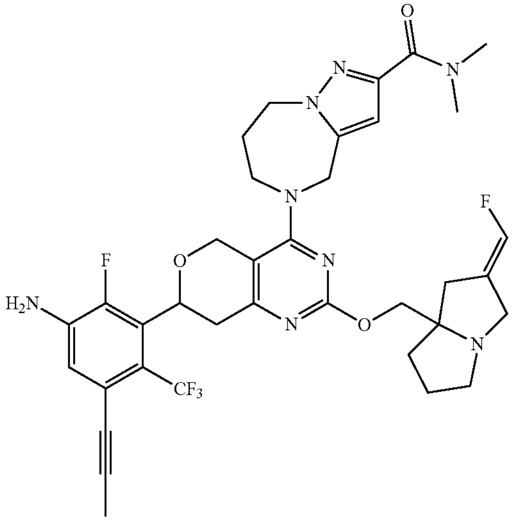
,
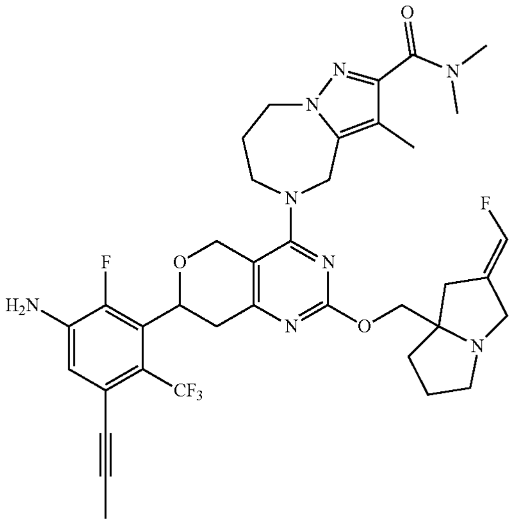
,
-continued
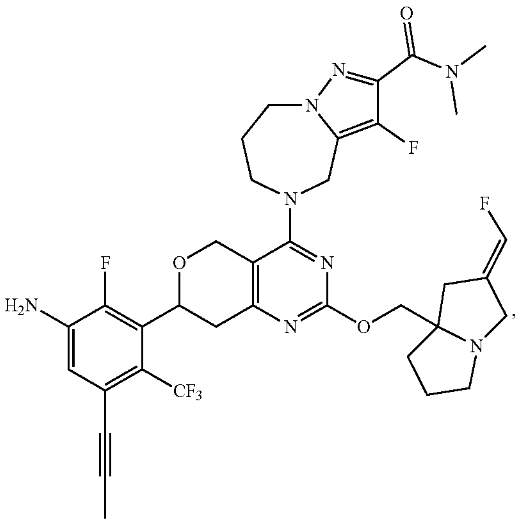
,
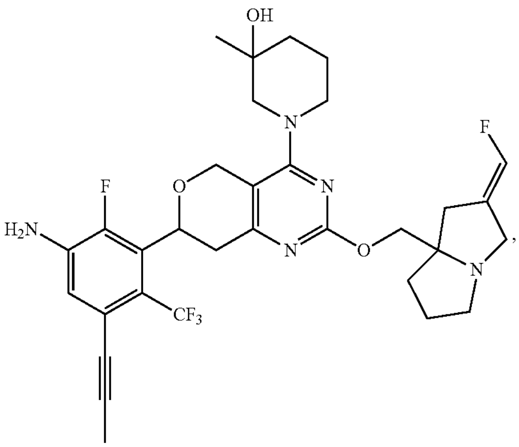
,
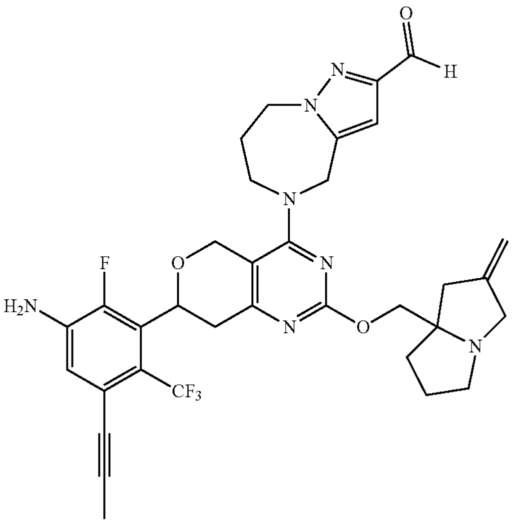
, -continued
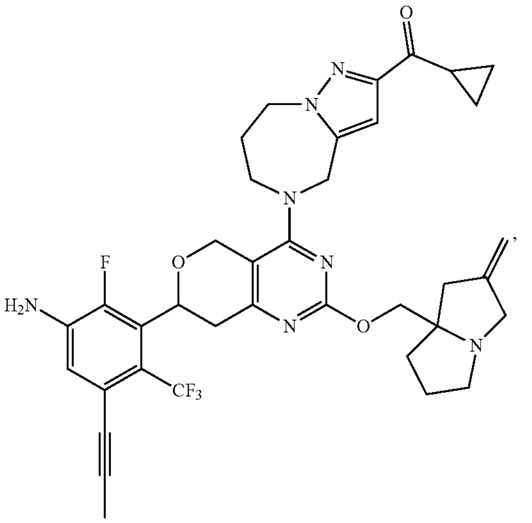
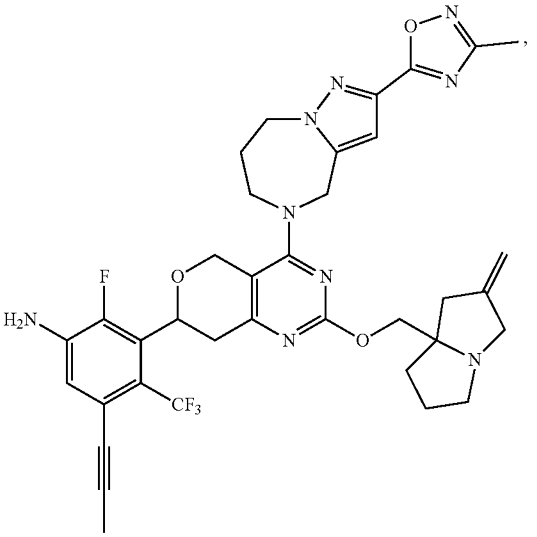
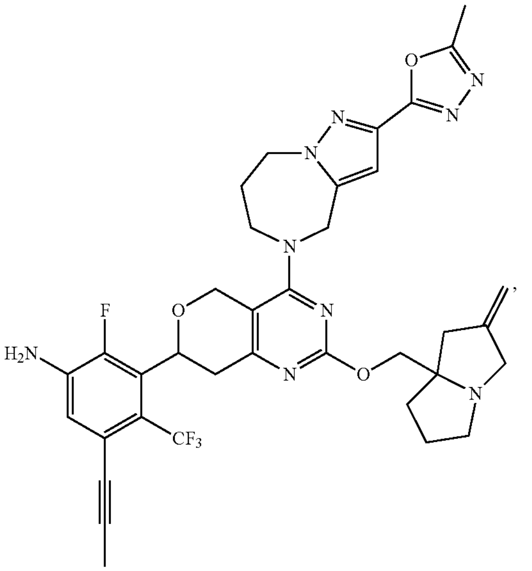
-continued
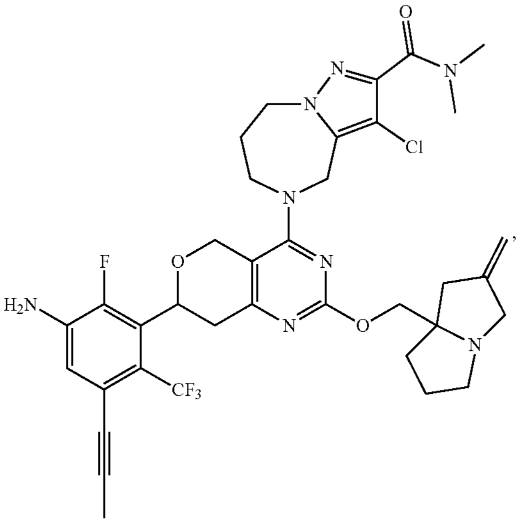
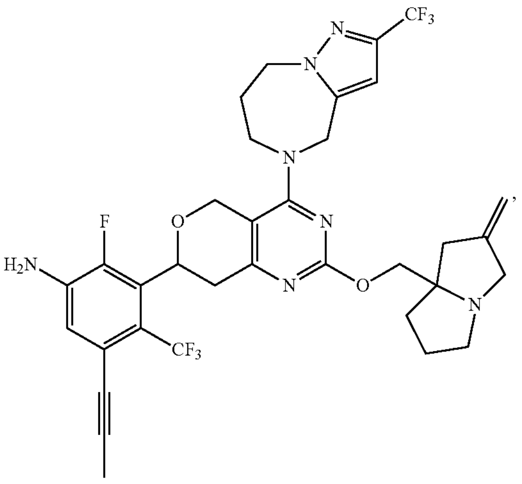
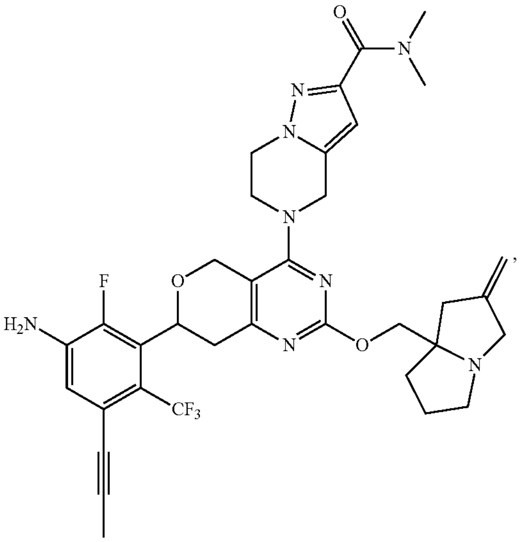

-continued
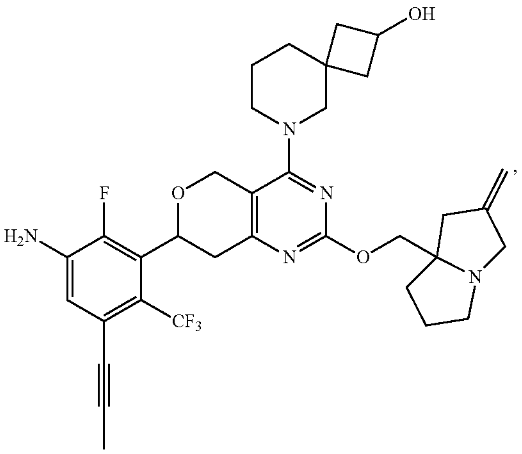
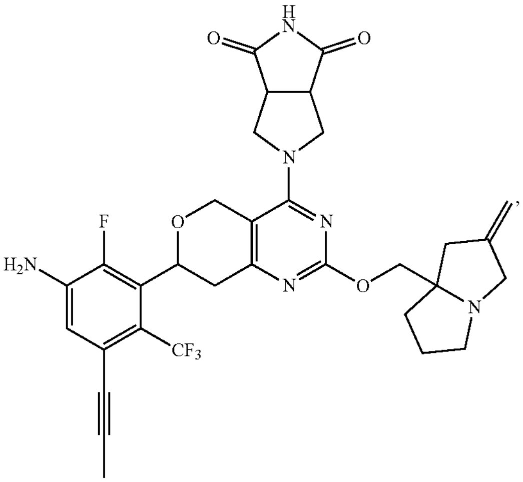
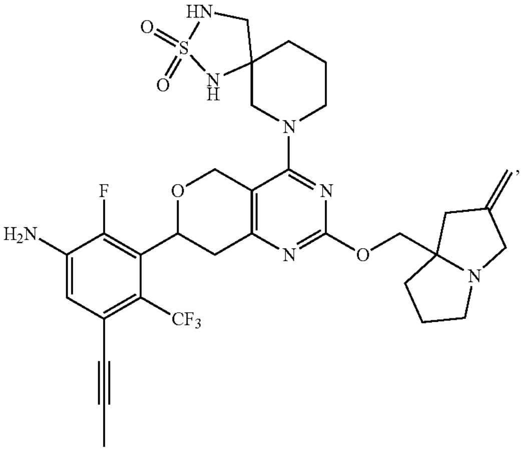
-continued
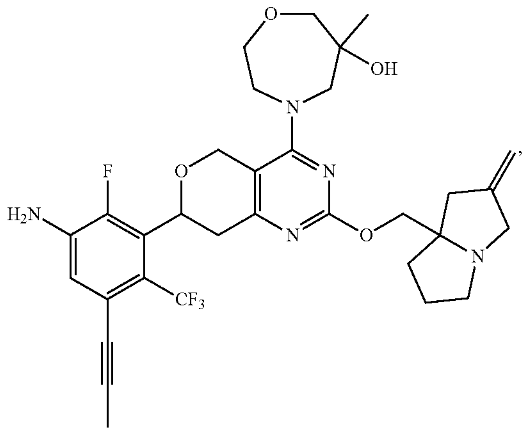
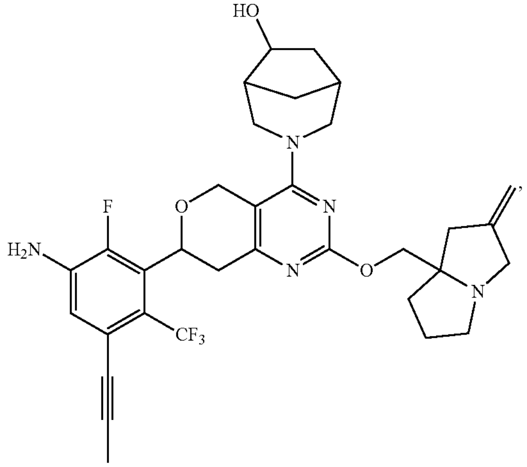
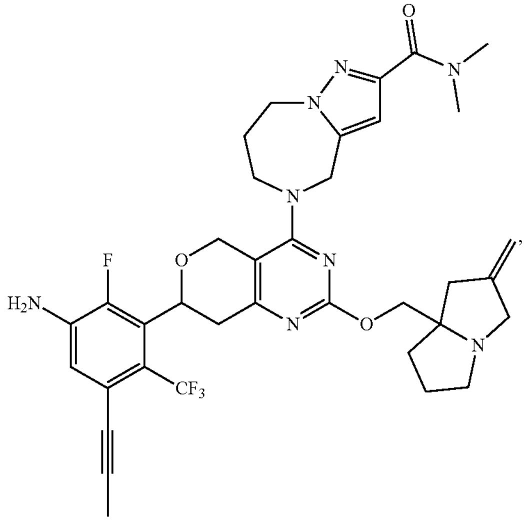

-continued
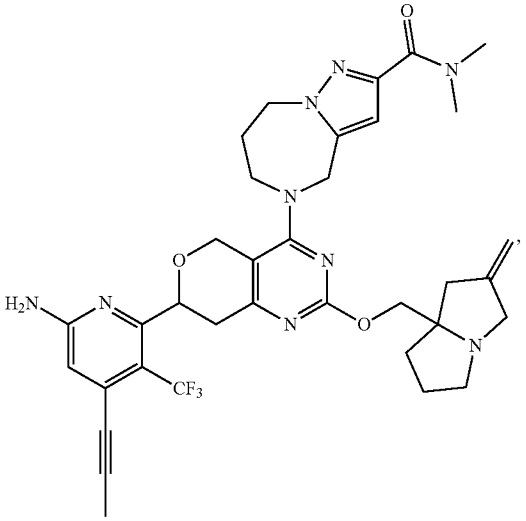
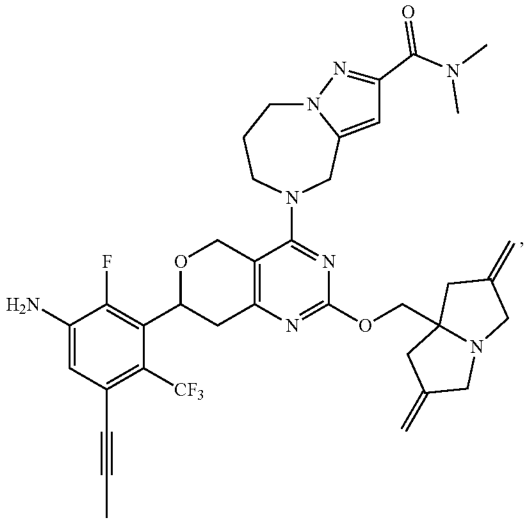
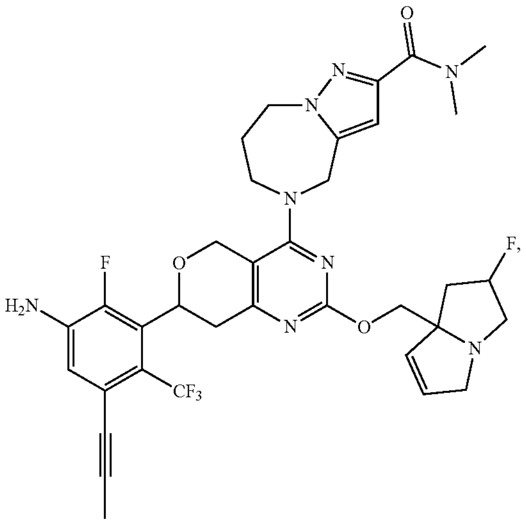
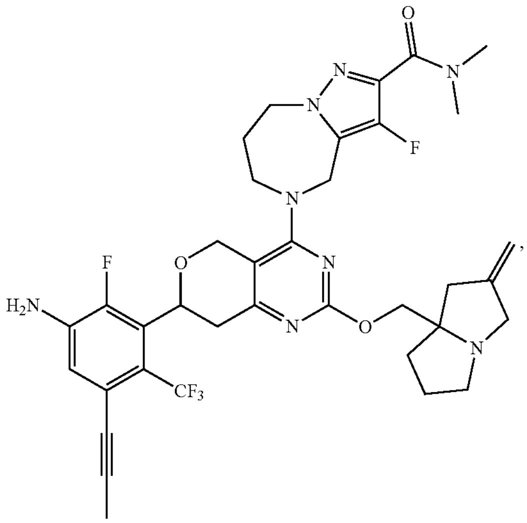
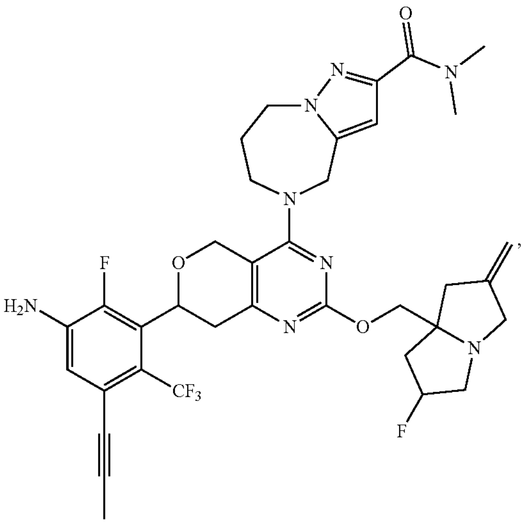
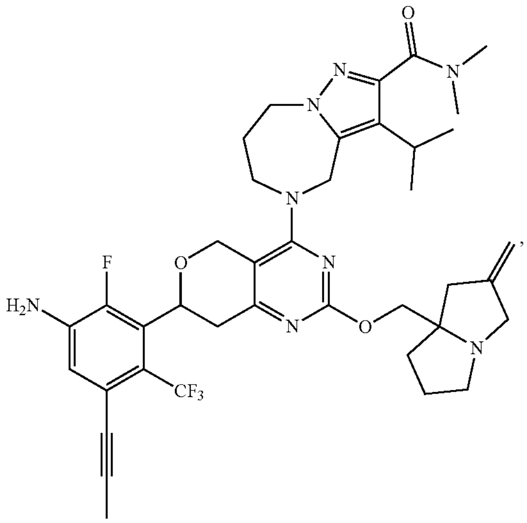

-continued
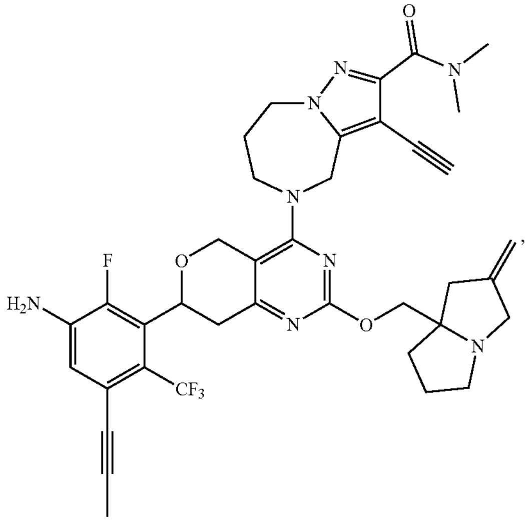
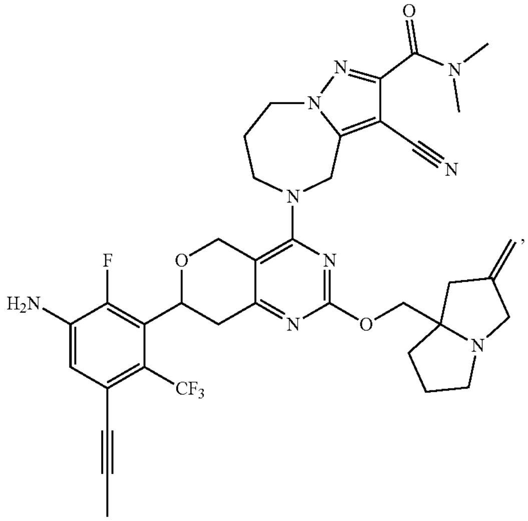
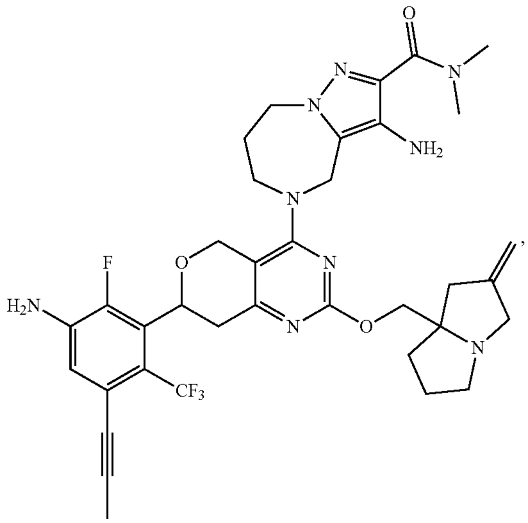
-continued
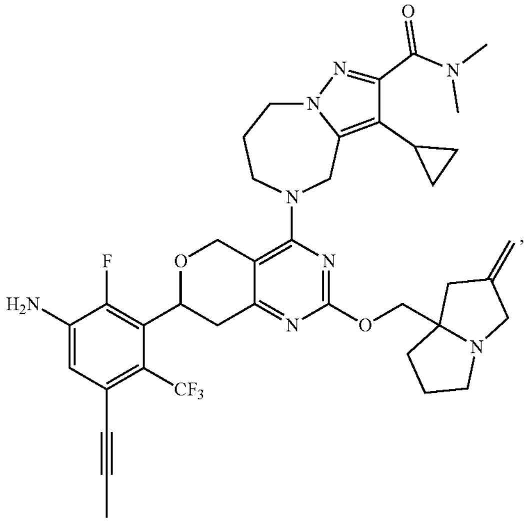
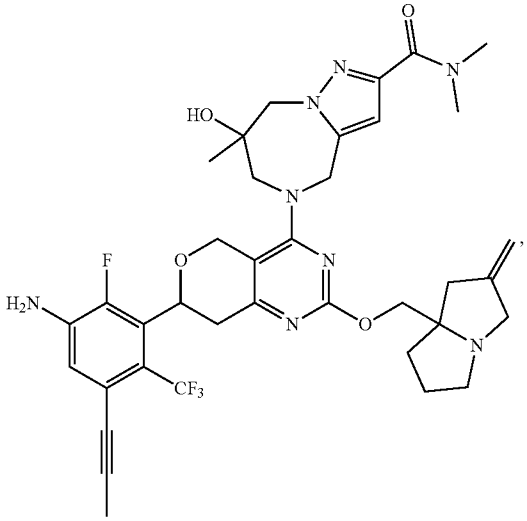
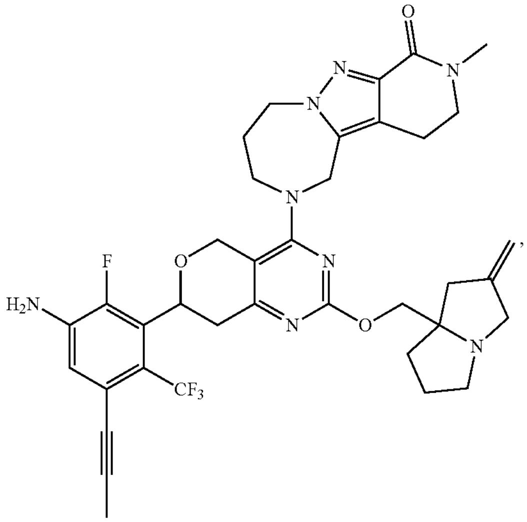

-continued
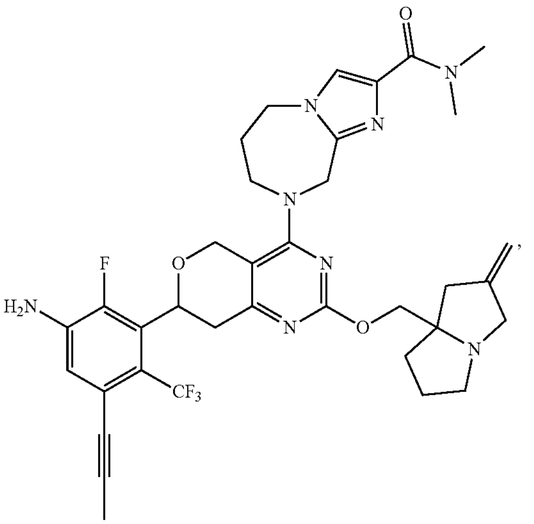
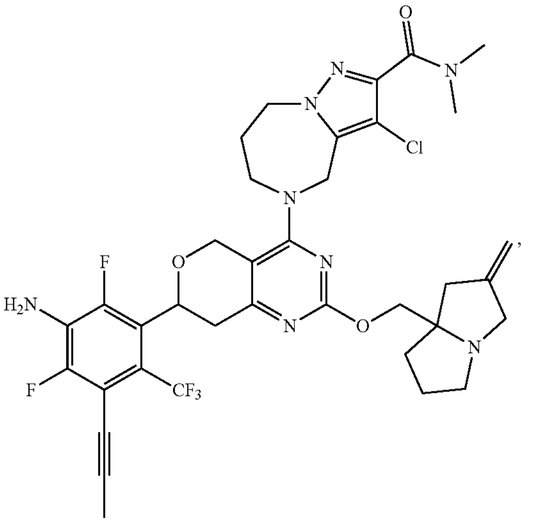
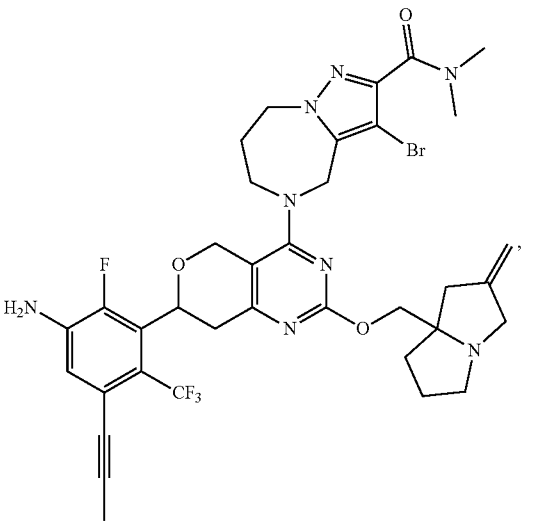
-continued
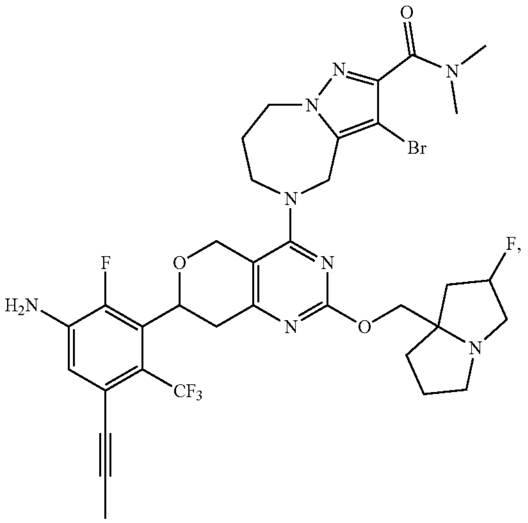
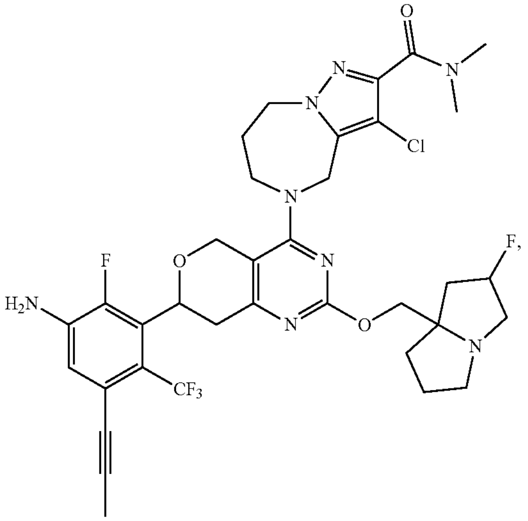
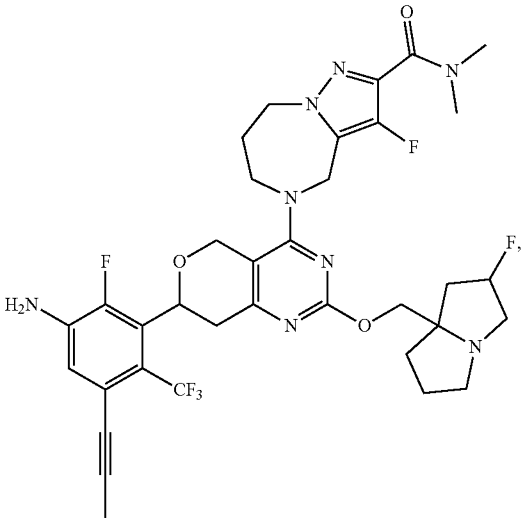

-continued
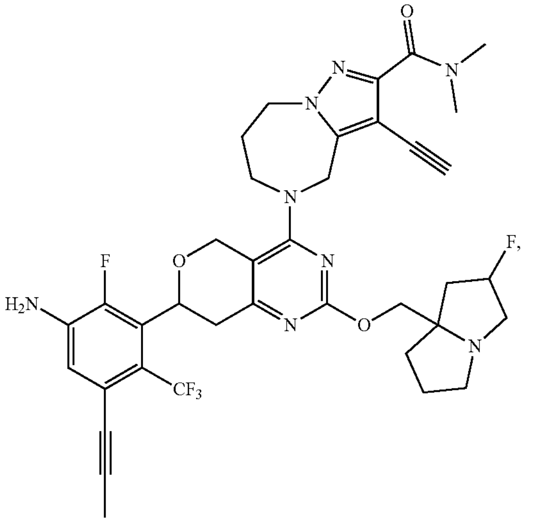
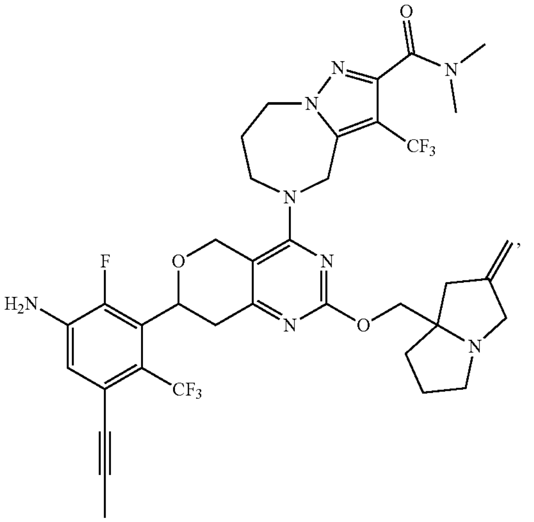
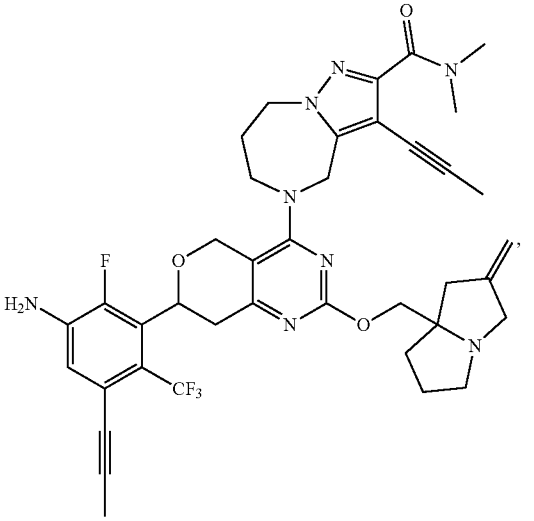
-continued
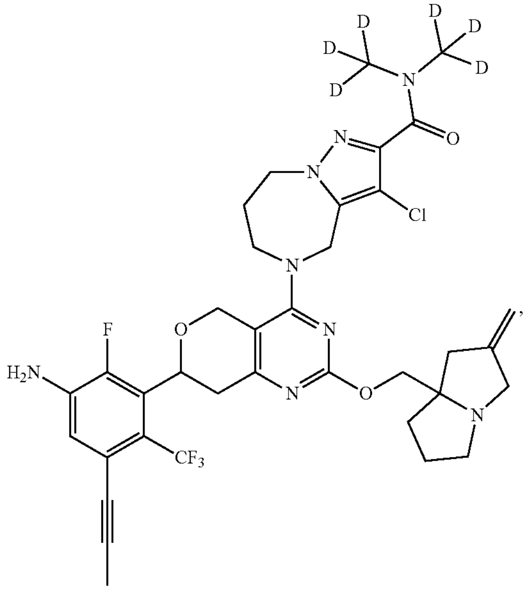
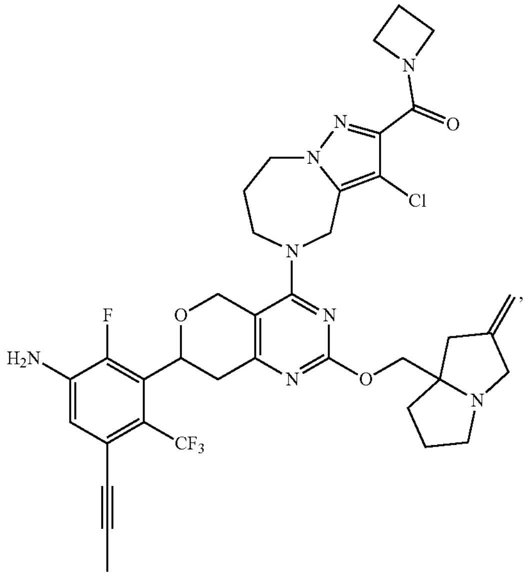
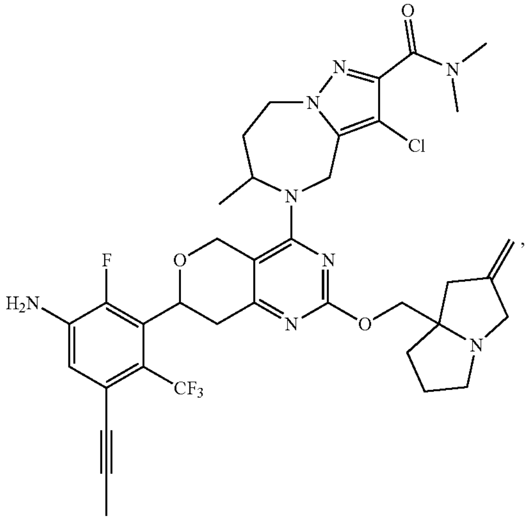
and -continued
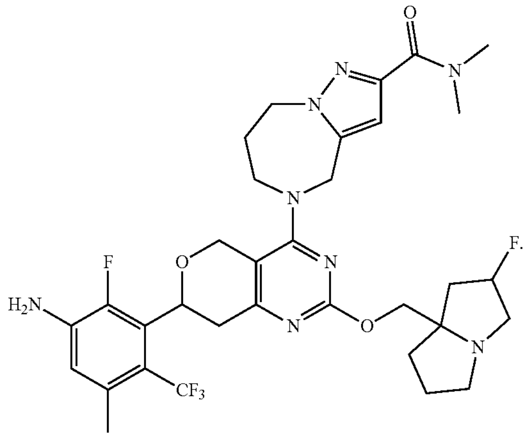
In some embodiments of the present invention, the compounds or pharmaceutically acceptable salts thereof are selected from:
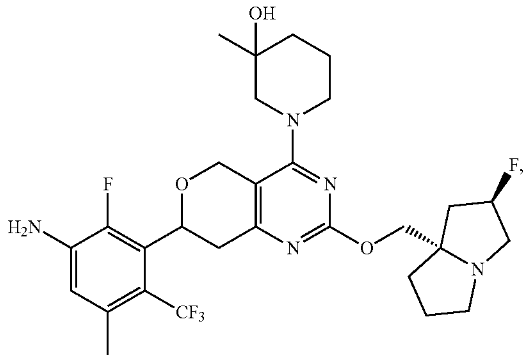
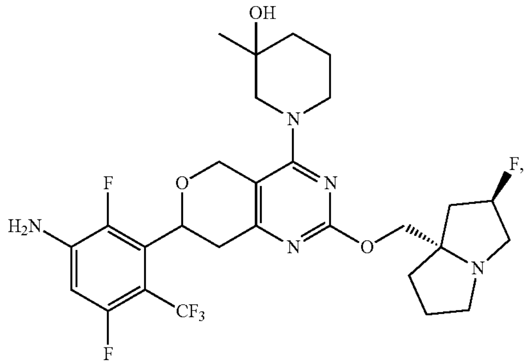
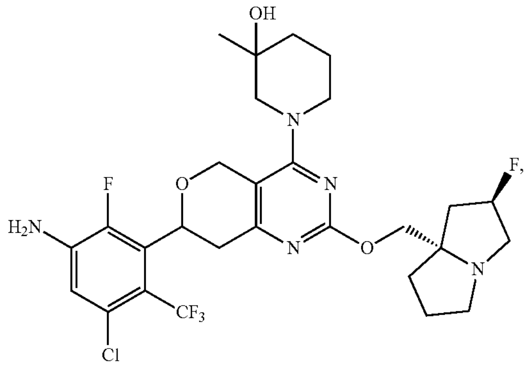
-continued
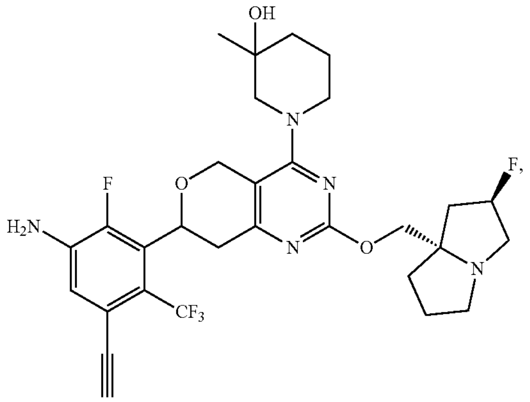
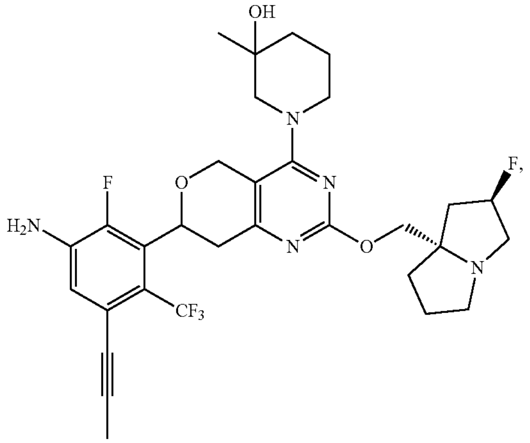
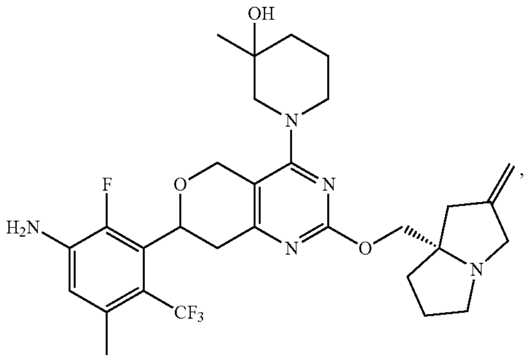
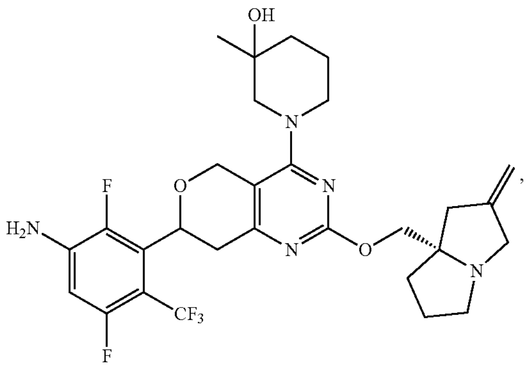

-continued
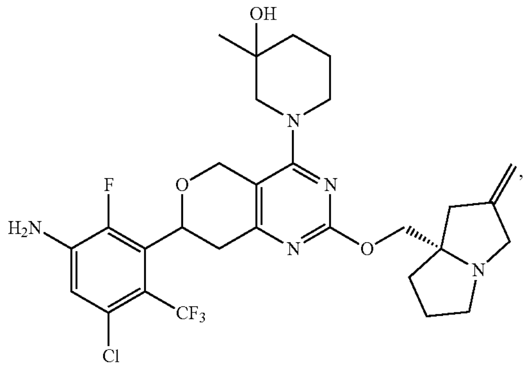
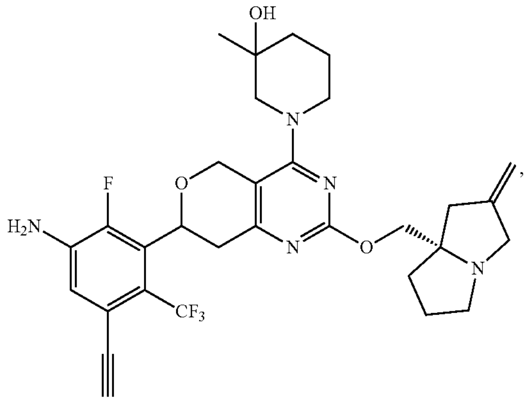
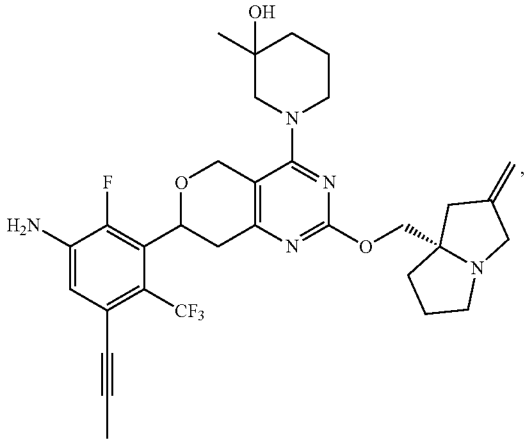
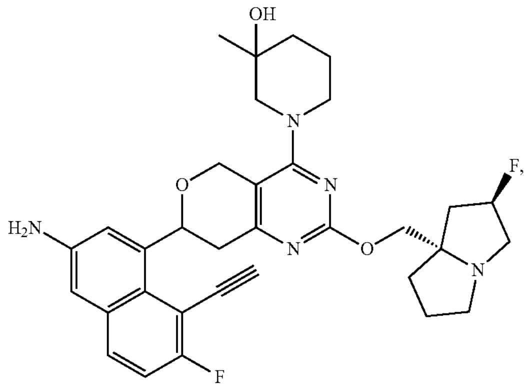
-continued
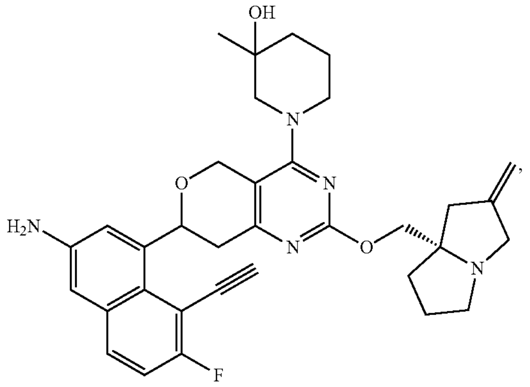
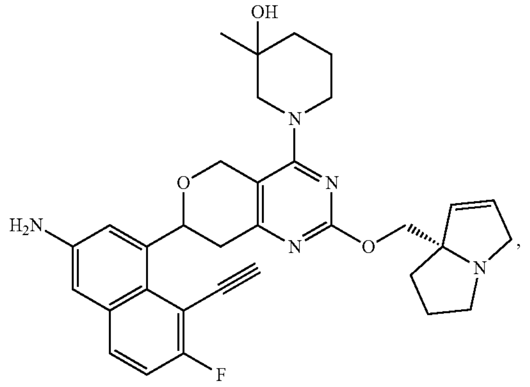
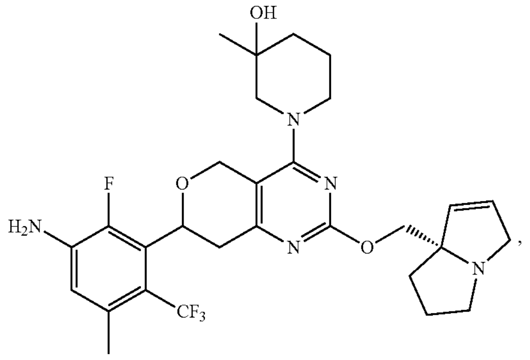
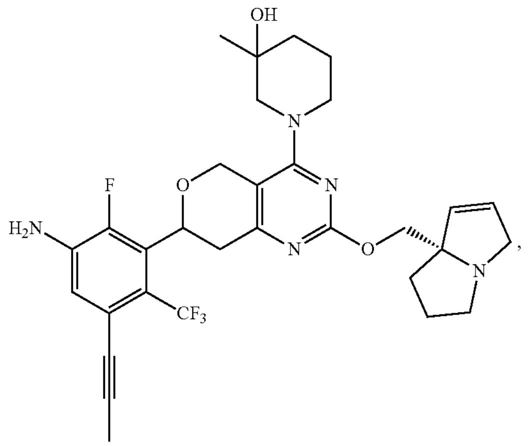

-continued
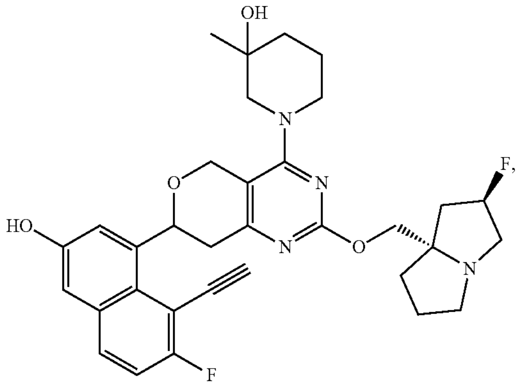
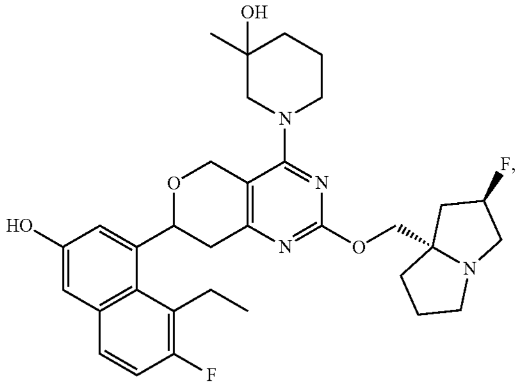
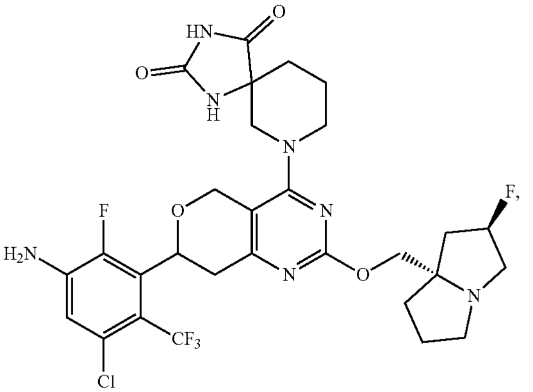
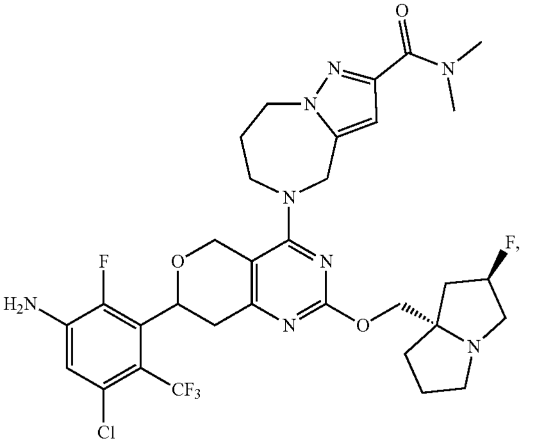
-continued
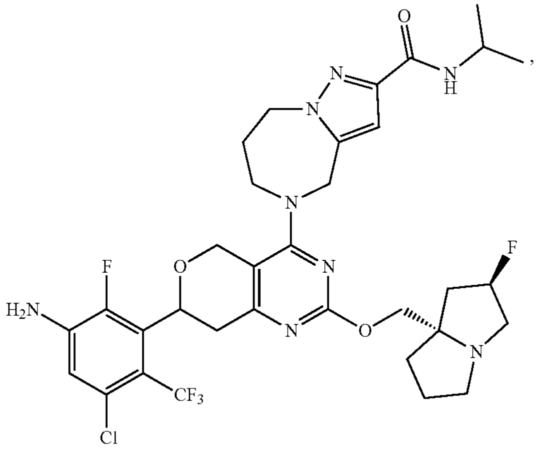
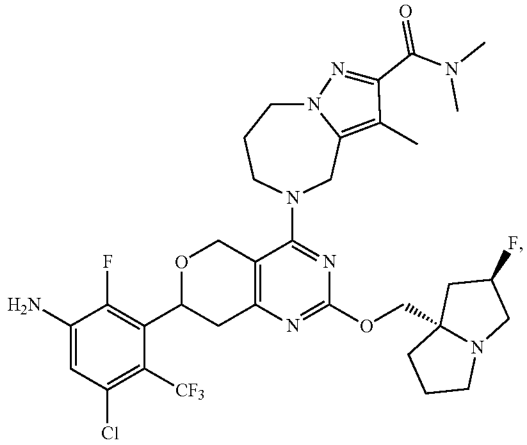
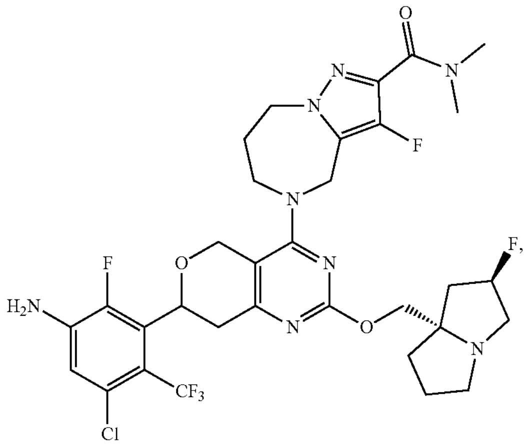

-continued
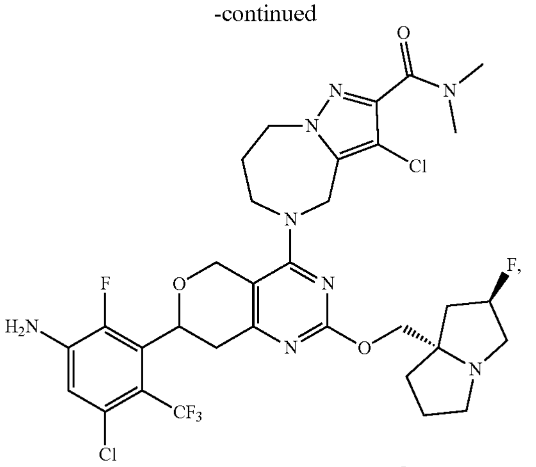
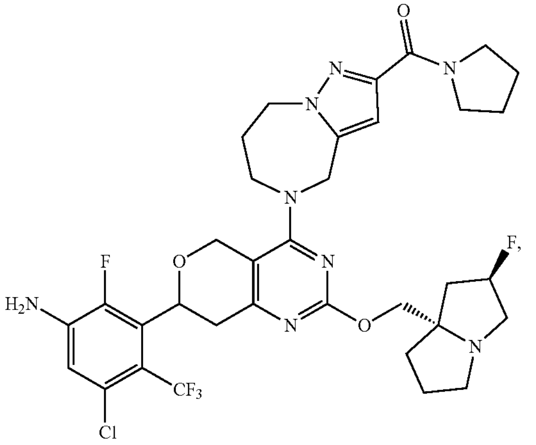
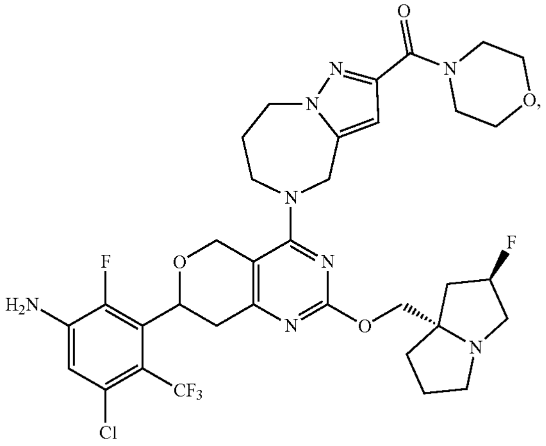
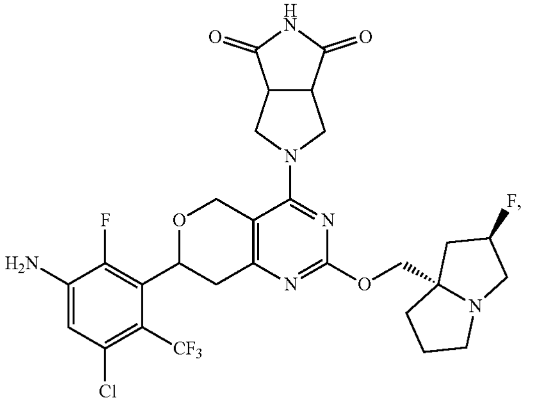
-continued
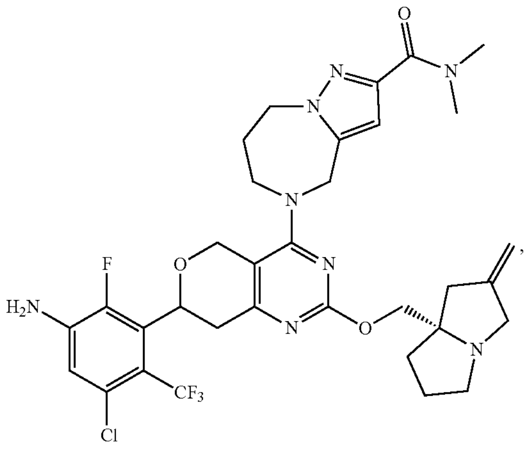
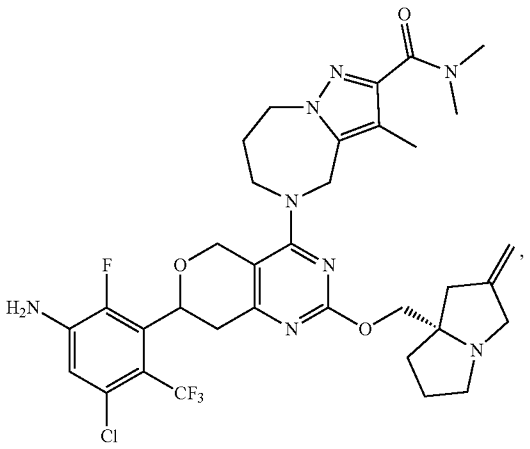
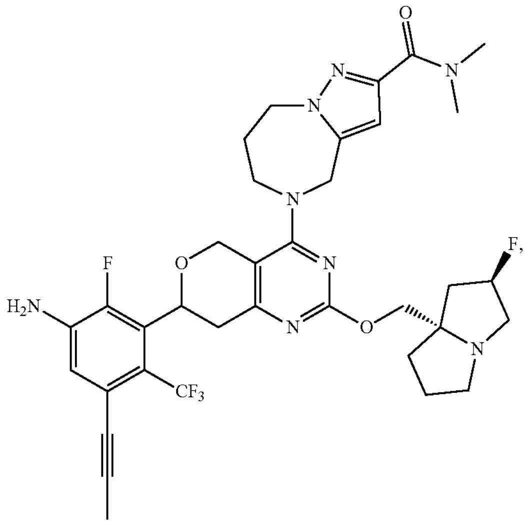

-continued
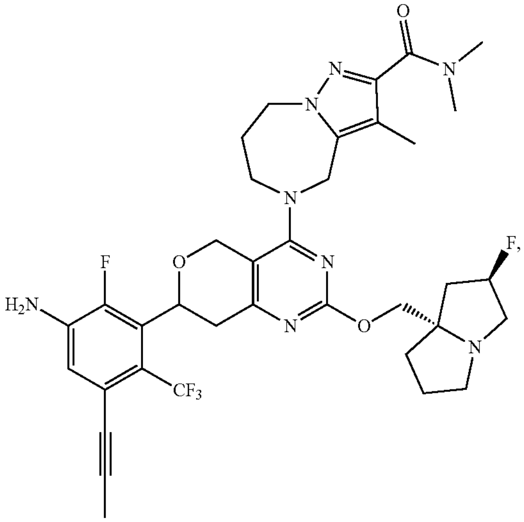
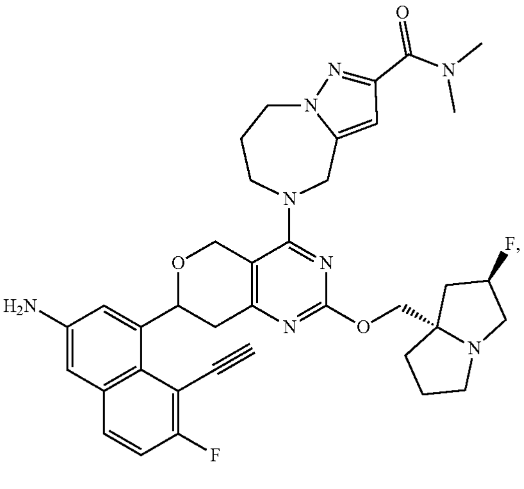
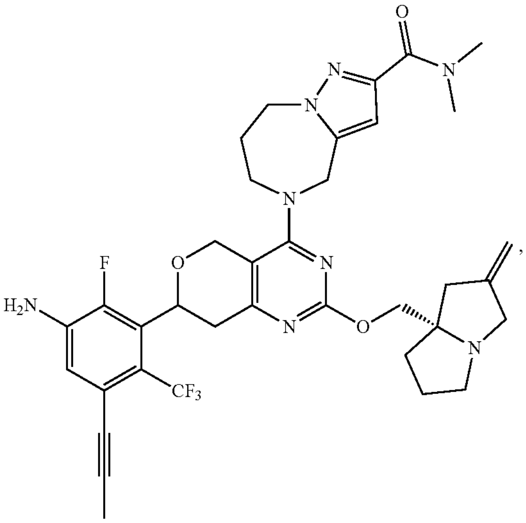
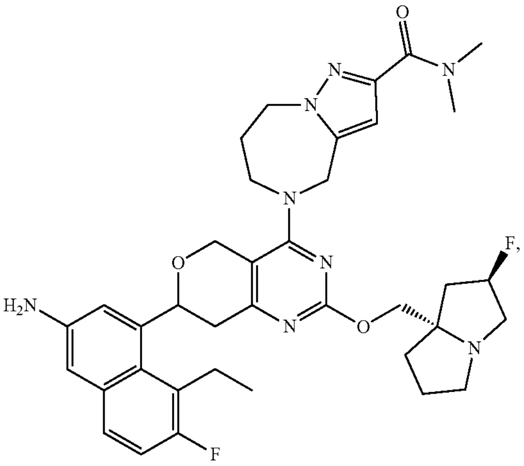
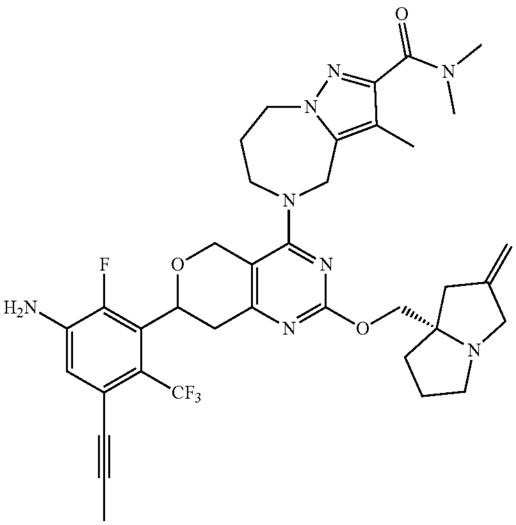
,
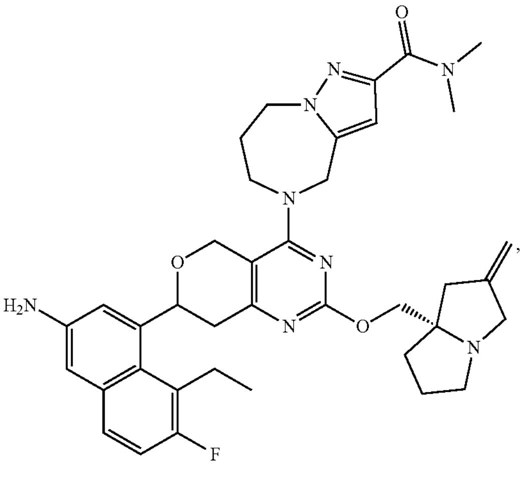

-continued
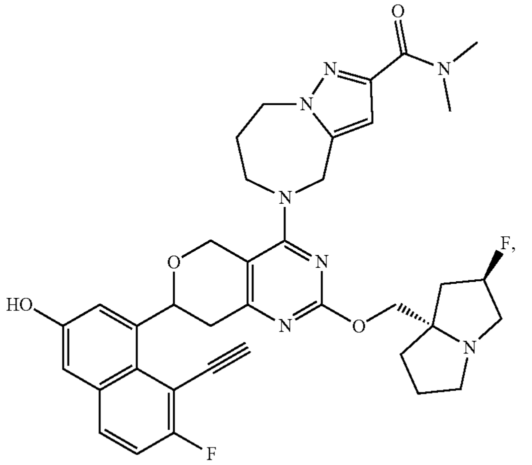
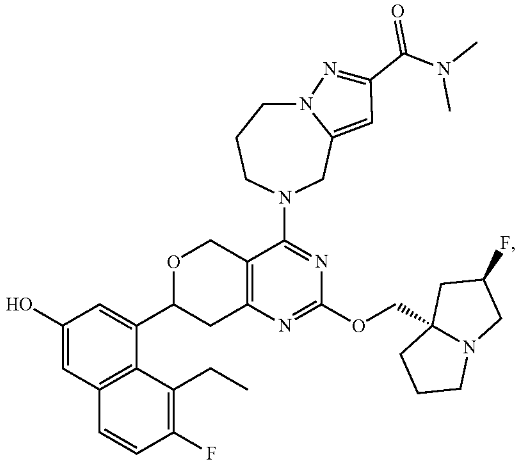
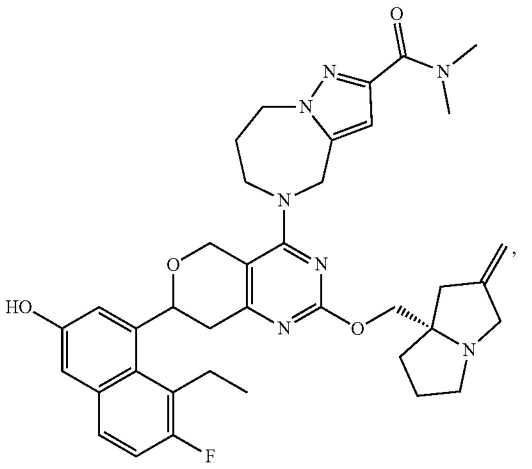
-continued
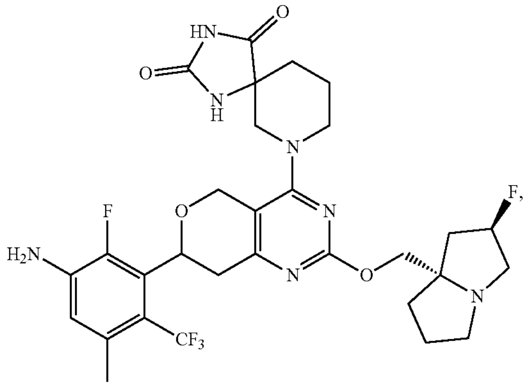
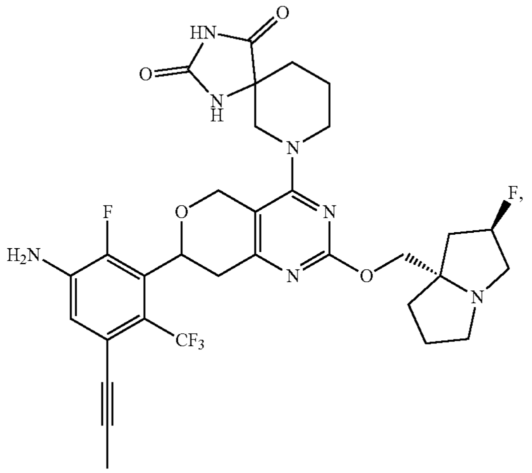
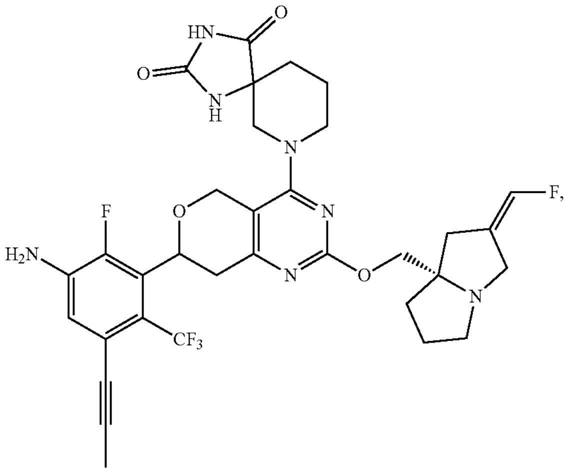

-continued
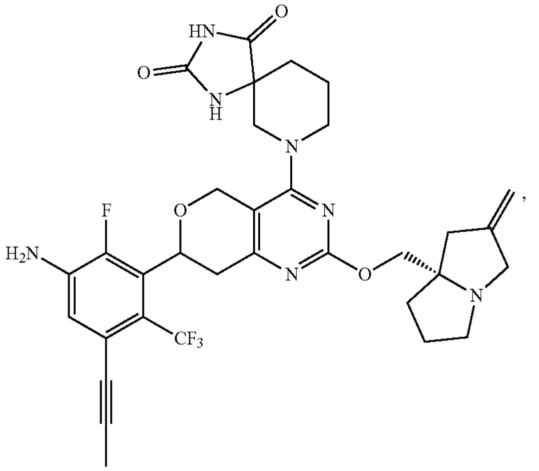
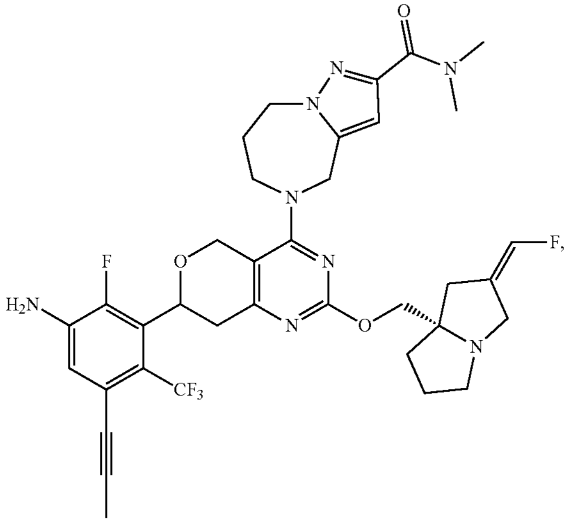
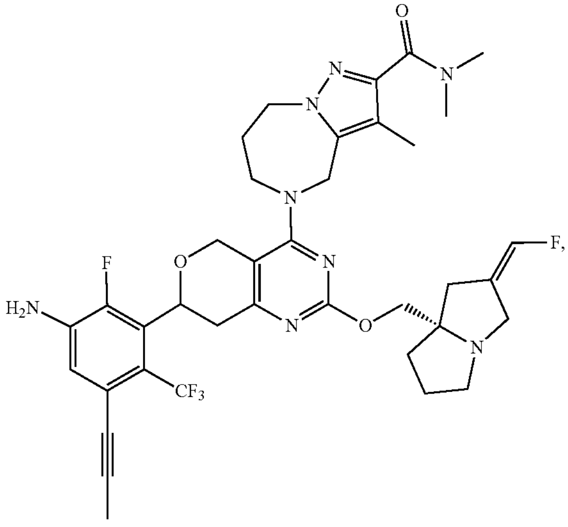
-continued
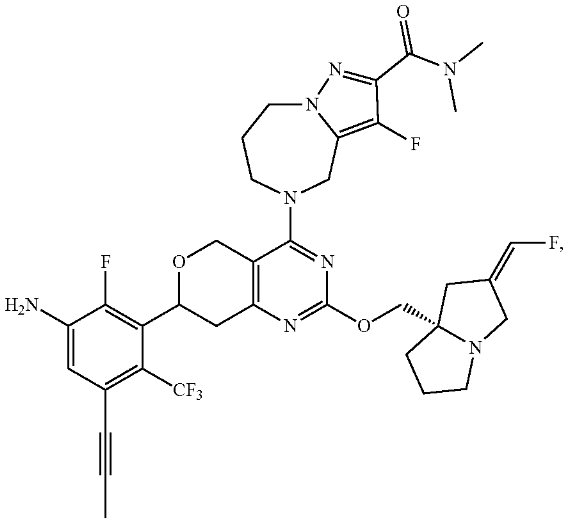
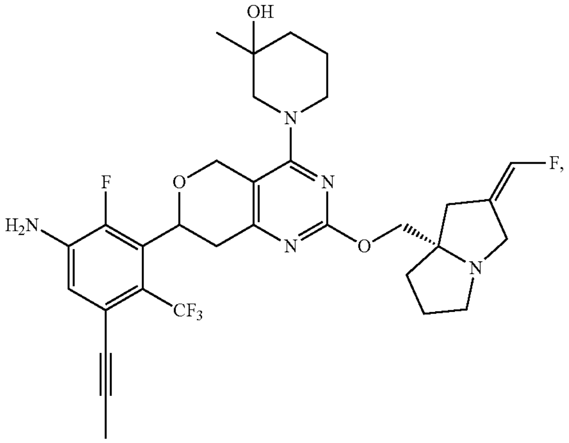
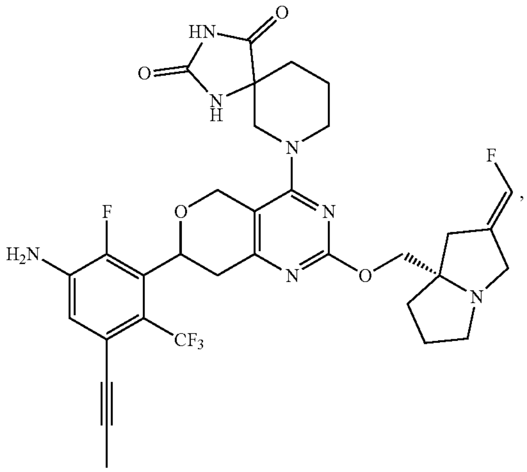

-continued
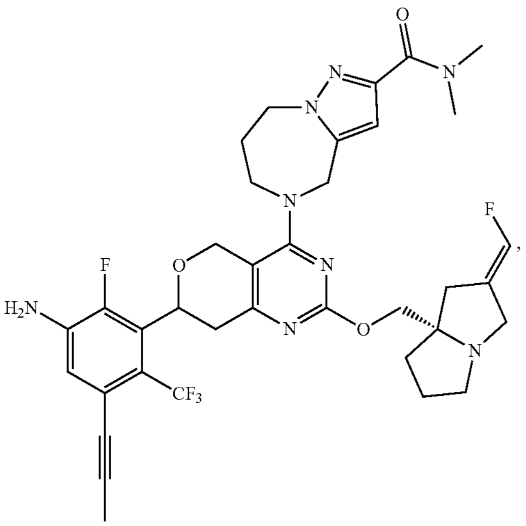
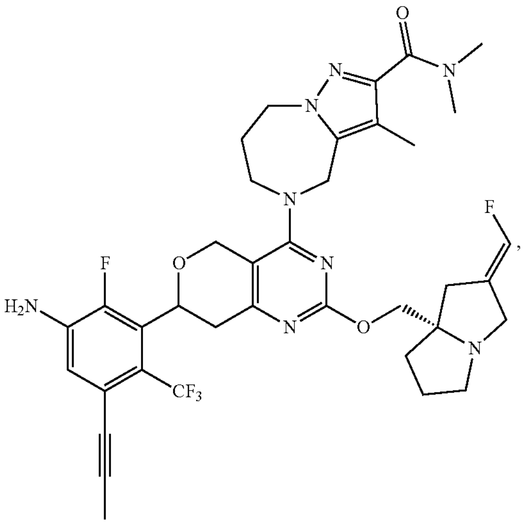
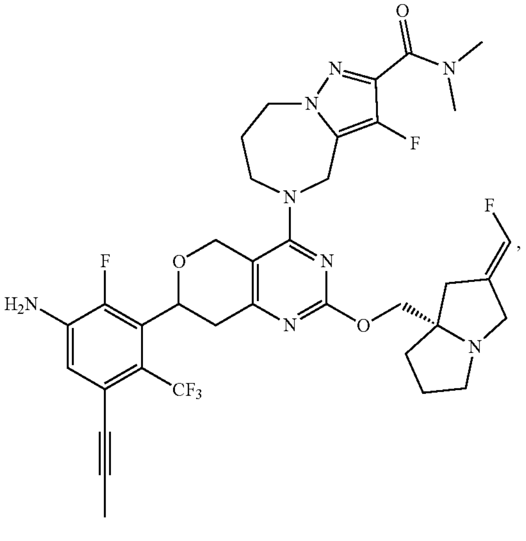
-continued
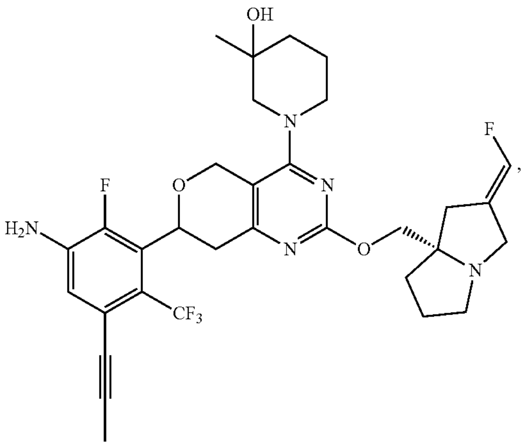
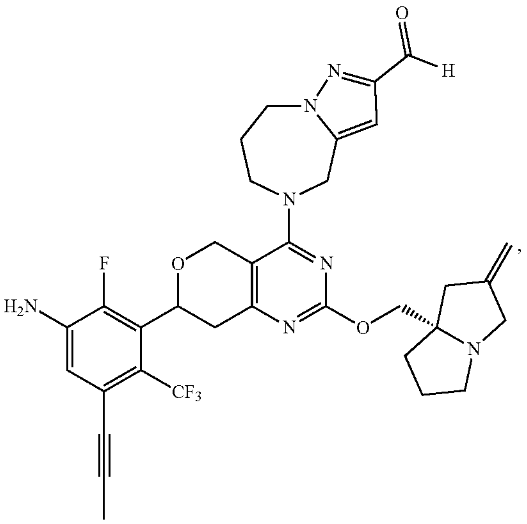
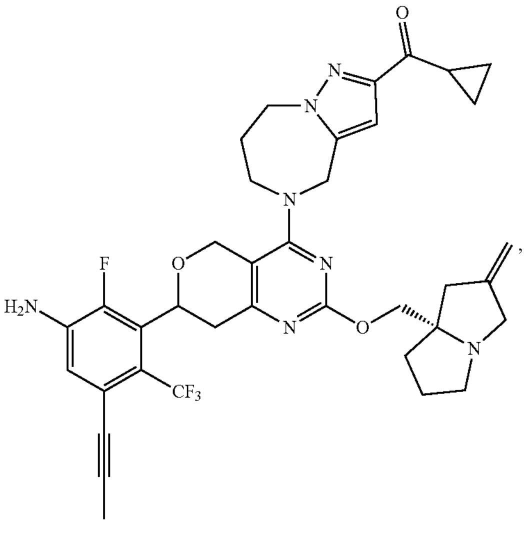

-continued
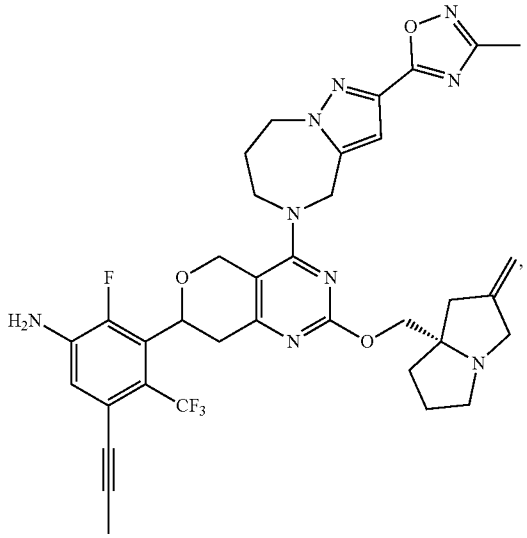
,
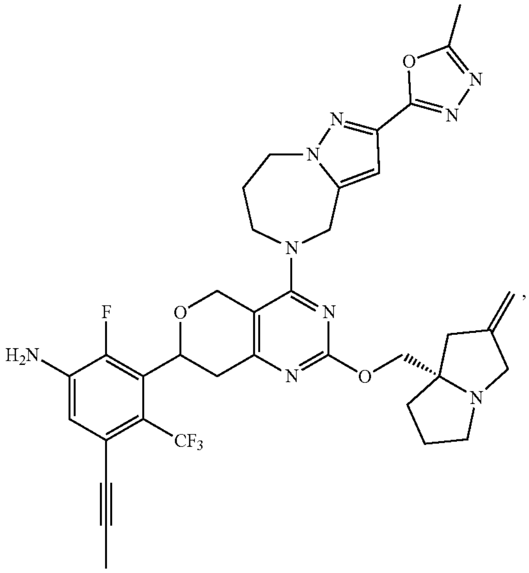
,
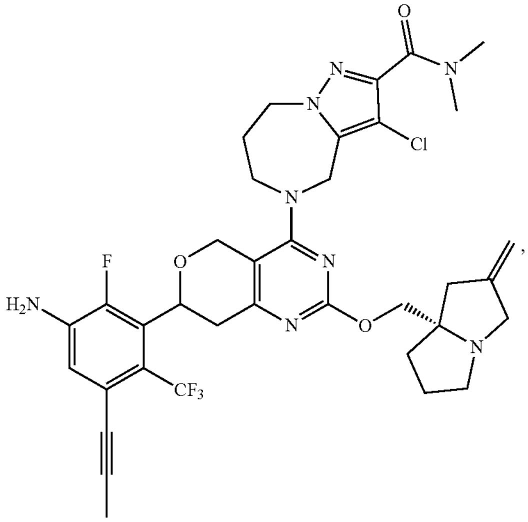
,
-continued
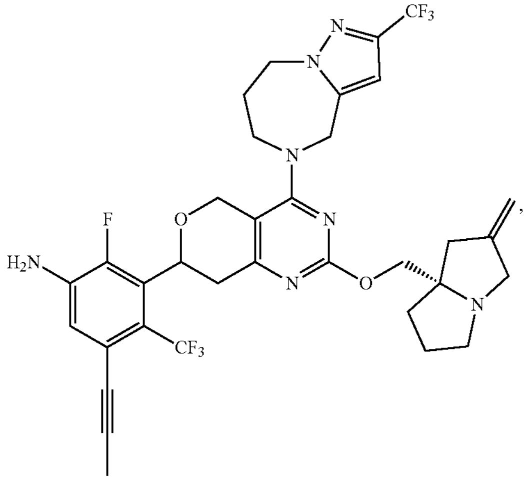
,
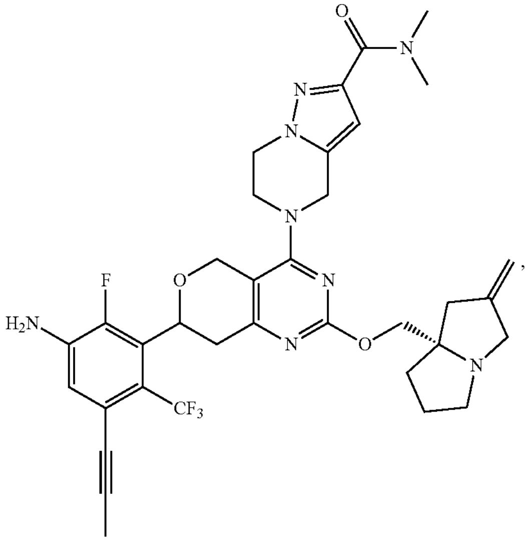
,
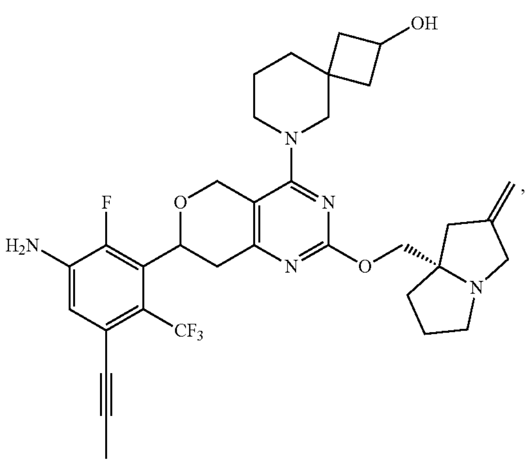
, -continued
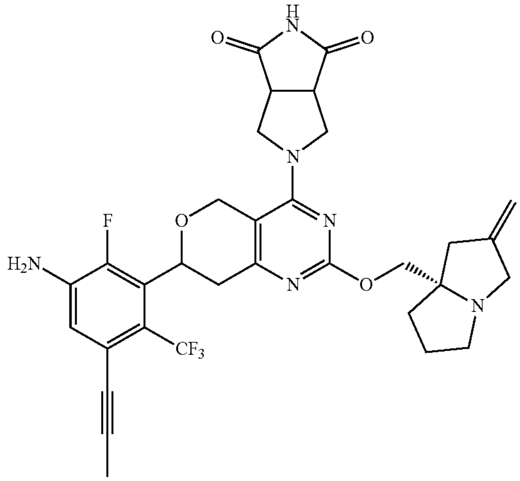,
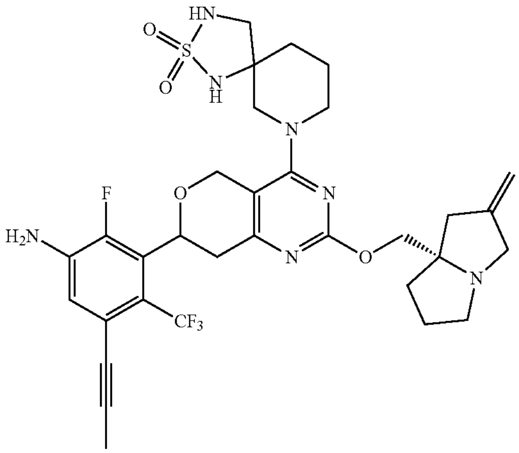,
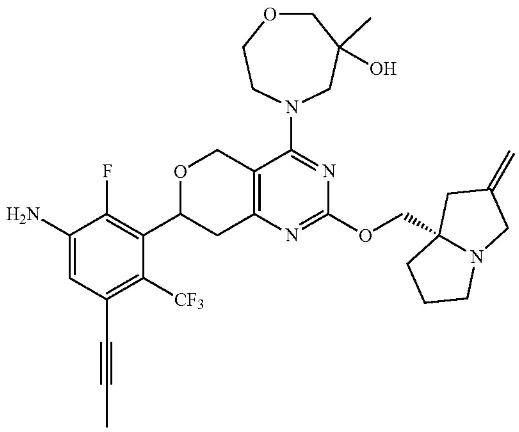,
-continued
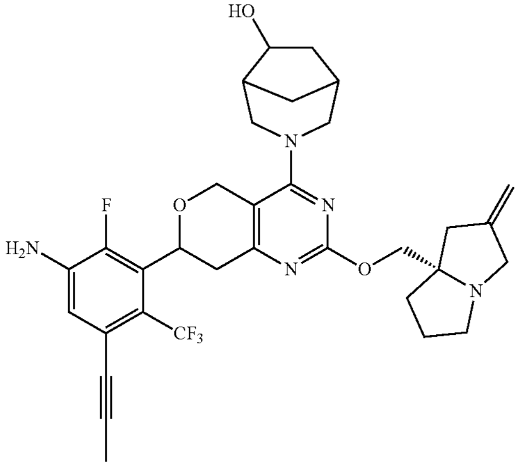,
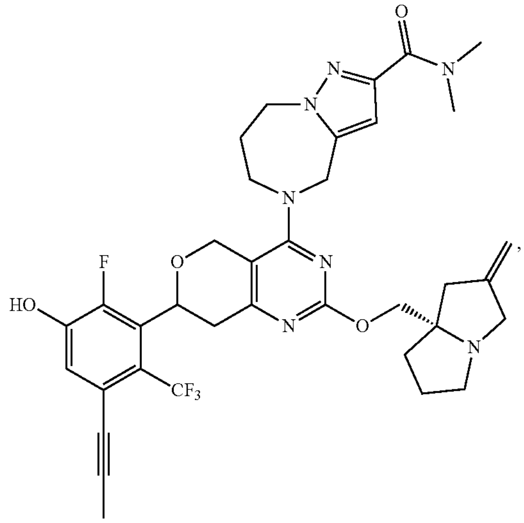,
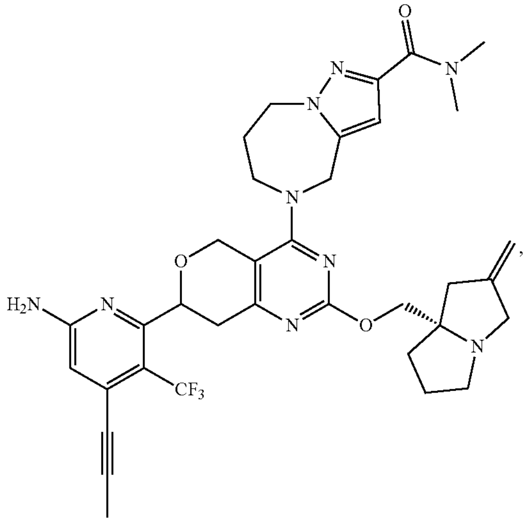, -continued
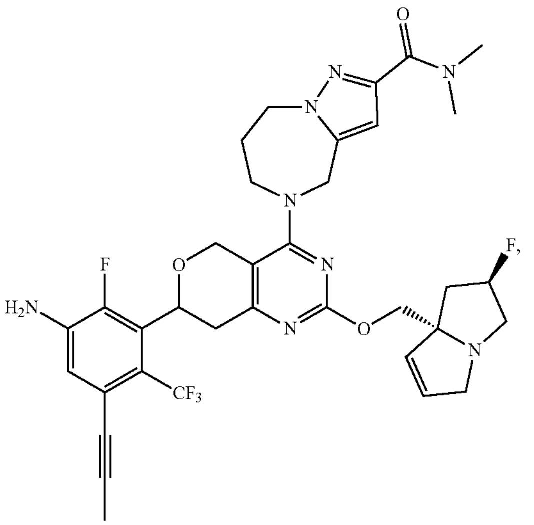
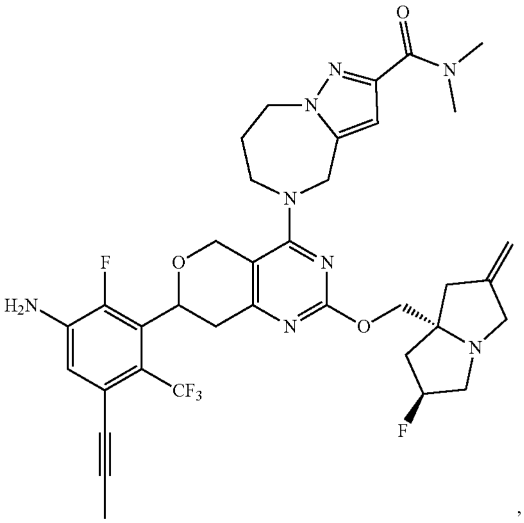
,
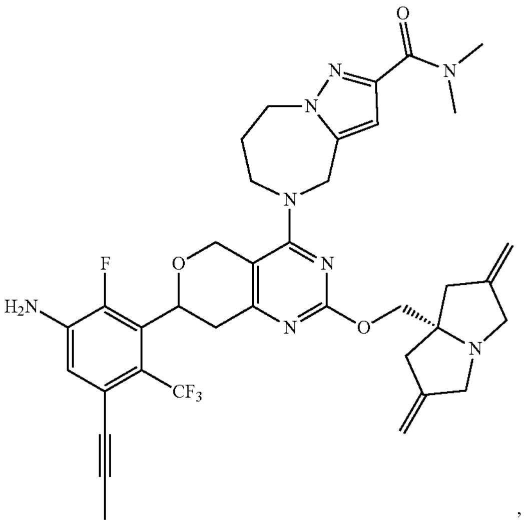
,
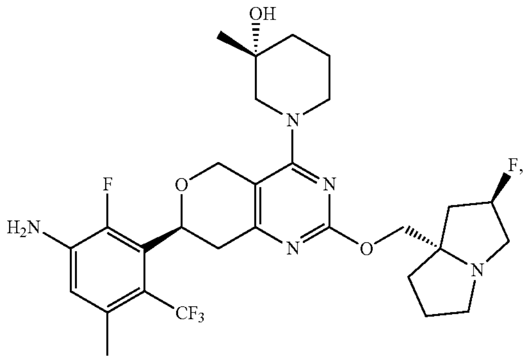
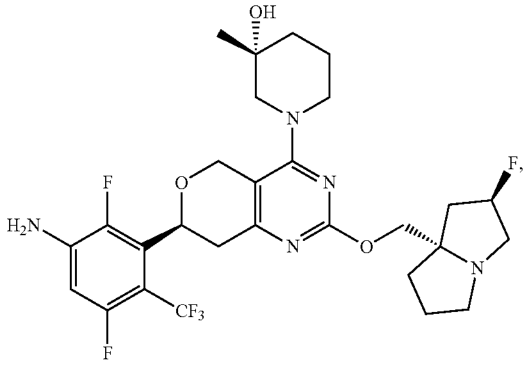
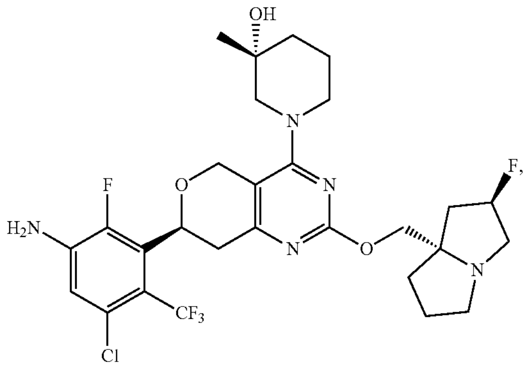
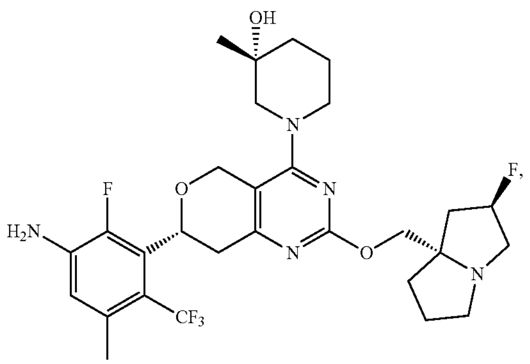

-continued
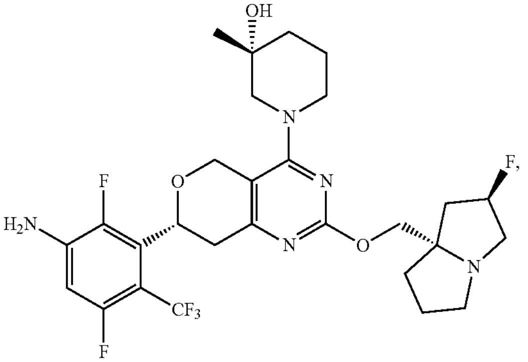
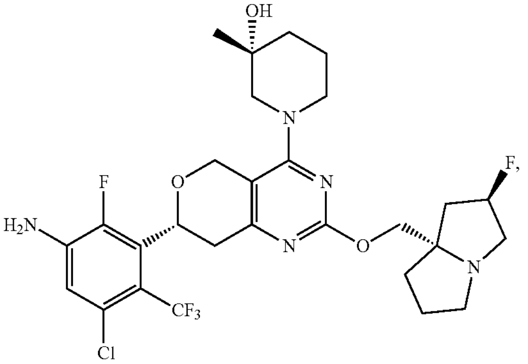
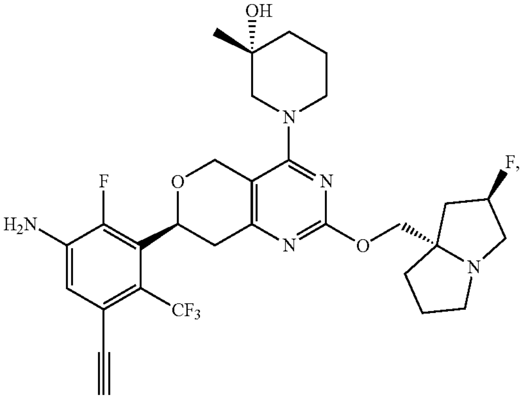
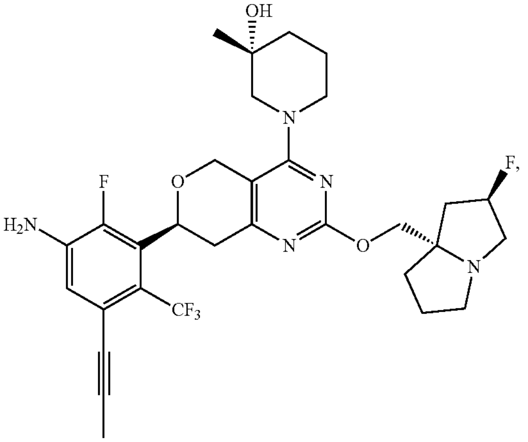
-continued
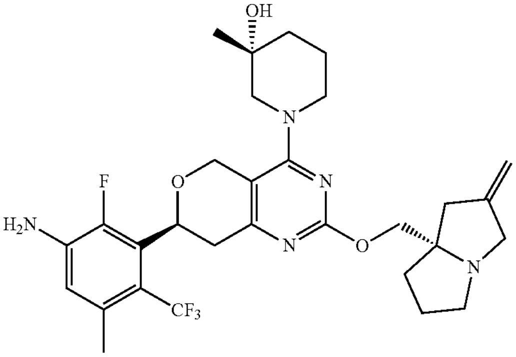
,
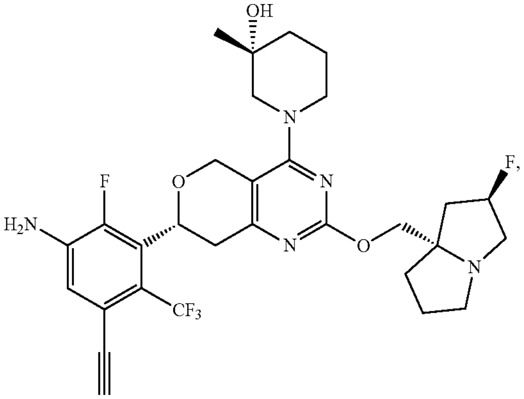
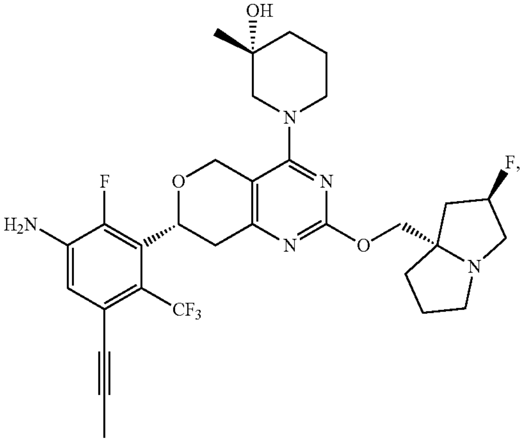
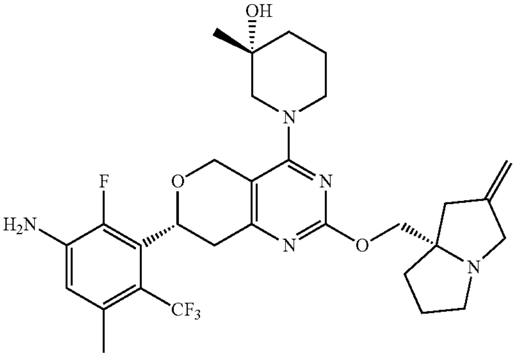
, -continued
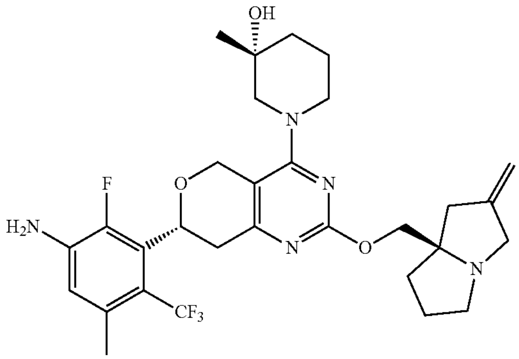
,
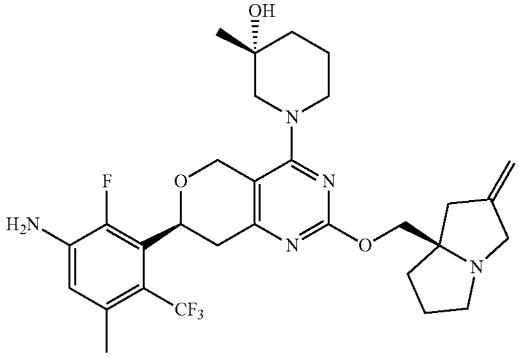
,
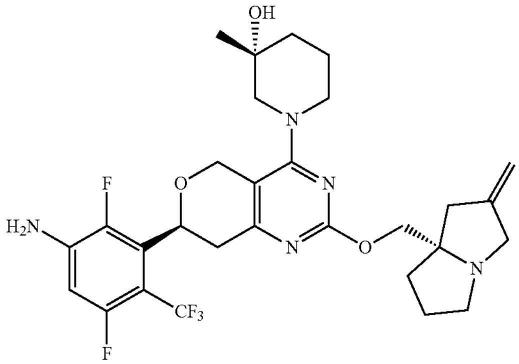
,
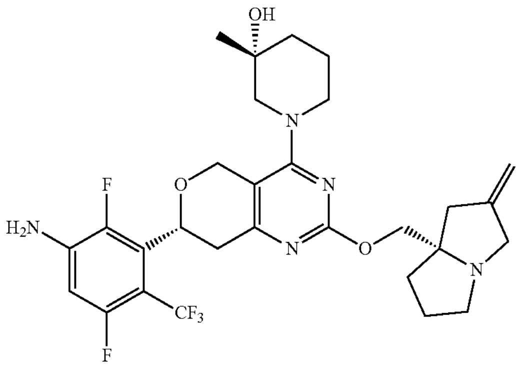
,
-continued
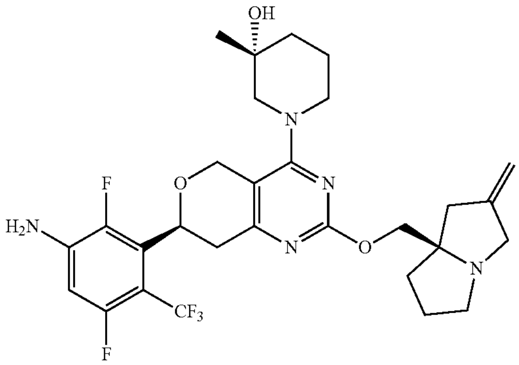
,
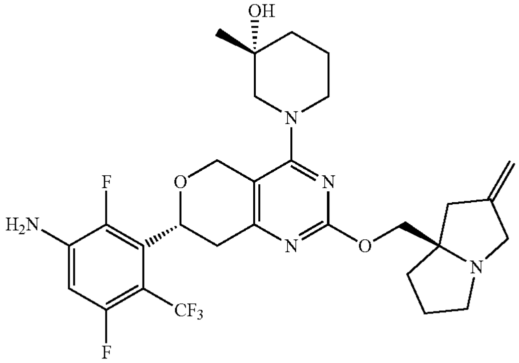
,
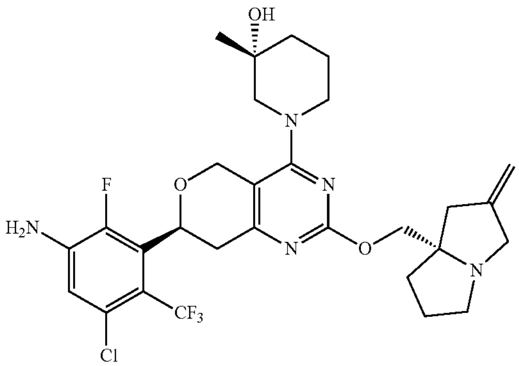
,
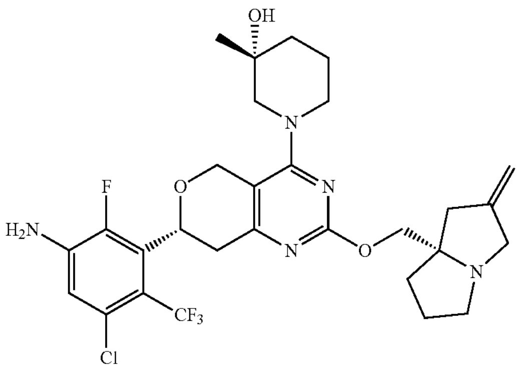
, -continued
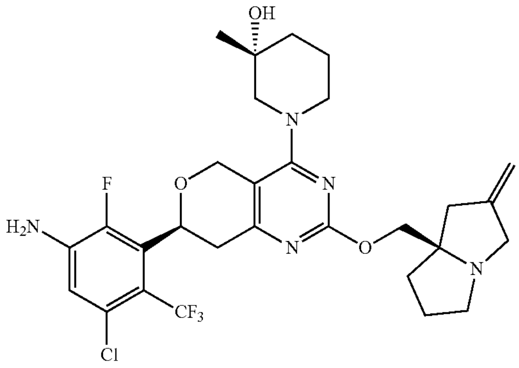
,
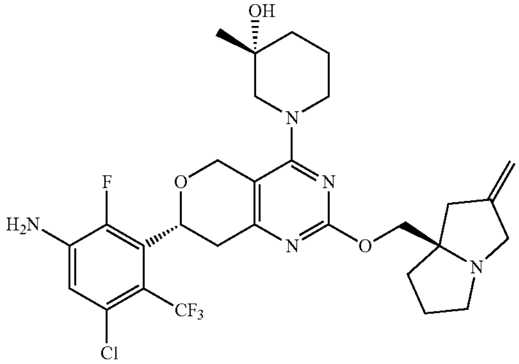
,
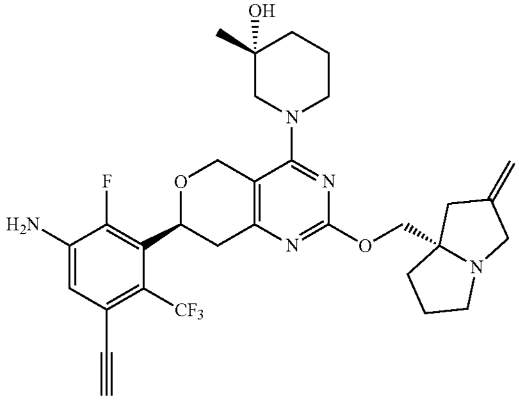
,
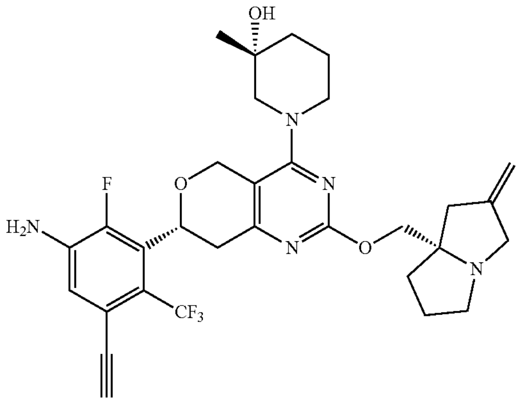
,
-continued
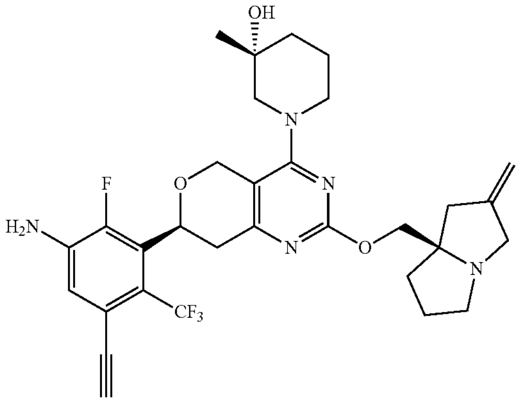
,
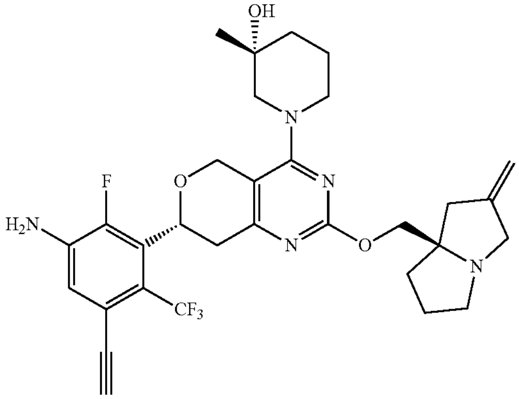
,
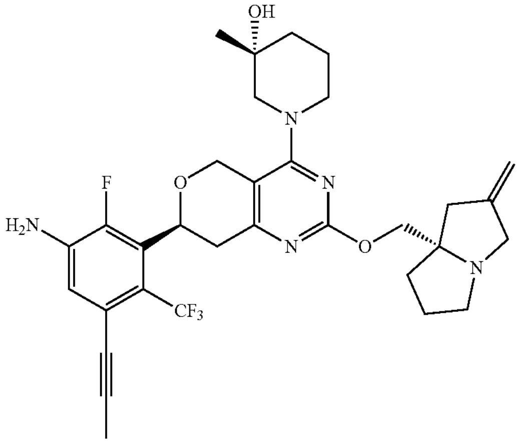
,
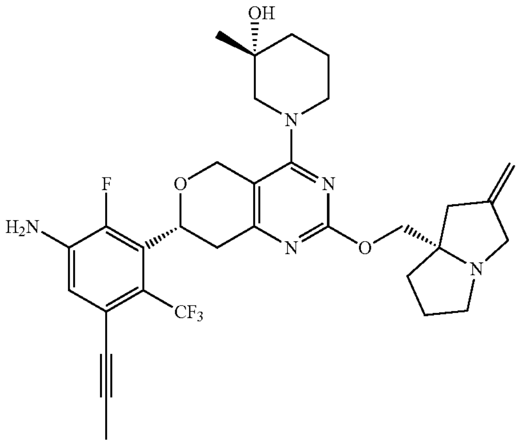
, -continued
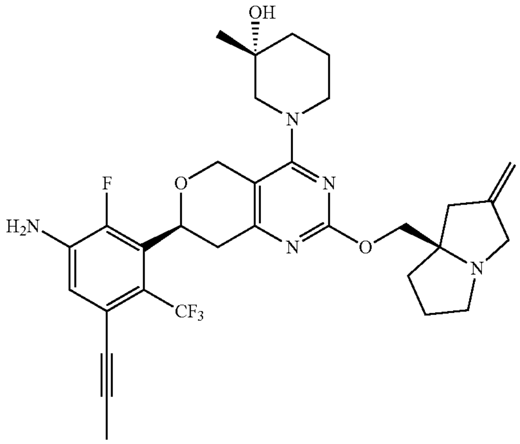
,
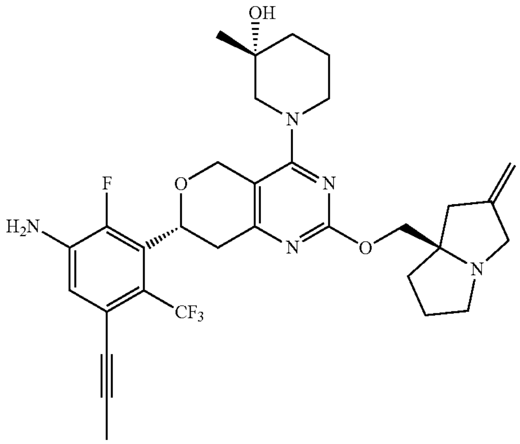
,
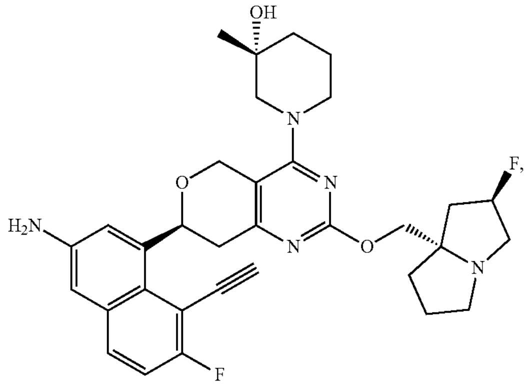
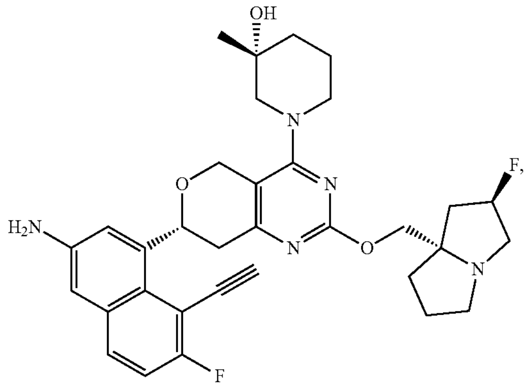
-continued
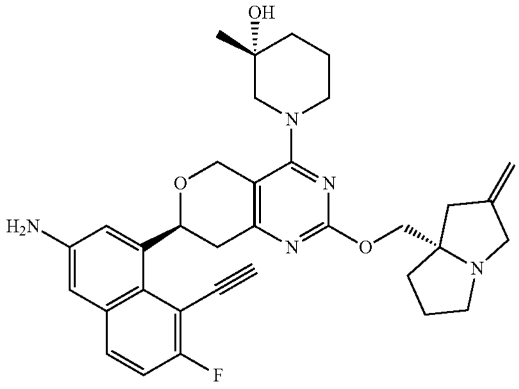
,
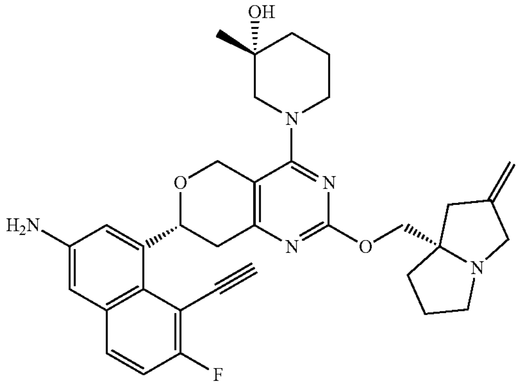
,
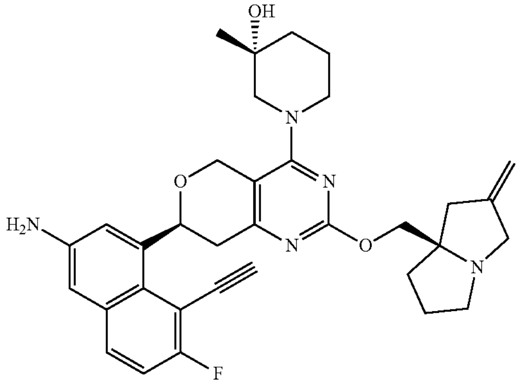
,
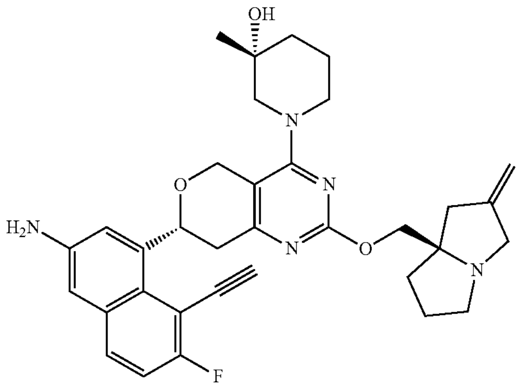
, -continued
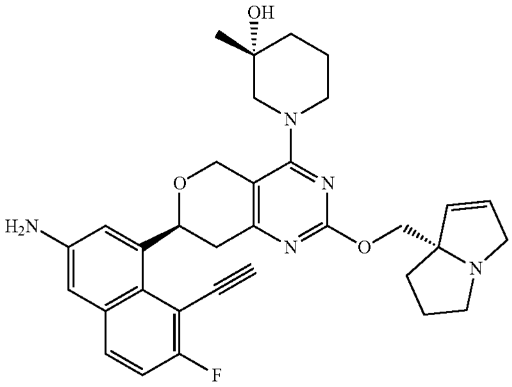
,
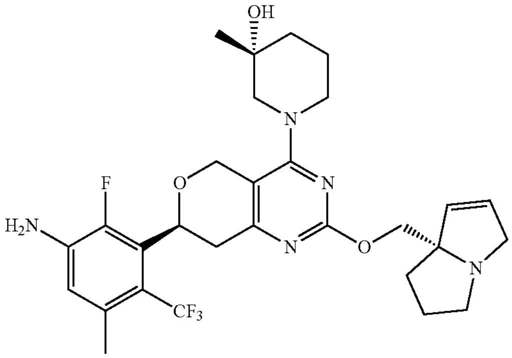
,
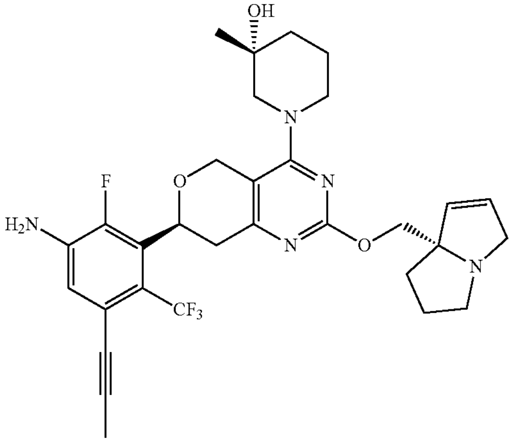
,
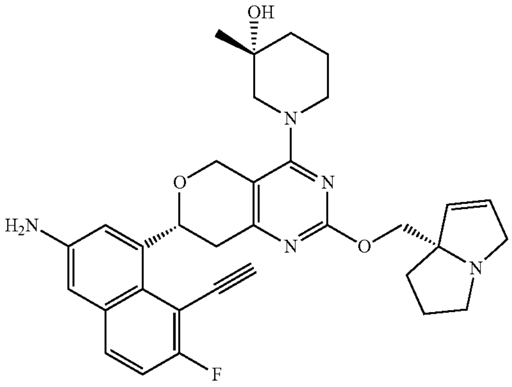
,
-continued
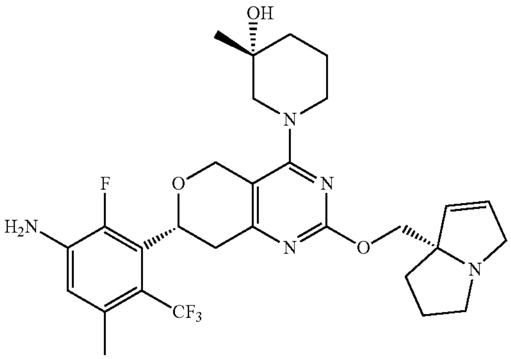
,
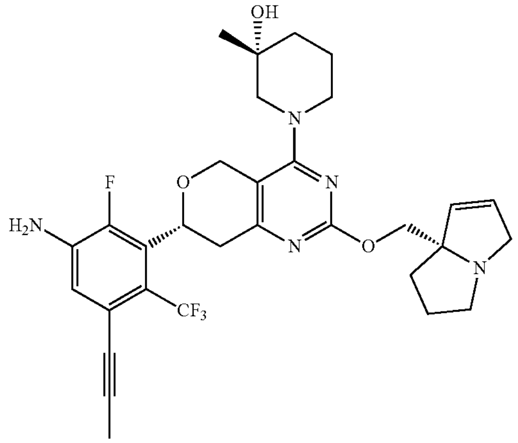
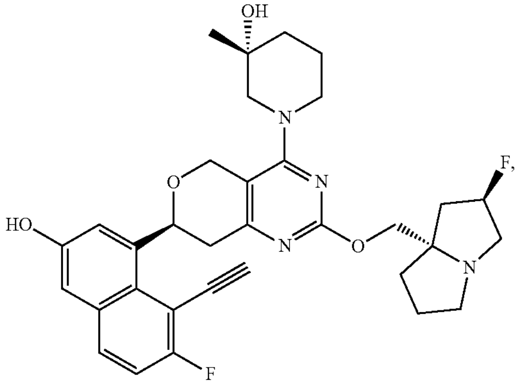
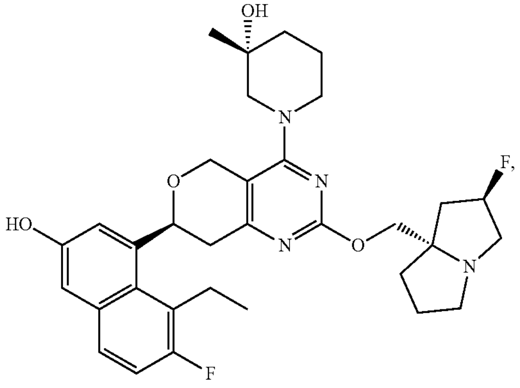

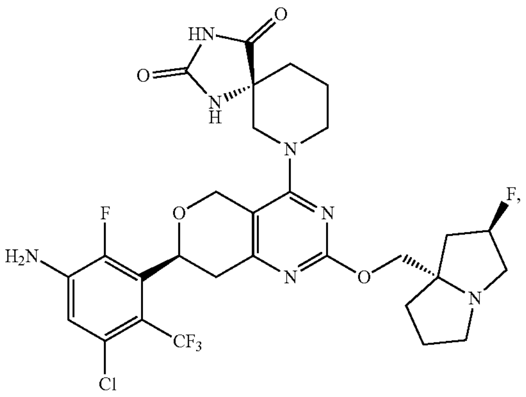
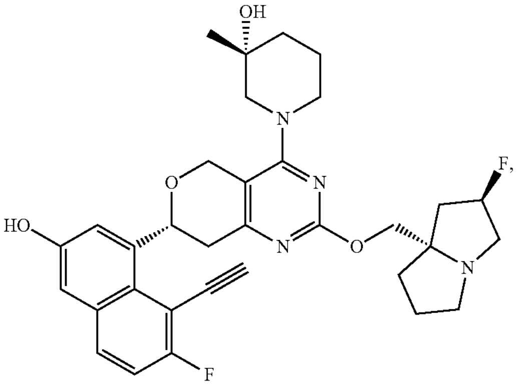
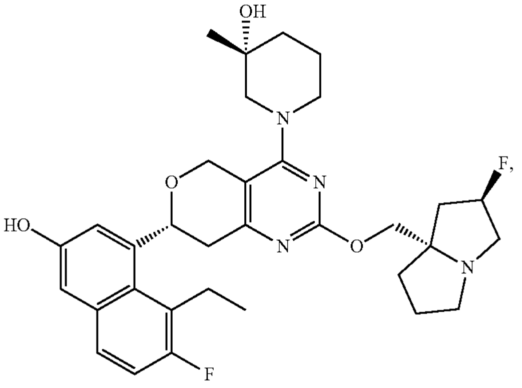
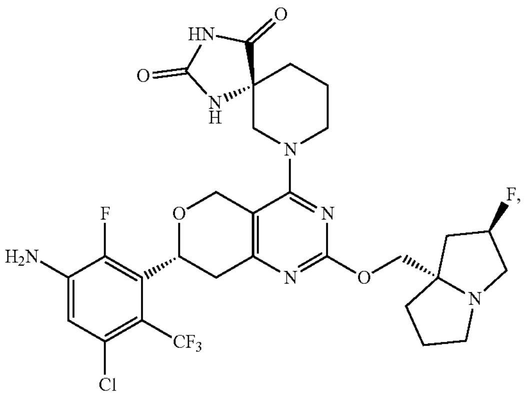
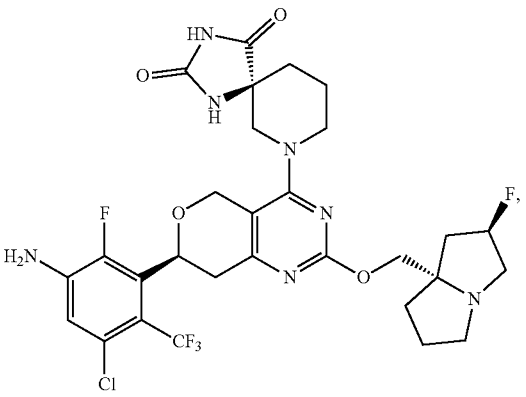
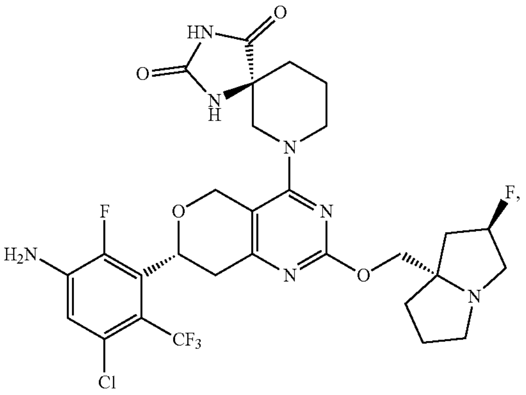
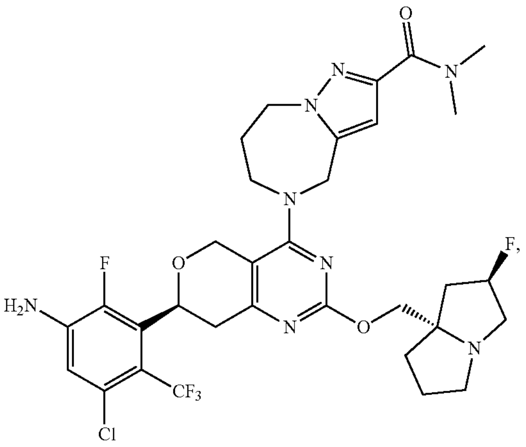
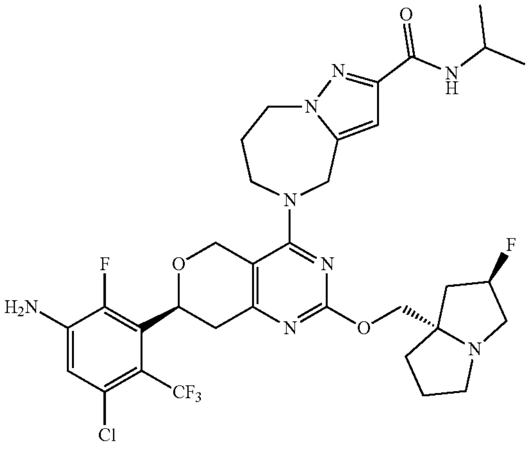
, -continued
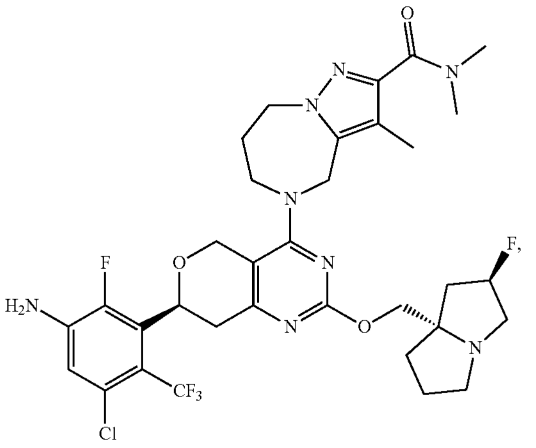
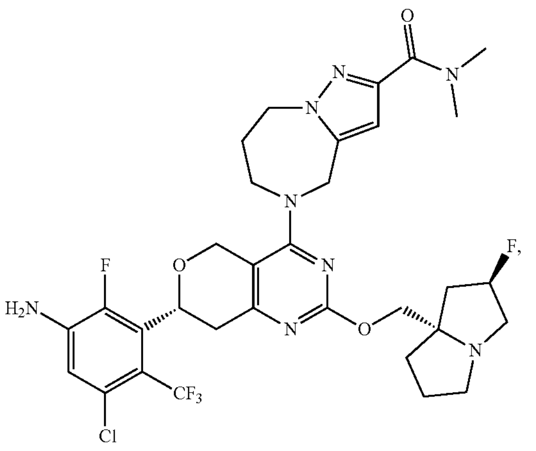
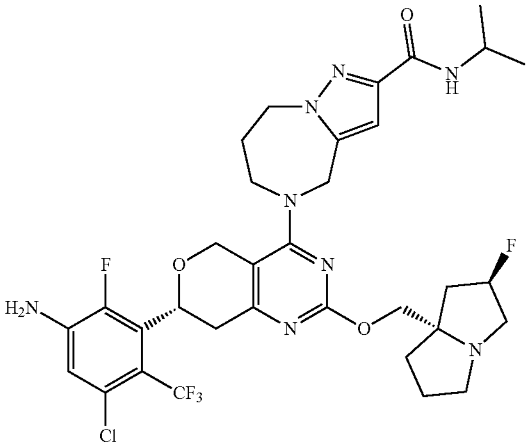
,
-continued
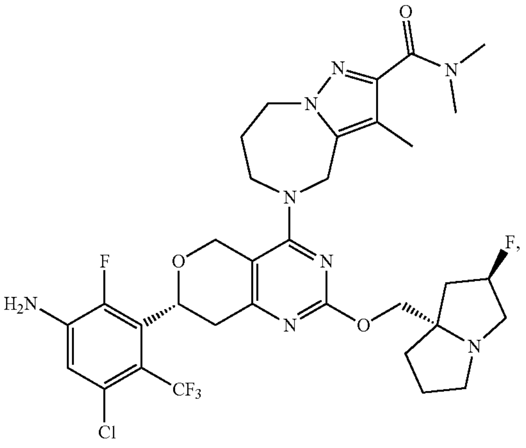
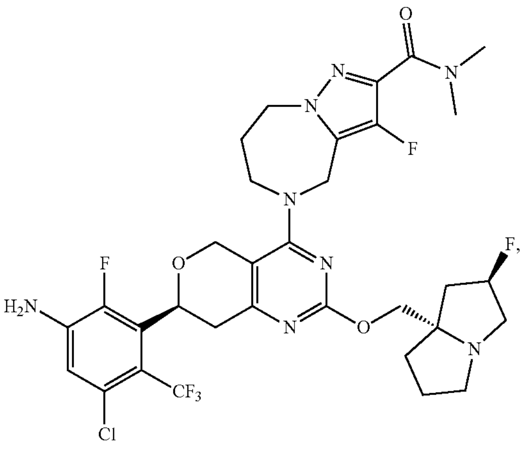
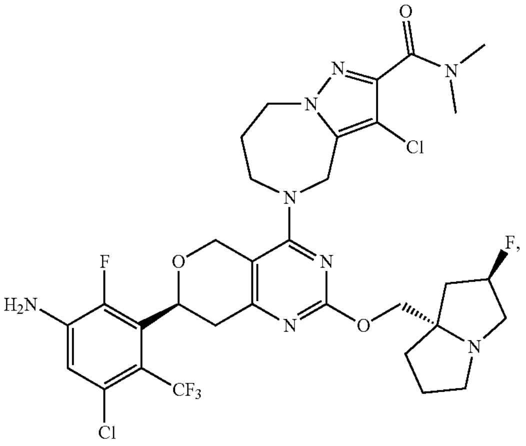

-continued
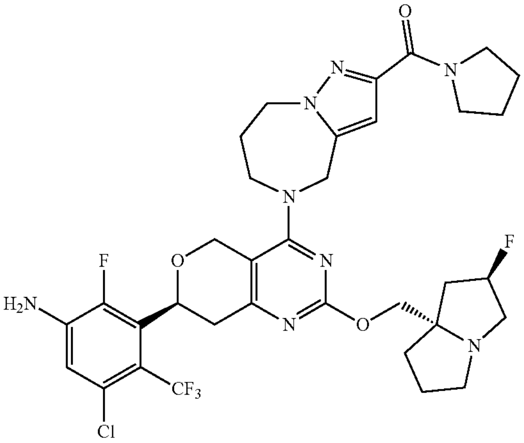
,
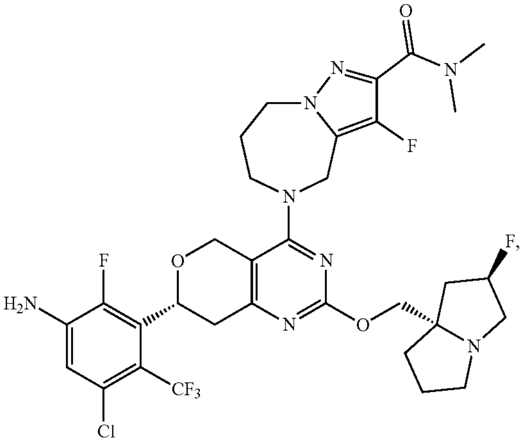
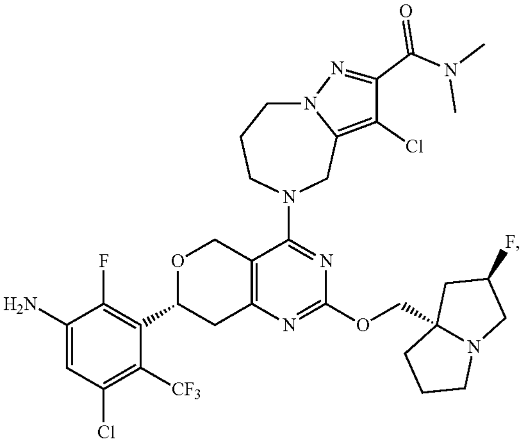
-continued
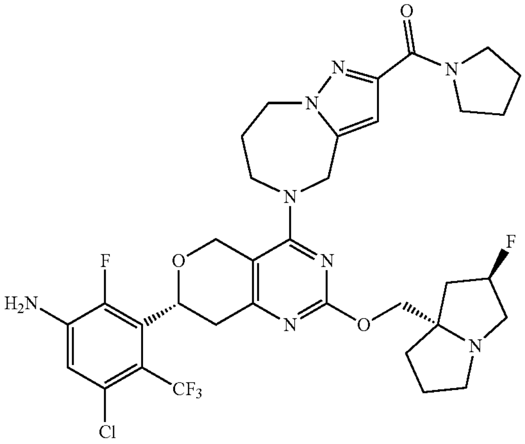
,
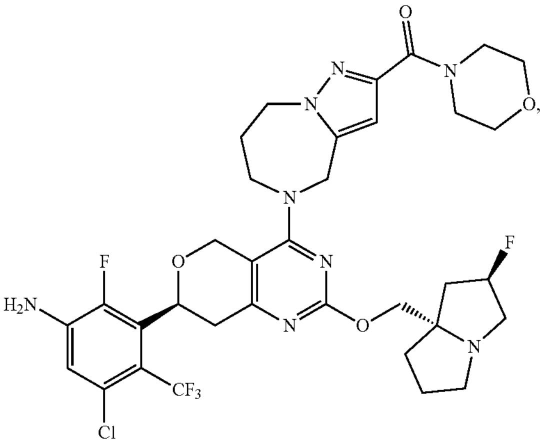
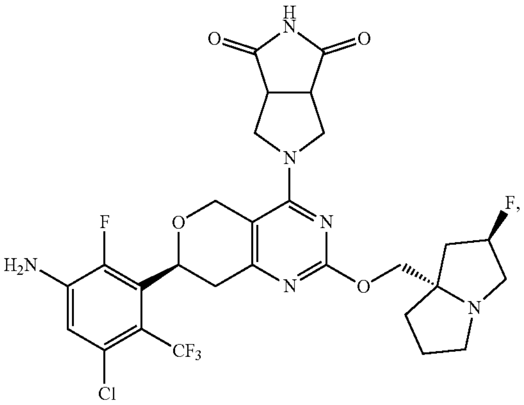

-continued
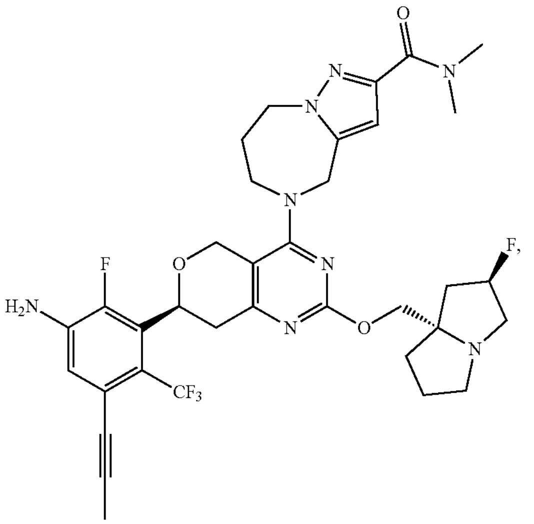
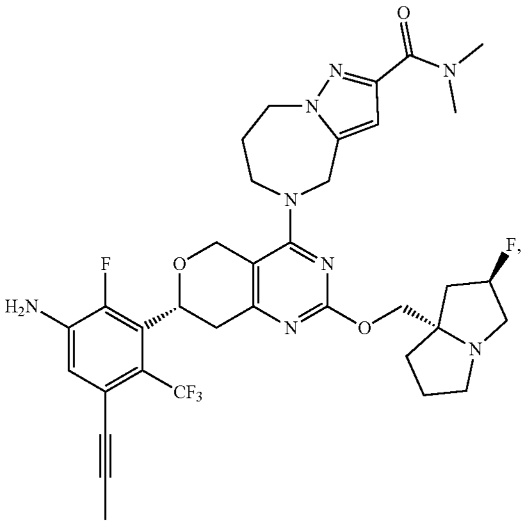
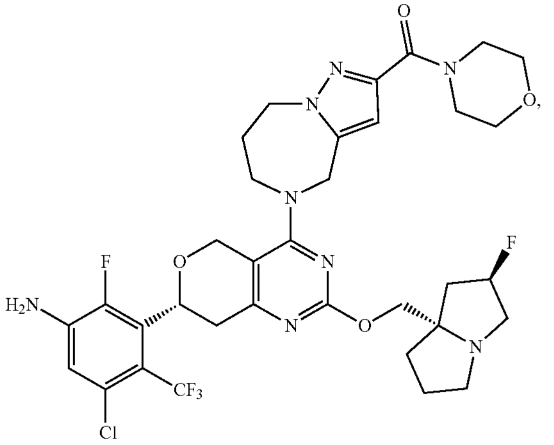
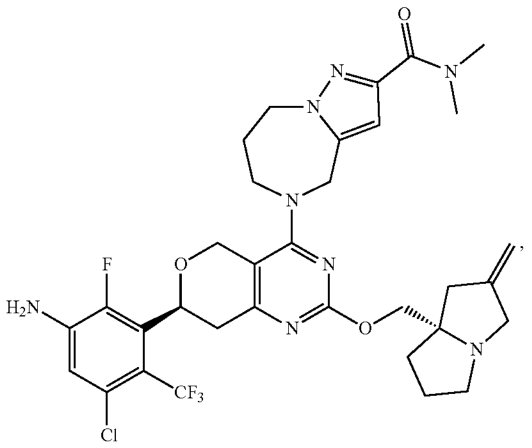
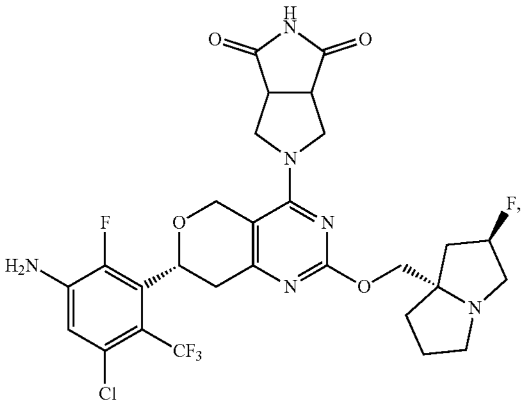
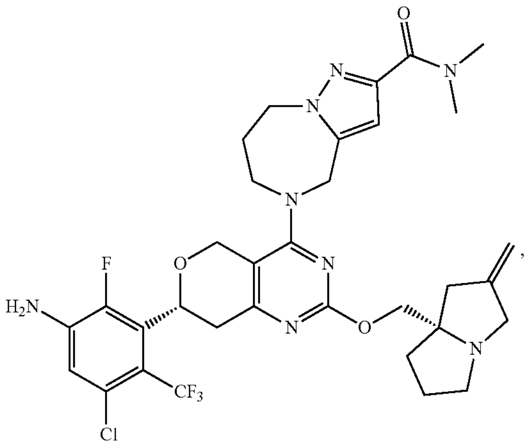

-continued
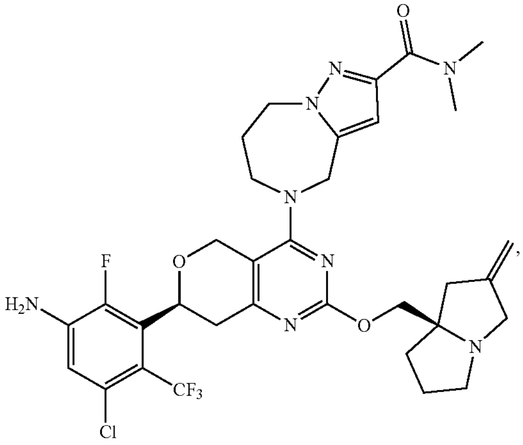
,
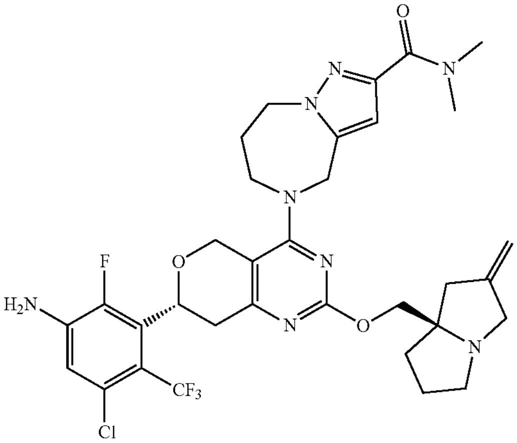
,
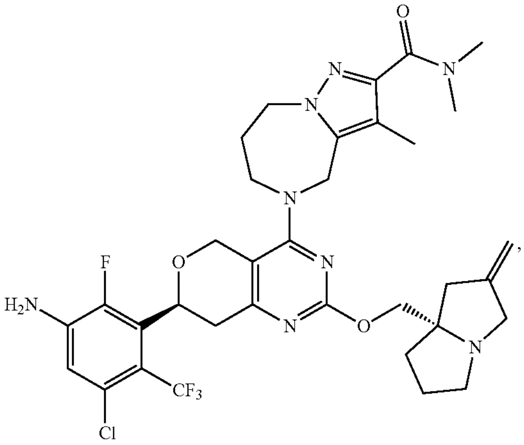
,
-continued
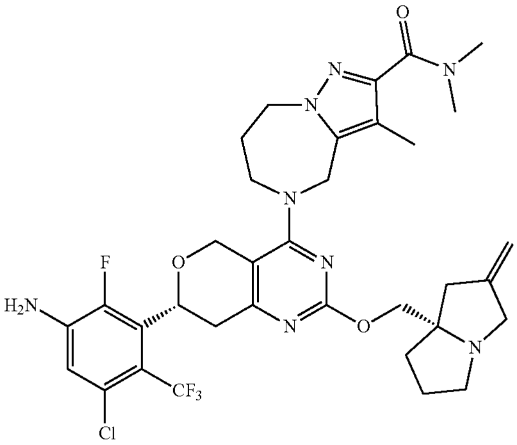
,
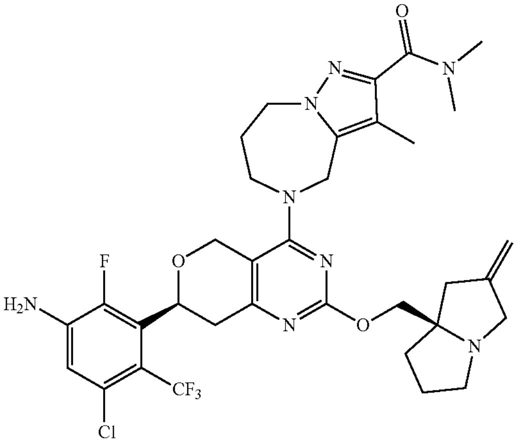
,
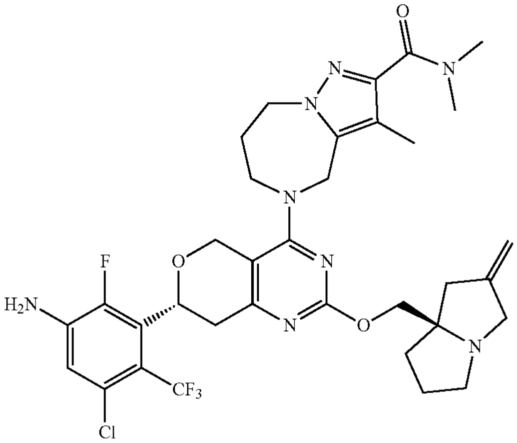
, -continued
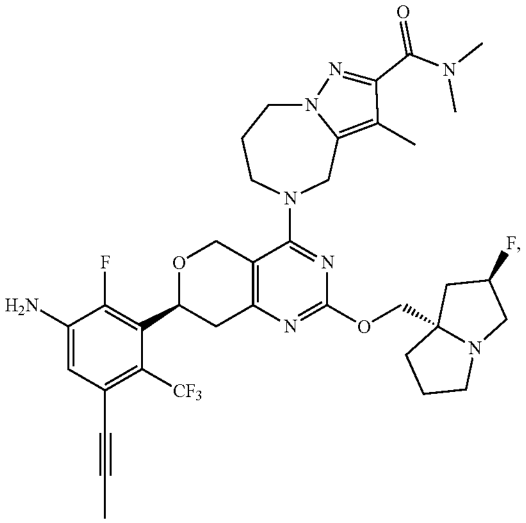
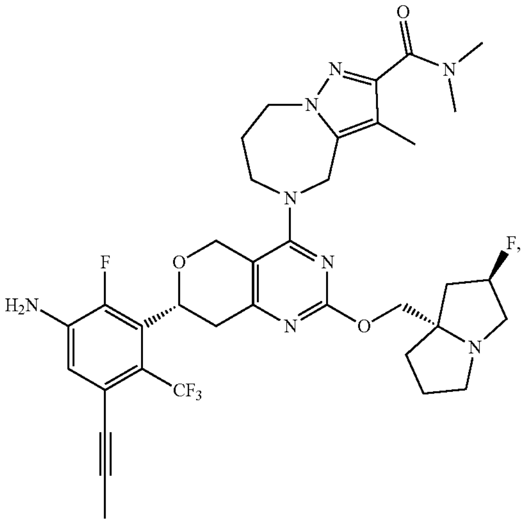
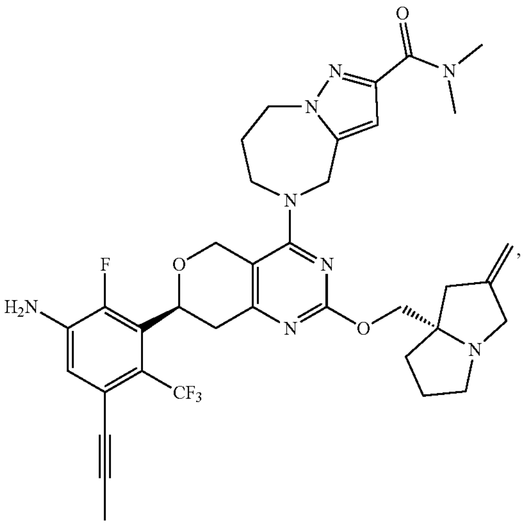
-continued
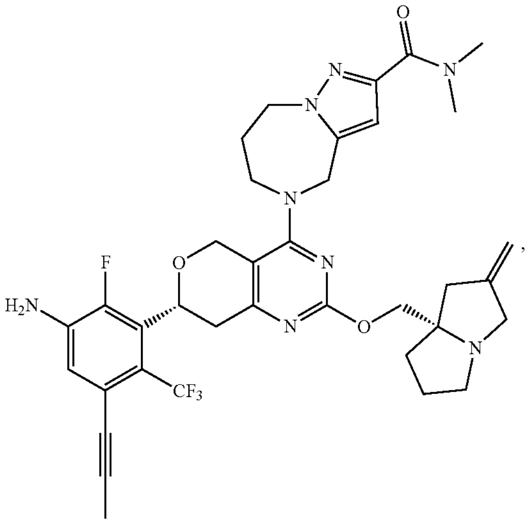
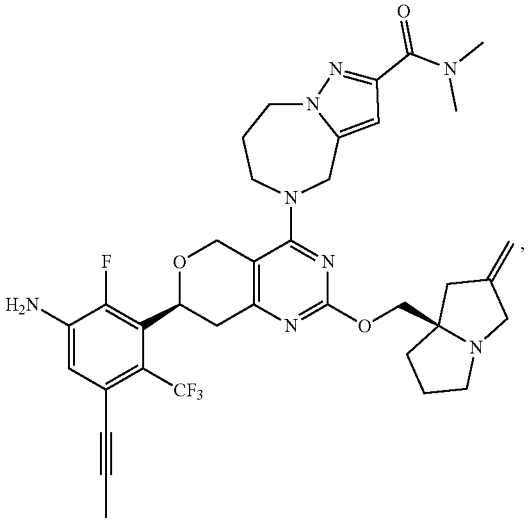
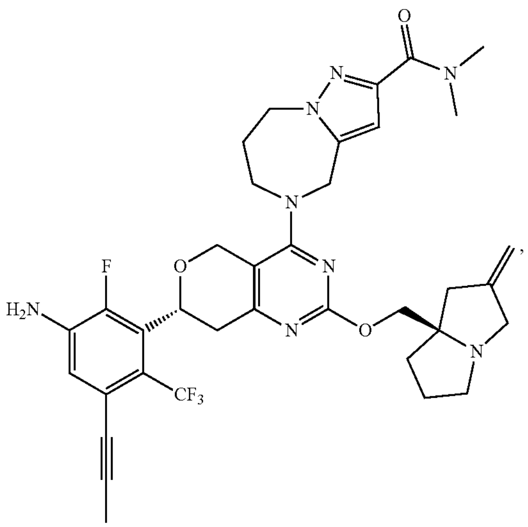

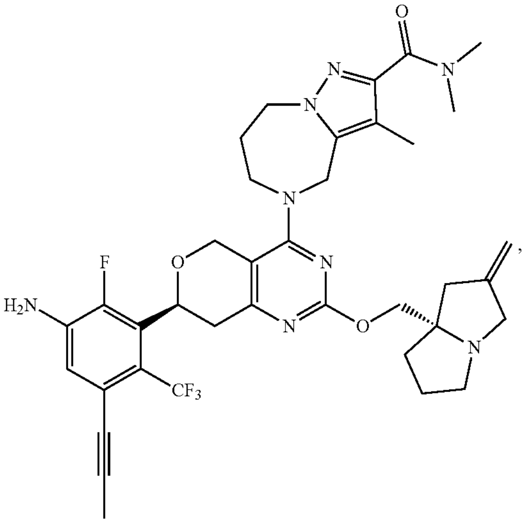
,
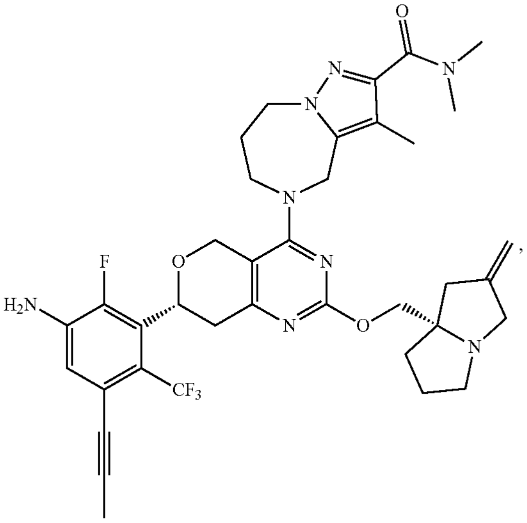
,
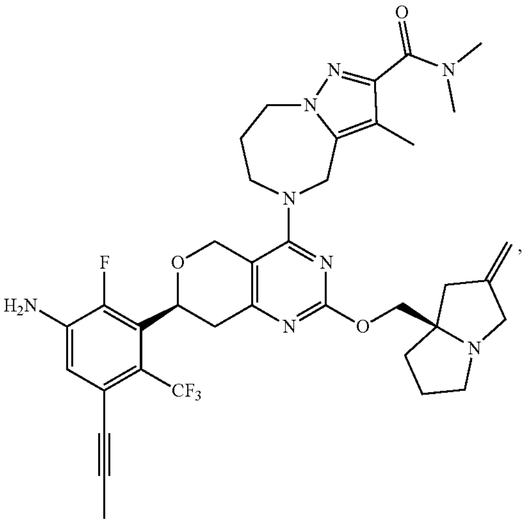
,
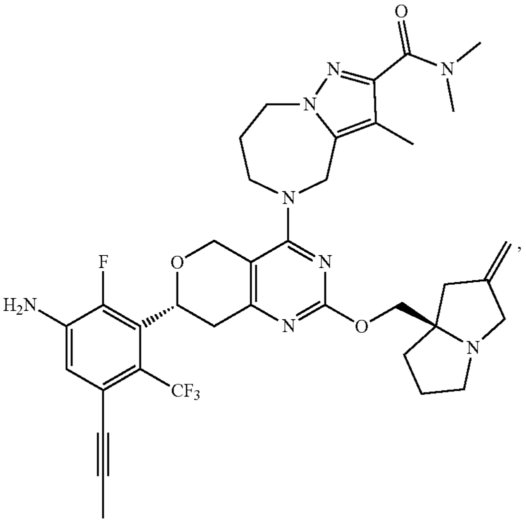
,
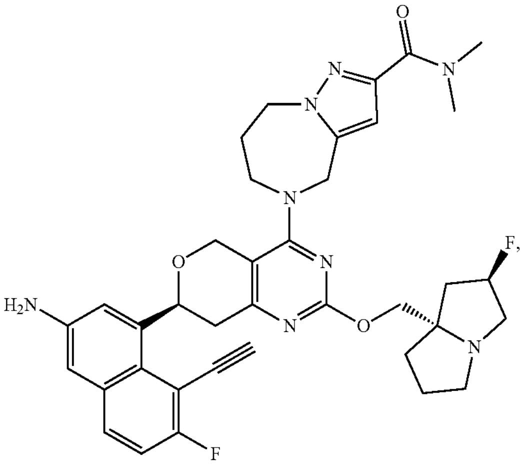
,
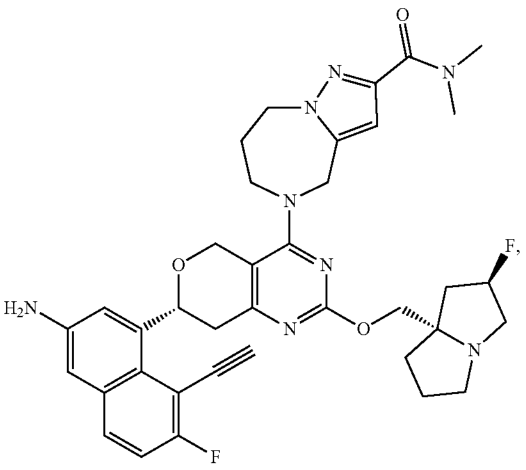
, -continued
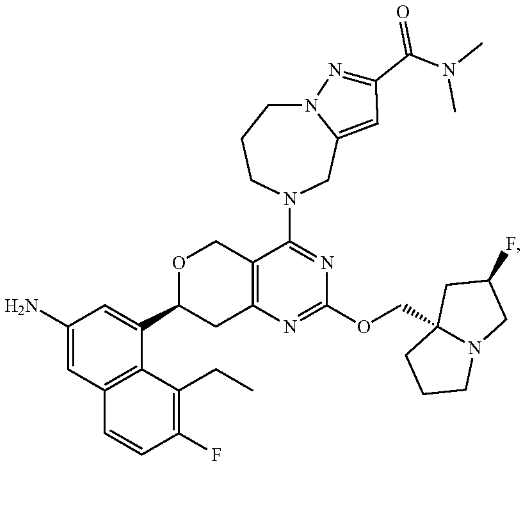
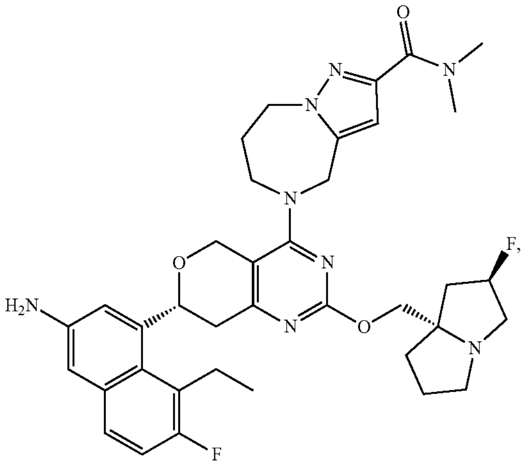
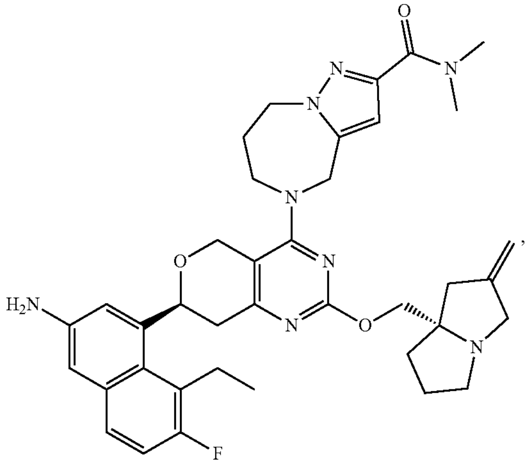
-continued
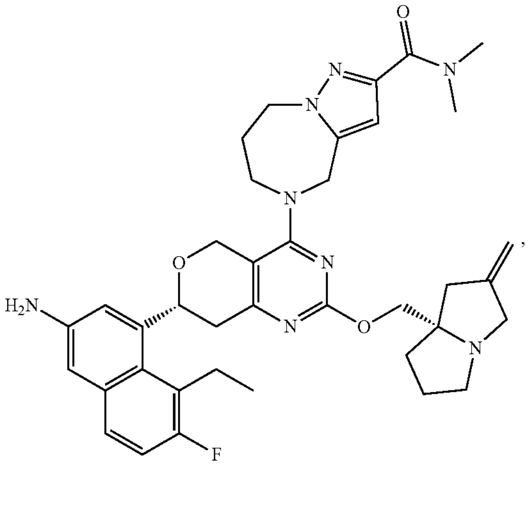
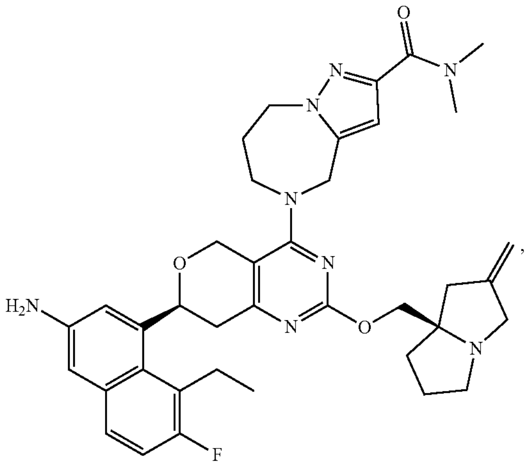
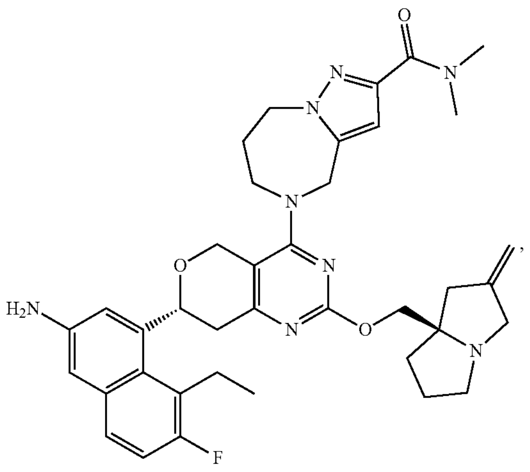

-continued
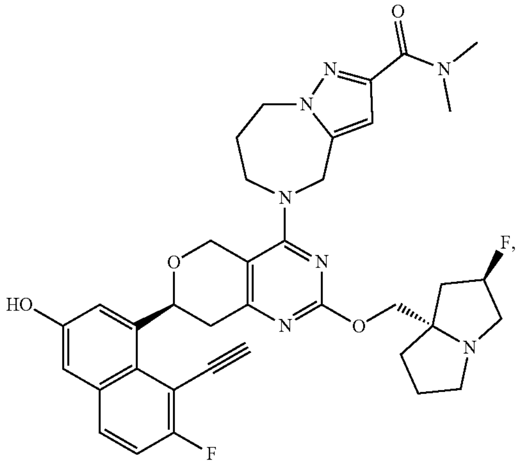
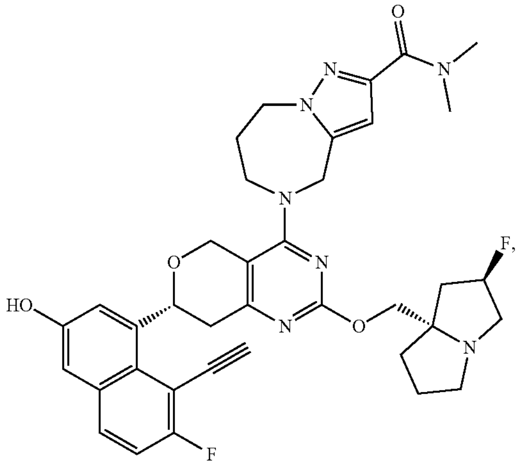
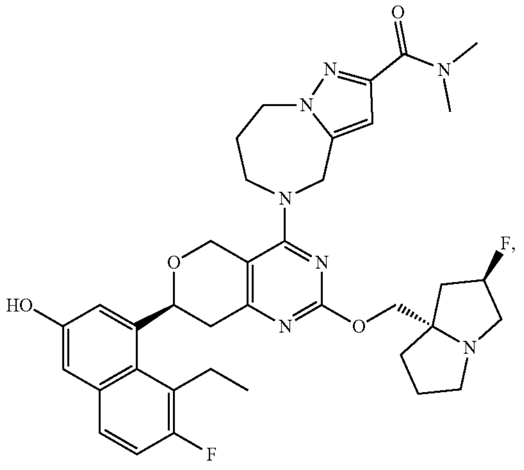
-continued
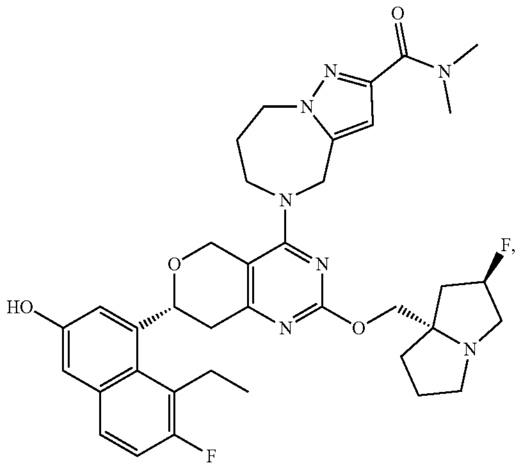
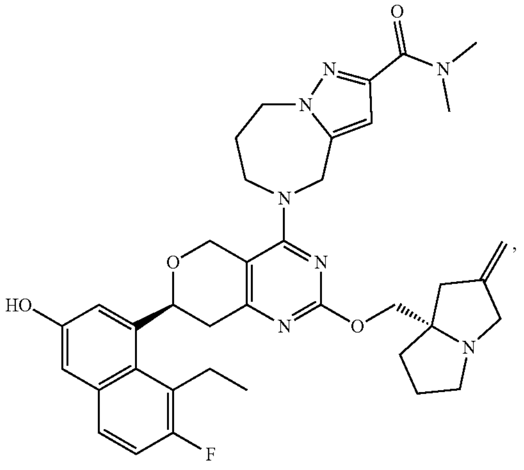
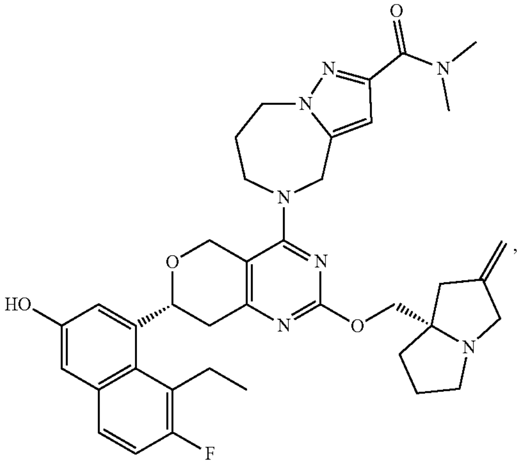

-continued
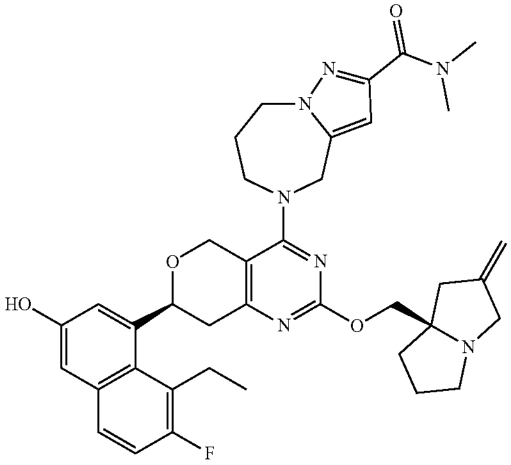
,
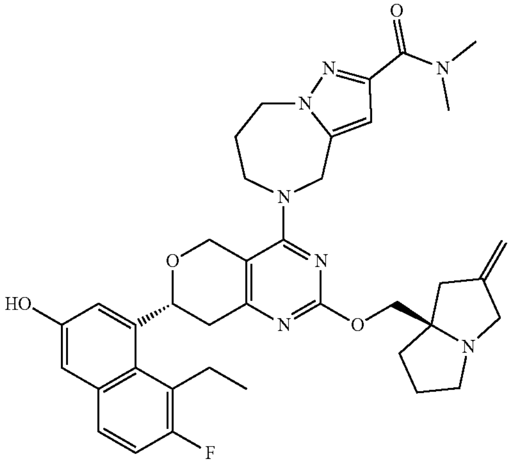
,
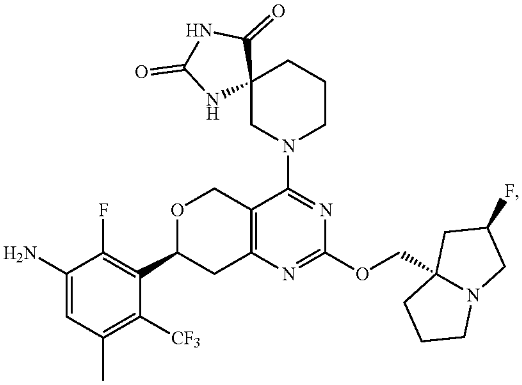
,
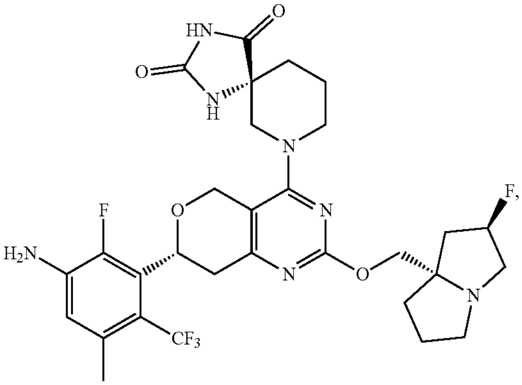
,
-continued
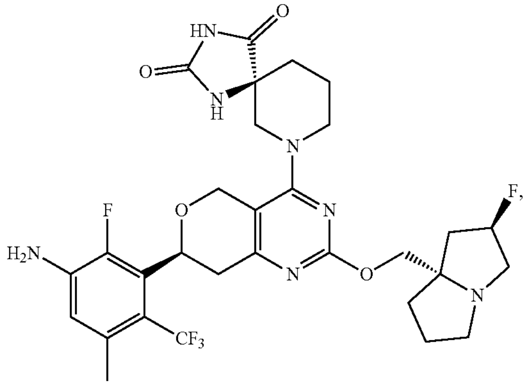
,
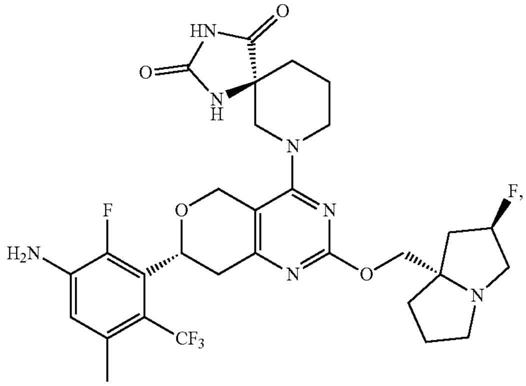
,
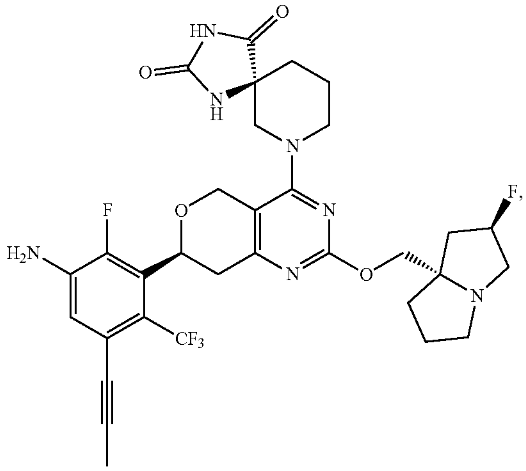
,
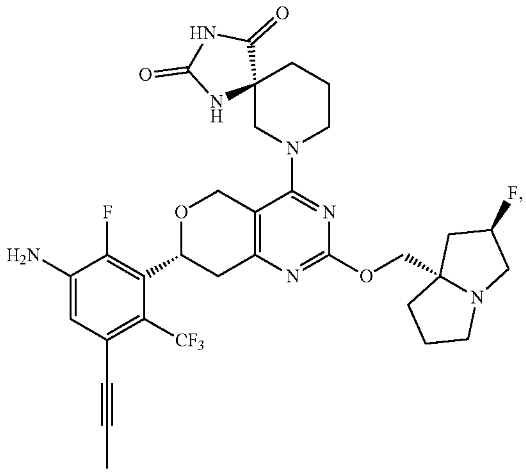
, -continued
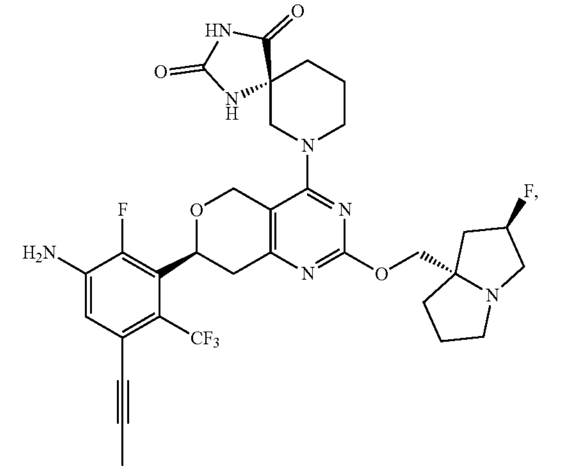
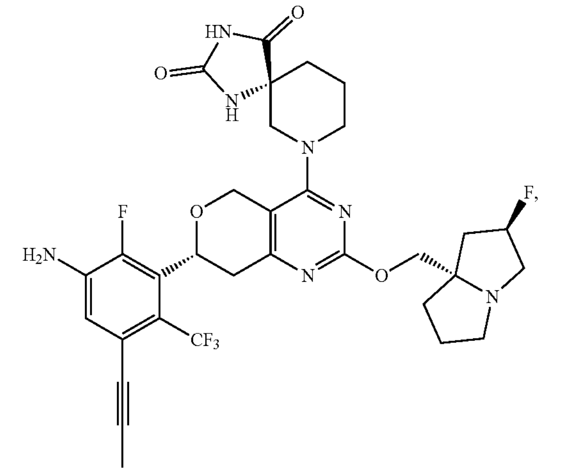
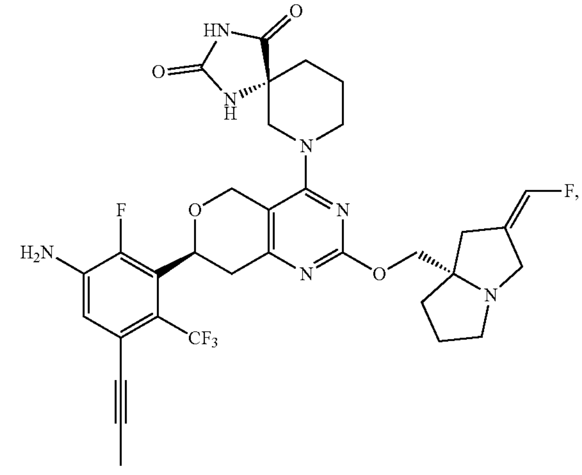
-continued
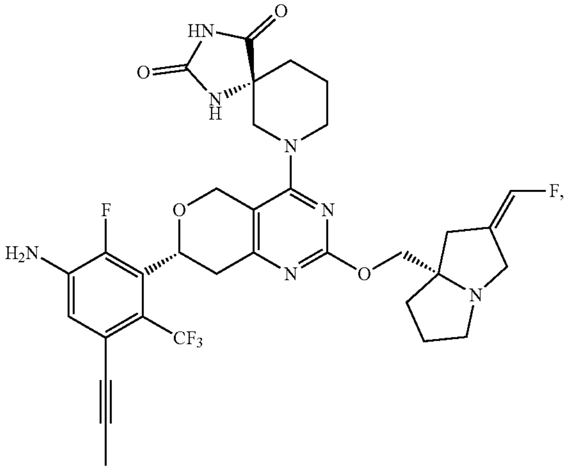
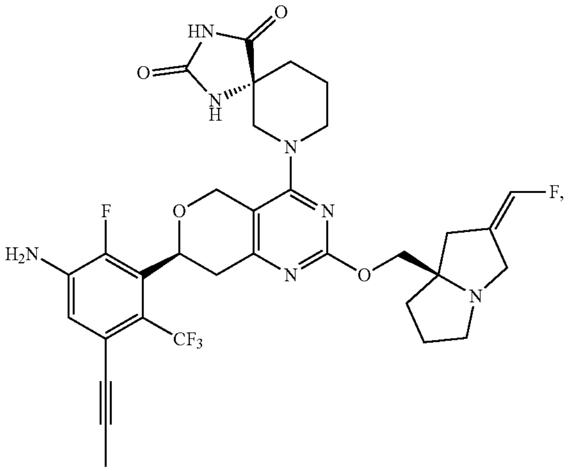
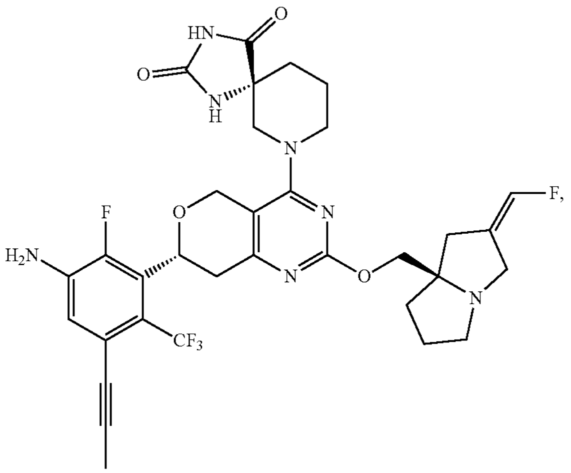

-continued
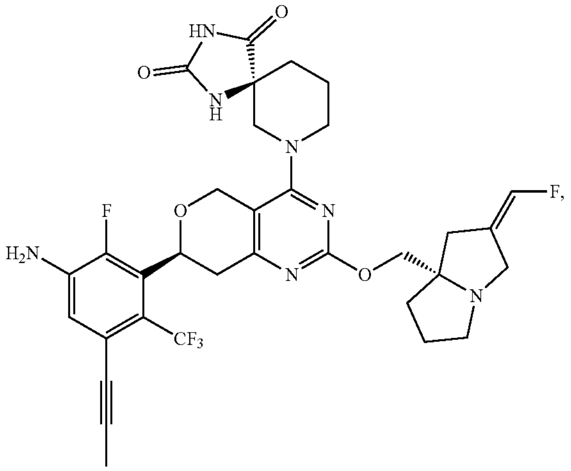
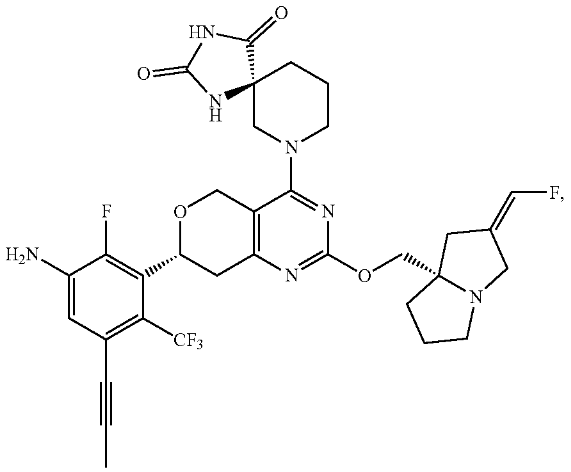
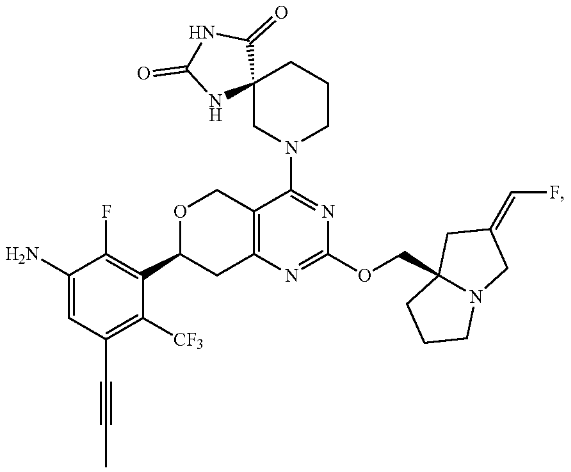
-continued
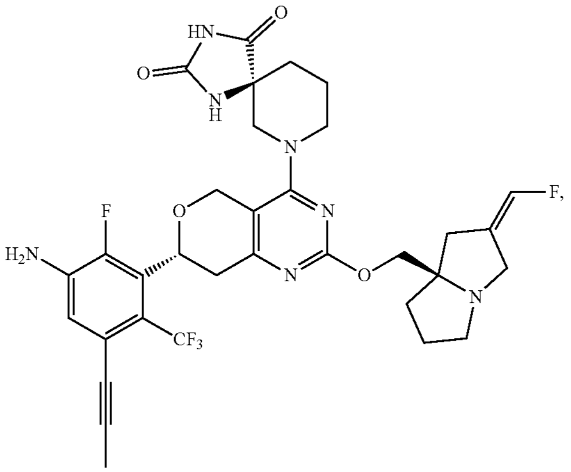
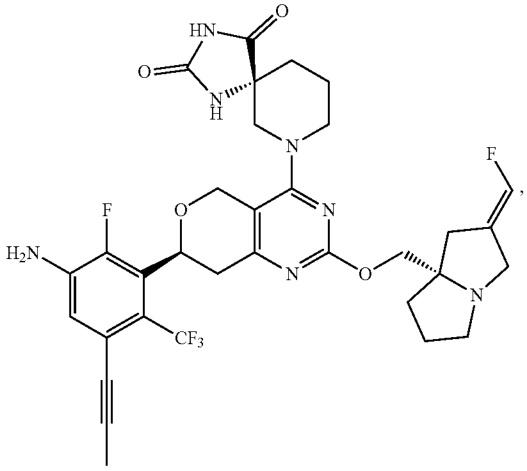
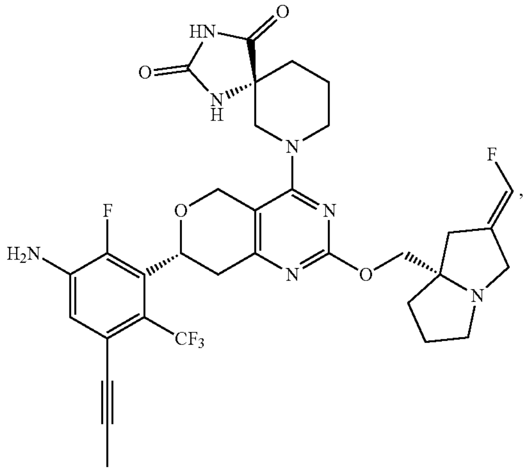

-continued
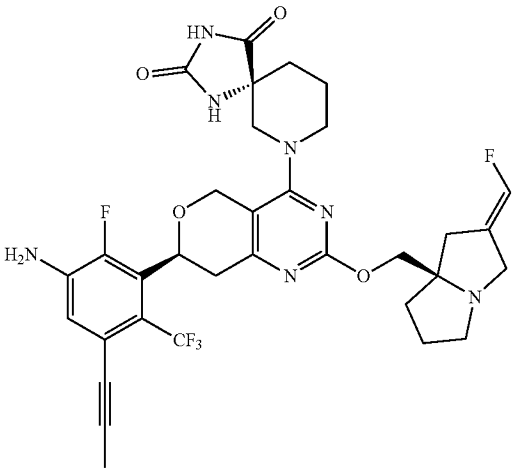
,
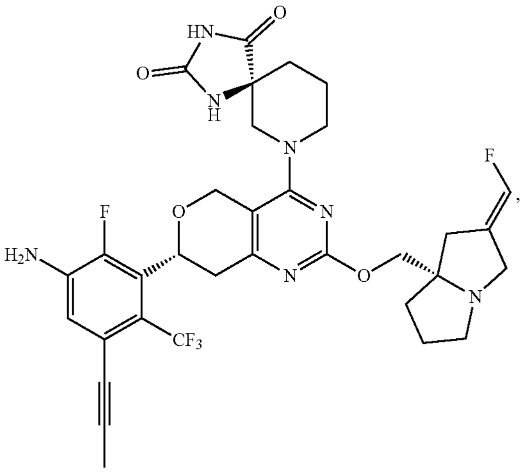
,
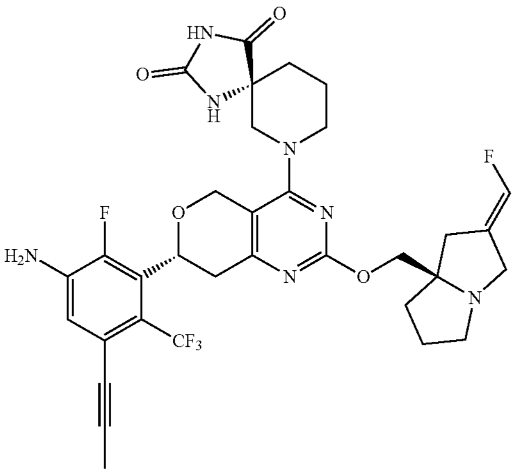
,
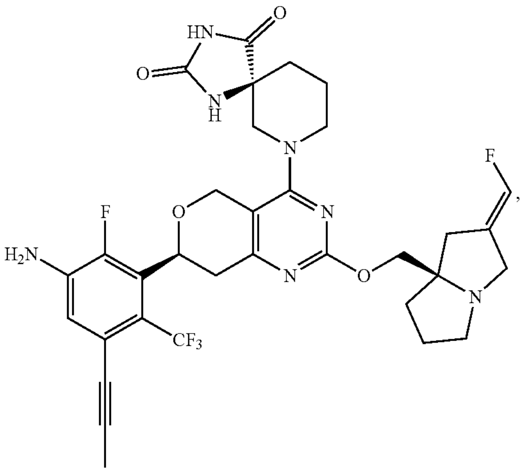
,
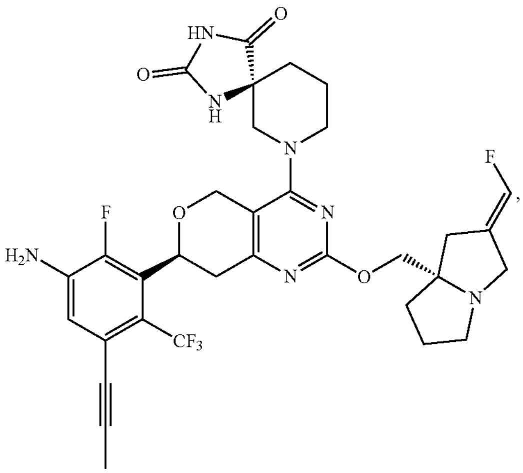
,
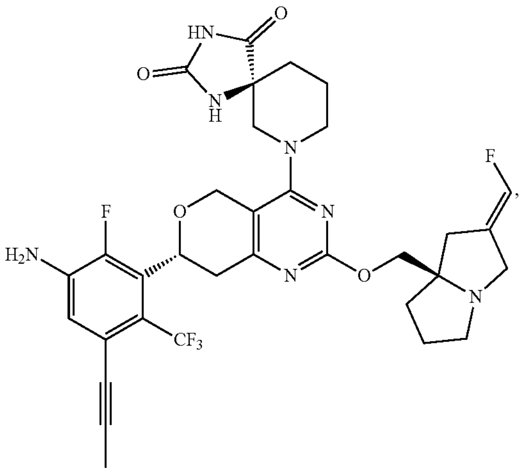
, -continued
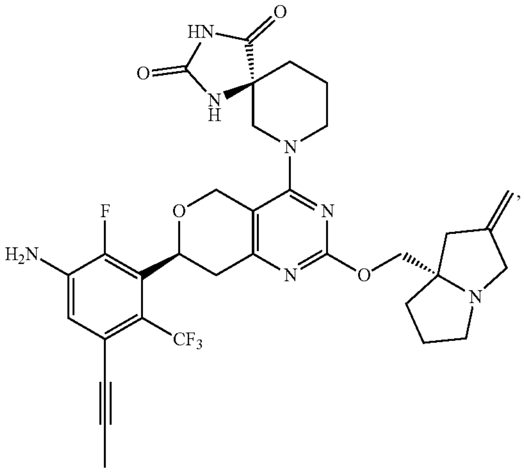
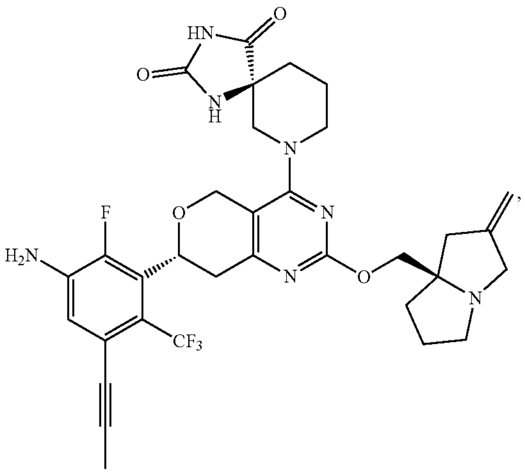
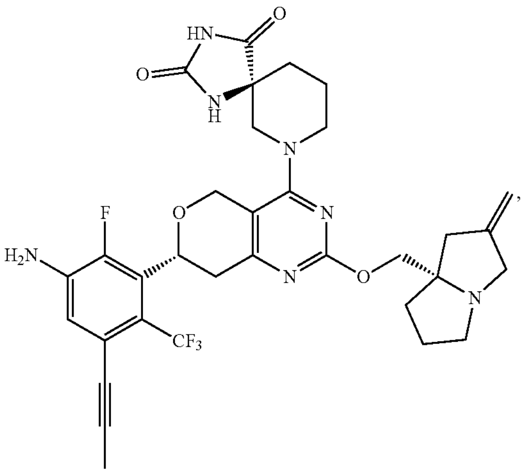
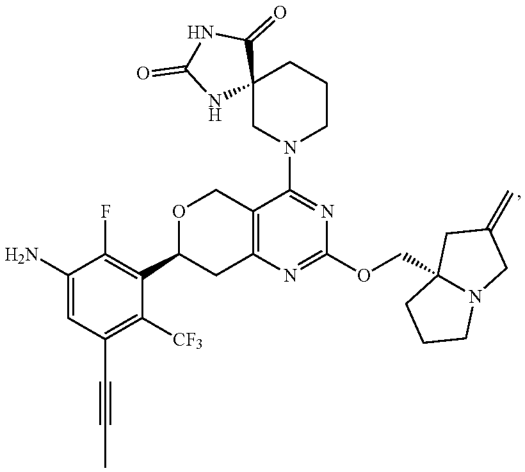
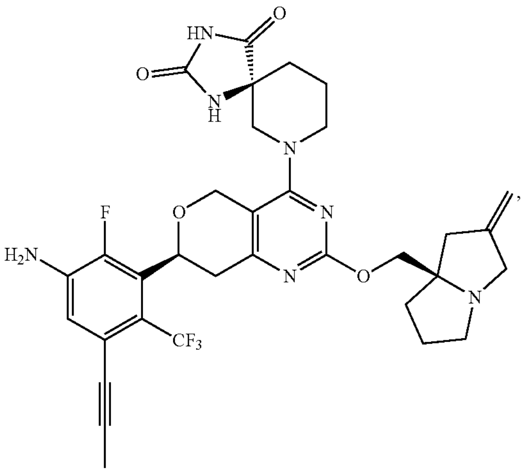
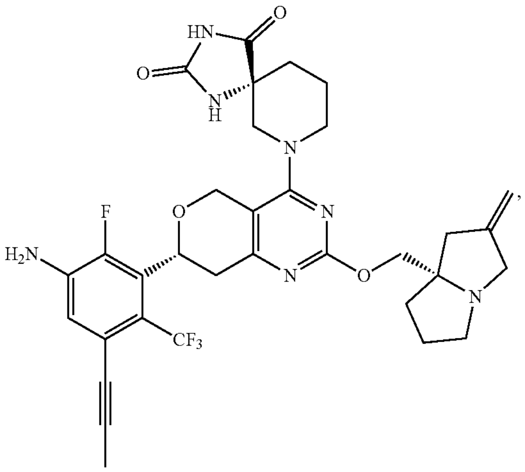

-continued
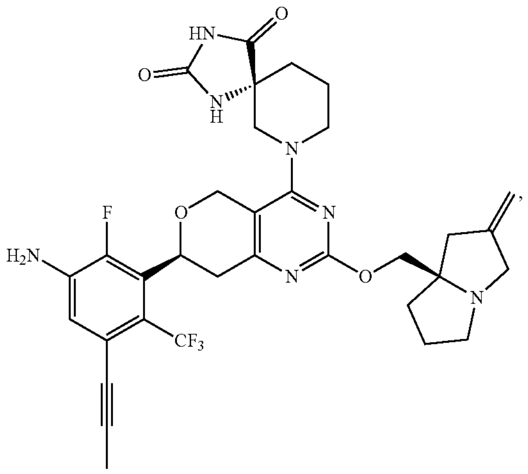
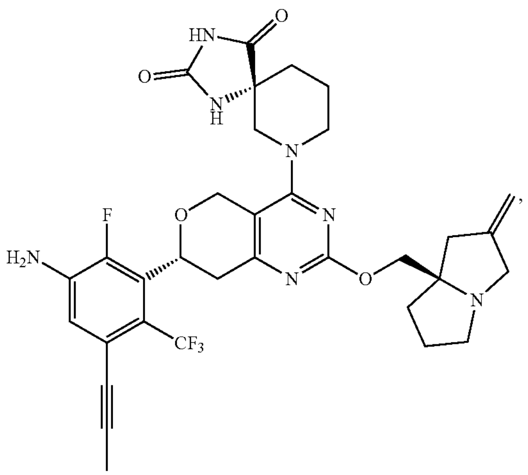
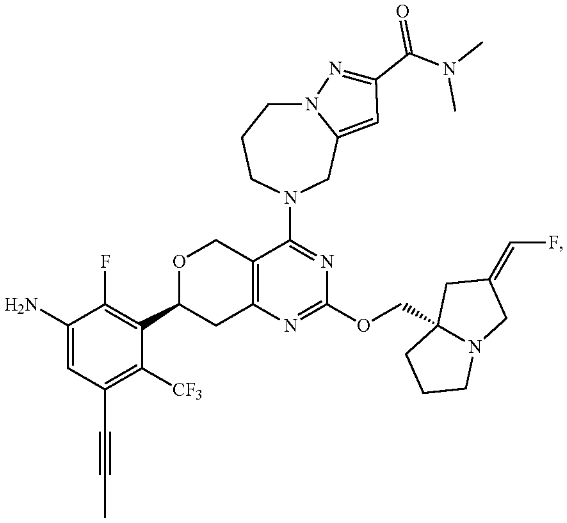
-continued
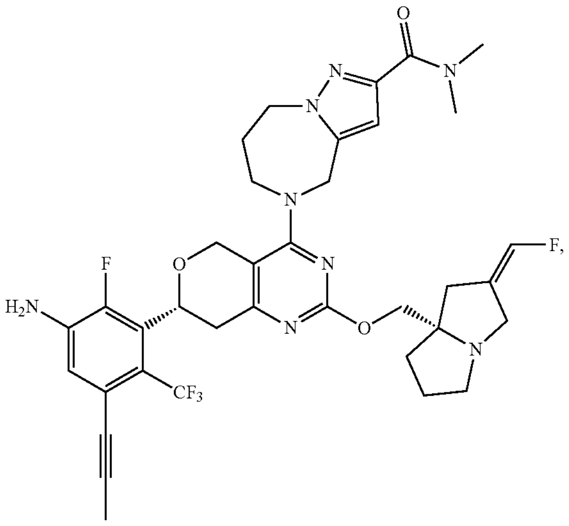
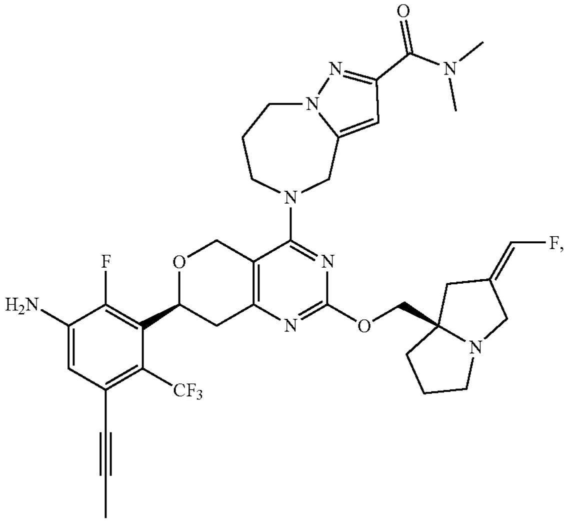
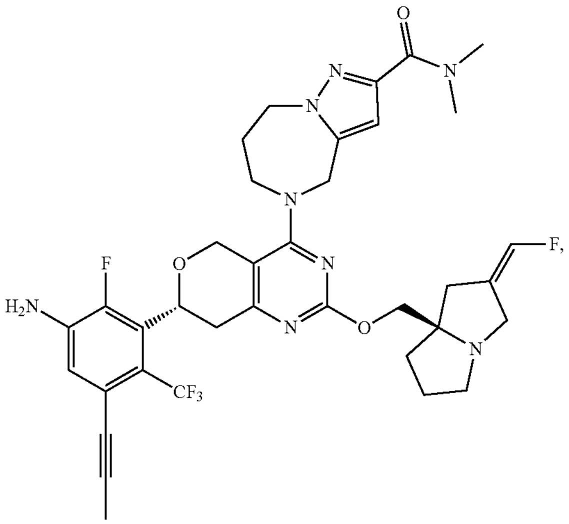

-continued
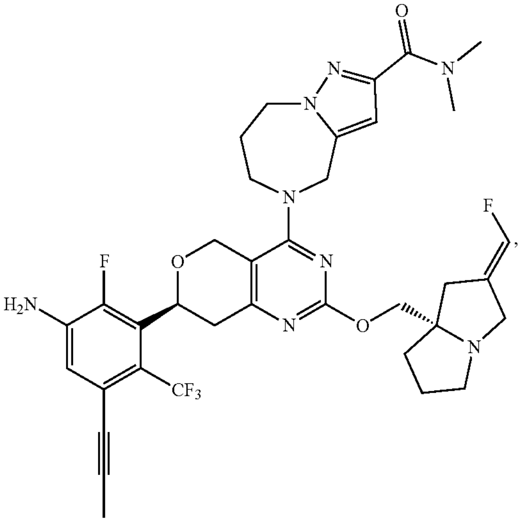
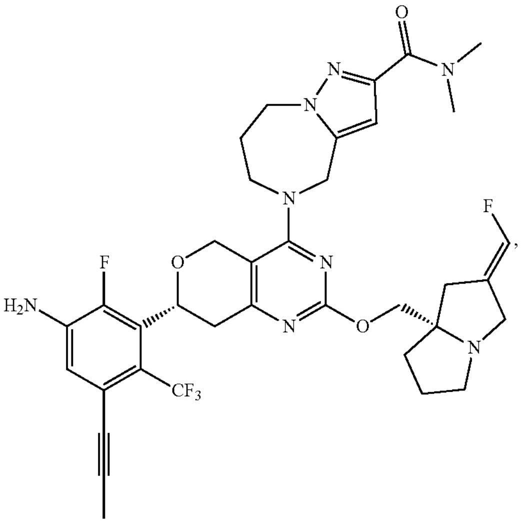
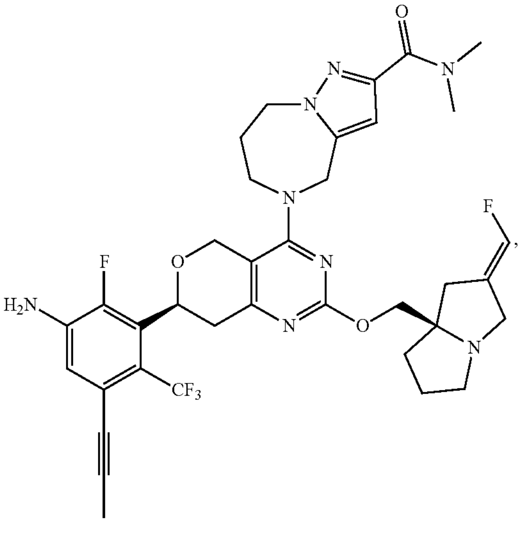
-continued
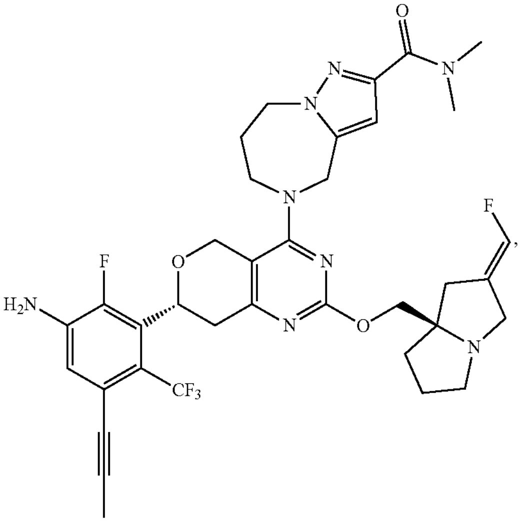
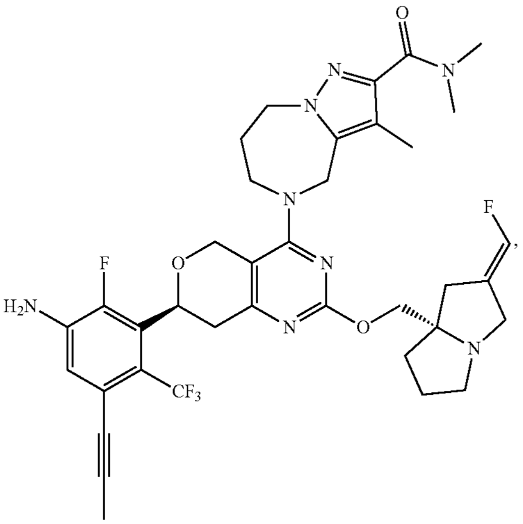
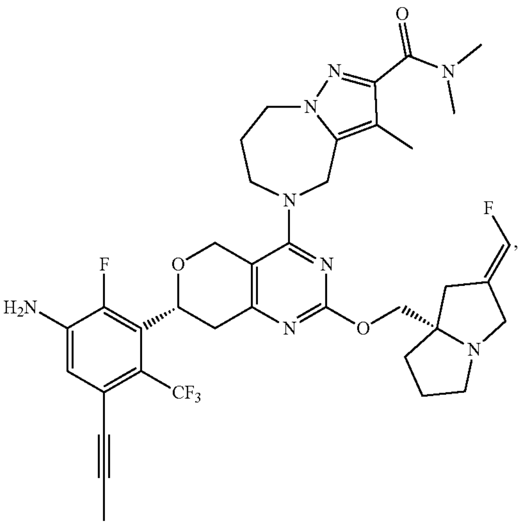

-continued
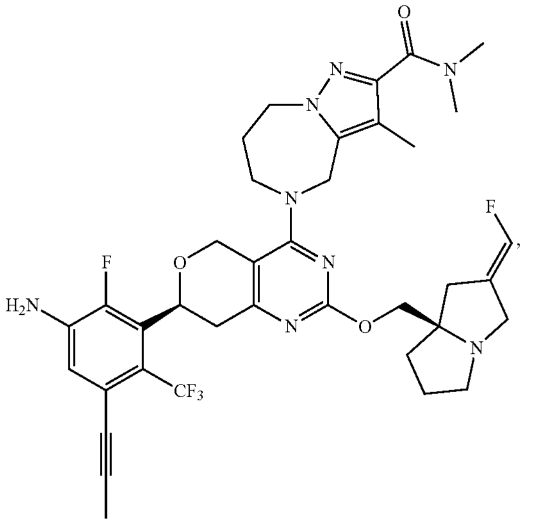
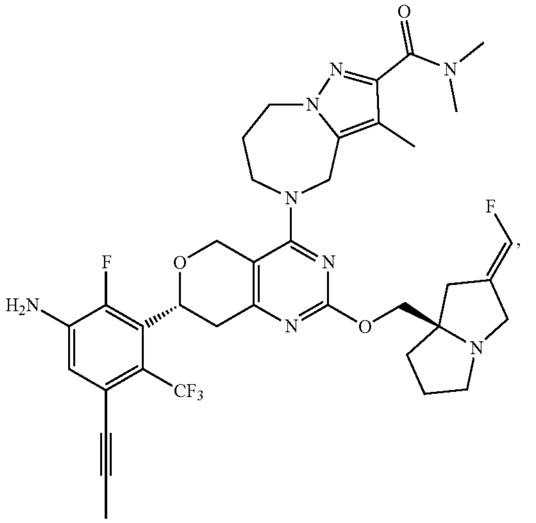
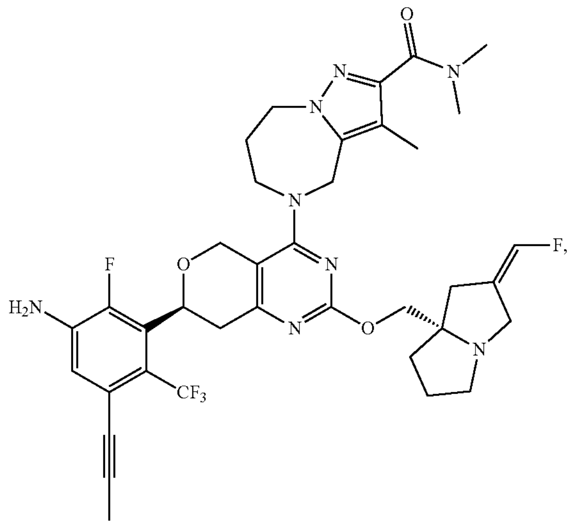
-continued
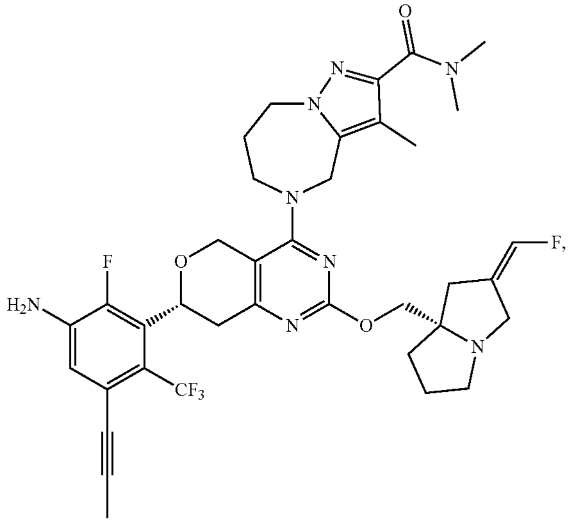
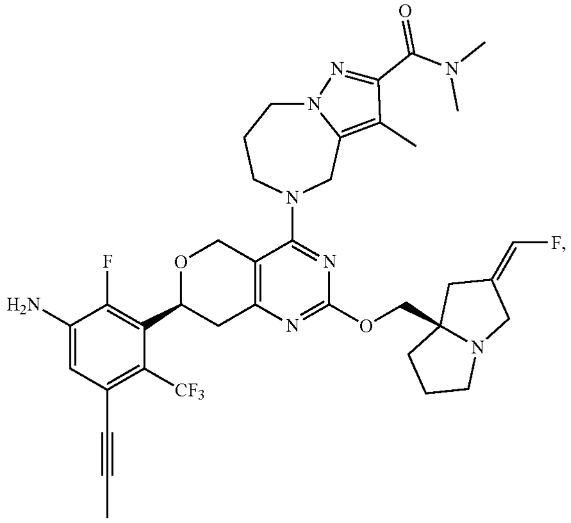
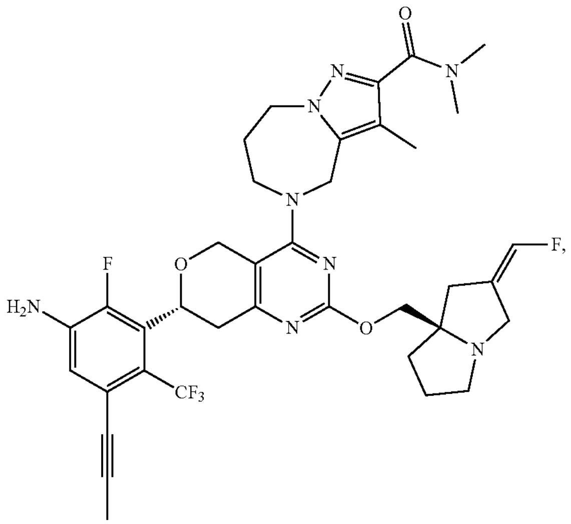

-continued
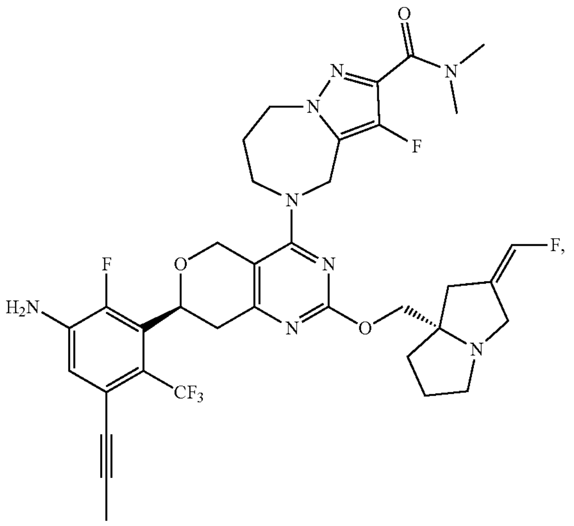
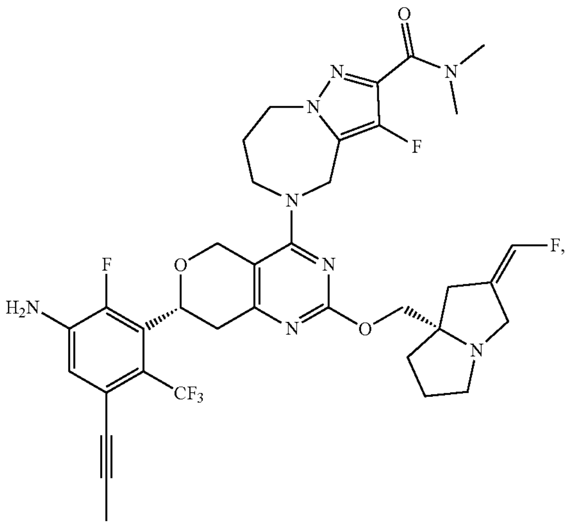
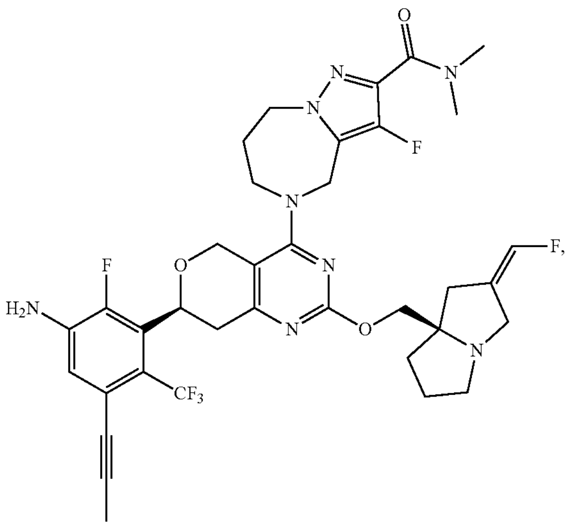
-continued
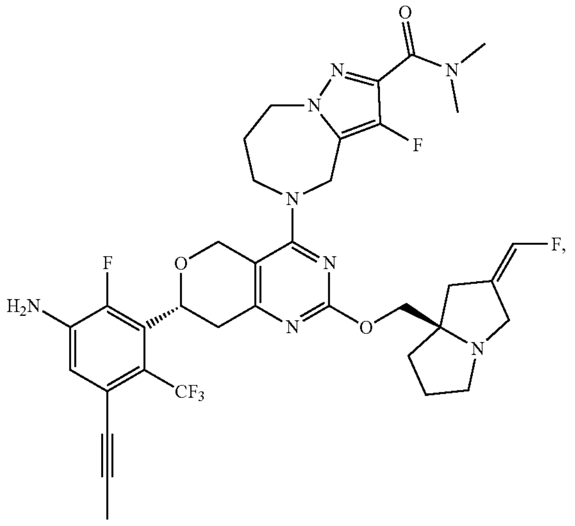
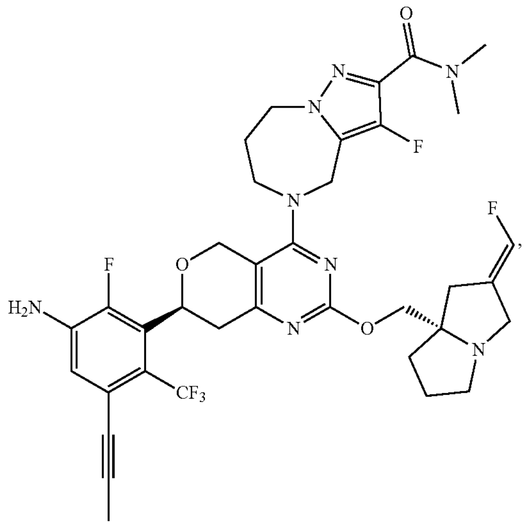
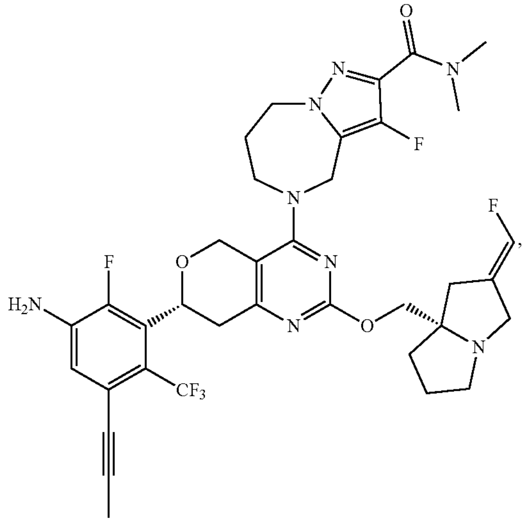

-continued
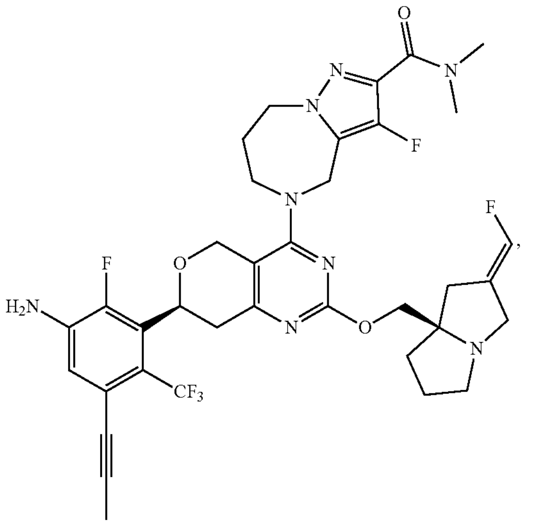
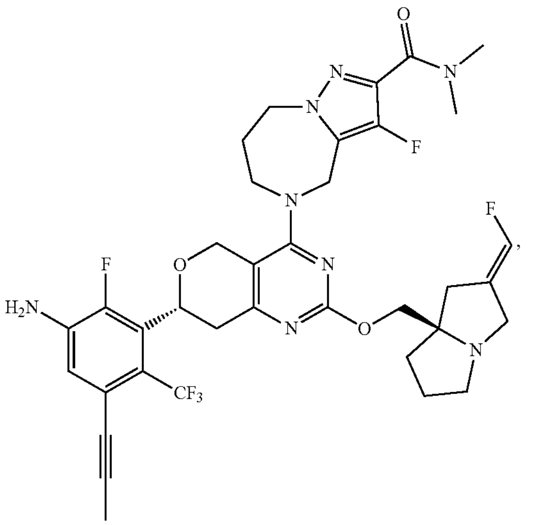
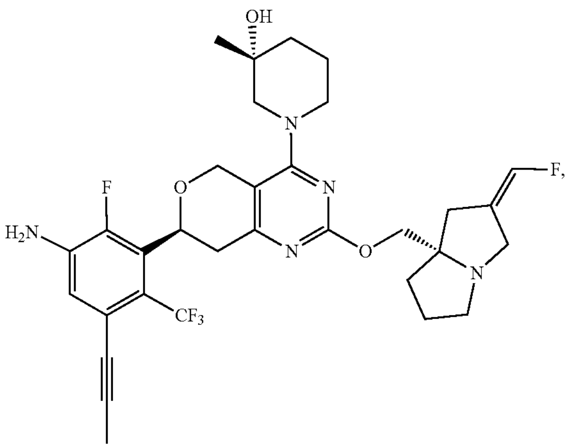
-continued
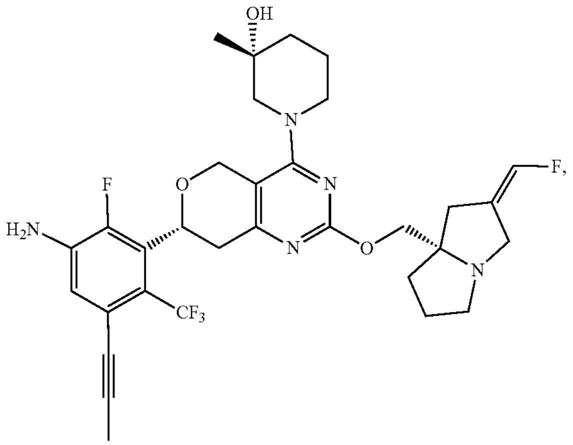
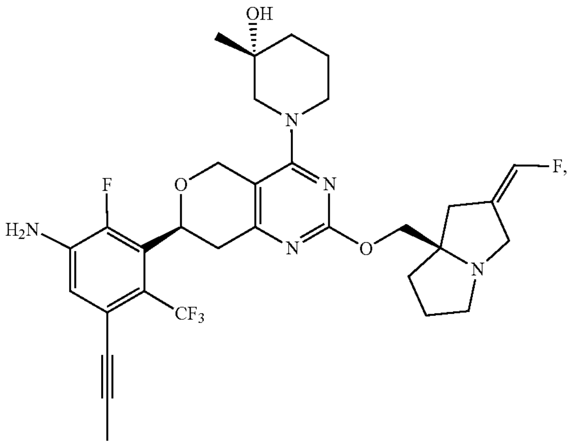
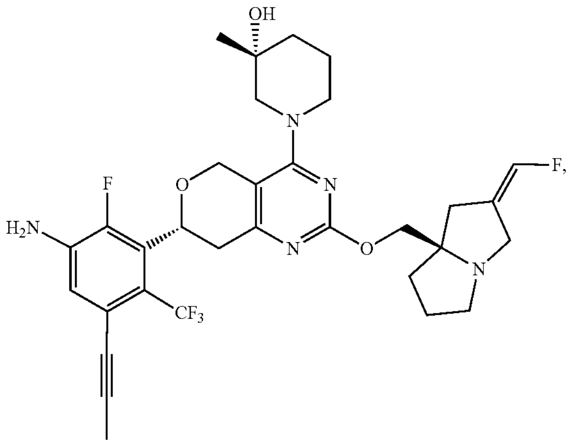

-continued
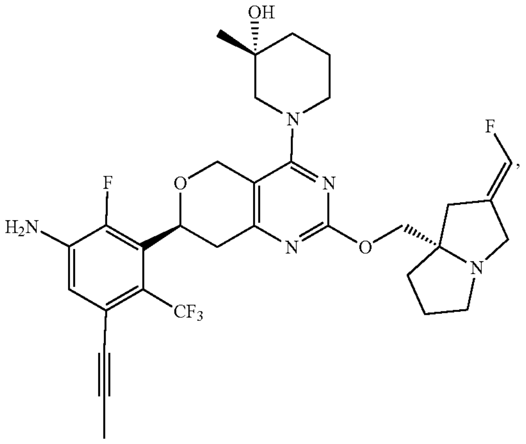
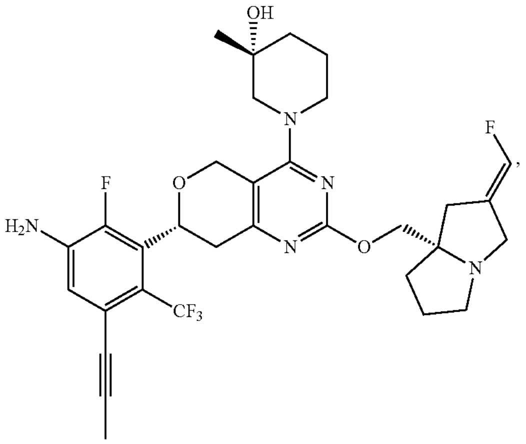
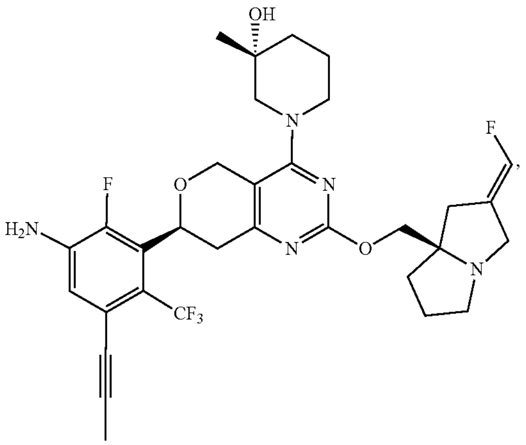
-continued
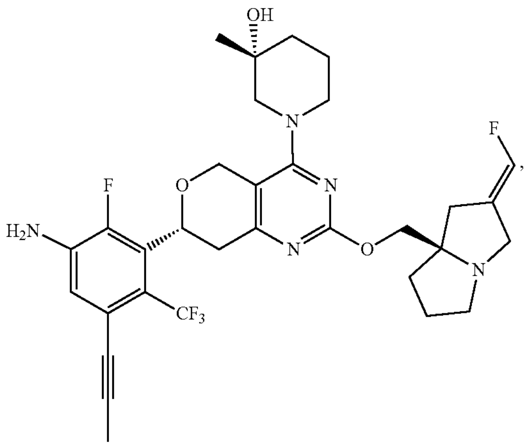
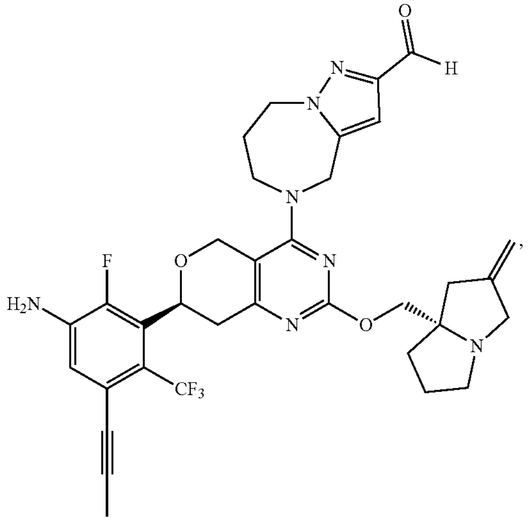
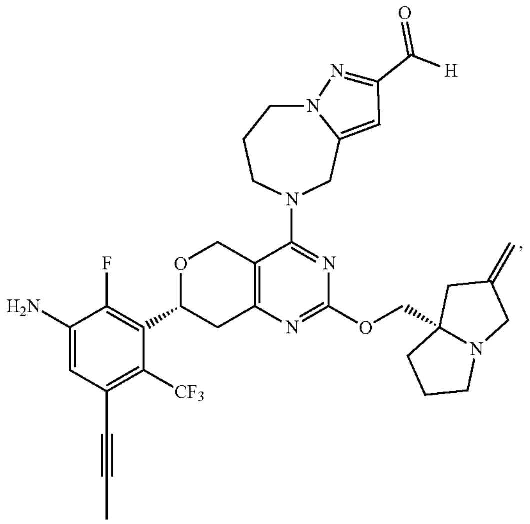

-continued
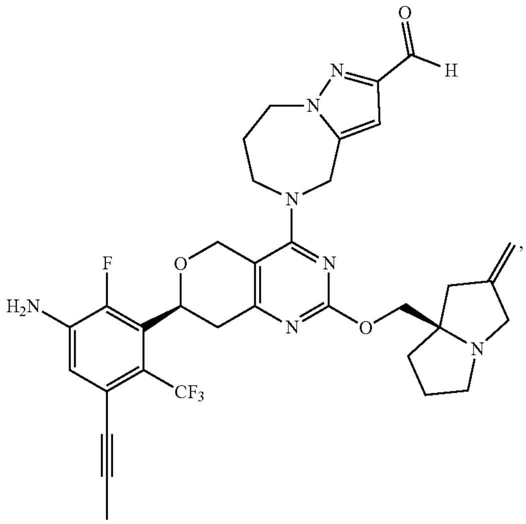
,
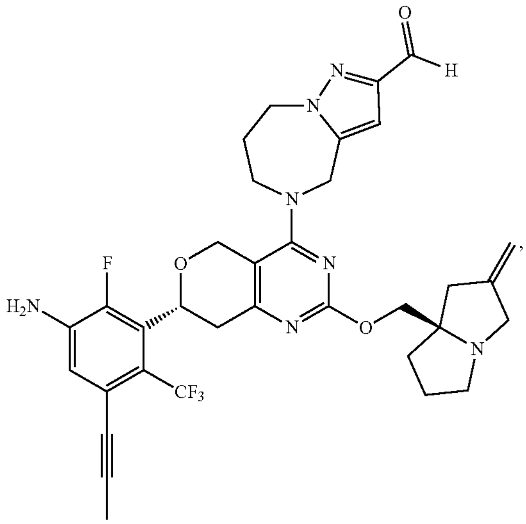
,
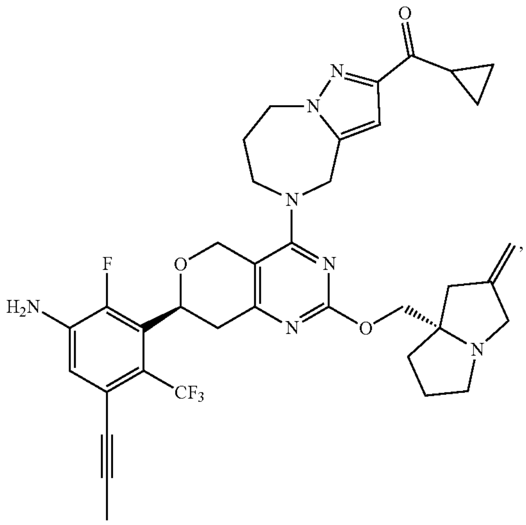
,
-continued
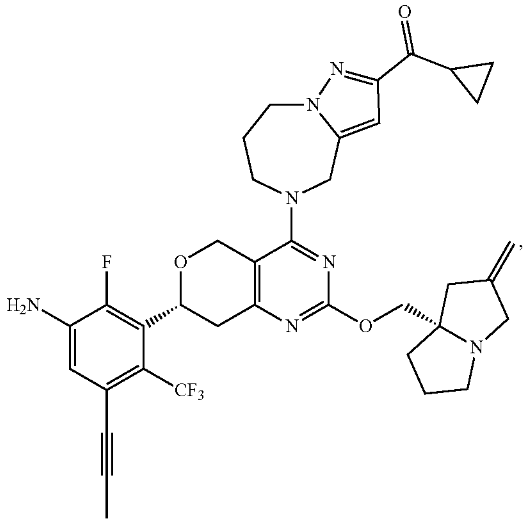
,
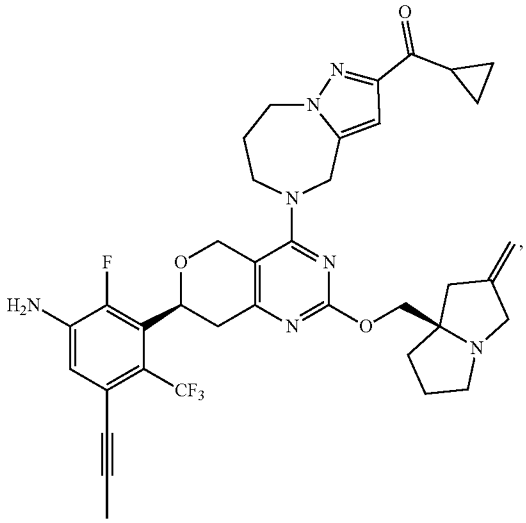
,
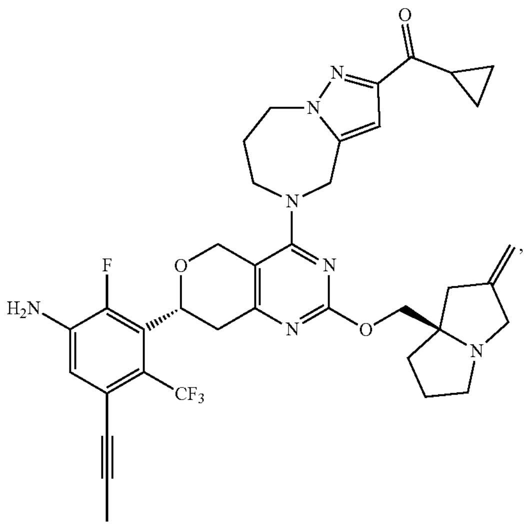
, -continued
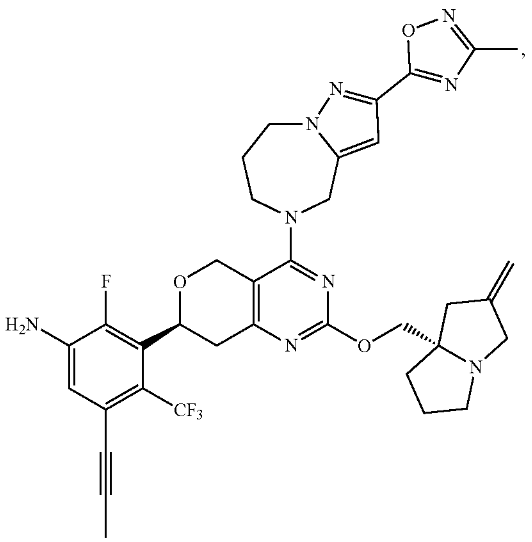
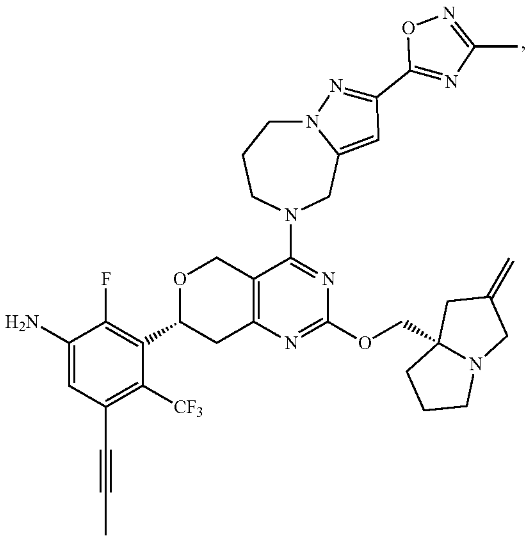
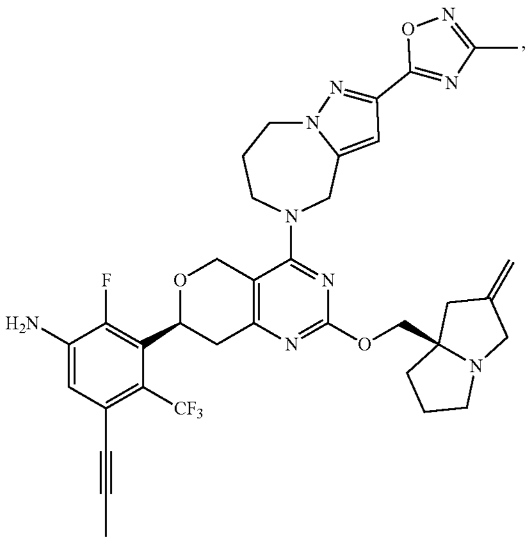
-continued
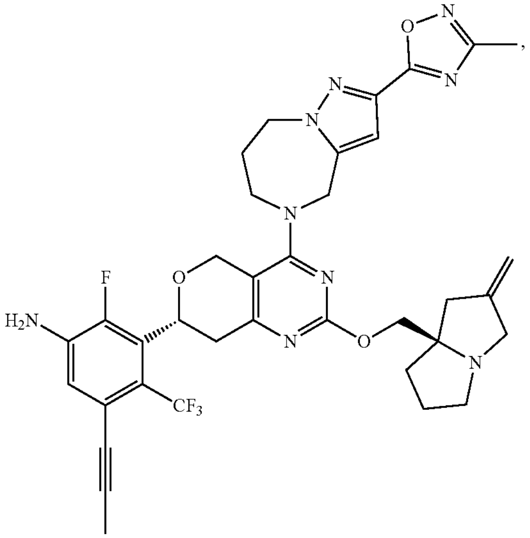
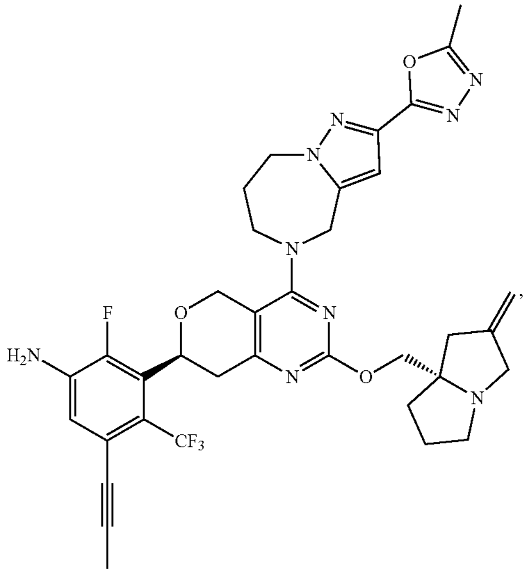
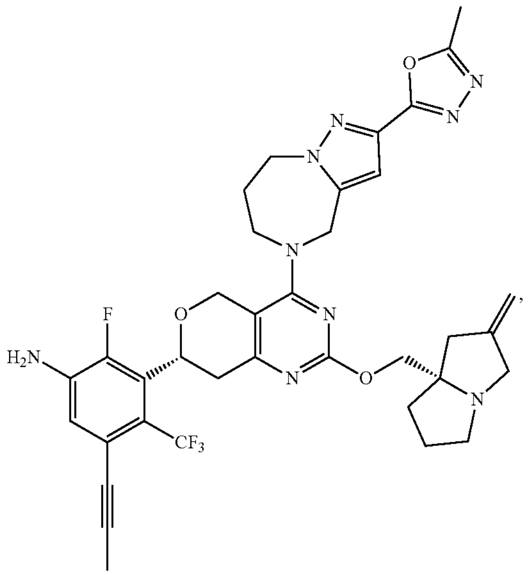

-continued
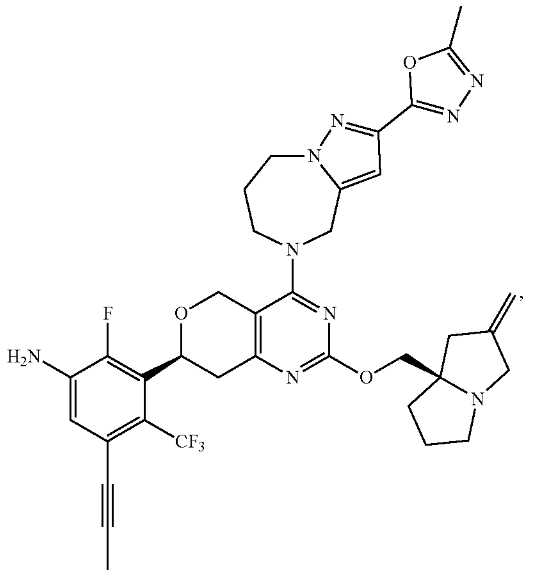
,
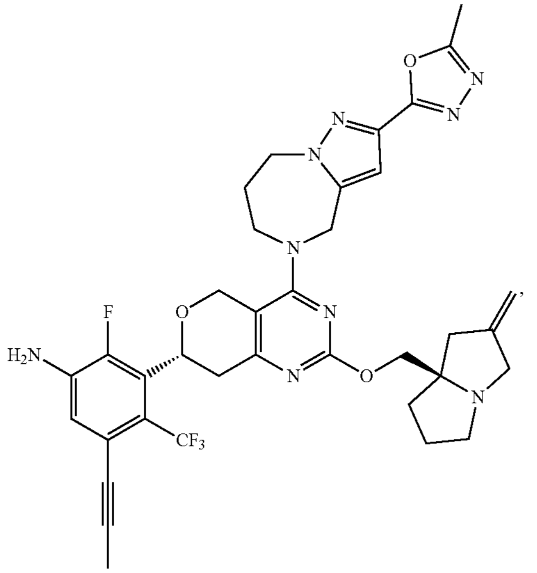
,
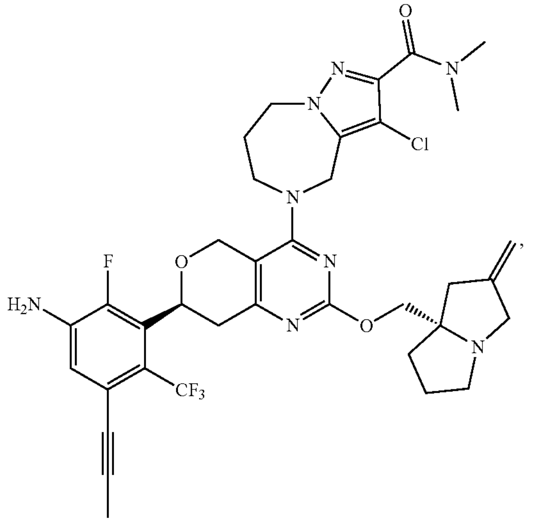
,
-continued
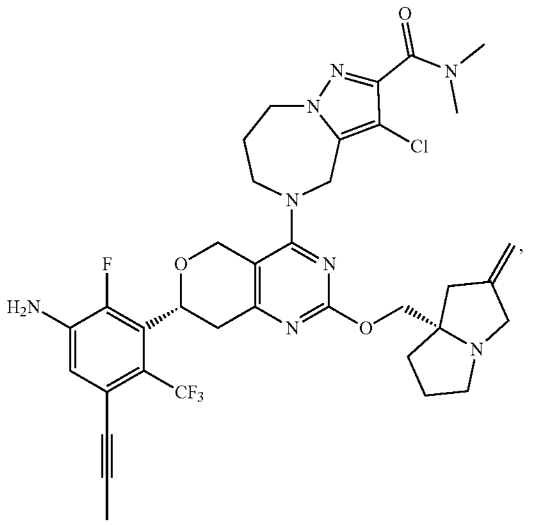
,
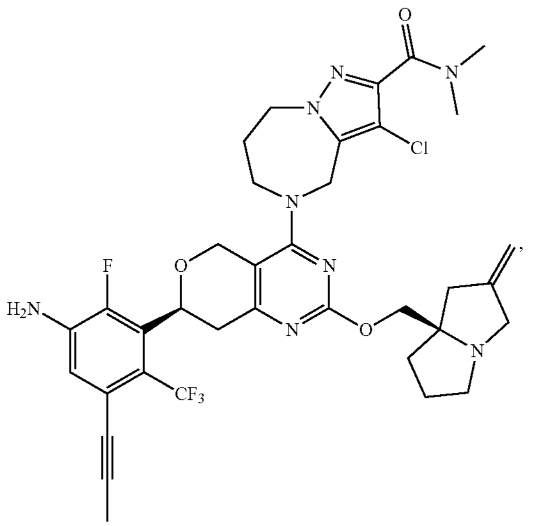
,
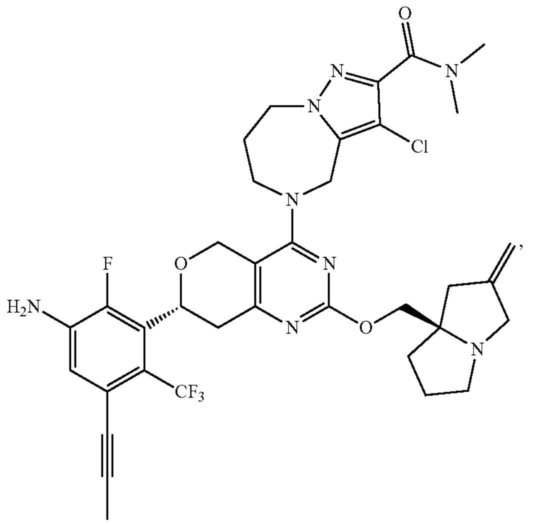
, -continued
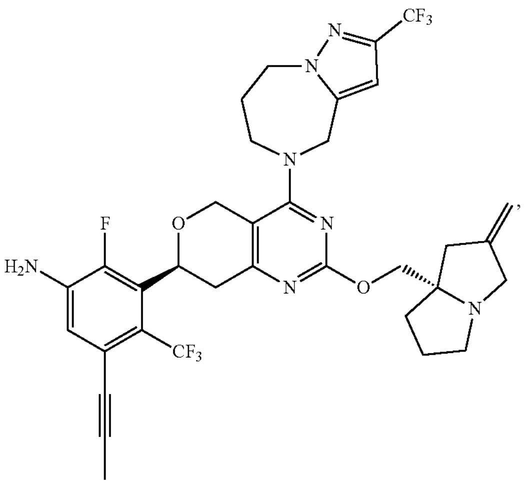
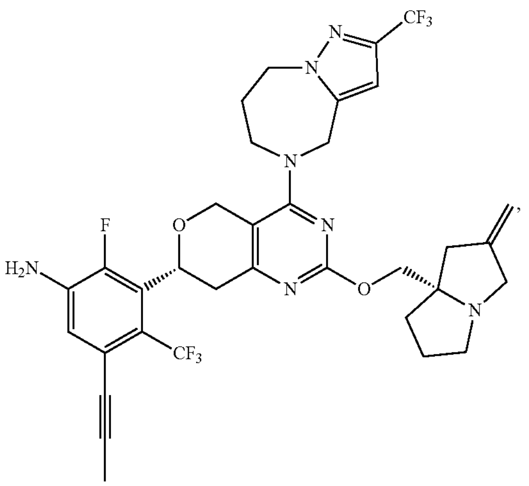
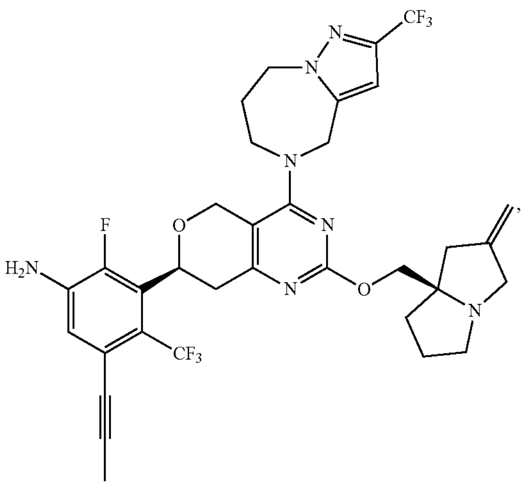
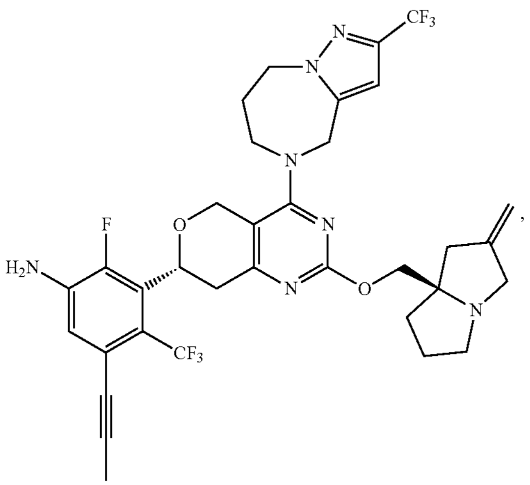
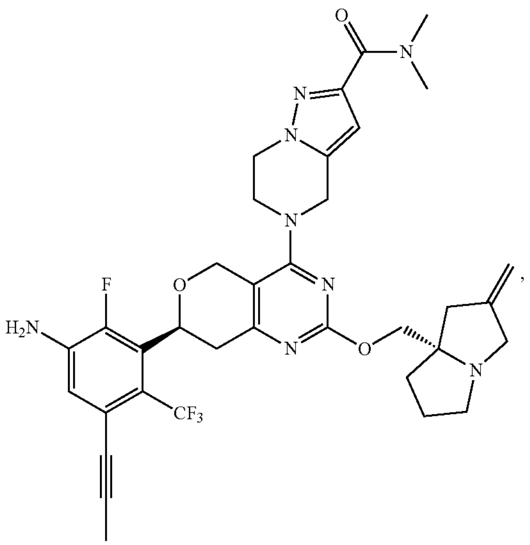
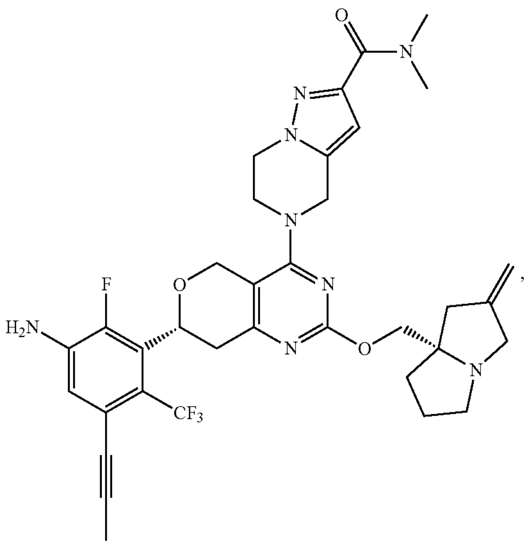

-continued
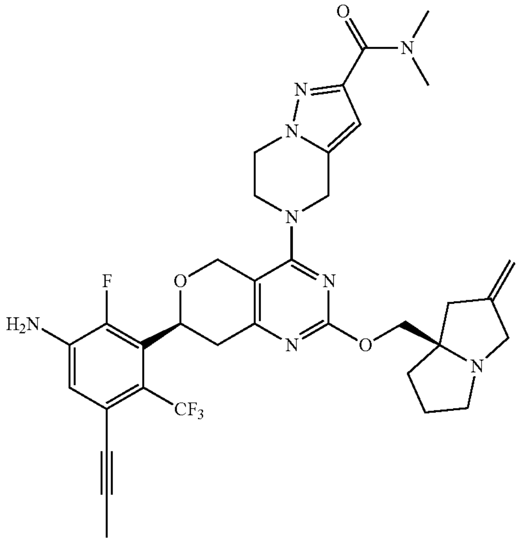
,
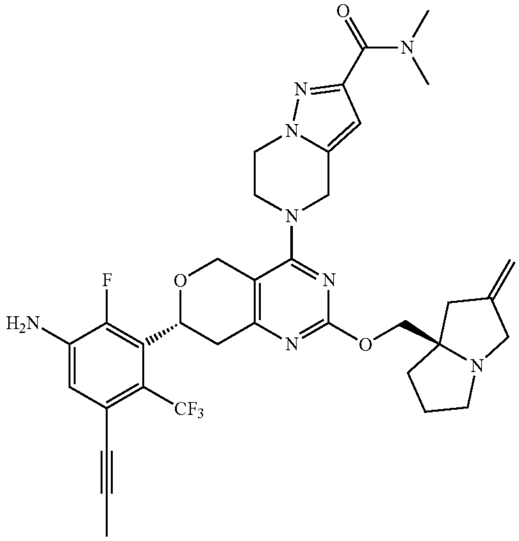
,
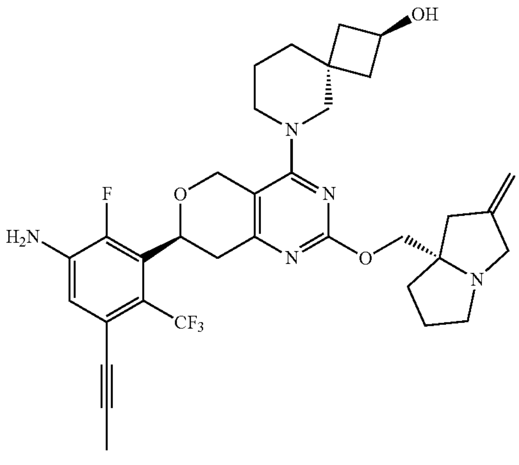
,
-continued
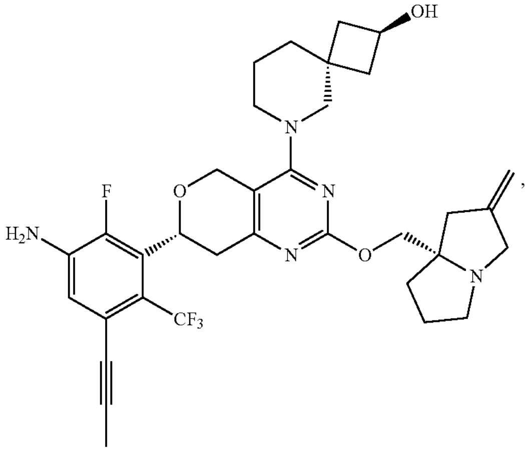
,
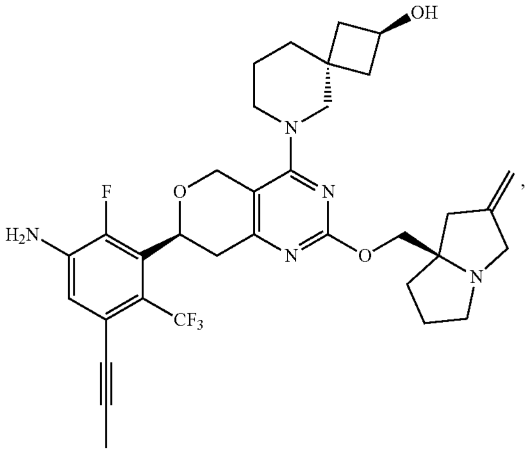
,
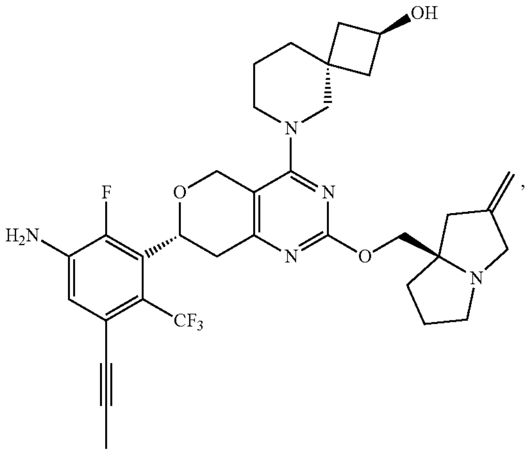
, -continued
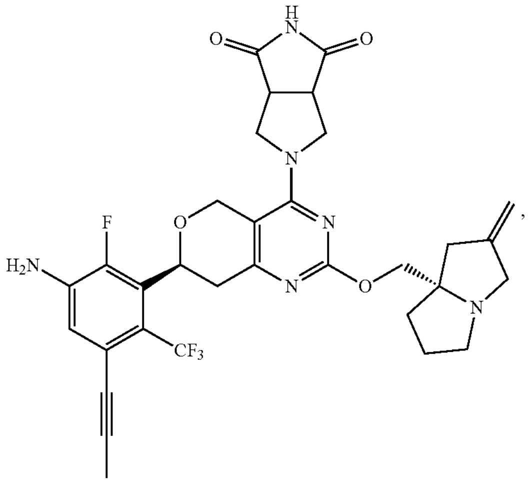
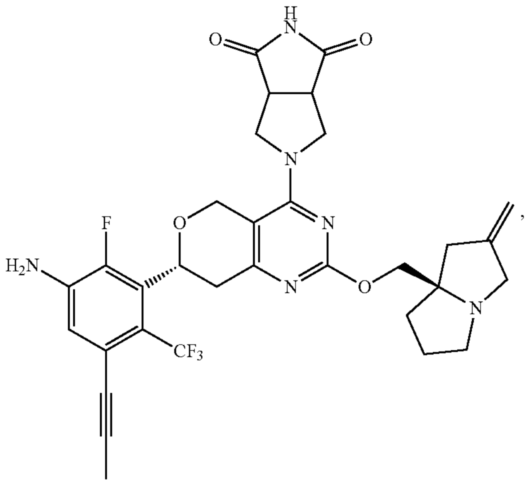
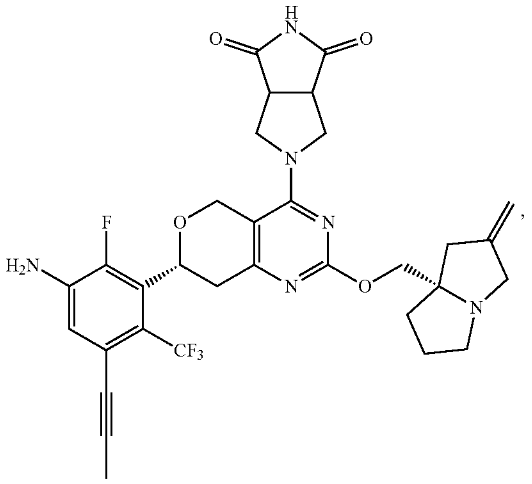
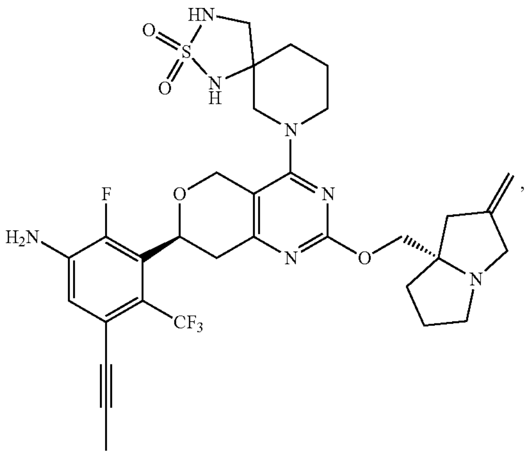
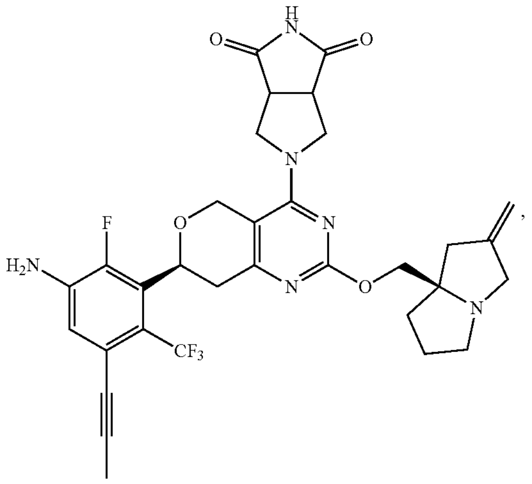
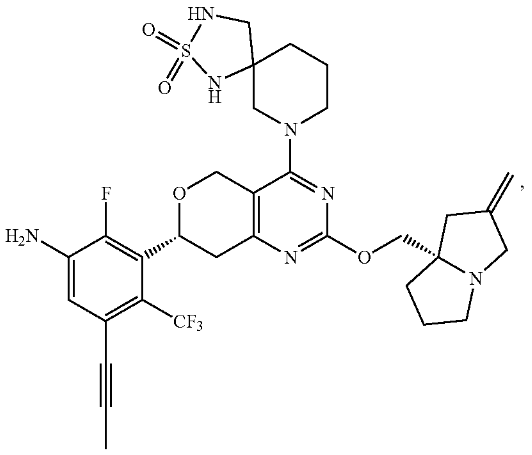

-continued
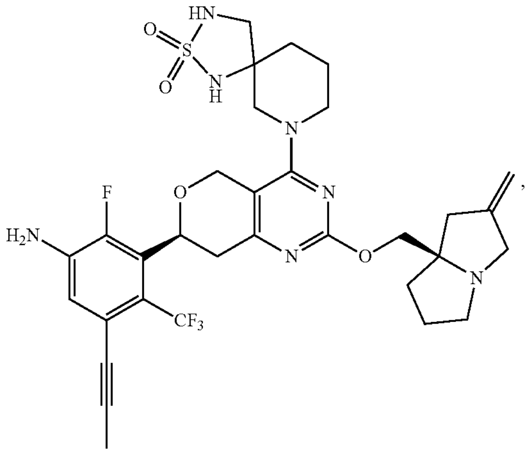
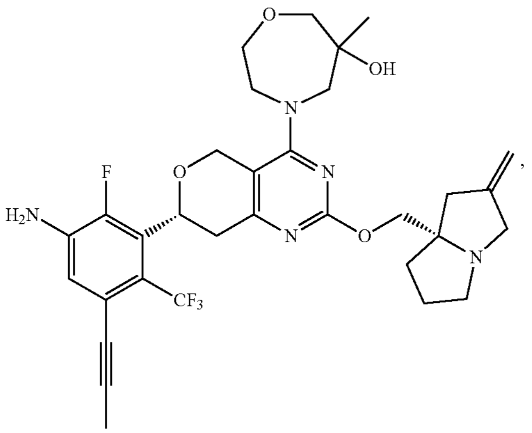
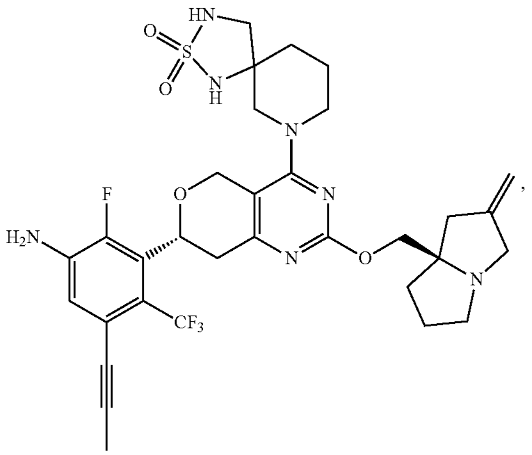
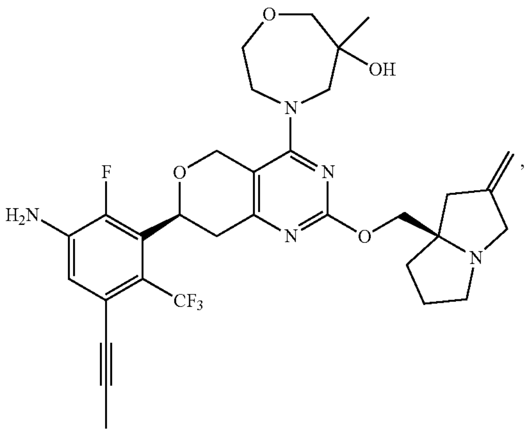
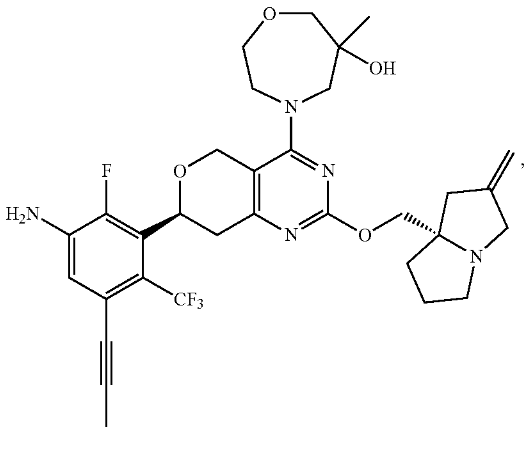
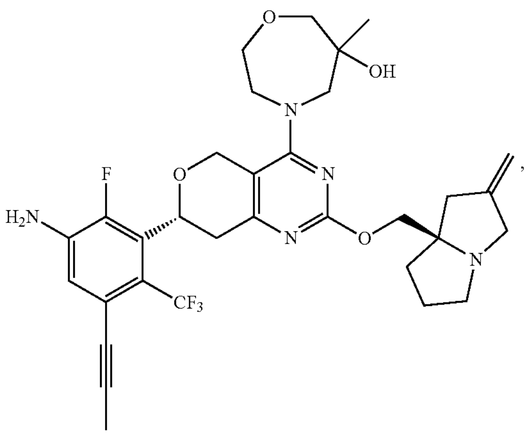
-continued -continued
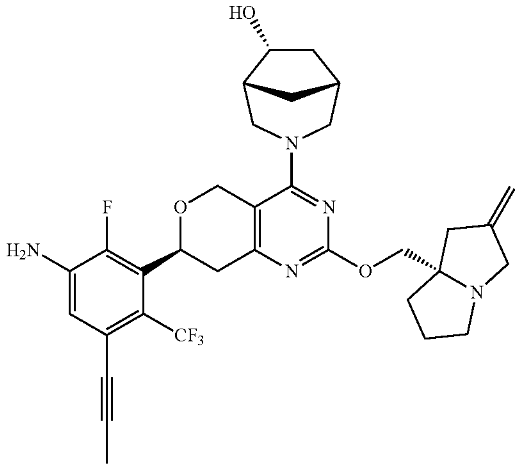
,
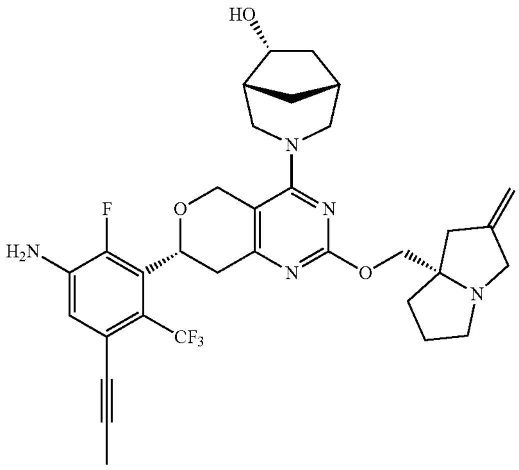
,
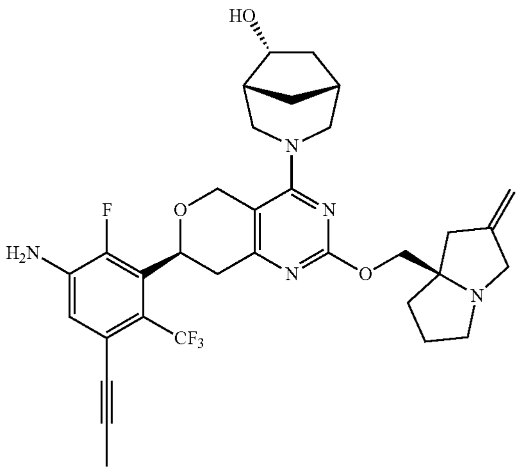
,
-continued
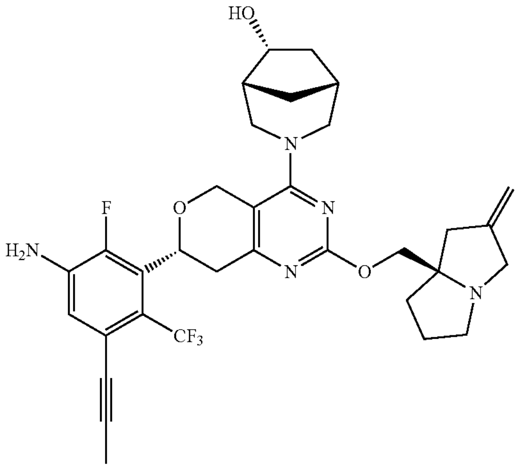
,
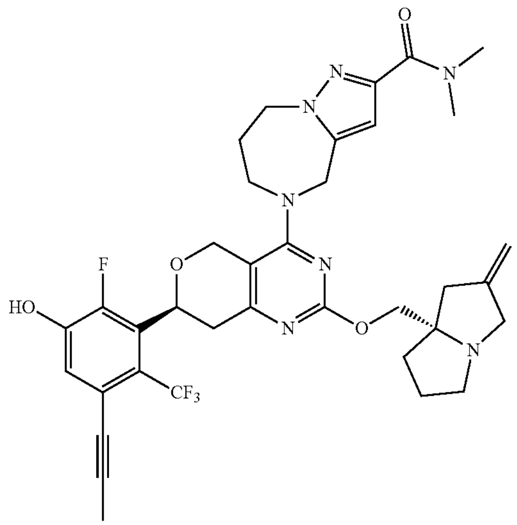
,
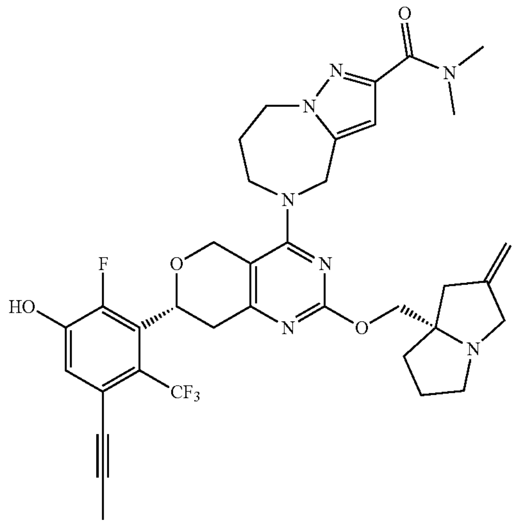
, -continued
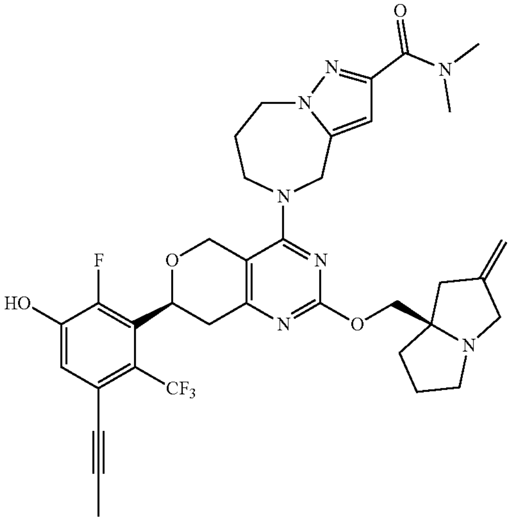
,
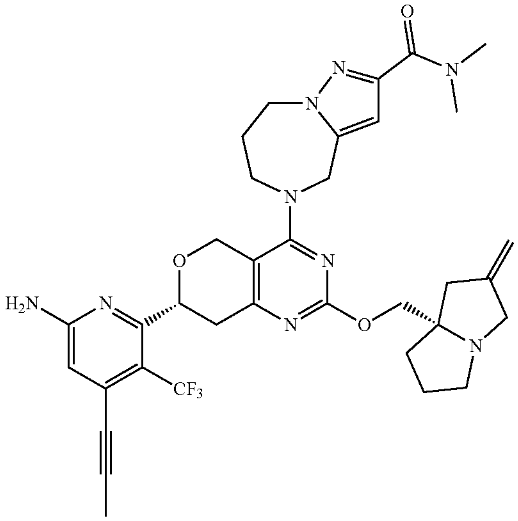
,
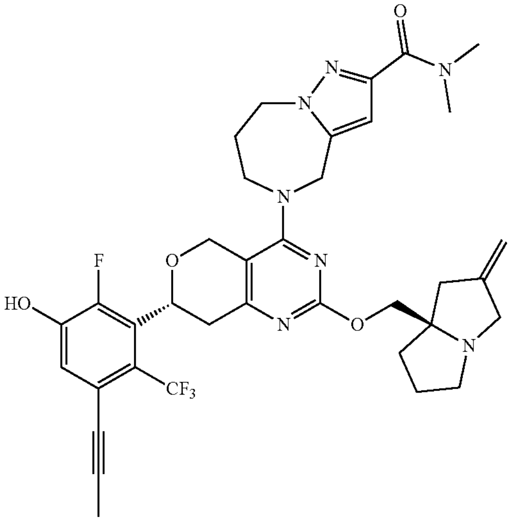
,
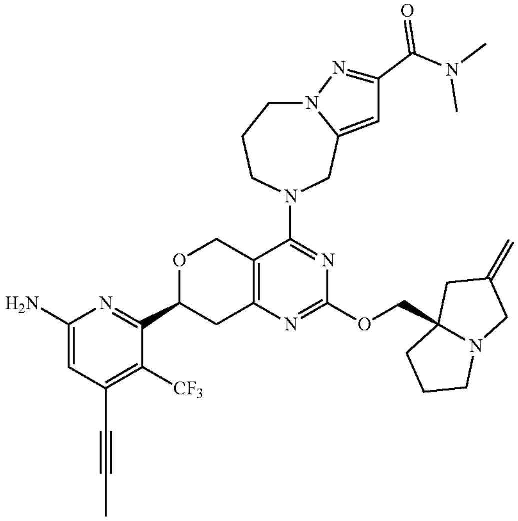
,
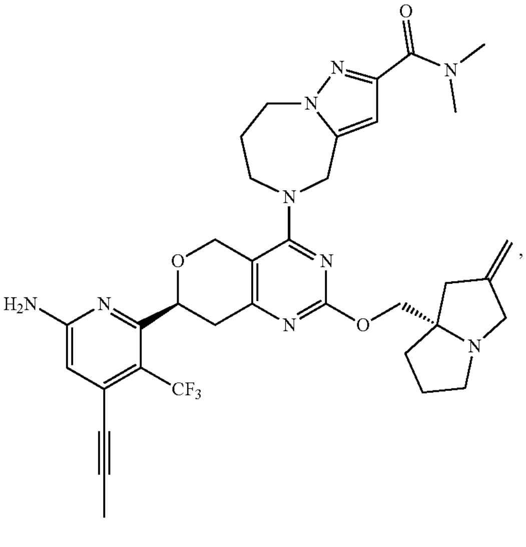
,
-continued
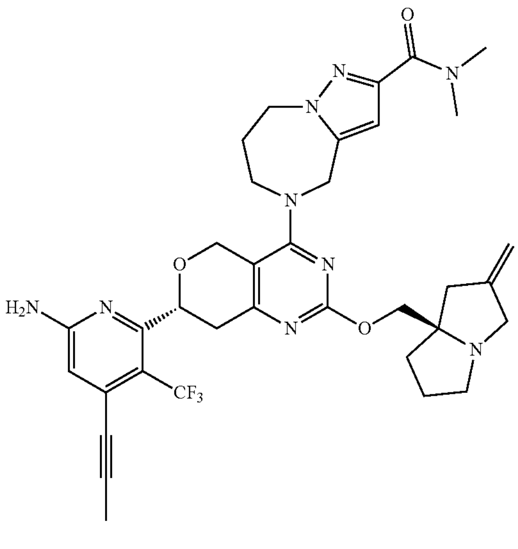
, -continued
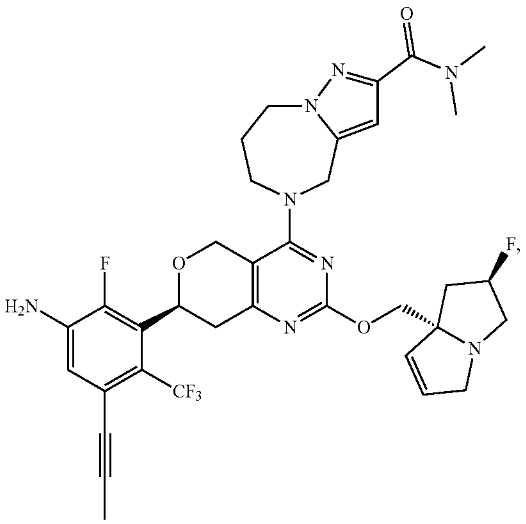
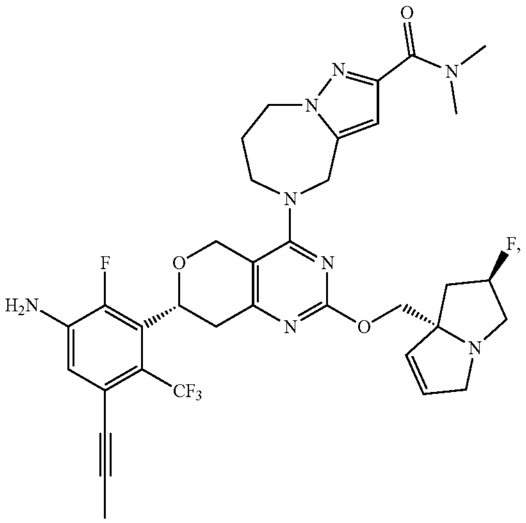
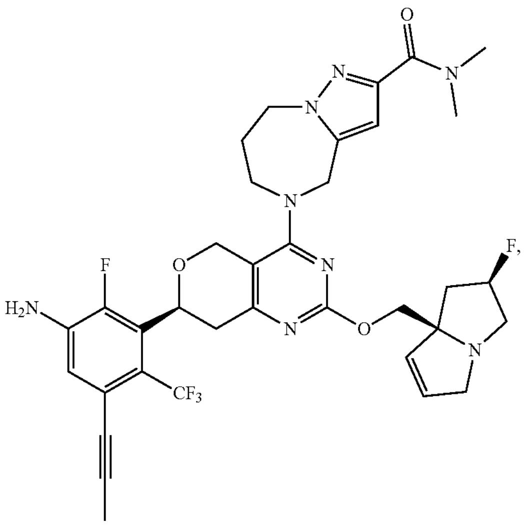
-continued
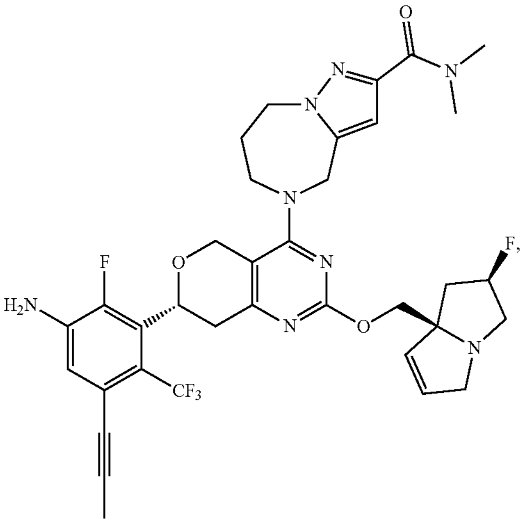
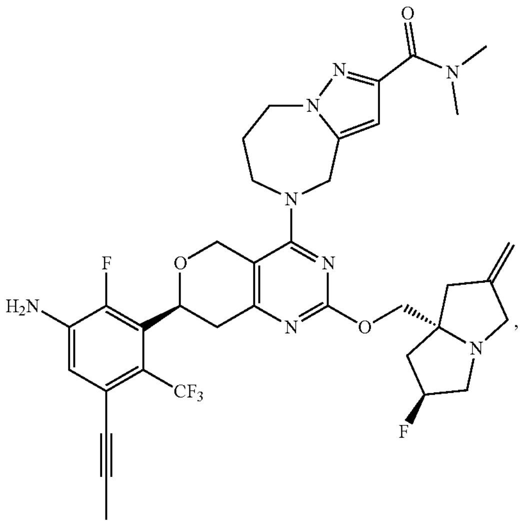
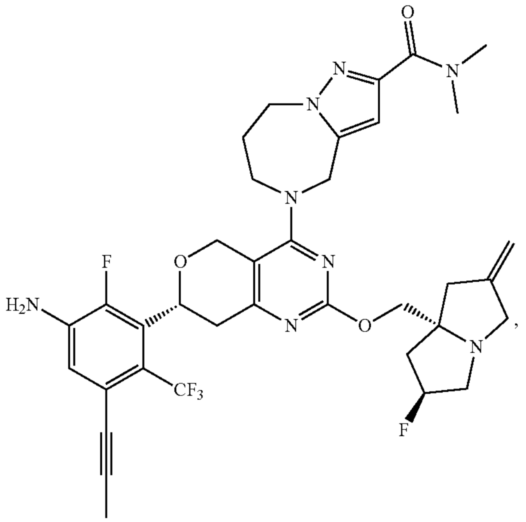

-continued
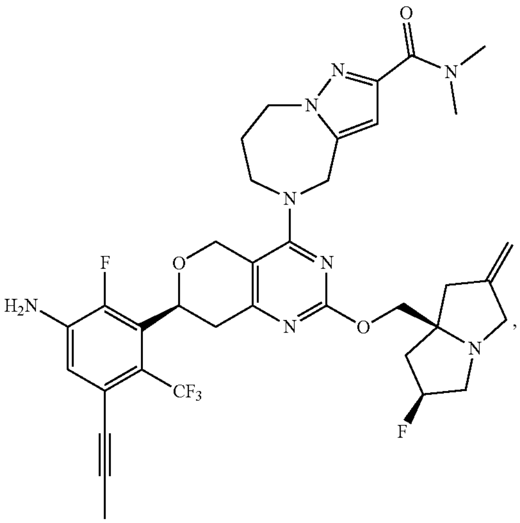
,
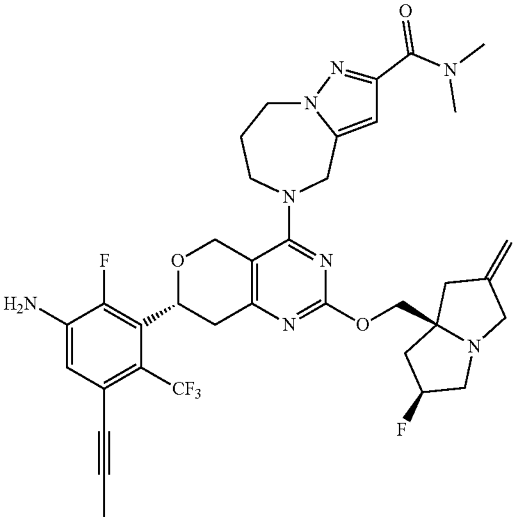
,
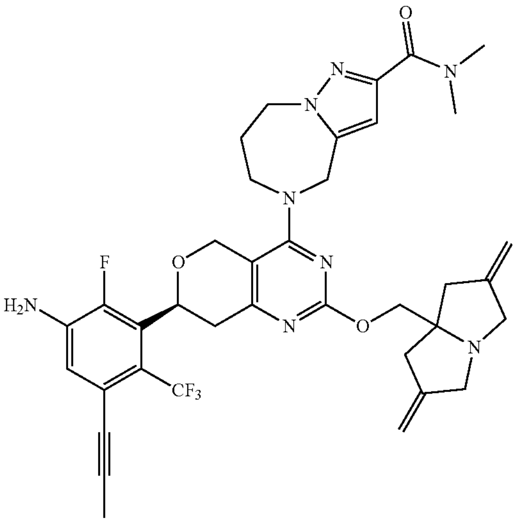
,
-continued
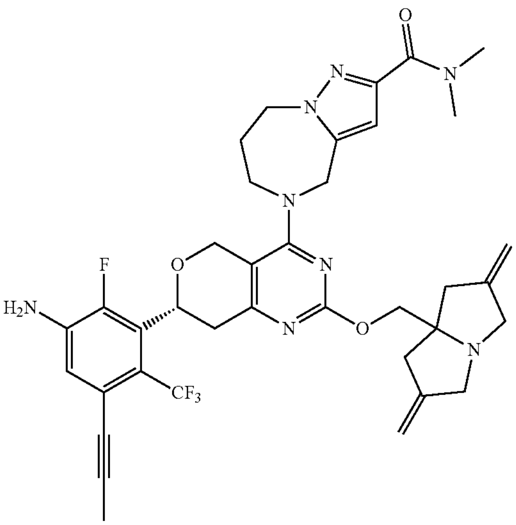
,
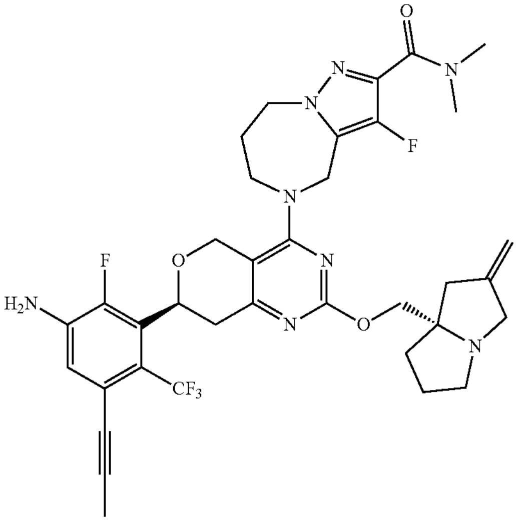
,
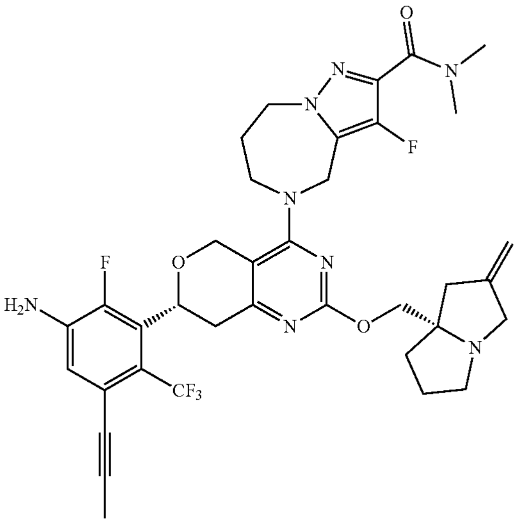
, -continued
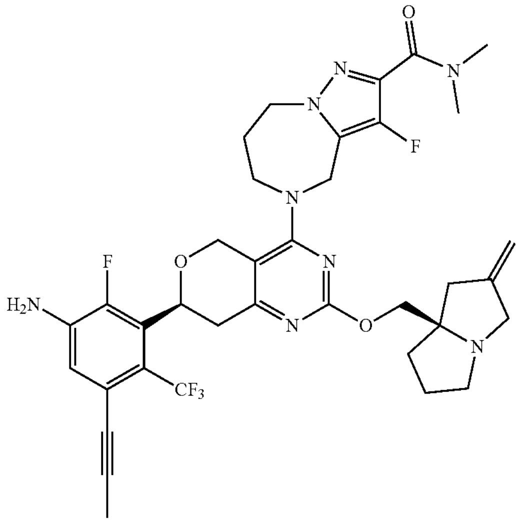
,
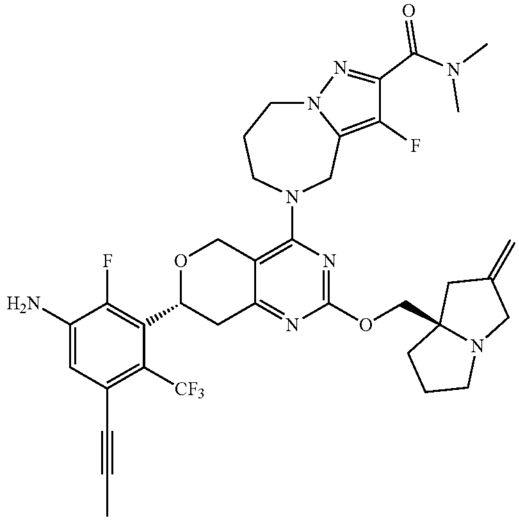
,
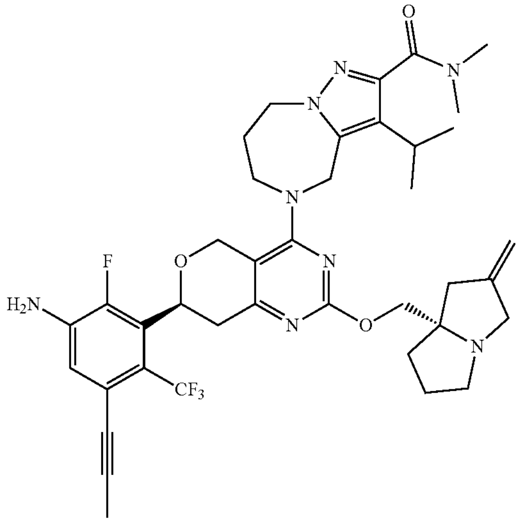
,
-continued
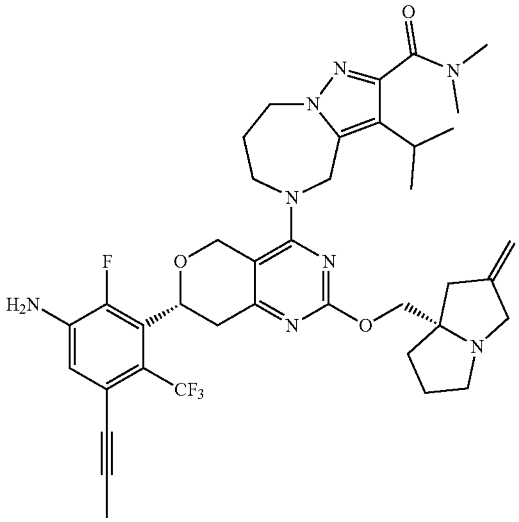
,
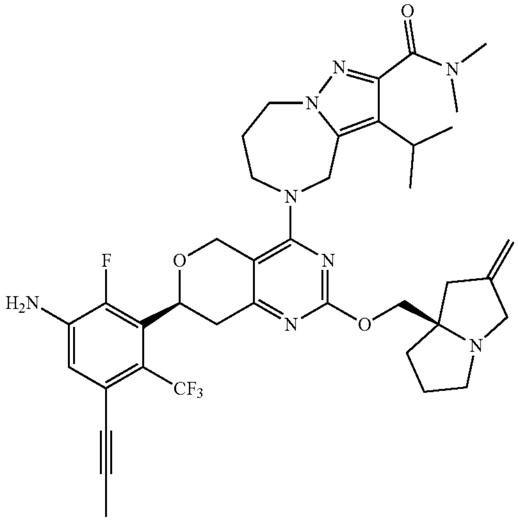
,
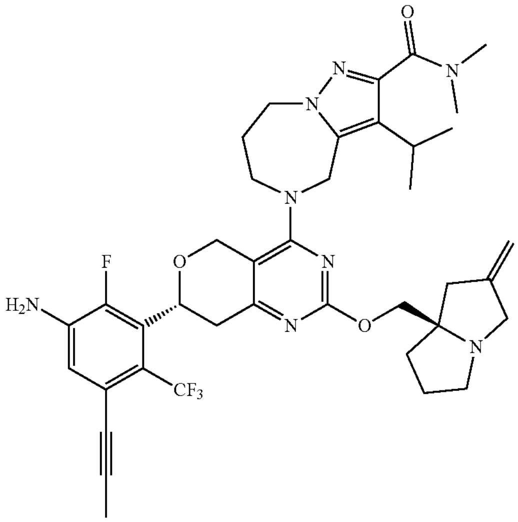
, -continued
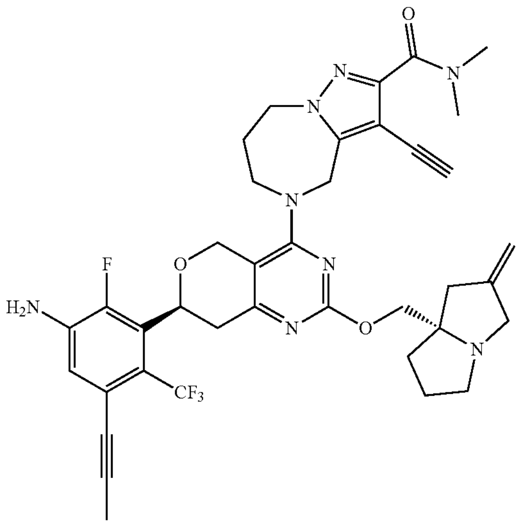
,
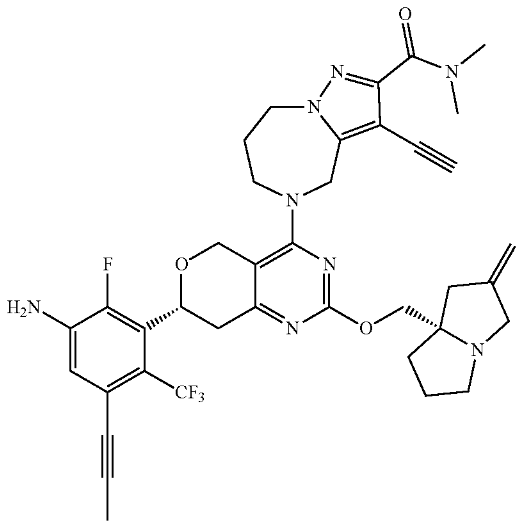
,
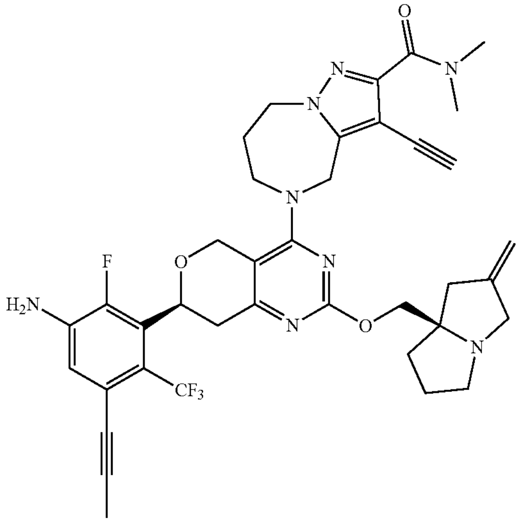
,
-continued
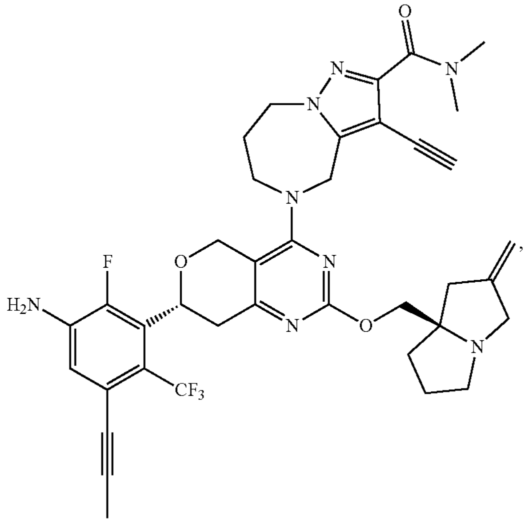
,
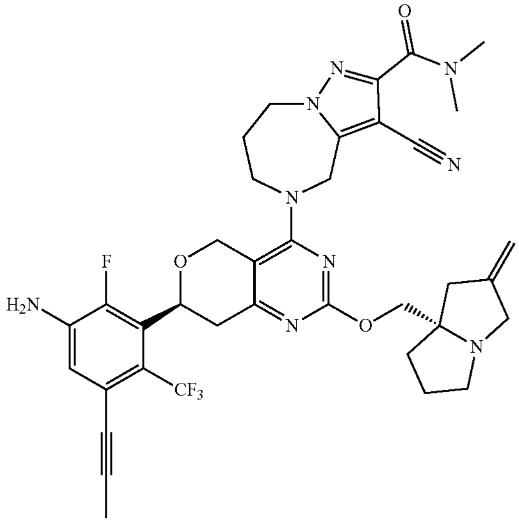
,
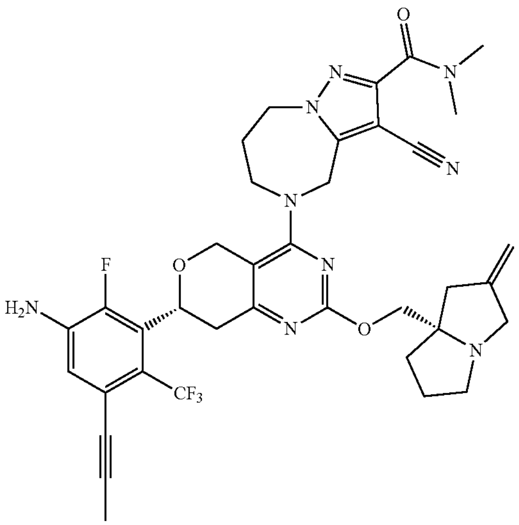
, -continued
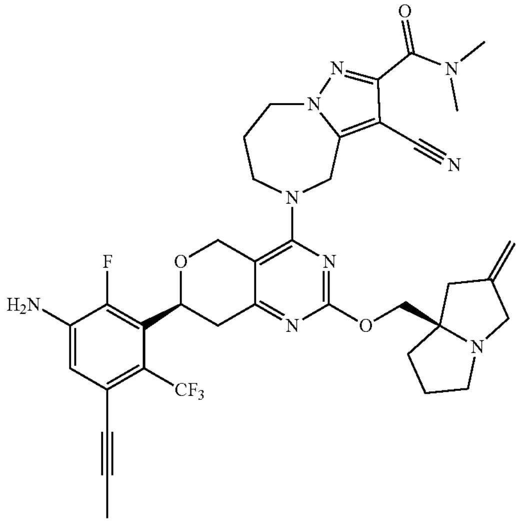
,
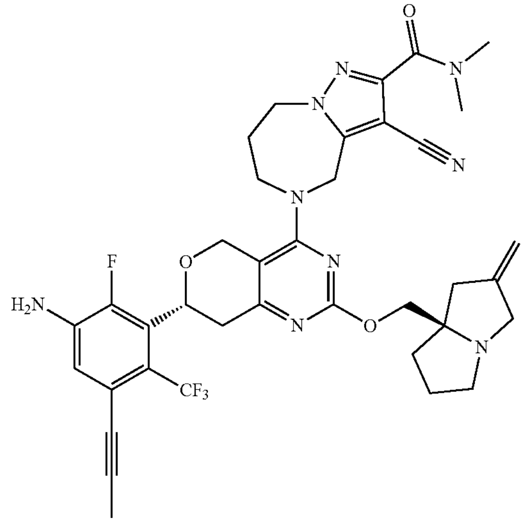
,
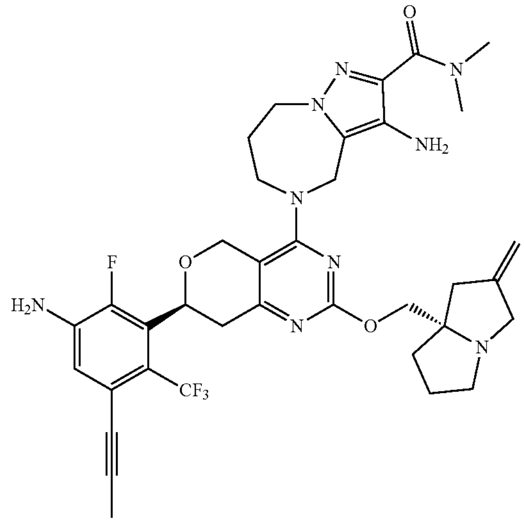
,
-continued
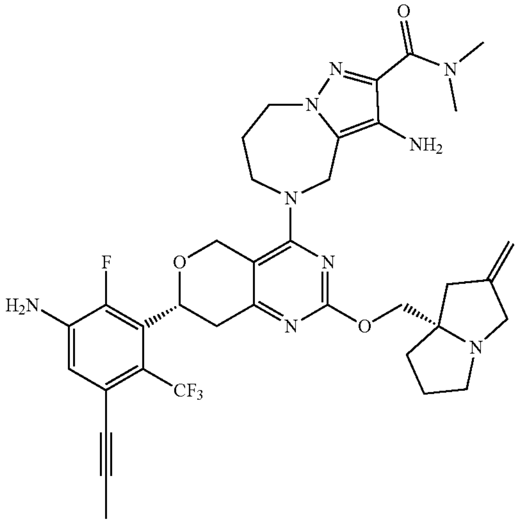
,
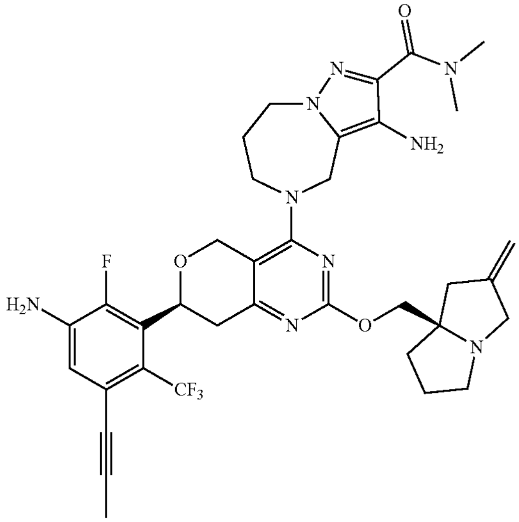
,
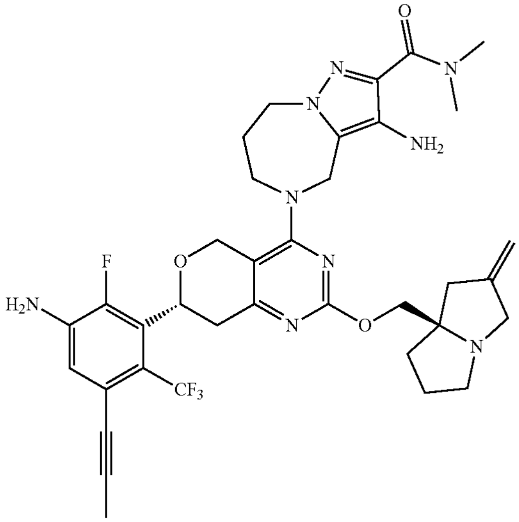
, -continued
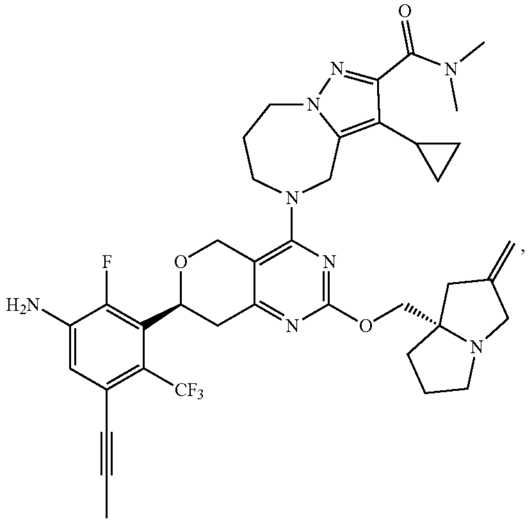
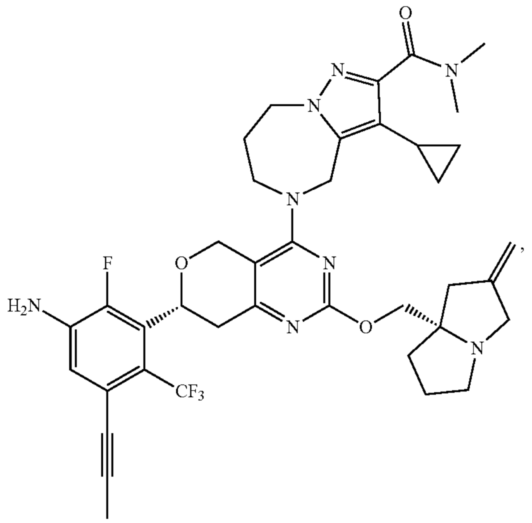
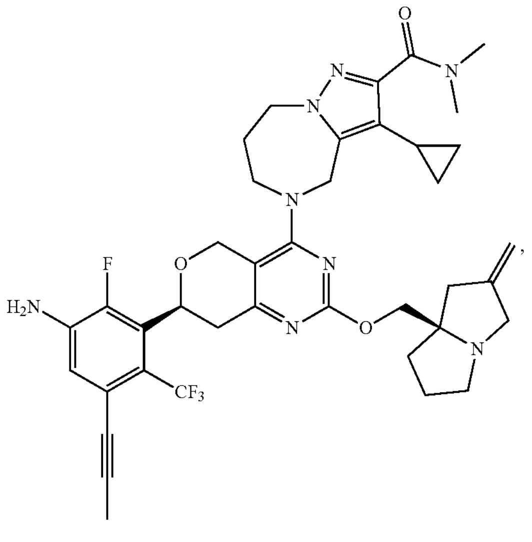
-continued
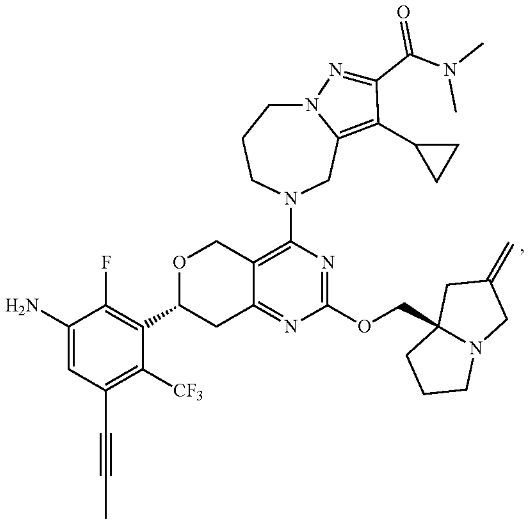
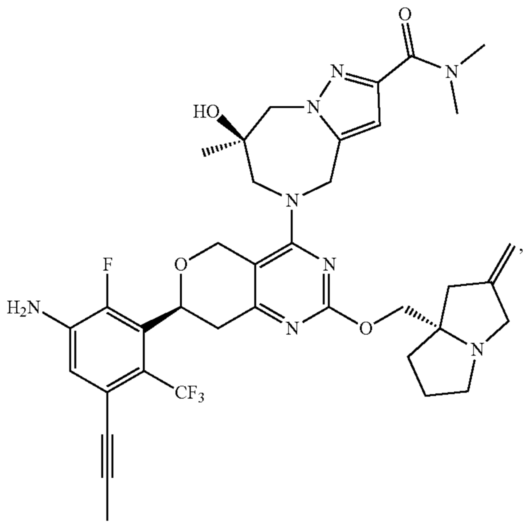
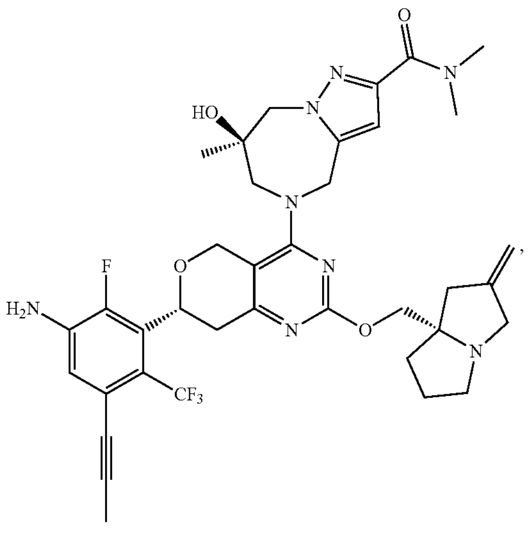

-continued
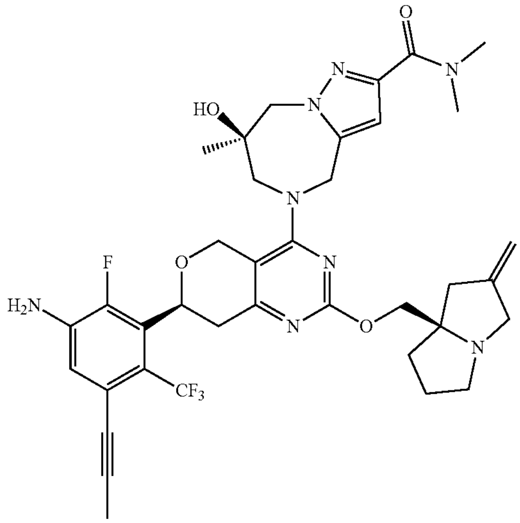
,
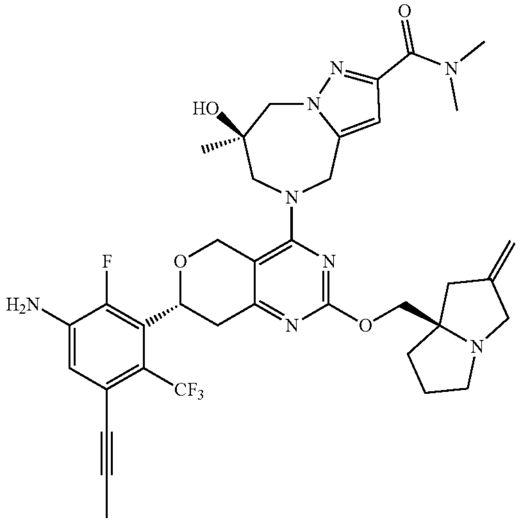
,
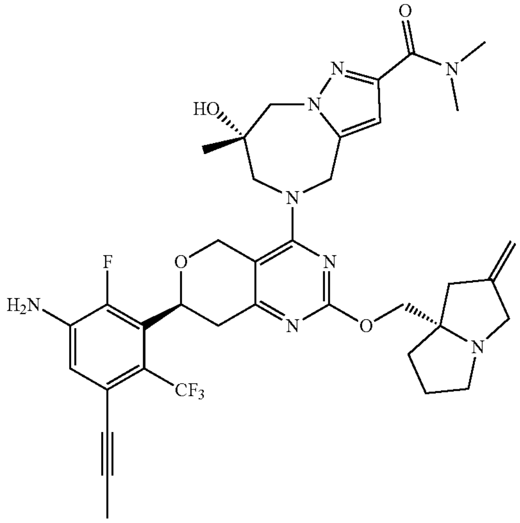
,
-continued
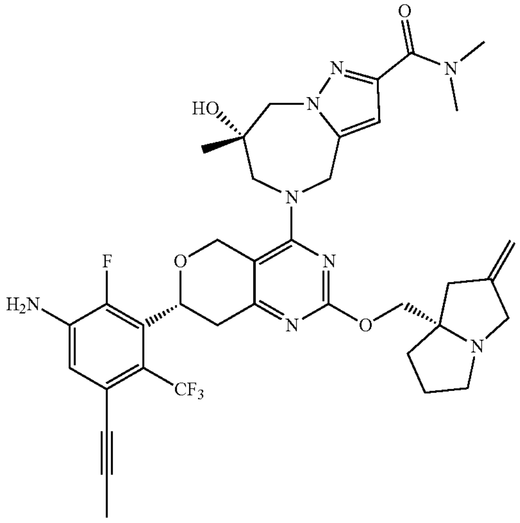
,
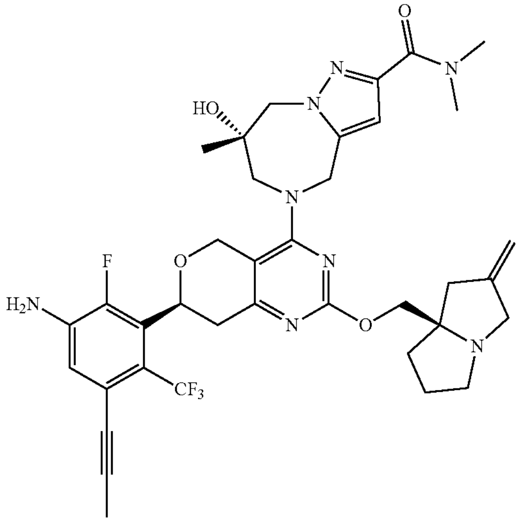
,
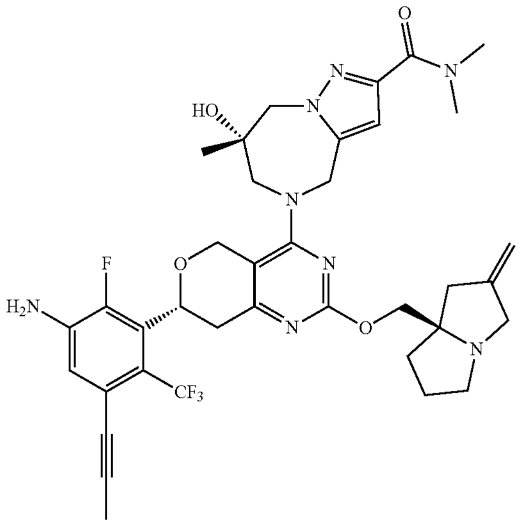
, -continued
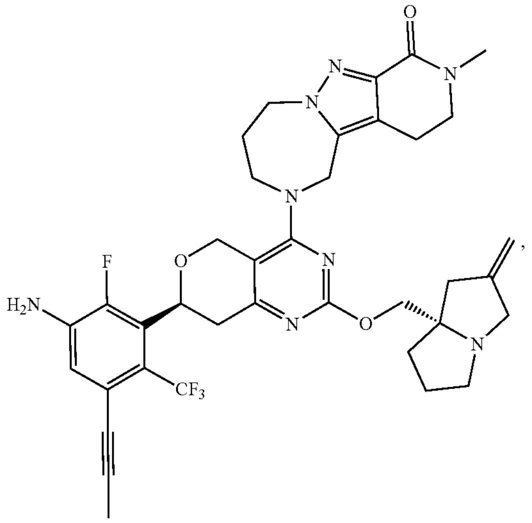
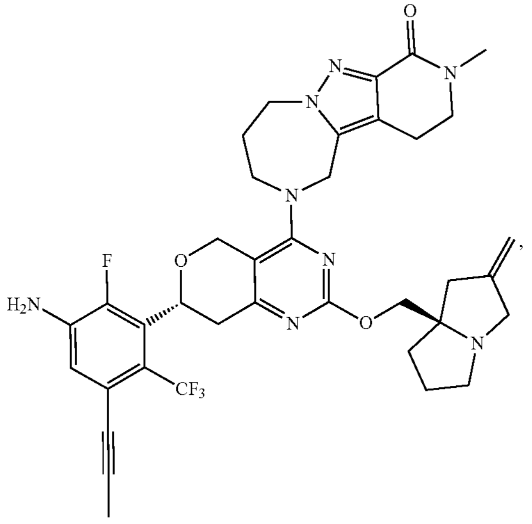
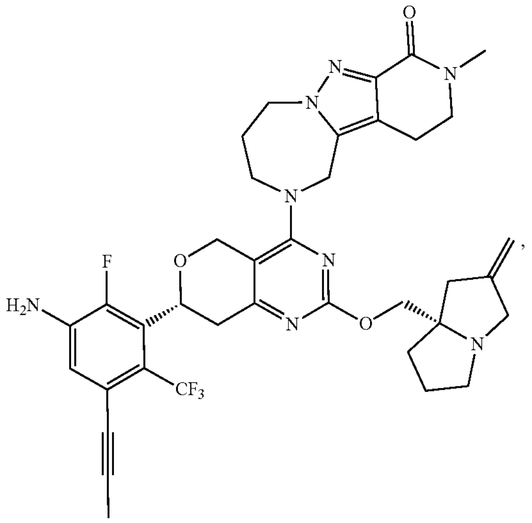
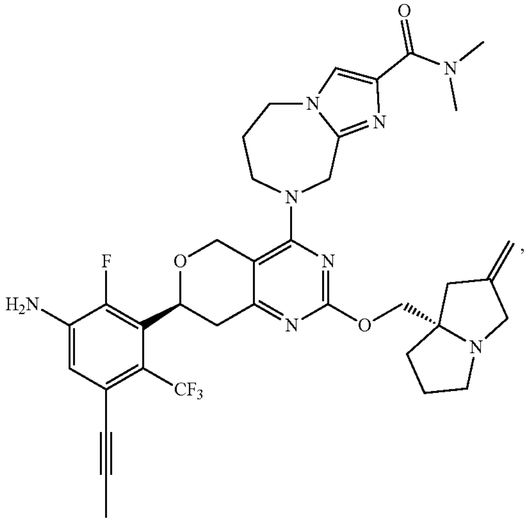
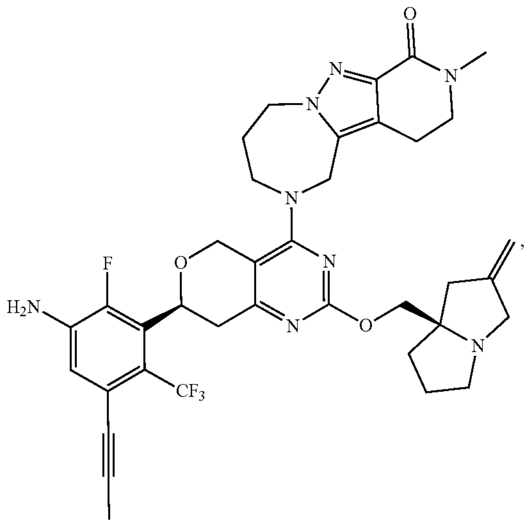
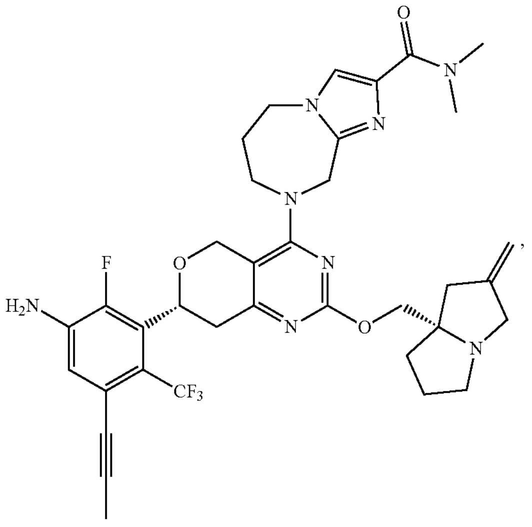

-continued
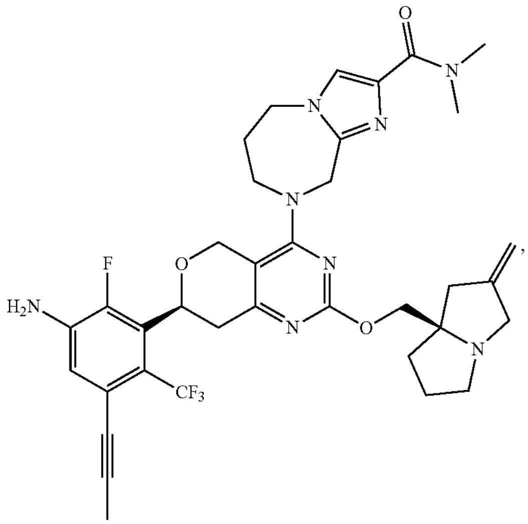
,
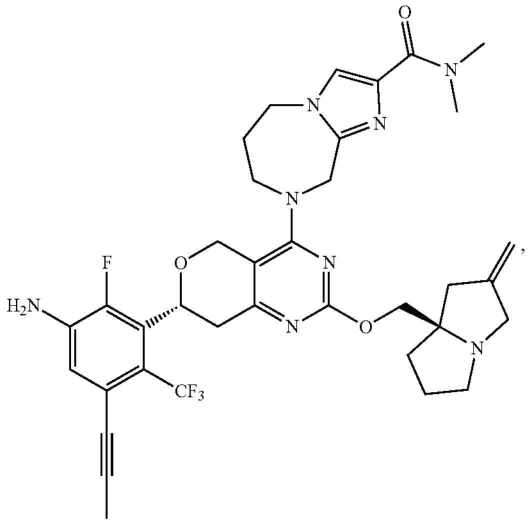
,
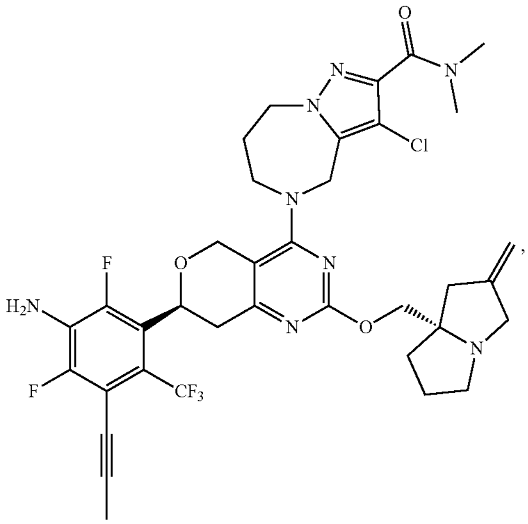
,
-continued
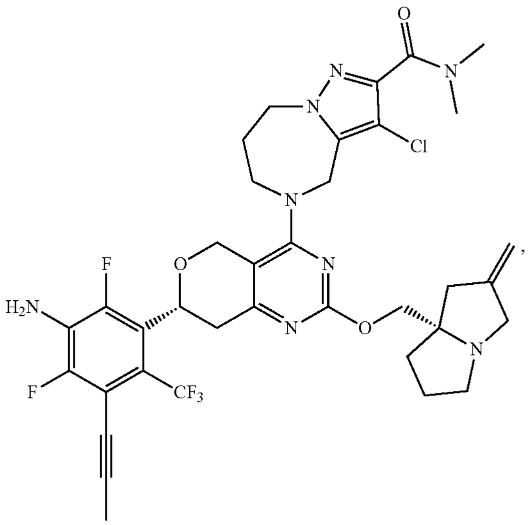
,
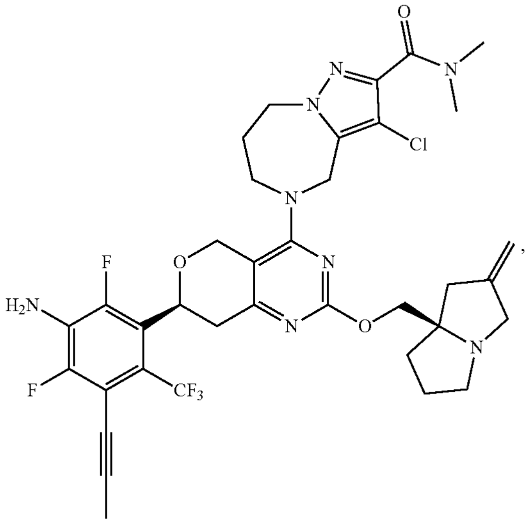
,
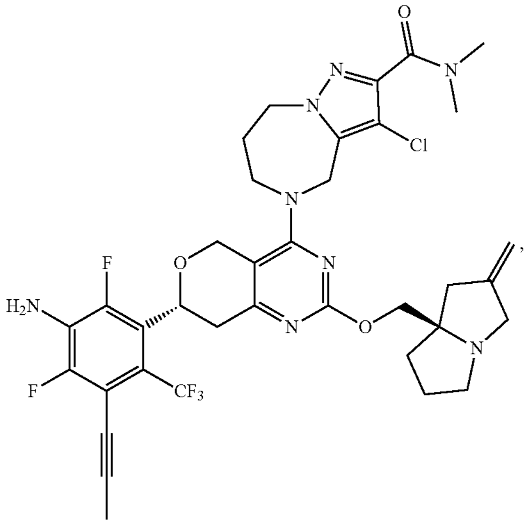
, -continued
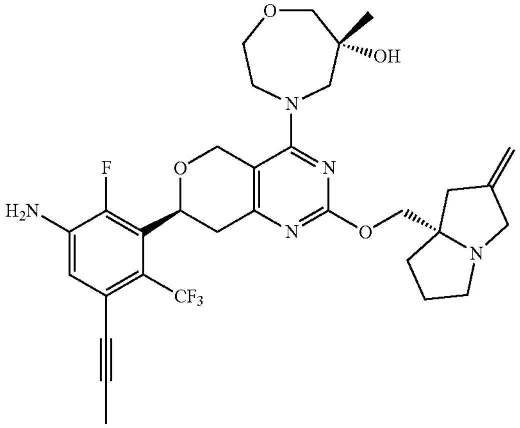
,
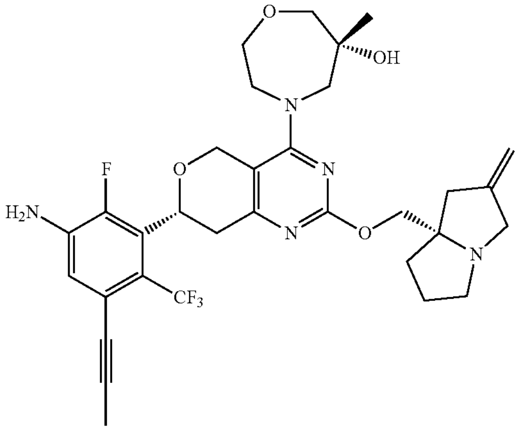
,
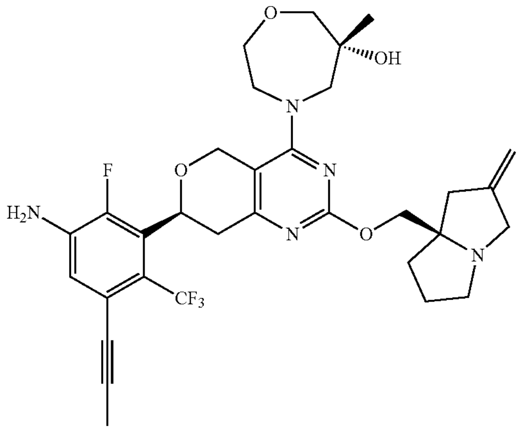
,
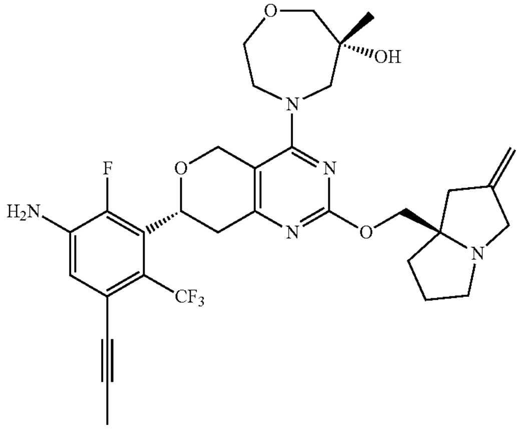
,
-continued
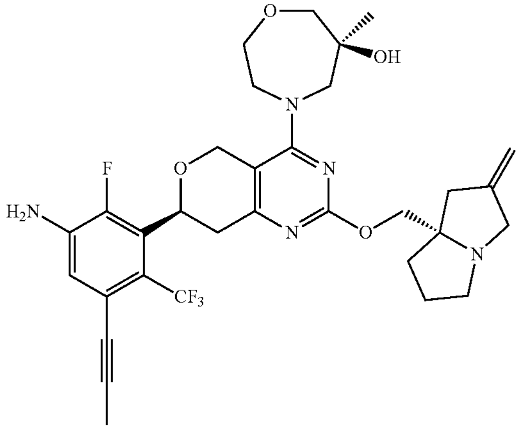
,
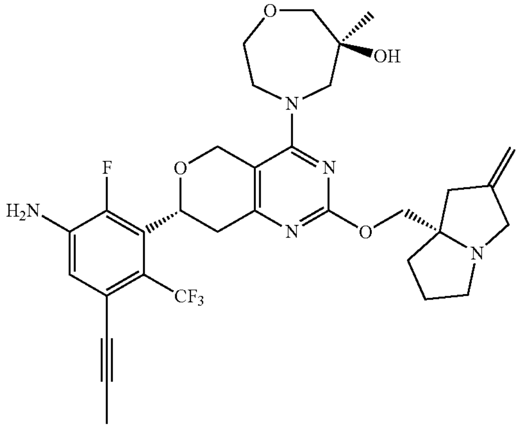
,
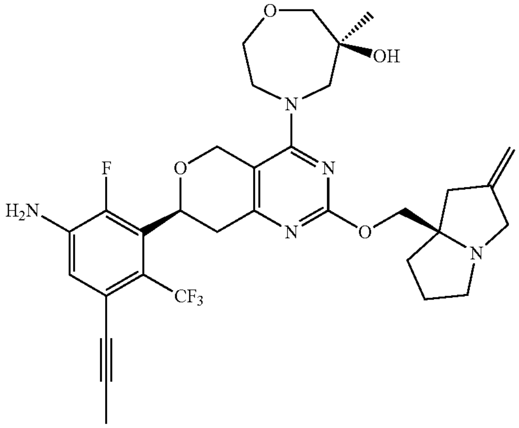
,
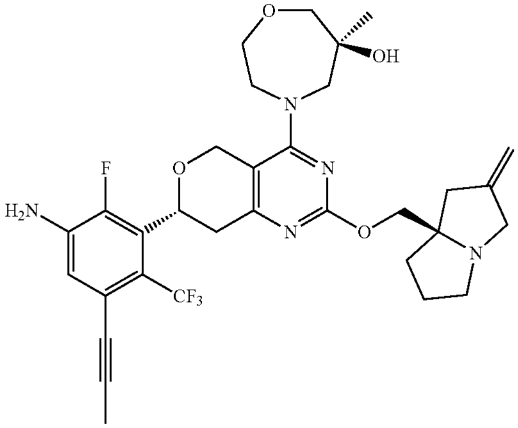
, -continued
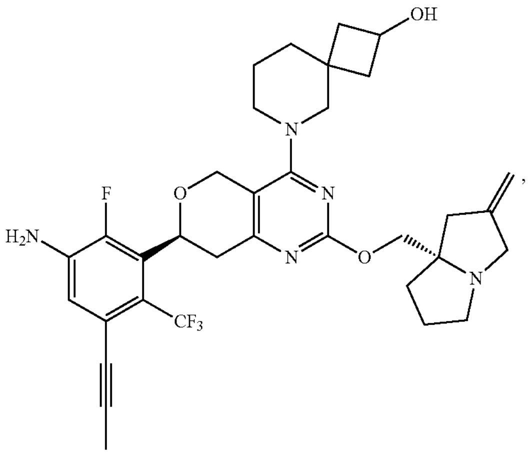
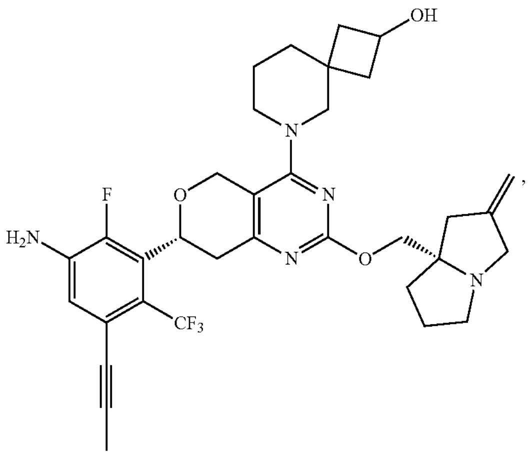
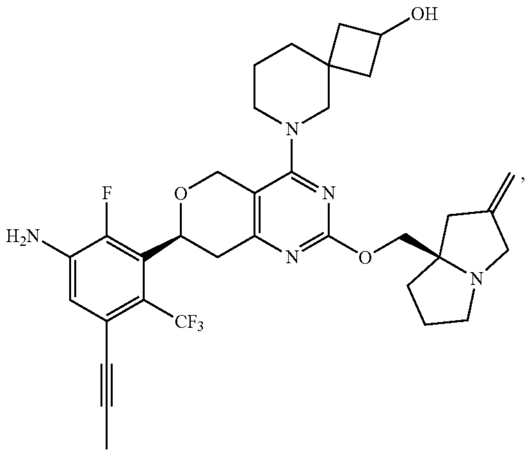
-continued
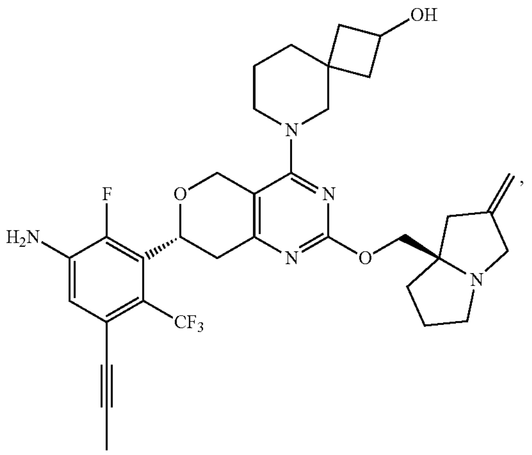
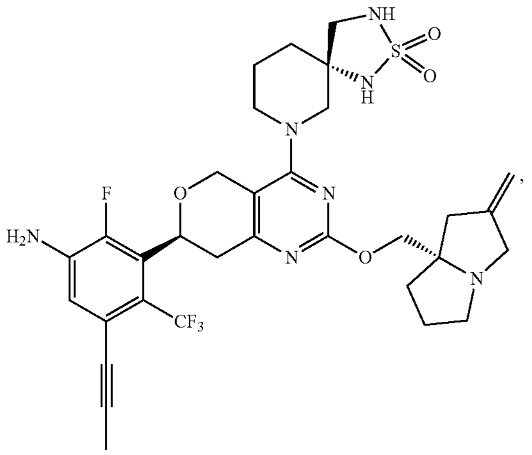
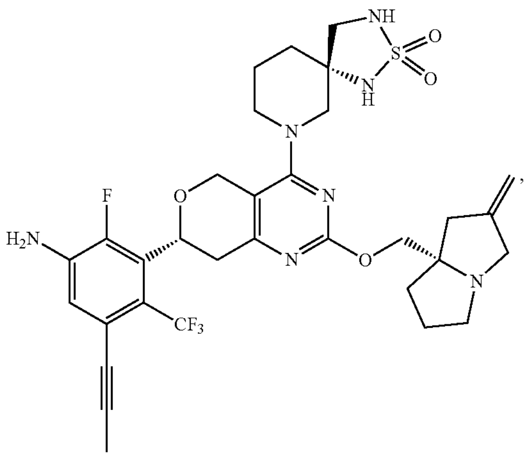

-continued
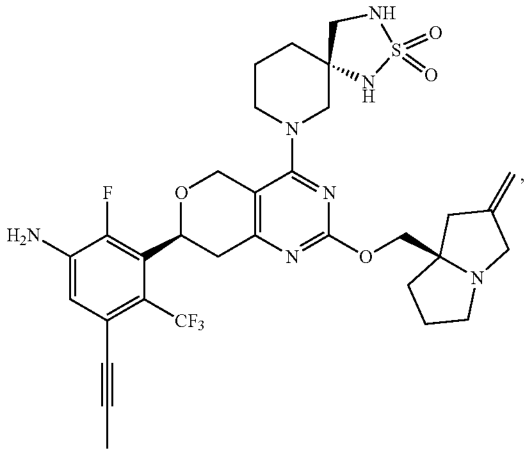
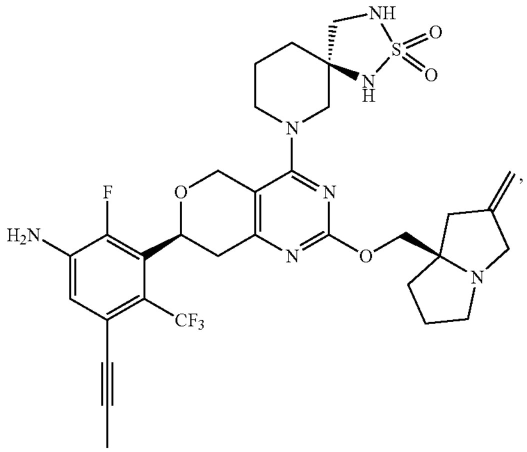
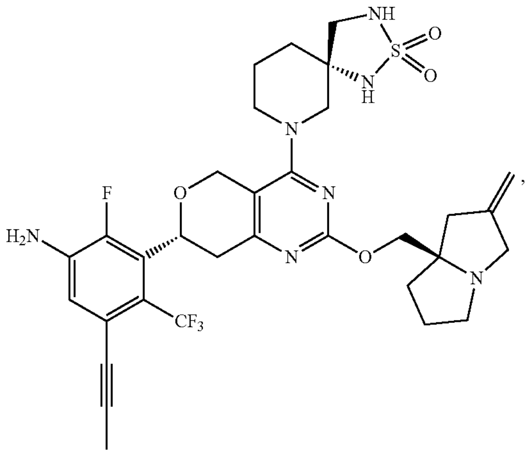
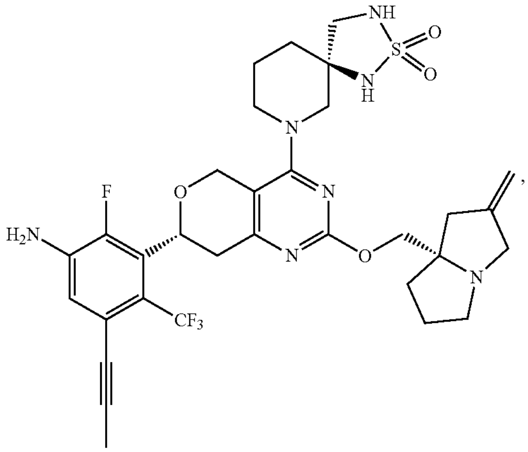
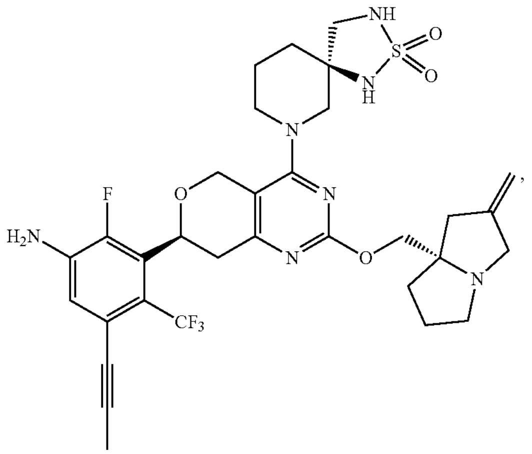
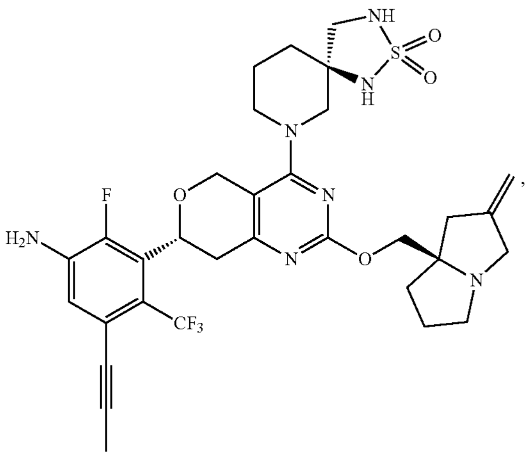

-continued
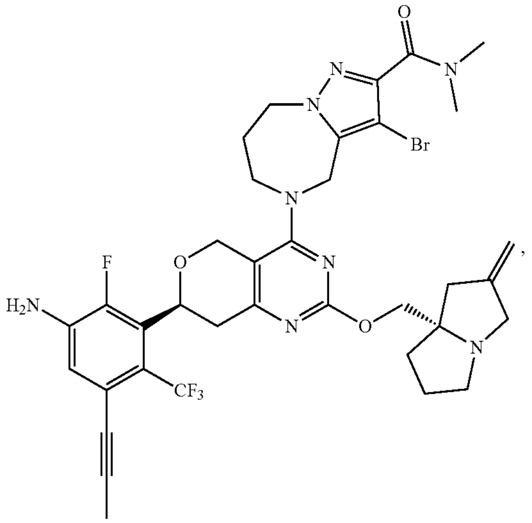
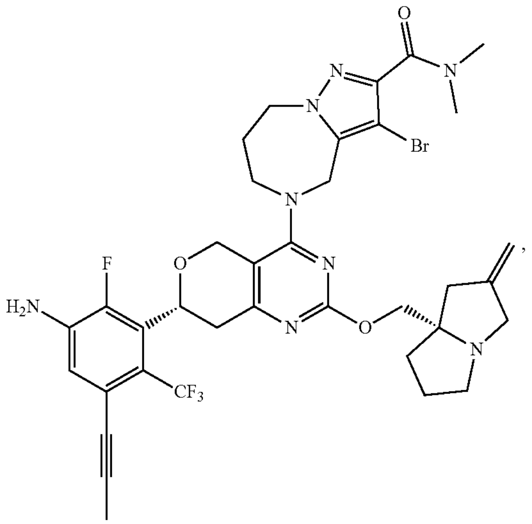
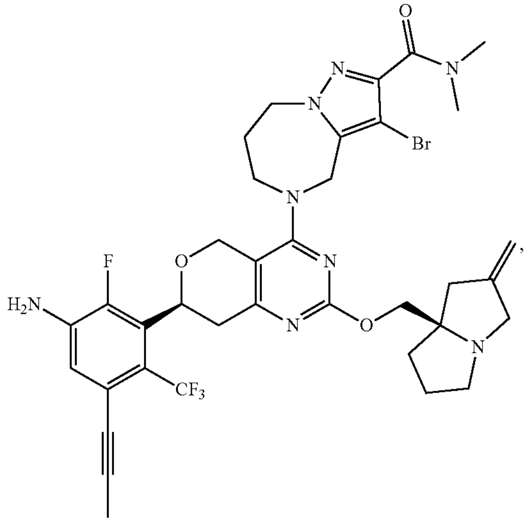
-continued
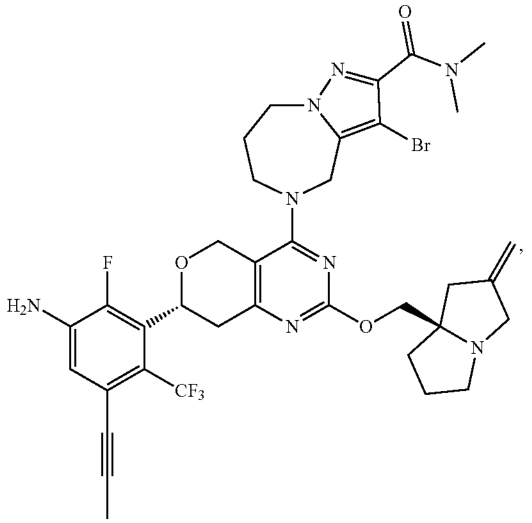
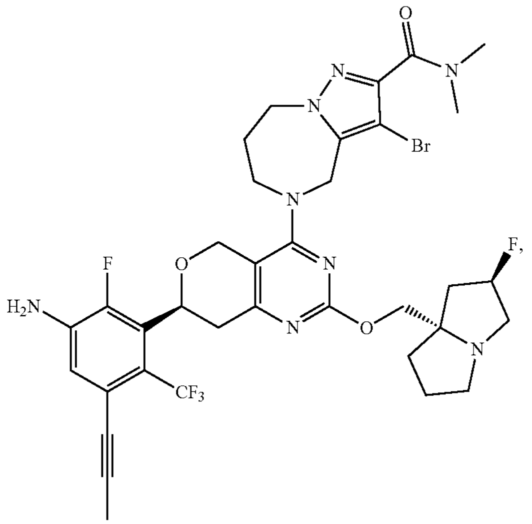
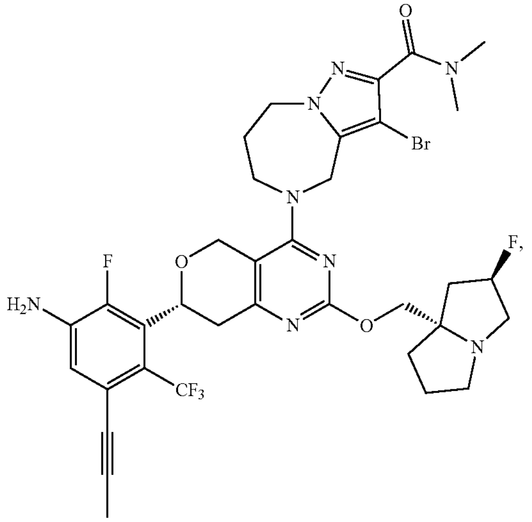

-continued
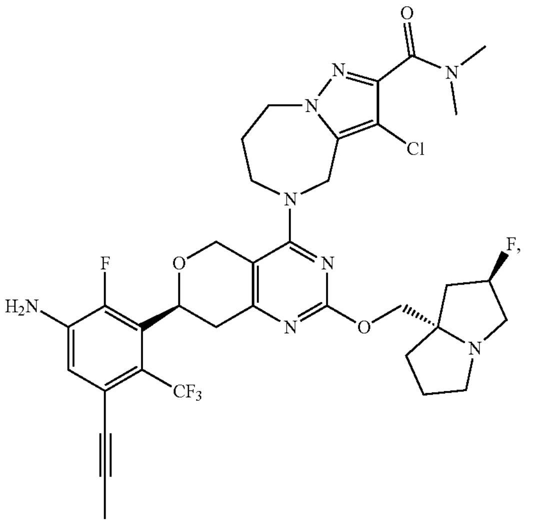
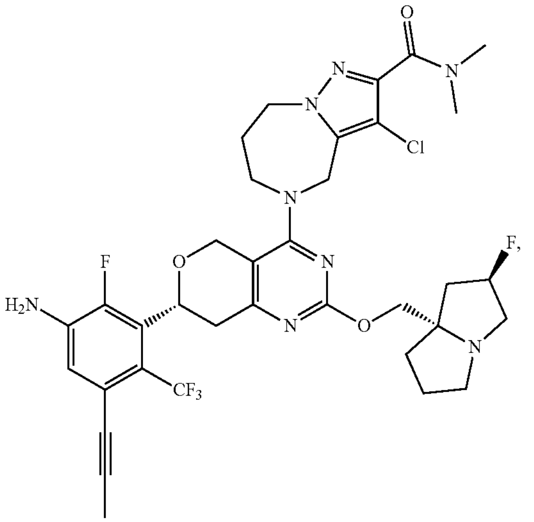
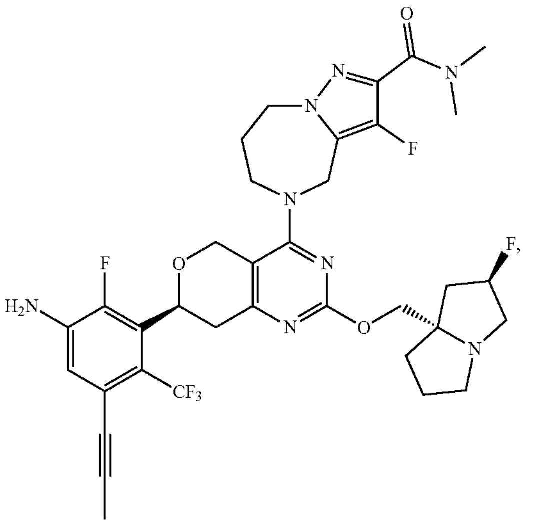
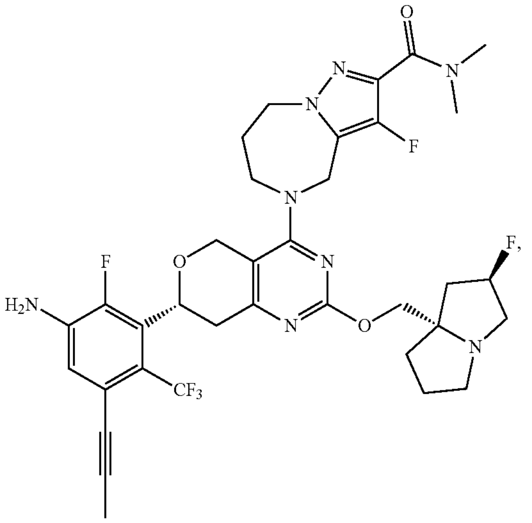
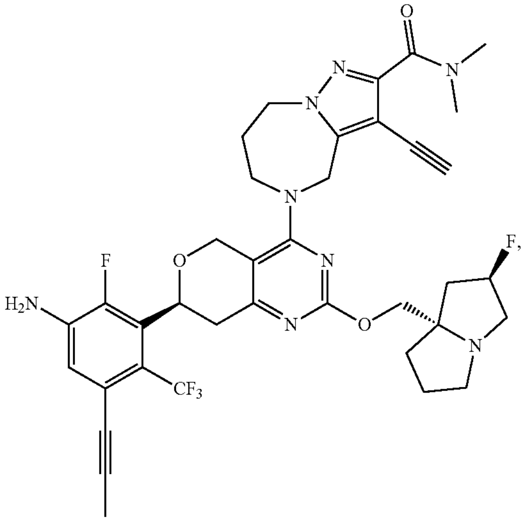
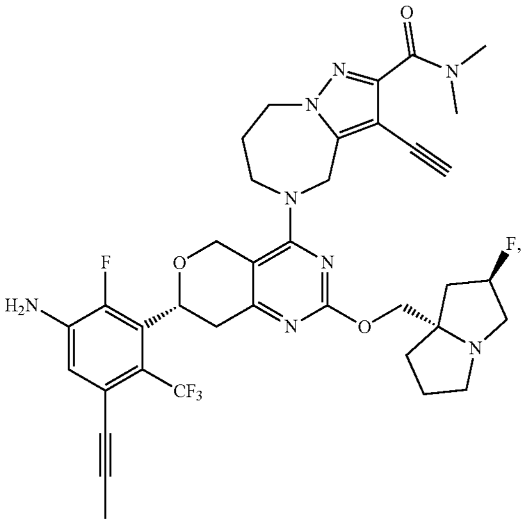

-continued
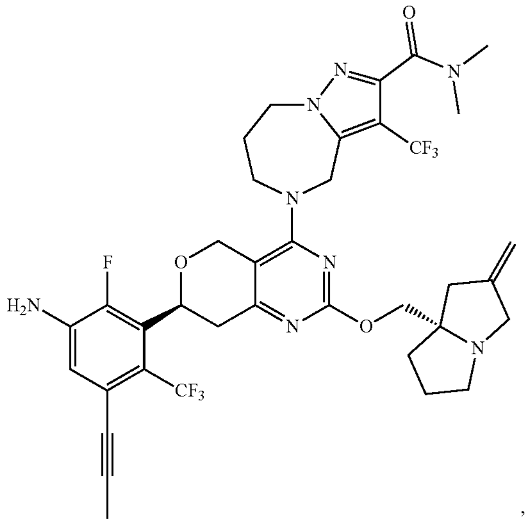
,
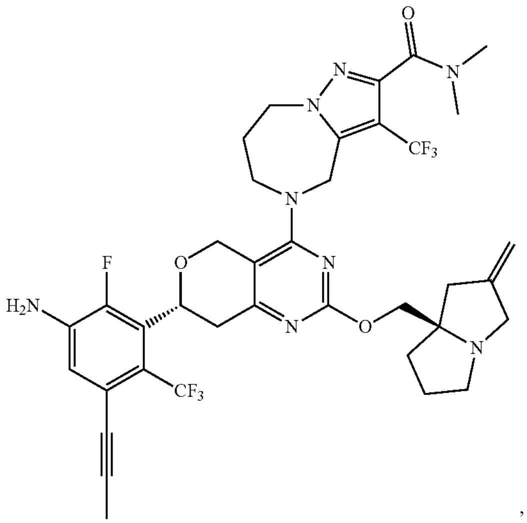
,
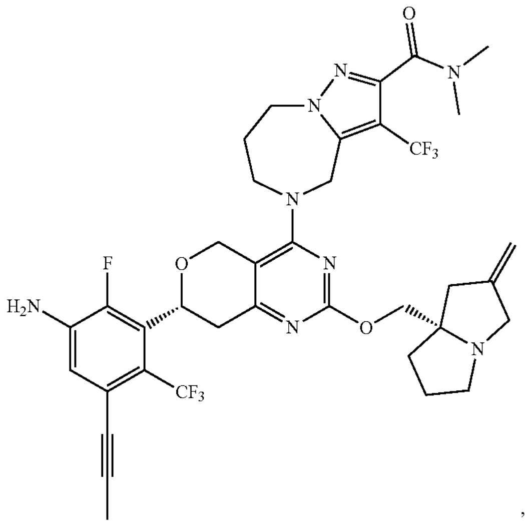
,
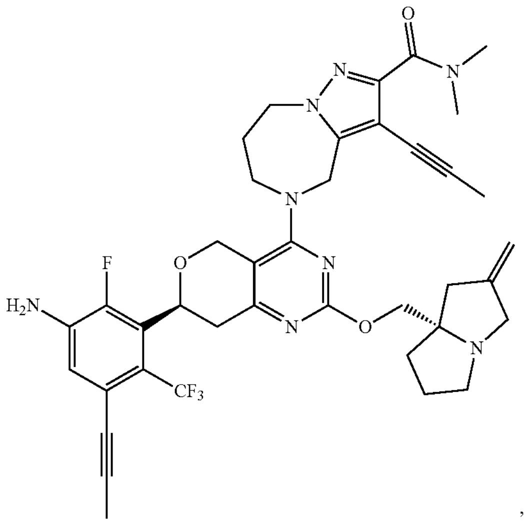 [SMILES: C#Cc1c(C(=O)N(C)C)nn2c1CN(c1nc(OC[C@@]34CCCN3CC(=C)C4)nc3c1CO[C@H](c1c(F)c(N)cc(C#CC)c1C(F)(F)F)C3)CCC2]
,
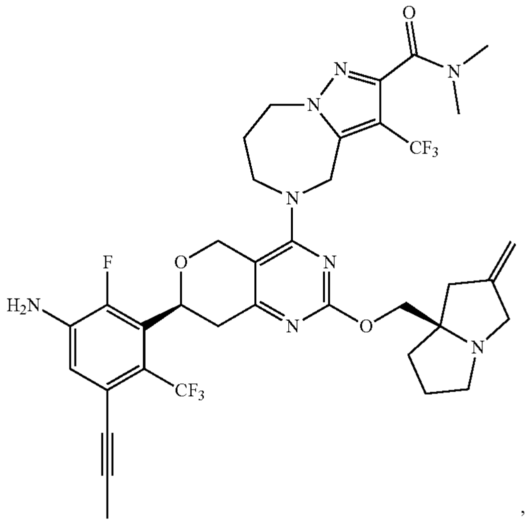
,
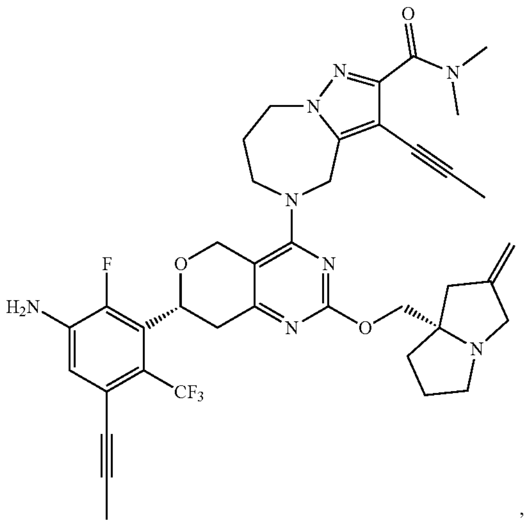
, -continued
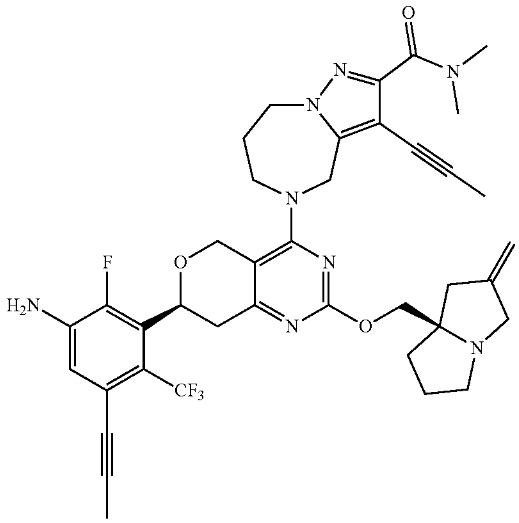
,
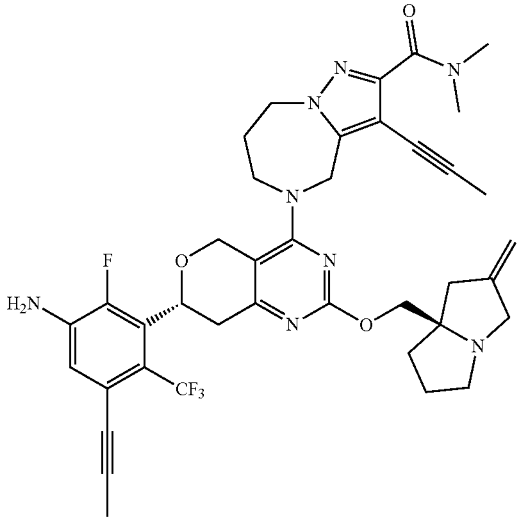
,
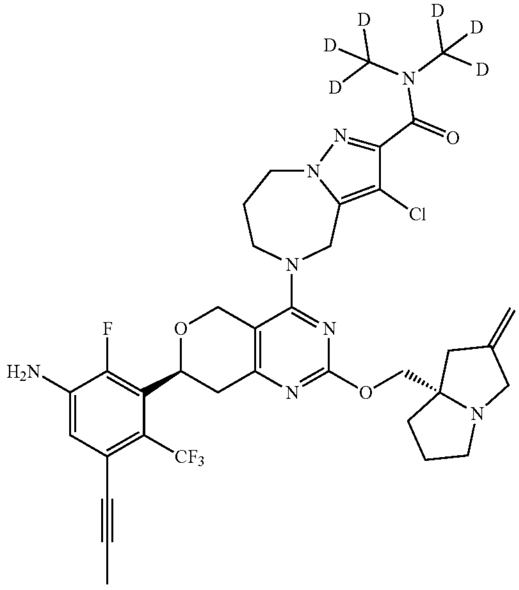
,
-continued
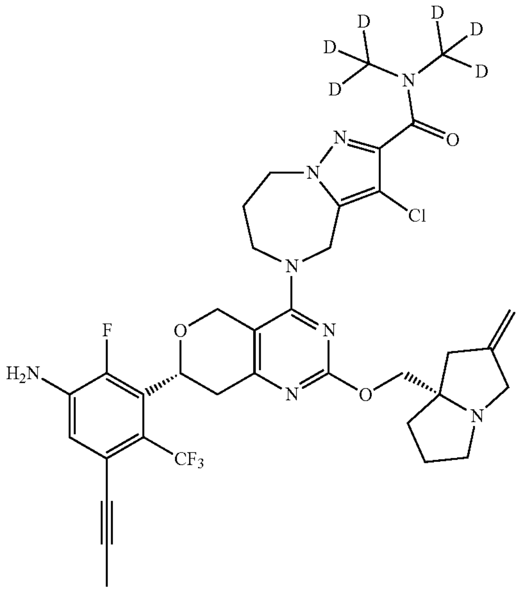
,
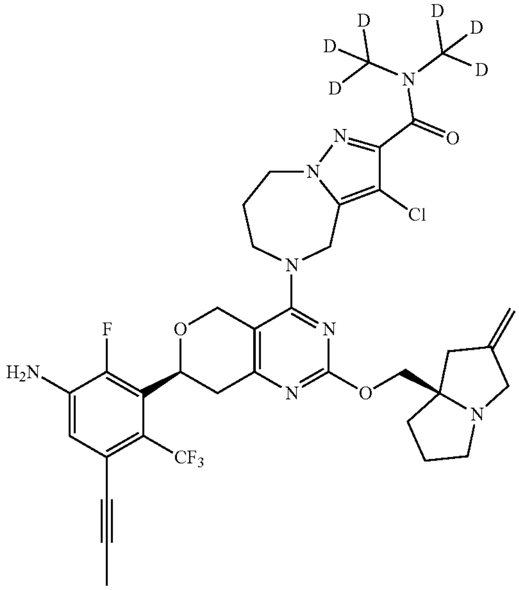
, -continued
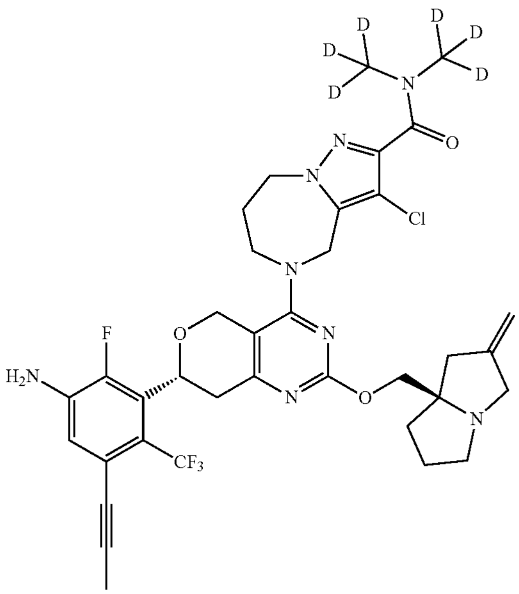
,
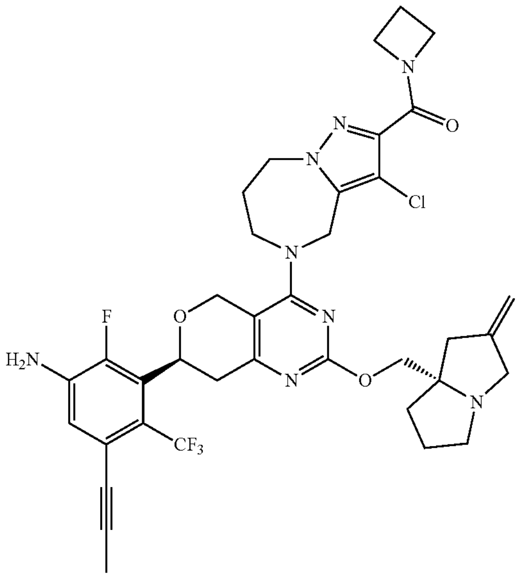
,
-continued
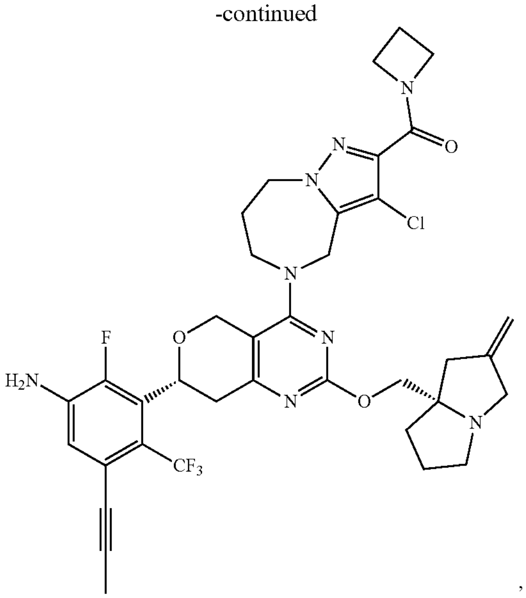
,
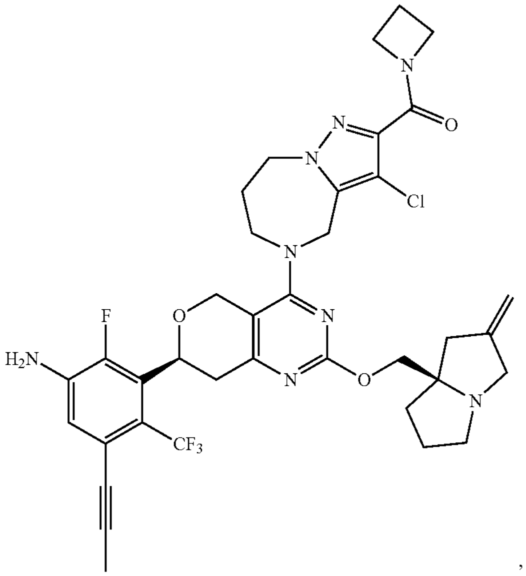
,
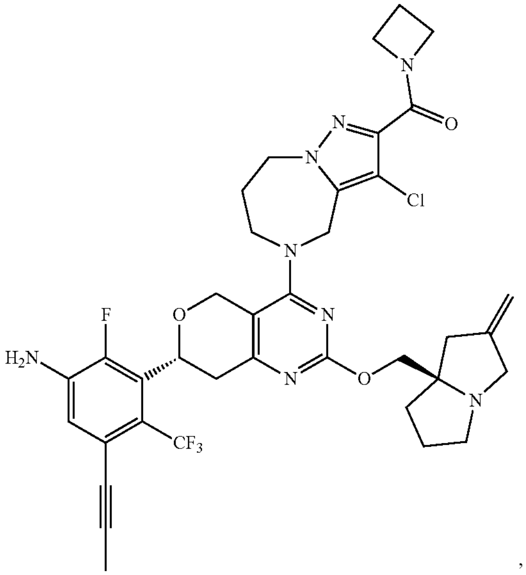
, -continued
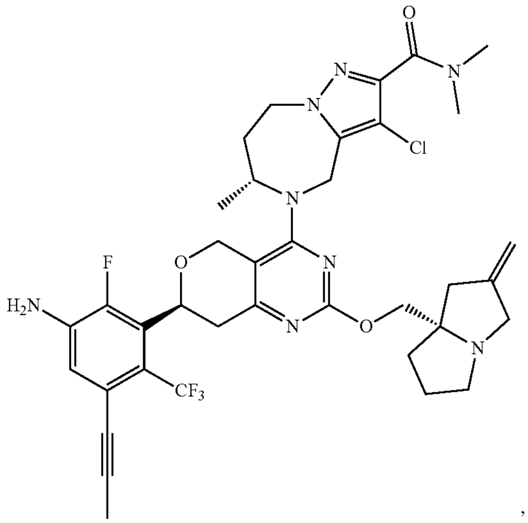
,
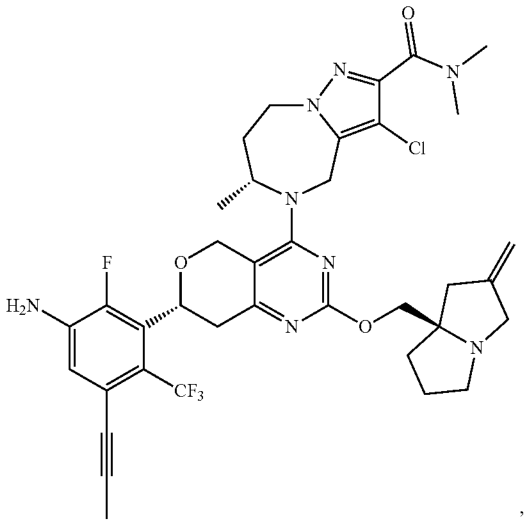
,
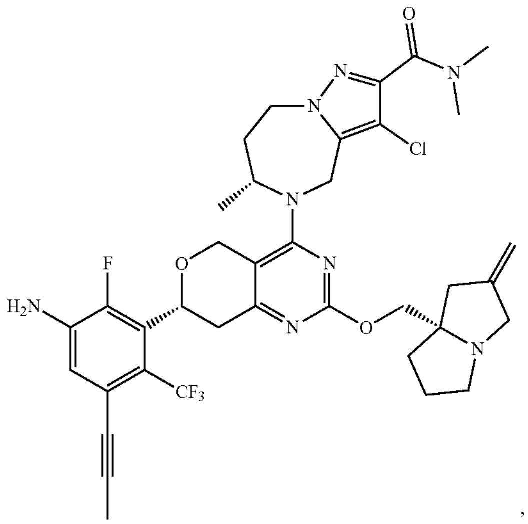
,
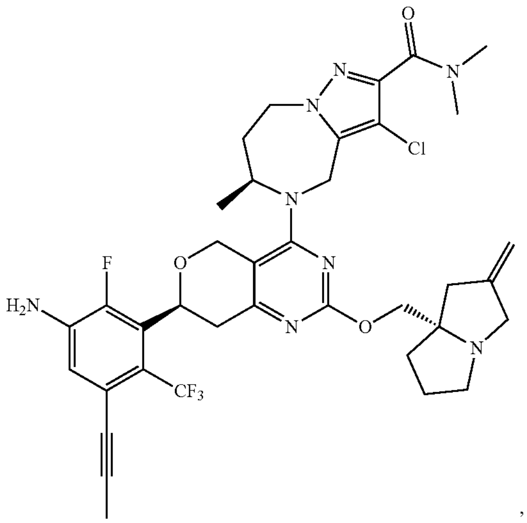
,
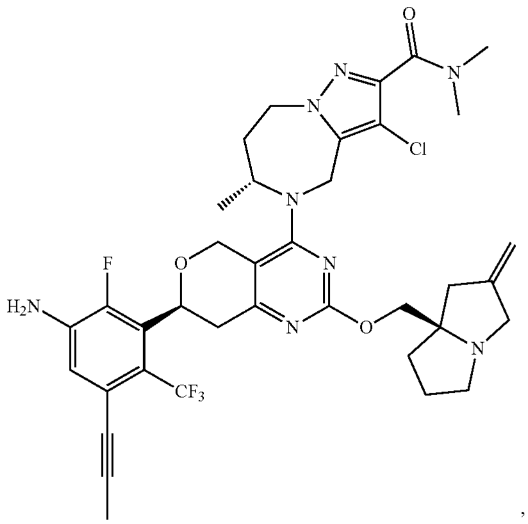
,
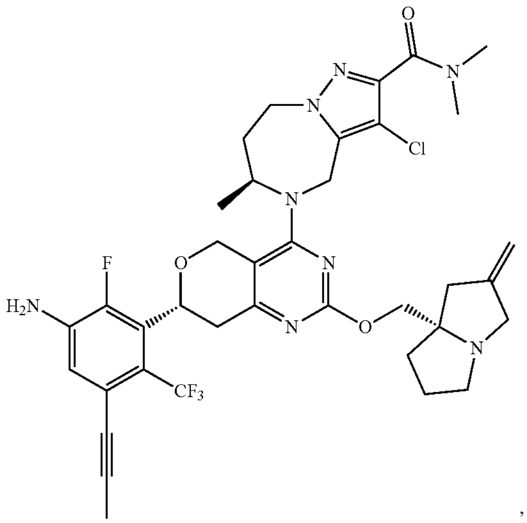
, -continued
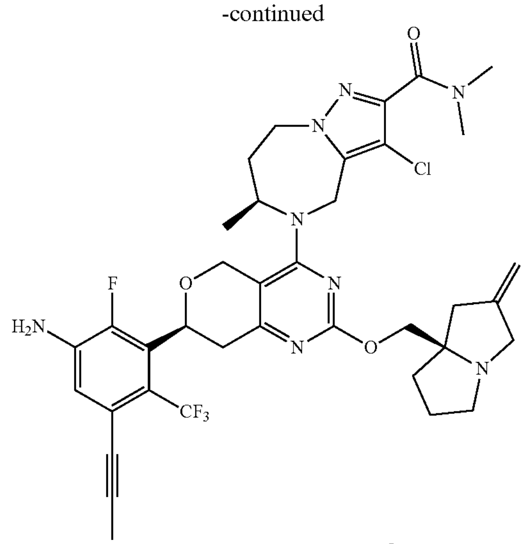
,
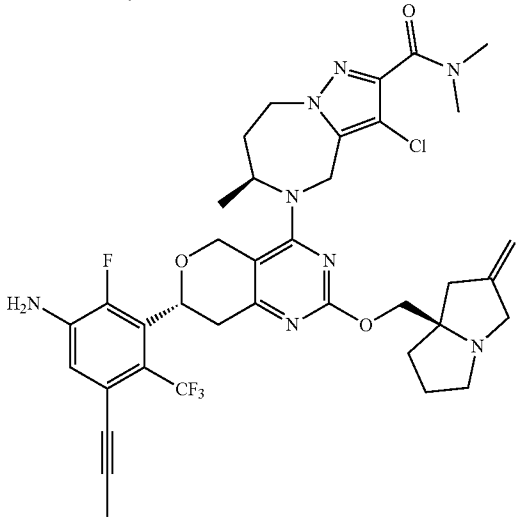
, and
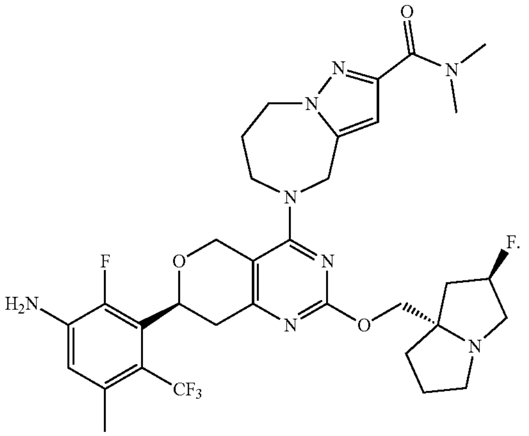
The present invention further provides the following synthesis methods:
Synthesis Method 1
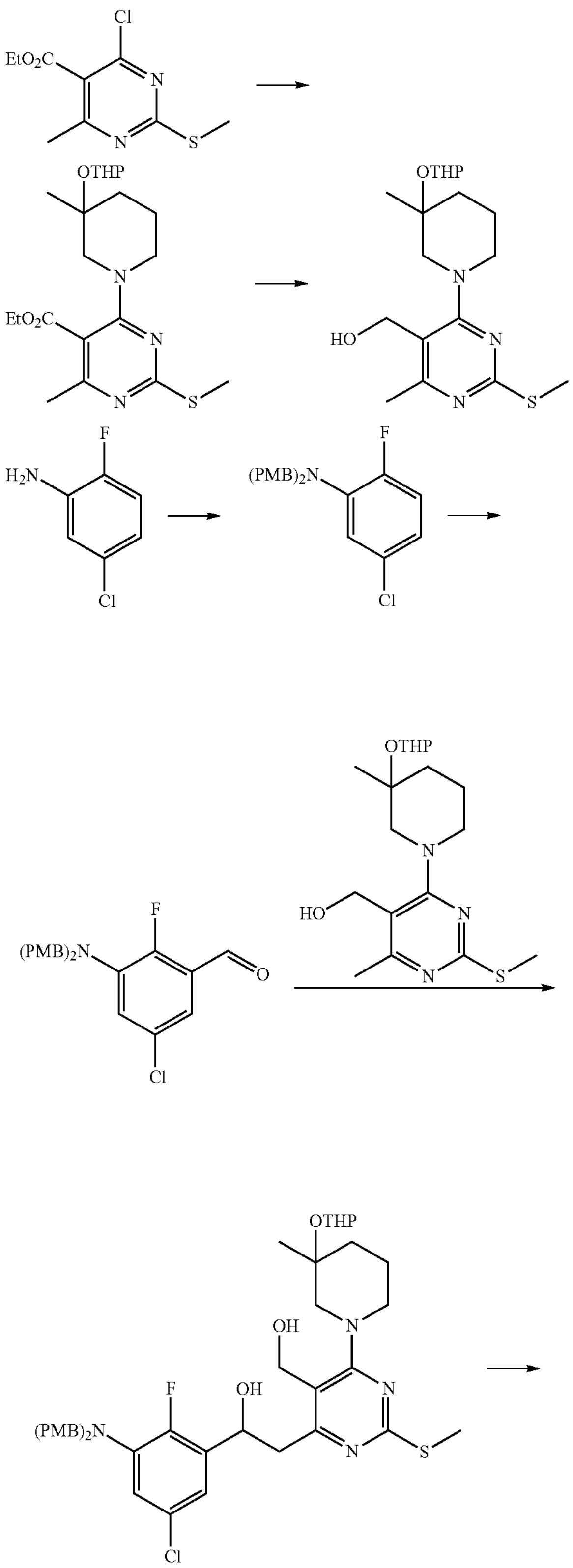

-continued
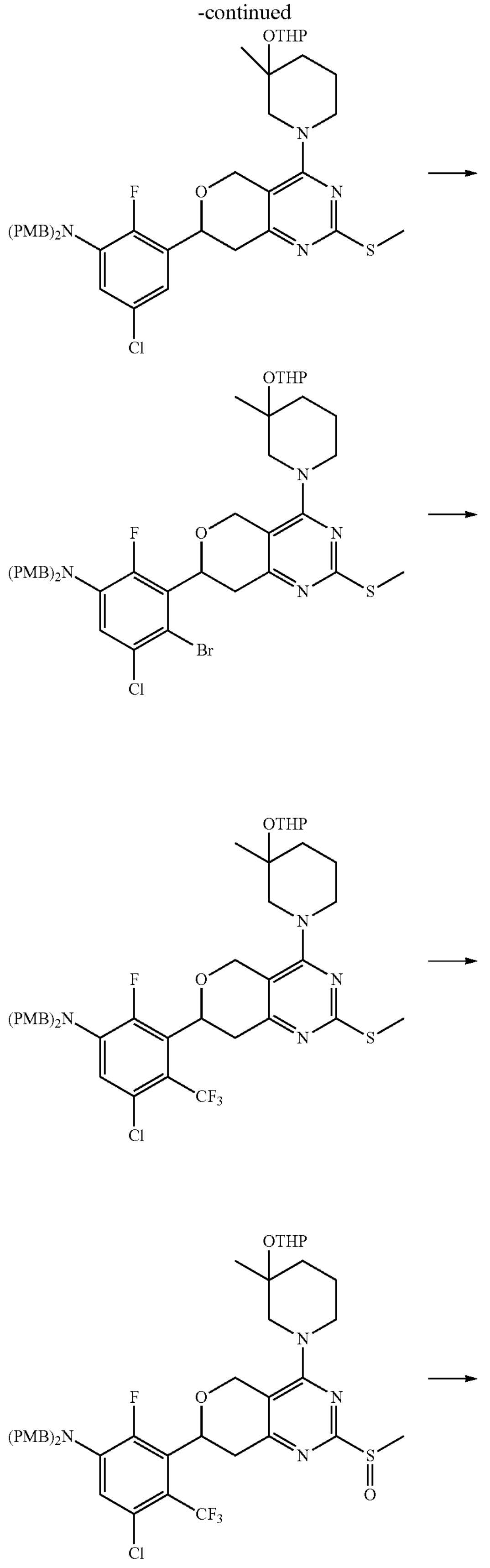
-continued
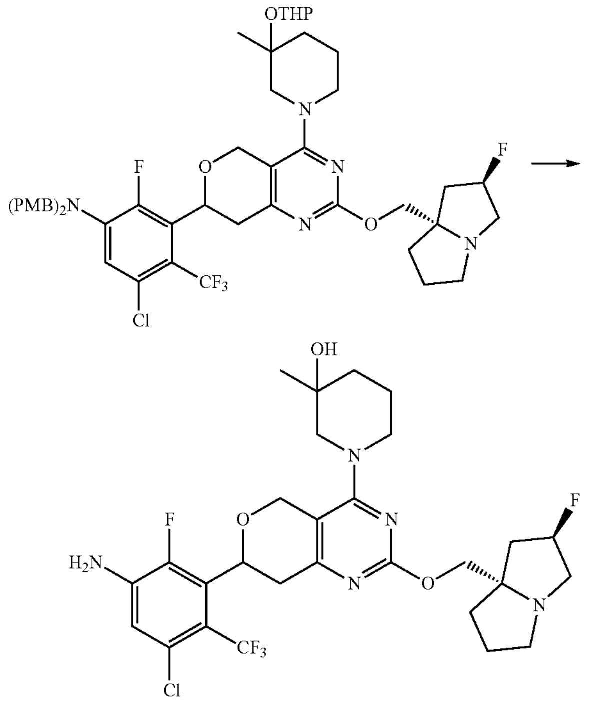
Synthesis Method 2
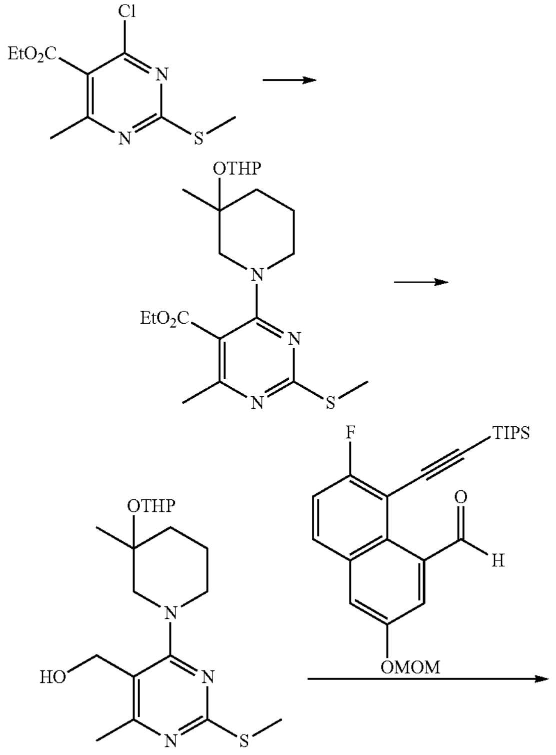

-continued
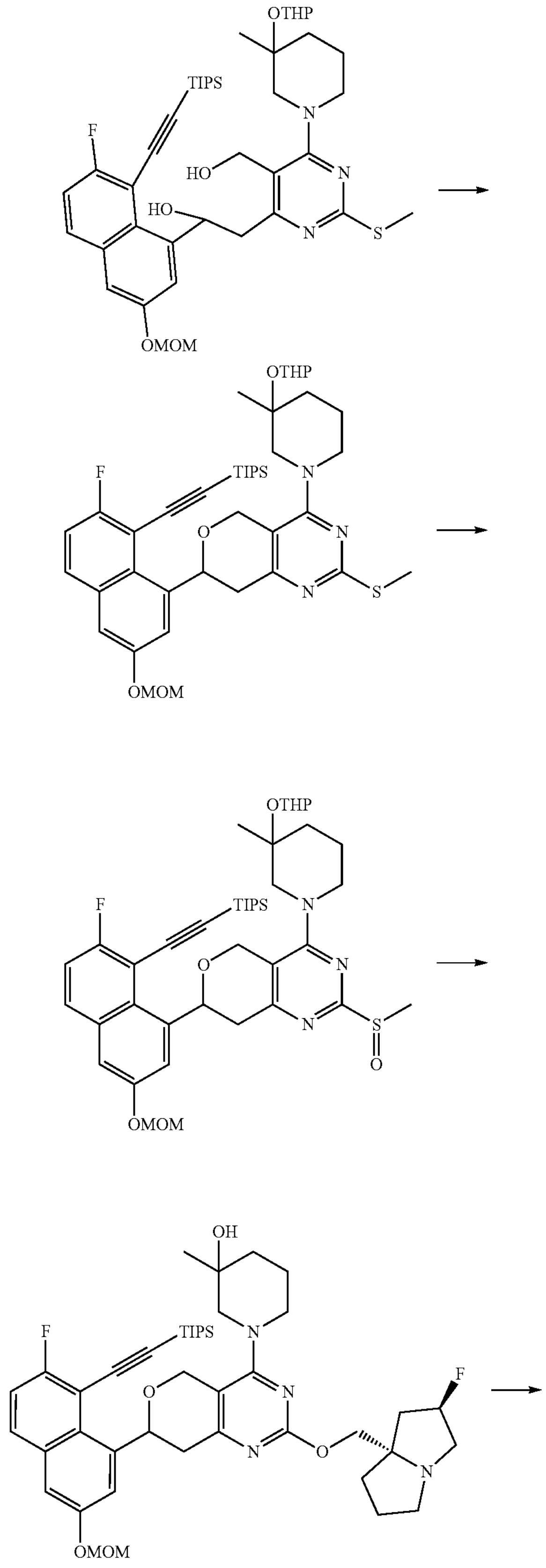
-continued
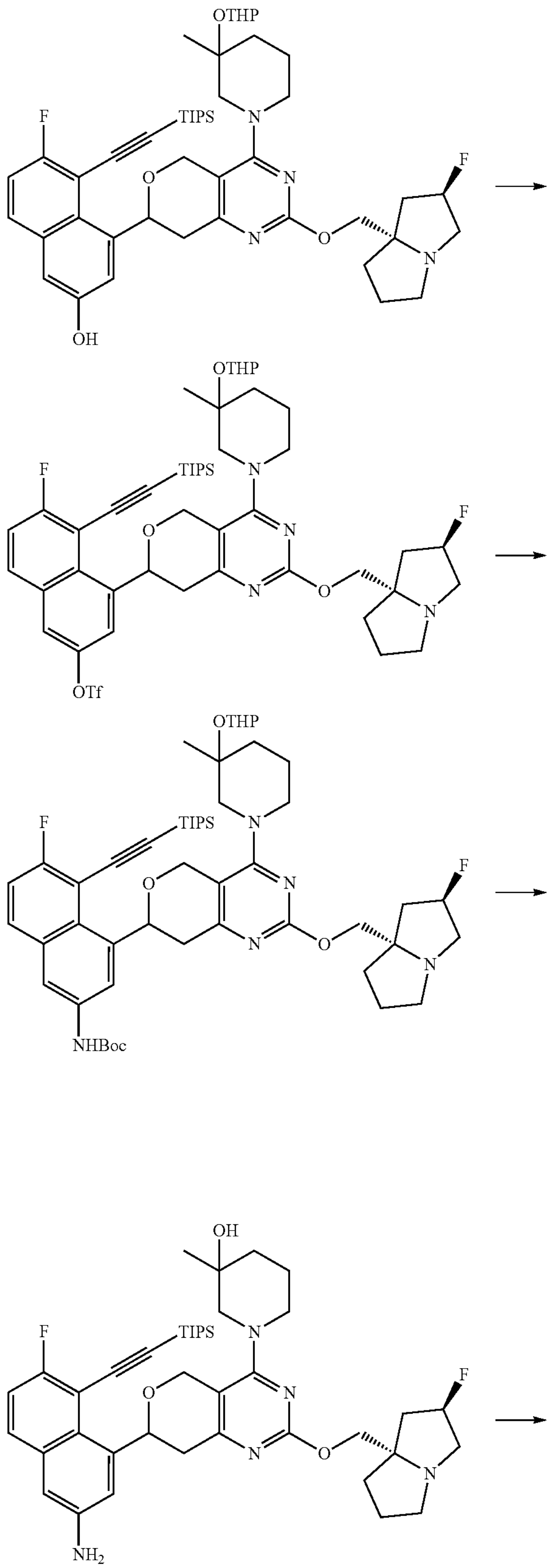

-continued

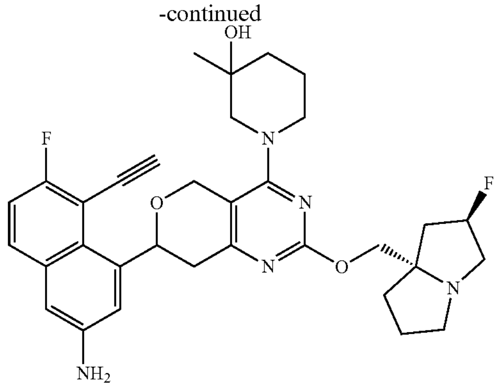

The present invention further provides use of the compounds or pharmaceutically acceptable salts thereof in the preparation of drugs for treating pan-KRAS related diseases.

The present invention further provides use of the compounds or pharmaceutically acceptable salts thereof in the preparation of drugs for treating tumor related diseases.

Test Method 1: H358 Cell Experiment

1. Purpose of the Experiment

The $IC_{50}$ of a compound for inhibition of H358 cell proliferation is tested.

2. Reagents

The main reagents used in the study include RPMI-1640 medium, penicillin/streptomycin antibiotics purchased from Wisent, and fetal bovine serum purchased from Biosera. The CellTiter-Glo (cell viability chemiluminescent assay) reagent was purchased from Promega. The NCI-H358 cell line was purchased from the Chinese Academy of Sciences cell bank.

3. Instrument

The main instrument used in the study is Nivo multilabel analyzer (PerkinElmer).

4. Methodology

1) NCI-H358 cells are seeded in a white 96-well plate at a density of 80 μL of cell suspension (containing 4,000 NCI-H358 cells) per well. The cell plate is incubated overnight in a carbon dioxide incubator.

2) The compound to be tested is diluted using a multichannel pipette by 5 times to the 9th concentration, that is, from 2 mM to 5.12 nM, and double replicates are set up. 78 μL of medium is added to an intermediate plate, and then the gradient-diluted compound is transferred at a density of 2 μL per well to the intermediate plate according to the corresponding position, mixed and transferred at a density of 20 μL per well to a cell plate. The concentration of the compound transferred into the cell plate ranges from 10 μM to 0.0256 nM. The cell plate is incubated in a carbon dioxide incubator for 5 days. Another cell plate is prepared, and the signal value read on the day of addition is taken as the maximum value (the Max value in the equation below) to be used in data analysis. A cell viability chemiluminescent assay reagent is added at a density of 25 μL per well to the cell plate and incubated at room temperature for 10 min to stabilize luminous signals. The readings are taken using a multilabel analyzer.

3) A cell viability chemiluminescent assay reagent is added at a density of 25 μL per well to the cell plate and incubated at room temperature for 10 min to stabilize luminous signals. The readings are taken using a multilabel analyzer.

Data Analysis:

The original data is converted into the inhibition rate using equation (Sample−Min)/(Max−Min)×100%, and the $IC_{50}$ value can be obtained by curve fitting through four parameters (GraphPad Prism "log(inhibitor) vs. response—Variable slope" mode).

Test Method 2. Antiproliferative Effects of Compounds in Tumor Cell Line AsPC-1

Research Objective

The experiment studies the antiproliferative effects of compounds by detecting the effects of the compounds on in vitro cell viability of the tumor cell line AsPC-1.

Experimental Materials

| Cell line | Tumor type | Growth characteristics | Culture method |
| --- | --- | --- | --- |
| AsPC-1 | Pancreatic cancer | Adherent growth | RPMI 1640 + 10% FBS |

Ultra Low Cluster-96-well plate (Corning-7007)

Greiner CELLSTAR 96-well plate (#655090)

Promega CellTiter-Glo 3D luminescence cell activity assay kit (Promega-G9683)

2104-10 EnVision reader, PerkinElmer

RPMI 1640, DMEM, PBS (phosphate buffer), FBS (fetal bovine serum), Antibiotic-antimycotic, L-glutamine, and DMSO (dimethyl sulfoxide)

Experimental Methods and Steps

Cell Culture

The tumor cell line is incubated in an incubator at 37° C., 5% $CO_2$ under the culture conditions shown by the culture method. Regular passage is conducted, and the cells in the logarithmic growth phase are taken for seeding.

Cell Seeding

The cells are stained with trypan blue and the number of living cells is counted.

The cell concentration is adjusted to a suitable concentration.

| Cell line | Density (per well) |
| --- | --- |
| AsPC-1 | 7,000 cells |

A cell suspension is added at a density of 135 μL per well to a ULA culture plate, and the same volume of cell-free medium is added to a blank control plate.

The ULA culture plate is centrifuged at room temperature and 1,000 rpm for 10 min immediately after seeding. Caution: Always handle follow-up actions with care after centrifuging to avoid unnecessary shaking.

The culture plate is incubated overnight in an incubator at 37° C., 5% $CO_2$, and 100% relative humidity.

Preparation of 10× Compound Working Fluid and Treatment of Cells with Compounds (Day 1)

After a 10× compound working fluid (DMSO 10× working fluid) is prepared, 15 μL of the 10× compound working fluid is added to a ULA culture plate, and 15 μL of a DMSO-cell medium mixture is added to a vehicle control and the blank control.

The 96-well cell plate is put back into the incubator and incubated for 120 h.

Sphere formation of the cells is observed daily until the end of the experiment.

CellTiter-Glo Luminescence Cell Viability Assay (Day 5)

The following steps are performed according to the instructions of the Promega CellTiter-Glo 3D luminescence cell activity assay kit (Promega #G9683).

A CellTiter-Glo 3D reagent is added at a density of 150 μL (equal to the volume of the cell medium per well) per well. The cell plate is wrapped in aluminum foil paper to avoid light.

The culture plate is shaken on an orbital shaker for 5 min.

The mixture is carefully blown up and down 10 times with a pipette to mix the mixture in the wells. It is necessary to ensure that cell spheres are sufficiently separated before proceeding to the next step.

The solution in the ULA plate is then transferred into a black plate (#655090) and placed at room temperature for 25 min to stabilize the luminous signals.

The luminous signals are detected on a 2104 EnVision reader.

Data Analysis

The inhibition rate (IR) of the detected compound is calculated using the following formula: IR (%)=(1−(RLU compound−RLU blank control)/(RLU vehicle control−RLU blank control))×100%. The inhibition rates of compounds with different concentrations are calculated in Excel, and then a diagram of inhibition curves is made and related parameters are calculated using GraphPad Prism software, including the minimum inhibition rate, maximum inhibition rate, and $IC_{50}$.

Technical Effects

The compounds of the present invention have good inhibitory activity on multiple KRAS mutant and KRAS amplified cells, and shows good tumor inhibitory effects in GP2D and Panc0403 cell lines.

Related Definitions

Unless otherwise noted, the following terms and phrases used herein are intended to have the following meanings. A particular term or phrase should not be considered ambiguous or unclear without a specific definition, but should be understood with its ordinary meaning. When a trade name appears in this article, it is intended to refer to the corresponding merchandise or active ingredients thereof.

The term "pharmaceutically acceptable" is used herein to refer to those compounds, materials, compositions and/or dosage forms that are within the bounds of sound medical judgment and are suitable for use in contact with human and animal tissues without excessive toxicity, irritation, allergic reactions or other problems or complications commensurate with a reasonable benefit/risk ratio.

The term "pharmaceutically acceptable salt" refers to a salt of a compound of the present invention prepared from a compound having a specific substituent found in the present invention and a relatively non-toxic acid or base. When the compounds of the present invention contain relatively acidic functional groups, base addition salts can be obtained by bringing such compounds into contact with a sufficient amount of base in a pure solution or a suitable inert solvent. When the compounds of the present invention contain relatively basic functional groups, acid addition salts can be obtained by bringing such compounds into contact with a sufficient amount of acid in a pure solution or a suitable inert solvent. Certain specific compounds of the present invention contain basic and acidic functional groups and can thus be converted into any base or acid addition salt.

The pharmaceutically acceptable salt of the present invention can be synthesized by conventional chemical methods from parent compounds containing acid groups or bases. In general, such salts are prepared by reacting the compounds in the form of a free acid or base with a stoichiometric appropriate base or acid in water or an organic solvent or a mixture of both.

Unless otherwise noted, the term "treatment" is intended to refer to all processes in which the progression of a disease may be slowed, interrupted, controlled, or stopped, but does not necessarily mean that all symptoms are eliminated.

The compounds of the present invention may be present in specific geometric or stereoisomer forms. The present invention envisages that all such compounds, including cis- and trans-isomers, (−)- and (+)-enantiomers, (R)- and (S)-enantiomers, diastereomers, (D)-isomers, (L)-isomers, racemic mixtures thereof, and other mixtures, such as enantiomers or diastereomerically enriched mixtures fall within the scope of the present invention. Additional asymmetric carbon atoms may be present in alkyl and other substituents. All of these isomers and mixtures thereof are included within the scope of the present invention.

The compounds of the present invention may include an atomic isotope in an unnatural proportion on one or more atoms constituting the compounds. For example, the compounds can be labeled with radioisotopes, such as tritium ($^3H$), iodine-125 ($^{125}I$), or C-14 ($^{14}C$). For example, hydrogen may be replaced by heavy hydrogen to form deuterated drugs, and the bond formed by deuterium and carbon is firmer than the bond formed by common hydrogen and carbon. Compared with undeuterated drugs, deuterated drugs have the advantages of reducing toxic and side effects, increasing drug stability, enhancing efficacy, prolonging the biological half-life of drugs, and the like. The conversion of all isotopic compositions of the compounds of the present invention, whether radioactive or not, is within the scope of the present invention.

The term "optional" or "optionally" refers to the possible but not necessary occurrence of an event or condition described subsequently, and the description includes the occurrence of the event or condition described and the non-occurrence of the event or condition.

The term "substituted" means that any one or more hydrogen atoms on a particular atom are substituted with a substituent (which may include heavy hydrogen and variants of hydrogen), as long as the valence of the particular atom is normal and the substituted compound is stable. When the substituent is oxygen (i.e., ═O), it means that two hydrogen atoms are substituted. The term "optionally substituted" means "may or may not be substituted", and unless otherwise specified, the type and number of substituents may be arbitrary on a chemically achievable basis.

When any variable (for example, R) appears more than once in the composition or structure of a compound, the definition of the variable in each case is independent. Thus, for example, if one group is substituted with 0-2 R, the group may optionally be substituted with two R to the most, and in each case R has an independent option. Furthermore, a combination of a substituent and/or variants thereof is permissible only if such a combination produces a stable compound.

When the number of linking groups is 0, e.g., $-(CRR)_0-$, it indicates that the linking group is a single bond.

When one of the variables is selected from a single bond, it indicates that the two groups linked thereby are directly linked, e.g., when L in A-L-Z represents a single bond, it indicates that the structure is actually A-Z.

When the listed linking groups do not indicate the linking direction, the linking direction is arbitrary. For example, when the linking group L in

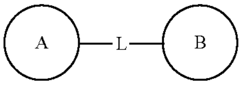

is -M-W—, the -M-W— can link ring A to ring B in the same direction as the reading order from left to right to form

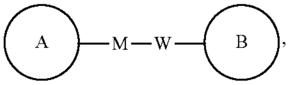, or link ring A to ring B in an opposite direction from the reading order from left to right to form

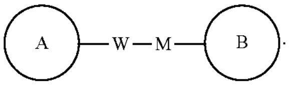.

A combination of the linking group, a substituent and/or variants thereof is permissible only if such a combination produces a stable compound.

Unless otherwise specified, when a group has one or more linkable sites, any one or more sites of the group may be linked to other groups through chemical bonds. When the chemical bonds are linked in a non-positional way, and a linking site has H atoms, the number of H atoms at the linking site may correspondingly reduce to the groups of the corresponding valence according to the number of the linking chemical bonds. The chemical bonds through which the sites are linked to other groups may be represented by a straight solid line (), a straight dashed line (), or a wavy line ().

For example, a straight solid line bond in —$OCH_3$ indicates linkage to other groups through the oxygen atom in the group; a straight dashed line bond in

indicates linkage to other groups through both ends of the nitrogen atom in the group; the wavy line in

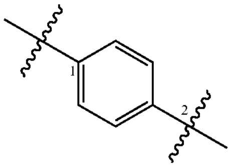 [SMILES: *c1ccc(*)cc1]

indicates linkage to other groups through the carbon atoms in the 1 and 2 positions in the phenyl group; and

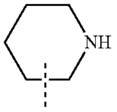

indicates that an arbitrary linkable site on the piperidyl may be linked to other groups through a chemical bond, at least including four linking modes, i.e.,

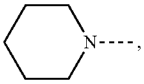, 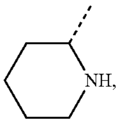, 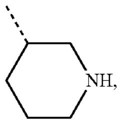, and 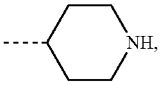, even if an H atom is drawn on the —N—,

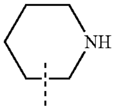

still includes the group of the linking mode

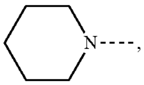, and only when one chemical bond is linked, the H at the site correspondingly reduces by one to become the corresponding monovalent piperidyl.

Unless otherwise noted, in some embodiments of the present invention, when ring B is selected from

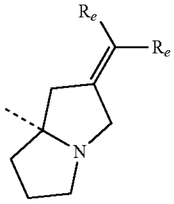 and 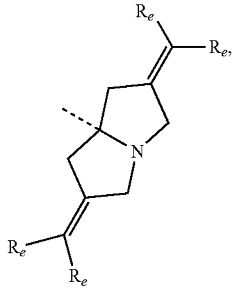, the

-continued

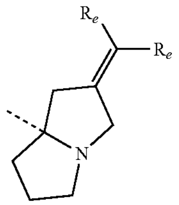

and

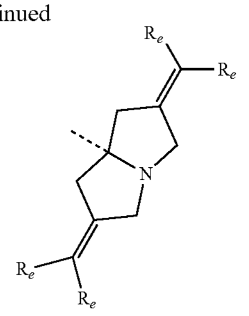

are independently substituted with 1, 2, 3, 4, 5 or 6 $R_e$, respectively, the substitution being indicated as substitution of a hexahydro-1H-pyrrolizine ring

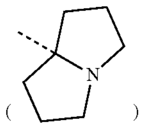

with $R_e$.

Unless otherwise noted, in some embodiments of the present invention, when a structural fragment

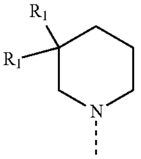

is substituted with $R_1$, the substitution is indicated as substitution of a piperidine ring

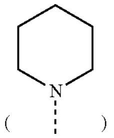

with $R_1$.

Unless otherwise noted, the absolute configuration of a three dimensional center is represented by a wedge-shaped solid line bond ( ) and a wedge-shaped dashed line bond ( ), the relative configuration of a three dimensional center is represented by a straight solid line bond ( ) and a straight dashed line bond ( ) the wedge-shaped solid bond ( ) or the wedge-shaped dashed line bond ( ) is represented by a wavy line ( ), or the straight solid line bond ( ) or the straight dashed line bond ( ) is represented by a wavy line ( ).

Unless otherwise noted, when a double-bond structure exists in the compound, e.g., a carbon-carbon double bond, a carbon-nitrogen double bond, and a nitrogen-nitrogen double bond, and each atom on the double bond is linked to two different substituents (in the double bond containing the nitrogen atom, a pair of lone-pair electrons on the nitrogen atom are considered as one substituent to which it is linked), if the atom on the double bond in the compound is linked to its substituent by a wavy line ( ), then a (Z)-type isomer, an (E)-type isomer, or a mixture of both of the compound is represented. For example, the following formula (A) represents that the compound exists as a single isomer represented by formula (A-1) or formula (A-2) or as a mixture of two isomers represented by formula (A-1) and formula (A-2); and the following formula (B) represents that the compound exists as a single isomer represented by formula (B-1) or formula (B-2) or as a mixture of two isomers represented by formula (B-1) and formula (B-2). The following formula (C) represents that the compound exists as a single isomer represented by formula (C-1) or formula (C-2) or as a mixture of two isomers represented by formula (C-1) and formula (C-2).

(A)

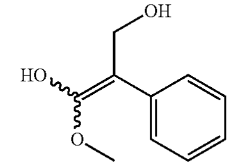

(A-1)

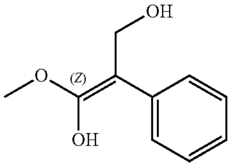

(A-2)

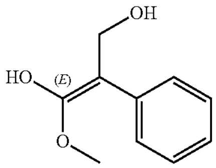

(B)

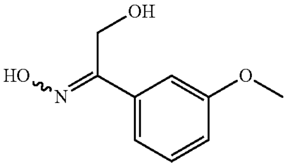

(B-1)

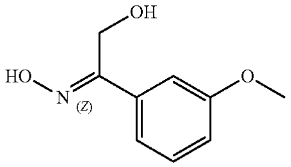

(B-2)

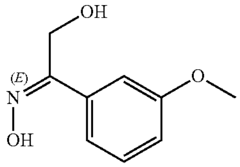

(C)

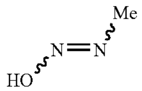

(C-1)

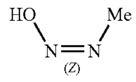

-continued (C-2)

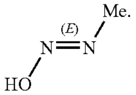

Unless otherwise noted, when a double-bond structure exists in the compound, e.g., a carbon-carbon double bond, a carbon-nitrogen double bond, and a nitrogen-nitrogen double bond, and each atom on the double bond is linked to two different substituents (in the double bond containing the nitrogen atom, a pair of lone-pair electrons on the nitrogen atom are considered as one substituent to which it is linked), if

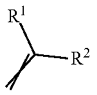

is used to represent between the atom on the double bond in the compound and its substituent, then a (Z)-type isomer, an (E)-type isomer, or a mixture of both of the compound is represented. Unless otherwise noted, the term "tautomer" or "tautomer form" refers to the fact that different functional isomers are in dynamic equilibrium and can quickly transform into each other at room temperature. If the tautomer is possible (e.g., in solution), the chemical equilibrium of the tautomer may be achieved. For example, proton tautomers (also known as prototropic tautomers) include inter-transformations by proton migration, such as keto-enol isomerization and imine-enamine isomerization. Valence tautomers include inter-transformations performed by the recombination of some bonding electrons. A specific example of keto-enol tautomerization is the tautomerization between two tautomers: pentane-2,4-dione and 4-hydroxy pentane-3-en-2-one.

Unless otherwise specified, $C_{n-n+m}$ or $C_n$—$C_{n+m}$ includes any case where n to n+m carbons are included, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; and similarly, n to n+m means that the number of atoms on a ring is n to n+m, for example, 3-12-membered rings include 3-membered rings, 4-membered rings, 5-membered rings, 6-membered rings, 7-membered rings, 8-membered rings, 9-membered rings, 10-membered rings, 11-membered rings, and 12-membered rings, and also include any range from n to n+m, for example, 3-12-membered rings include 3-6-membered rings, 3-9-membered rings, 5-6-membered rings, 5-7-membered rings, 6-7-membered rings, 6-8-membered rings, and 6-10-membered rings.

Unless otherwise noted, the term "enriched in an isomer", "isomer enriched", "enriched in an enantiomer", or "enantiomer enriched" means that the content of one of the isomers or enantiomers is less than 100% and that the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise noted, the term "isomer excess" or "enantiomer excess" refers to the difference between the relative percentages of two isomers or enantiomers. For example, if the content of one isomer or enantiomer is 90% and the content of the other isomer or enantiomer is 10%, the isomer or enantiomer excess (ee value) is 80%.

Unless otherwise specified, the term "halogenin" or "halogen" itself or as part of another substituent represents a fluorine, chlorine, bromine or iodine atom.

Unless otherwise specified, the term "$C_{1-3}$ alkyl" is used to represent a saturated hydrocarbon group consisting of 1 to 3 carbon atoms in a straight or branched chain. The $C_{1-3}$ alkyl includes $C_{1-2}$ and $C_{2-3}$ alkyl, and the like, which may be monovalent (e.g., methyl), bivalent (e.g., methylene), or multivalent (e.g., hypomethyl). Examples of $C_{1-3}$ alkyl include, but are not limited to, methyl (Me), ethyl (Et), propyl (including n-propyl and isopropyl), and the like.

Unless otherwise specified, the term "$C_{1-4}$ alkoxy" refers to those alkyl groups containing 1 to 4 carbon atoms that are linked to the remainder of a molecule by an oxygen atom. The $C_{1-4}$ alkoxy includes $C_{1-3}$, $C_{1-2}$, $C_{2-4}$, $C_4$ and $C_3$ alkoxy, and the like. Examples of $C_{1-4}$ alkoxy include, but are not limited to, methoxy, ethoxy, propoxy (including n-propoxy and isopropoxy), butoxy (including n-butoxy, isobutoxy, s-butoxy and t-butoxy), and the like.

Unless otherwise specified, "$C_{2-4}$ alkenyl" is used to represent a hydrocarbon group consisting of 2 to 4 carbon atoms including at least one carbon-carbon double bond in a straight or branched chain, where the carbon-carbon double bond may be located anywhere in the group. The $C_{2-4}$ alkenyl includes $C_2$-3, $C_4$, $C_3$ and $C_2$ alkenyl, and the like; and the $C_{2-4}$ alkenyl may be monovalent, divalent, or multivalent. Examples of $C_{2-4}$ alkenyl includes, but are not limited to, vinyl, propylene, butenyl, interbutadienyl, and the like. Unless otherwise specified, "$C_{2-3}$ alkenyl" is used to represent a hydrocarbon group consisting of 2 to 3 carbon atoms including at least one carbon-carbon double bond in a straight or branched chain, where the carbon-carbon double bond may be located anywhere in the group. The $C_{2-3}$ alkenyl includes $C_3$ and $C_2$ alkenyl; and the $C_{2-3}$ alkenyl may be monovalent, divalent, or multivalent. Examples of $C_{2-3}$ alkenyl include, but are not limited to, vinyl, propylene, and the like.

Unless otherwise specified, "$C_{2-4}$ alkynyl" is used to represent a hydrocarbon group consisting of 2 to 4 carbon atoms including at least one carbon-carbon triple bond in a straight or branched chain, where the carbon-carbon triple bond may be located anywhere in the group. The $C_{2-4}$ alkynyl includes $C_{2-3}$, $C_4$, $C_3$ and $C_2$ alkynyl, and the like, and may be monovalent, divalent, or multivalent. Examples of $C_{2-4}$ alkynyl include, but are not limited to, acetynyl, propynyl, butynyl, and the like.

Unless otherwise specified, "$C_{3-6}$ cycloalkyl" represents a saturated cyclic hydrocarbon group consisting of 3 to 6 carbon atoms, which is a monocyclic and bicyclic system, and the $C_{3-6}$ cycloalkyl includes $C_{3-5}$, $C_{4-5}$ and $C_{5-6}$ cycloalkyl, and the like, and may be monovalent, bivalent, or multivalent. Examples of $C_{3-6}$ cycloalkyl include, but are not limited to, cyclopropyl, cyclobutyl, cyclopentyl, cyclohexyl, and the like.

Unless otherwise specified, the term "5-12-membered heterocyclic alkenyl" itself or in combination with other terms represents, respectively, a partially unsaturated cyclic group consisting of 5 to 12 ring atoms containing at least one carbon-carbon double bond, the 1, 2, 3 or 4 ring atoms thereof being heteroatoms independently selected from O, S, and N, and the remainder being carbon atoms, wherein the carbon atoms are optionally oxygenated (i.e., C(O)), the nitrogen atoms are optionally quaternized, and the nitrogen and sulfur heteroatoms are optionally oxidized (i.e., NO and $S(O)_p$, p being 1 or 2). Single ring, double ring and triple ring systems are included, wherein the double ring and triple ring systems include spirocyclic, fused cyclic and endocyclic systems, and any ring of the system is non-aromatic. In addition, in the case of the "5-12-membered heterocyclic alkenyl", the heteroatom may occupy the position where the heterocyclic alkenyl is linked to the remainder of the molecule. The 5-12-membered heterocyclic alkenyl includes 5-10-membered, 5-8-membered, 5-6-membered, 4-5-membered, 4-membered, 5-membered and 6-membered heterocyclic alkenyl, and the like.

Unless otherwise specified, the term "5-6-membered heterocyclic alkenyl" itself or in combination with other terms represents, respectively, a partially unsaturated cyclic group consisting of 5 to 6 ring atoms containing at least one carbon-carbon double bond, the 1, 2, 3 or 4 ring atoms thereof being heteroatoms independently selected from O, S, and N, and the remainder being carbon atoms, wherein the carbon atoms are optionally oxygenated (i.e., C(O)), the nitrogen atoms are optionally quaternized, and the nitrogen and sulfur heteroatoms are optionally oxidized (i.e., NO and $S(O)_p$, p being 1 or 2). Single ring and double ring systems are included, wherein the double ring system includes spirocyclic, fused cyclic and endocyclic systems, and any ring of the system is non-aromatic. In addition, in the case of the "5-6-membered heterocyclic alkenyl", the heteroatom may occupy the position where the heterocyclic alkenyl is linked to the remainder of the molecule. The 5-6-membered heterocyclic alkenyl includes 5-membered and 6-membered heterocyclic alkenyl, and the like. Examples of 5-6-membered heterocyclic alkenyl include, but are not limited to,

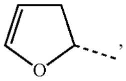,
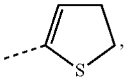,
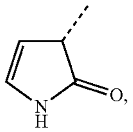,
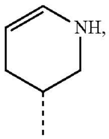, or
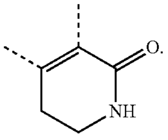.

Unless otherwise specified, the term "4-6-membered heterocyclic alkyl" itself or in combination with other terms represents, respectively, a saturated cyclic group consisting of 4 to 6 ring atoms, the 1, 2, 3 or 4 ring atoms thereof being heteroatoms independently selected from O, S, and N, and the remainder being carbon atoms, wherein the carbon atoms are optionally oxygenated (i.e., C(O)), the nitrogen atoms are optionally quaternized, and the nitrogen and sulfur heteroatoms are optionally oxidized (i.e., NO and $S(O)_p$, p being 1 or 2). Single ring and double ring systems are included, wherein the double ring system includes spirocyclic, fused cyclic and endocyclic systems. In addition, in the case of the "4-6-membered heterocyclic alkyl", the heteroatom may occupy the position where the heterocyclic alkyl is linked to the remainder of the molecule. The 4-6-membered heterocyclic alkyl includes 5-6-membered, 4-membered, 5-membered and 6-membered heterocyclic alkyl, and the like. Examples of 4-6-membered heterocyclic alkyl include, but are not limited to, azacyclobutyl, oxacyclobutyl, thiacyclobutyl, pyrrolidinyl, pyrazolidinyl, imidazolidinyl, tetrahydrothienyl (including tetrahydrothiophene-2-yl, tetrahydrothiophene-3-yl, and the like), tetrahydrofuryl (including tetrahydrofuran-2-yl, and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl,1,2-oxazinyl, 1,2-thiazinyl, or hexahydropyridazinyl, and the like.

Unless otherwise specified, the term "5-6-membered heterocyclic alkyl" itself or in combination with other terms represents, respectively, a saturated cyclic group consisting of 5 to 6 ring atoms, the 1, 2, 3 or 4 ring atoms thereof being heteroatoms independently selected from O, S, and N, and the remainder being carbon atoms, wherein the carbon atoms are optionally oxygenated (i.e., C(O)), the nitrogen atoms are optionally quaternized, and the nitrogen and sulfur heteroatoms are optionally oxidized (i.e., NO and $S(O)_p$, p being 1 or 2). Single ring and double ring systems are included, wherein the double ring system includes spirocyclic, fused cyclic and endocyclic systems. In addition, in the case of the "5-6-membered heterocyclic alkyl", the heteroatom may occupy the position where the heterocyclic alkyl is linked to the remainder of the molecule. The 5-6-membered heterocyclic alkyl includes 5-membered and 6-membered heterocyclic alkyl. Examples of 5-6-membered heterocyclic alkyl include, but are not limited to, pyrrolidinyl, pyrazolidinyl, imidazolidinyl, tetrahydrothienyl (including tetrahydrothiophene-2-yl, tetrahydrothiophene-3-yl, and the like), tetrahydrofuryl (including tetrahydrofuran-2-yl, and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl,1,2-oxazinyl, 1,2-thiazinyl, and hexahydropyridazinyl.

Unless otherwise specified, the term "7-12-membered tricyclic heterocyclic alkyl" itself or in combination with other terms represents, respectively, a tricyclic saturated cyclic group consisting of 7 to 12 ring atoms, the 1, 2, 3 or 4 ring atoms thereof being heteroatoms independently selected from O, S, and N, and the remainder being carbon atoms, wherein the carbon atoms are optionally oxygenated (i.e., C(O)), the nitrogen atoms are optionally quaternized, and the nitrogen and sulfur heteroatoms are optionally oxidized (i.e., NO and $S(O)_p$, p being 1 or 2). The 7-12-membered tricyclic heterocyclic alkyl includes spirocyclic, fused cyclic and endocyclic systems. In addition, in the case of the "7-12-membered tricyclic heterocyclic alkyl", the heteroatom may occupy the position where the heterocyclic alkyl is linked to the remainder of the molecule. The 7-12-membered tricyclic heterocyclic alkyl includes 7-10-membered, 7-8-membered, 8-10-membered, 8-12-membered, 9-10-membered, 9-12-membered, 10-12-membered, 9-membered and 10-membered heterocyclic alkyl, and the like.

Unless otherwise specified, the terms "5-10-membered heteroaromatic ring" and "5-10-membered heteroaryl" in the present invention may be used interchangeably, and the term "5-10-membered heteroaryl" represents a cyclic group consisting of 5 to 10 ring atoms and having a conjugated π electron system, the 1, 2, 3 or 4 ring atoms thereof being heteroatoms independently selected from O, S and N, and the remainder being carbon atoms. The 5-10-membered heteroaryl may be a monocyclic, fused bicyclic, or fused tricyclic system in which every ring is aromatic, wherein the nitrogen atom is optionally quaternized and the nitrogen and sulfur heteroatoms are optionally oxidized (i.e., NO and $S(O)_p$, p being 1 or 2). The 5-10-membered heteroaryl may be linked to the remainder of the molecule by heteroatoms or carbon atoms. The 5-10-membered heteroaryl includes 5-8-membered, 5-7-membered, 5-6-membered, 5-membered and 6-membered heteroaryl, and the like. Examples of the 5-10-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (1H-1,2,3-triazolyl, 2H-1,2,3-triazolyl, 1H-1,2,4-triazolyl, 4H-1,2,4-triazolyl, and the like), tetrazolyl, isoxazolyl (3-isoxazolyl, 4-isoxazolyl, 5-isoxazolyl, and the like), thiazolyl (including 2-thiazolyl, 4-thiazolyl, 5-thiazolyl, and the like), furyl (including 2-furyl, 3-furyl, and the like), thienyl (including 2-thienyl, 3-thienyl, and the like), pyridinyl (including 2-pyridinyl, 3-pyridinyl, 4-pyridinyl, and the like), pyrazinyl, pyrimidinyl (including 2-pyrimidinyl, 4-pyrimidinyl, and the like), benzothiazolyl (including 5-benzothiazolyl, and the like), purinyl, benzimidazolyl (including 2-benzimidazolyl, and the like), benzoxazolyl, indolyl (including 5-indolyl, and the like), isoquinolyl (including 1-isoquinolyl, 5-isoquinolyl, and the like), quinoxalinyl (including 2-quinoxalinyl, 5-quinoxalinyl, and the like), or quinolinyl (including 3-quinolinyl, 6-quinolinyl, and the like).

Unless otherwise specified, the terms "5-6-membered heteroaromatic ring" and "5-6-membered heteroaryl" in the present invention may be used interchangeably, and the term "5-6-membered heteroaryl" represents a monocyclic group consisting of 5 to 6 ring atoms and having a conjugated $\pi$ electron system, the 1, 2, 3 or 4 ring atoms thereof being heteroatoms independently selected from O, S and N, and the remainder being carbon atoms, wherein the nitrogen atom is optionally quaternized and the nitrogen and sulfur heteroatoms are optionally oxidized (i.e., NO and $S(O)_p$, p being 1 or 2). The 5-6-membered heteroaryl may be linked to the remainder of the molecule by heteroatoms or carbon atoms. The 5-6-membered heteroaryl includes 5-membered and 6-membered heteroaryl. Examples of the 5-6-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (1H-1,2,3-triazolyl, 2H-1,2,3-triazolyl, 1H-1,2,4-triazolyl, 4H-1,2,4-triazolyl, and the like), tetrazolyl, isoxazolyl (3-isoxazolyl, 4-isoxazolyl, 5-isoxazolyl, and the like), thiazolyl (including 2-thiazolyl, 4-thiazolyl, 5-thiazolyl, and the like), furyl (including 2-furyl, 3-furyl, and the like), thienyl (including 2-thienyl, 3-thienyl, and the like), pyridinyl (including 2-pyridinyl, 3-pyridinyl, 4-pyridinyl, and the like), pyrazinyl, or pyrimidinyl (including 2-pyrimidinyl, 4-pyrimidinyl, and the like).

Unless otherwise specified, the terms "5-6-membered nitrogen-containing heteroaromatic ring" and "5-6-membered nitrogen-containing heteroaryl" in the present invention may be used interchangeably, and the term "5-6-membered nitrogen-containing heteroaryl" represents a monocyclic group consisting of 5 to 6 ring atoms and having a conjugated 71 electron system, the 1, 2, 3 or 4 ring atoms thereof being heteroatoms independently selected from O, S and N, at least one heteroatom being N, and the remainder being carbon atoms, wherein the nitrogen atom is optionally quaternized and the nitrogen and sulfur heteroatoms are optionally oxidized (i.e., NO and $S(O)_p$, p being 1 or 2). The 5-6-membered heteroaryl may be linked to the remainder of the molecule by heteroatoms or carbon atoms. The 5-6-membered heteroaryl includes 5-membered and 6-membered heteroaryl. Examples of the 5-6-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (1H-1,2,3-triazolyl, 2H-1,2,3-triazolyl, 1H-1,2,4-triazolyl, 4H-1,2,4-triazolyl, and the like), tetrazolyl, isoxazolyl (3-isoxazolyl, 4-isoxazolyl, 5-isoxazolyl, and the like), thiazolyl (including 2-thiazolyl, 4-thiazolyl, 5-thiazolyl, and the like), pyridinyl (including 2-pyridinyl, 3-pyridinyl, 4-pyridinyl, and the like), pyrazinyl, or pyrimidinyl (including 2-pyrimidinyl, 4-pyrimidinyl, and the like).

The compound of the present invention may be prepared by a variety of synthetic methods well known to those skilled in the art, including, but not limited to, the specific embodiments listed below, embodiments formed by combination with other chemical synthetic methods, and equivalent substitution methods well known to those skilled in the art, and the preferred embodiments include, but are not limited to, embodiments of the present invention.

The compound of the present invention can be structurally confirmed by conventional methods well known to those skilled in the art, and if the present invention relates to an absolute configuration of the compound, the absolute configuration can be confirmed by conventional technical means in the art. For example, using a single crystal X ray diffraction (SXRD) method, diffraction intensity data is collected from cultured single crystals by a Bruker D8 venture diffractometer, the light source being CuKα radiation, and the scanning mode being (p/o scan; and after the relevant data is collected, further the crystal structure is analyzed by a direct method (Shelxs97) to confirm the absolute configuration.

The solvent used in the present invention is commercially available. The present invention uses the following abbreviations: DMF for N,N-dimethylformamide; DIPEA for N,N-diisopropylethylamine; DCM for dichloromethane; m-CPBA for m-chloroperoxybenzoic acid; NBS for N-bromosuccinimide; HATU for 2-(7-azobenzotriazole)-N,N,N',N'-tetramethylurea hexafluorophosphate; NCS for N-chlorosuccinimide; and Dess-Martin periodinane for (1,1,1-triacetyloxy)-1,1-dihydro-1,2-phenioyl-3(1H)-one.

Compounds are named in accordance with the general nomenclature in the art or using ChemDraw® software, and commercially available compounds are named using a Suppliers Directory.

DETAILED DESCRIPTION OF THE INVENTION

The present invention is described in detail below by the embodiments, which does not imply any adverse limitation to the present invention. The present invention has been described in detail herein, and specific embodiments thereof are also disclosed. It will be apparent to those skilled in the art that a variety of modifications and improvements to specific embodiments of the present invention may be made without departing from the spirit and scope of the present invention.

Embodiment 1

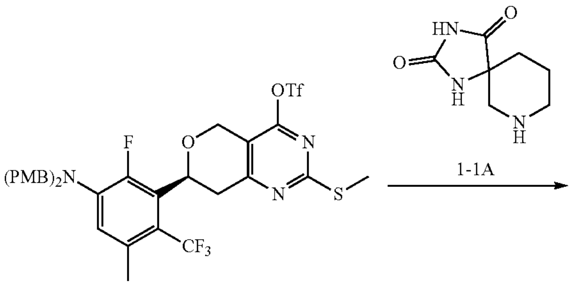

1-1

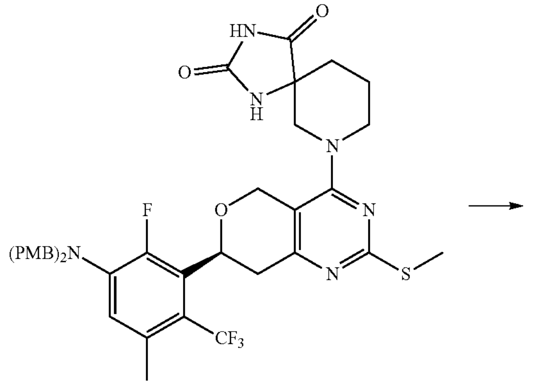

1-2

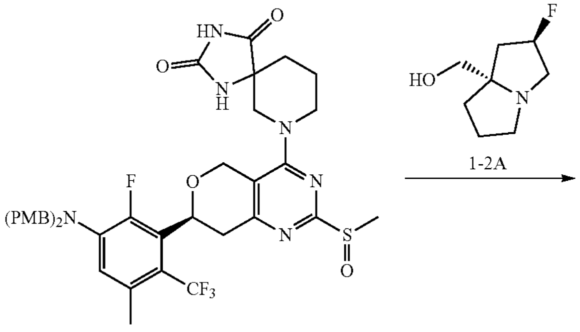

1-3

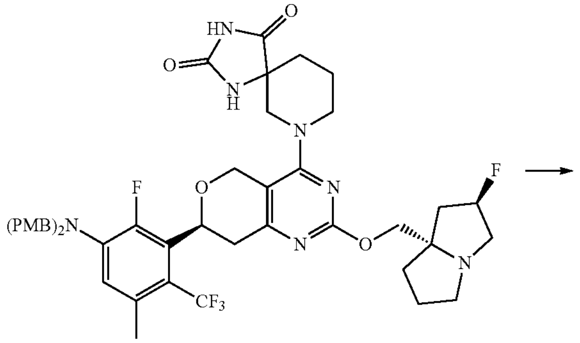

1-4

-continued

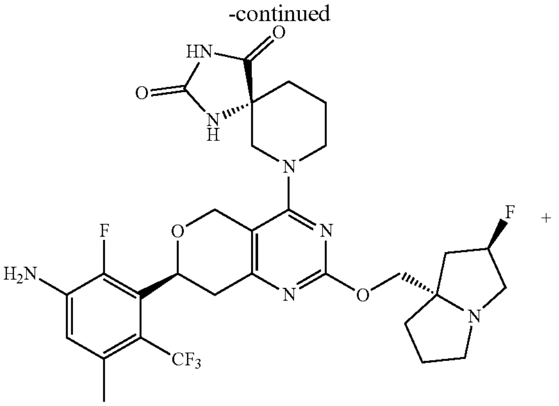

1A or 1B

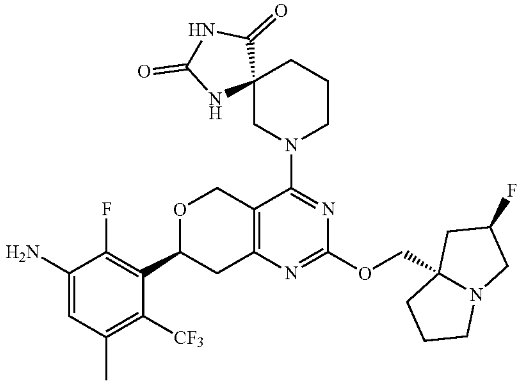

1B or 1A

Step 1: Synthesis of Compound 1-2

Compounds 1-1 (1 g, 1.31 mmol) and 1-1A (444.20 mg, 2.63 mmol) were weighed and dissolved with DMF (50 mL). DIPEA (1.70 g, 13.13 mmol, 2.29 mL) was added to react at 100° C. for 2 h. The reaction solution was quenched with water (50 mL), extracted with ethyl acetate (50 mL×2), washed with water (30 mL), and concentrated. Compound 1-2 was obtained, with MS m/z=781.5 $[M+H]^+$.

Step 2: Synthesis of Compound 1-3

Compound 1-2 (1.06 g, 1.36 mmol) was weighed and dissolved with DCM (30 mL). m-CPBA (276.34 mg, 1.36 mmol, 85% purity) was added at 0° C. to react at 25° C. for 1 h. The reaction solution was concentrated to obtain compound 1-3, with MS m/z=797.5 $[M+H]^+$.

Step 3: Synthesis of Compound 1-4

Compound 1-2A (847.12 mg, 5.32 mmol) was dissolved with anhydrous tetrahydrofuran (20 mL). Sodium tert-butanol (511.38 mg, 5.32 mmol) was added to react at 0° C. for 30 min. Compound 1-3 (1.06 g, 1.33 mmol) was added to react at 25° C. for 1 h. 20 mL of a saturated ammonium chloride solution was added to the reaction solution. The reaction solution was extracted with ethyl acetate (20 mL×2), washed with 20 mL of a saturated table salt solution, dried with anhydrous sodium sulfate, and concentrated to obtain compound 1-4. MS m/z=892.6 $[M+H]^+$.

Step 4: Synthesis of Hydrochlorides of Compounds 1A and 1B

Compound 1-4 (0.7 g, 784.82 mol) was dissolved with dichloromethane (5 mL). Trifluoroacetic acid (1 mL) was added to react at 25° C. for 2 h. After the reaction, the reaction solution was concentrated directly. By HPLC) (Phenomenex C18 150×40 mm×5 μm; mobile phase: [water (0.05% HCl)-acetonitrile]; acetonitrile %: 10-30%), the hydrochloride of compound 1A and hydrochloride of compound 1B were obtained. Analysis method: Chromatographic column: ChromCore 120 C18 3 μm, 3.0×30 mm; mobile phase: [water (0.04% trifluoroacetic acid)-acetonitrile (0.02% trifluoroacetic acid)]; gradient: acetonitrile (0.02% trifluoroacetic acid) %: 10-80%, 7 min_220&254 nm); retention time: 1A (Rt=2.694 min), MS m/z=652.3 $[M+H]^+$, 1B (Rt=2.848 min), MS m/z=652.2 $[M+H]^+$.

1A: $^1H$ NMR (400 MHz, $CD_3OD$) δ 6.90-6.66 (m, 1H), 5.75-5.45 (m, 1H), 5.39-5.22 (m, 1H), 5.00-4.94 (m, 2H), 4.79-4.63 (m, 3H), 4.24-4.07 (m, 1H), 4.02-3.81 (m, 3H), 3.71-3.62 (m, 1H), 3.61-3.54 (m, 1H), 3.51-3.44 (m, 1H), 3.42-3.35 (m, 1H), 3.17-3.04 (m, 1H), 2.71-2.46 (m, 3H), 2.27-2.17 (m, 1H), 2.23 (dt, J=4.1, 13.1 Hz, 6H), 2.10-1.99 (m, 1H), 1.96-1.78 (m, 2H).

1B: $^1H$ NMR (400 MHz, $CD_3OD$) δ 7.43-7.34 (m, 1H), 7.06-6.90 (m, 1H), 6.88-6.76 (m, 1H), 5.74-5.50 (m, 1H), 5.35-5.20 (m, 1H), 5.02-4.96 (m, 1H), 4.78-4.72 (m, 2H), 4.52-4.39 (m, 1H), 4.20-4.07 (m, 1H), 4.05-3.77 (m, 4H), 3.53-3.38 (m, 3H), 3.13-2.99 (m, 1H), 2.78-2.58 (m, 2H), 2.53-2.43 (m, 1H), 2.40 (br d, J=3.8 Hz, 3H), 2.37-2.31 (m, 2H), 2.28-2.15 (m, 1H), 2.12-2.01 (m, 1H), 2.00-1.89 (m, 2H).

Embodiment 2

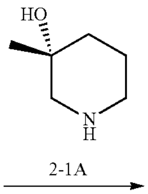

2-1A 1-1

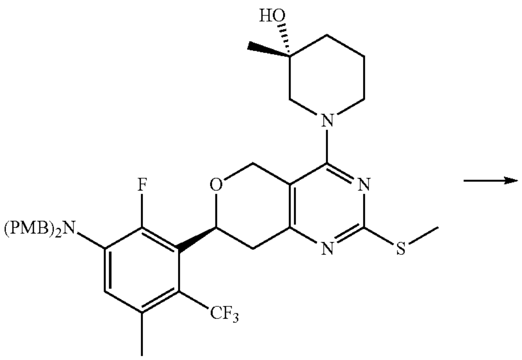

2-1

-continued

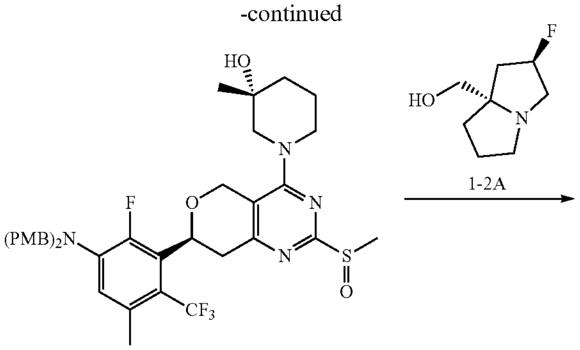

1-2A 2-2

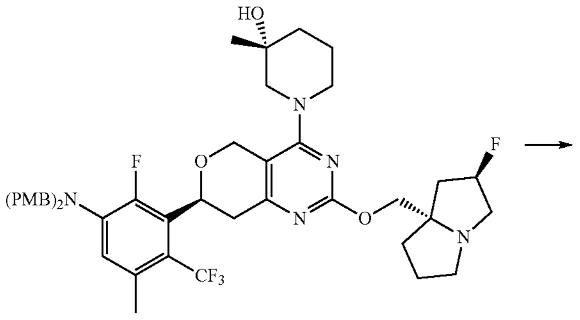

2-3

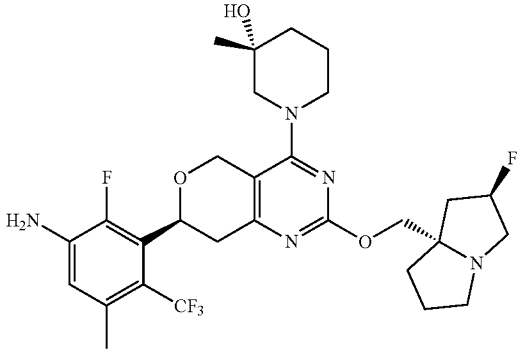

2

Step 1: Synthesis of Compound 2-1

Compounds 1-1 (800 mg, 1.05 mmol) and 2-1A (175.18 mg, 1.16 mmol) were weighed and DMF (10 mL) was added. DIPEA (407.21 mg, 3.15 mmol, 548.80 μL) was added to react at 100° C. for 2 h. The reaction solution was quenched with water (50 mL), extracted with ethyl acetate (50 mL×2), washed with water (30 mL), concentrated, and separated by column chromatography (petroleum ether:ethyl acetate=10:1) to obtain compound 2-1, with MS m/z=727.3 $[M+H]^+$.

Step 2: Synthesis of Compound 2-2

Compound 2-1 (620 mg, 853.03 μmol) was weighed and dissolved with DCM (20 mL). m-CPBA (173.18 mg, 853.03 μmol, 85% purity) was added to react at 25° C. for 1 h. The reaction solution was diluted with 50 mL of dichloromethane, washed with 30 mL of a saturated table salt solution, dried with anhydrous sodium sulfate, filtered, concentrated, and separated by column chromatography (dichloromethane:methanol=20:1), to obtain compound 2-2, with MS m/z=743.3 $[M+H]^+$.

Step 3: Synthesis of Compound 2-3

Compound 1-2A (128.59 mg, 807.73 μmol) was dissolved with anhydrous tetrahydrofuran (10 mL). Sodium tert-butanol (77.62 mg, 807.73 μmol) was added to react at 25° C. for 30 min. Compound 2-2 (300 mg, 403.87 μmol) was added to react at 25° C. for 1 h. The reaction solution was diluted with 60 mL of ethyl acetate, washed with 30 mL of a saturated table salt solution, dried with anhydrous sodium sulfate, filtered, and concentrated to obtain compound 2-3. MS m/z=838.4 $[M+H]^+$.

Step 4: Synthesis of Hydrochloride of Compound 2

Compound 2-3 (0.3 g, 358.03 μmol) was dissolved with dichloromethane (3 mL). Trifluoroacetic acid (3 mL) was added to react at 25° C. for 2 h. After the reaction, the reaction solution was concentrated directly. By HPLC) (Phenomenex C18 150×40 mm×5 μm; mobile phase: [water (0.05% HCl)-acetonitrile]; acetonitrile %: 5-35%, 10 min), the hydrochloride of compound 2 was obtained. MS m/z=598.4 $[M+H]^+$. $^1H$ NMR (400 MHz, $CD_3OD$) δ ppm 6.85-6.67 (m, 1H), 5.69-5.52 (m, 1H), 5.32-5.22 (m, 1H), 5.00-4.94 (m, 1H), 4.80-4.74 (m, 3H), 4.61-4.34 (m, 1H), 4.06-3.83 (m, 4H), 3.55-3.36 (m, 3H), 3.25-3.10 (m, 1H), 3.07-2.95 (m, 1H), 2.82-2.61 (m, 2H), 2.54-2.44 (m, 1H), 2.42-2.30 (m, 5H), 2.30-2.17 (m, 1H), 2.14-1.98 (m, 1H), 1.89-1.65 (m, 3H), 1.34-1.25 (m, 3H).

Embodiment 3

1-1

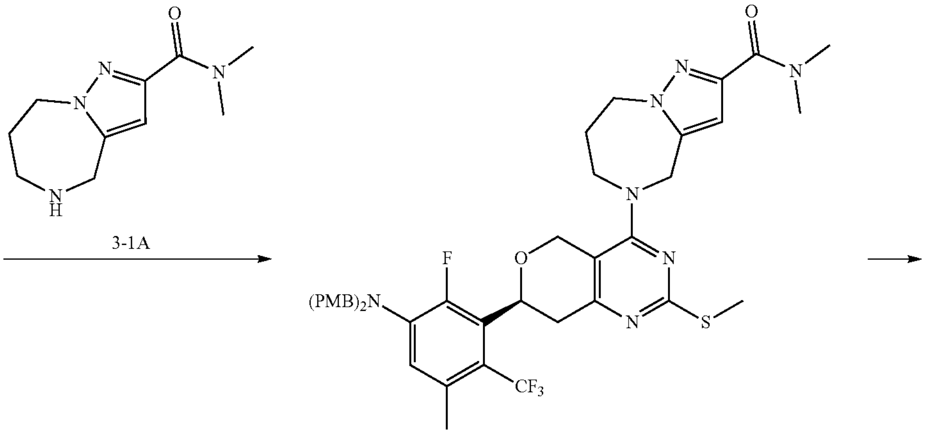

3-1A 3-1

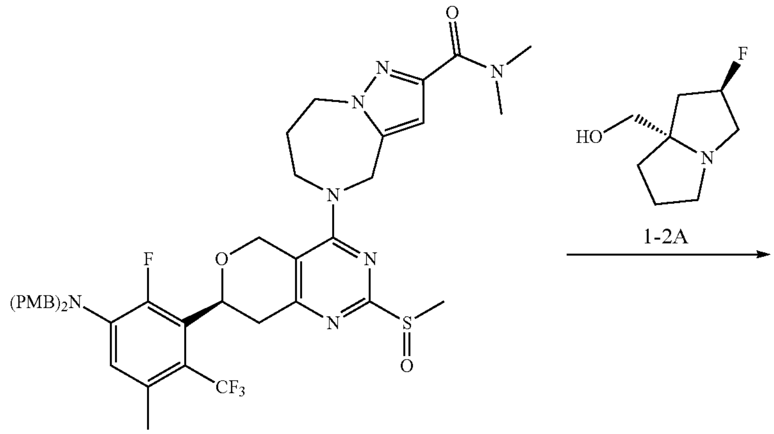

1-2A 3-2

-continued

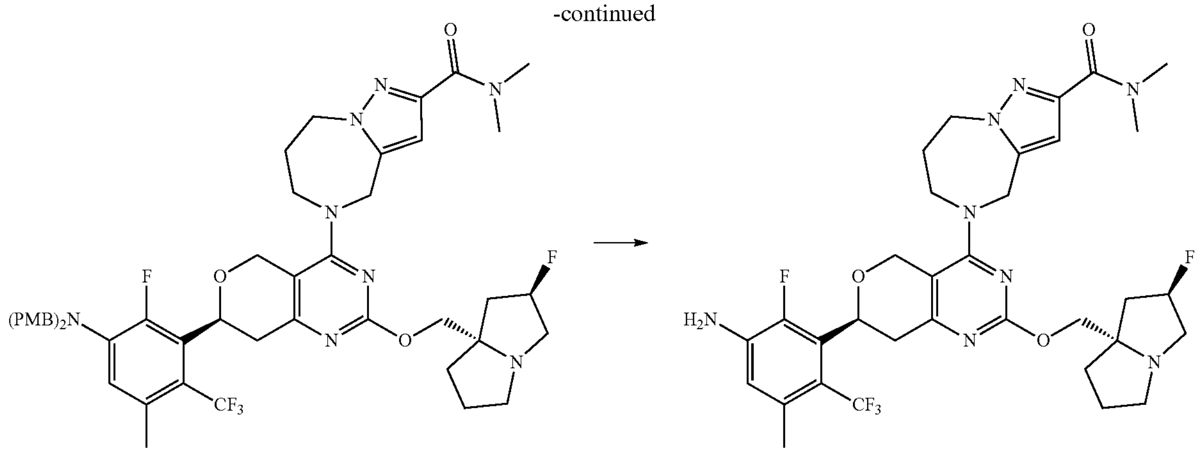

3-3 3

Step 1: Synthesis of Compound 3-1

Compounds 1-1 (300 mg, 0.39 mmol) and 3-1A (144.57 mg, 0.59 mmol) were weighed and DMF (5 mL) was added. DIPEA (152.70 mg, 1.18 mmol, 205.80 L) was added to react at 100° C. for 1 h. The reaction solution was concentrated directly and separated by column chromatography (petroleum ether:ethyl acetate=4:1-1:1) to obtain compound 3-1, with MS m/z=820.5 $[M+H]^+$.

Step 2: Synthesis of Compound 3-2

Compound 3-1 (320 mg, 390.29 mol) was weighed and dissolved with DCM (5 mL). m-CPBA (79.24 mg, 390.29 mol, 85% purity) was added to react at 25° C. for 0.5 h. The reaction solution was diluted with 40 mL of dichloromethane, washed with 20 mL of a saturated table salt solution, dried with anhydrous sodium sulfate, filtered, concentrated, and separated by column chromatography (dichloromethane:methanol=20:1), to obtain compound 3-2, with MS m/z=836.5 $[M+H]^+$.

Step 3: Synthesis of Compound 3-3

Compound 1-2A (91.42 mg, 574.23 mol) was dissolved with anhydrous tetrahydrofuran (5 mL). Sodium tert-butanol (55.19 mg, 574.23 mol) was added to react at 25° C. for 30 min. Compound 3-2 (300 mg, 358.89 μmol) was added to react at 25° C. for 1 h. The reaction solution was diluted with 40 mL of ethyl acetate, washed with 20 mL of a saturated table salt solution, dried with anhydrous sodium sulfate, filtered, and concentrated to obtain compound 3-3. MS m/z=931.7 $[M+H]^+$.

Step 4: Synthesis of Hydrochloride of Compound 3

Compound 3-3 (310 mg, 332.97 mol) was dissolved with dichloromethane (3 mL). Trifluoroacetic acid (3 mL) was added to react at 25° C. for 1 h. After the reaction, the reaction solution was concentrated. By high performance liquid chromatography (HPLC) (Phenomenex C18 150×40 mm×5 μm; mobile phase: [water (0.05% HCl)-acetonitrile]; acetonitrile %: 13-43%, 10 min), the hydrochloride of compound 3 was obtained. MS m/z=691.4[M+H]+. 1H NMR (400 MHz, CD3OD) δ ppm 7.08-6.91 (m, 1H), 6.87-6.71 (m, 1H), 5.77-5.47 (m, 1H), 5.35-5.15 (m, 2H), 4.99 (brs, 3H), 4.89-4.81 (m, 1H), 4.78-4.69 (m, 1H), 4.67-4.55 (m, 1H), 4.53-4.43 (m, 1H), 4.21-4.05 (m, 2H), 4.03-3.80 (m, 3H), 3.53-3.34 (m, 5H), 3.20-2.99 (m, 4H), 2.80-2.61 (m, 2H), 2.60-2.51 (m, 1H), 2.50-2.17 (m, 8H).

Embodiment 4

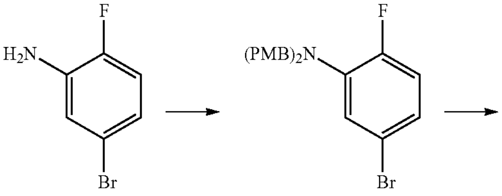

4-1 4-2

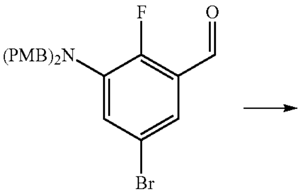

4-3

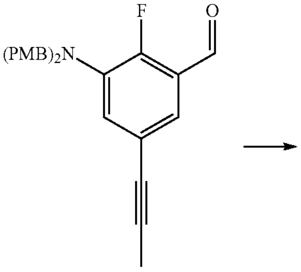

4-4

-continued
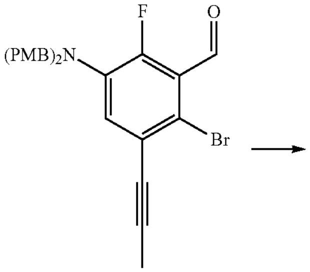
4-5
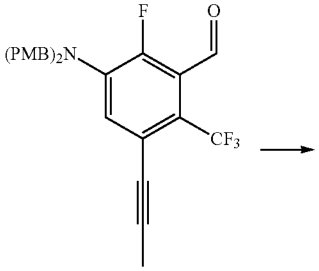
4-6
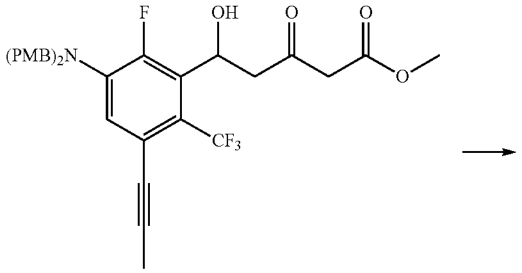
4-7
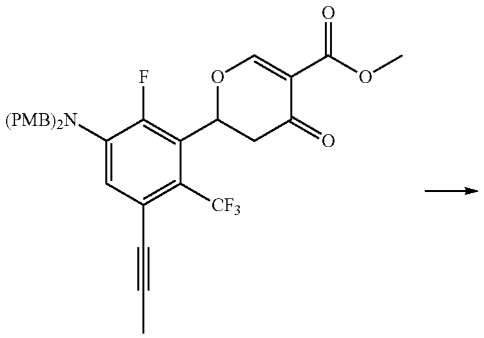
4-8
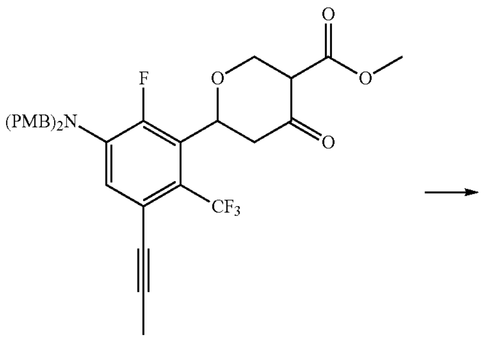
4-9
-continued
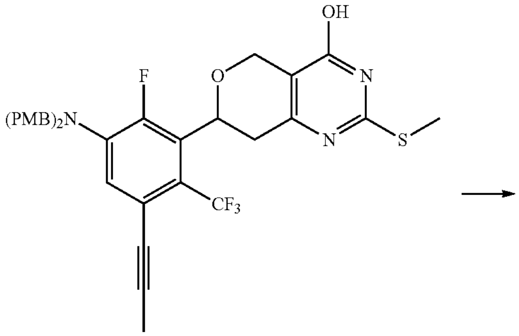
4-10
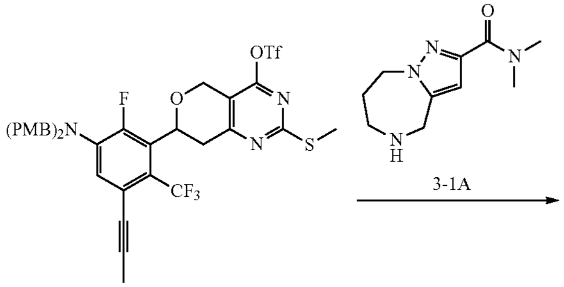
4-11
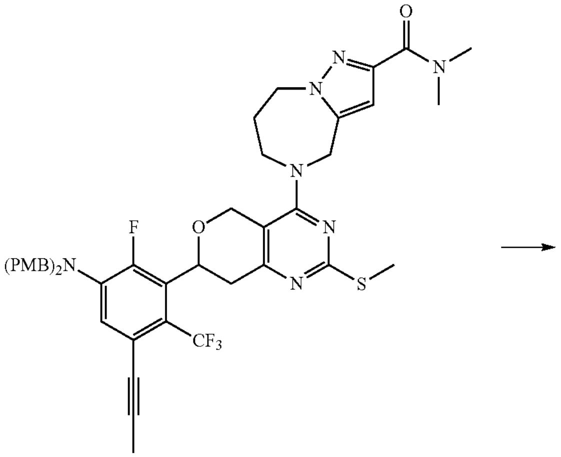
4-12
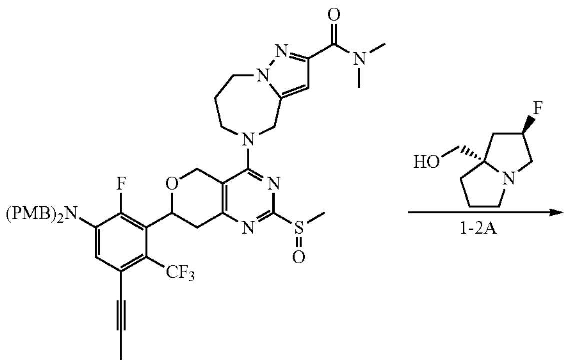
4-13

-continued

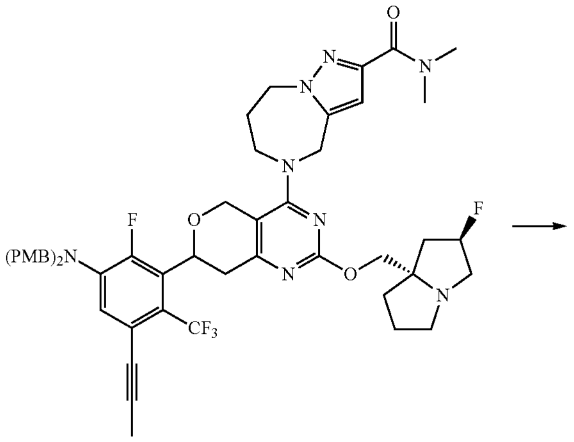

4-14

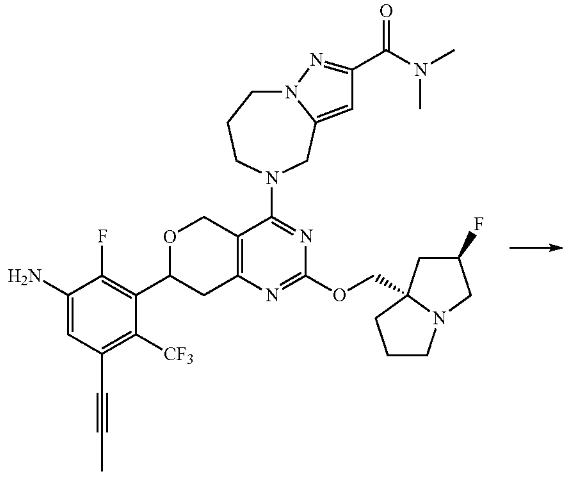

4

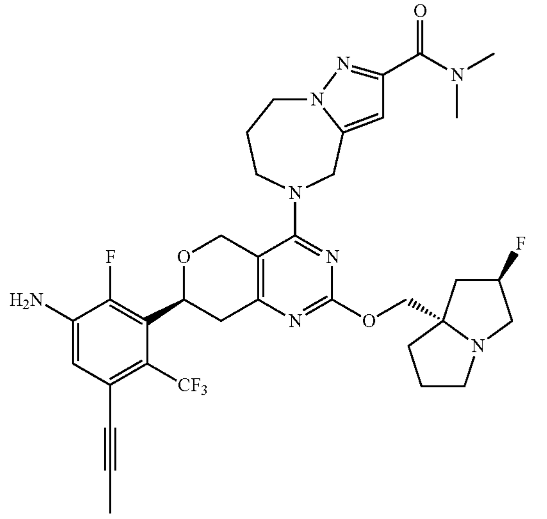

4A or 4B

+

-continued

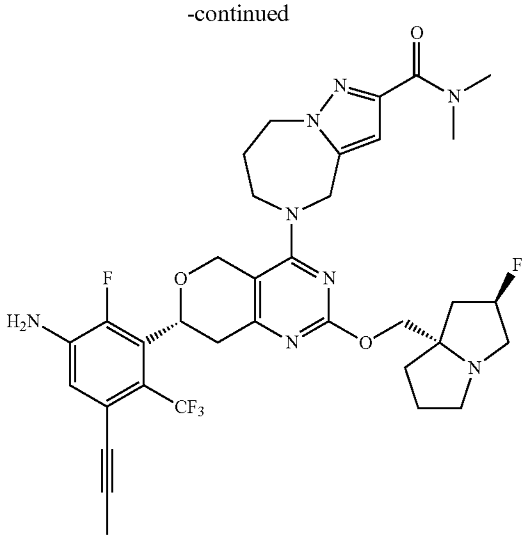

4B or 4A

Step 1: Synthesis of Compound 4-2

Compound 4-1 (480 g, 2.53 mol) was weighed and DMF (2,500 mL) was added. 4-methoxybenzyl chloride (5.18 mol, 702.79 mL), potassium carbonate (872.82 g, 6.32 mol), and potassium iodide (419.35 g, 2.53 mol) were added to react at 65° C. for 2 h. The reaction solution was quenched with water (1,000 mL), extracted with ethyl acetate (1,000 mL×3), and concentrated under reduced pressure in an organic phase to obtain compound 4-2, with MS m/z=430.0 $[M+H]^+$.

Step 2: Synthesis of Compound 4-3

Compound 2,2,6,6-tetramethylpiperidine (220.59 g, 1.56 mol, 265.13 mL) was weighed and THF (3,000 mL) was added. n-butyl lithium (2.5 M, 499.73 mL) was added at −5° C., stirred for 0.5 h, and cooled to −60° C. Compound 4-2 (280 g, 624.67 mmol) was added and stirred for 0.5 h. Finally, DMF (228.28 g, 3.12 mol, 240.30 mL) was added. The reaction was continued for 0.5 h. The reaction solution was quenched by pouring into water (1,000 mL), adjusted to pH 7 with hydrochloric acid, extracted with ethyl acetate (1,000 mL×3), concentrated under reduced pressure, and separated by column chromatography (petroleum ether:ethyl acetate=10:1) to obtain compound 4-3.

Step 3: Synthesis of Compound 4-4

Compound 4-3 (370 g, 807.30 mmol) was weighed. Toluene (1,500 mL), dichlorobis[di-tert-butyl-(4-dimethylaminophenyl)phosphine]palladium (2.86 g, 4.04 mmol, 2.86 mL), and tri-butyl(1-propargynyl)tin (265.69 g, 807.30 mmol) were added to react at 120° C. for 2 h under nitrogen protection. The reaction solution was concentrated under reduced pressure and separated by column chromatography (petroleum ether: ethyl acetate=5:1) to obtain compound 4-4. MS m/z=418.1 $[M+H]^+$.

Step 4: Synthesis of Compound 4-5

Compound 4-4 (450 g, 970.13 mmol) was weighed and DMF (100 mL) was added. N-bromosuccinimide (189.93 g, 1.07 mol) was added to react at 25° C. for 2 h. Supplementary N-bromosuccinimide (17.27 g, 97.01 mmol) was added to continue to react for 3 h. The reaction solution was spin dried directly and separated by column chromatography (petroleum ether: ethyl acetate=5:1) to obtain compound 4-5. MS m/z=496.0 $[M+H]^+$.

Step 5: Synthesis of Compound 4-6

Compound 4-5 (55 g, 110.81 mmol) was weighted and DMF (300 mL) was added. Methyl fluorosulfonyl difluoroacetate (42.57 g, 221.61 mmol, 28.19 mL) and cuprous iodide (42.21 g, 221.61 mmol) were added to react at 110° C. for 2 h under nitrogen protection. The reaction solution was quenched with 500 mL of water and extracted with ethyl acetate (600 mL×3. The extracted organic phases were mixed, washed with water (800 mL×2) and a saturated table salt solution (800 mL) in sequence, dried with anhydrous sodium sulfate, filtered, and concentrated. The organic phase was separated by column chromatography (petroleum ether: ethyl acetate=10:1) to obtain compound 4-6. MS m/z=485.9 $[M+H]^+$.

Step 6: Synthesis of Compound 4-7

Methyl acetoacetate (18.42 g, 158.61 mmol, 17.10 mL) was added dropwise to a tetrahydrofuran solution (350 mL) of sodium hydrogen (6.34 g, 158.61 mmol, 60% purity) at 0° C. to react for 15 min. The reaction solution was cooled to −20° C. Then n-butyl lithium (2.5 M, 63.44 mL) was added dropwise and stirred for 15 min after the dropwise addition. Then a tetrahydrofuran solution (350 mL) of compound 4-6 (35 g, 72.10 mmol) was added to react for 0.5 h. The reaction solution was quenched with 200 mL of a saturated ammonium chloride solution and extracted with ethyl acetate (300 mL×2). The extracted organic phases were mixed, washed with a saturated table salt solution (400 mL), dried with anhydrous sodium sulfate, filtered, and concentrated. The organic phase was separated by column chromatography (petroleum ether: ethyl acetate=10:1-1:1) to obtain compound 4-7. MS m/z=624.2 $[M+Na]^+$.

Step 7: Synthesis of Compound 4-8

Compound 4-7 (38 g, 63.17 mmol) was weighed and dichloromethane (300 mL) was added. Then N, N-dimethylformamide dimethyl acetal (9.03 g, 75.80 mmol) was added to react at 25° C. for 16 h. The reaction solution was cooled to 0° C. Boron trifluoride ether (10.76 g, 75.80 mmol, 9.32 mL) was added. The system was stirred at 0° C. for 1 h. 200 mL of a saturated sodium bicarbonate solution was added to the system. The organic phase was separated. The aqueous phase was extracted with 200 mL of dichloromethane. The extracted organic phases were mixed, washed with 250 mL of a saturated table salt solution, dried with anhydrous sodium sulfate, filtered, and concentrated. The organic phase was separated by column chromatography (petroleum ether: ethyl acetate=10:1-1:1) to obtain compound 4-8. MS m/z=612.1 $[M+H]^+$.

Step 8: Synthesis of Compound 4-9

Compound 4-8 (30 g, 49.05 mmol) was weighed and tetrahydrofuran (300 mL) was added. Lithium tributylborohydride (1 M, 53.96 mL) was added at −60° C. to react at −60° C. for 1 h. The reaction was quenched with 200 mL of water to the system. The reaction solution was extracted with ethyl acetate (300 mL×2). The extracted organic phases were mixed, washed with a saturated table salt solution (300 mL), dried with anhydrous sodium sulfate, filtered, and concentrated. The organic phase was separated by column chromatography (petroleum ether: ethyl acetate=10:1-5:1) to obtain compound 4-9. MS m/z=614.1 $[M+H]^+$.

Step 9: Synthesis of Compound 4-10

Compound 4-9 (20 g, 32.59 mmol) was weighed and ethanol (200 mL) was added. Then 2-methyl-2-thiourea sulfate (27.22 g, 97.78 mmol) and sodium carbonate (6.91 g, 65.19 mmol) were added to react at 50° C. for 13 h. The reaction solution was concentrated and 40 mL of water was added. The reaction solution was extracted with ethyl acetate (50 mL×2). The extracted organic phases were mixed, washed with 60 mL of a saturated table salt solution, dried with anhydrous sodium sulfate, filtered, and concentrated to obtain compound 4-10. MS m/z=654.3 $[M+H]^+$.

Step 10: Synthesis of Compound 4-11

Compound 4-10 (21 g, 32.13 mmol) was weighed and DMF (200 mL) was added. Then N, N-diisopropylethylamine (12.46 g, 96.38 mmol, 16.79 mL) and N-phenylbis (trifluoromethane sulfonyl)imine (13.77 g, 38.55 mmol) were added to react at 25° C. for 1 h. 300 mL of water was added to the system. The reaction solution was extracted with ethyl acetate (300 mL×3), washed with water (400 mL×2) and a saturated table salt solution (400 mL) in sequence, dried with anhydrous sodium sulfate, filtered, and concentrated. The organic phase was separated by column chromatography (petroleum ether: ethyl acetate=10:1) to obtain compound 4-11.

Step 11: Synthesis of Compound 4-12

Compounds 4-11 (5 g, 6.36 mmol) and 3-1A (2.34 g, 9.55 mmol) were weighed and DMF (15 mL) was added. DIPEA (2.47 g, 19.09 mmol, 3.33 mL) was added to react at 100° C. for 1 h. The reaction solution was concentrated directly and separated by column chromatography (petroleum ether: ethyl acetate=1:1) to obtain compound 4-12, with MS m/z=844.3 $[M+H]^+$.

Step 12: Synthesis of Compound 4-13

Compound 4-12 (5.3 g, 6.28 mmol) was weighed and dissolved with DCM (60 mL). m-CPBA (1.27 g, 6.28 mmol, 85% purity) was added to react at 25° C. for 0.5 h. The reaction solution was diluted with 100 mL of dichloromethane, washed with 80 mL of a saturated table salt solution, dried with anhydrous sodium sulfate, filtered, and concentrated to obtain compound 4-13, with MS m/z=860.5 $[M+H]^+$.

Step 13: Synthesis of Compound 4-14

Compound 1-2A (1.30 g, 8.16 mmol) was dissolved with anhydrous tetrahydrofuran (60 mL). Sodium tert-butanol (784.51 mg, 8.16 mmol) was added to react at 25° C. for 30 min. Compound 4-13 (5.4 g, 6.28 mmol) was added to react at 25° C. for 0.5 h. The reaction solution was diluted with 300 mL of ethyl acetate, washed with 200 mL of a saturated table salt solution, dried with anhydrous sodium sulfate, filtered, concentrated, and separated by column chromatography (dichloromethane:methanol=20:1) to obtain compound 4-14. MS m/z=955.8 [M+H]$^+$.

Step 14: Synthesis of Compounds 4A and 4B

Compound 4-14 (3.4 g, 3.56 mmol) was dissolved with dichloromethane (10 mL). Trifluoroacetic acid (5 mL) was added to react at 20° C. for 1 h. The reaction solution was concentrated, adjusted to pH 9-11 with a saturated sodium carbonate solution, and extracted with dichloromethane (100 mL×2). The extracted organic phases were mixed, dried with anhydrous sodium sulfate, filtered, concentrated, and separated by column chromatography (dichloromethane:methanol=20:1) to obtain compound4. SFC separation was carried out (chromatographic column: DAICEL CHIRALCEL OD (250 mm×50 mm, 10 m); mobile phase: [supercritical $CO_2$-methanol (0.1% ammonia)]; methanol (0.1% ammonia) %: 40-40%) to obtain compound 4A and compound 4B. Chiral SFC analysis was carried out (chromatographic column: DAICEL CHIRALCEL OD-3 (150 mm×4.6 mm, 3 μm); mobile phase: [supercritical $CO_2$-methanol (0.05% diethylamine)]; (methanol (0.05% diethylamine)) %: 40-40%), compound 4A, Rt=3.084 min, ee value 99%; compound 4B, Rt=5.110 min, ee value 98%.

Compound 4A: MS m/z=715.4 [M+H]$^+$, $^1$H NMR (400 MHz, $CD_3OD$) δ ppm 6.98-6.86 (m, 1H), 6.73-6.58 (m, 1H), 5.40-5.21 (m, 1H), 5.20-5.12 (m, 1H), 4.84 (brs, 4H), 4.58-4.40 (m, 2H), 4.15-4.04 (m, 2H), 4.00-3.82 (m, 2H), 3.34 (s, 6H), 3.37-3.17 (m, 1H), 3.12-3.06 (m, 3H), 3.06-2.98 (m, 1H), 2.90-2.80 (m, 1H), 2.35-2.21 (m, 2H), 2.20-2.06 (m, 3H), 2.05-2.02 (m, 3H), 2.01-1.84 (m, 3H). Compound 4B: MS m/z=715.4 [M+H]$^+$.

Embodiment 5

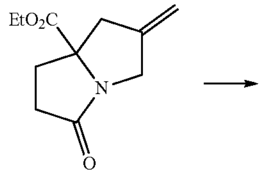

5-1

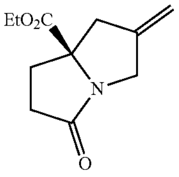

or

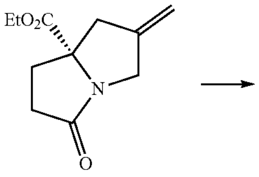

5-1A

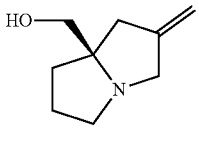

or

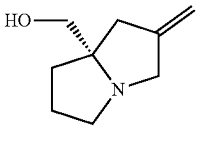

5-2

-continued

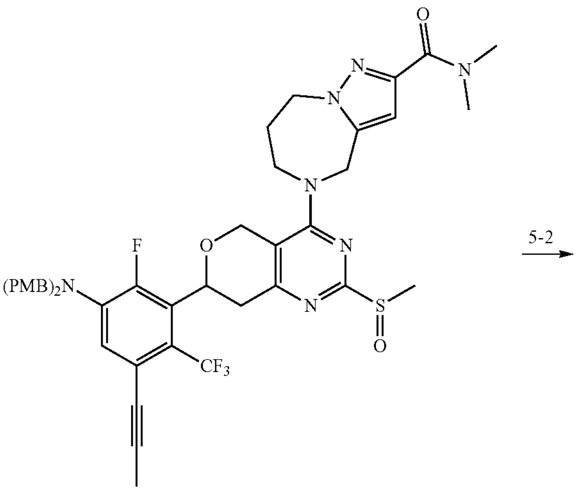

4-13

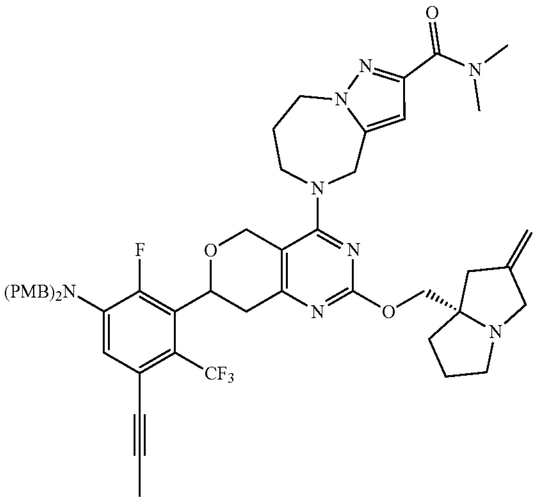

or

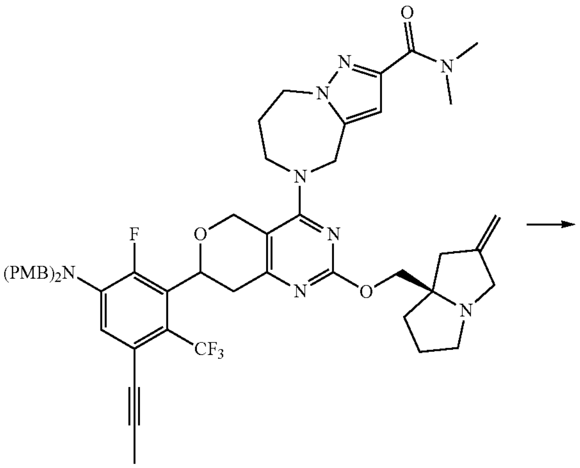

5-3

-continued
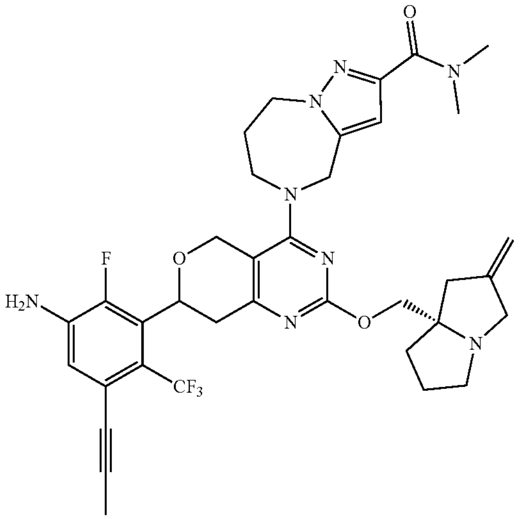
or
-continued
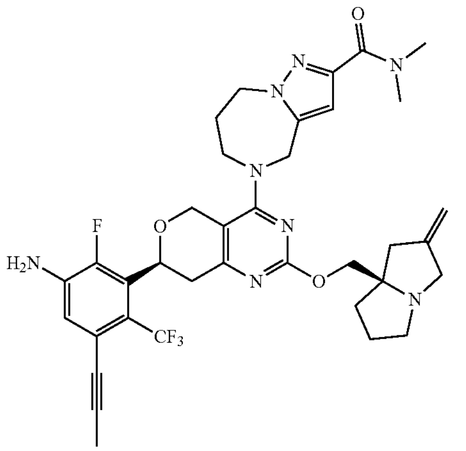
or
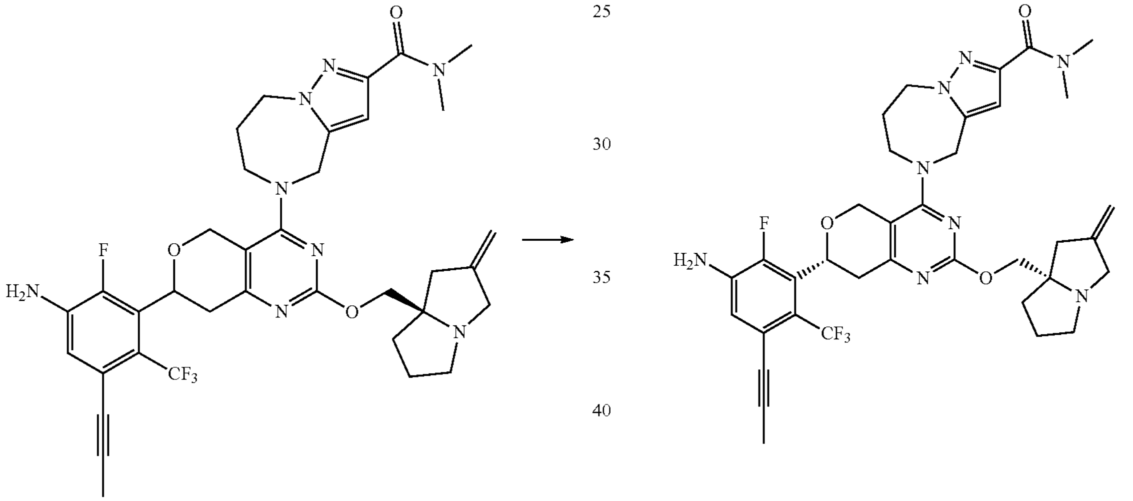
or
5
5A + 5B
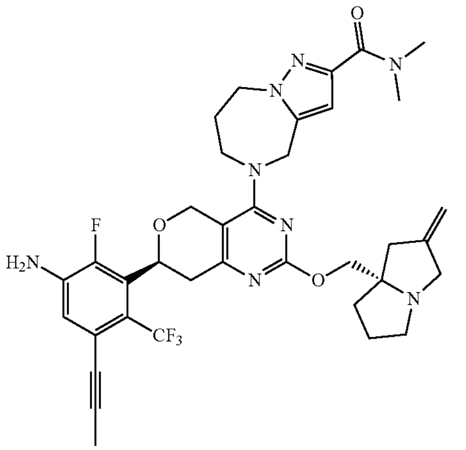
or
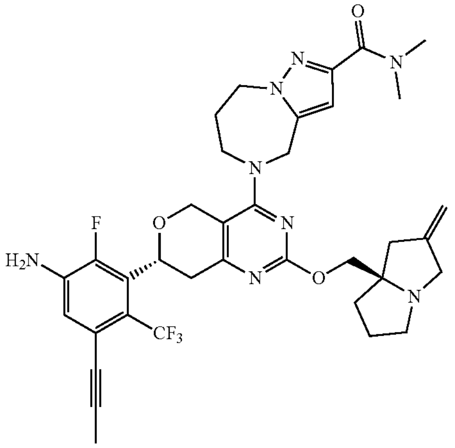
5A -continued

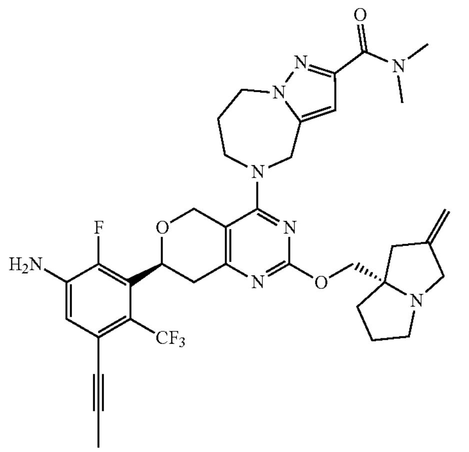

or

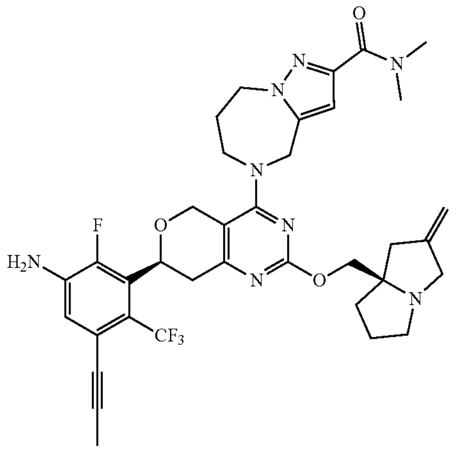

or

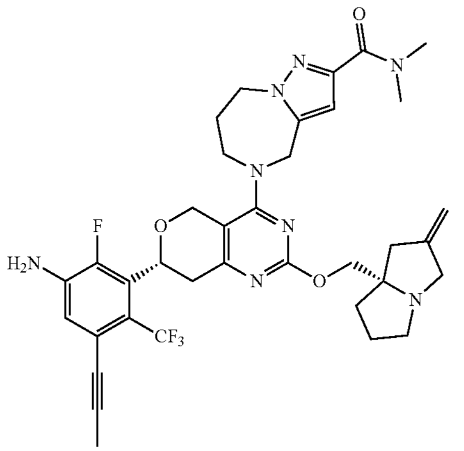

or

-continued

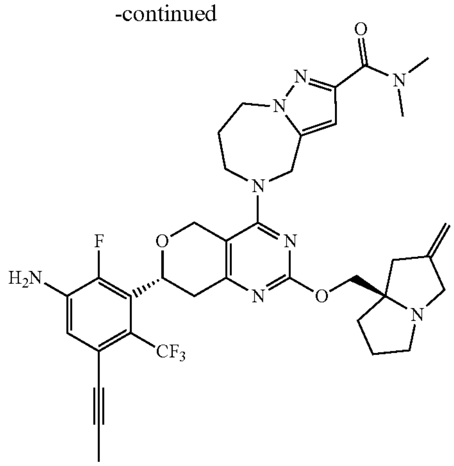

5B

Step 1: Synthesis of Intermediate 5-1A

SFC analysis of compound 5-1 was carried out (chromatographic column: Chiralpak IH-3, 100×4.6 mm I.D., 3 μm; mobile phases: A (supercritical $CO_2$) and B (EtOH, containing 0.1% isopropylamine); gradient: B %=10-50%, running time 3.7 min), and peak times: 1.266 min and 1.521 min, where compound 5-1A is at 1.521 min. Then supercritical fluid chromatography (SFC) purification was carried out (chromatographic column: ChiralPak IH, 250×50 mm, 10 μm; mobile phase: [supercritical $CO_2$-ethanol (0.1% ammonia)]; ethanol (0.1% ammonia) %: 20-20%), to obtain compound 5-1A, SFC analysis (chromatographic column: Chiralpak IH-3, 100×4.6 mm I.D., 3 μm; mobile phase: A (supercritical $CO_2$) and B (EtOH, containing 0.1% isopropylamine); 10 gradient: B %=10-50%, 4 min; flow rate: 3.4 mL/min; wavelength: 220 nm; pressure: 2000 psi); compound 5-1A, Rt=1.489 min, ee value 98.8%. $^1$H NMR (400 MHz, $CDCl_3$) δ=4.99-4.86 (m, 2H), 4.26-3.95 (m, 3H), 3.59 (m, 1H), 3.01-2.88 (m, 1H), 2.88-2.15 (m, 4H), 1.91 (s, 1H), 1.20-1.09 (m, 3H).

Step 2: Synthesis of Intermediate 5-2

Lithium aluminum tetrahydroxide (1.55 g, 40.15 mmol) was dissolved with anhydrous tetrahydrofuran (30 mL) and cooled to 0° C. An anhydrous tetrahydrofuran (20 mL) solution of compound 5-1A (2.8 g, 13.38 mmol) was added under nitrogen protection to react at 70° C. for 1 h. 1.5 mL of water was added to the reaction solution at 0° C. 1.5 mL of a 15% sodium hydroxide solution was added. Then 4.5 mL of water was added and stirred for 20 min. The reaction solution was filtered. The filter cake was washed with 10 mL of tetrahydrofuran, and the filtrate was concentrated to obtain compound 5-2. $^1$H NMR (400 MHz, $CDCl_3$) δ=4.99-4.86 (m, 2H), 4.28-3.95 (m, 3H), 3.61-3.59 (m, 1H), 3.00-2.88 (m, 1H), 2.74-2.27 (m, 4H), 1.91 (s, 1H), 1.20-1.08 (m, 3H).

Step 3: Synthesis of Compound 5-3

Compound 5-2 (88.20 mg, 575.63 mol) was dissolved with anhydrous tetrahydrofuran (5 mL). Sodium tert-butanol (55.32 mg, 575.63 mol) was added to react at 25° C. for 30 min. Compound 4-13 (330 mg, 383.75 mol) was added to react at 25° C. for 0.5 h. The reaction solution was diluted with 30 mL of ethyl acetate, washed with 20 mL of a saturated table salt solution, dried with anhydrous sodium sulfate, filtered, and concentrated to obtain compound 5-3. MS m/z=949.1 [M+H]$^+$.

Step 4: Synthesis of Compounds 5A and 5B

Compound 5-3 (360 mg, 379.33 mol) was dissolved with dichloromethane (2 mL). Trifluoroacetic acid (2 mL) was added to react at 25° C. for 1 h. The reaction solution was concentrated and separated by HPLC (chromatographic column: Xtimate C18 150×40 mm×5 μm; mobile phase: [water (0.05% HCl)-acetonitrile]; acetonitrile %: 10-40%; 10 min), to obtain the hydrochloride of compound 5. SFC separation was carried out (chromatographic column: DAICEL CHIRALCEL OD (250 mm×30 mm, 10 m); mobile phase: [supercritical $CO_2$-ethanol (0.1% ammonia)]; ethanol (0.1% ammonia) %: 40-40%) to obtain compounds 5A and 5B. Chiral SFC analysis was carried out (chromatographic column: DAICEL CHIRALCEL OD-3 (150 mm×4.6 mm, 3 μm); mobile phase: [supercritical $CO_2$-ethanol (0.05% diethylamine)]; ethanol (0.05% diethylamine) %: 40-40%), compound 5A, Rt=0.848 min, ee value 100%; compound 5B, Rt=2.371 min, ee value 99%.

Compound 5A: MS m/z=709.3 [M+H]$^+$, $^1$H NMR (400 MHz, $CD_3C_1$) 6 ppm 6.93-6.85 (m, 1H), 6.84-6.77 (m, 1H), 5.36-5.22 (m, 2H), 5.20-5.11 (m, 1H), 4.89-4.41 (m, 10H), 4.18-3.99 (m, 3H), 3.97-3.77 (m, 2H), 3.61-3.48 (m, 1H), 3.42-3.26 (m, 4H), 3.17-3.04 (m, 4H), 3.01-2.88 (m, 2H), 2.73-2.61 (m, 1H), 2.56-2.42 (m, 1H), 2.35-2.23 (m, 2H), 2.21-2.12 (m, 2H), 2.10-2.04 (m, 3H). Compound 5B: MS m/z=709.3 [M+H]$^+$.

Embodiment 6

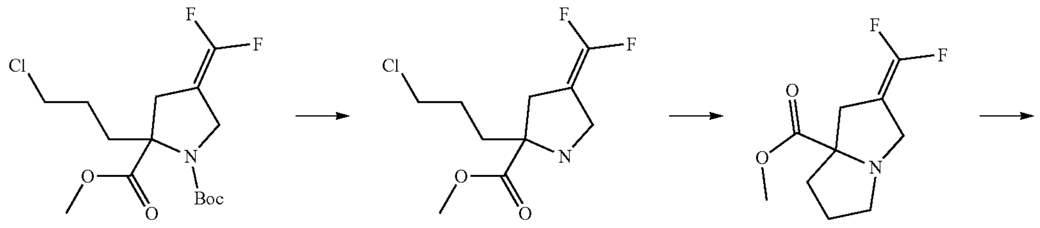

6-1 6-2 6-3

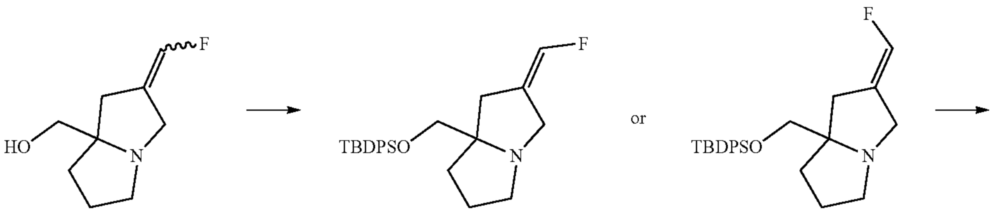

or 6-4 6-5

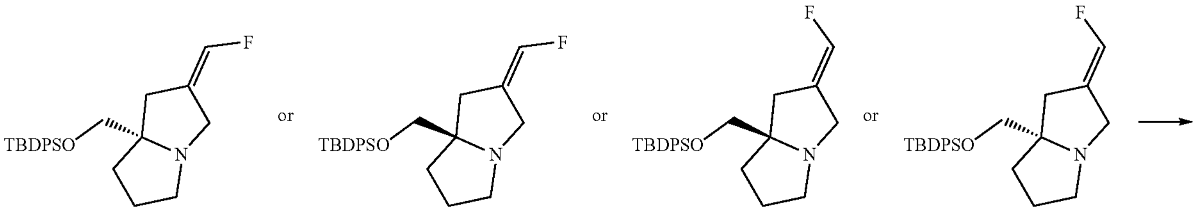

or or or 6-6

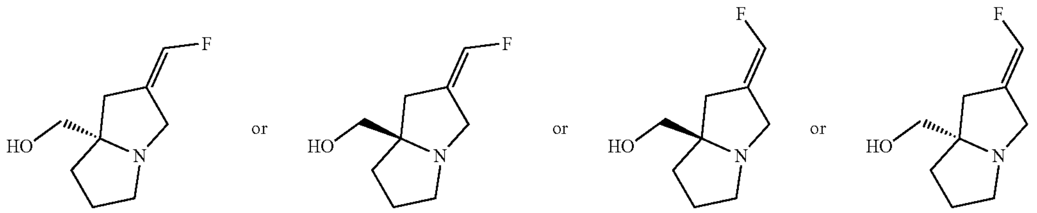

or or or 6-7

-continued
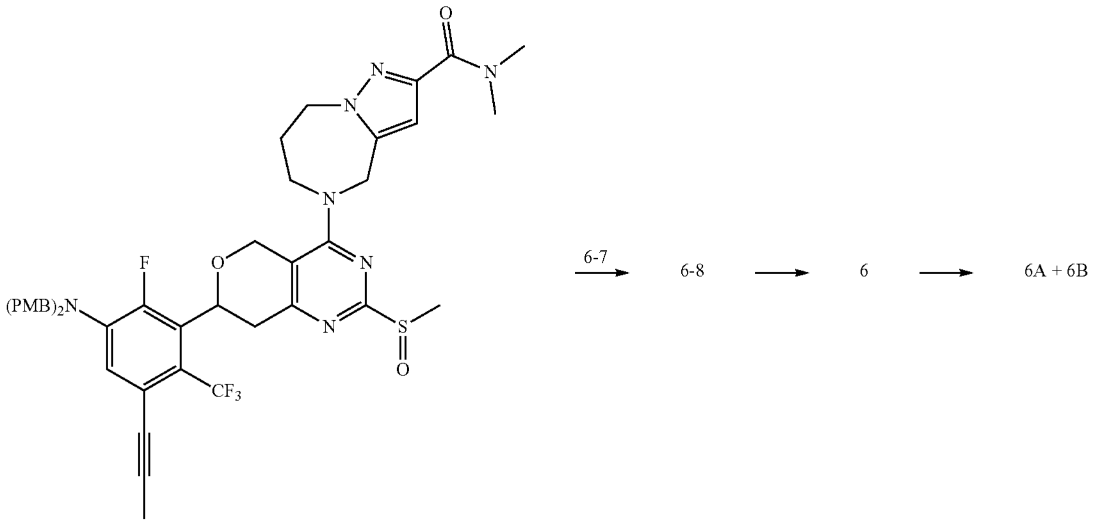
4-13
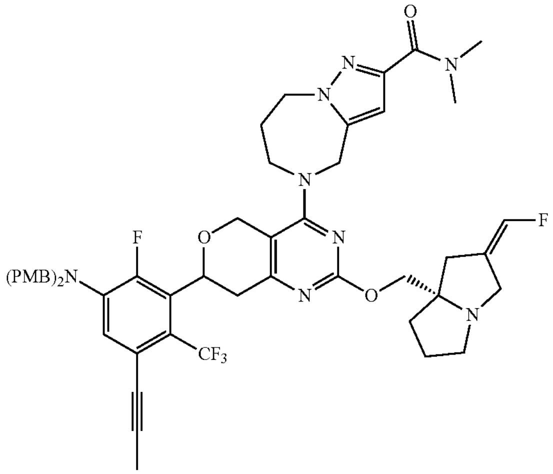
or
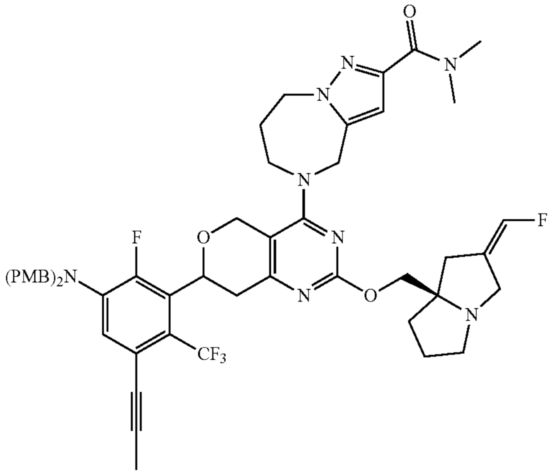
or
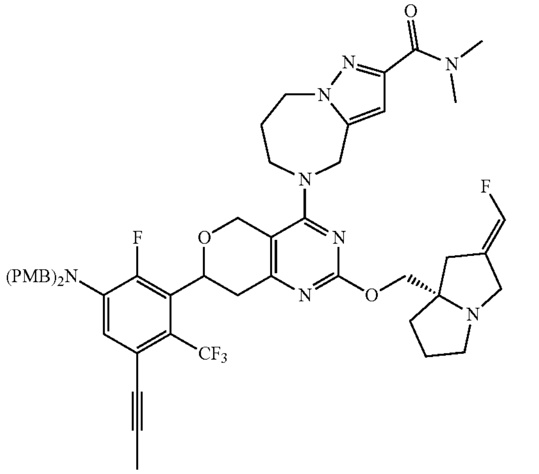
or
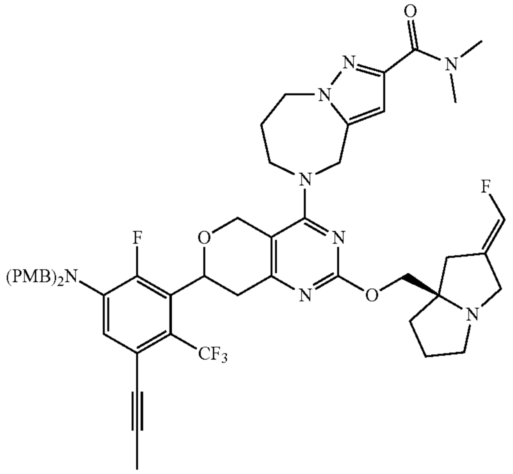
6-8

-continued
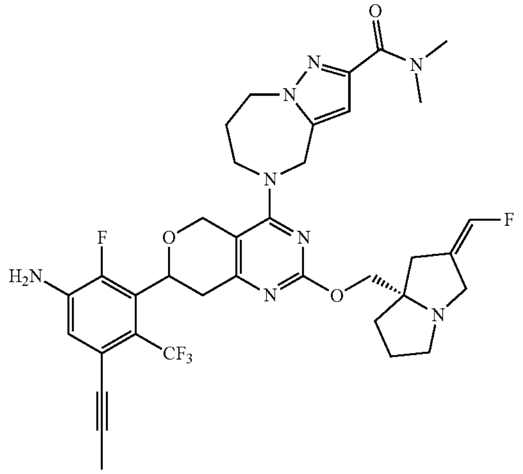
or
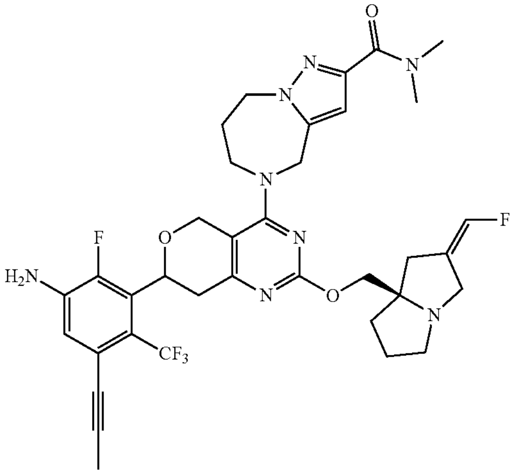
or
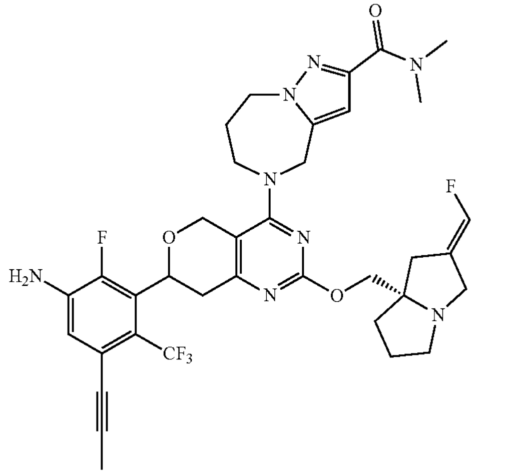
or
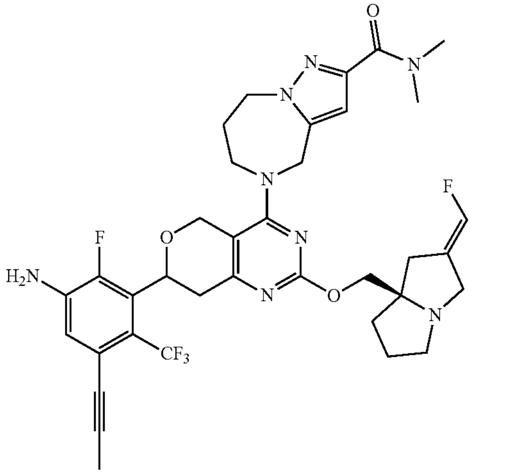
6
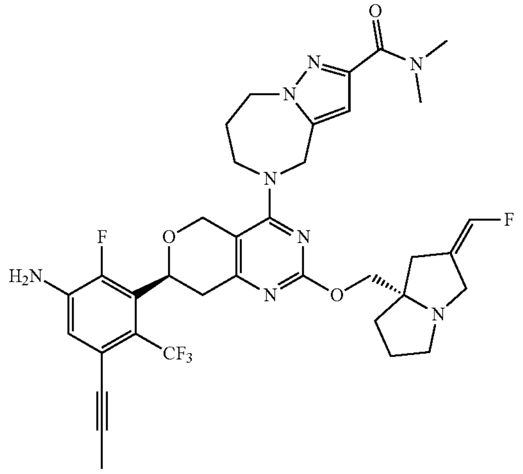
or
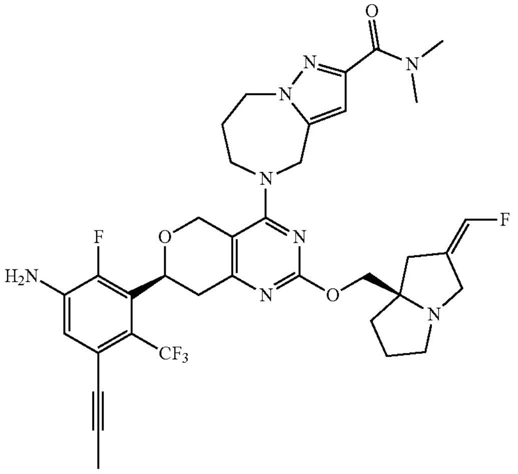
or -continued

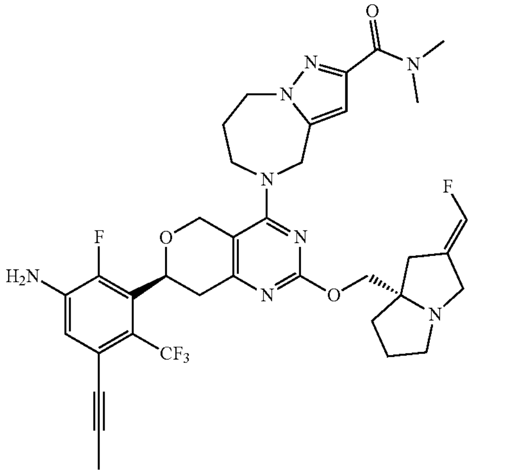

or

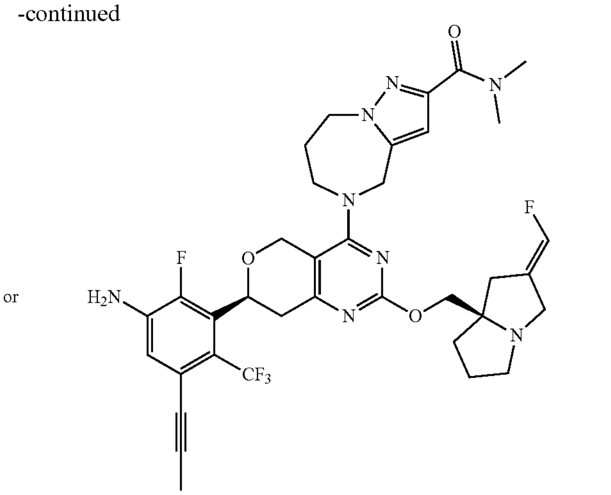

or

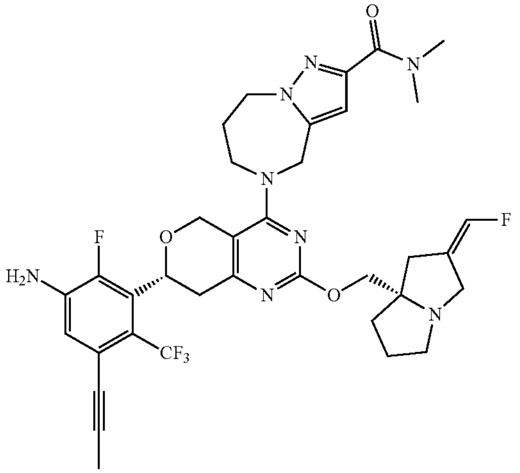

or

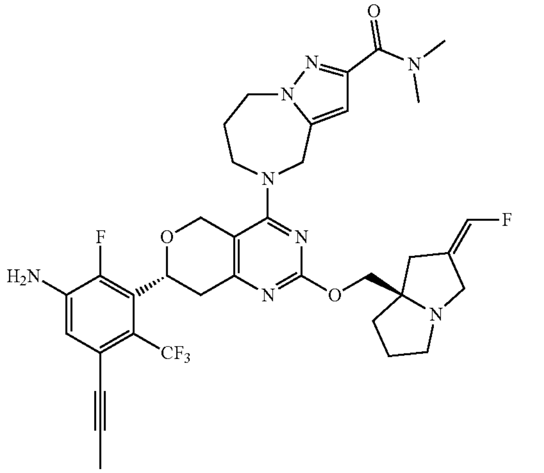

or

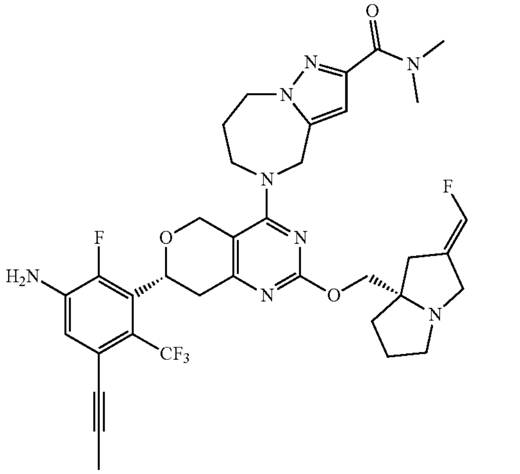

or

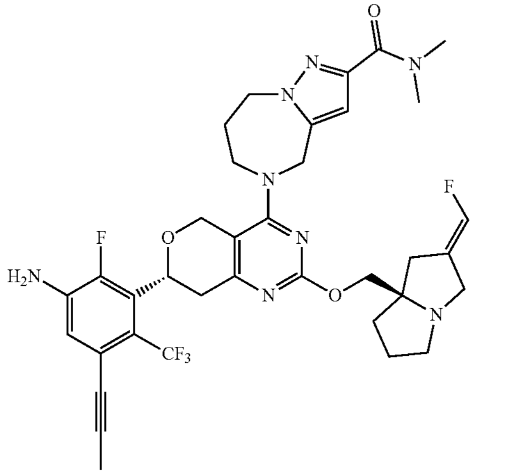

6A or 6B

Step 1: Synthesis of Intermediate 6-2

Compound 6-1 (20 g, 56.53 mmol) was dissolved with hydrochloric acid/ethyl acetate (4 M, 120 mL), to react at 25° C. for 2 h. The reaction solution was concentrated directly to obtain crude product 6-2. The crude product was used directly in the next step.

Step 2: Synthesis of Intermediate 6-3

Crude product 6-2 (20 g) was dissolved with DMF (65 mL) and potassium carbonate (14.2 g, 102 mmol) was added, to react at 25° C. for 12 h. The reaction solution was diluted with 500 mL of ethyl acetate, washed with water (300 mL×2), washed with saturated salt (300 mL), dried with anhydrous sodium sulfate, filtered, and concentrated to obtain the crude product. The crude product was purified by column chromatography (petroleum ether:ethyl acetate=2:1) to obtain compound 6-3.

Step 3: Synthesis of Intermediate 6-4

Compound 6-3 (7 g, 32.23 mmol) was dissolved with 2-methyltetrahydrofuran (75 mL). Red aluminum (37.2 g, 129 mmol, 35.8 mL, 70% purity) was added slowly at 10° C. under nitrogen protection after three times of nitrogen substitution, to react at 25° C. for 12 h. The reaction solution was quenched with dropwise a 26.0% sodium tartrate aqueous solution, and extracted with 2-methyltetrahydrofuran (200 mL). The aqueous phase was extracted with 2-methyltetrahydrofuran (50 mL×3). The organic phases were mixed, washed with 50 mL of a saturated table salt solution, dried with anhydrous sodium sulfate, filtered, and concentrated to obtain compound 6-4.

Step 4: Synthesis of Intermediate 6-5

Compound 6-4 (2.2 g, 13 mmol) was dissolved with DCM (30 mL). Imidazole (3.5 g, 53 mmol), 4-dimethylaminopyridine (160 mg, 1.3 mmol), and tert-butyl diphenylchlorosilane (7.2 g, 25 mmol) were added, to react at 45° C. for 12 h. Water (50 mL) was added to the reaction solution to separate the organic phase. The aqueous phase was extracted with dichloromethane (40 mL). The organic phases were mixed, washed with 40 mL saturated salt, dried with anhydrous sodium sulfate, filtered, and concentrated. Methyl tert-butyl ether (10 mL), n-heptane (21 mL), and a hydrochloric acid solution (2 M, 21 mL) were added. The aqueous phase was separated, washed with a mixed solvent (20 mL×3) of methyl tert-butyl ether and n-heptane (1:2), adjusted to pH 7 with a sodium carbonate aqueous solution, and extracted with 200 mL of ethyl acetate. The organic phases were mixed, washed with 20 mL of saturated salt, dried with anhydrous sodium sulfate, filtered, and concentrated to obtain the crude product. The crude product was separated by column chromatography (petroleum ether: ethyl acetate=10:1), and the first point ($R_f$=0.6, the other isomer: $R_f$=0.5) was separated to obtain crude intermediate 6-5.

Step 5: Synthesis of Intermediate 6-6

SFC analysis of compound 6-5 (2 g, 4.6 mmol) was carried out (chromatographic column: Chiralpak IC-3 50×4.6 mm I.D., 3 m; mobile phases: A (supercritical $CO_2$) and B (methanol, 25 containing 0.05% diethylamine); gradient: B %=5-10%, flow rate: 3 mL/min), peak times: 2.117 min and 2.980 min, where intermediate 6-6 is at 2.117 min. Chiral SFC separation was carried out for separation and purification (chromatographic column: DAICEL CHIRALPAK IC (250 mm×30 mm, 10 μm); mobile phase: [supercritical $CO_2$-methanol (0.1% ammonia)]; methanol (0.1% ammonia) %: 25-25%, 4.5 min), to obtain compound 6-6. SFC analytical method (chromatographic column: Chiralpak IC-3 50×4.6 mm I.D., 3 m; mobile phases: A (supercritical $CO_2$) and B (methanol, containing 0.05% diethylamine); gradient: B %=5-10%, flow rate: 3 mL/min), Rt=2.014 min, ee value 98%. MS m/z=410.3[M+H]$^+$.

Step 6: Synthesis of Intermediate 6-7

Compound 6-6 (1.2 g, 2.93 mmol) was dissolved with 24 mL of 1,4-dioxane and concentrated hydrochloric acid (12 M, 7.20 mL) was added, to react at 95° C. for 12 h. The reaction solution was cooled, diluted with 10 mL of water, and washed with 10 mL of ethyl acetate. The aqueous phase was freeze-dried to obtain the hydrochloride of compound 6-7. The hydrochloride was dissolved with methanol (20 mL). 2 g of potassium carbonate was added. The reaction solution was filtered, concentrated, then dissolved with tetrahydrofuran (20 mL), filtered, and concentrated, to obtain compound 6-7.

Step 7: Synthesis of Compound 6-8

Compound 6-7 (92.58 mg, 540.74 mol) was dissolved with anhydrous tetrahydrofuran (5 mL). Sodium tert-butanol (51.97 mg, 540.74 mol) was added to react at 25° C. for 30 min. Compound 4-13 (310 mg, 360.49 mol) was added to react at 25° C. for 0.5 h. The reaction solution was diluted with 30 mL of ethyl acetate, washed with 20 mL of a saturated table salt solution, dried with anhydrous sodium sulfate, filtered, and concentrated to obtain compound 6-8. MS m/z=967.3 [M+H]$^+$.

Step 8: Synthesis of Compounds 6A and 6B

Compound 6-8 (345 mg, 356.76 mol) was dissolved with dichloromethane (2 mL). Trifluoroacetic acid (2 mL) was added to react at 25° C. for 1 h. The reaction solution was concentrated and separated by HPLC (chromatographic column: Xtimate C18 150×40 mm×5 μm; mobile phase: [water (0.05% HCl)-acetonitrile]; acetonitrile %: 10-40%; 10 min), to obtain the hydrochloride of compound 6. SFC separation was carried out (chromatographic column: DAICEL CHIRALCEL OD (250 mm×30 mm, 10 m); mobile phase: [supercritical $CO_2$-methanol (0.1% ammonia)]; methanol (0.1% ammonia) %: 40-40%) to obtain compounds 6A and 6B. Chiral SFC analysis was carried out (chromatographic column: DAICEL CHIRALCEL OD-3 (150 mm×4.6 mm, 3 μm); mobile phase: [supercritical $CO_2$-methanol (0.05% diethylamine)]; methanol (0.05% diethylamine) %: 40-40%), compound 6A, Rt=3.658 min, ee value 99.9%; compound 6B, Rt=7.041 min, ee value 99.9%.

Compound 6A: MS m/z=727.3 [M+H]$^+$, $^1$H NMR (400 MHz, $CD_3OD$) δ ppm 6.90-6.64 (m, 2H), 6.60-6.55 (m, 1H), 5.13-5.01 (m, 1H), 4.84 (brs, 2H), 4.69-4.57 (m, 2H), 4.47-4.38 (m, 2H), 4.37-4.26 (m, 3H), 4.06-3.96 (m, 1H), 3.90-3.75 (m, 2H), 3.72-3.62 (m, 1H), 3.26-3.23 (m, 3H), 3.19-3.10 (m, 2H), 3.04-2.93 (m, 3H), 2.88-2.62 (m, 3H), 2.36-2.23 (m, 1H), 2.02 (s, 5H), 1.93-1.87 (m, 3H). Compound 6B: MS m/z=727.3 [M+H]$^+$.

Embodiment 7

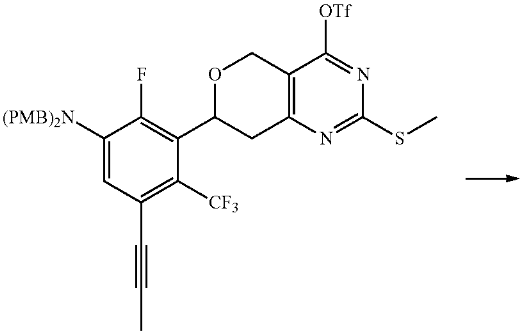

4-11

-continued
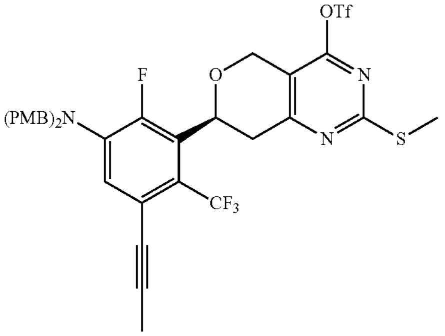
or
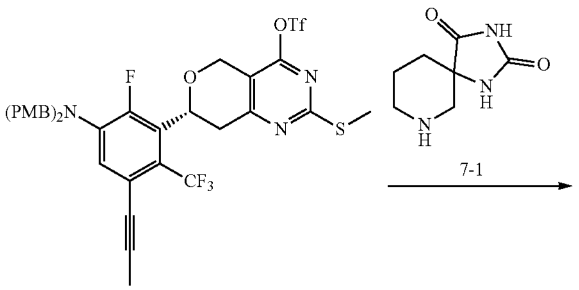
4-11B
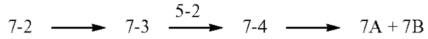
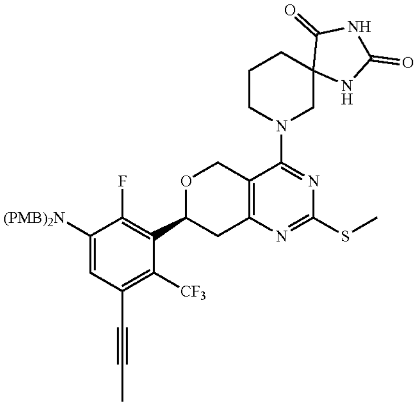
or
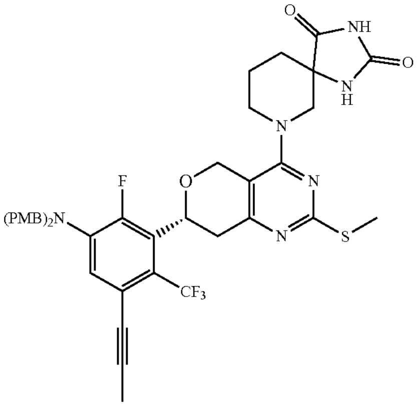
7-2
-continued
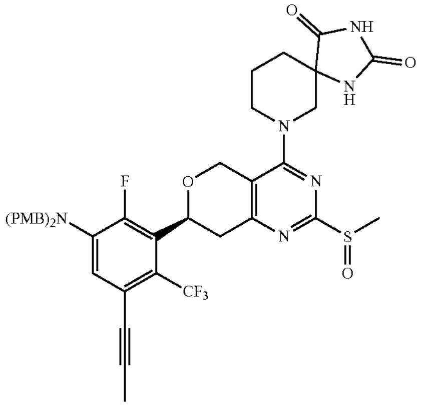
or
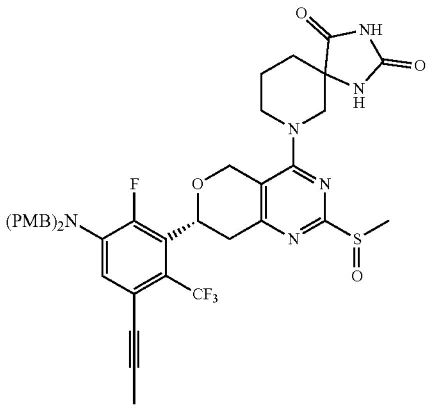
7-3
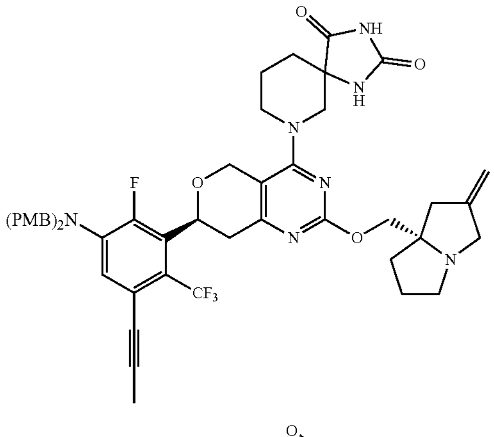
or
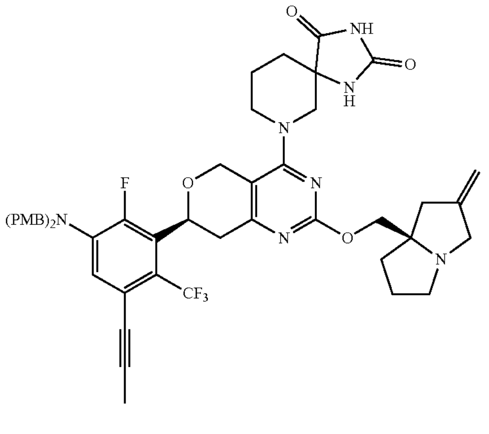
or -continued
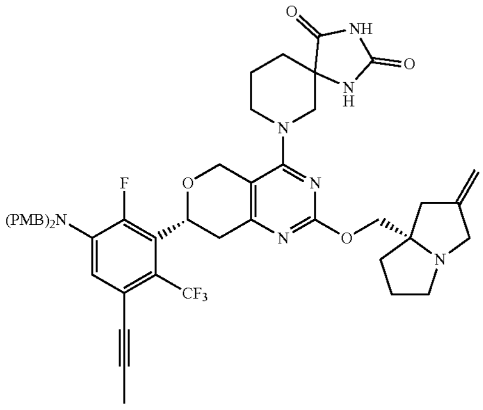
or
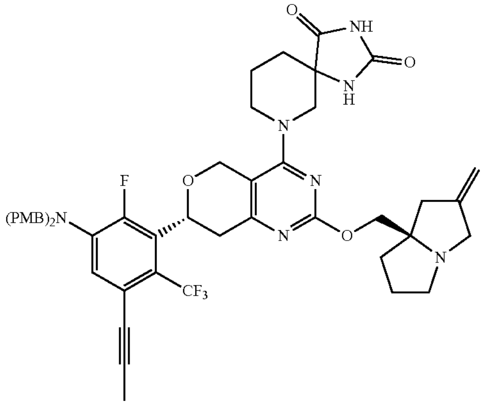
7-4
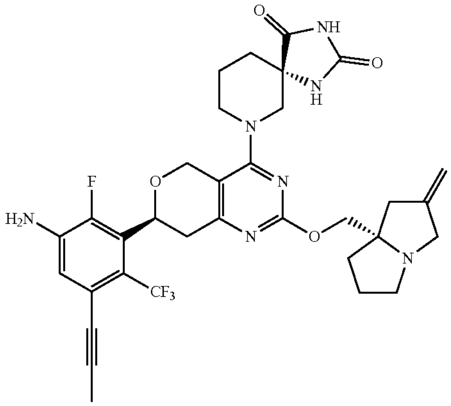
or
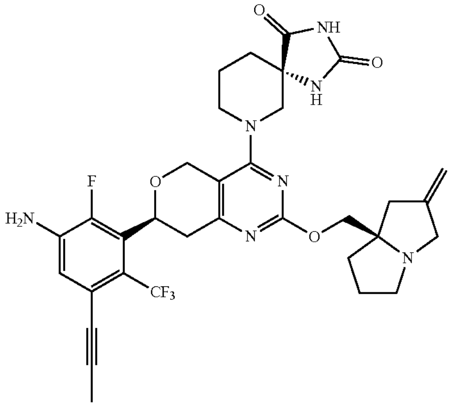
or
-continued
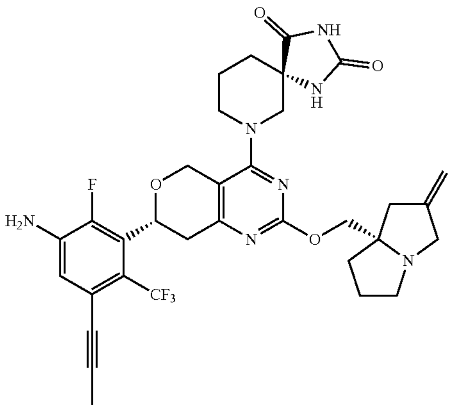
or
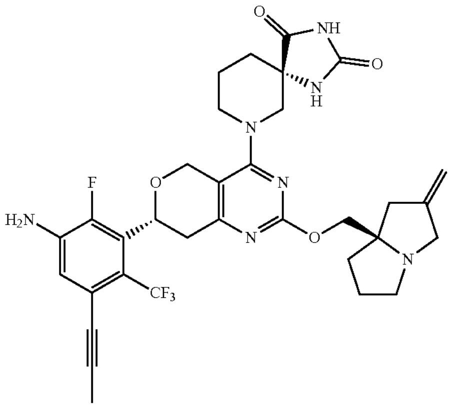
7Aor 7B
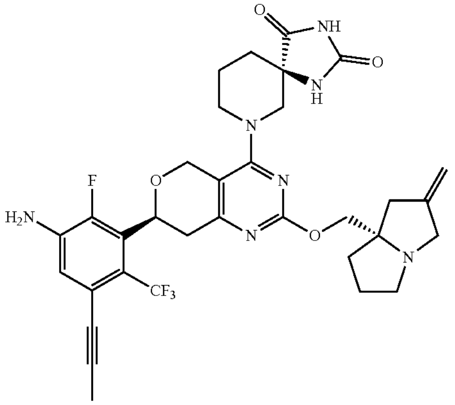
or -continued

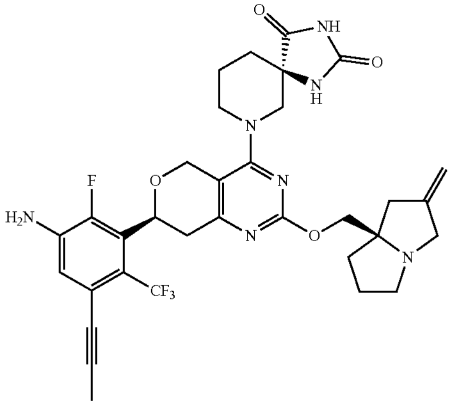

or

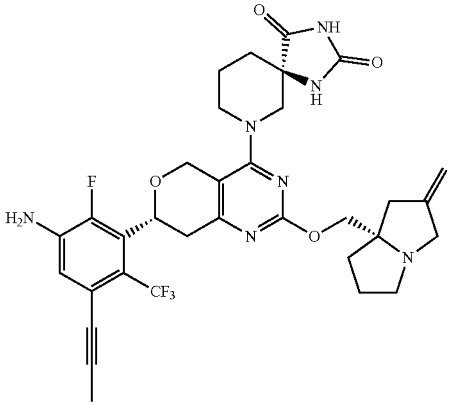

or

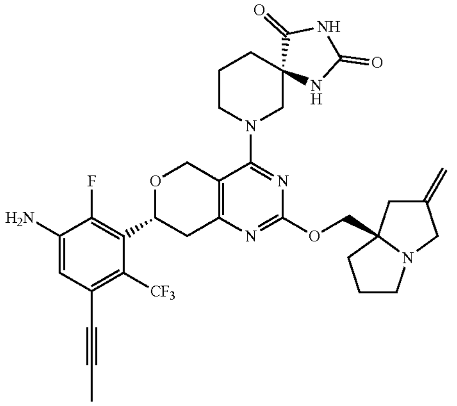

7B or 7A

Step 1: Synthesis of Intermediate 4-11B

SFC separation of compound 4-11 was carried out (chromatographic column: DAICEL CHIRALPAK IG (250 mm×50 mm, 10 m); mobile phase [supercritical $CO_2$-ethanol (0.1% ammonia)]; ethanol (0.1% ammonia) %: 25-25%) to obtain compound 4-11B and an isomer thereof. Chiral SFC analysis was carried out (chromatographic column: ChiralPak IG-3 (100 mm×4.6 mm, 3 μm); mobile phase: [supercritical $CO_2$-ethanol (0.05% diethylamine)]; (ethanol (0.05% diethylamine)) %: 5-40%), compound 4-11B, Rt=3.055 min, ee value 99%; isomer, Rt=2.574 min, ee value 99%.

Step 2: Synthesis of Intermediate 7-2

Compound 4-11B (0.4 g, 509.07 mol) was weighed and dissolved with DMF (15 mL). Compound 7-1 (125.62 mg, 610.88 mol) was weighed and added. Then DIPEA (197.38 mg, 1.53 mmol) was added to the reaction system to react at 100° C. for 1 h. Water (15 mL) was added to the reaction solution. The reaction solution was extracted with ethyl acetate (20 mL×3). The organic phases were mixed, washed with water (30 mL), dried with anhydrous sodium sulfate, and concentrated under reduced pressure to obtain the crude product. The crude product was purified by column chromatography (petroleum ether:ethyl acetate=3:1) to obtain compound 7-2, with MS m/z=805.6 $[M+H]^+$.

Step 3: Synthesis of Intermediate 7-3

Compound 7-2 (381.80 mg, 474.37 mol) was weighed and dissolved with DCM (10 mL). m-CPBA (96.31 mg, 474.37 mol, 85% purity) was added to react at 25° C. for 1 h. Water (15 mL) was added to the reaction solution. The reaction solution was diluted with 100 mL of dichloromethane, washed with 80 mL of a saturated table salt solution, dried with anhydrous sodium sulfate, filtered, and concentrated under reduced pressure to obtain compound 7-3, MS m/z=821.6 $[M+H]^+$.

Step 4: Synthesis of Intermediate 7-4

Compound 5-2 (286.64 mg, 1.87 mmol) was dissolved with anhydrous tetrahydrofuran (20 mL). Sodium tert-butyl alcohol (179.79 mg, 1.87 mmol) was added. The reaction system reacted at 0° C. for 1 h. Compound 7-3 (383.90 mg, 467.69 mol) was added to react at 0° C. for 1 h. Water (15 mL) was added to the reaction solution. The reaction solution was diluted with 100 mL of ethyl acetate, washed with 100 mL of a saturated table salt solution, dried with anhydrous sodium sulfate, filtered, concentrated, and separated by column chromatography (dichloromethane:methanol=20:1) to obtain compound 7-4. MS m/z=910.5 $[M+H]^+$.

Step 5: Synthesis of Compounds 7A and 7B

Compound 7-4 (0.2833 g, 311.33 mol) was dissolved with dichloromethane (15 mL). Trifluoroacetic acid (4.33 g, 38.01 mmol, 2.82 mL) was added to react at 20° C. for 1 h. The reaction solution was concentrated, adjusted to pH 10 with a saturated sodium carbonate solution, and extracted with dichloromethane (100 mL×2). The organic phases were mixed, dried with anhydrous sodium sulfate, filtered, and concentrated to obtain the crude product. The crude product was separated by HPLC (chromatographic column: Phenomenex C18 80×40 mm×3 m; mobile phase: [water (0.05% ammonia)-acetonitrile]; acetonitrile %: 41-71% over 8 min) to obtain compound 7A and compound 7B. Chiral SFC analysis (chromatographic column: DAICEL CHIRALCEL AS-3 (100 mm×4.6 mm, 3 μm); mobile phase: [supercritical $CO_2$-methanol (0.05% diethylamine)]; (methanol (0.05% diethylamine)) %: 40-40%), compound 7A, Rt=1.445 min, ee value 97.4%, MS m/z=670.3 $[M+H]^+$. Compound 7B, Rt=0.863 min, ee value 94.9%, MS m/z=670.3 $[M+H]^+$.

Embodiment 8
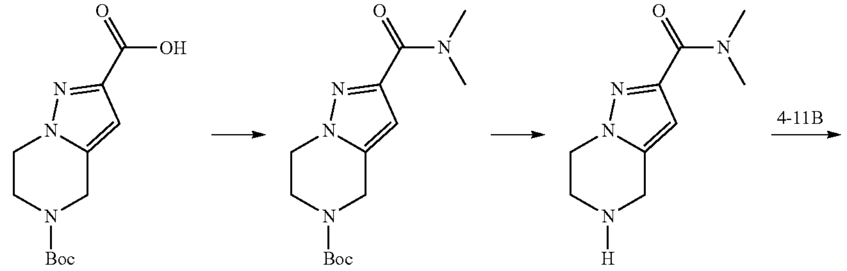
8-1 8-2 8-3
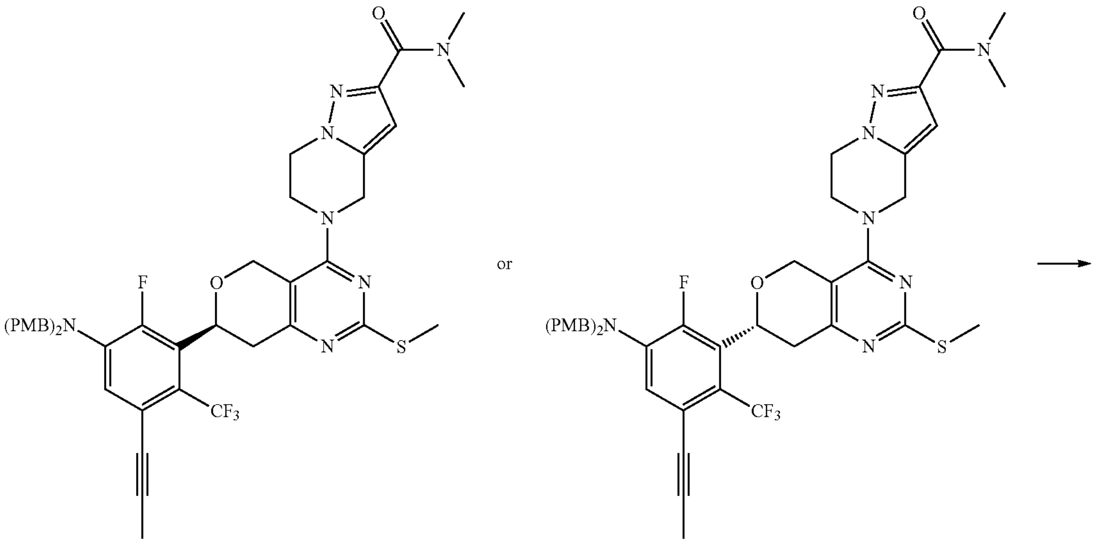
or
8-4
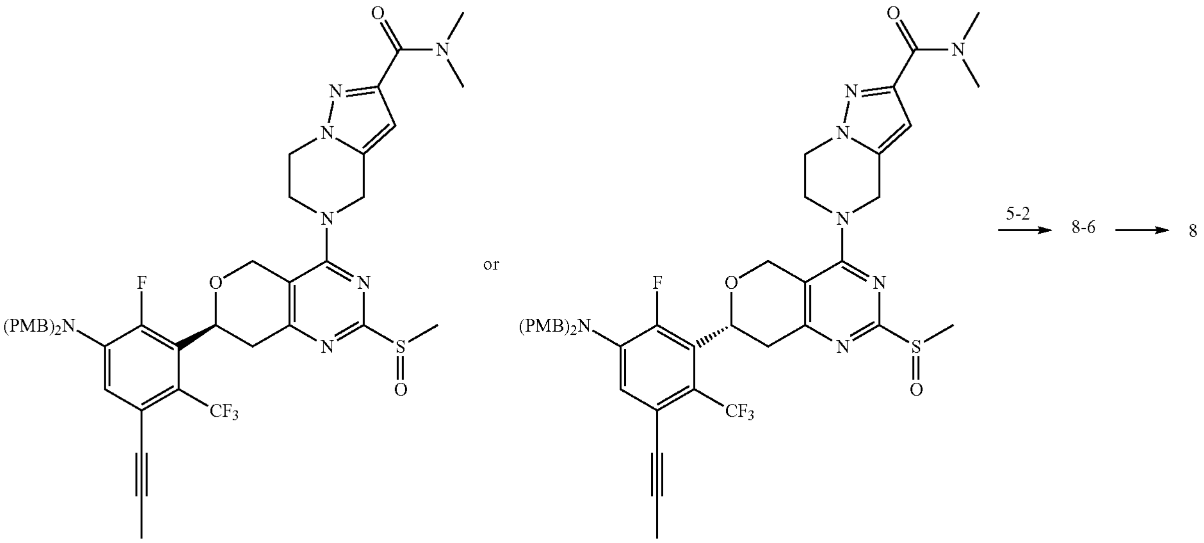
or
8-5

-continued
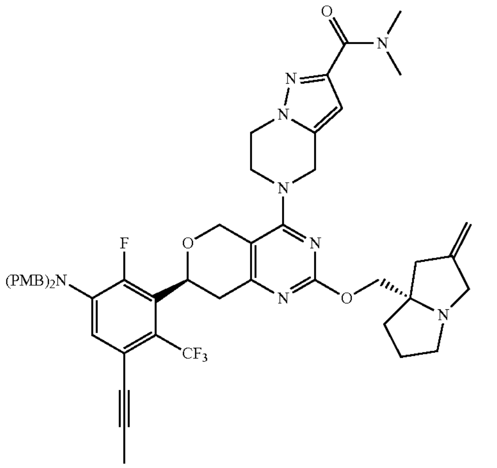
or
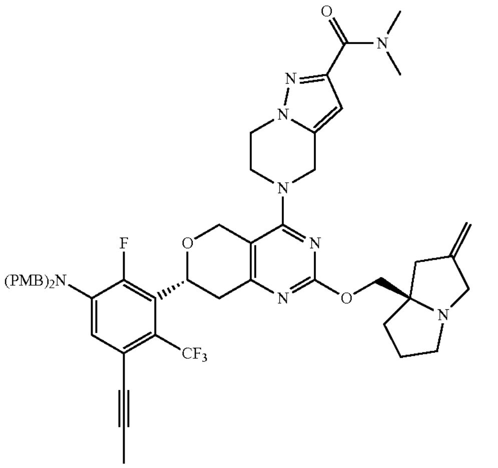
or
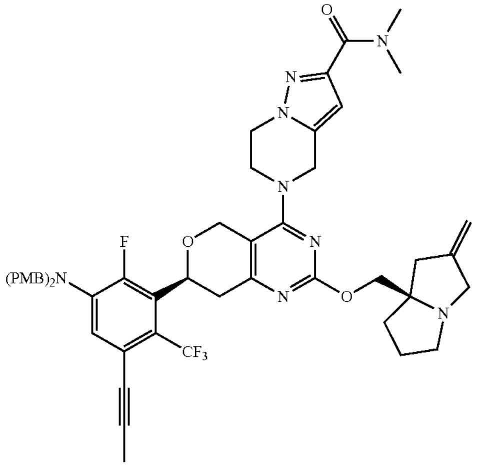
or
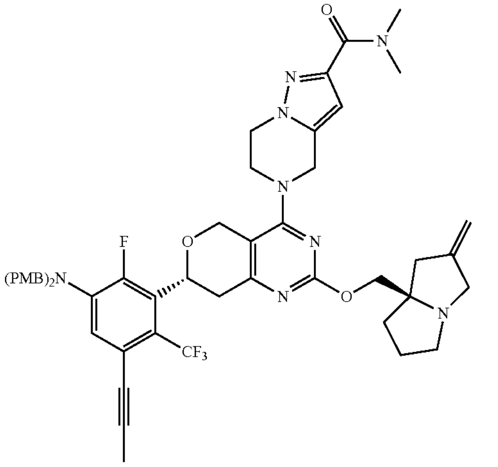
8-6
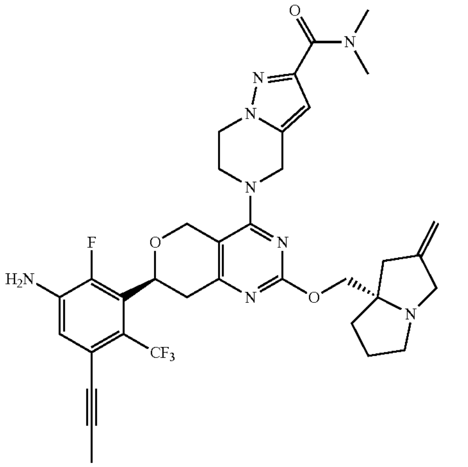
or
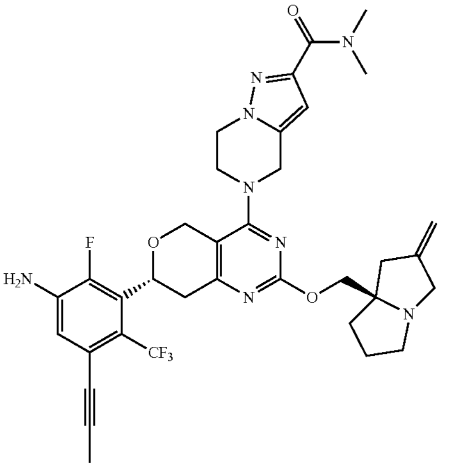
or -continued

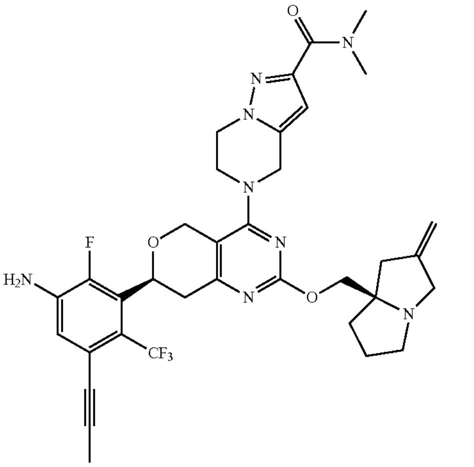

or

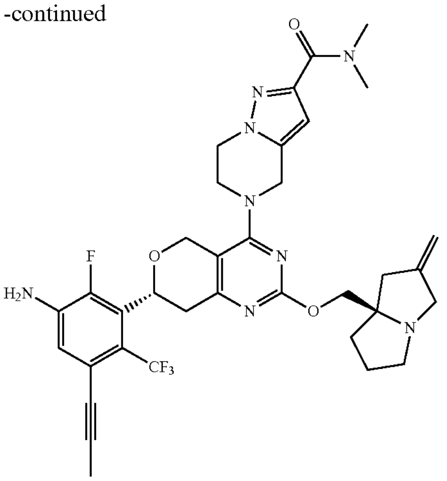

8

Step 1: Synthesis of Intermediate 8-2

Compound 8-1 (0.2 g, 710.86 μmol) was weighed and dissolved with DMF (5 mL). O-(7-azabenzotriazole-1-YL)-N, N, N, N-tetramethylurea hexafluorophosphine (351.38 mg, 924.12 μmol), DIPEA (367.50 mg, 2.84 mmol, 495.28 μL), and dimethylamine hydrochloride (173.90 mg, 2.13 mmol) were added to the reaction system to react at room temperature of 18° C. for 2 h. Water (20 mL) was added to the reaction solution. The reaction solution was extracted with ethyl acetate (20 mL×3). The organic phases were mixed, washed with water (30 mL), dried with anhydrous sodium sulfate, and concentrated under reduced pressure to obtain compound 8-2, with MS m/z=295.2 $[M+H]^+$.

Step 2: Synthesis of Hydrochloride of Intermediates 8-3

Compound 8-2 (209 mg, 674.54 μmol) was weighed. A 4M hydrochloric acid/ethyl acetate solution (5 mL) was added. The reaction system reacted at room temperature of 18° C. for 2 h. The reaction solution was concentrated under reduced pressure to obtain the hydrochloride of compound 8-3, with MS m/z=195.1 $[M+H]^+$.

Step 3: Synthesis of Intermediate 8-4

Compound 4-11B (0.2 g, 254.53 μmol) was weighed and dissolved with DMF (8 mL). The hydrochloride of compound 8-3 (59.33 mg) was added. DIPEA (98.69 mg, 763.60 μmol) was measured and added to the reaction system to react at 100° C. for 1 h. The reaction solution was quenched with water (20 mL), extracted with ethyl acetate (20 mL×3). The organic phases were mixed, washed with water (30 mL), dried with anhydrous sodium sulfate, and concentrated by rotary evaporation at low pressure. The crude product was purified by column chromatography (petroleum ether:ethyl acetate=1:1) to obtain compound 8-4, with MS m/z=830.6 $[M+H]^+$.

Step 4: Synthesis of Intermediate 8-5

Compound 8-4 (0.099 g, 119.29 mol) was weighed and dissolved with DCM (10 mL). m-CPBA (24.22 mg, 119.29 mol, 85% purity) was added to react at 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated under reduced pressure to obtain the crude product. The crude product was purified by column chromatography (dichloromethane:methanol=20:1), to obtain compound 8-5, MS m/z=846.6 $[M+H]^+$.

Step 5: Synthesis of Intermediate 8-6

Compound 5-2 (46.73 mg, 305.00 mol) was dissolved with anhydrous tetrahydrofuran (10 mL). Sodium tert-butanol (29.31 mg, 305.00 mol) was added. The reaction system reacted at 0° C. for 1 h. Compound 8-5 (129 mg, 152.50 mol) was added to react at 0° C. for 1 h. Water (20 mL) was added to the reaction solution. The reaction solution was diluted with 100 mL of ethyl acetate, washed with 100 mL of a saturated table salt solution, dried with anhydrous sodium sulfate, filtered, concentrated under reduced pressure, and separated by column chromatography (dichloromethane:methanol=20:1) to obtain compound 8-6. MS m/z=935.5 $[M+H]^+$.

Step 6: Synthesis of Hydrochloride of Compound 8

Compound 8-6 (0.142 g, 151.87 mol) was dissolved with dichloromethane (15 mL). Trifluoroacetic acid (2.11 g, 18.54 mmol, 1.38 mL) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 10-40%, 10 min), to obtain the hydrochloride of compound 8. MS m/z=695.2 $[M+H]^+$. 1H NMR (400 MHz, MeOD) δ=6.96 (d, J=8.5 Hz, 1H), 6.69-6.47 (m, 1H), 5.39-5.32 (m, 2H), 5.30-5.21 (m, 1H), 5.13-5.04 (m, 2H), 4.95 (br d, J=5.0 Hz, 2H), 4.69-4.56 (m, 2H), 4.55-4.42 (m, 2H), 4.41-4.31 (m, 2H), 4.06-3.98 (m, 1H), 3.98-3.91 (m, 1H), 3.87-3.77 (m, 1H), 3.47-3.36 (m, 3H), 3.30-3.22 (m, 2H), 3.20-2.98 (m, 5H), 2.91-2.81 (m, 1H), 2.51-2.40 (m, 1H), 2.33-2.12 (m, 3H), 2.04 (s, 3H).

Embodiment 9
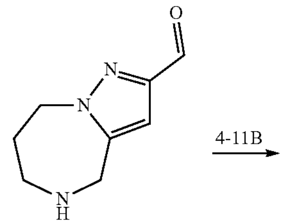
9-1
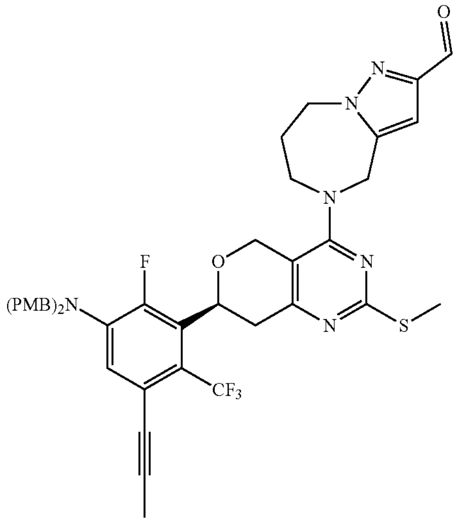
or
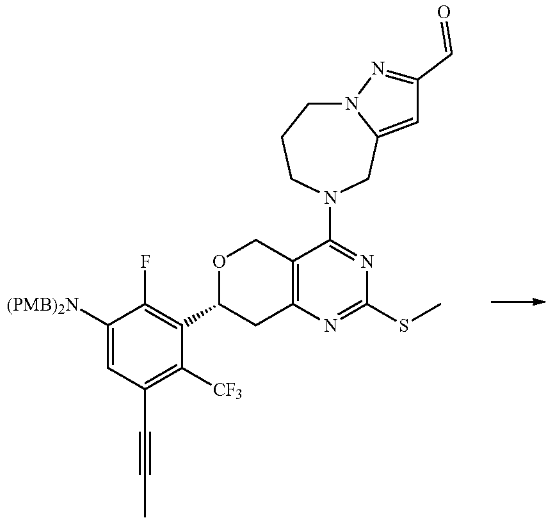
9-2
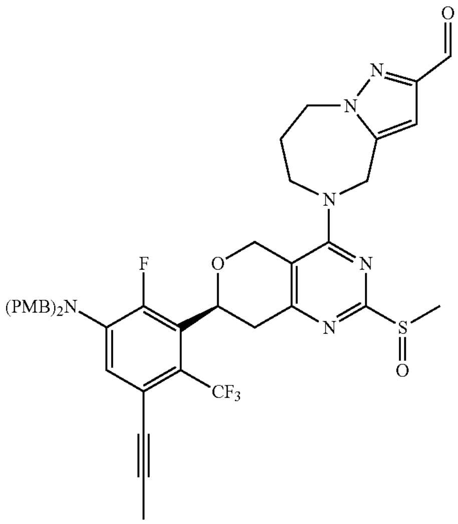
or
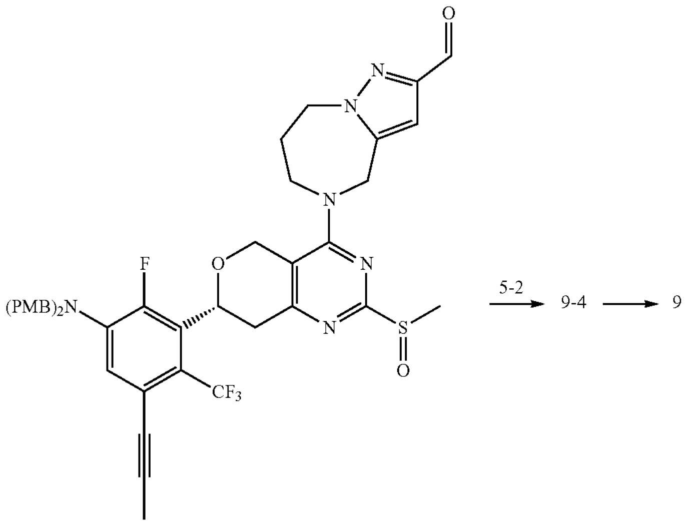
9-3

-continued
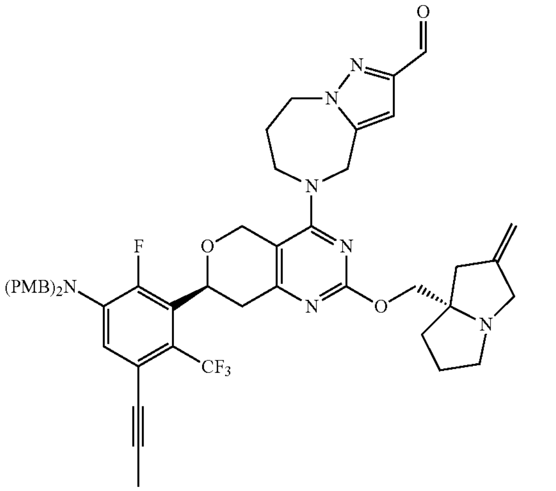
or
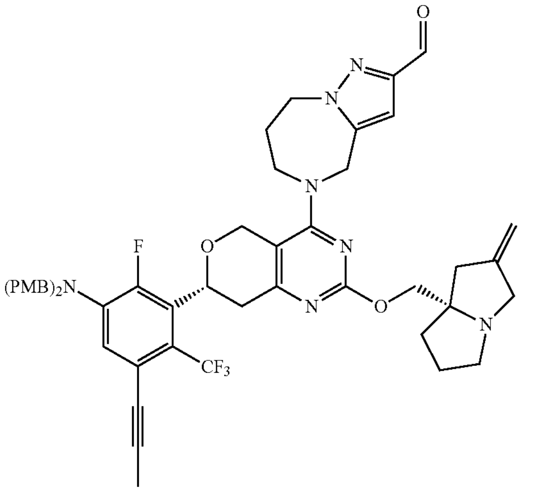
or
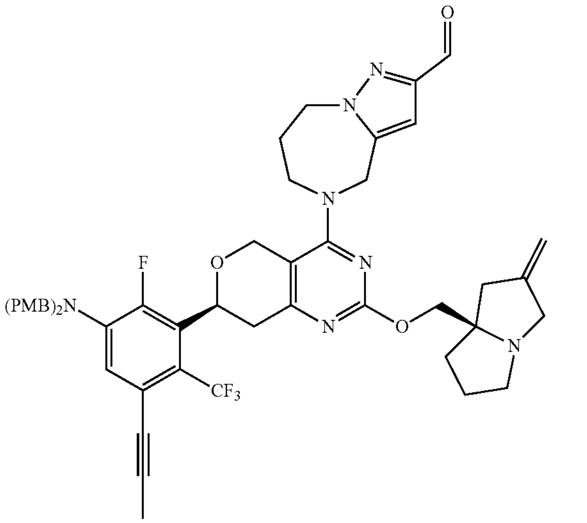
or
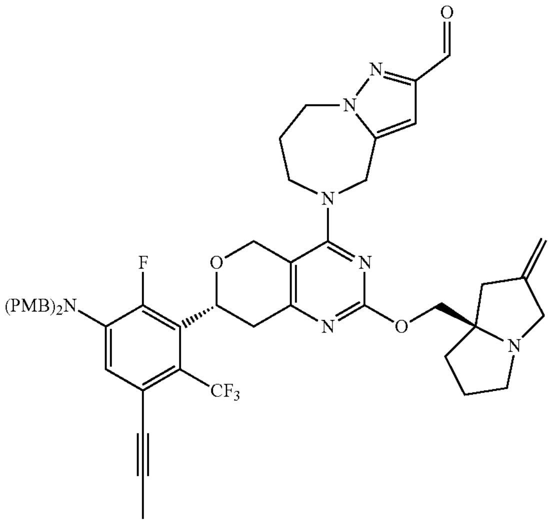
9-4
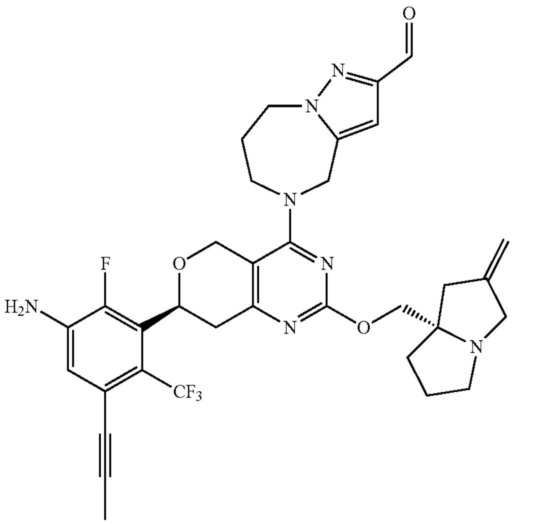
or
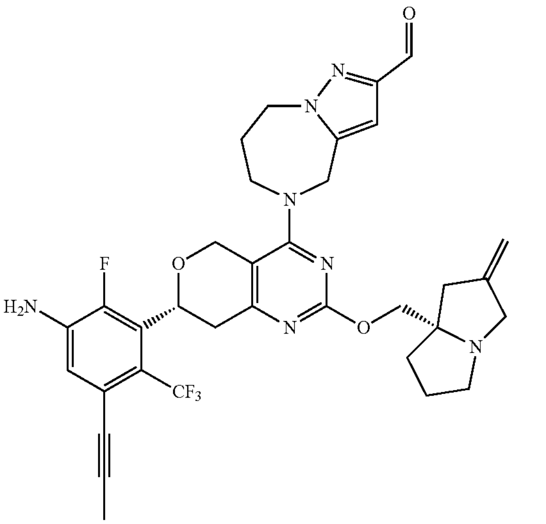
or -continued

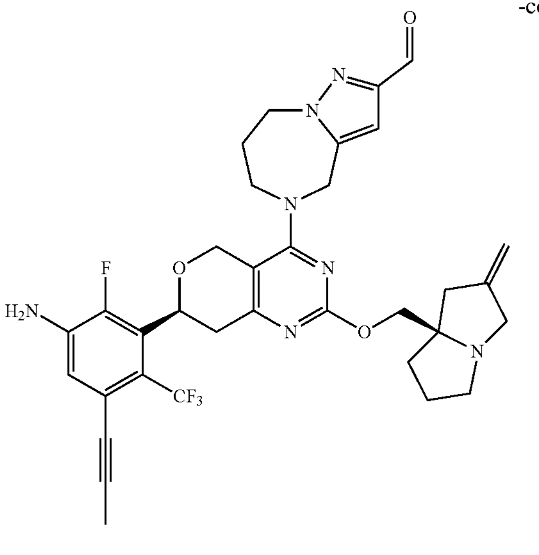

or

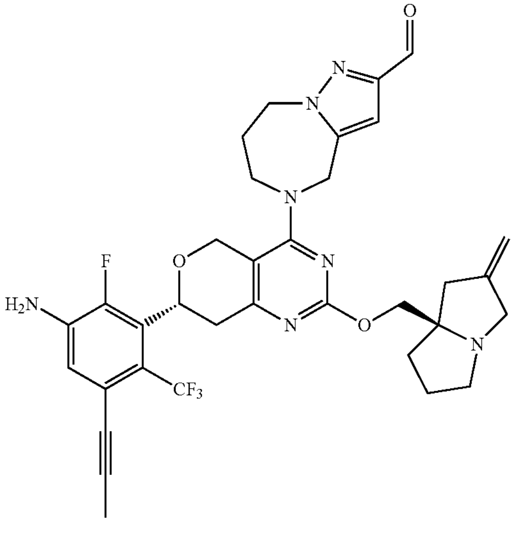

9

Step 1: Synthesis of Intermediate 9-2

Compound 4-11B (0.2 g, 254.53 kmol) was weighed and dissolved with DMF (15 mL). Compound 9-1 (61.59 mg, 305.44 kmol) was added. Then DIPEA (98.69 mg, 763.60 kmol, 133.00 μL) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated. A crude product was purified by column chromatography (petroleum ether: ethyl acetate=1:1), to obtain compound 9-2, MS m/z=801.6 $[M+H]^+$.

Step 2: Synthesis of Intermediate 9-3

Compound 9-2 (158.80 mg, 198.29 mol) was weighed and dissolved with DCM (10 mL). m-CPBA (40.26 mg, 198.29 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated under reduced pressure, to obtain compound 9-3, with MS m/z=817.4 $[M+H]^+$.

Step 3: Synthesis of Intermediate 9-4

Compound 5-2 (60.44 mg, 394.44 mol) was dissolved with anhydrous tetrahydrofuran (10 mL). Sodium tert-butanol (37.91 mg, 394.44 mol) was added. The reaction system reacted at 0° C. for 1 h. Compound 9-3 (0.1611 g, 197.22 mol) was added to react at 0° C. for 1 h. The reaction solution was quenched with water (20 mL), extracted with ethyl acetate (20 mL×3), washed with 50 mL of a saturated table salt solution, dried with anhydrous sodium sulfate, filtered, concentrated under reduced pressure, and separated by column chromatography (dichloromethane:methanol 20:1), to obtain compound 9-4. MS m/z=906.7 $[M+H]^+$.

Step 4: Synthesis of Hydrochloride of Compound 9

Compound 9-4 (127.44 mg, 140.66 mol) was dissolved with dichloromethane (15 mL). Trifluoroacetic acid (1.96 g, 17.17 mmol, 1.28 mL) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 9. MS m/z=666.3 $[M+H]^+$.

Embodiment 10

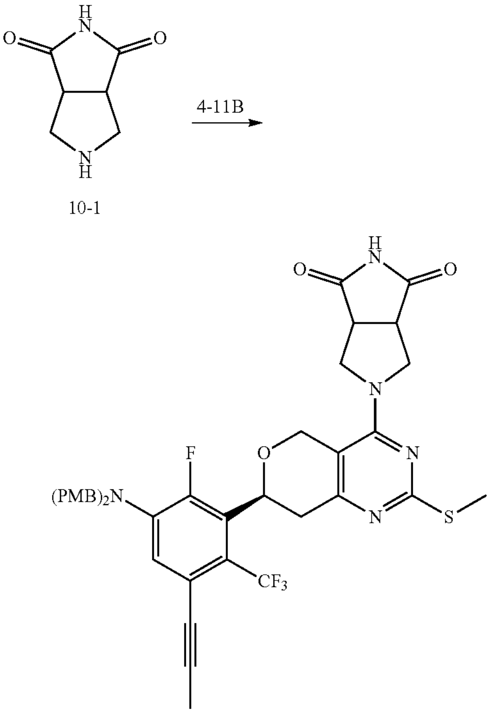

10-1 or

-continued
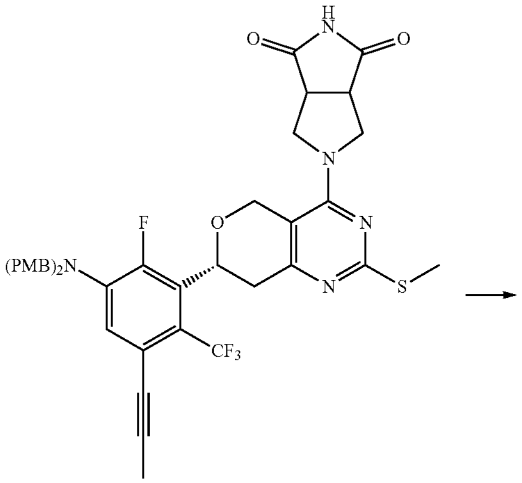
10-2
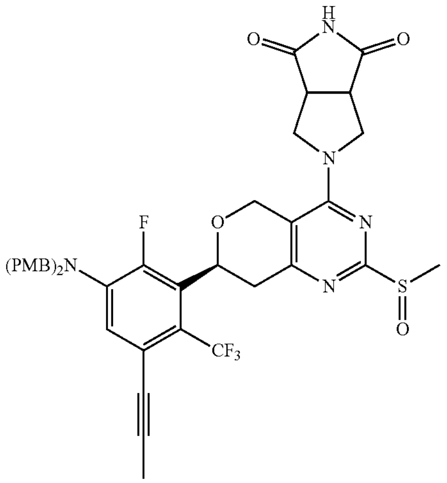
or
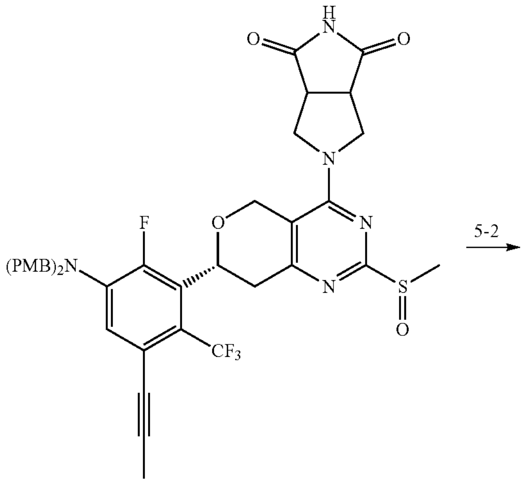
10-3
10-4 → 10
-continued
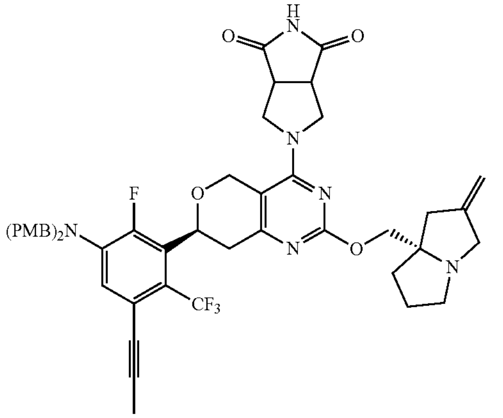
or
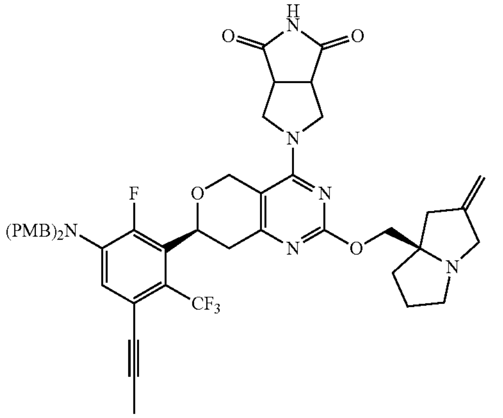
or
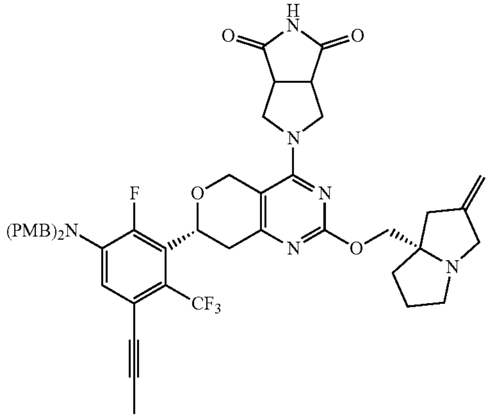
or
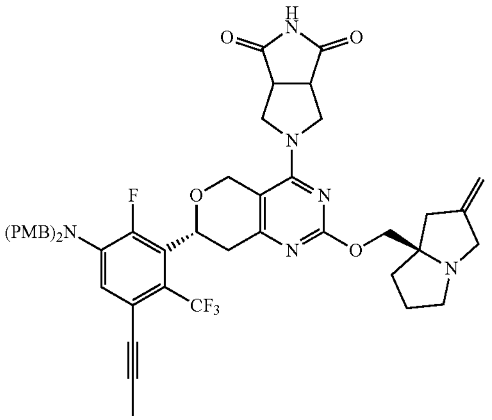
10-4

-continued

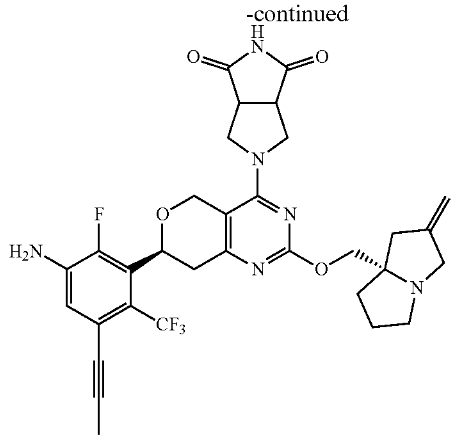

or

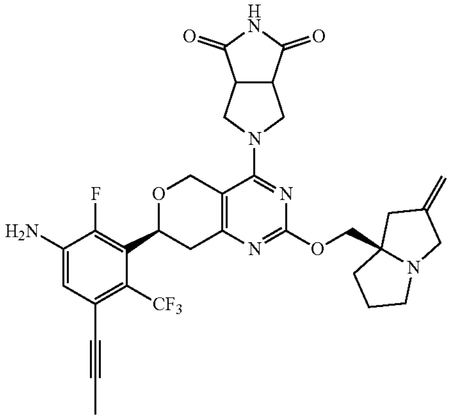

or

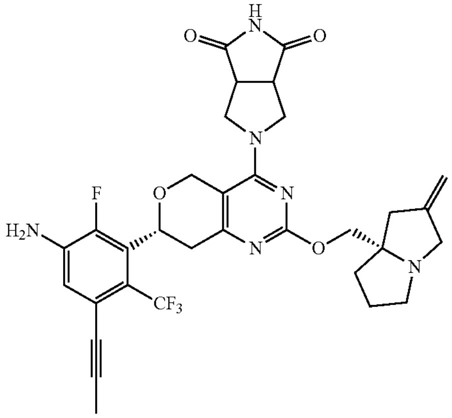

or

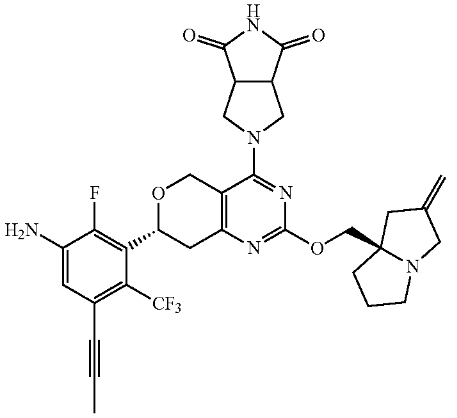

10

Step 1: Synthesis of Intermediate 10-2

Compound 4-11B (0.205 g, 260.90 mol) was weighed and dissolved with DMF (15 mL). Compound 10-1 (55.29 mg, 313.08 mol) was added. Then DIPEA (101.16 mg, 782.69 mol, 136.33 μL) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated. The crude product was purified by column chromatography (petroleum ether:ethyl acetate=1:1), to obtain compound 10-2, with MS m/z=776.3 $[M+H]^+$.

Step 2: Synthesis of Intermediate 10-3

Compound 10-2 (0.202 g, 260.37 mol) was weighed and dissolved with DCM (10 mL). m-CPBA (52.86 mg, 260.37 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated, to obtain compound 10-3, with MS m/z=792.5 $[M+H]^+$.

Step 3: Synthesis of Intermediate 10-4

Compound5-2 (79.34 mg, 517.80 mol) was dissolved with anhydrous tetrahydrofuran (10 mL). Sodium tert-butanol (49.76 mg, 517.80 mol) was added. The reaction system reacted at 0° C. for 1 h. Compound 10-3 (0.1611 g, 197.22 mol) was added to react at 0° C. for 1 h. The reaction solution was quenched with water (20 mL), extracted with ethyl acetate (30 mL×3), washed with 100 mL of a saturated table salt solution, dried with anhydrous sodium sulfate, filtered, concentrated under reduced pressure, and separated by column chromatography (dichloromethane:methanol=20:1), to obtain compound 10-4. MS m/z=881.7 $[M+H]^+$.

Step 4: Synthesis of Hydrochloride of Compound 10

Compound 10-4 (0.1338 g, 151.89 mol) was dissolved with dichloromethane (5 mL). Trifluoroacetic acid (5 mL) was added to react at 20° C. for 1 h. The reaction solution was concentrated to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 10. MS m/z=641.1 $[M+H]^+$.

Embodiment 11

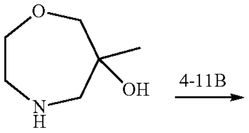

11-1

-continued
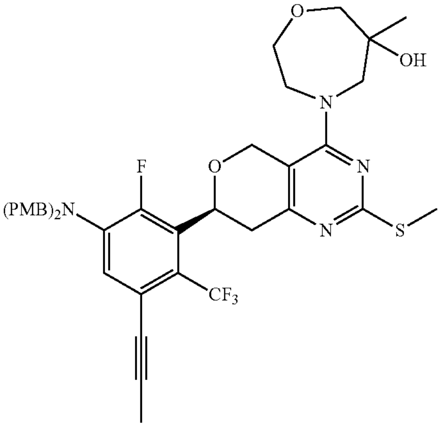
or
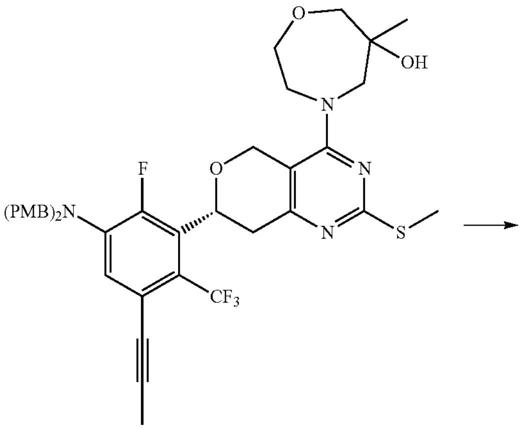
11-2
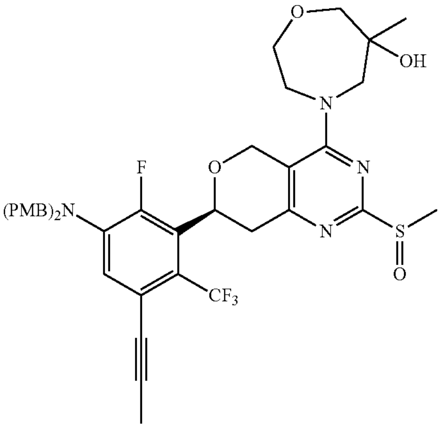
or
-continued
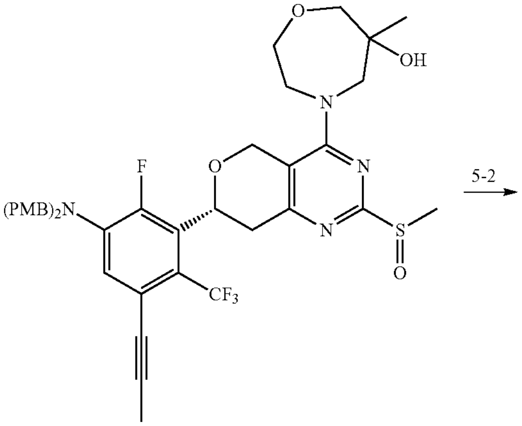
11-3
11-4 → 11A + 11B
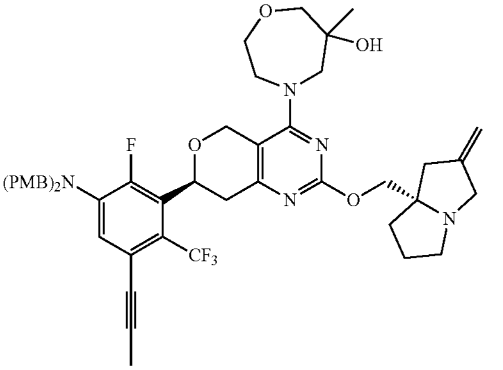
or
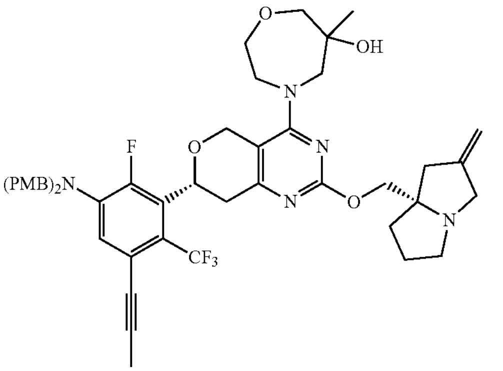
or
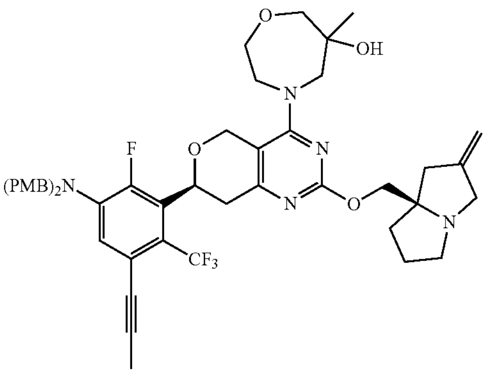
or -continued
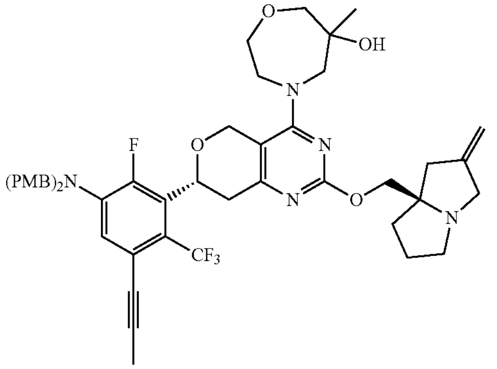
11-4
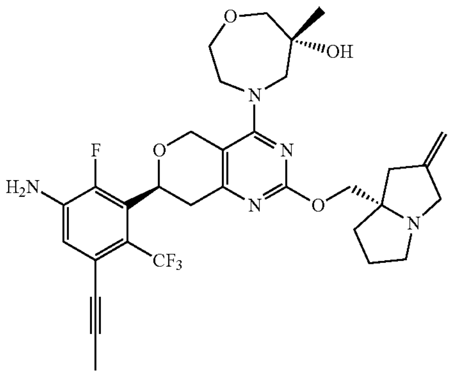
or
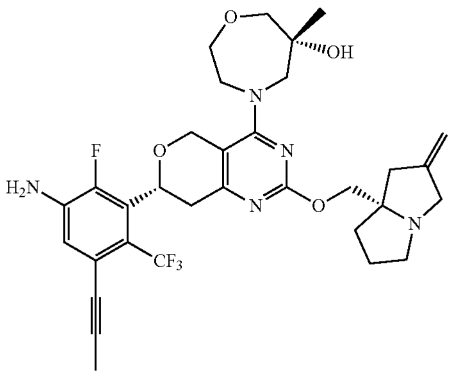
or
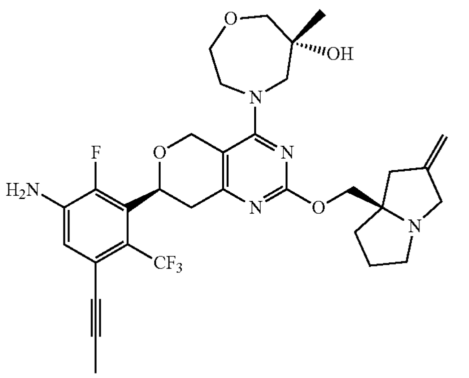
or
-continued
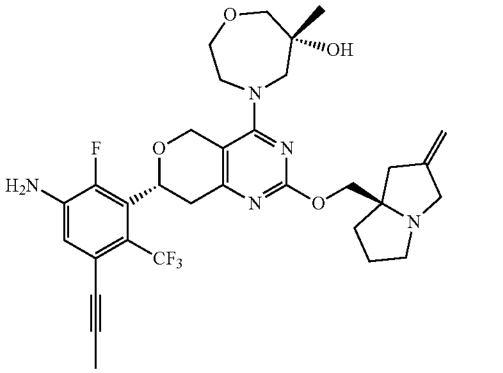
11A or 11B
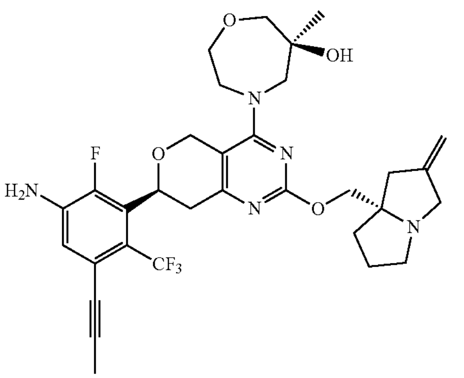
or
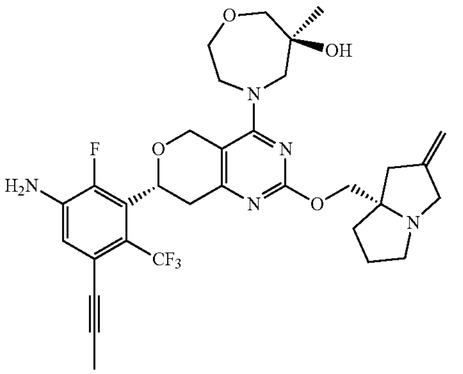
or
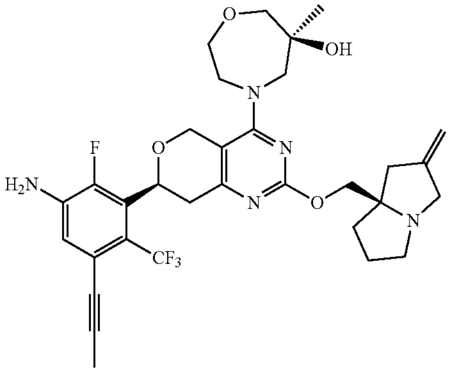
or -continued

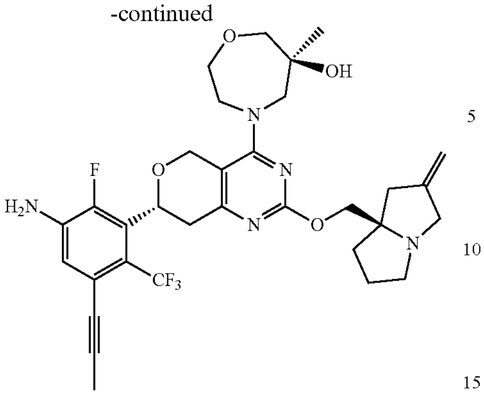

11B or 11A

Step 1: Synthesis of Intermediate 11-2

Compound 4-11B (0.48 g, 610.88 mol) was weighed and dissolved with DMF (15 mL). Compound 11-1 (96.16 mg, 733.06 mol) was added. Then DIPEA (236.85 mg, 1.83 mmol, 319.21 L) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated under reduced pressure to obtain the crude product. The crude product was purified by column chromatography (petroleum ether:ethyl acetate=1:1), to obtain compound 11-2, with MS m/z=767.4 $[M+H]^+$.

Step 2: Synthesis of Intermediate 11-3

Compound 11-2 (452.40 mg, 589.95 mol) was weighed and dissolved with DCM (10 mL). m-CPBA (119.77 mg, 589.95 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated under reduced pressure, to obtain compound 11-3, with MS m/z=783.5 $[M+H]^+$.

Step 3: Synthesis of Intermediate 11-4

Compound 5-2 (180.46 mg, 1.18 mmol) was dissolved with anhydrous tetrahydrofuran (20 mL). Sodium tert-butyl alcohol (113.19 mg, 1.18 mmol) was added. The reaction system reacted at 0° C. for 1 h. Compound 11-3 (0.461 g, 588.88 mol) was added to react at 0° C. for 1 h. The reaction solution was quenched with water (20 mL), extracted with ethyl acetate (30 mL×3), washed with 100 mL of a saturated table salt solution, dried with anhydrous sodium sulfate, filtered, concentrated under reduced pressure, and separated by column chromatography (dichloromethane:methanol=20:1), to obtain compound 11-4. MS m/z=872.5 $[M+H]^+$.

Step 4: Synthesis of Hydrochloride of Compound 11A and Hydrochloride of 11B

Compound 11-4 (0.2 g, 229.37 mol) was dissolved with dichloromethane (5 mL). Trifluoroacetic acid (3.19 g, 28.00 mmol, 2.08 mL) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 11A and the hydrochloride of compound 11B. Analysis method: Chromatographic column: ChromCore 120 C18 3 μm, 3.0×30 mm; mobile phase: [water (0.04% trifluoroacetic acid)-acetonitrile (0.02% trifluoroacetic acid)]; acetonitrile (0.02% trifluoroacetic acid) %: 10-80%, 7 min); retention time: 11A (Rt=2.902 min), MS m/z=632.2 $[M+H]^+$; 11B (Rt=3.020 min), MS m/z=632.2 $[M+H]^+$.

Embodiment 12

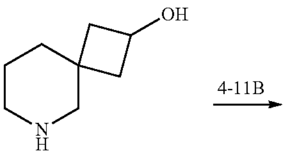

12-1

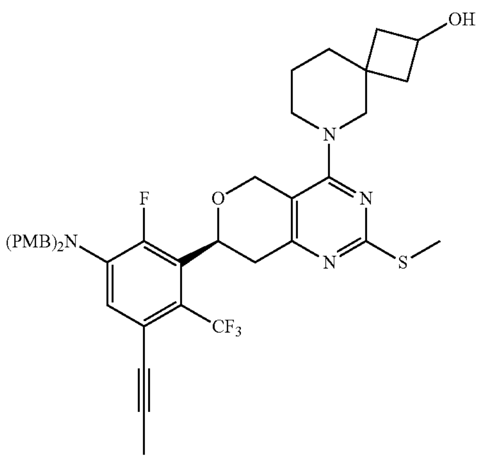

or

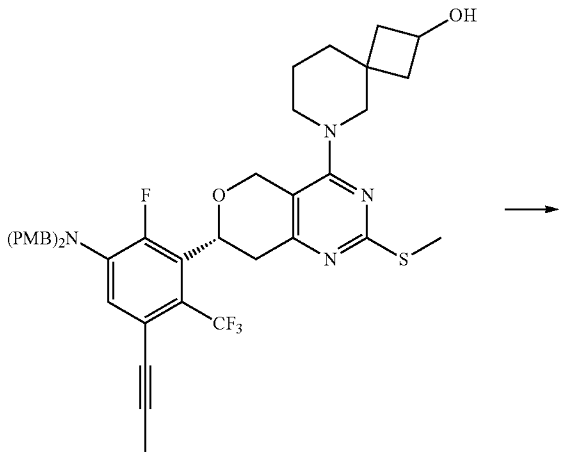

12-2

-continued
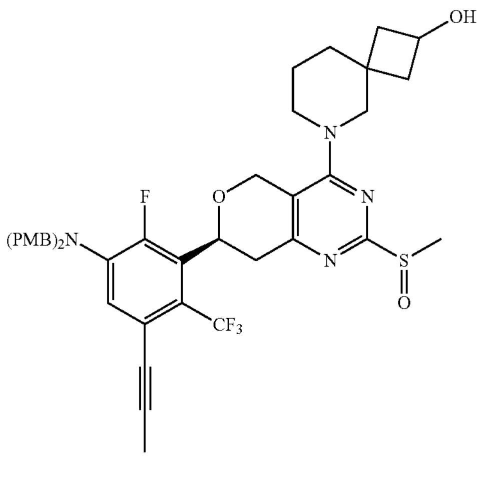
or
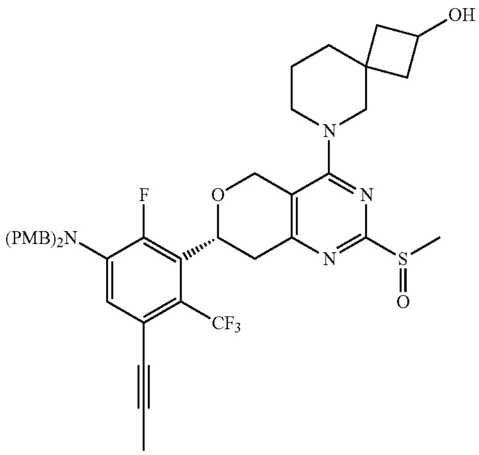
5-2
12-3
12-4
12
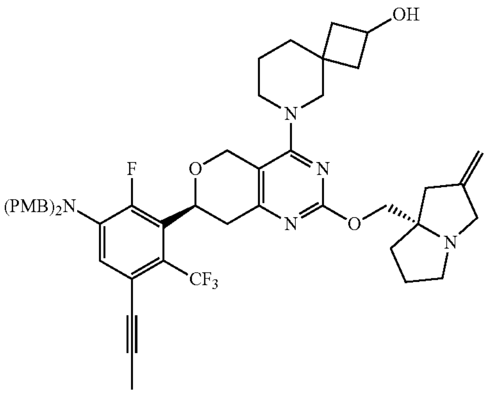
or
-continued
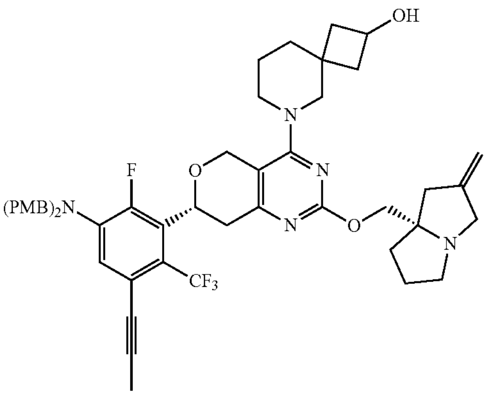
or
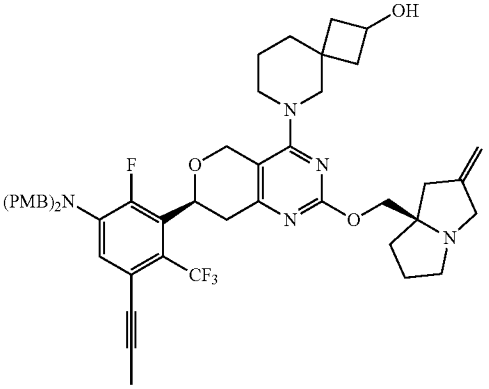
or
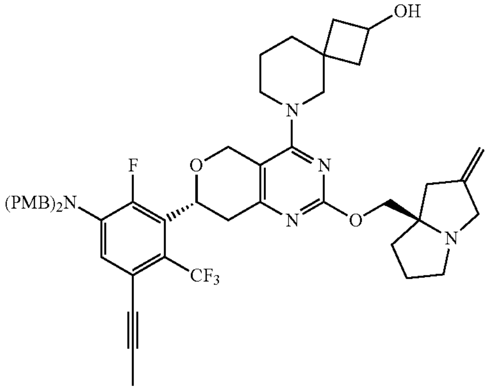
12-4
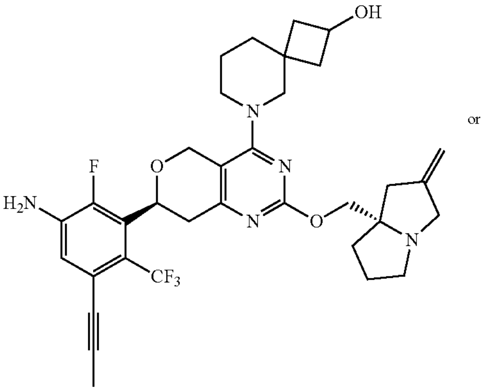
or -continued

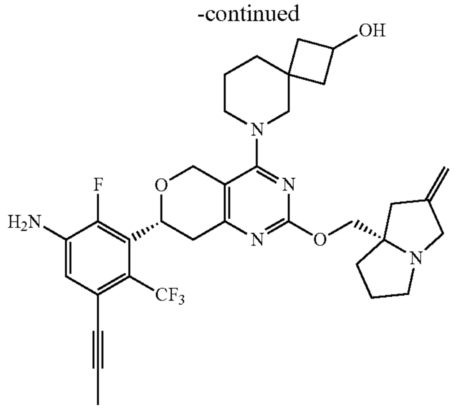

or

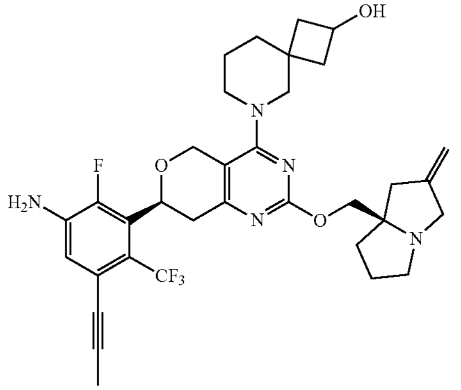

or

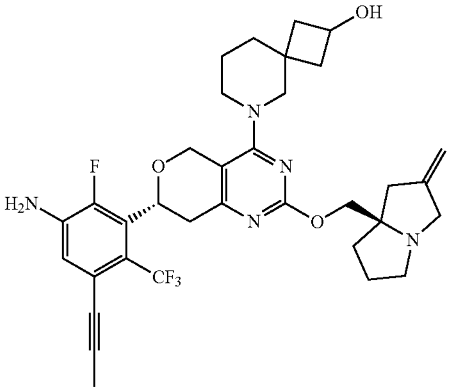

12

Step 1: Synthesis of Intermediate 12-2

Compound 4-11B (0.2 g, 254.53 mol) was weighed and dissolved with DMF (15 mL). Compound 12-1 (54.27 mg, 305.44 mol) was added. Then DIPEA (98.69 mg, 763.60 mol, 133.00 L) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated under reduced pressure to obtain the crude product. The crude product was purified by column chromatography (petroleum ether:ethyl acetate=1:1) to obtain compound 12-2, with MS m/z=777.4 [M+H]$^+$.

Step 2: Synthesis of Intermediate 12-3

Compound 12-2 (0.1976 g, 254.35 mol) was weighed and dissolved with DCM (10 mL). m-CPBA (51.67 mg, 254.35 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated under reduced pressure, to obtain compound 12-3, with MS m/z=793.6 [M+H]$^+$.

Step 3: Synthesis of Intermediate 12-4

Compound 5-2 (77.68 mg, 507.01 mol) was dissolved with anhydrous tetrahydrofuran (20 mL). Sodium tert-butanol (48.73 mg, 507.01 mol) was added. The reaction system reacted at 0° C. for 1 h. Compound 12-3 (0.201 g, 253.51 mol) was added to react at 0° C. for 1 h. The reaction solution was quenched with water (20 mL), extracted with ethyl acetate (30 mL×3), washed with 100 mL of a saturated table salt solution, dried with anhydrous sodium sulfate, filtered, concentrated under reduced pressure, and separated by column chromatography (dichloromethane:methanol=20:1), to obtain compound 12-4. MS m/z=882.5 [M+H]$^+$.

Step 4: Synthesis of Hydrochloride of Compound 12

Compound 12-4 (0.221 g, 250.57 mol) was dissolved with dichloromethane (5 mL). Trifluoroacetic acid (3.49 g, 30.59 mmol, 2.27 mL) was added to react at 20° C. for 1 h. The reaction solution was concentrated under reduced pressure to obtain the crude product. The crude product was separated by HPLC (chromatographic column: Xtimate C18 150×40 mm×5 m; mobile phase: [water (0.05% HCl)-acetonitrile]; acetonitrile %: 20-50%, 10 min), to obtain the hydrochloride of compound 12. MS m/z=642.4 [M+H]$^+$.

Embodiment 13

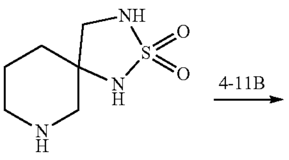

13-1

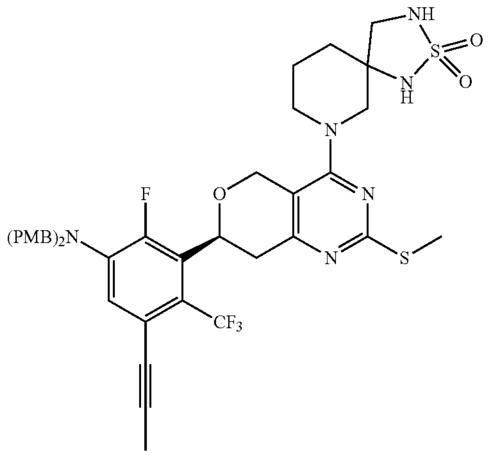

or

-continued
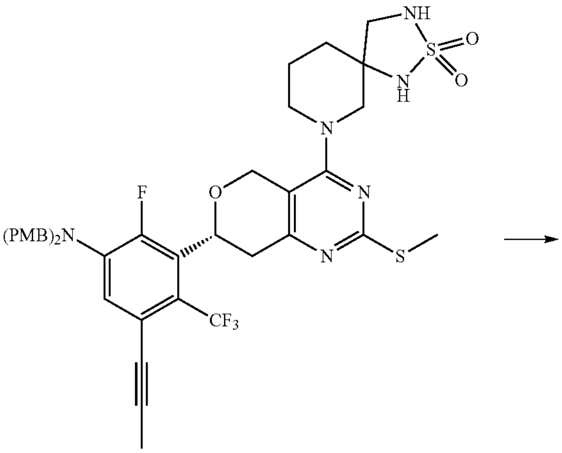
13-2
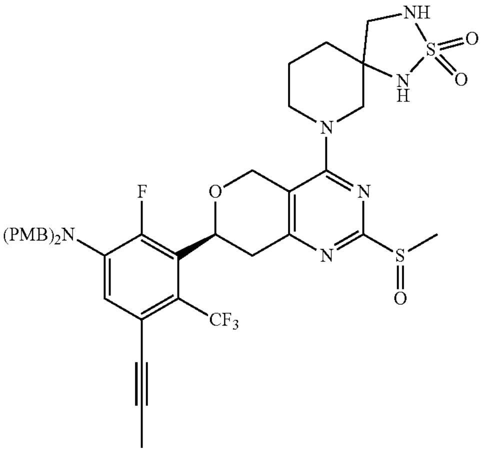
or
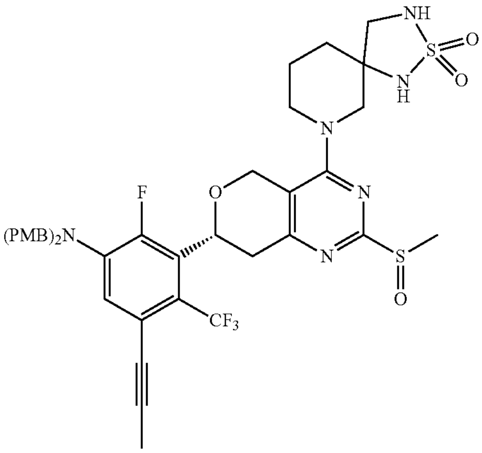
13-3
-continued
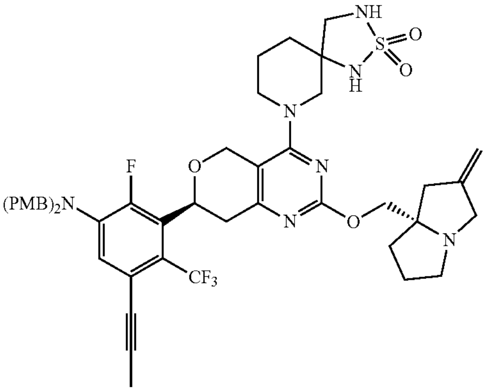
or
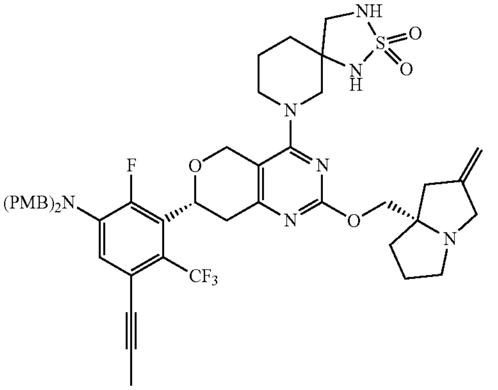
or
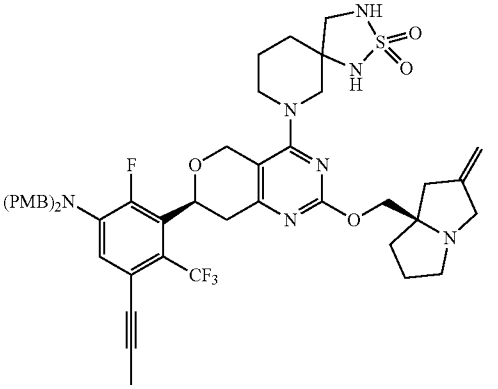
or
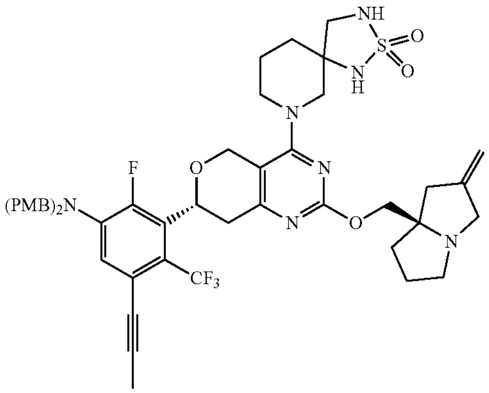
13-4
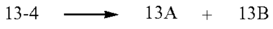

-continued
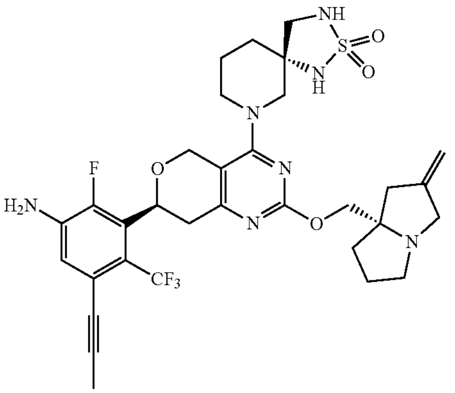
or
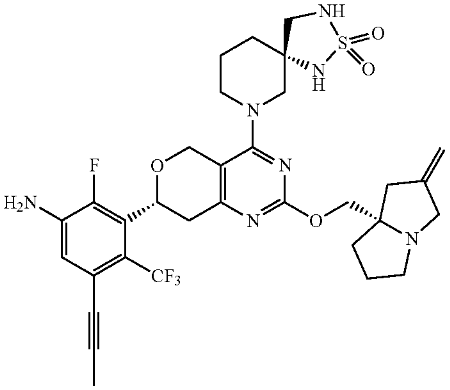
or
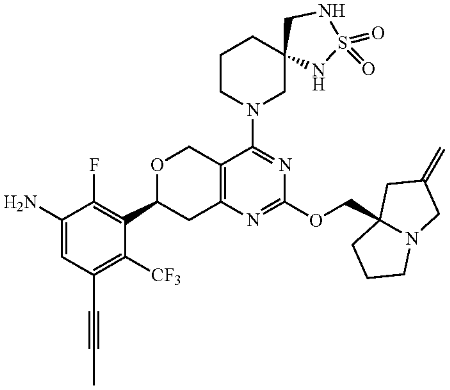
or
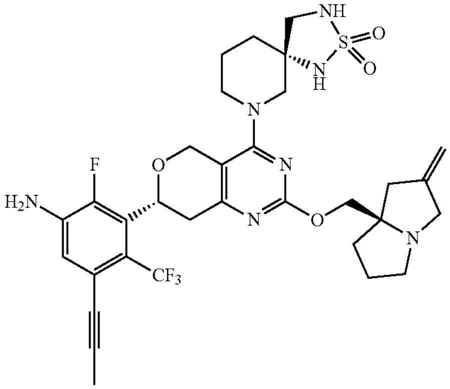
13A or 13B
-continued
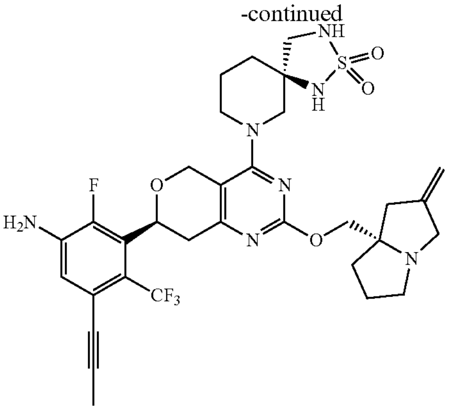
or
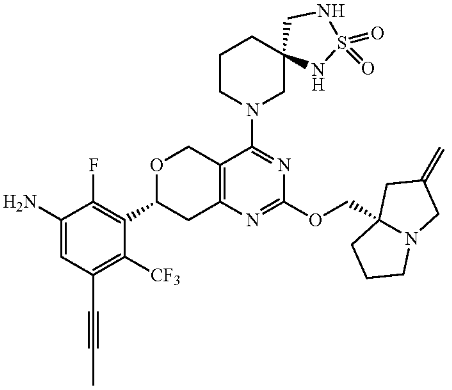
or
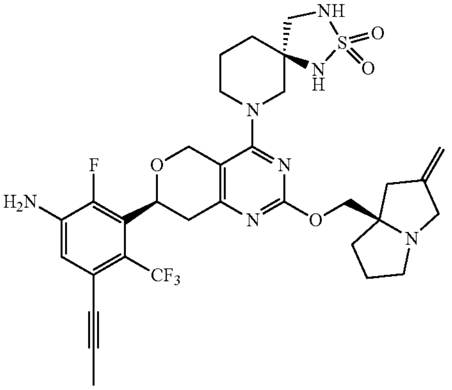
or
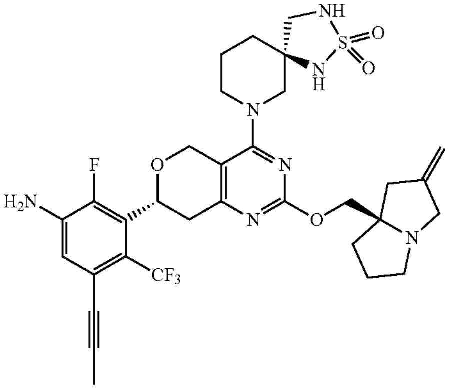
13B or 13A
Step 1: Synthesis of Intermediate 13-2
Compound 4-11B (0.35 g, 445.44 mol) was weighed and dissolved with DMF (15 mL). Compound 13-1 (121.72 mg, 534.52 mol) was added. Then DIPEA (172.70 mg, 1.34 mmol, 232.76 L) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated under reduced pressure to obtain the crude product. The crude product was purified by column chromatography (petroleum ether:ethyl acetate=1:1) to obtain compound 13-2, with MS m/z=827.4 $[M+H]^+$.

Step 2: Synthesis of Intermediate 13-3

Compound 13-2 (0.4165 g, 503.68 mol) was weighed and dissolved with DCM (10 mL). m-CPBA (102.26 mg, 503.68 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated, to obtain compound 13-3, with MS m/z=843.5 $[M+H]^+$.

Step 3: Synthesis of Intermediate 13-4

Compound 5-2 (154.33 mg, 1.01 mmol) was dissolved with anhydrous tetrahydrofuran (20 mL). Sodium tert-butanol (96.80 mg, 1.01 mmol) was added. The reaction system reacted at 0° C. for 1 h. Compound13-3 (0.4245 g, 503.61 mol) was added to react at 0° C. for 1 h. The reaction solution was quenched with water (20 mL), extracted with ethyl acetate (30 mL×3), washed with 100 mL of a saturated table salt solution, dried with anhydrous sodium sulfate, filtered, concentrated under reduced pressure, and separated by column chromatography (dichloromethane:methanol=20:1), to obtain compound 13-4. MS m/z=932.4 $[M+H]^+$.

Step 4: Synthesis of Hydrochlorides of Compounds 13A and 13B

Compound 13-4 (0.293 g, 314.26 mol) was dissolved with dichloromethane (15 mL). Trifluoroacetic acid (4.37 g, 38.36 mmol, 2.85 mL) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochlorides of compounds 13A and 13B. Analysis method: Chromatographic column: ChromCore 120 C18 3 μm, 3.0×30 mm; mobile phase: [water (0.04% trifluoroacetic acid)-acetonitrile (0.02% trifluoroacetic acid)]; acetonitrile (0.02% trifluoroacetic acid) %: 10-80%, 7 min); retention time: 13A (Rt=2.891 min), MS m/z=692.2 $[M+H]^+$; 13B (Rt=3.126 min), MS m/z=692.2 $[M+H]^+$.

Embodiment 14

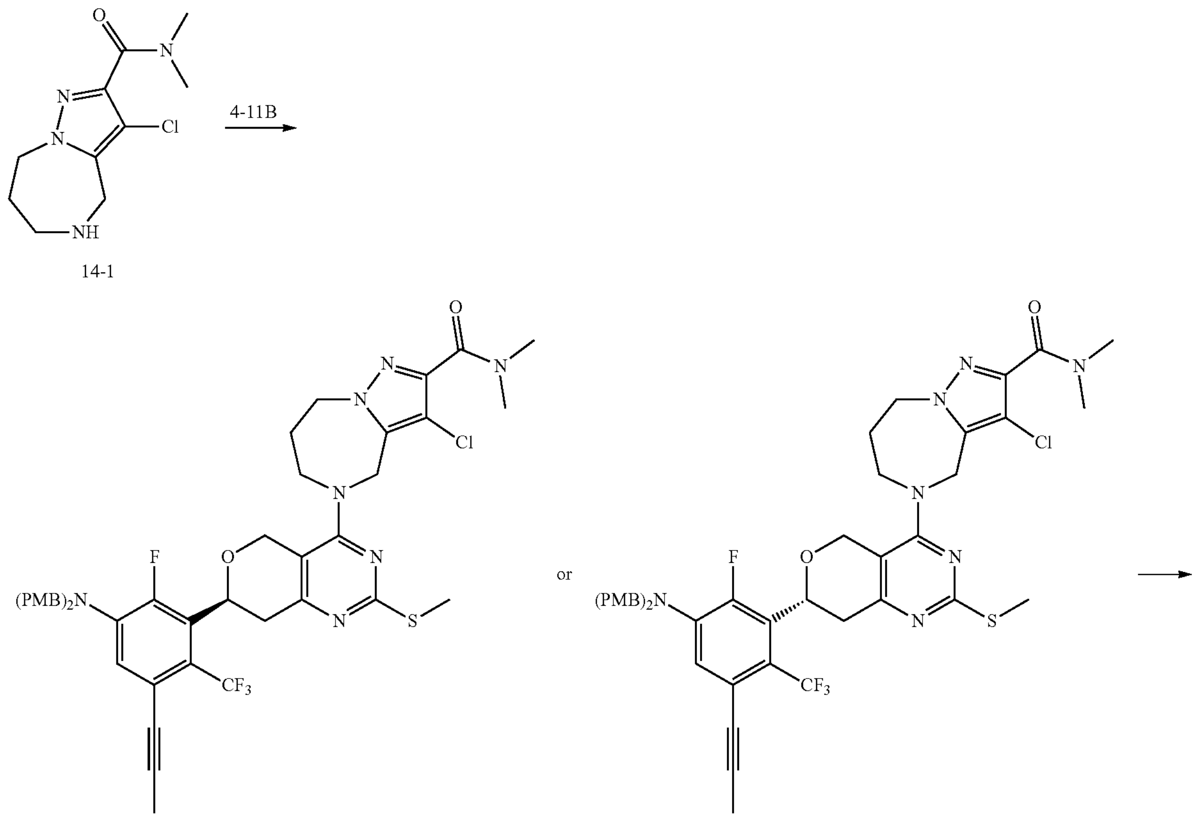

14-1 or 14-2

-continued
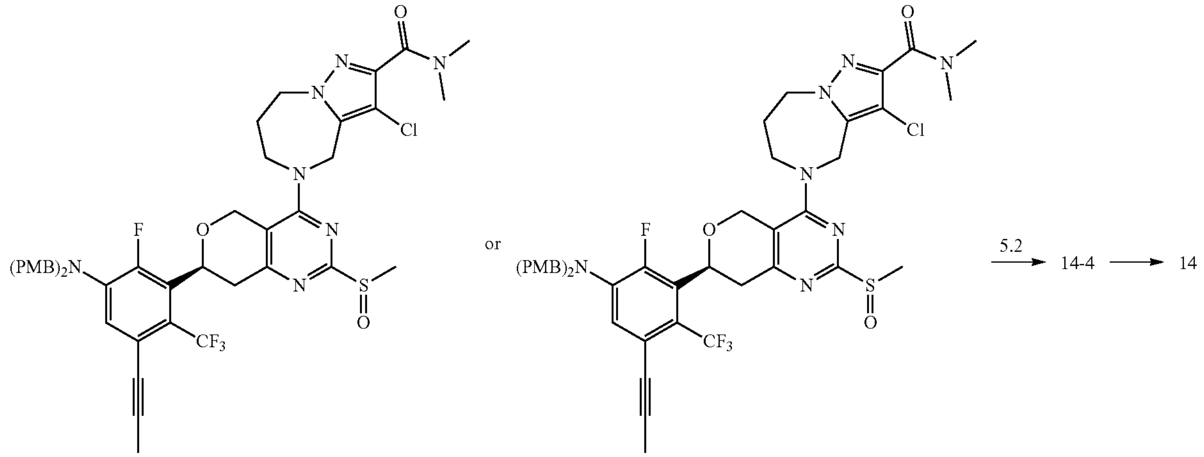
14-3
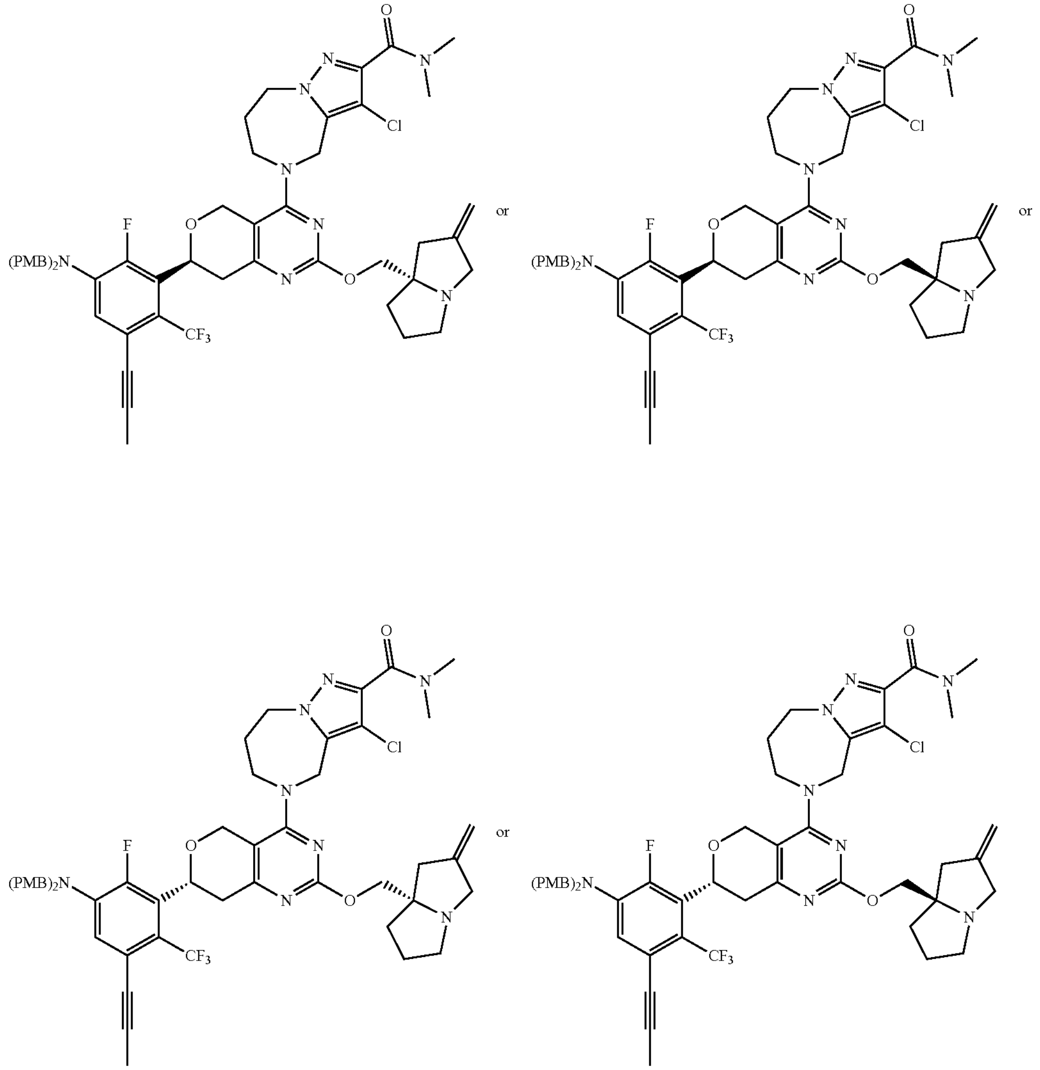
14-4

-continued

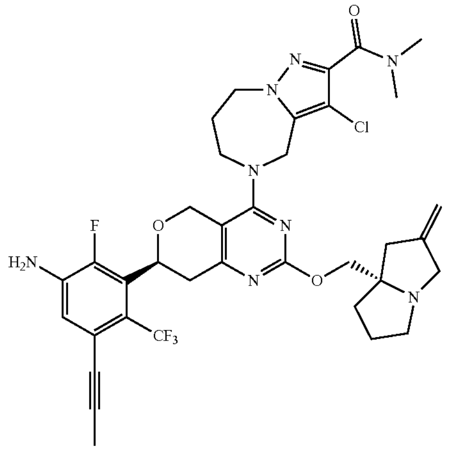

or

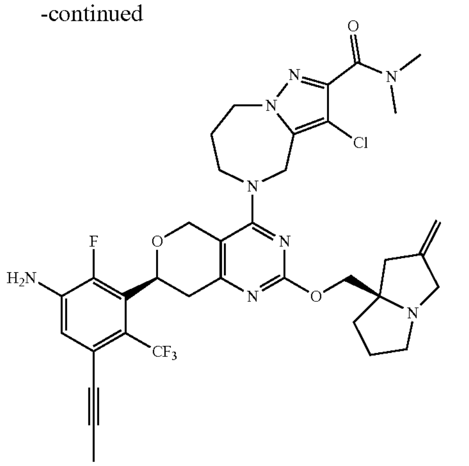

or

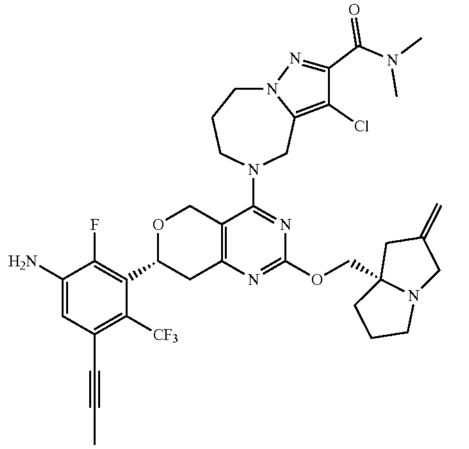

or

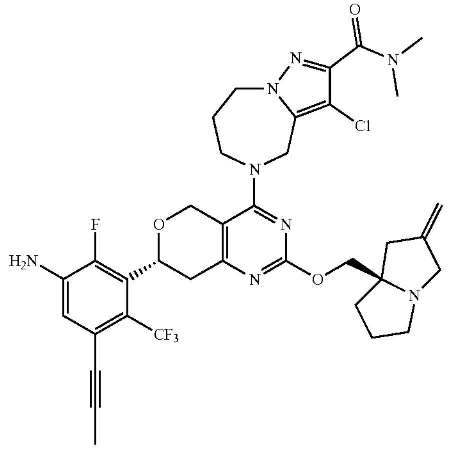

14

Step 1: Synthesis of Intermediate 14-2

Compound 4-11B (200.00 mg, 254.53 μmol) was weighed and dissolved with DMF (10 mL). The hydrochloride of compound 14-1 (106.21 mg) was added. Then DIPEA (98.69 mg, 763.60 μmol, 133.01 μL) was added to react at 100° C. for 1 h. The reaction solution was concentrated under reduced pressure to obtain the crude product. The crude product was purified by column chromatography (dichloromethane:methanol=10:1) to obtain compound 14-2, with MS m/z=878.6 $[M+H]^+$.

Step 2: Synthesis of Intermediate 14-3

Compound 14-2 (200.23 mg, 227.95 μmol) was weighed and dissolved with DCM (10 mL). m-CPBA (39.34 mg, 227.95 μmol, 85% purity) was added to react at room temperature of 25° C. for 1 h. The reaction solution was concentrated under reduced pressure to obtain compound 14-3, with MS m/z=894.3 $[M+H]^+$.

Step 3: Synthesis of Intermediate 14-4

Compound 5-2 (61.67 mg, 402.52 μmol) was dissolved with anhydrous tetrahydrofuran (5 mL). Sodium tert-butanol (38.68 mg, 402.52 μmol) was added. The reaction system reacted at 0° C. for 1 h. Compound 14-3 (180 mg, 201.26 μmol) was added to react at 0° C. for 1 h. The reaction solution was quenched with water (10 mL), adjusted to pH=6 with 1N diluted hydrochloric acid, and extracted with ethyl acetate (100 mL×2). The organic phases were mixed, dried with anhydrous sodium sulfate, filtered, concentrated under reduced pressure, and separated by column chromatography (dichloromethane:methanol=10:1) to obtain compound 14-4. MS m/z=983.8 $[M+H]^+$.

Step 4: Synthesis of Compound 14 and Hydrochloride of Compound 14

Compound 14-4 (118 mg, 119.98 mol) was dissolved with trifluoroacetic acid (5 mL) to react at 25° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia)-acetonitrile]; acetonitrile %: 52-82% over 8 min) to obtain compound 14. MS m/z=743.2 $[M+H]^+$.

The crude product was separated by HPLC in a hydrochloric acid condition (chromatographic column: Xtimate C18 150×40 mm×5 μm; mobile phase: [water (0.05% HCl)-acetonitrile]; acetonitrile %: 17-47%, 10 min), to obtain the hydrochloride of compound 14. Chiral SFC analysis was carried out (chromatographic column: DAICEL CHIRALCEL OD-3 (50 mm×4.6 mm, 3 μm); mobile phase: [supercritical $CO_2$-ethanol (0.05% diethylamine)]; ethanol (0.05% diethylamine) %: 40-40%), Rt=0.745 min. MS m/z=743.2

[M+H]+. $^1$H NMR (400 MHz, $CD_3OD$) δ=7.00-6.93 (m, 1H), 5.34 (br d, J=5.9 Hz, 2H), 5.27-5.15 (m, 2H), 5.09 (br d, J=14.0 Hz, 1H), 5.00-4.93 (m, 2H), 4.83 (br d, J=11.8 Hz, 1H), 4.65 (br d, J=11.9 Hz, 1H), 4.59-4.51 (m, 1H), 4.37-4.27 (m, 2H), 4.17 (br d, J=13.4 Hz, 1H), 3.96-3.89 (m, 2H), 3.85-3.76 (m, 1H), 3.35-3.31 (m, 1H), 3.29-3.19 (m, 1H), 3.16 (s, 3H), 3.13-3.09 (m, 3H), 3.08-2.97 (m, 2H), 2.83 (br d, J=16.3 Hz, 1H), 2.62-2.48 (m, 1H), 2.47-2.33 (m, 2H), 2.31-2.13 (m, 3H), 2.04 (s, 3H).
Embodiment 15
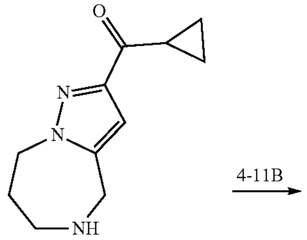
15-1
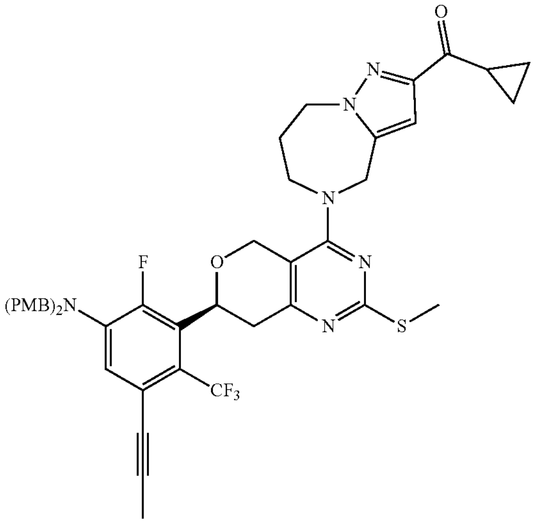
or
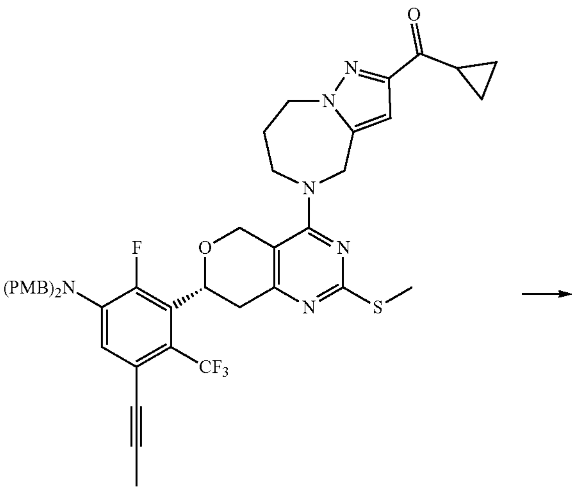
15-2
-continued
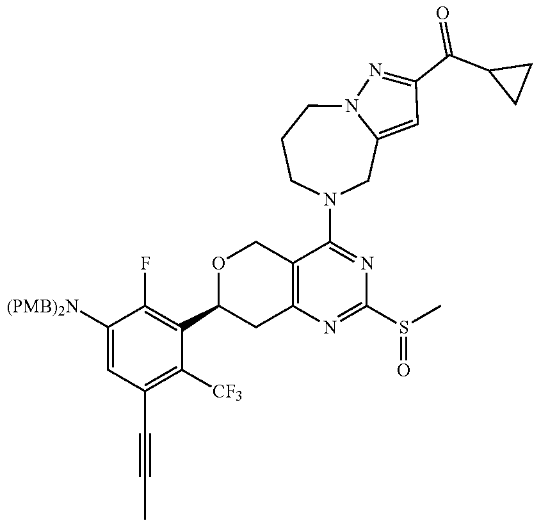
or
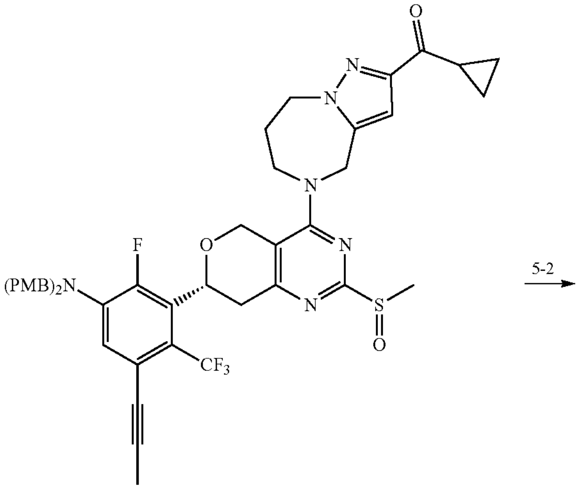
15-3
15-4 15
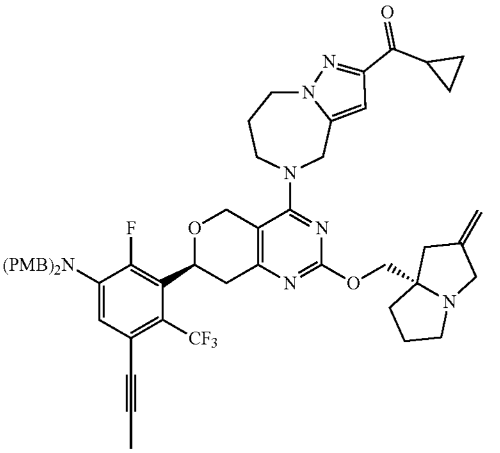
or -continued
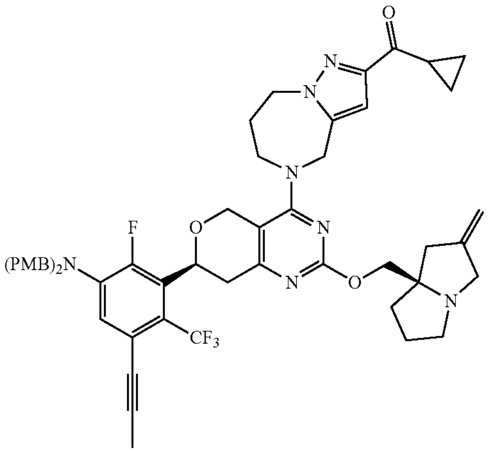
or
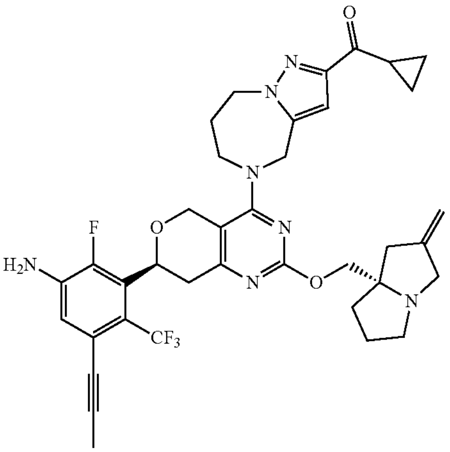
or
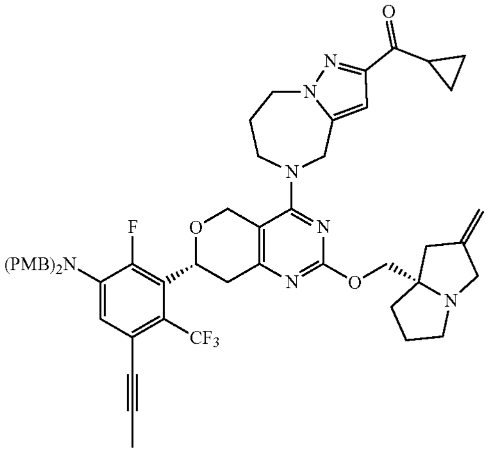
15-4
-continued
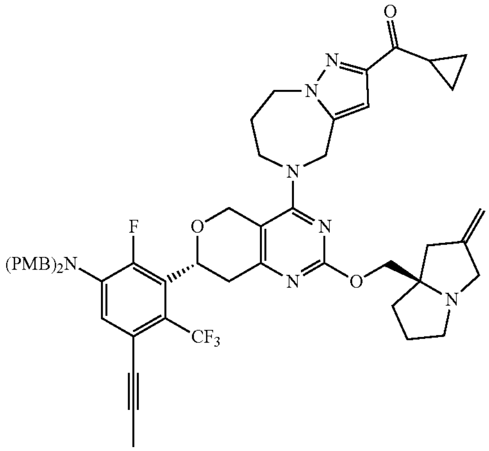
or
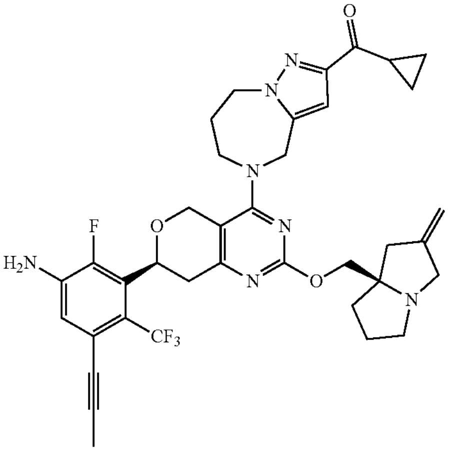
or
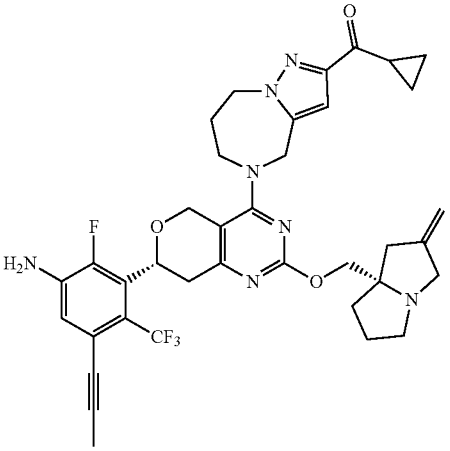
or -continued

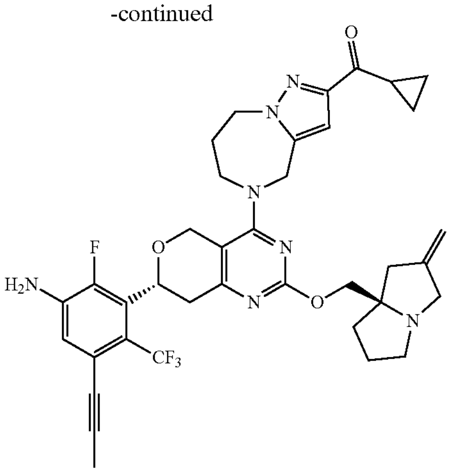

15

Step 1: Synthesis of Intermediate 15-2

Compound 4-11B (200.00 mg, 254.53 mol) was weighed and dissolved with DMF (10 mL). The hydrochloride of compound 15-1 (92.29 mg, 381.80 mol) was added. Then DIPEA (98.69 mg, 763.60 mol) was added to react at 100° C. for 1 h. The reaction solution was concentrated under reduced pressure to obtain the crude product. The crude product was purified by column chromatography (dichloromethane:methanol=10:1) to obtain compound 15-2, with MS m/z=841.6 $[M+H]^+$.

Step 2: Synthesis of Intermediate 15-3

Compound 15-2 (150.00 mg, 178.37 mol) was weighed and dissolved with DCM (10 mL). m-CPBA (30.78 mg, 178.37 mol, 85% purity) was added to react at room temperature of 25° C. for 1 h. The reaction solution was concentrated under reduced pressure to obtain compound 15-3, with MS m/z=857.6 $[M+H]^+$.

Step 3: Synthesis of Intermediate 15-4

Compound 5-2 (46.49 mg, 303.41 mol) was dissolved with anhydrous tetrahydrofuran (5 mL). Sodium tert-butanol (29.16 mg, 303.41 mol) was added. The reaction system reacted at 0° C. for 1 h. Compound 15-3 (130 mg, 151.71 mol) was added to react at 0° C. for 1 h. The reaction solution was quenched with water (10 mL), adjusted to pH=6 with 1N diluted hydrochloric acid, and extracted with ethyl acetate (100 mL×2). The organic phases were mixed, dried with anhydrous sodium sulfate, filtered, concentrated under reduced pressure, and separated by column chromatography (dichloromethane:methanol=10:1) to obtain compound 15-4. MS m/z=946.8 $[M+H]^+$.

Step 4: Synthesis of Hydrochloride of Compound 15

Compound 15-4 (100 mg, 105.70 mol) was dissolved with trifluoroacetic acid (5 mL) to react at 25° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 15. MS m/z=706.3 $[M+H]^+$.

Embodiment 16

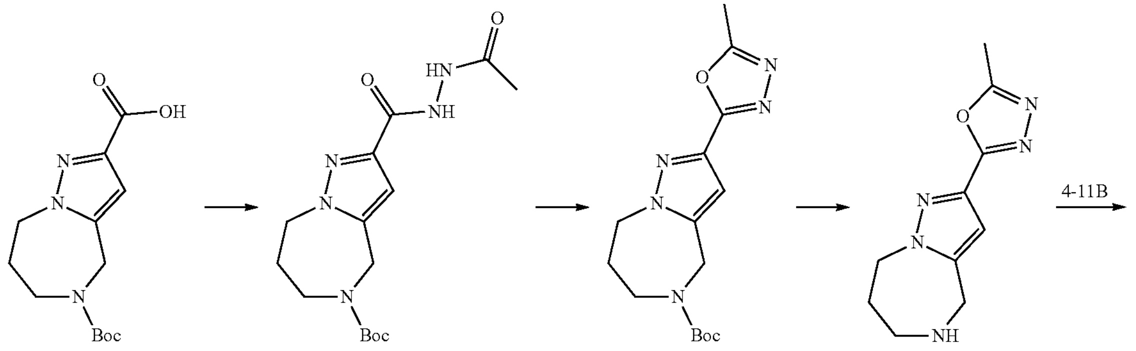

16-1 16-2 16-3 16-4

-continued
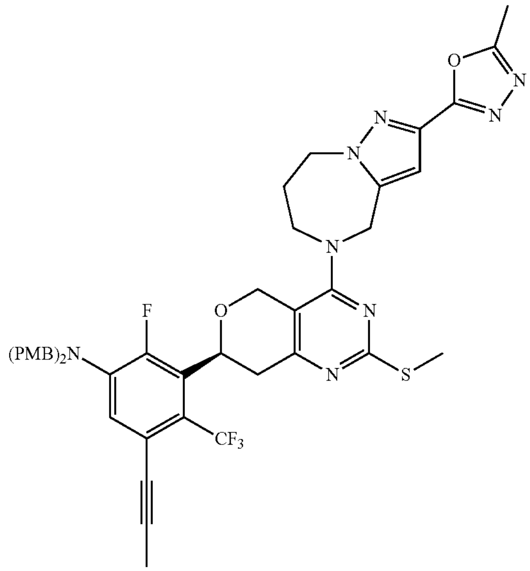
or
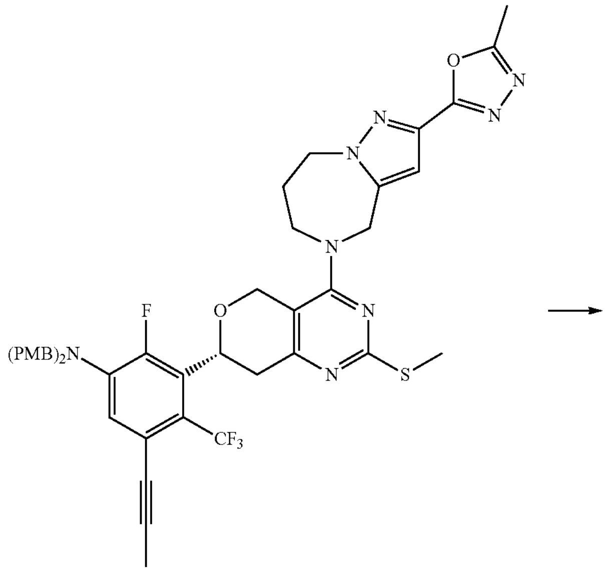
16-5
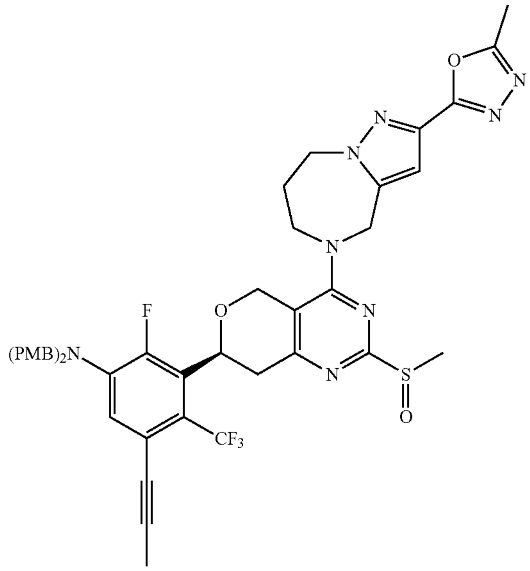
or
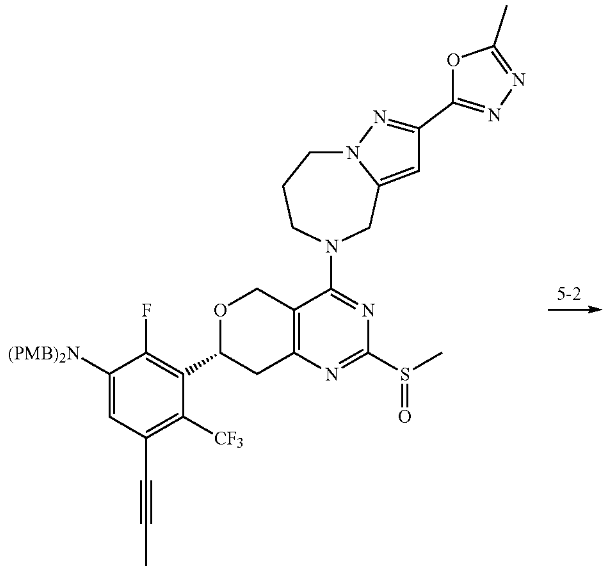
16-6
16-7
16

-continued
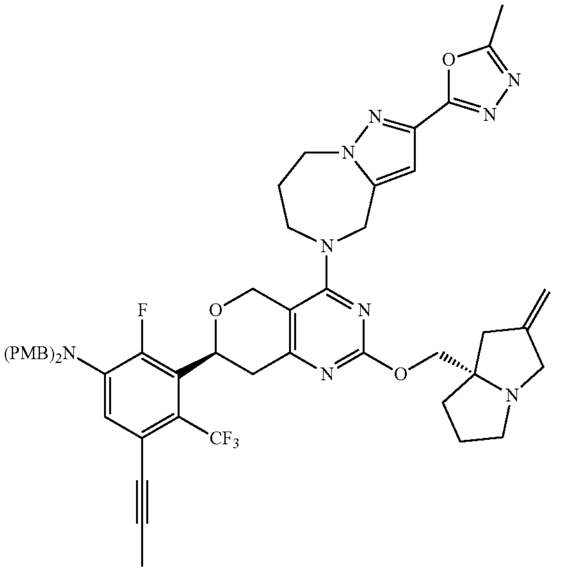
or
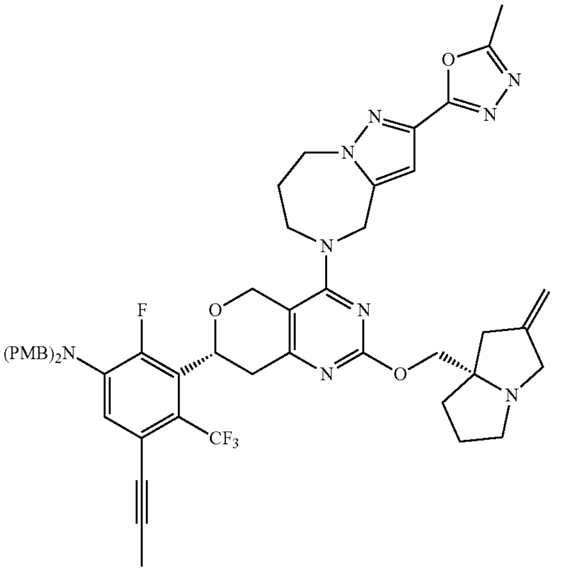
or
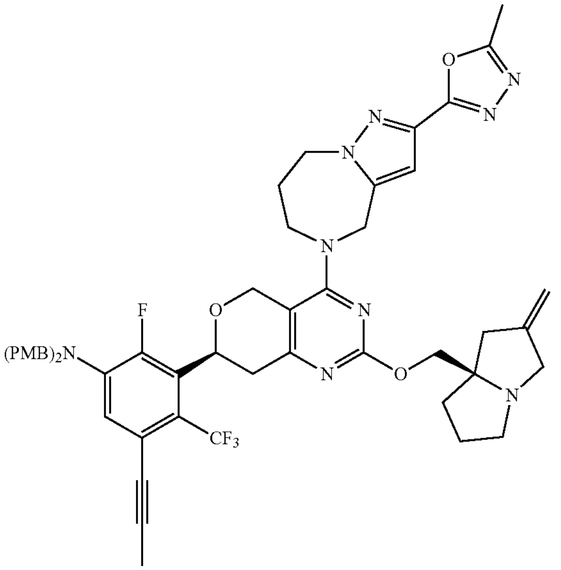
or
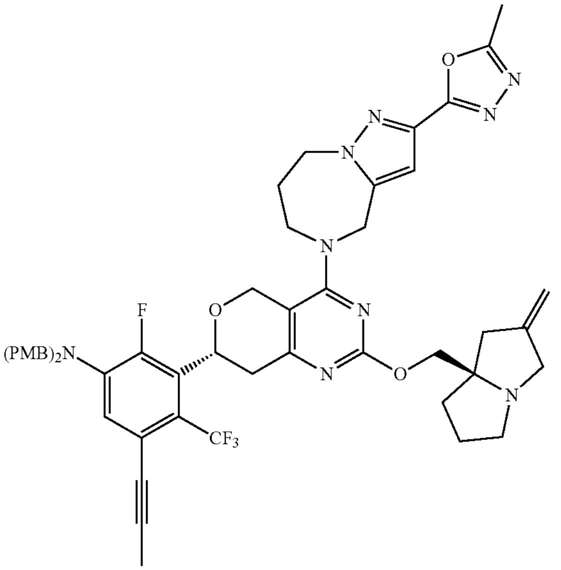
16-7

-continued

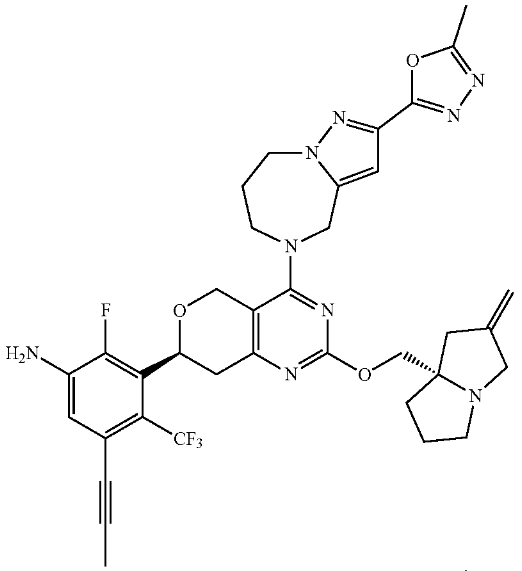

or

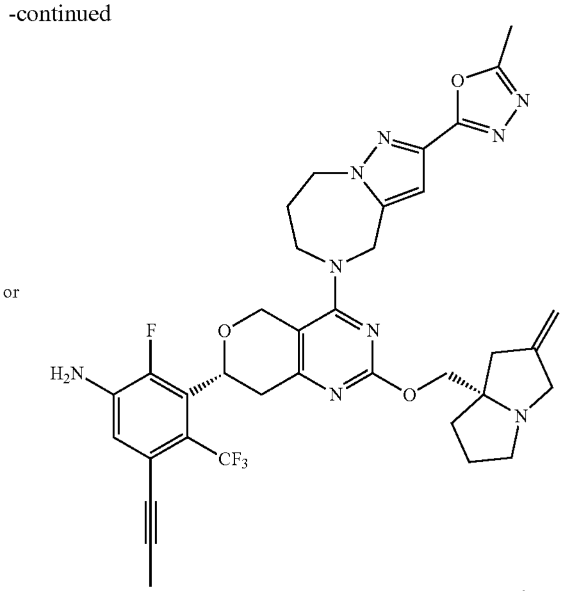

or

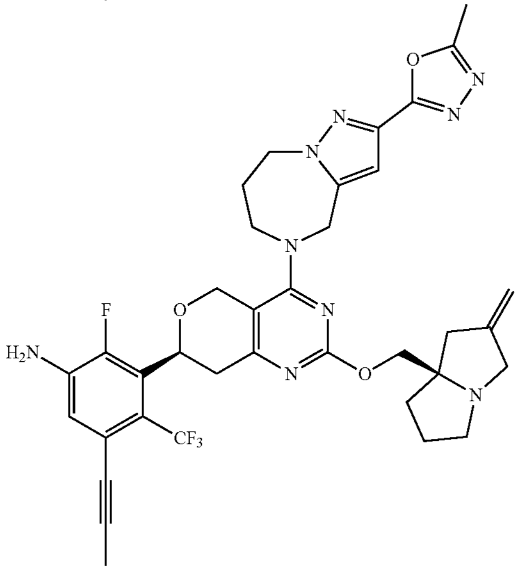

or

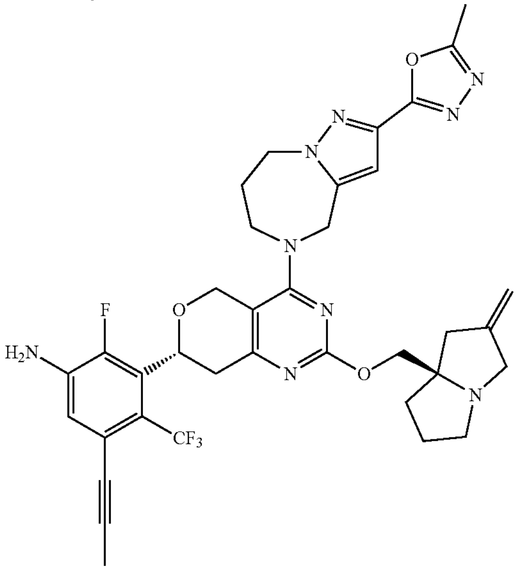

16

Step 1: Synthesis of Intermediate 16-2

Compound 16-1 (500 mg, 1.78 mmol) was weighed and dissolved with DMF (5 mL). 0-(7-azabenzotriazole-1-YL)-N,N,N,N-tetramethylurea hexafluorophosphine (810.99 mg, 2.13 mmol), and triethylamine (539.57 mg, 5.33 mmol, 742.18 L) were added and stirred at 25° C. for 1 h. Then 2-(2-fluorophenyl)acetylhydrazide hydrochloride (235.78 mg, 2.13 mmol) was added to react at 25° C. for 16 h. The reaction solution was extracted with ethyl acetate (20 mL×2). The organic phases were mixed, dried with anhydrous sodium sulfate, filtered, concentrated under reduced pressure, and separated by column chromatography (dichloromethane:methanol=10:1) to obtain compound 16-2. MS m/z=338.2 $[M+H]^+$.

Step 2: Synthesis of Intermediate 16-3

Triphenylphosphine (777.45 mg, 2.96 mmol) and elemental iodine (752.31 mg, 2.96 mmol) were weighed and dissolved with dichloromethane (10 mL) at 0° C. After dissolution, DIPEA (766.17 mg, 5.93 mmol) was added. Then a tetrahydrofuran solution (10 mL) of compound 16-2 (500 mg, 1.48 mmol) was added and stirred to react at 20° C. for 6 h. The reaction solution was extracted with ethyl acetate (20 mL×2). The organic phases were mixed, dried with anhydrous sodium sulfate, filtered, concentrated under reduced pressure, and separated by column chromatography (dichloromethane:methanol=10:1) to obtain compound 16-3. MS m/z=320.2 $[M+H]^+$.

Step 3: Synthesis of Hydrochloride of Intermediates 16-4

Compound 16-3 (1 g, 1.41 mmol) was weighed and dissolved with a 4M hydrochloric acid/ethyl acetate solution (10 mL) and stirred at 25° C. for 1 h. The reaction solution was concentrated under reduced pressure to obtain the hydrochloride of compound 16-4.

Step 4: Synthesis of Intermediate 16-5

Compound 4-11B (200.00 mg, 254.53 mol) was weighed and dissolved with DMF (10 mL). The hydrochloride of compound 16-4 (97.63 mg) was added. Then DIPEA (148.03 mg, 1.15 mmol, 199.50 L) was added to react at 100° C. for 1 h. The reaction solution was concentrated under reduced pressure to obtain the crude product. The crude product was purified by column chromatography (dichloromethane:methanol=10:1), to obtain compound 16-5, with MS m/z=855.5 $[M+H]^+$.

Step 5: Synthesis of Intermediate 16-6

Compound 16-5 (120 mg, 140.37 mol) was weighed and dissolved with DCM (10 mL). m-CPBA (24.22 mg, 140.37 mol, 85% purity) was added to react at room temperature of 25° C. for 1 h. The reaction solution was concentrated under reduced pressure to obtain compound 16-6, with MS m/z=871.4 $[M+H]^+$.

Step 6: Synthesis of Intermediate 16-7

Compound 5-2 (35.19 mg, 229.64 mol) was dissolved with anhydrous tetrahydrofuran (5 mL). Sodium tert-butanol (22.07 mg, 229.64 mol) was added. The reaction system reacted at 0° C. for 1 h. Compound 16-6 (100 mg, 114.82 mol) was added to react at 0° C. for 1 h. The reaction solution was quenched with water (10 mL), adjusted to pH=6 with 1N diluted hydrochloric acid, and extracted with ethyl acetate (100 mL×2). The organic phases were mixed, dried with anhydrous sodium sulfate, filtered, concentrated, and separated by column chromatography (dichloromethane:methanol=10:1) to obtain compound 16-7. MS m/z=960.8 $[M+H]^+$.

Step 7: Synthesis of Compound 16

Compound 16-7 (70 mg, 72.91 mol) was dissolved with trifluoroacetic acid (5 mL) to react at 25° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia)-acetonitrile]; acetonitrile %: 52-82% over 8 min), to obtain compound 16. MS m/z=720.2 $[M+H]^+$.

Embodiment 17

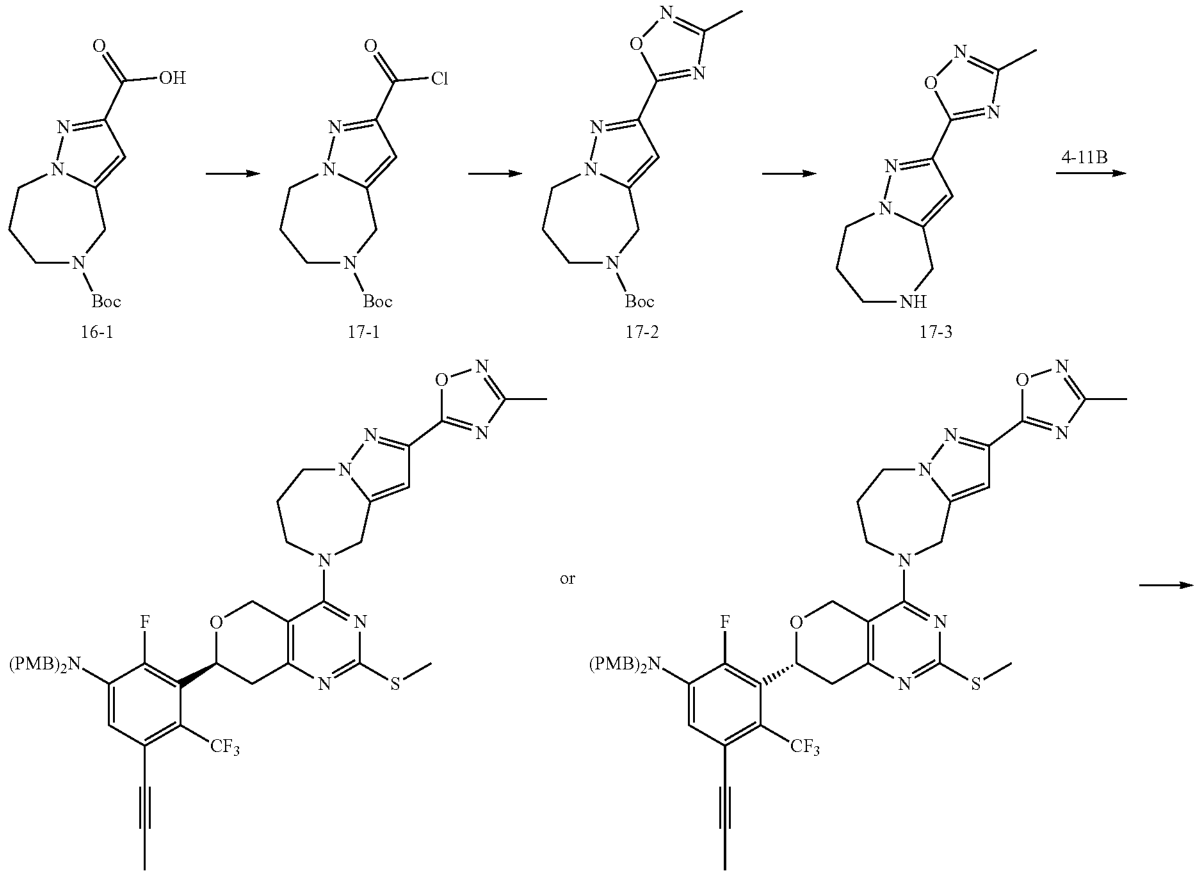

16-1 17-1 17-2 17-3 or 17-4

-continued
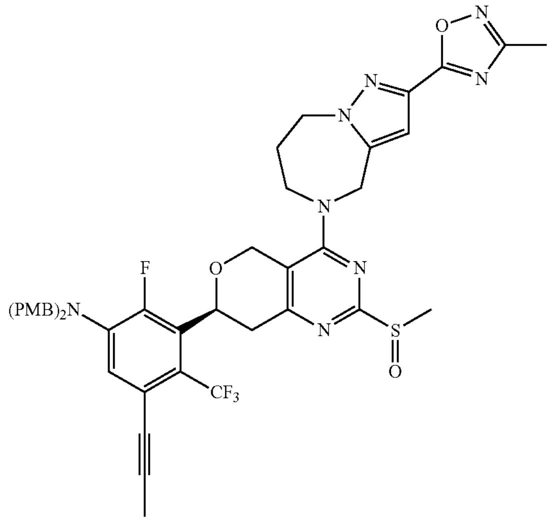
or
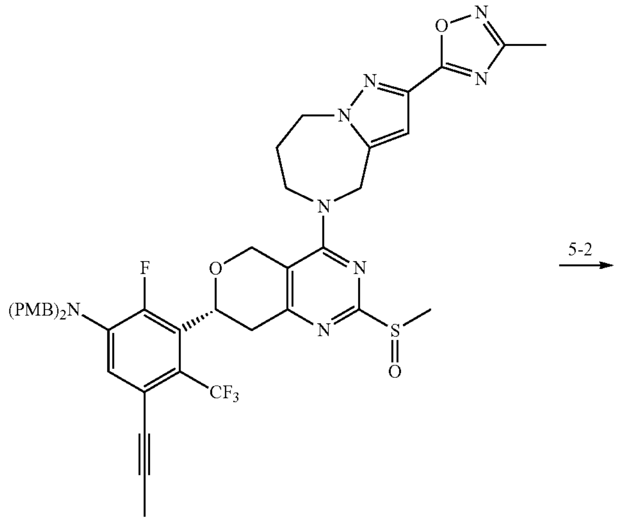
17-5
17-6 17
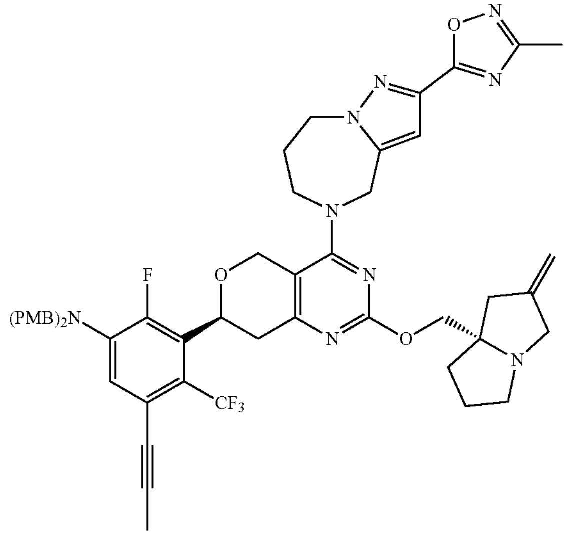
or
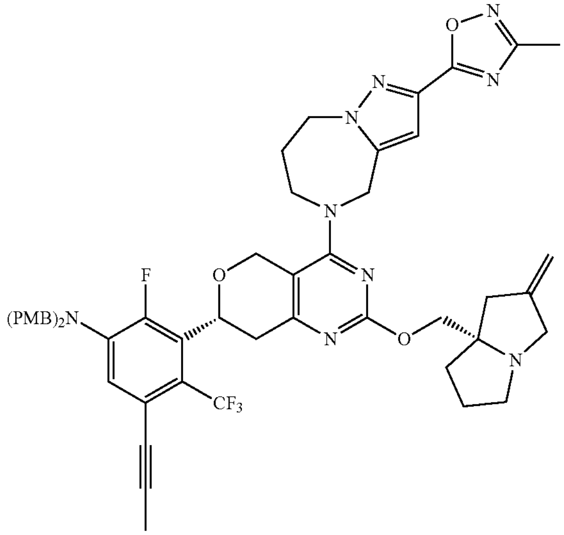
or
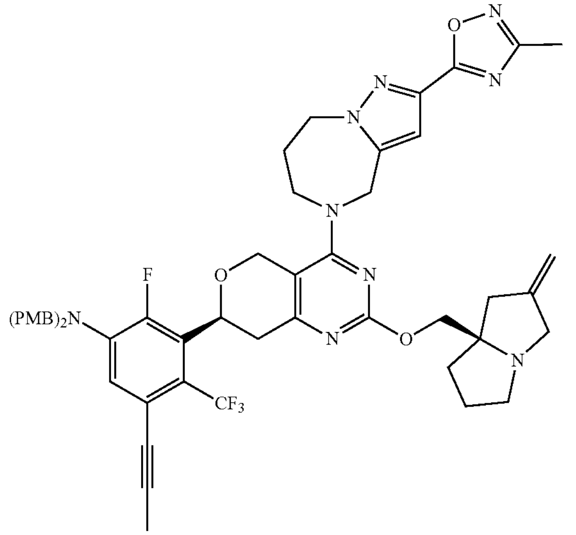
or
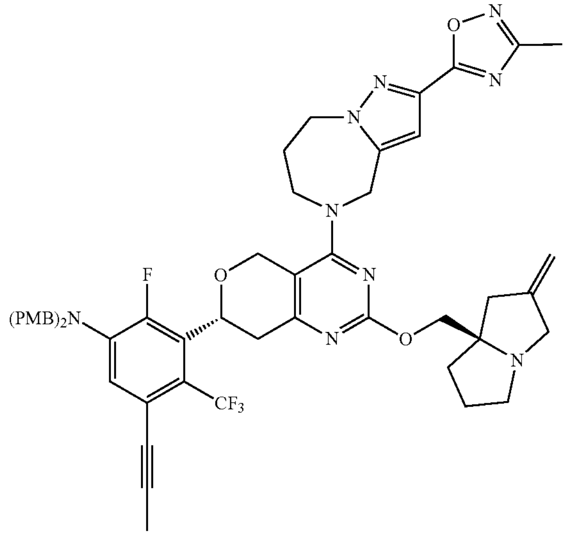
17-6

-continued

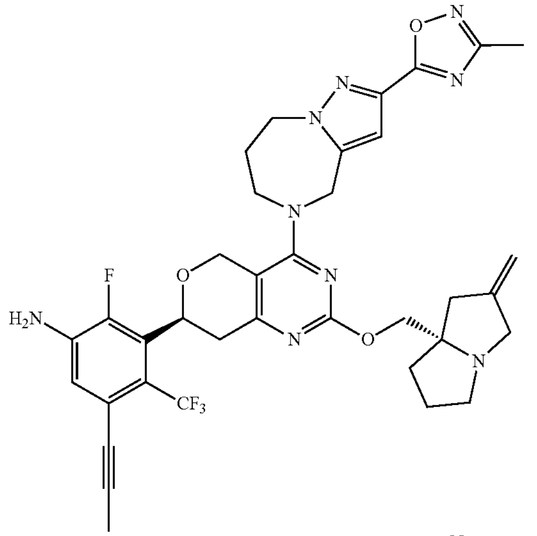

or

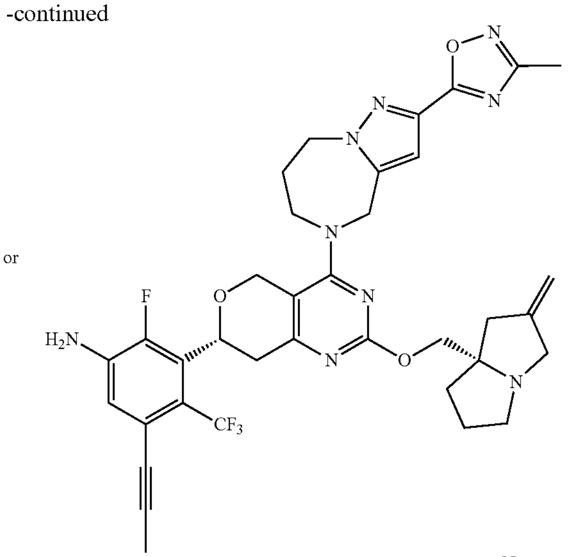

or

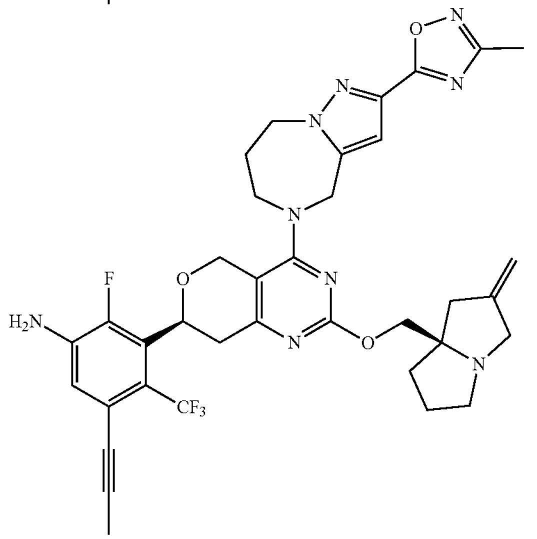

or

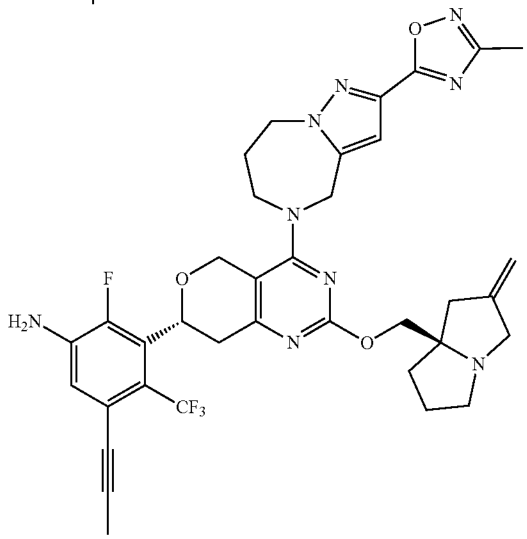

17

Step 1: Synthesis of Intermediate 17-1

Compound 16-1 (500 mg, 1.78 mmol) was weighed and dissolved with dichloromethane (10 mL). Oxalic chloride (451.22 mg, 3.55 mmol, 311.18 L) and DMF (12.99 mg, 177.74 mol, 13.67 μL) were added to react at 25° C. for 2 h. The reaction solution was concentrated under reduced pressure to obtain compound 17-1. MS m/z=300.1 $[M+H]^+$.

Step 2: Synthesis of Intermediate 17-2

Compound 17-1 (400 mg, 1.33 mmol) was weighed and dissolved with acetonitrile (10 mL). DIPEA (517.39 mg, 4.00 mmol, 697.29 L) and N-hydroxyacetamidine (118.63 mg, 1.60 mmol) were added to react at 150° C. for 0.5 h under microwave. The reaction solution was concentrated under reduced pressure and separated by column chromatography (petroleum ether:ethyl acetate=2:1) to obtain compound 17-2. MS m/z=320.2 $[M+H]^+$.

Step 3: Synthesis of Hydrochloride of Intermediates 17-3

Compound 17-2 (260 mg, 814.13 mol) was weighed and dissolved with a 4M hydrochloric acid/ethyl acetate solution (10 mL) and stirred at 25° C. for 1 h. The reaction solution was concentrated under reduced pressure to obtain the hydrochloride of compound 17-3.

Step 4: Synthesis of Intermediate 17-4

Compound 4-11B (300 mg, 381.80 mol) was weighed and dissolved with DMF (10 mL). The hydrochloride of compound 17-3 (146.44 mg) was added. Then DIPEA (148.03 mg, 1.15 mmol, 199.50 L) was added to react at 100° C. for 1 h. The reaction solution was concentrated under reduced pressure to obtain the crude product. The crude product was purified by column chromatography (dichloromethane: methanol=10:1), to obtain compound 17-4, with MS m/z=855.4 $[M+H]^+$.

Step 5: Synthesis of Intermediate 17-5

Compound 17-4 (150 mg, 175.46 mol) was weighed and dissolved with DCM (10 mL). m-CPBA (30.28 mg, 175.46 mol, 85% purity) was added to react at room temperature of 25° C. for 1 h. The reaction solution was concentrated under reduced pressure to obtain compound 17-5, with MS m/z=871.3 [M+H]+.

Step 6: Synthesis of Intermediate 17-6

Compound 5-2 (52.78 mg, 344.47 mol) was dissolved with anhydrous tetrahydrofuran (5 mL). Sodium tert-butanol (33.10 mg, 344.47 mol) was added. The reaction system reacted at 0° C. for 1 h. Compound 17-5 (150.00 mg, 172.23 mol) was added to react at 0° C. for 1 h. The reaction solution was quenched with water (10 mL), adjusted to pH=6 with 1N diluted hydrochloric acid, and extracted with ethyl acetate (100 mL×2). The organic phases were mixed, dried with anhydrous sodium sulfate, filtered, concentrated under reduced pressure, and separated by column chromatography (dichloromethane:methanol=10:1) to obtain compound 17-6. MS m/z=960.5 [M+H]+.

Step 7: Synthesis of Compound 17

Compound 17-6 (130 mg, 135.41 mol) was dissolved with trifluoroacetic acid (5 mL) to react at 25° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia)-acetonitrile]; acetonitrile %: 52-82% over 8 min), to obtain compound 17. MS m/z=720.3 [M+H]+.

Embodiment 18

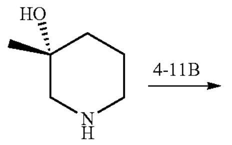

2-1A

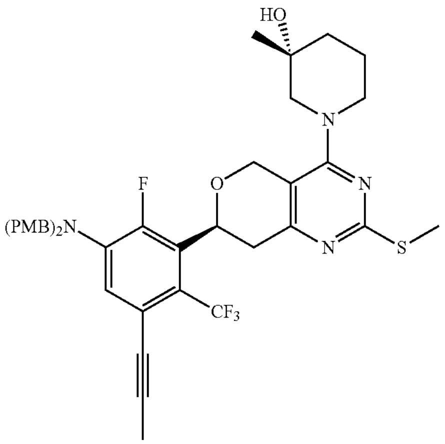

or

-continued

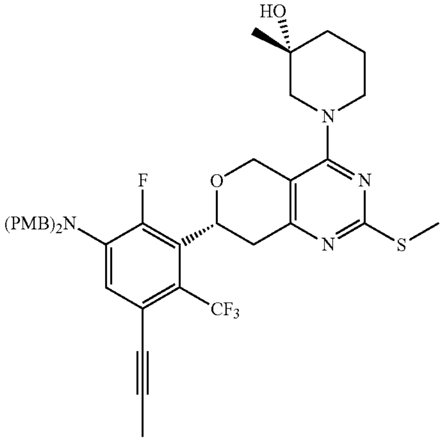

18-1

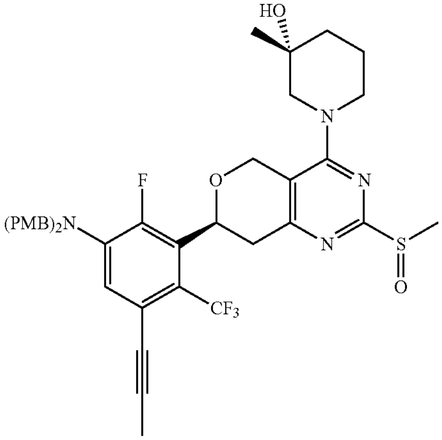

or

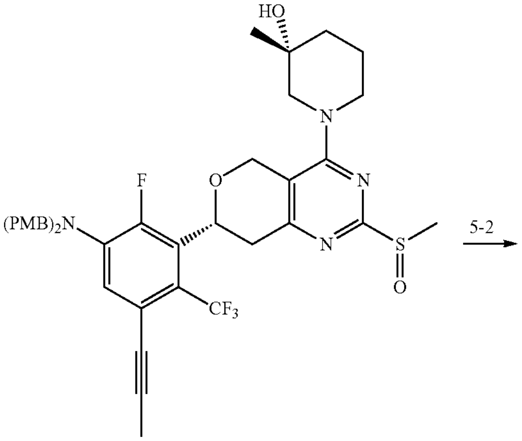

18-2

18-3

18

-continued
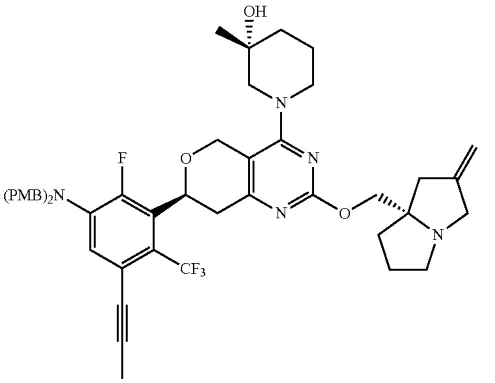
or
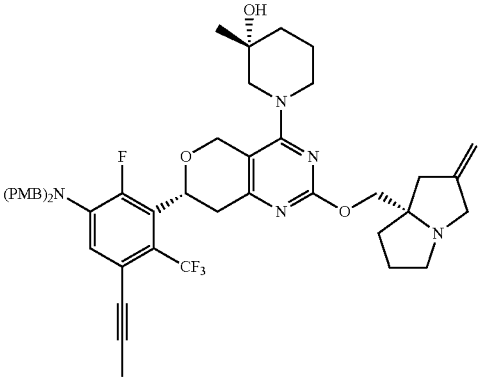
or
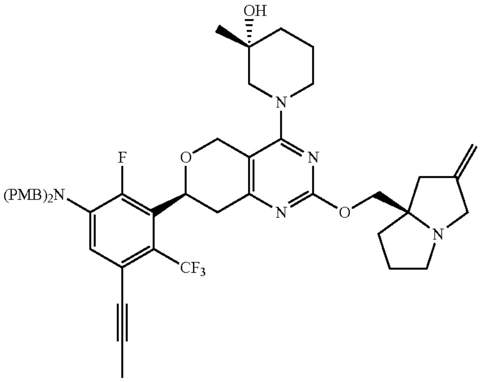
or
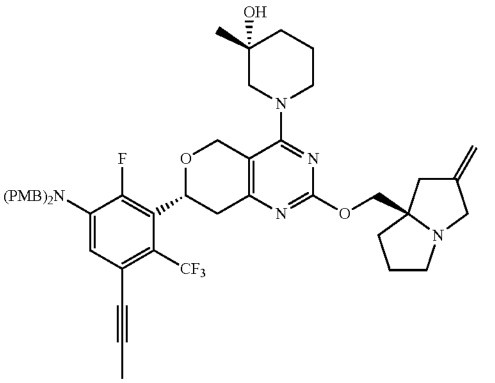
18-3
-continued
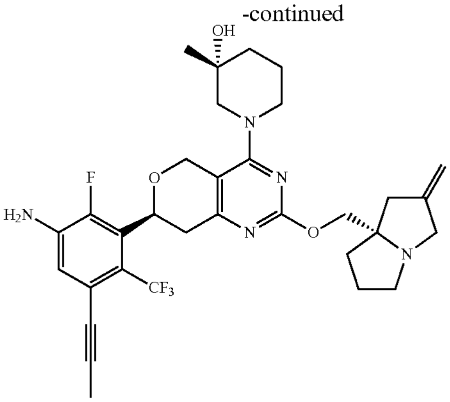
or
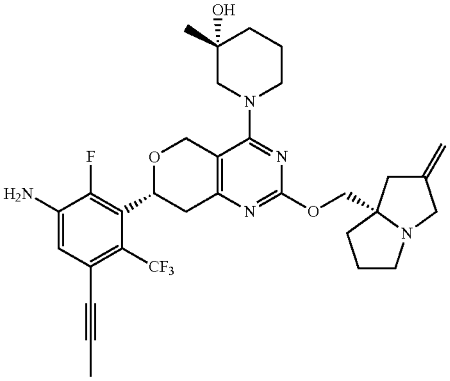
or
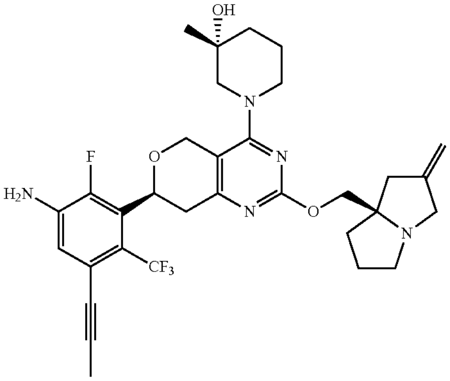
or
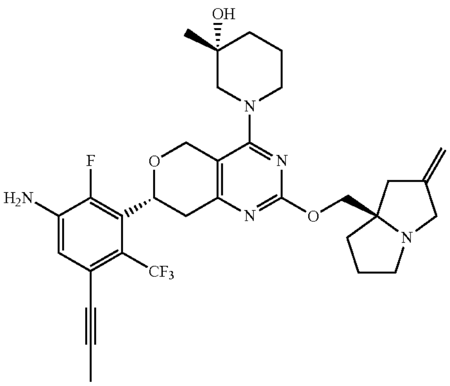
18
Step 1: Synthesis of Intermediate 18-1
Compound 4-11B (0.15 g, 190.90 mol) was weighed and dissolved with DMF (15 mL). Compound 2-1A (34.74 mg, 229.08 mol) was added. Then DIPEA (74.02 mg, 572.70 mol, 99.75 L) was added to react at 100° C. for 1 h. The reaction solution was quenched with water (20 mL), diluted with 100 mL of ethyl acetate, washed with 100 mL of a saturated table salt solution, dried with anhydrous sodium sulfate, filtered, and concentrated under reduced pressure to obtain the crude product. The crude product was purified by column chromatography (petroleum ether:ethyl acetate=2:1) to obtain compound 18-1, with MS m/z=751.5 $[M+H]^+$.

Step 2: Synthesis of Intermediate 18-2

Compound 18-1 (106.5 mg, 141.84 mol) was weighed and dissolved with DCM (10 mL). m-CPBA (28.80 mg, 141.84 mol, 85% purity) was added to react at room temperature of 25° C. for 1 h. The reaction solution was quenched with water (15 mL), diluted with 100 mL of dichloromethane, washed with 80 mL of a saturated table salt solution, dried with anhydrous sodium sulfate, filtered, and concentrated under reduced pressure, to obtain compound 18-2, with MS m/z=767.5 $[M+H]^+$.

Step 3: Synthesis of Intermediate 18-3

Compound 5-2 (86.32 mg, 563.35 mol) was dissolved with anhydrous tetrahydrofuran (20 mL). Sodium tert-butanol (54.14 mg, 563.35 mol) was added. The reaction system reacted at 0° C. for 1 h. Compound 18-2 (0.108 g, 140.84 mol) was added to react at 0° C. for 1 h. The reaction solution was quenched with water (20 mL), extracted with ethyl acetate (30 mL×3), washed with 100 mL of a saturated table salt solution, dried with anhydrous sodium sulfate, filtered, concentrated, and separated by column chromatography (dichloromethane:methanol=20:1) to obtain compound 18-3. MS m/z=856.7 $[M+H]^+$.

Step 4: Synthesis of Hydrochloride of Compound 18

Compound 18-3 (120.4 mg, 140.66 mol) was dissolved with dichloromethane (5 mL). Trifluoroacetic acid (1.96 g, 17.17 mmol, 1.28 mL) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 10-40%, 10 min), to obtain the hydrochloride of compound 18. MS m/z=616.3 $[M+H]^+$.

Embodiment 19

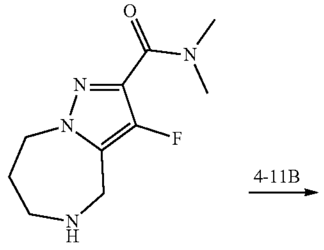

19-1

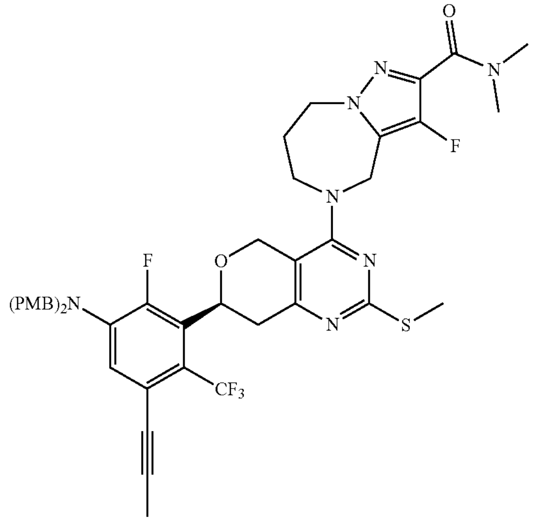

or

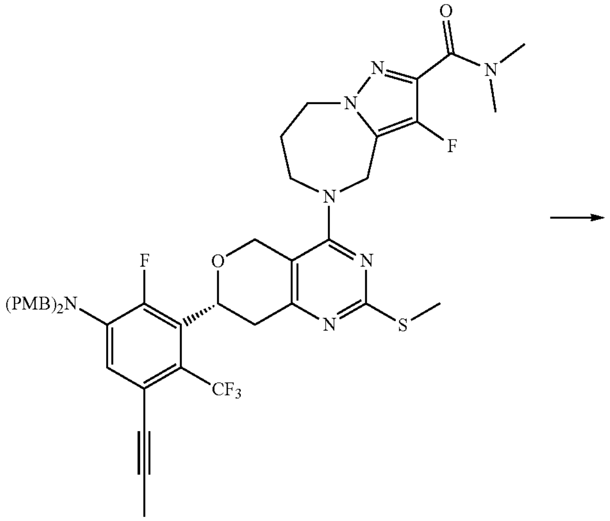

19-2

-continued
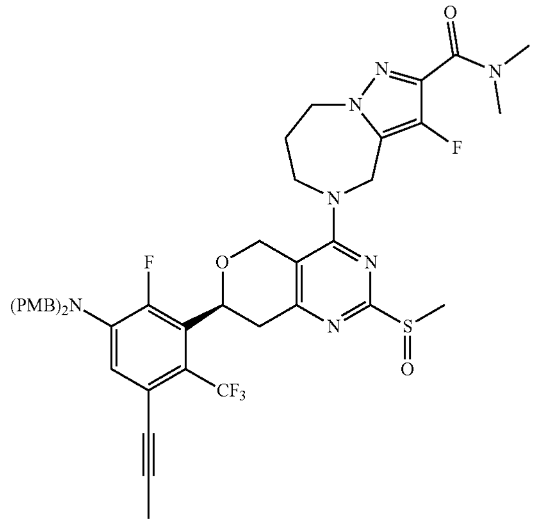
or
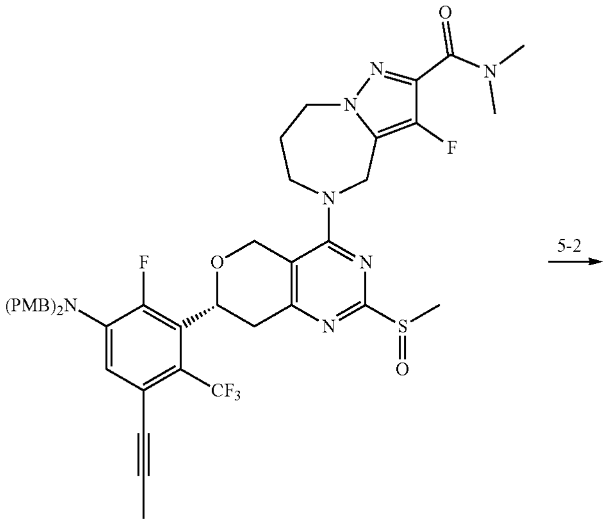
19-3
19-4 19
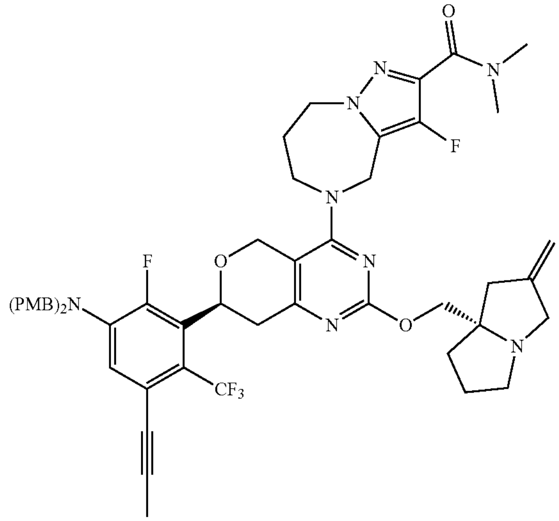
or
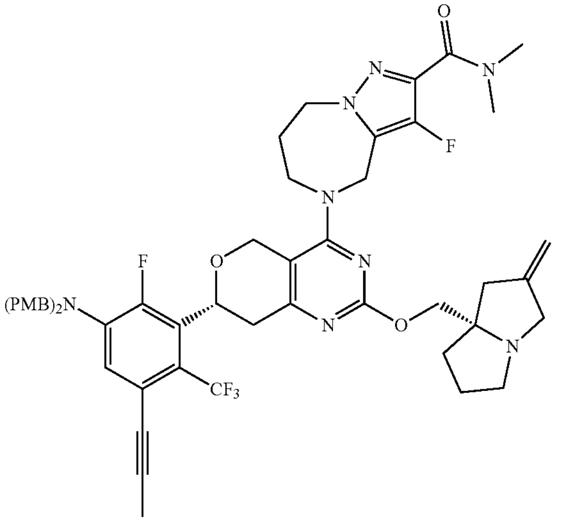
or
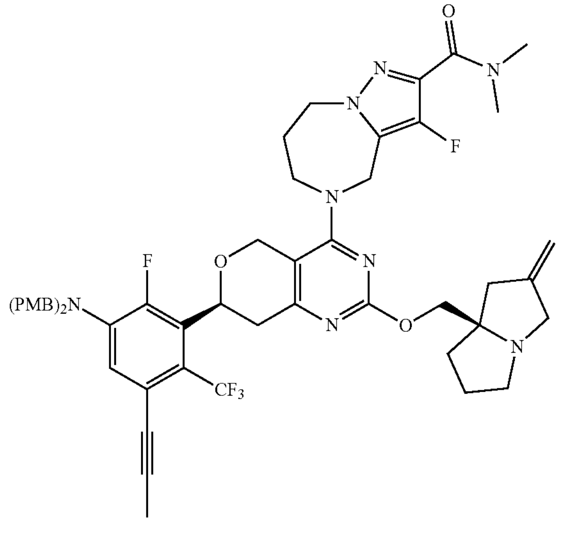
or
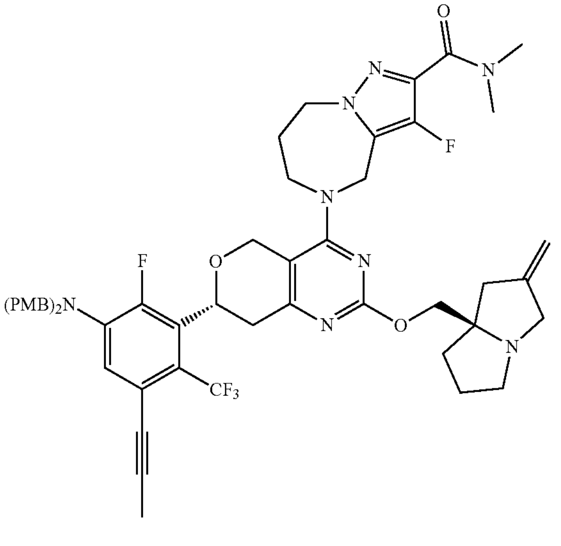
19-4

-continued

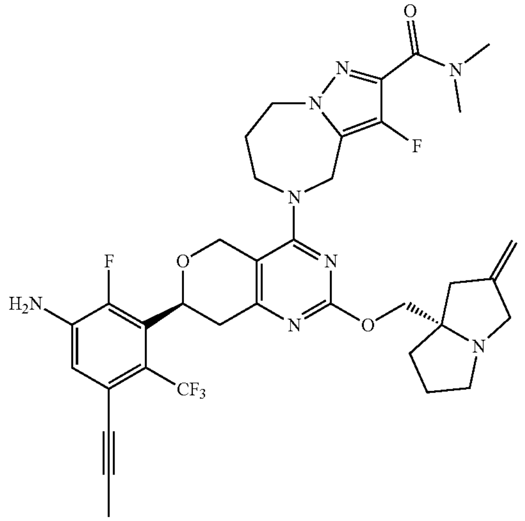

or

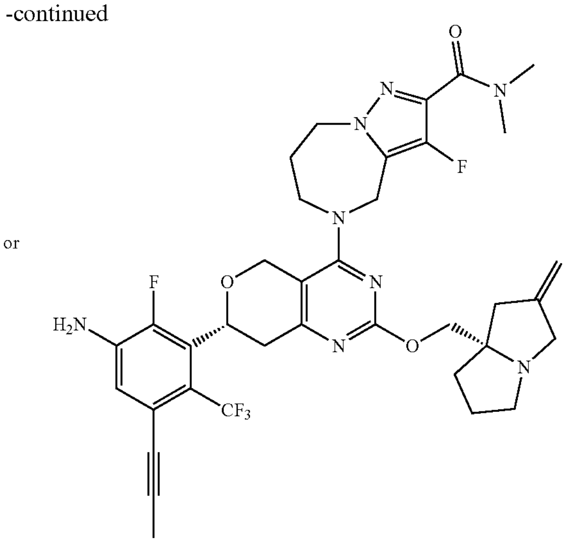

or

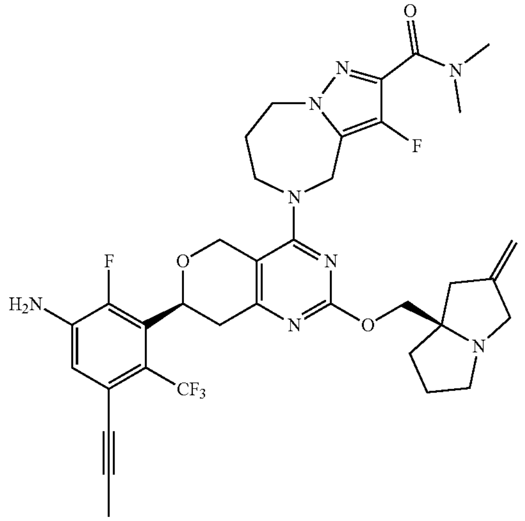

or

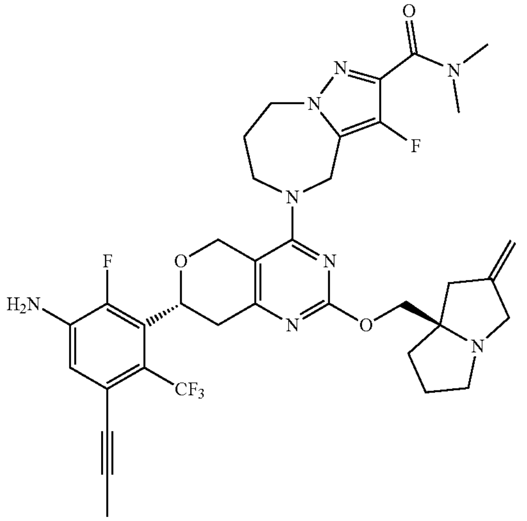

19

Step 1: Synthesis of Intermediate 19-2

Compound 4-11B (150 mg, 190.90 μmol) was weighed and dissolved with DMF (5 mL). Compound 19-1 (40 mg, 152.26 μmol) was added. Then DIPEA (74.02 mg, 572.70 μmol, 99.75 μL) was added to react at 100° C. for 1 h. The reaction solution was concentrated under reduced pressure to obtain the crude product. The crude product was purified by column chromatography (dichloromethane:methanol=10:1), to obtain compound 19-2, with MS m/z=862.6 $[M+H]^+$.

Step 2: Synthesis of Intermediate 19-3

Compound 19-2 (120 mg, 139.22 mol) was weighed and dissolved with DCM (10 mL). m-CPBA (24.03 mg, 139.22 mol, 85% purity) was added to react at room temperature of 25° C. for 0.5 h. The reaction solution was quenched with water (15 mL), diluted with 100 mL of dichloromethane, washed with 80 mL of a saturated table salt solution, dried with anhydrous sodium sulfate, filtered, and concentrated under reduced pressure, to obtain compound 19-3, with MS m/z=878.3 $[M+H]^+$.

Step 3: Synthesis of Intermediate 19-4

Compound 5-2 (41.89 mg, 273.37 mol) was dissolved with anhydrous tetrahydrofuran (20 mL). Sodium tert-butyl alcohol (26.27 mg, 273.37 mol) was added at 0° C. The reaction system reacted at 0° C. for 1 h. 5 mL of a tetrahydrofuran solution of compound 19-3 (120 mg, 136.69 mol) was added to react at 0° C. for 1 h. The reaction solution was quenched with water (20 mL), adjusted to approximately pH=6 with diluted hydrochloric acid, extracted with ethyl acetate (30 mL×3), washed with 100 mL of a saturated table salt solution, dried with anhydrous sodium sulfate, filtered, concentrated, and separated by column chromatography (dichloromethane:methanol=10:1) to obtain compound 19-4. MS m/z=967.5 $[M+H]^+$.

Step 4: Synthesis of Compound 19

Compound 19-4 (80 mg, 82.73 mol) was dissolved with dichloromethane (5 mL). Trifluoroacetic acid (5 mL) was added to react at 25° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia+10 mM ammonium bicarbonate)-acetonitrile]; acetonitrile %: 53-83%, 9 min), to obtain compound 19. MS m/z=727.2 $[M+H]^+$.

Embodiment 20
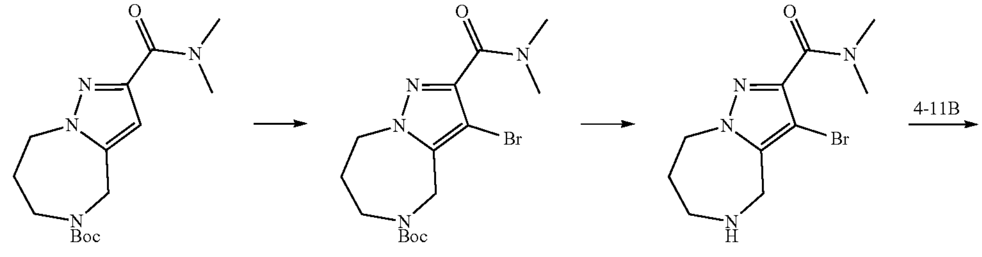
20-1 20-2 20-3
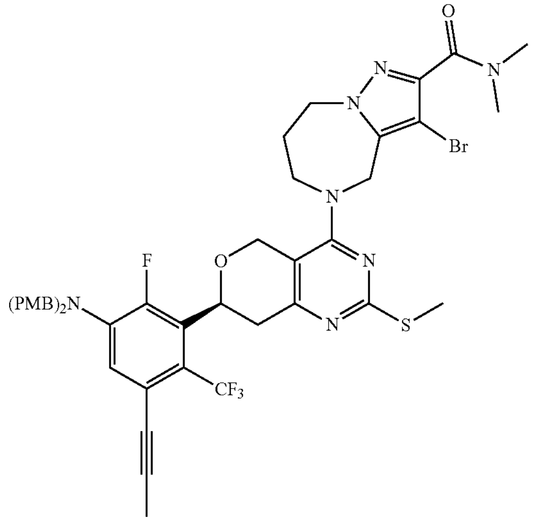
or
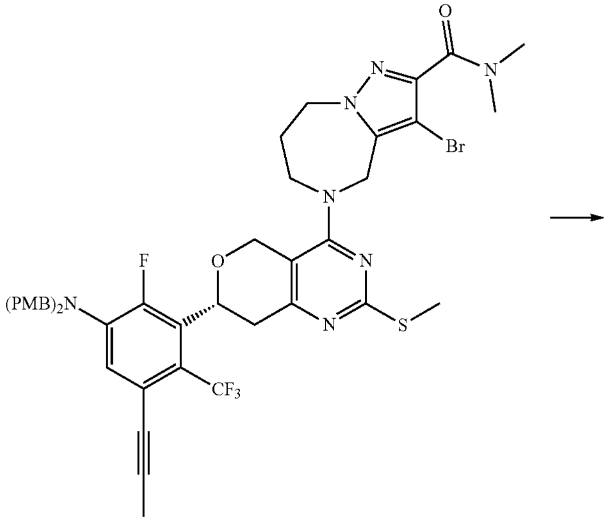
20-4
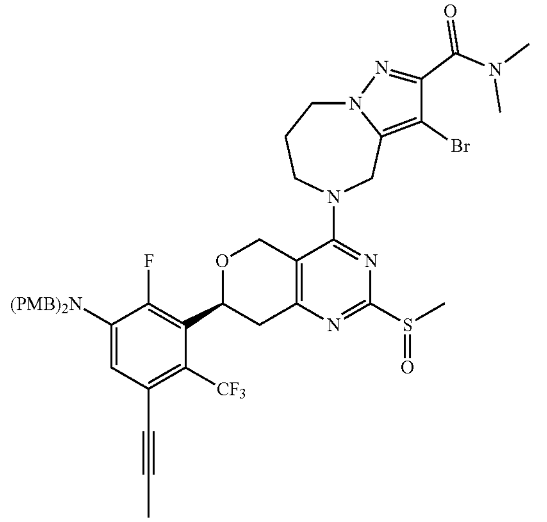
or
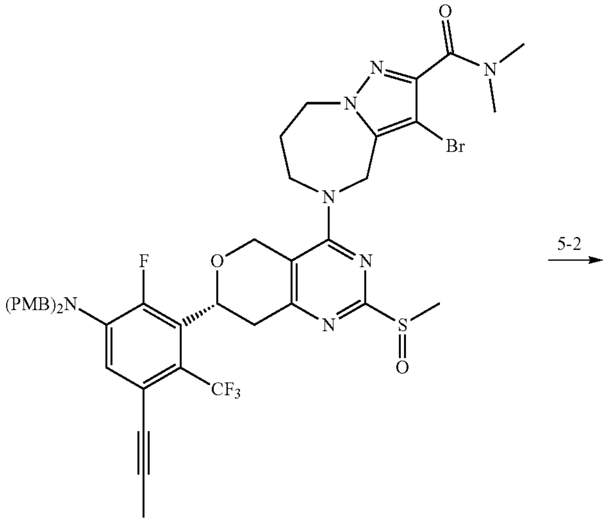
20-5
20-6 20

-continued
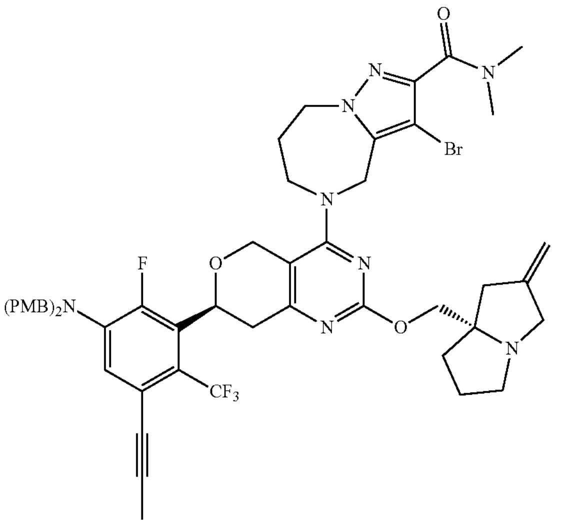
or
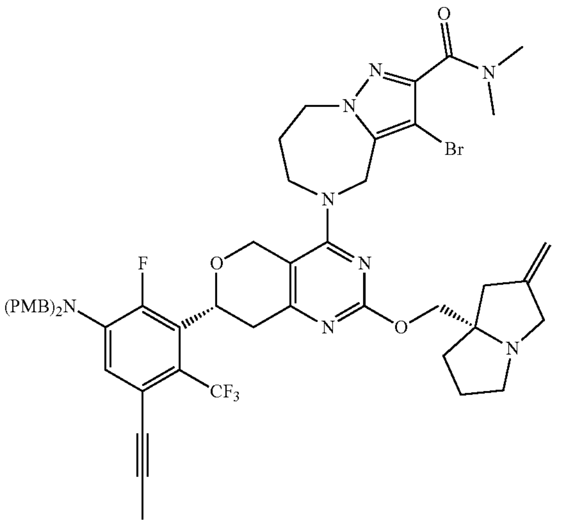
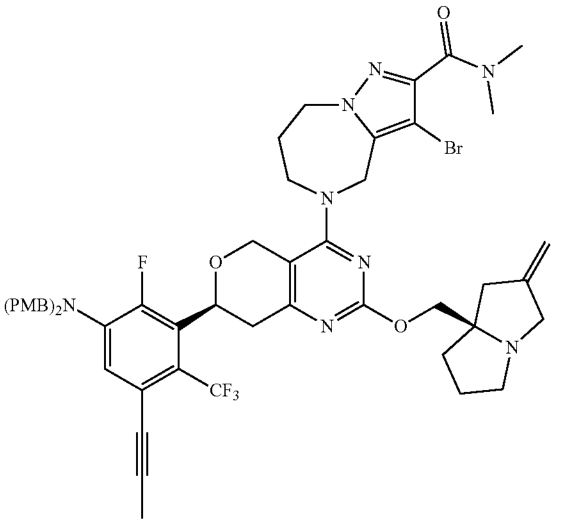
or
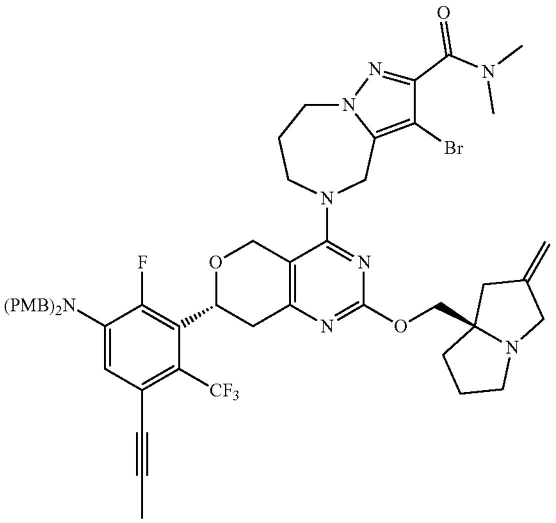
20-6
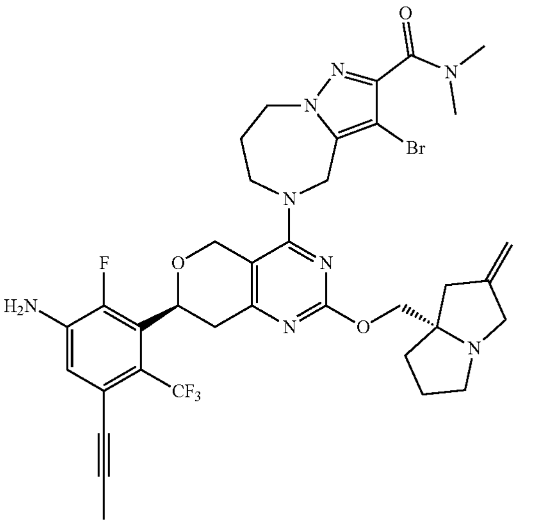
or
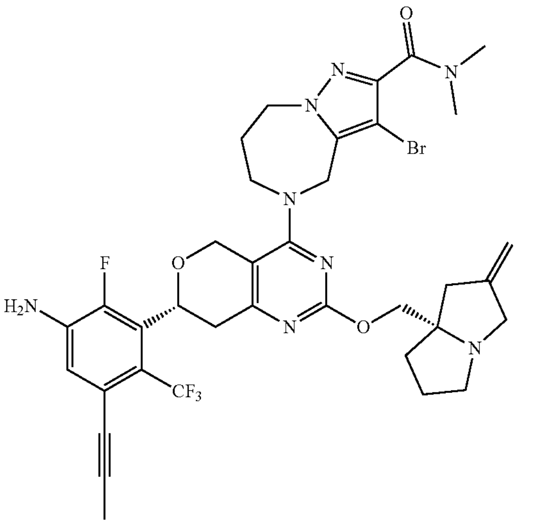
or -continued

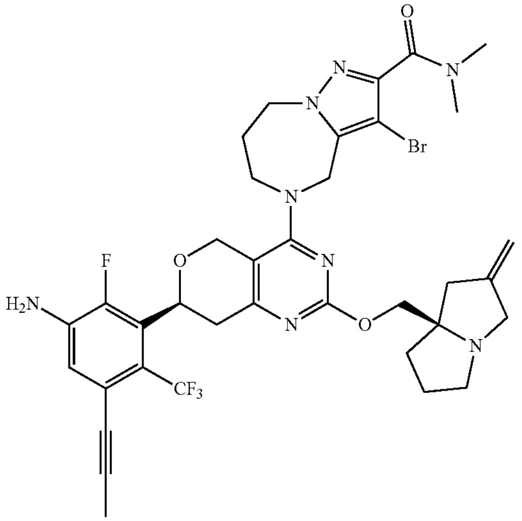

or

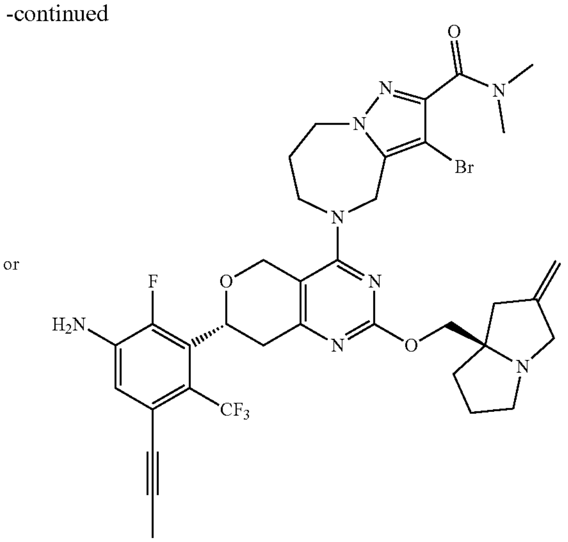

20

Step 1: Synthesis of Intermediate 20-2

Compound 20-1 (400 mg, 1.30 mmol) was weighed and dissolved with DMF (10 mL). NBS (346.30 mg, 1.95 mmol) was added to react at 25° C. for 1 h. The reaction solution was extracted with ethyl acetate (30 mL×3), washed with water (30 mL×3), and dried with anhydrous sodium sulfate to obtain the crude product. The crude product was purified by column chromatography (dichloromethane:methanol=10:1) to obtain compound 20-2. MS m/z=387.0, 389.0 $[M+H]^+$.

Step 2: Synthesis of Hydrochloride of Intermediates 20-3

Compound 20-2 (250 mg, 645.54 mol) was weighed and dissolved with hydrogen chloride/ethyl acetate (4 M, 10 mL) to react at 25° C. for 1 h. The reaction solution was concentrated under reduced pressure to obtain the hydrochloride of compound 20-3. MS m/z=287.0, 289.1 $[M+H]^+$.

Step 3: Synthesis of Intermediate 20-4

Compound 4-11B (200 mg, 254.53 mol) was weighed and dissolved with DMF (5 mL). The hydrochloride of compound 20-3 (123.56 mg) was added. Then DIPEA (98.69 mg, 763.60 mol) was added to react at 100° C. for 1 h. The reaction solution was concentrated under reduced pressure to obtain the crude product. The crude product was purified by column chromatography (dichloromethane:methanol=10:1), to obtain compound 20-4, with MS m/z=922.1, 924.0 $[M+H]^+$.

Step 4: Synthesis of Intermediate 20-5

Compound 20-4 (180 mg, 195.05 mol) was weighed and dissolved with DCM (10 mL). m-CPBA (33.66 mg, 195.05 mol, 85% purity) was added to react at room temperature of 25° C. for 0.5 h. The reaction solution was quenched with water (15 mL), diluted with 20 mL of dichloromethane, washed with 20 mL of a saturated table salt solution, dried with anhydrous sodium sulfate, filtered, and concentrated under reduced pressure, to obtain compound 20-5, with MS m/z=938.2, 940.15$[M+H]^+$.

Step 5: Synthesis of Intermediate 20-6

Compound 5-2 (39.17 mg, 255.64 mol) was dissolved with anhydrous tetrahydrofuran (20 mL). Sodium tert-butyl alcohol (24.57 mg, 255.64 mol) was added at 0° C. The reaction system reacted at 0° C. for 1 h. 5 mL of a tetrahydrofuran solution of compound 20-5 (120 mg, 127.82 mol) was added to react at 0° C. for 1 h. The reaction solution was quenched with water (20 mL), adjusted to approximately pH=6 with diluted hydrochloric acid, extracted with ethyl acetate (30 mL×3), washed with 100 mL of a saturated table salt solution, dried with anhydrous sodium sulfate, filtered, concentrated, and separated by column chromatography (dichloromethane:methanol=10:1) to obtain compound 20-6. MS m/z=1027.4, 1029.5 $[M+H]^+$.

Step 6: Synthesis of Compound 20

Compound 20-6 (100 mg, 97.28 mol) was dissolved with trifluoroacetic acid (5 mL) to react at 25° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia+10 mM ammonium bicarbonate)-acetonitrile]; acetonitrile %: 45-75%, 8 min), to obtain compound 20. MS m/z=787.1, 789.05 $[M+H]^+$.

Embodiment 21

20-5

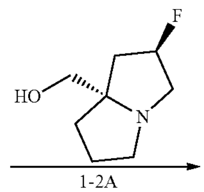

1-2A

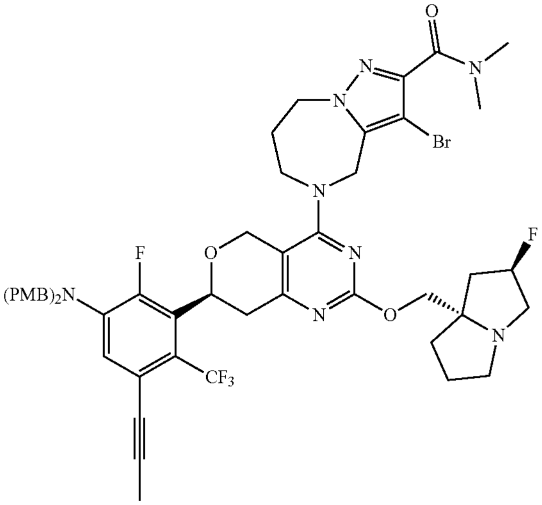

or

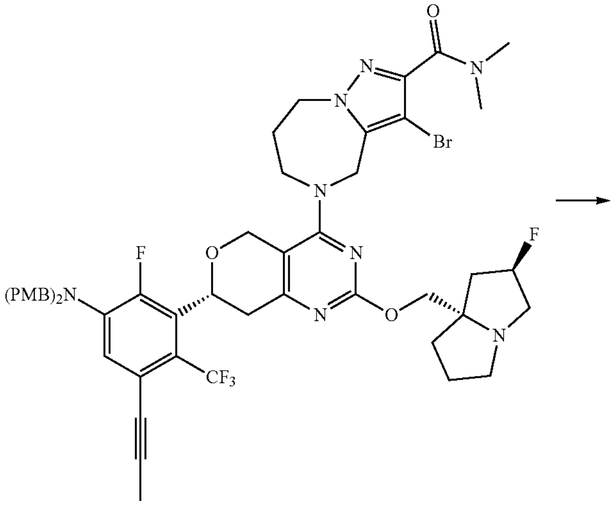

21-1

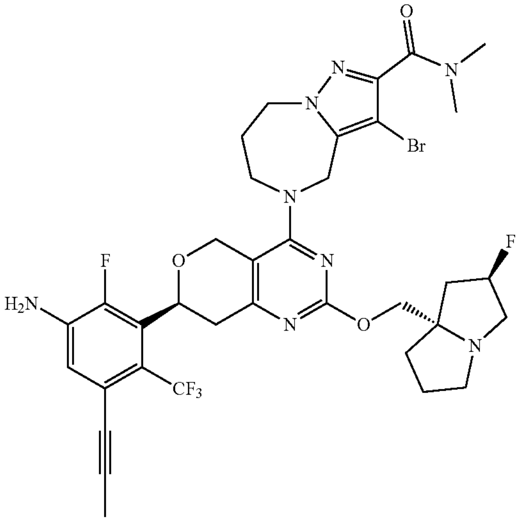

or

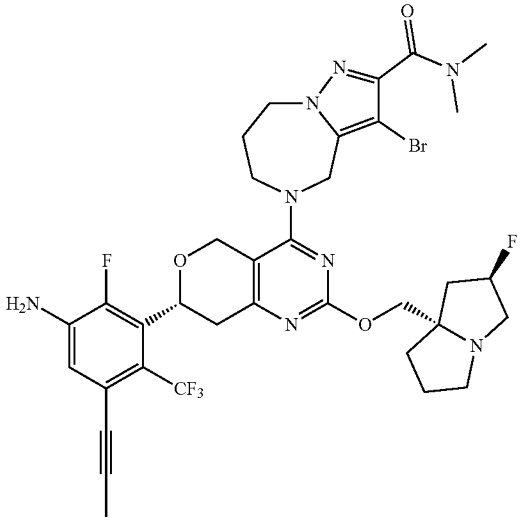

21

Step 1: Synthesis of Intermediate 21-1

Compound 1-2A (291.78 mg, 1.83 mmol) and sodium tert-butanol (140.91 mg, 1.47 mmol) were dissolved with anhydrous tetrahydrofuran (3 mL) to react at −15° C. for 15 min. A tetrahydrofuran (2 mL) solution of compound 20-5 (0.35 g, 366.56 mol) was added dropwise to react at −15-0° C. for 1 h. 5 mL of saturated ammonium chloride was added to the reaction solution. The reaction solution was extracted with ethyl acetate (10 mL×3). The organic phases were mixed, washed with a saturated table salt solution (20 mL×2), dried with anhydrous sodium sulfate, filtered, and concentrated under reduced pressure to obtain compound 21-1. MS m/z=1033.2, 1035.2[M+H]$^+$.

Step 2: Synthesis of Hydrochloride of Compound 21

Compound 21-1 (100 mg, 96.7 mol) was dissolved with dichloromethane (5 mL). Trifluoroacetic acid (771.96 mg, 6.77 mmol) was added to react at 18° C. for 16 h. The reaction solution was concentrated under reduced pressure to obtain the crude product. The crude product was separated by HPLC (chromatographic column: Phenomenex Luna C18 75×30 mm×3 m; mobile phase: [water (0.04% HCl)-acetonitrile]; acetonitrile %: 15-45%, 8 min), to obtain the hydrochloride of compound 21. MS m/z=793.1, 795.1 [M+H]$^+$.

Embodiment 22

14-3

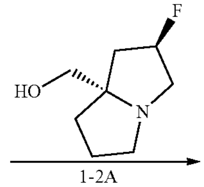

1-2A

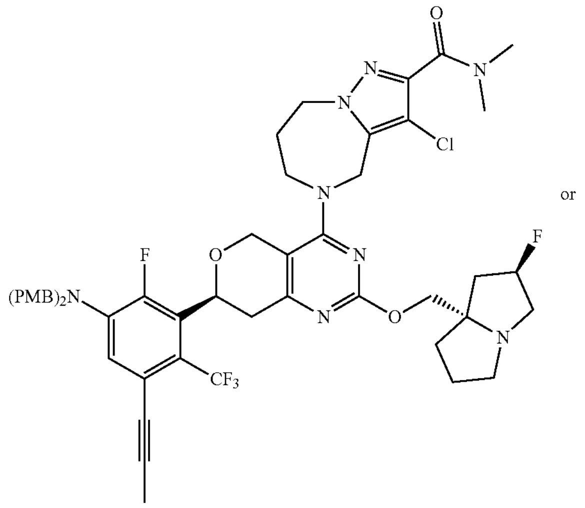

or

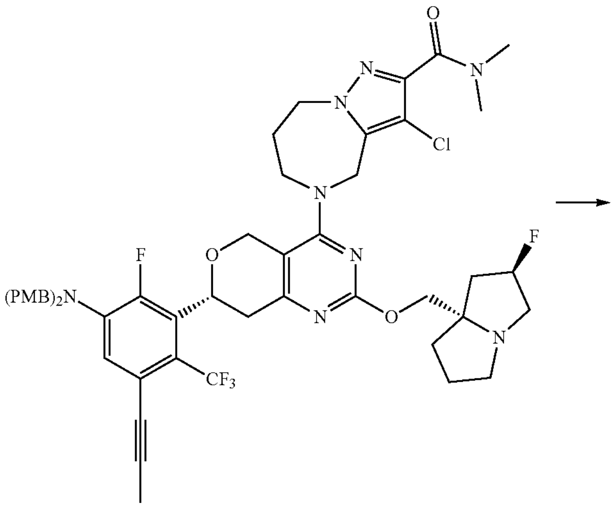

22-1

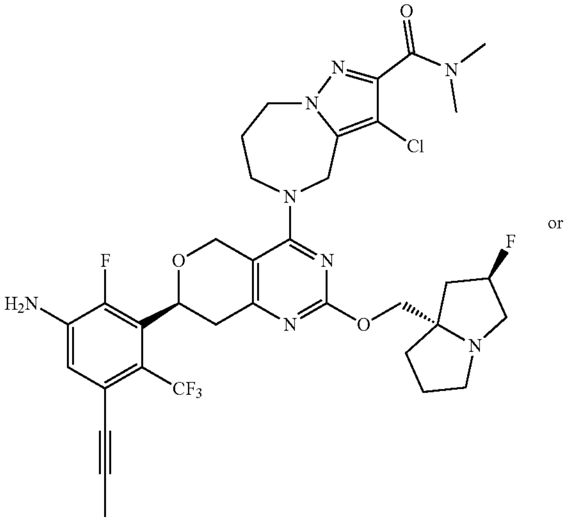

or

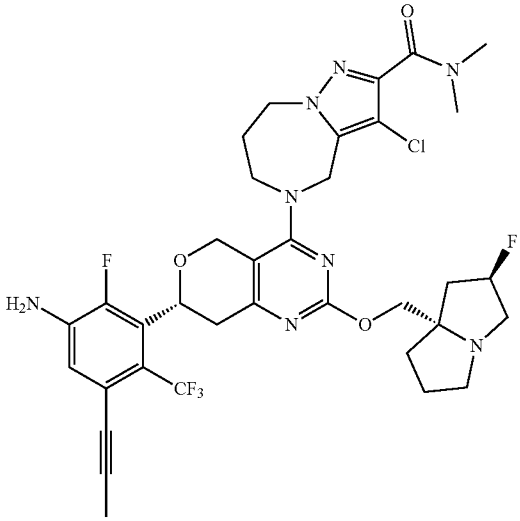

22

Step 1: Synthesis of Intermediate 22-1

Compound 1-2A (35.60 mg, 223.62 μmol) was dissolved with anhydrous tetrahydrofuran (15 mL). Sodium tert-butyl alcohol (21.49 mg, 223.62 μmol) was added to react at 0° C. for 60 min. A tetrahydrofuran (5 mL) solution of compound 14-3 (0.1 g, 111.81 μmol) was added dropwise to react at 0° C. for 1 h. The reaction solution was quenched with 5 mL of saturated ammonium chloride and extracted with ethyl acetate (10 mL×3). The organic phases were mixed, washed with a saturated table salt solution (20 mL×2), dried with anhydrous sodium sulfate, and concentrated to obtain compound 22-1. MS m/z=989.4 $[M+H]^+$.

Step 2: Synthesis of Hydrochloride of Compound 22

Compound 22-1 (0.077 g, 77.82 mol) was dissolved with dichloromethane (15 mL). Trifluoroacetic acid (1.08 g, 9.50 mmol) was added to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 22. MS m/z=749.2 [M+H]$^+$.

Embodiment 23

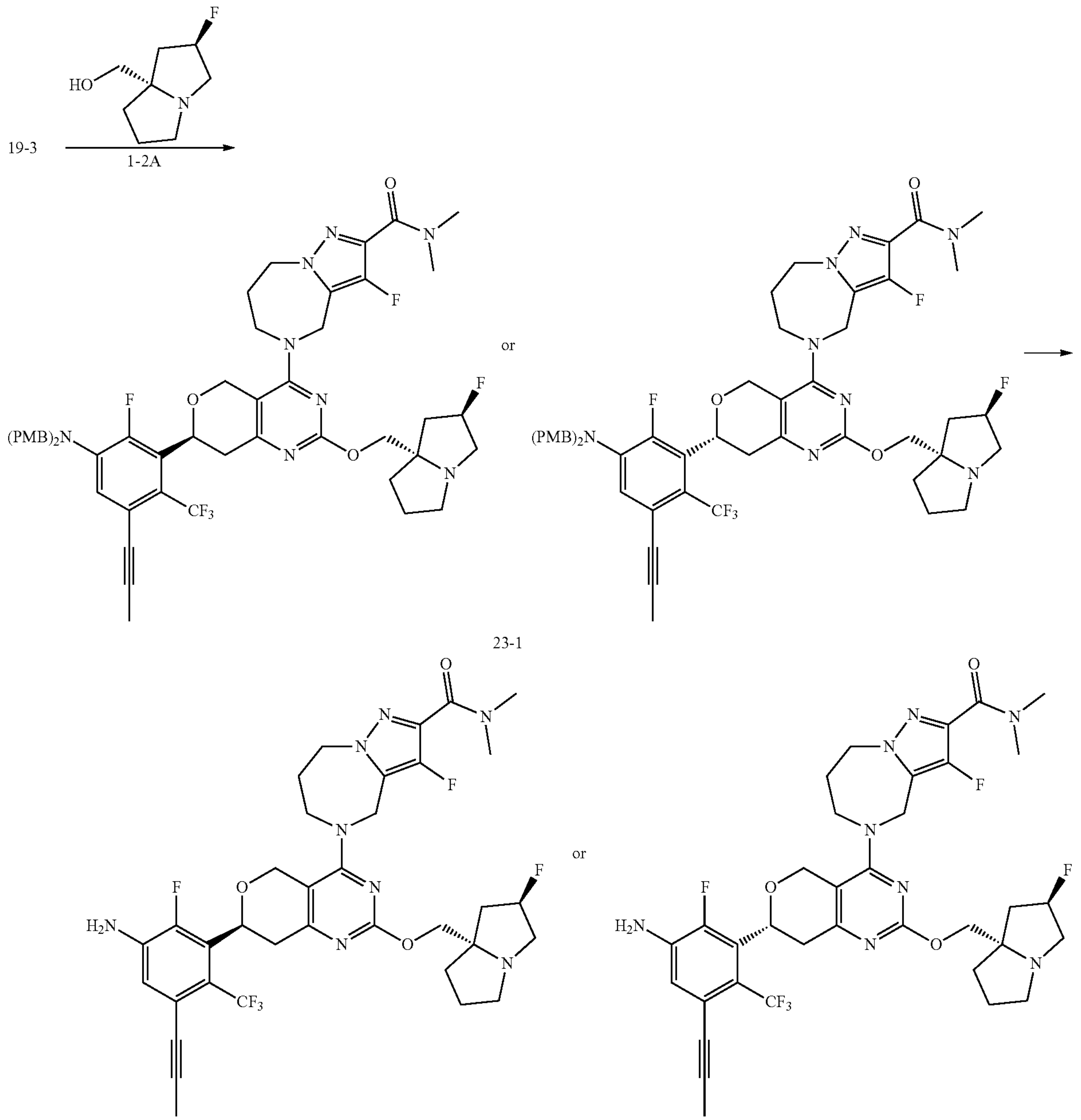

19-3

1-2A or 23-1 or

23

Step 1: Synthesis of Intermediate 23-1

Compound 1-2A (15.41 mg, 96.82 mol) was dissolved with anhydrous tetrahydrofuran (0.5 mL) and cooled to −15° C. under nitrogen protection. Sodium tert-butyl alcohol (7.44 mg, 77.46 mol) was added to react at −15° C. for 0.25 h. A tetrahydrofuran (0.5 mL) solution of compound 19-3 (17 mg, 19.36 mol) was added dropwise to react at −15° C. for 1 h. The reaction solution was quenched with 3 mL of saturated ammonium chloride and extracted with ethyl acetate (2 mL×3). The organic phases were mixed, washed with a saturated table salt solution (5 mL×2), dried with anhydrous sodium sulfate, and concentrated to obtain compound 23-1. MS m/z=973.2 [M+H]$^+$.

Step 2: Synthesis of Hydrochloride of Compound 23

Compound 23-1 (23 mg, 23.64 mol) was dissolved with dichloromethane (1 mL). Trifluoroacetic acid (539.04 mg, 4.73 mmol) was added at −10° C. to react at 20° C. for 2 h. The reaction solution was concentrated under reduced pressure to obtain the crude product. The crude product was separated by HPLC (chromatographic column: Phenomenex Luna C18 75×30 mm×3 m; mobile phase: [water (0.04% HCl)-acetonitrile]; acetonitrile %: 20-50%, 8 min), to obtain the hydrochloride of compound 23. MS m/z=733.2 $[M+H]^+$. $^1H$ NMR (400 MHz, MeOD) δ ppm 6.93 (d, J=8.4 Hz, 1H) 5.68-5.51 (m, 1H), 5.17-5.12 (m, 3H), 4.97-4.95 (m, 1H), 4.75-4.72 (m, 1H), 4.64 (s, 3H), 4.44-4.36 (m, 1H), 4.05 (s, 2H), 3.97-3.84 (m, 3H), 3.51-3.42 (m, 2H), 3.31-3.27 (m, 3H), 3.08 (s, 3H), 2.99-2.94 (m, 1H), 2.71-2.58 (m, 2H), 2.53-2.44 (m, 1H), 2.43-2.28 (m, 3H), 2.27-2.07 (m, 2H), 2.02 (s, 3H).
Embodiment 24
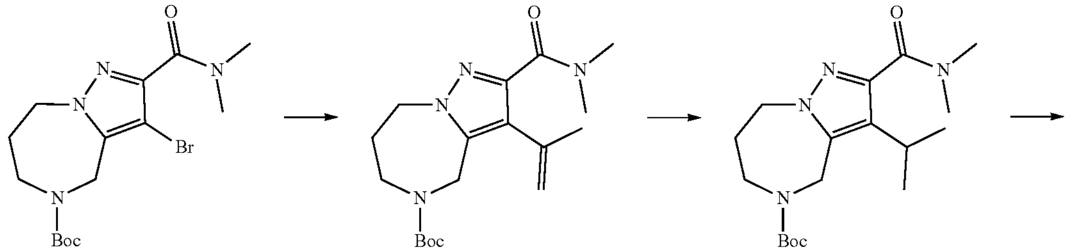
20-2 24-1 24-2
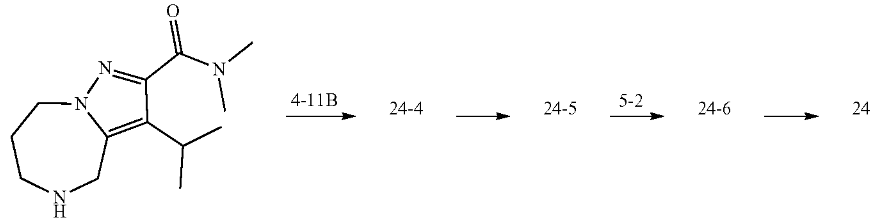
24-3
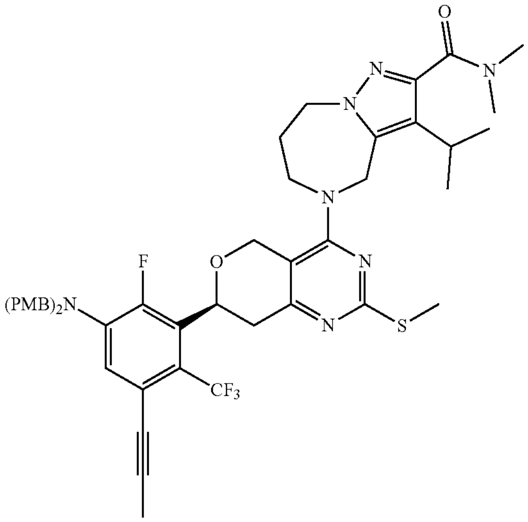
or
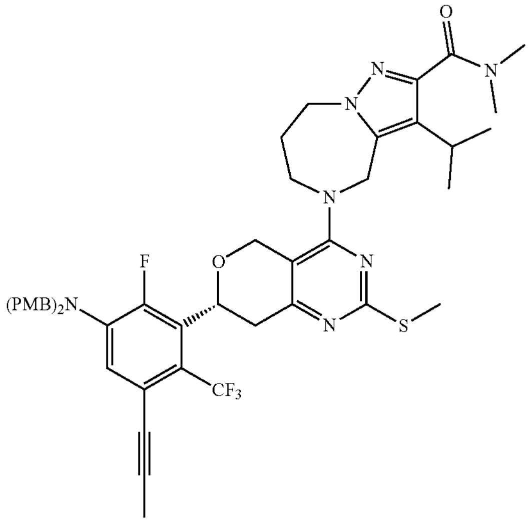
24-4

-continued
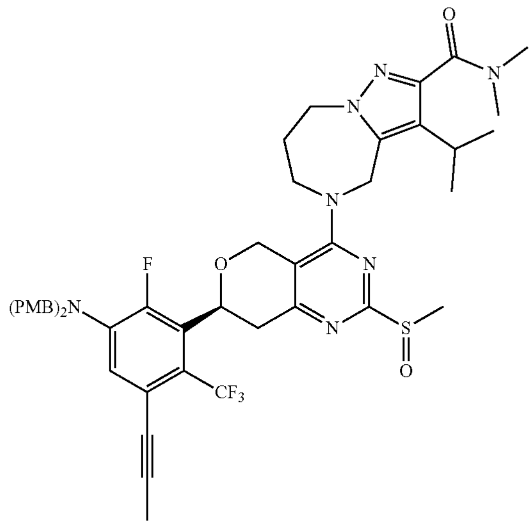
or
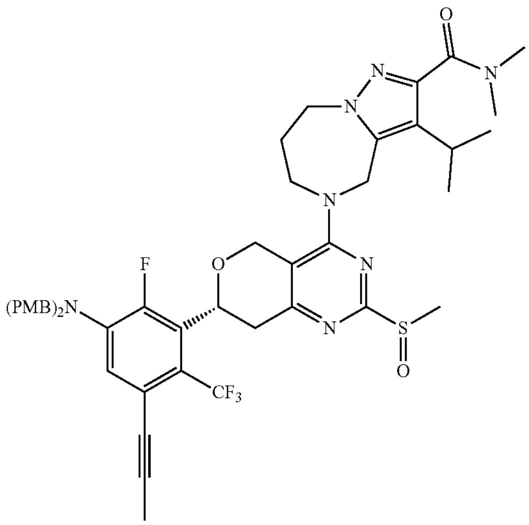
24-5
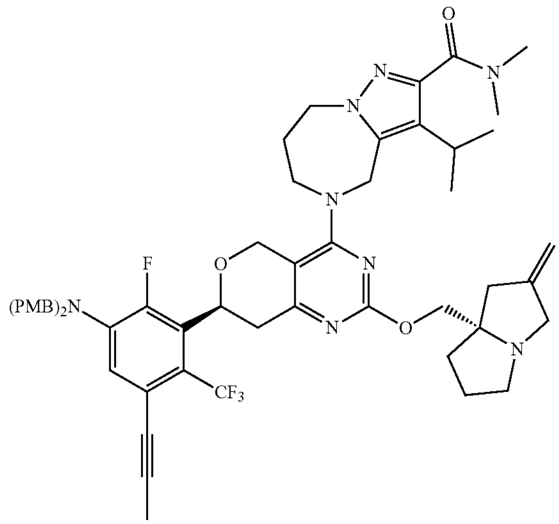
or
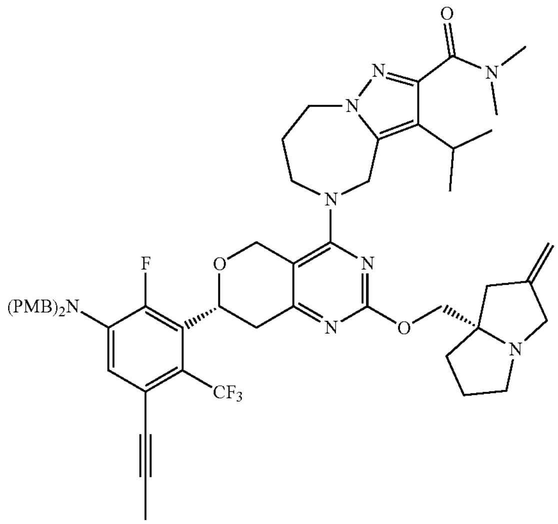
or
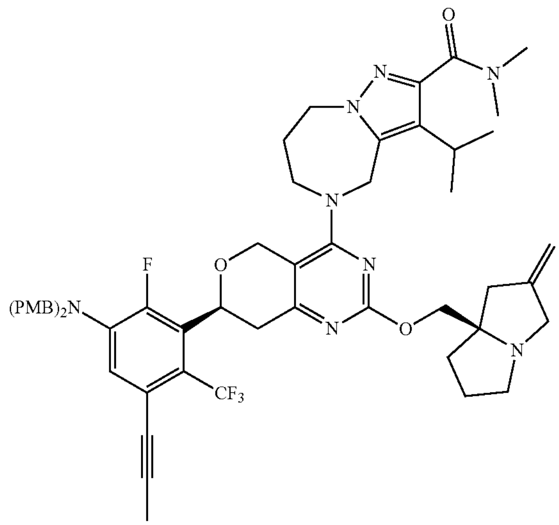
or
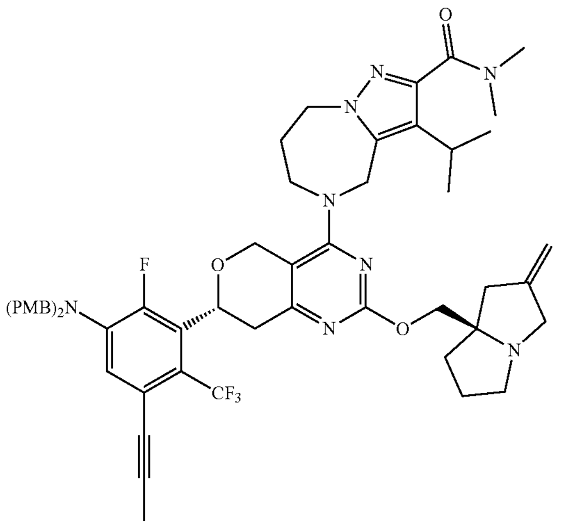
24-6

-continued

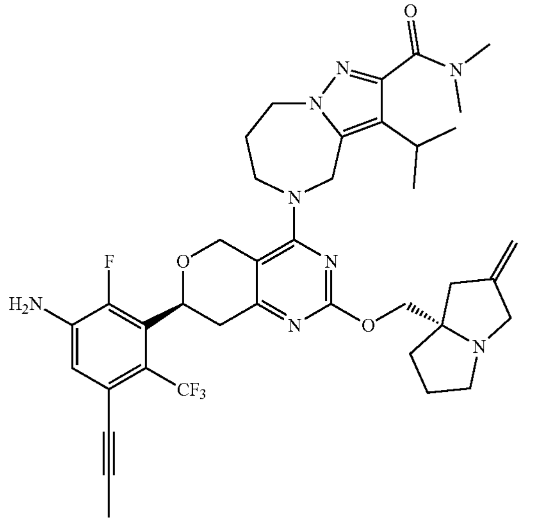

or

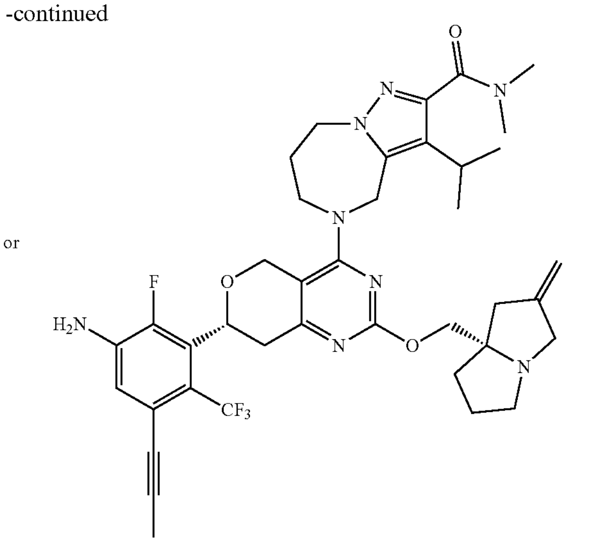

or

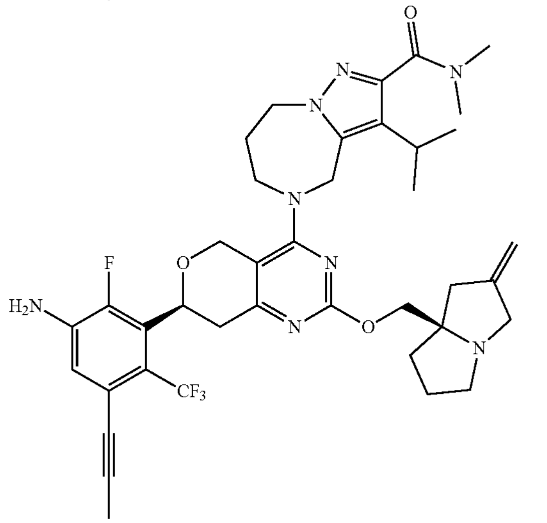

or

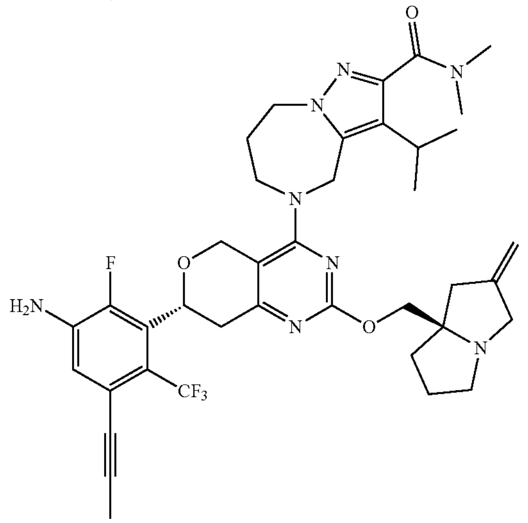

24

Step 1: Synthesis of Intermediate 24-1

Compound 20-2 (0.1 g, 258.22 mol), water (0.3 mL), 1,4-dioxane (1.5 mL), isopropenylboronic acid pinacol ester (56.41 mg, 335.68 mol), and potassium carbonate (178.44 mg, 1.29 mmol) were added to a reaction flask. Bis(tri-butylphosphine) palladium (13.20 mg, 25.82 mol) was added under nitrogen protection to react at 80° C. for 12 h. The reaction solution was cooled to room temperature. 2 mL of water was added to the reaction solution. The reaction solution was extracted with ethyl acetate (2 mL×2). The organic phase was dried with anhydrous sodium sulfate, filtered, and concentrated under reduced pressure. Purification was carried out by thin layer chromatography (dichloromethane:methanol=10:1) to obtain compound 24-1. MS m/z=349.0 [M+H]+.

Step 2: Synthesis of Intermediate 24-2

Under argon protection, methanol (2 mL), wet palladium hydroxide on carbon (20 mg, 14.24 mol, 10% purity), and compound 24-1 (39 mg, 111.93 mol) were added into a reaction flask to react at 15 Psi and 20° C. for 16 h with hydrogen introduced. The reaction solution was filtered, and the filter cake was washed with 10 mL of methanol. The filtrate was collected and concentrated under reduced pressure to obtain compound 24-2. MS m/z=351.2 [M+H]+.

Step 3: Synthesis of Hydrochloride of Intermediates 24-3

Compound 24-2 (0.04 g, 114.14 mol) and hydrochloric acid/methanol (4 M, 0.5 mL) were added to a reaction flask to react at 20° C. for 0.5 h. The reaction solution was concentrated under reduced pressure directly to obtain the hydrochloride of compound 24-3. MS m/z=251.2[M+H]+.

Step 4: Synthesis of Intermediate 24-4

Compound 4-11B (60 mg, 76.36 mol) was weighed and dissolved with DMF (1 mL). The hydrochloride of compound 24-3 (32.85 mg) was added. Then DIPEA (1 mL) was added to react at 50° C. for 1 h. The reaction solution was cooled to room temperature. 2 mL of water was added to the reaction solution. The reaction solution was extracted with ethyl acetate (3 mL×4). The organic phase was washed with a saturated table salt solution (5 mL), dried with anhydrous sodium sulfate, filtered, and concentrated under reduced pressure. Purification was carried out by thin layer chromatography (dichloromethane:methanol=10:1) to obtain compound 24-4. MS m/z=886.3[M+H]$^+$.

Step 5: Synthesis of Intermediate 24-5

Compound 24-4 (68 mg, 76.75 mol) was weighed and dissolved with DCM (1 mL). m-CPBA (10.91 mg, 53.72 mol, 85% purity) was added to react at room temperature of 20° C. for 1 h. The reaction solution was diluted with 5 mL of dichloromethane, washed with 3 mL of a 5% sodium thiosulfate solution and 5 mL of a saturated table salt solution twice, dried with anhydrous sodium sulfate, filtered, and concentrated under reduced pressure. Purification was carried out by thin layer chromatography (dichloromethane:methanol=10:1) to obtain compound 24-5, with MS m/z=902.2[M+H]$^+$.

Step 6: Synthesis of Intermediate 24-6

Compound 5-2 (19.53 mg, 127.49 mol) was dissolved with anhydrous tetrahydrofuran (0.5 mL). Sodium tert-butyl alcohol (9.80 mg, 101.99 mol) was added at −15° C. The reaction system reacted at −15° C. for 0.25 h. 0.5 mL of a tetrahydrofuran solution of compound 24-5 (23 mg, 25.50 mol) was added to react at 0° C. for 1 h. 3 mL of a saturated ammonium chloride aqueous solution was added to the reaction solution. The reaction solution was extracted with ethyl acetate (2 mL×3). The organic phase was washed with a saturated table salt solution (5 mL), dried with anhydrous sodium sulfate, filtered, and concentrated under reduced pressure. Purification was carried out by thin layer chromatography (dichloromethane:methanol=10:1) to obtain compound 24-6, with MS m/z=991.3[M+H]$^+$.

Step 7: Synthesis of Compound 24

Compound 24-6 (22 mg, 22.20 mol) was dissolved with dichloromethane (1 mL). Trifluoroacetic acid (253.10 mg, 2.22 mmol) was added at −10° C. to react at −10° C. for 2 h. The reaction solution was concentrated under reduced pressure to obtain the crude product. The crude product was separated by HPLC (chromatographic column: Waters Xbridge BEH C18 100×30 mm) 5 m; mobile phase: [water (10 mM ammonium bicarbonate)-acetonitrile]; acetonitrile %: 30-60%, 8 min), to obtain compound 24. MS m/z=751.3 [M+H]$^+$. $^1$H NMR (400 MHz, MeOD) δ ppm 6.90-6.80 (d, J=8.4 Hz, 1H), 5.34-5.25 (m, 1H), 5.21-5.13 (m, 1H), 4.98-4.78 (m, 3H), 4.63 (d, J=13.6 Hz, 1H), 4.50-4.39 (m, 3H), 4.10 (s, 2H), 3.99 (d, J=14.4 Hz, 1H), 3.75-3.57 (m, 2H), 3.23-3.11 (m, 1H), 3.00-3.17 (m, 6H), 2.93 (s, 3H), 2.84-2.78 (m, 1H), 2.66-2.77 (m, 2H), 2.44-2.34 (m, 1H), 2.26-2.04 (m, 3H), 2.02 (s, 3H), 1.98-1.77 (m, 3H), 1.22 (d, J=7.2 Hz, 3H), 1.17 (d, J=6.8 Hz, 3H).

Embodiment 25

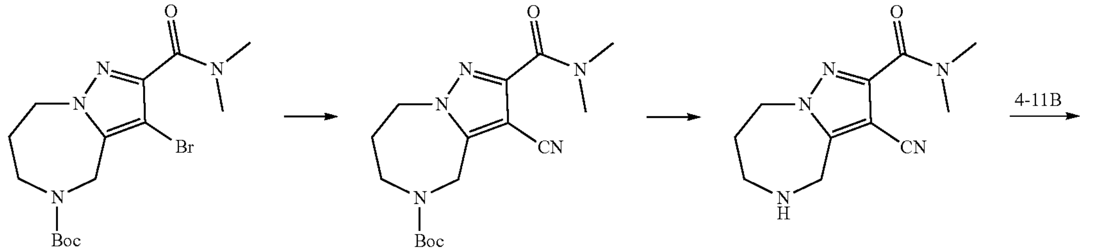

20-2

25-1

25-2

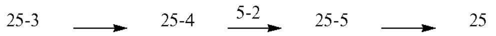

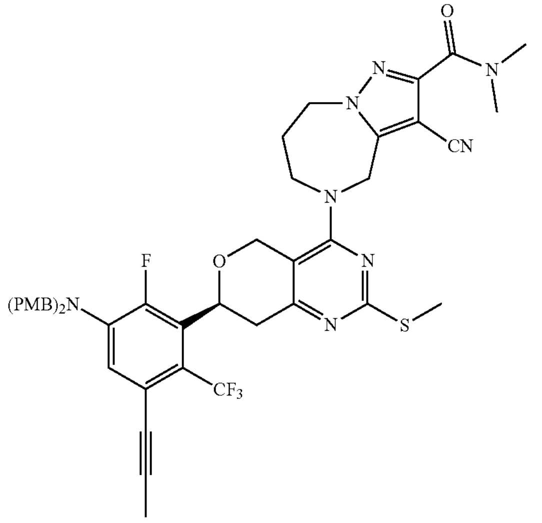

or

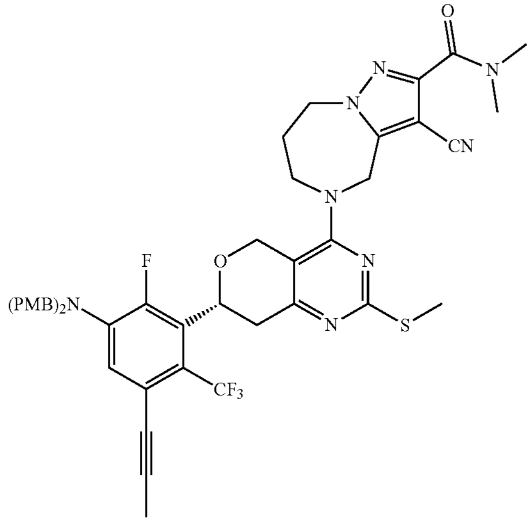

25-3

-continued
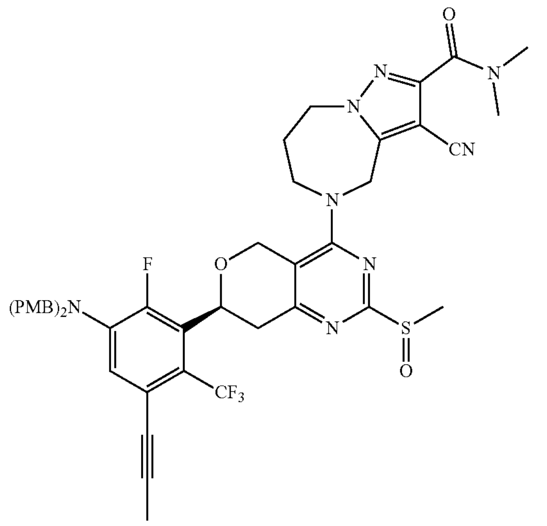
or
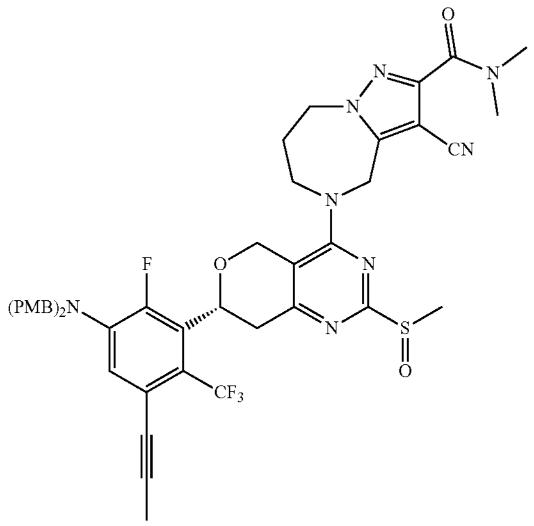
25-4
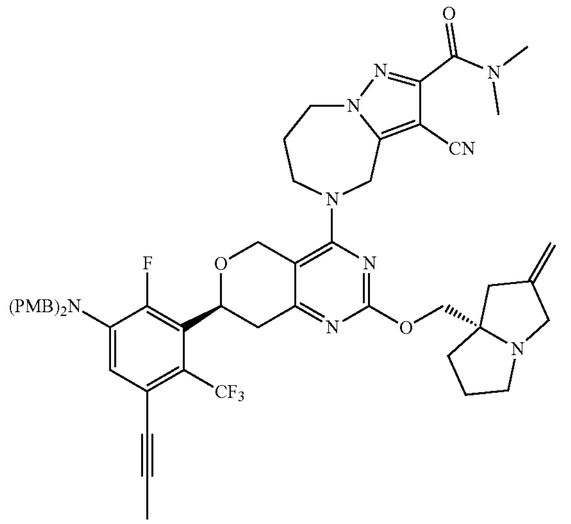
or
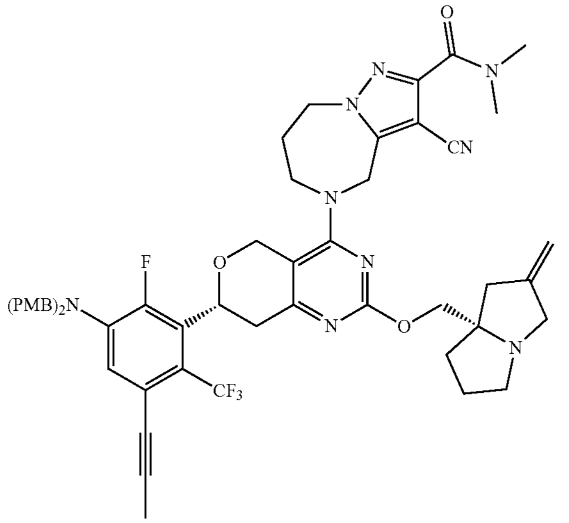
or
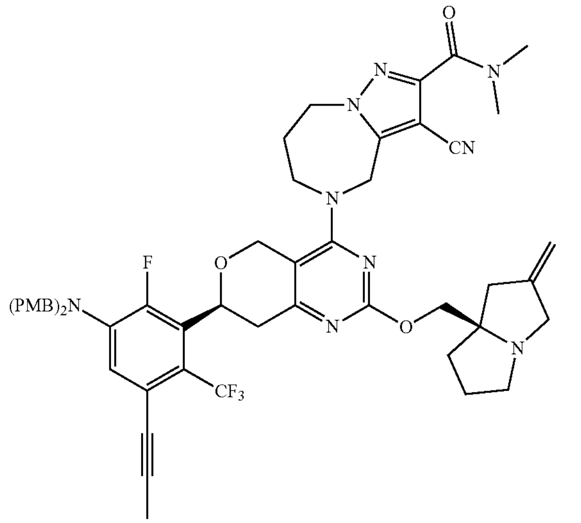
or
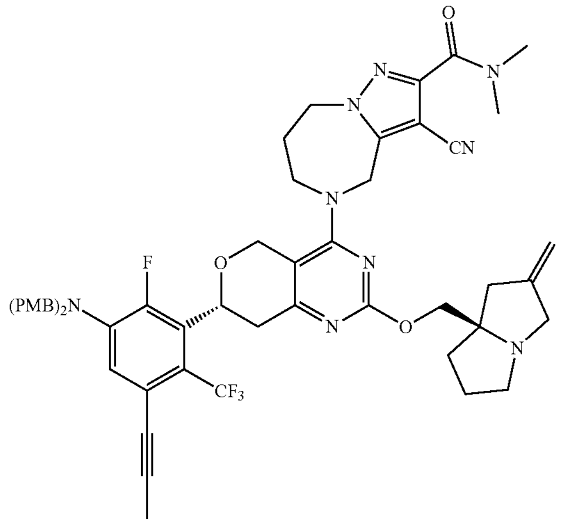
25-5

-continued

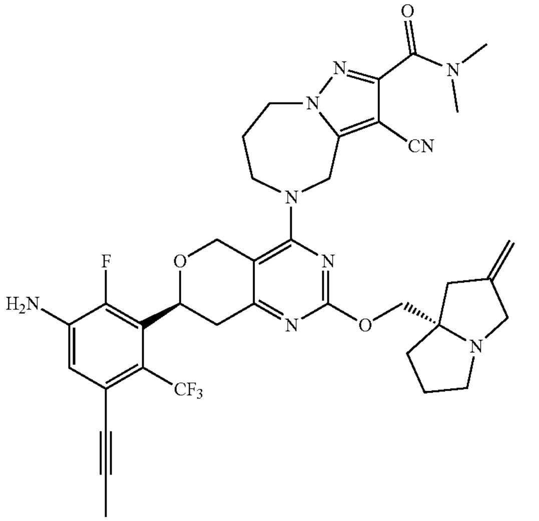

or

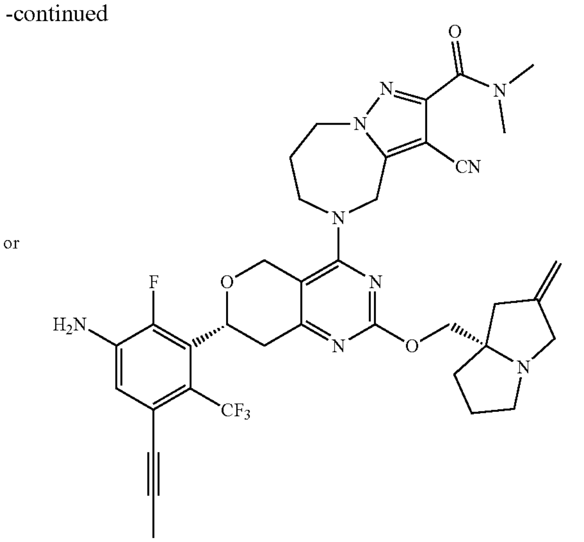

or

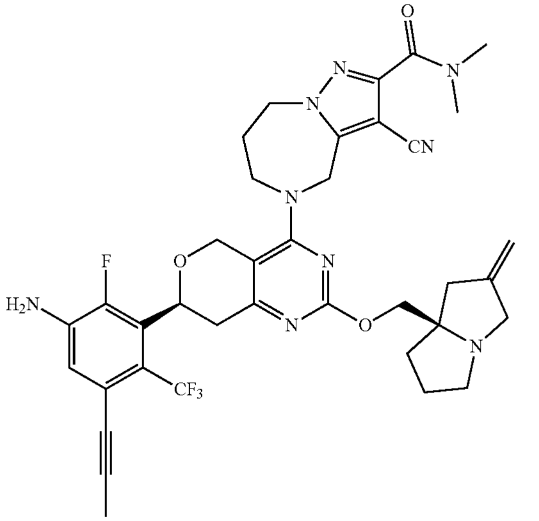

or

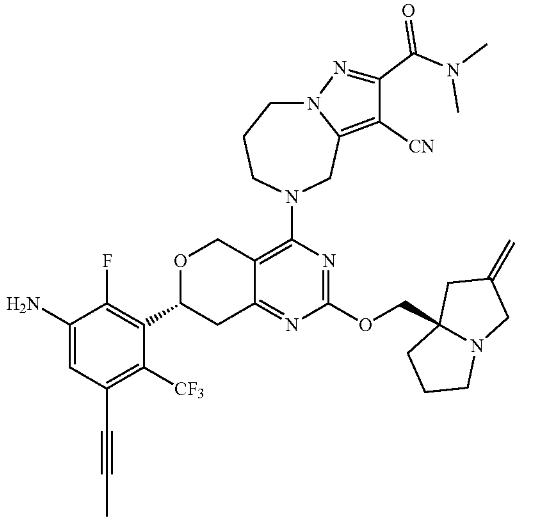

Step 1: Synthesis of Intermediate 25-1

Compound 20-2 (0.15 g, 387.33 mol), N,N-dimethylformamide (3 mL), and copper cyanide (104.07 mg, 1.16 mmol) were added to a dry reaction flask. 1,1-bis(diphenylphosphorus) ferrocene palladium chloride (28.34 mg, 38.73 mol) and tris(dibenzylacetone) dipalladium (35.47 mg, 38.73 mol) were added under nitrogen protection, and heated to 120° C. to react for 12 h. The reaction solution was cooled to room temperature. 10 mL of water was added to the reaction solution. The reaction solution was extracted with ethyl acetate (5 mL×4). The organic phase was washed with a saturated table salt solution (10 mL), dried with anhydrous sodium sulfate, filtered, and concentrated under reduced pressure. Purification was carried out by thin layer chromatography (dichloromethane:methanol=10:1) to obtain compound 25-1, with MS m/z=333.9[M+H]$^+$.

Step 2: Synthesis of Hydrochloride of Intermediates 25-2

Compound 25-1 (80 mg, 239.96 mol) and hydrochloric acid/ethyl acetate (4 M, 2 mL) were added to a reaction flask to react at 20° C. for 1 h. The reaction solution was concentrated under reduced pressure directly to obtain the hydrochloride of compound 25-2. MS m/z=234.2 [M+H]$^+$.

Step 3: Synthesis of Intermediate 25-3

Compound 4-11B (120 mg, 152.72 mol) was weighed and dissolved with DMF (2 mL). The hydrochloride of compound 25-2 (82.39 mg) was added. Then DIPEA (59.21 mg, 458.16 mol) was added to react at 50° C. for 1 h. The reaction solution was cooled to room temperature. 2 mL of water was added to the reaction solution. The reaction solution was extracted with ethyl acetate (3 mL×4). The organic phase was washed with a saturated table salt solution (5 mL), dried with anhydrous sodium sulfate, filtered, and concentrated under reduced pressure. Purification was carried out by thin layer chromatography (dichloromethane: methanol=10:1) to obtain compound 25-3. MS m/z=869.2 [M+H]$^+$.

Step 4: Synthesis of Intermediate 25-4

Compound 25-3 (90 mg, 103.57 mol) was weighed and dissolved with DCM (2 mL). m-CPBA (14.72 mg, 72.50 mol, 85% purity) was added to react at room temperature of 20° C. for 1 h. The reaction solution was diluted with 5 mL of dichloromethane, washed with 3 mL of a 5% sodium thiosulfate solution and 5 mL of a saturated table salt solution twice, dried with anhydrous sodium sulfate, filtered, and concentrated under reduced pressure. Purification was carried out by thin layer chromatography (dichloromethane: methanol=10:1) to obtain compound 25-4, with MS m/z=885.1 [M+H]$^+$.

Step 5: Synthesis of Intermediate 25-5

Compound 5-2 (65.79 mg, 429.41 mol) was dissolved with anhydrous tetrahydrofuran (1 mL). Sodium tert-butyl alcohol (33.01 mg, 343.53 mol) was added at −15° C. The reaction system reacted at −15° C. for 0.25 h. 1 mL of a tetrahydrofuran solution of compound 25-4 (76 mg, 85.88 mol) was added to continue to react for 1 h. 5 mL of a saturated ammonium chloride aqueous solution was added to the reaction solution. The reaction solution was extracted with ethyl acetate (5 mL×3). The organic phase was washed with a saturated table salt solution (10 mL), dried with anhydrous sodium sulfate, filtered, and concentrated under reduced pressure to obtain compound 25-5, with MS m/z=974.2 [M+H]$^+$.

Step 6: Synthesis of Compound 25

Compound 25-5 (96 mg, 98.56 mol) was dissolved with dichloromethane (1 mL). Trifluoroacetic acid (2.25 g, 19.71 mmol, 1.46 mL) was added at −10° C. to react at 20° C. for 2 h. The reaction solution was concentrated under reduced pressure to obtain the crude product. The crude product was separated by HPLC (chromatographic column: Waters Xbridge BEH C18 100×30 mm 5 m; mobile phase: [water (10 mM ammonium bicarbonate)-acetonitrile]; acetonitrile %: 25-55%, 8 min), to obtain compound 25. MS m/z=734.2 [M+H]$^+$. $^1$H NMR (400 MHz, $CDCl_3$) δ ppm 6.87 (d, J=8.38 Hz, 1H), 5.20-5.18 (m, 1H), 5.07-4.77 (m, 4H), 4.75-4.64 (m, 2H), 4.60-4.47 (m, 1H), 4.41-4.31 (m, 1H), 4.06 (s, 3H), 4.01-3.56 (m, 4H), 3.36-3.22 (m, 4H), 3.19-3.04 (m, 4H), 2.97-2.90 (m, 1H), 2.78-2.69 (m, 1H), 2.65-2.61 (m, 1H), 2.41-2.25 (m, 2H), 2.21-2.13 (m, 2H), 2.04 (s, 3H), 1.96-1.84 (m, 2H), 1.79-1.65 (m, 2H).

Embodiment 26

21-1

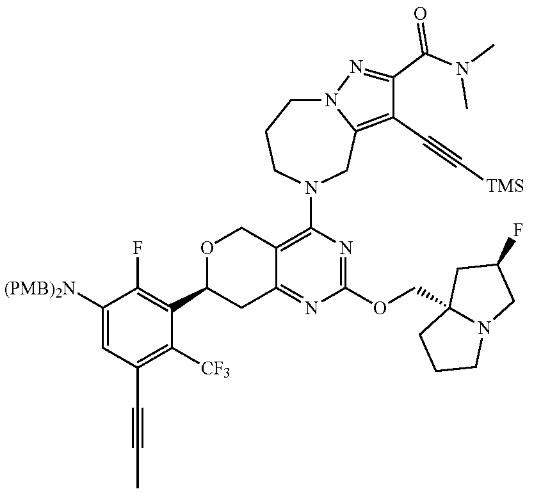

or

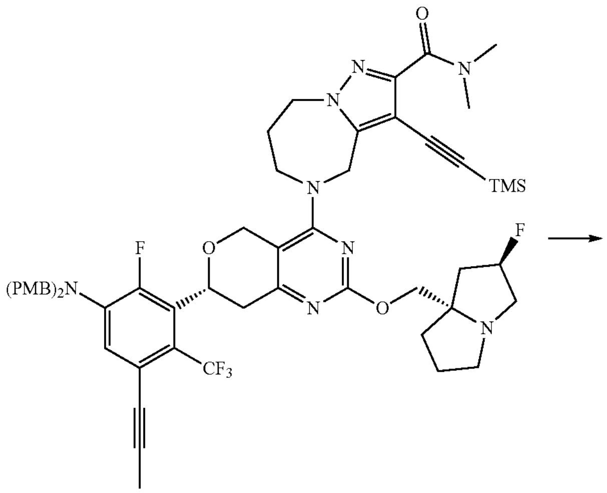

26-1

-continued

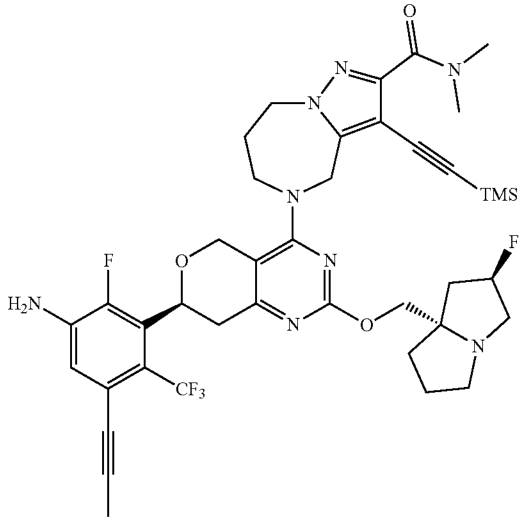

or

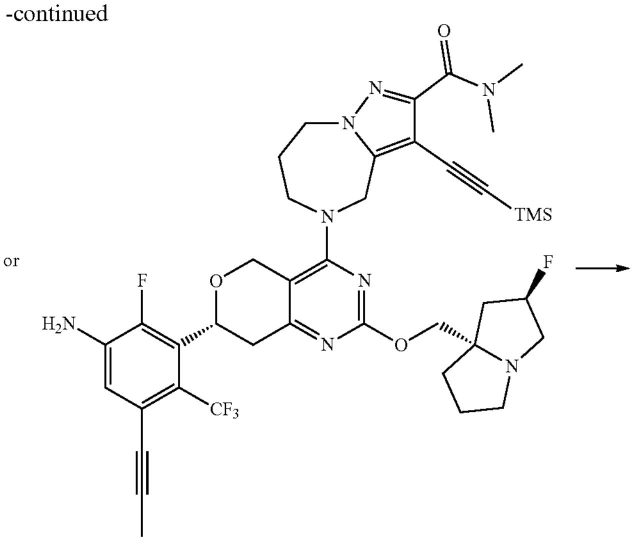

26-2

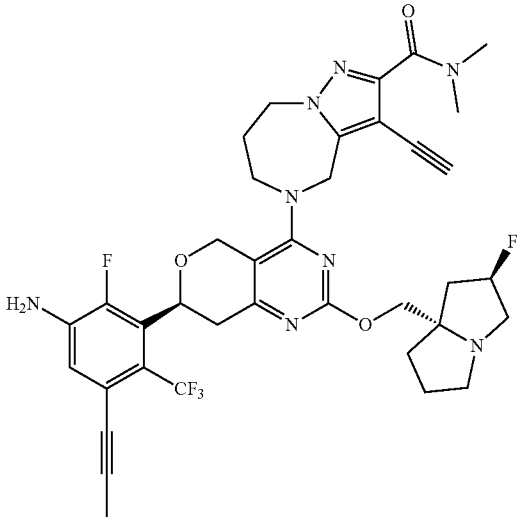

or

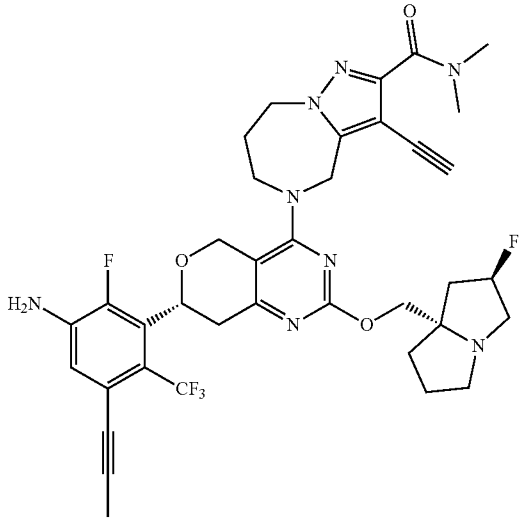

26

Step 1: Synthesis of Intermediate 26-1

Compound 21-1 (50 mg, 48.36 mol) and tributyl(trimethylsilylethynyl)tin (112.37 mg, 290.16 mol) were dissolved with anhydrous toluene (2 mL). Tetrakis(triphenylphosphine)palladium (11.18 mg, 9.67 mol) was added to react at 130° C. for 16 h under nitrogen protection. The reaction solution was concentrated. 5 mL of water was added to the reaction solution. The reaction solution was extracted with ethyl acetate (3 mL×2), washed with a saturated table salt solution (3 mL×2), dried with anhydrous sodium sulfate, and concentrated to obtain compound 26-1. MS m/z=1051.3 $[M+H]^+$.

Step 2: Synthesis of Trifluoroacetate of Intermediate 26-2

Compound 26-1 (50 mg, 47.56 mol) was dissolved with anhydrous dichloromethane (2 mL). Trifluoroacetic acid (612.82 mg, 5.37 mmol) was added to react at 15° C. for 1 h. The reaction solution was concentrated under reduced pressure to obtain the trifluoroacetate of compound 26-2. MS m/z=811.2 $[M+H]^+$.

Step 3: Synthesis of Compound 26

The trifluoroacetate of compound 26-2 (0.1 g) was dissolved with anhydrous methanol (2.5 mL). Potassium carbonate (34.09 mg, 246.63 mol) was added to react at 18° C. for 2 h. The reaction solution was concentrated. Water (10 mL) and ethyl acetate (5 mL×2) were added to separate the solution. The organic phases were mixed, washed with a saturated table salt solution (5 mL×2), dried with anhydrous sodium sulfate, and concentrated. The crude product was separated by HPLC (chromatographic column: Phenomenex Luna C18 75×30 mm×3 m; mobile phase: [water (0.04% HCl)-acetonitrile]; acetonitrile %: 20-50%, 8 min). The separated solution was adjusted to pH=9 with a saturated sodium bicarbonate solution, concentrated under reduced pressure to remove the organic phase, extracted with ethyl acetate (5 mL×2), concentrated under reduced pressure, and freeze-dried to obtain compound 26. MS m/z=739.2$[M+H]^+$.

Embodiment 27
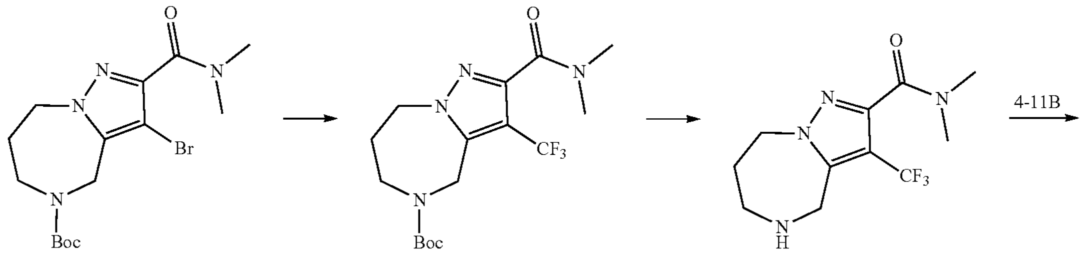
20-2 27-1 27-2
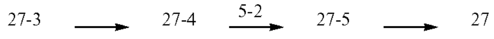
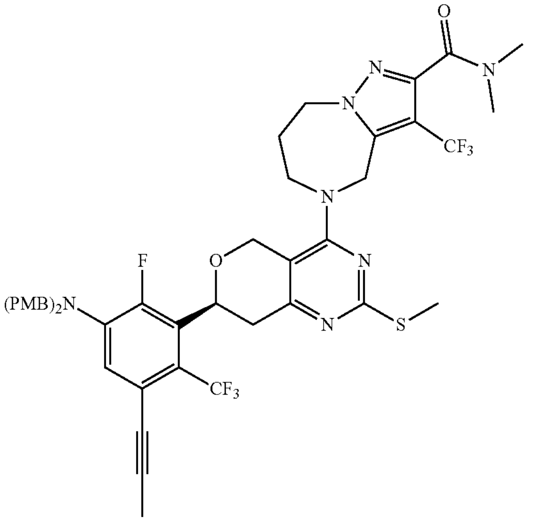
or
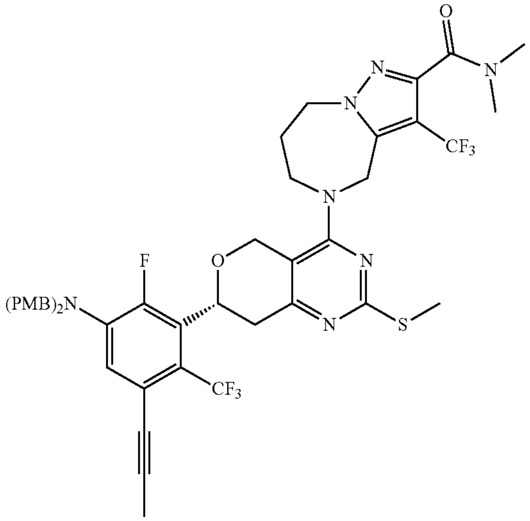
27-3
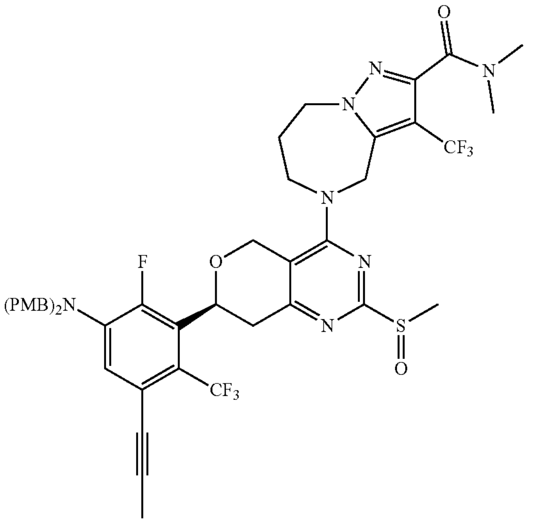
or
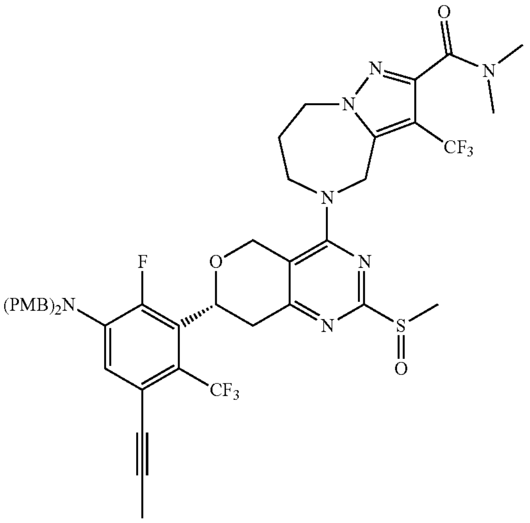
27-4

-continued
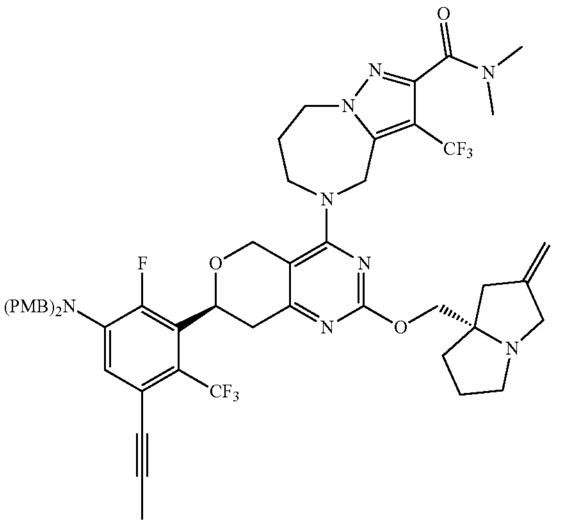
or
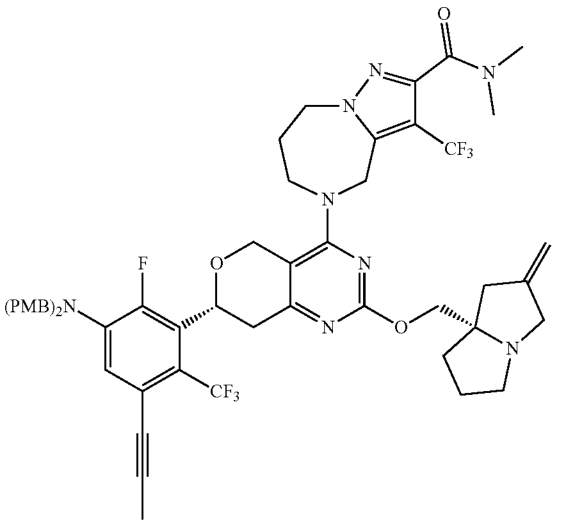
or
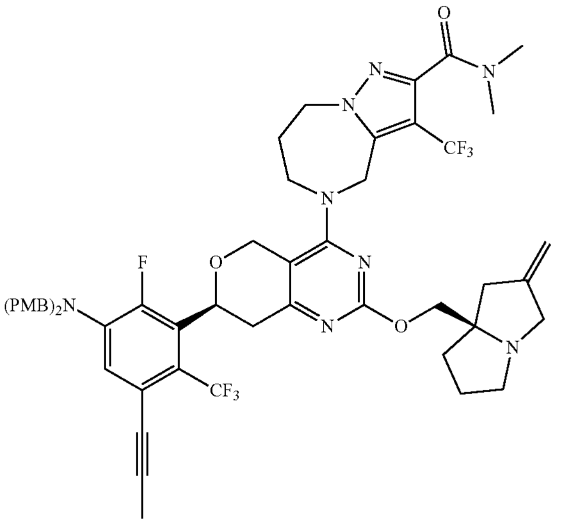
or
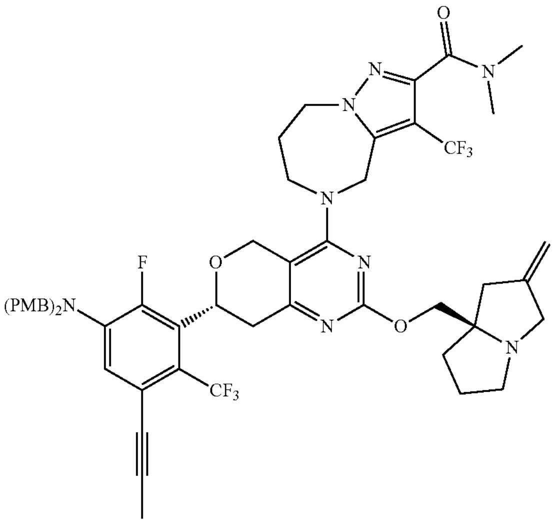
27-5
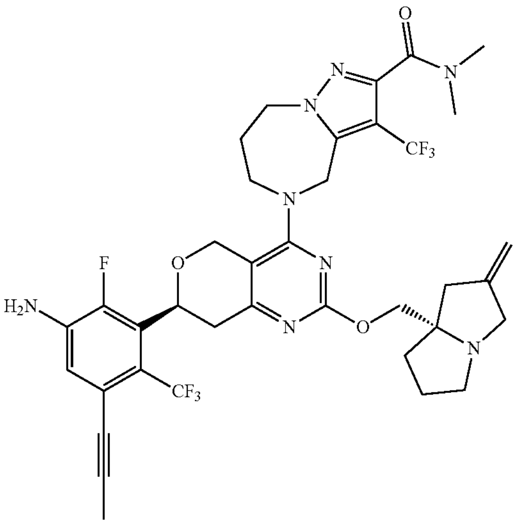
or
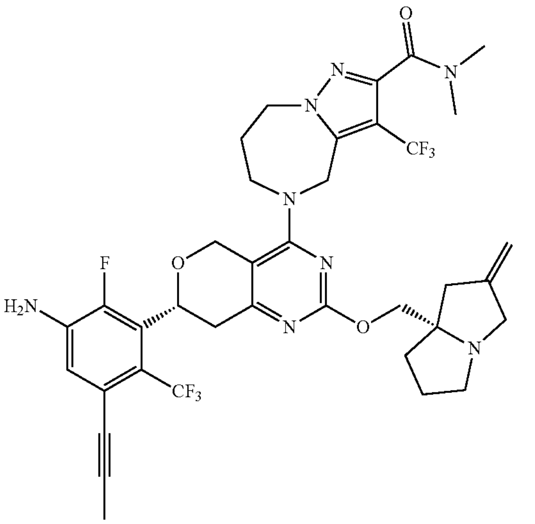
or -continued

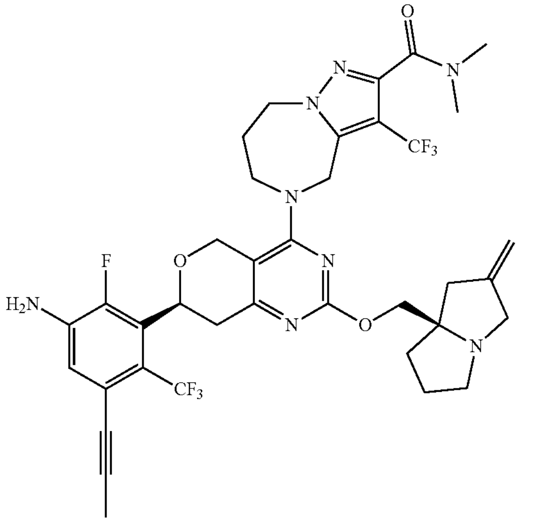

or

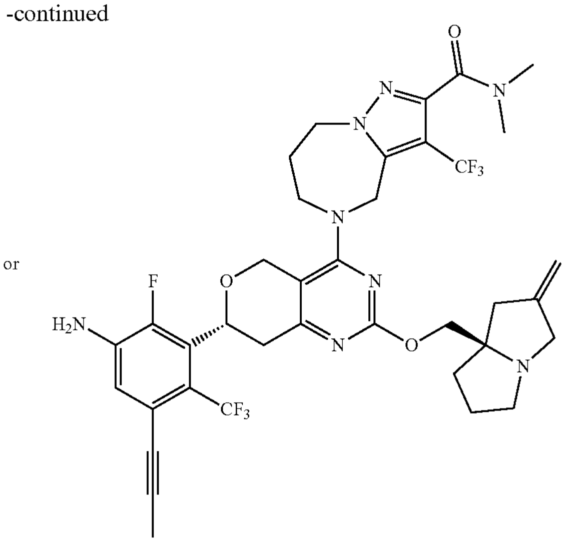

27

Step 1 Synthesis of Intermediate 27-1

Compound 20-2 (0.2 g, 516.43 μmol) and N, N-dimethylformamide (2.5 mL) were added to a dry reaction flask. Methyl fluorosulfonyl difluoroacetate (496.07 mg, 2.58 mmol) and cuprous iodide (196.71 mg, 1.03 mmol) were added to react at 100° C. for 10 h. 5 mL of water was added to the reaction solution. The reaction solution was extracted with ethyl acetate (5 mL×2), washed with a saturated table salt solution (5 mL×2), dried with anhydrous sodium sulfate, and concentrated. The crude product was separated by HPLC (chromatographic column: Phenomenex luna C18 100×40 mm×3 am; mobile phase: [water (0.04% HCl)-acetonitrile]; acetonitrile %: 30-60%, 18.0 min). The separated solution was adjusted to pH=8-9 and concentrated under reduced pressure to remove the organic phase. The aqueous phase was extracted with ethyl acetate (5 mL×2). The organic phases were mixed, washed with 3 mL of a saturated table salt solution, dried with anhydrous sodium sulfate, and concentrated to obtain compound 27-1. MS m/z=377.1 $[M+H]^+$.

Step 2: Synthesis of Hydrochloride of Intermediates 27-2

Compound 27-1 (90 mg, 239.12 mol) and hydrochloric acid/ethyl acetate (4 M, 2.5 mL) were added to a reaction flask to react at 18° C. for 2 h. The reaction solution was concentrated under reduced pressure to obtain the hydrochloride of compound 27-2. MS m/z=277.1 $[M+H]^+$.

Step 3: Synthesis of Intermediate 27-3

Compound 4-11B (100 mg, 127.27 mol) was weighed and dissolved with DMF (1 mL). The hydrochloride of compound 27-2) (42.19 mg) was added. Then DIPEA (49.34 mg, 381.80 mol) was added to react at 50° C. for 1 h. The reaction solution was cooled to room temperature. Water (10 mL) was added. The reaction solution was extracted with ethyl acetate (5 mL×3) and separated. The organic phases were mixed, extracted with a saturated table salt solution (5 mL×2), separated, dried with anhydrous sodium sulfate, filtered, and concentrated under reduced pressure to obtain compound 27-3. MS m/z=912.1 $[M+H]^+$.

Step 4: Synthesis of Intermediate 27-4

Compound 27-3 (0.14 g, 153.52 mol) was weighed and dissolved with DCM (2.5 mL). m-CPBA (46.57 mg, 230.28 mol, 85% purity) was added to react at 18° C. for 1 h. The reaction solution was quenched with 20 mL of a 5% sodium sulfite solution and extracted with dichloromethane (10 mL×2). The organic phases were mixed, washed with a saturated table salt solution (20 mL×2), dried with anhydrous sodium sulfate, and concentrated to obtain compound 27-4, MS m/z=944.1 $[M+H]^+$.

Step 5: Synthesis of Intermediate 27-5

Compound 5-2 (113.63 mg, 741.58 mol) was dissolved with anhydrous tetrahydrofuran (1 mL). Sodium tert-butyl alcohol (57.01 mg, 593.27 mol) was added at −15° C. The reaction system reacted at −15° C. for 0.25 h. 2 mL of a tetrahydrofuran solution of compound 27-4 (0.14 g, 148.32 μmol) was added to continue to react for 1 h. 5 mL of a saturated ammonium chloride aqueous solution was added to the reaction solution. The reaction solution was extracted with ethyl acetate (5 mL×3). The organic phase was washed with a saturated table salt solution (10 mL), dried with anhydrous sodium sulfate, filtered, and concentrated under reduced pressure to obtain compound 27-5, MS m/z=1017.6 $[M+H]^+$.

Step 6: Synthesis of Hydrochloride of Compound 27

Compound 27-5 (0.12 g, 117.99 mol) was dissolved with dichloromethane (2.5 mL). Trifluoroacetic acid (766.83 mg, 6.73 mmol) was added at 18° C. to react at 18° C. for 16 h. The reaction solution was concentrated under reduced pressure to obtain the crude product. The crude product was separated by HPLC (chromatographic column: Phenomenex Luna C18 75×30 mm×3 μm; mobile phase: [water (0.04% HCl)-acetonitrile]; acetonitrile %: 20-50%, 8 min), to obtain the hydrochloride of compound 27. MS m/z=777.2 $[M+H]^+$. 1H NMR (400 MHz, MeOD) δ=7.00-6.90 (m, 1H), 5.31-5.06 (m, 4H), 5.02-4.80 (m, 2H), 4.79-4.61 (m, 2H), 4.59-4.30 (m, 4H), 4.10-3.70 (m, 4H), 3.52-3.40 (m, 2H), 3.24-3.08 (m, 2H), 3.02-2.93 (m, 6H), 2.49-2.40 (m, 1H), 2.38-2.27 (m, 3H), 2.13-1.84 (m, 6H).

Embodiment 28
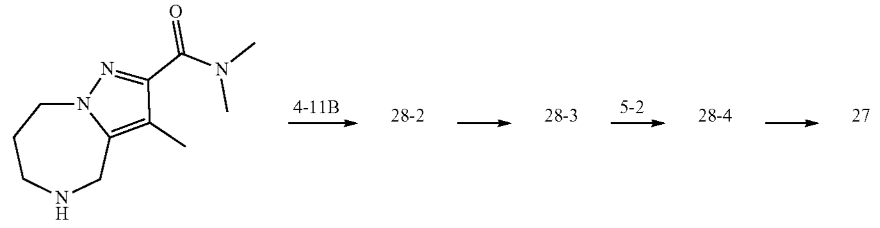
28-1
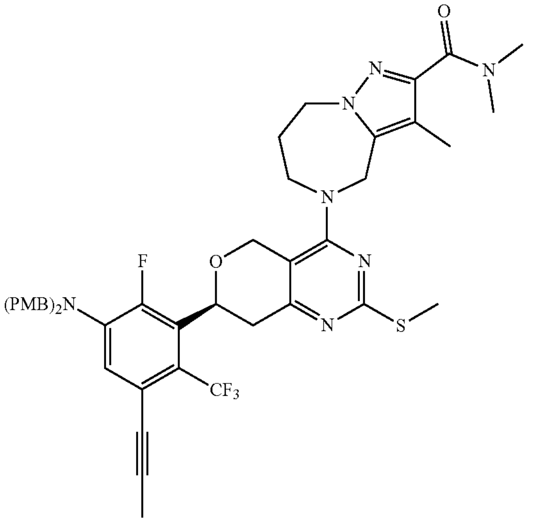
or
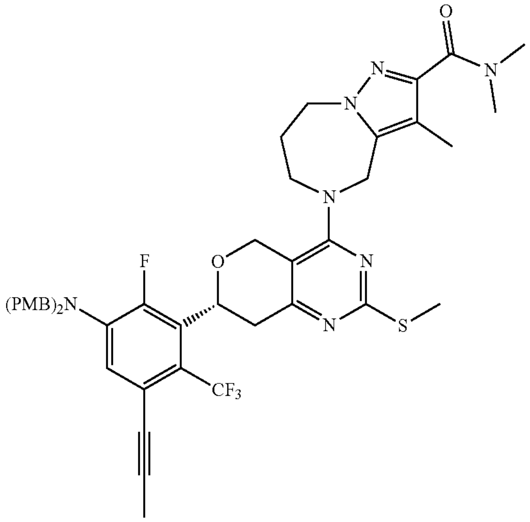
28-2
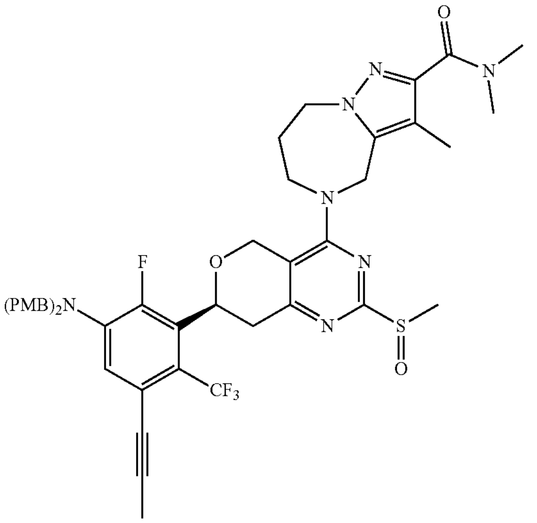
or
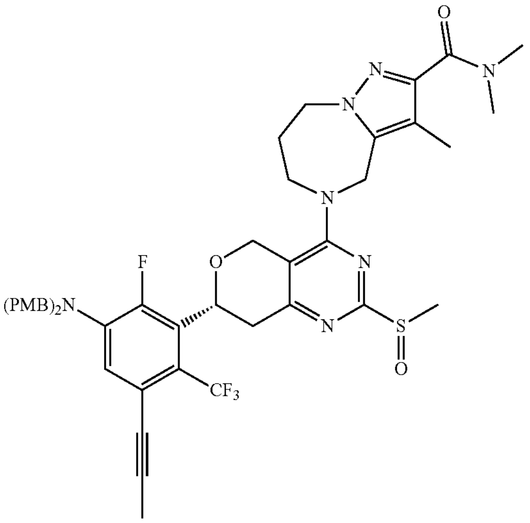
28-3

-continued
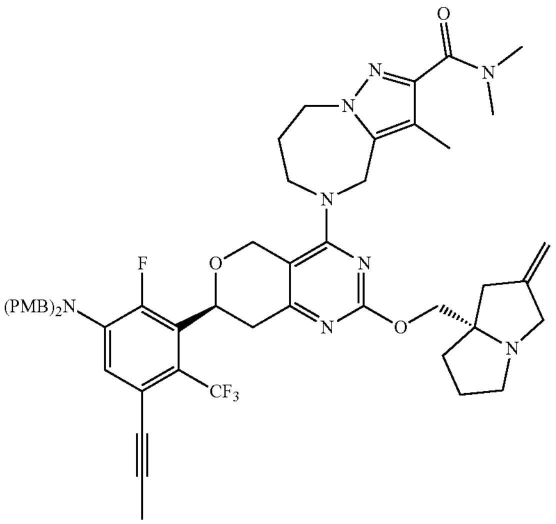
or
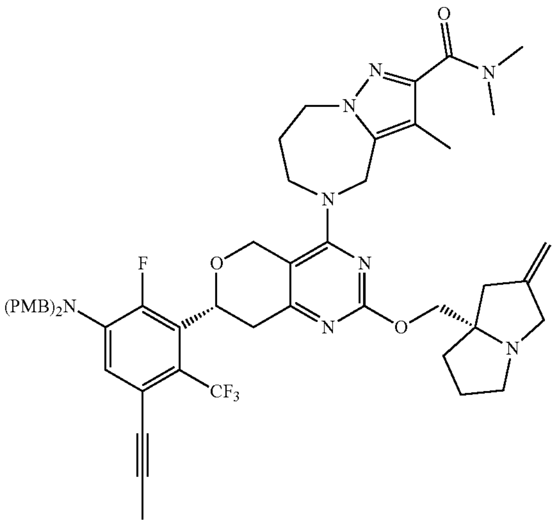
or
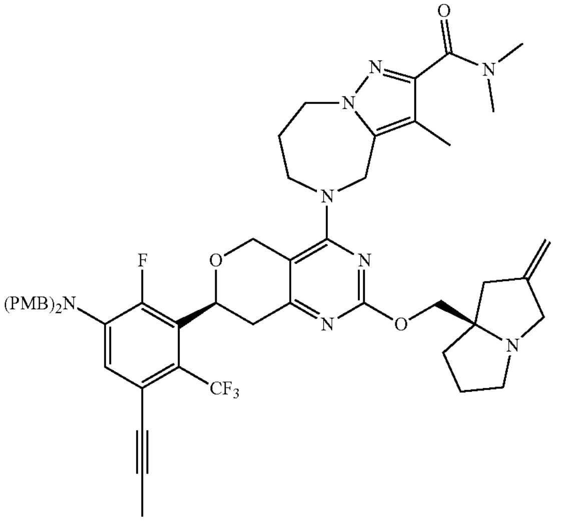
or
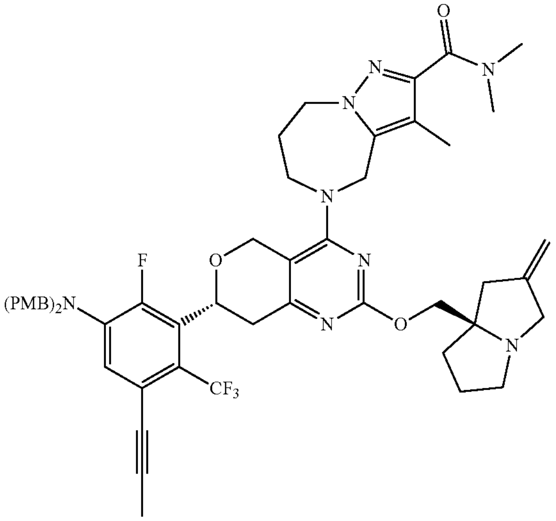
28-4
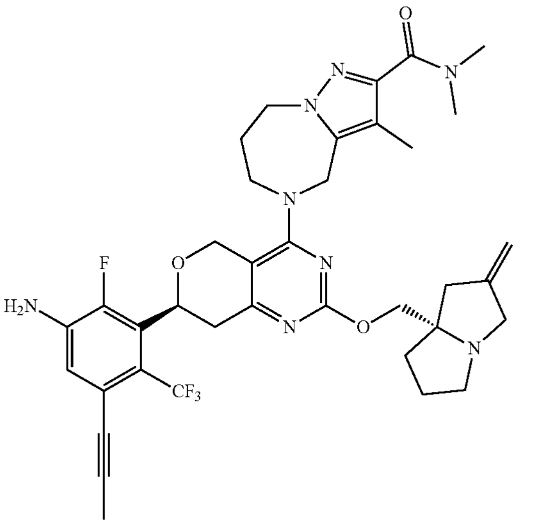
or
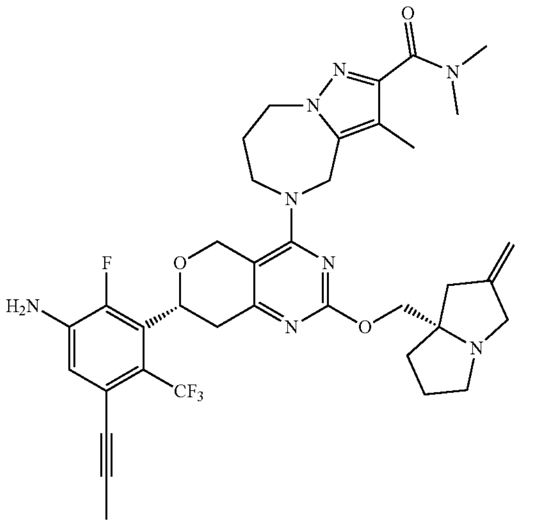
or -continued

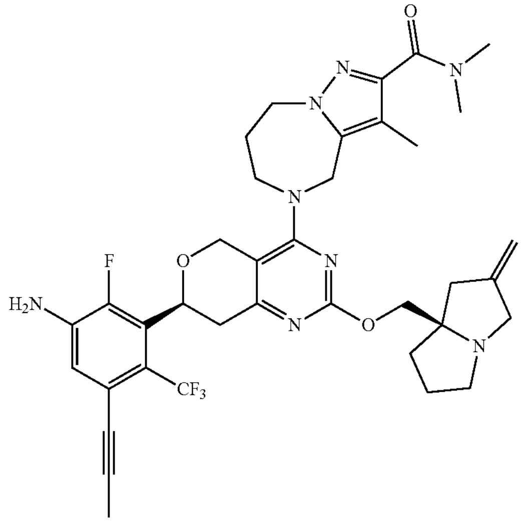

or

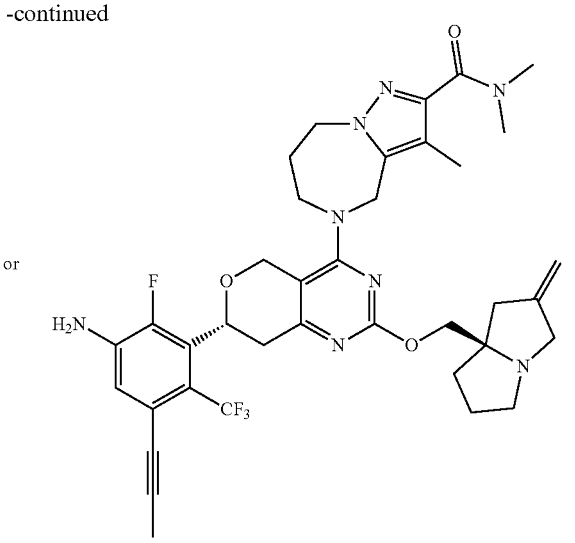

28

Step 1: Synthesis of Intermediate 28-2

Compound 4-11B (0.22 g, 279.99 μmol) was weighed and dissolved with DMF (20 mL). Compound 28-1 (0.1 g, 449.87 mol) was added. Then DIPEA (180.93 mg, 1.40 mmol) was added to react at 100° C. for 1 h. The reaction solution was cooled to room temperature, quenched with saturated ammonium chloride (10 mL), extracted with ethyl acetate (10 mL×3), and separated. The organic phases were mixed, extracted with a saturated table salt solution (10 mL), separated, dried with anhydrous sodium sulfate, filtered, and concentrated under reduced pressure to obtain compound 28-2. MS m/z=858.3 $[M+H]^+$.

Step 2: Synthesis of Intermediate 28-3

Compound 28-2 (0.154 g, 179.50 mol) was weighed and dissolved with DCM (10 mL). m-CPBA (36.44 mg, 179.50 mol, 85% purity) was added to react at room temperature of 25° C. for 1 h. The reaction solution was quenched with water (10 mL) and extracted with dichloromethane (10 mL×2). The organic phases were mixed, washed with a saturated table salt solution (20 mL×2), dried with anhydrous sodium sulfate, and concentrated to obtain compound 28-3, with MS m/z=874.3 $[M+H]^+$.

Step 3: Synthesis of Intermediate 28-4

Compound 5-2 (56.50 mg, 368.76 mol) was dissolved with anhydrous tetrahydrofuran (10 mL). Sodium tert-butoxide (35.44 mg, 368.76 mol) was added at 0° C. The reaction system reacted at 0° C. for 1 h. Compound 28-3 (161.14 mg, 184.38 mol) was added to continue to react for 1 h. 5 mL of a water solution was added to the reaction solution. The reaction solution was extracted with ethyl acetate (10 mL×3). The organic phase was washed with a saturated table salt solution (20 mL), dried with anhydrous sodium sulfate, filtered, and concentrated to obtain compound 28-4, MS m/z=963.4 $[M+H]^+$.

Step 4: Synthesis of Hydrochloride of Compound 28

Compound 28-4 (0.173 g, 179.63 mol) was dissolved with dichloromethane (15 mL). Trifluoroacetic acid (2.50 g, 21.93 mmol) was added at 20° C. to react at 20° C. for 1 h. The reaction solution was concentrated under reduced pressure to obtain the crude product. The crude product was separated by HPLC (chromatographic column: Xtimate C18 150×40 mm×5 μm; mobile phase: [water (0.05% HCl)-acetonitrile]; acetonitrile %: 20-50%, 10 min), to obtain the hydrochloride of compound 28. MS m/z=723.2 $[M+H]^+$. $^1H$ NMR (400 MHz, MeOH) δ=6.99-6.90 (m, 1H), 5.38-5.29 (m, 2H), 5.26-5.11 (m, 2H), 5.10-4.95 (m, 2H), 4.75-4.66 (m, 2H), 4.55-4.47 (m, 1H), 4.38-4.28 (m, 2H), 4.20-4.07 (m, 1H), 4.00-3.90 (m, 2H), 3.85-3.69 (m, 2H), 3.42-3.35 (m, 1H), 3.28-3.20 (m, 2H), 3.20-3.07 (m, 6H), 3.05-2.95 (m, 2H), 2.91-2.79 (m, 1H), 2.43-2.16 (m, 8H), 2.08-2.01 (m, 3H).

Embodiment 29

20-6 → 29-1 → 29

-continued
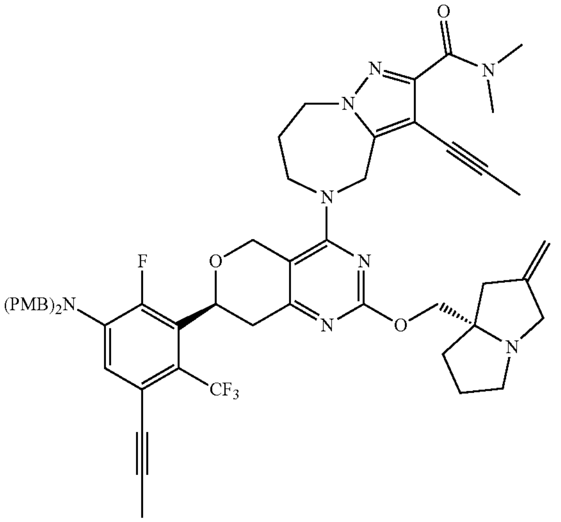
or
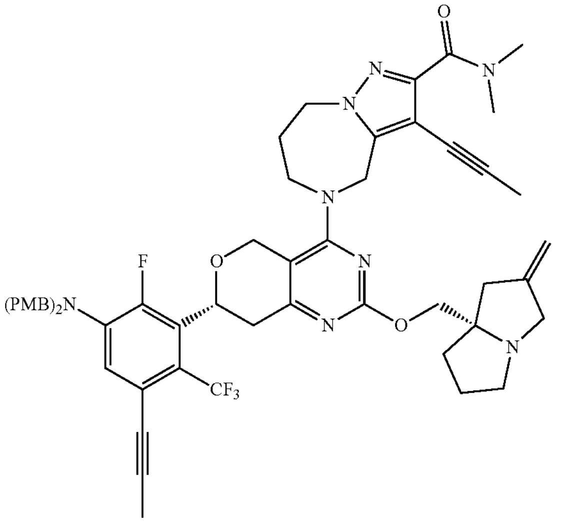
or
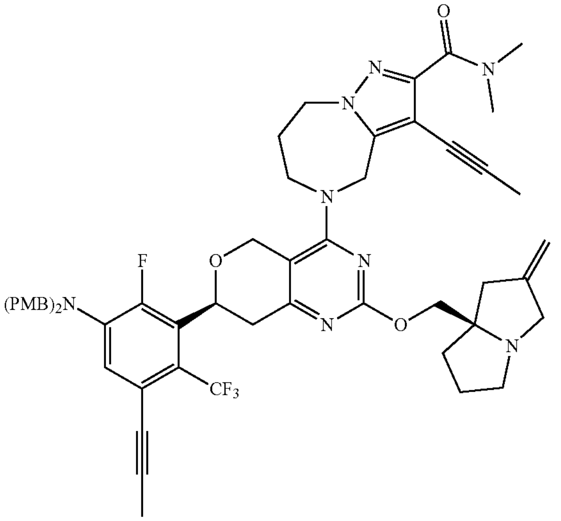
or
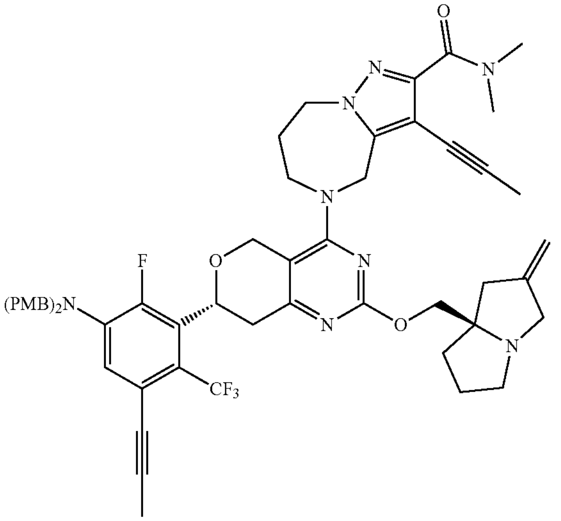
29-1
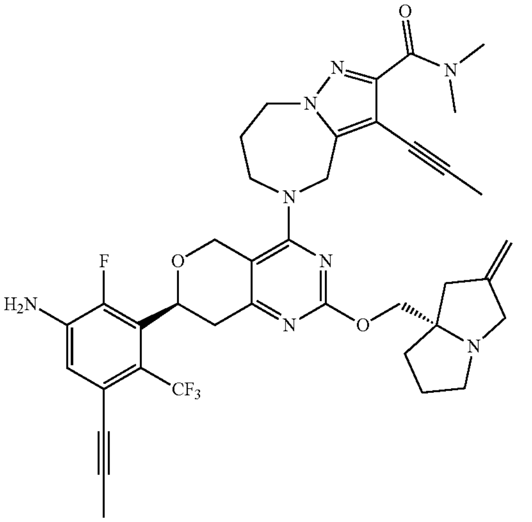
or
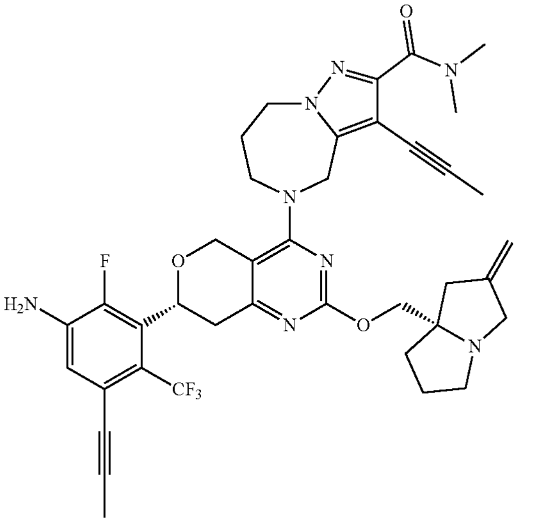
or -continued

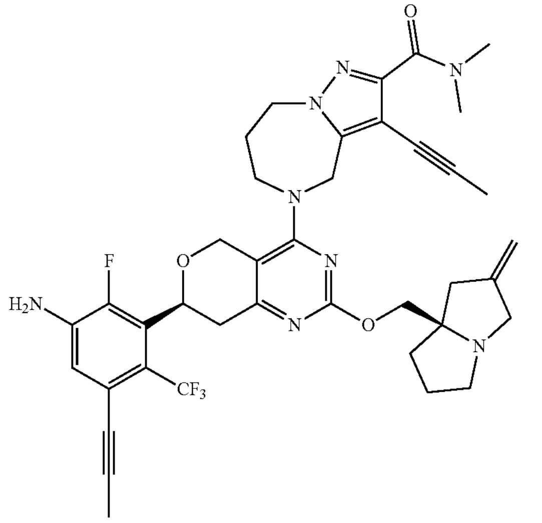

or

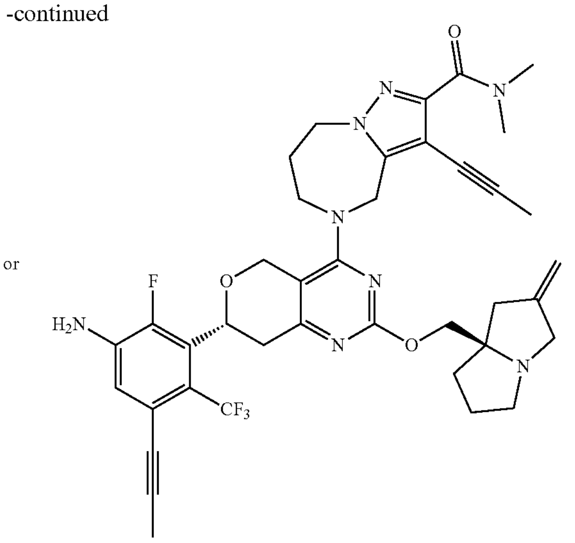

29

Step 1: Synthesis of Intermediate 29-1

Compound 20-6 (0.15 g, 145.92 mol) and tri-butyl (1-propargynyl)tin (384.20 mg, 1.17 mmol) were dissolved with anhydrous toluene (6 mL). Dichlorobis[di-tert-butyl-(4-dimethylaminophenyl)phosphine]palladium (31.00 mg, 43.78 mol) was added under nitrogen protection to react at 120° C. for 24 h with the nitrogen pumped and replaced for 5 times. The reaction solution was quenched with 5 mL of water and filtered with diatomite. The filter cake was washed with ethyl acetate. The filtrate was extracted with ethyl acetate (10 mL×2), washed with 10 mL of a saturated table salt solution, dried with anhydrous sodium sulfate, and concentrated to obtain compound 29-1. MS m/z=987.7 $[M+H]^+$.

Step 2: Synthesis of Compound 29

Compound 29-1 (67.2 mg, 68.08 mol) was dissolved with dichloromethane (15 mL). Trifluoroacetic acid (212.92 mg, 1.87 mmol) was added at 20° C. to react at 20° C. for 1 h. The reaction solution was concentrated under reduced pressure to obtain the crude product. The crude product was separated by HPLC (chromatographic column: Welch Xtimate C18 150×25 mm×5 m; mobile phase: [water (0.05% ammonia+10 mM ammonium bicarbonate)-acetonitrile]; acetonitrile %: 40-70%, 9 min), to obtain compound 29. MS m/z=747.3 $[M+H]^+$.

Embodiment 30

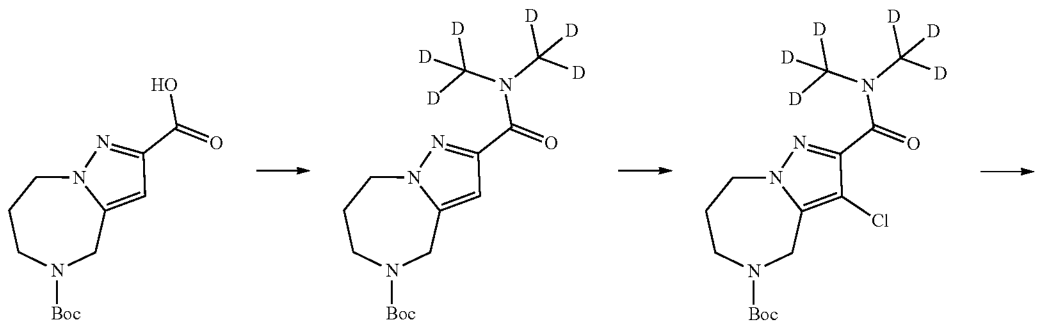

30-1 30-2 30-3

-continued
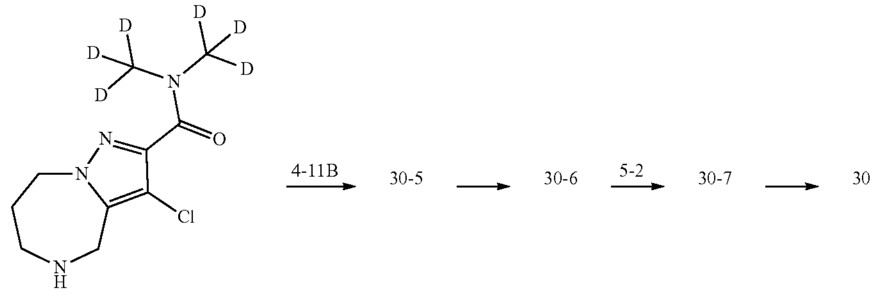
30-4
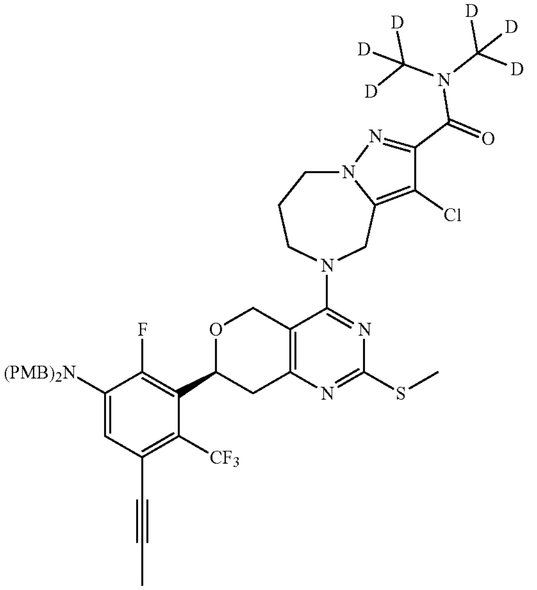
or
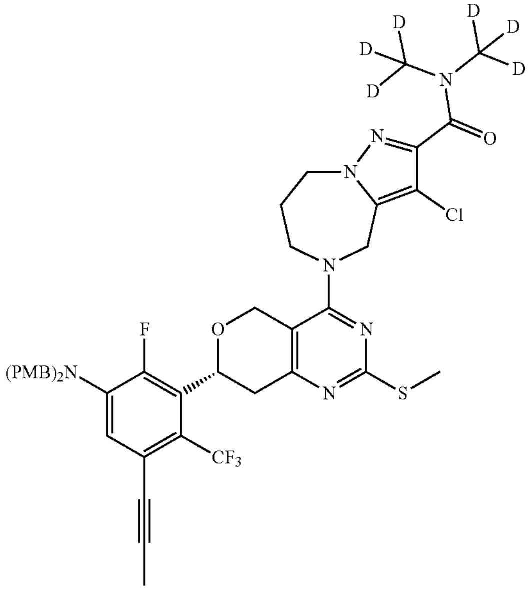
30-5
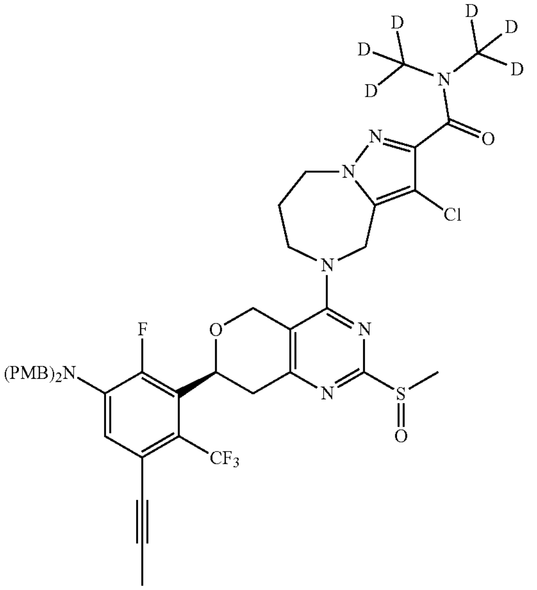
or
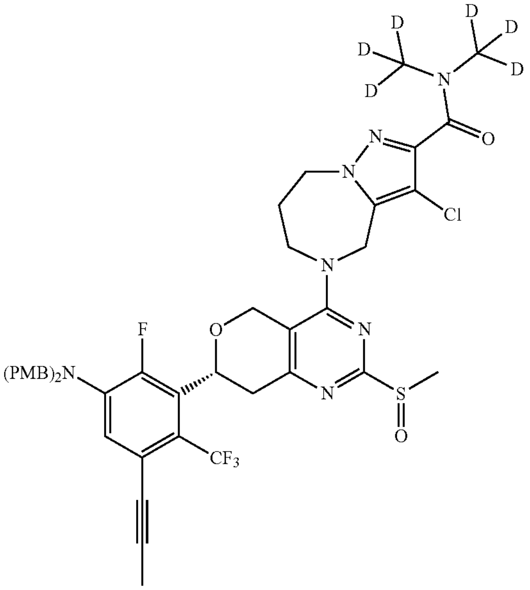
30-6

-continued
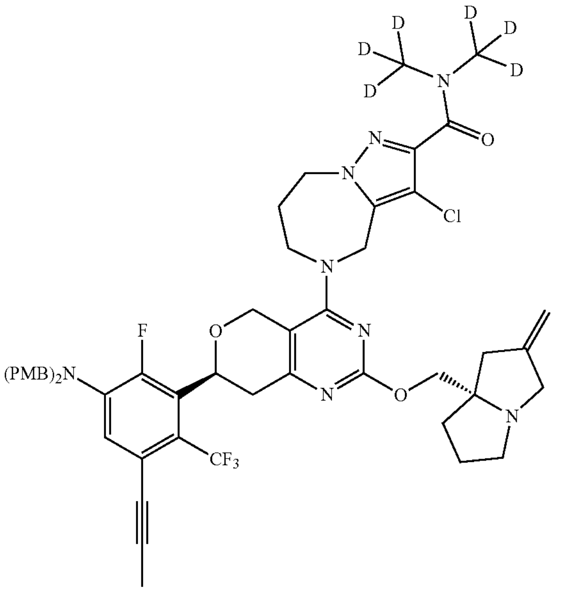
or
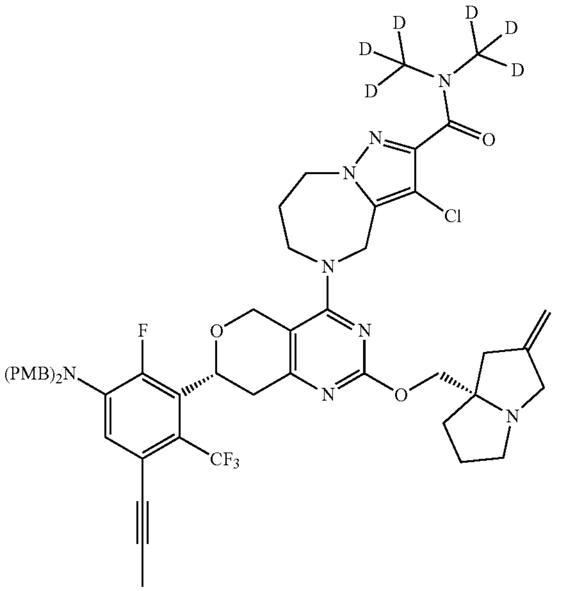
or
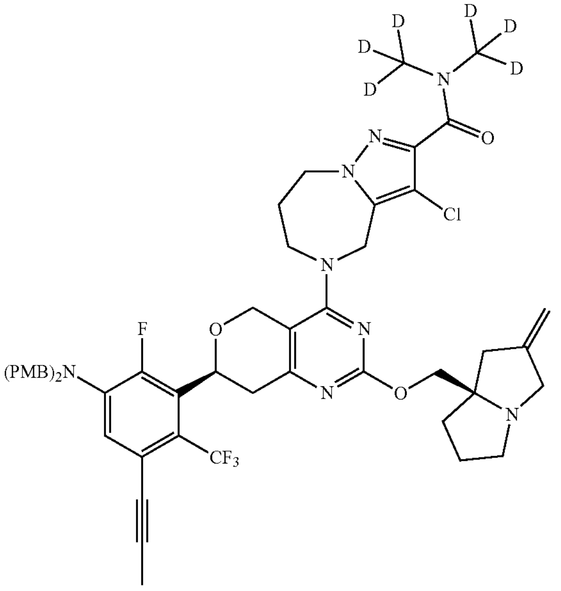
or
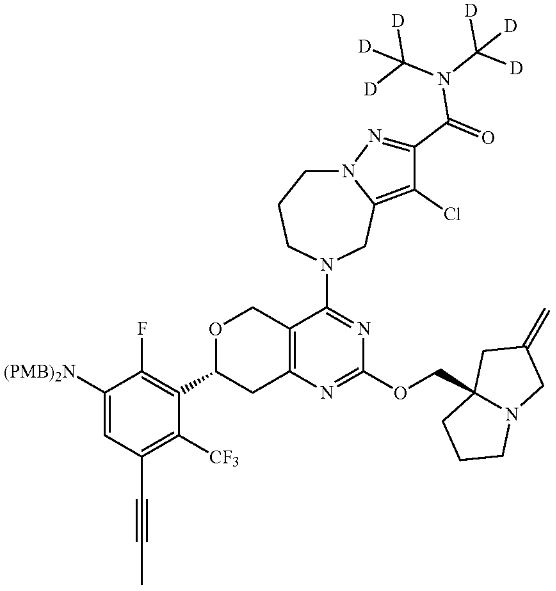

-continued

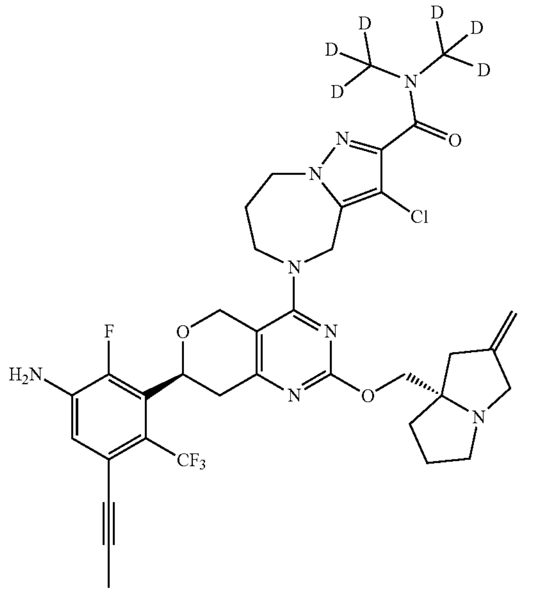

or

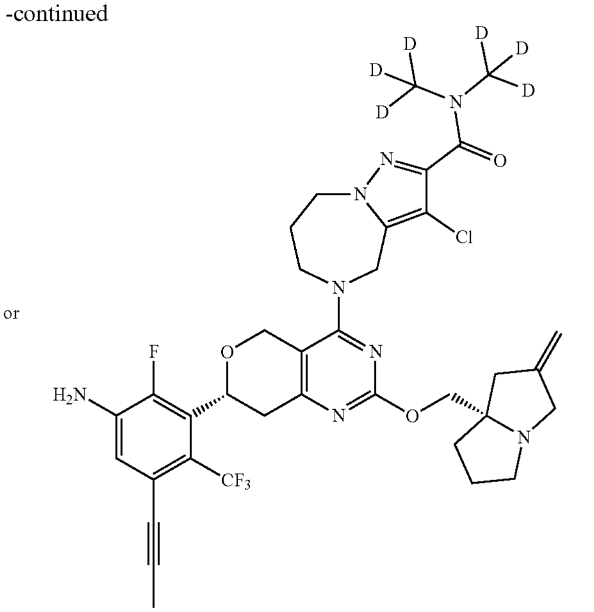

or

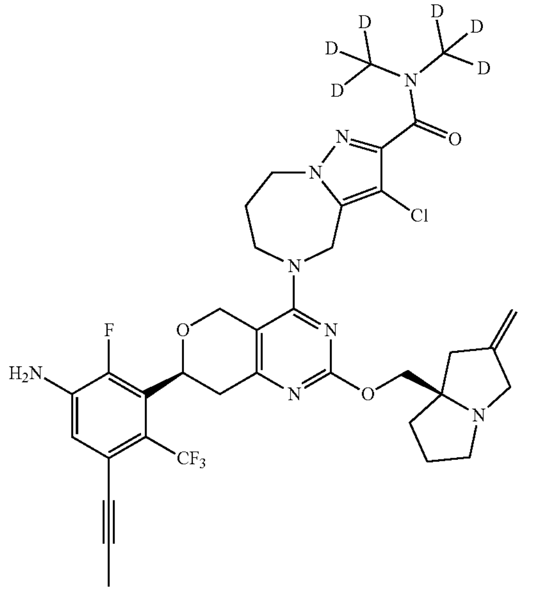

or

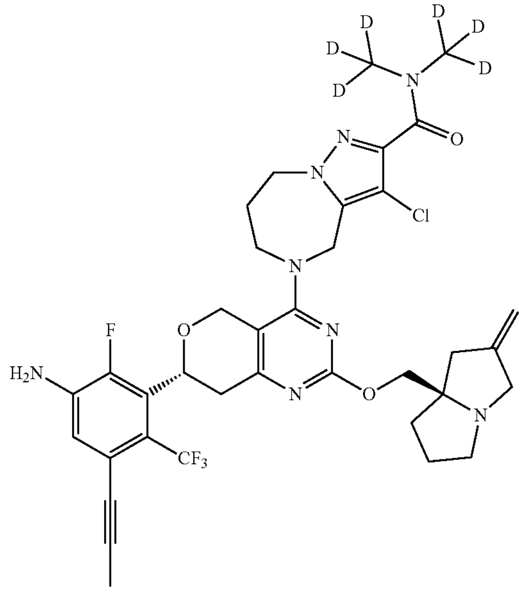

Step 1: Synthesis of Intermediate 30-2

Compound 30-1 (0.25 g, 844.27 mol) was weighed and dissolved with DMF (5 ml). HATU (417.32 mg, 1.10 mmol), DIPEA (436.46 mg, 3.38 mmol, 588.22 L) and dimethyl-d6-aminohydrochloride (314.18 mg, 2.53 mmol) were added to the solution to react at room temperature of 18° C. for 1 h. The reaction solution was quenched with 5 mL of water, extracted with ethyl acetate (10 mL×3), washed with 10 mL of a saturated table salt solution, dried with anhydrous sodium sulfate, and concentrated under reduced pressure to obtain compound 30-2. MS m/z=315.2 $[M+H]^+$.

Step 2: Synthesis of Compound 30-3

Compound 30-2 (264.97 mg, 800.60 mol) was weighed and dissolved with DMF (3 mL). NCS (160.36 mg, 1.20 mmol) was added to the reaction system to react at 55° C. for 2 h. The reaction solution was quenched with 5 mL of water, extracted with ethyl acetate (10 mL×3), washed with 10 mL of a saturated table salt solution, dried with anhydrous sodium sulfate, concentrated under reduced pressure, and purified by column chromatography (petroleum ether: ethyl acetate=1:1), to obtain compound 30-3. MS m/z=349.2 $[M+H]^+$.

Step 3: Synthesis of Hydrochloride of Compound 30-4

Compound 30-3 (0.27 g, 735.26 mol) was weighed. Hydrogen chloride/ethyl acetate (15 mL) was added to react at 18° C. for 1 h. The reaction solution was concentrated under reduced pressure to obtain the hydrochloride of compound 30-4. MS m/z=249.2 $[M+H]^+$.

Step 4: Synthesis of Compound 30-5

Compound 4-11B (0.2 g, 254.53 mol) was weighed and dissolved with DMF (5 mL). The hydrochloride of compound 30-4 (145.19 mg) was added. Then DIPEA (98.69 mg, 763.60 mol) was added to react at 100° C. for 1 h. The reaction solution was cooled to room temperature. Water (10 mL) was added. The reaction solution was extracted with ethyl acetate (5 mL×3) and separated. The organic phases were mixed, extracted with a saturated table salt solution (5 mL×2), separated, dried with anhydrous sodium sulfate, filtered, and concentrated under reduced pressure to obtain compound 30-5. MS m/z=884.3 $[M+H]^+$.

Step 5: Synthesis of Intermediate 30-6

Compound 30-5 (0.214 g, 241.97 mol) was weighed and dissolved with DCM (10 mL). m-CPBA (49.13 mg, 241.97 mol, 85% purity) was added to react at room temperature of 18° C. for 1 h. The reaction solution was quenched with water (10 mL) and extracted with dichloromethane (10 mL×3). The organic phases were mixed, washed with a saturated table salt solution (20 mL), dried with anhydrous sodium sulfate, and concentrated to obtain compound 30-6, MS m/z=900.3 $[M+H]^+$.

Step 6: Synthesis of Intermediate 30-7

Compound 5-2 (71.47 mg, 466.45 mol) was dissolved with anhydrous tetrahydrofuran (5 mL). Sodium tert-butoxide (44.83 mg, 466.45 mol) was added at 0° C. The reaction system reacted at 0° C. for 1 h. 5 mL of a tetrahydrofuran solution of compound 30-6 (0.21 g, 233.23 mol) was added to continue to react for 1 h. The reaction solution was quenched with 5 mL of water and extracted with ethyl acetate (5 mL×3. The organic phase was washed with a saturated table salt solution (10 mL), dried with anhydrous sodium sulfate, filtered, concentrated under reduced pressure, and purified by column chromatography (dichloromethane:methanol=10:1), to obtain compound 30-7, MS m/z=989.4 $[M+H]^+$.

Step 7: Synthesis of Hydrochloride of Compound 30

Compound 30-7 (0.22 g, 222.33 mol) was dissolved with dichloromethane (15 mL). Trifluoroacetic acid (5.65 g, 49.53 mmol) was added at 20° C. to react at 20° C. for 1 h. The reaction solution was concentrated under reduced pressure to obtain the crude product. The crude product was separated by HPLC (chromatographic column: Xtimate C18 150×40 mm×5 m; mobile phase: [water (0.05% HCl)-acetonitrile]; acetonitrile %: 17-47%, 14 min), to obtain the hydrochloride of compound 30. MS m/z=749.3 $[M+H]^+$. $^1H$ NMR (400 MHz, MeOD) δ=7.01-6.91 (m, 1H), 5.39-5.29 (m, 2H), 5.26-5.19 (m, 1H), 5.16-5.00 (m, 4H), 4.76-4.69 (m, 1H), 4.59-4.44 (m, 2H), 4.41-4.21 (m, 2H), 4.17-4.06 (m, 1H), 4.01-3.85 (m, 2H), 3.84-3.73 (m, 1H), 3.30-3.20 (m, 2H), 3.09-2.95 (m, 2H), 2.86-2.72 (m, 1H), 2.56-2.10 (m, 6H), 2.08-1.97 (m, 3H).

Embodiment 31

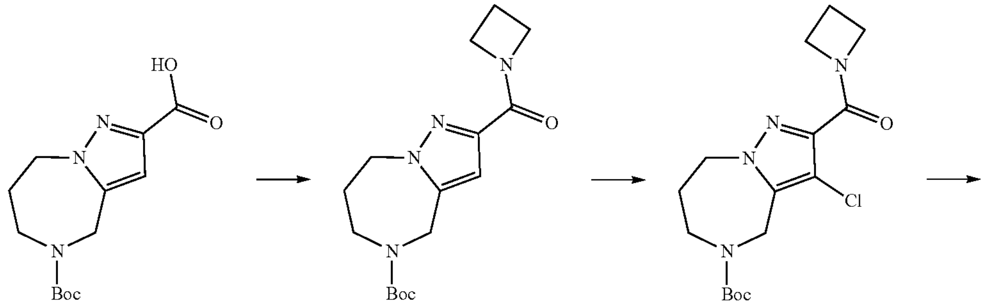

30-1 31-2 31-3

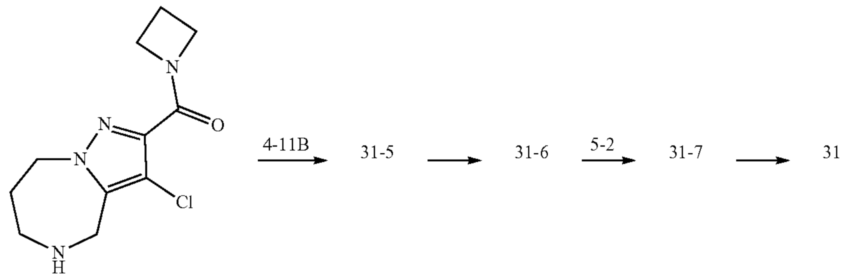

31-4

-continued
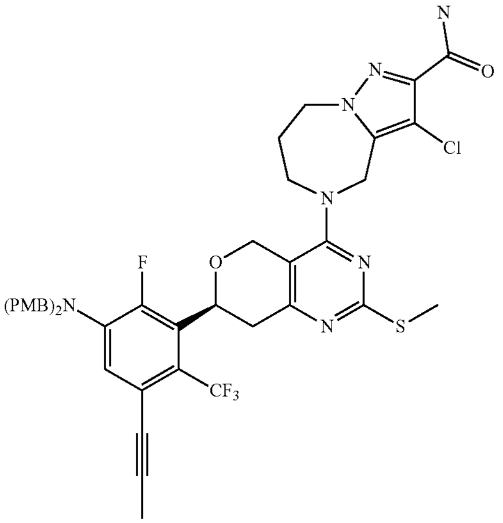
or
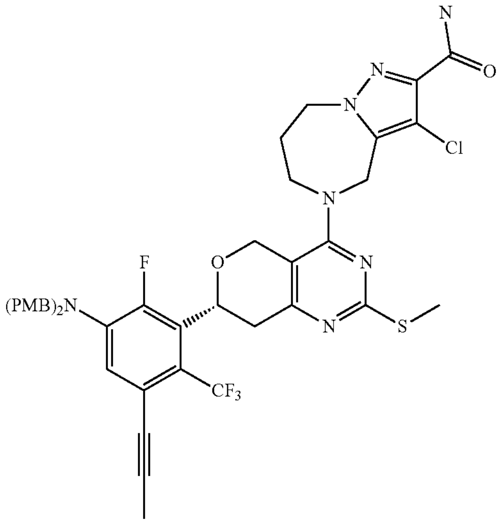
31-5
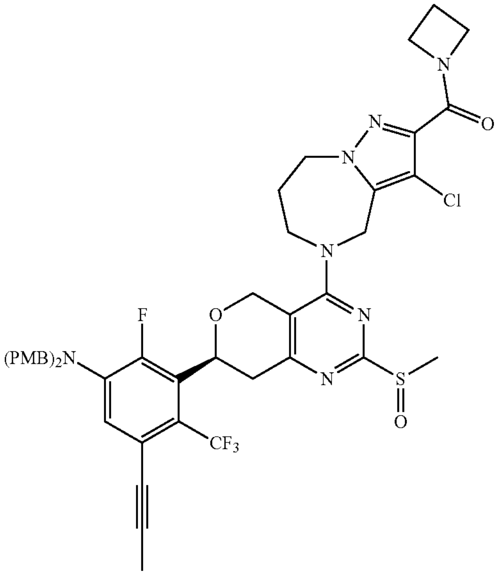
or
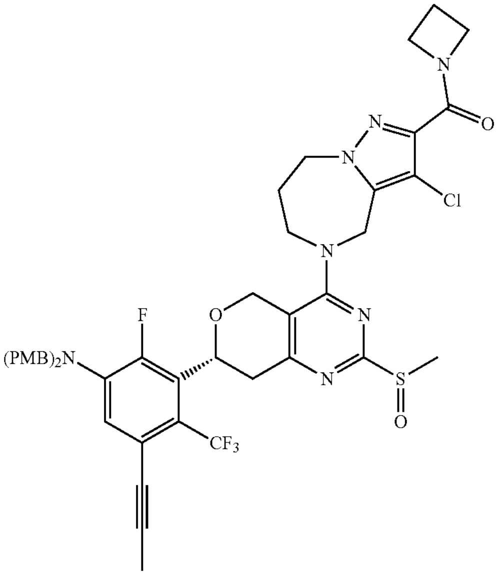
31-6

-continued
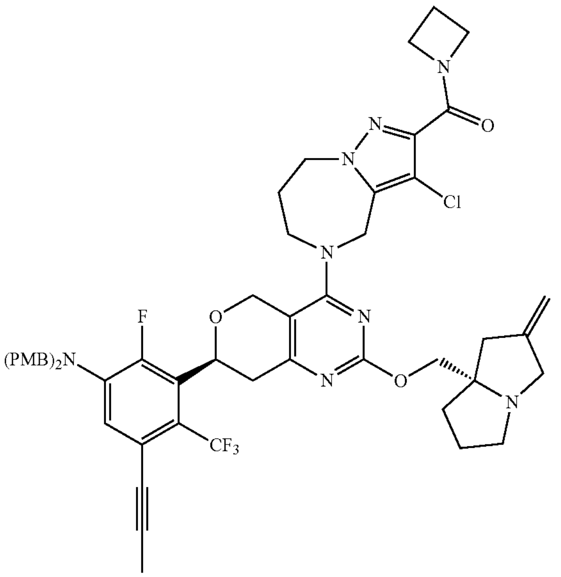
or
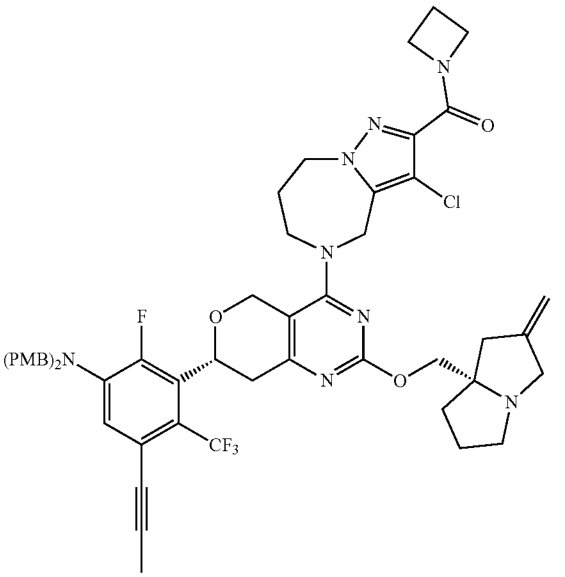
or
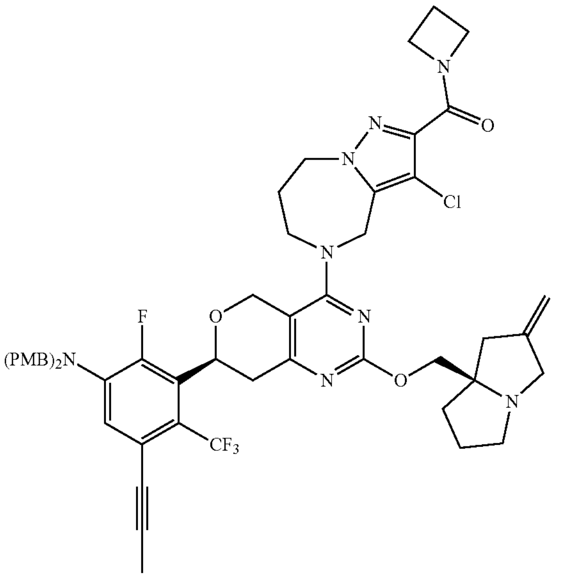
or
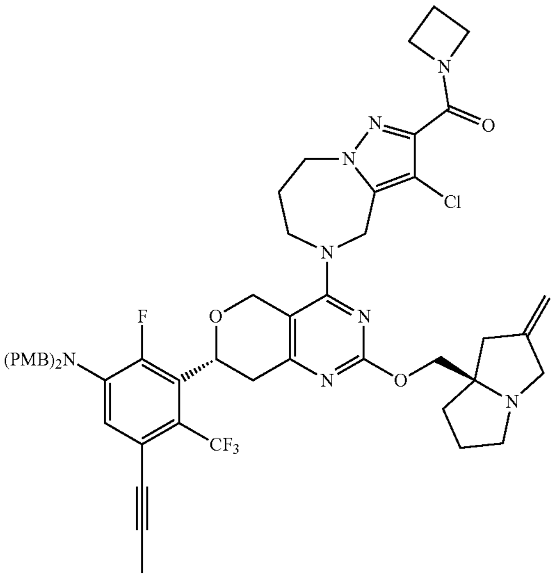
31-7

-continued

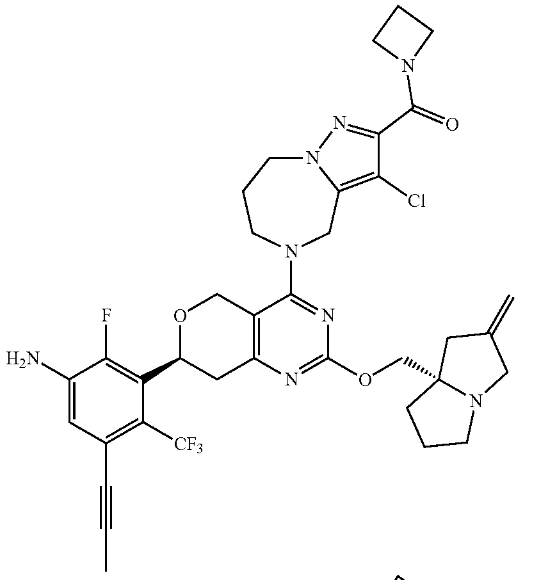

or

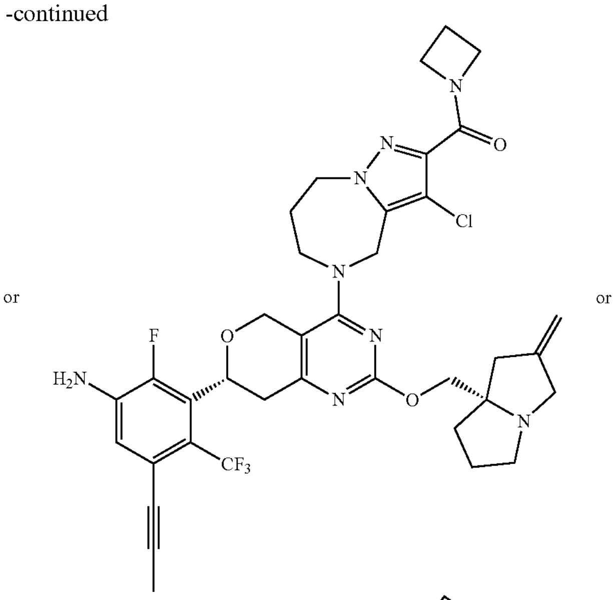

or

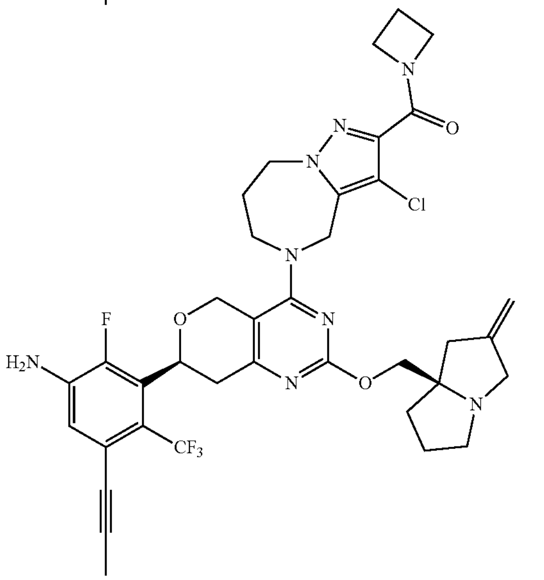

or

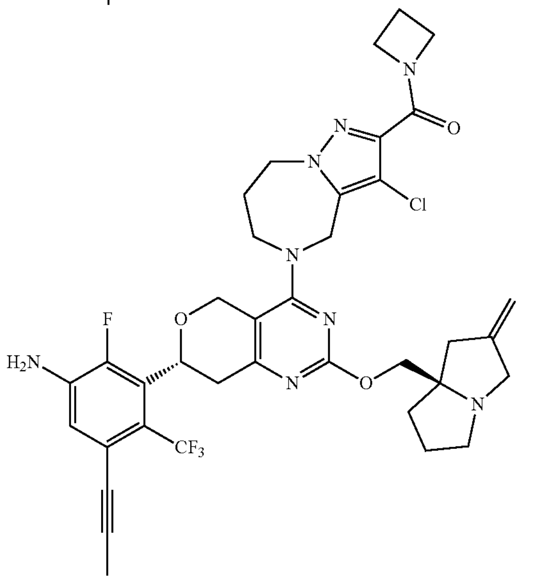

31

Step 1: Synthesis of Intermediate 31-2

Compound 30-1 (0.25 g, 844.27 μmol) was weighed and dissolved with DMF (5 ml). HATU (417.32 mg, 1.10 mmol), DIPEA (436.46 mg, 3.38 mmol, 588.22 μL) and azetidine hydrochloride (236.96 mg, 2.53 mmol) were added to the solution to react at room temperature of 18° C. for 2 h. The reaction solution was quenched with 5 mL of water, extracted with ethyl acetate (10 mL×3), washed with 10 mL of a saturated table salt solution, dried with anhydrous sodium sulfate, and concentrated under reduced pressure to obtain compound 31-2. MS m/z=321.2 $[M+H]^+$.

Step 2: Synthesis of Compound 31-3

Compound 31-2 (0.27 g, 800.60 mol) was weighed and dissolved with DMF (3 mL). NCS (160.36 mg, 1.20 mmol) was added to the reaction system to react at 55° C. for 2 h. The reaction solution was quenched with 5 mL of water, extracted with ethyl acetate (10 mL×3), washed with 10 mL of a saturated table salt solution, dried with anhydrous sodium sulfate, concentrated under reduced pressure, and purified by column chromatography (petroleum ether:ethyl acetate=1:1), to obtain compound 31-3. MS m/z=355.2 $[M+H]^+$.

Step 3: Synthesis of Trifluoroacetate of Compound 31-4

Compound 31-3 (0.06 g, 160.64 mol) was weighed. Trifluoroacetic acid (18.32 mg, 160.64 mol) was added to react at 18° C. for 1 h. The reaction solution was concentrated under reduced pressure to obtain the trifluoroacetate of compound 31-4. MS m/z=255.1 $[M+H]^+$.

Step 4: Synthesis of Compound 31-5

Compound 4-11B (0.05 g, 63.63 mol) was weighed and dissolved with DMF (5 mL). The trifluoroacetate of compound 31-4 (28.16 mg) was added. Then DIPEA (24.67 mg, 190.90 mol) was added to react at 100° C. for 1 h. The reaction solution was cooled to room temperature. Water (10 mL) was added. The reaction solution was extracted with ethyl acetate (5 mL×3) and separated. The organic phases were mixed, extracted with a saturated table salt solution (5 mL×2), separated, dried with anhydrous sodium sulfate, filtered, and concentrated under reduced pressure to obtain compound 31-5. MS m/z=890.3 [M+H]$^+$.

Step 5: Synthesis of Intermediate 31-6

Compound 31-5 (0.278 g, 312.22 mol) was weighed and dissolved with DCM (10 mL). m-CPBA (63.39 mg, 312.23 mol, 85% purity) was added to react at room temperature of 18° C. for 1 h. The reaction solution was quenched with water (10 mL) and extracted with dichloromethane (10 mL×3). The organic phases were mixed, washed with a saturated table salt solution (20 mL), dried with anhydrous sodium sulfate, and concentrated to obtain compound 31-6, MS m/z=906.3 [M+H]$^+$.

Step 6: Synthesis of Intermediate 31-7

Compound 5-2 (81.14 mg, 529.58 mol) was dissolved with anhydrous tetrahydrofuran (5 mL). Sodium tert-butoxide (50.89 mg, 529.58 mol) was added at 0° C. The reaction system reacted at 0° C. for 1 h. 5 mL of a tetrahydrofuran solution of compound 31-6 (0.24 g, 264.79 mol) was added to continue to react for 1 h. The reaction solution was quenched with 5 mL of water and extracted with ethyl acetate (5 mL×3. The organic phase was washed with a saturated table salt solution (10 mL), dried with anhydrous sodium sulfate, filtered, and concentrated under reduced pressure. and purified by column chromatography (dichloromethane:methanol=10:1), to obtain compound 31-7, MS m/z=995.4 [M+H]$^+$.

Step 7: Synthesis of Hydrochloride of Compound 31

Compound 31-7 (0.05 g, 50.23 mol) was dissolved with dichloromethane (15 mL). Trifluoroacetic acid (157.08 mg, 1.38 mmol) was added at 20° C. to react at 20° C. for 1 h. The reaction solution was concentrated under reduced pressure to obtain the crude product. The crude product was separated by HPLC (chromatographic column: Phenomenex C18 80×40 mm×3 m; mobile phase: [water (0.05% ammonia+10 mM ammonium bicarbonate)-acetonitrile]; acetonitrile %: 57-87%, 8 min), to obtain the hydrochloride of compound 31. MS m/z=755.2 [M+H]$^+$.

Embodiment 32

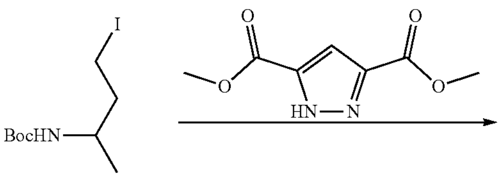

32-1

-continued

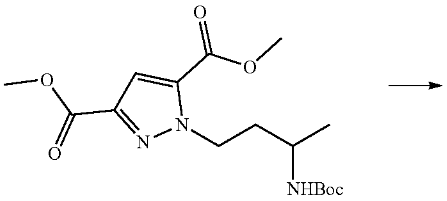

32-2

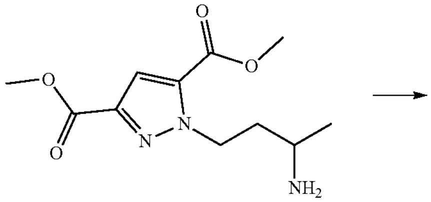

32-3

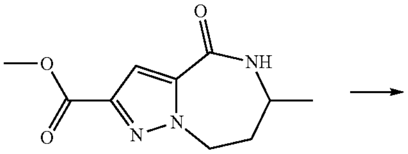

32-4

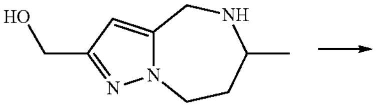

32-5

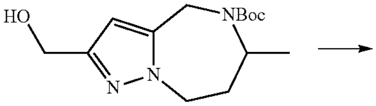

32-6

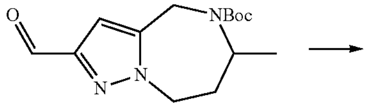

32-7

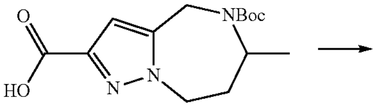

32-8

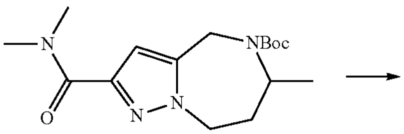

32-9

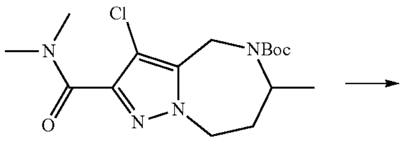

32-10

-continued
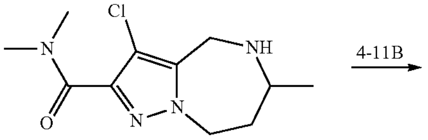
32-11
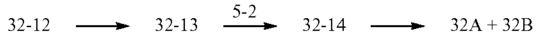
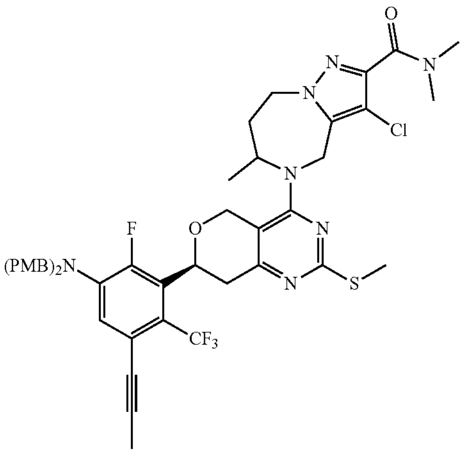
or
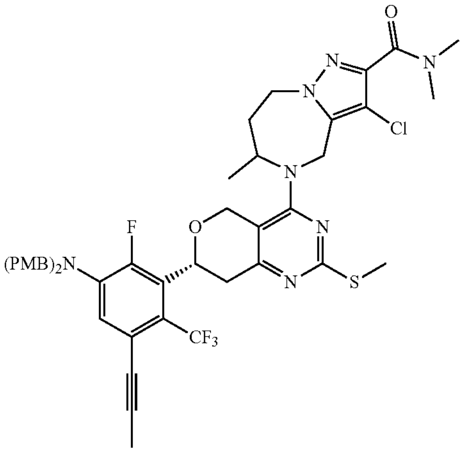
32-12
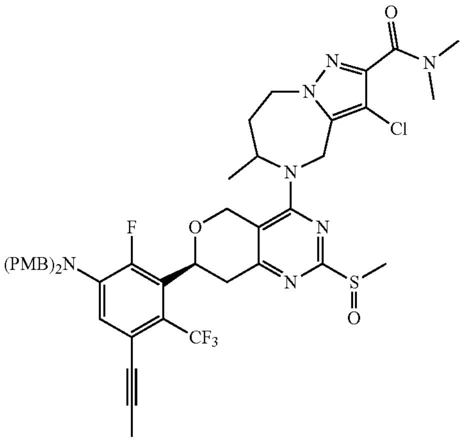
or
-continued
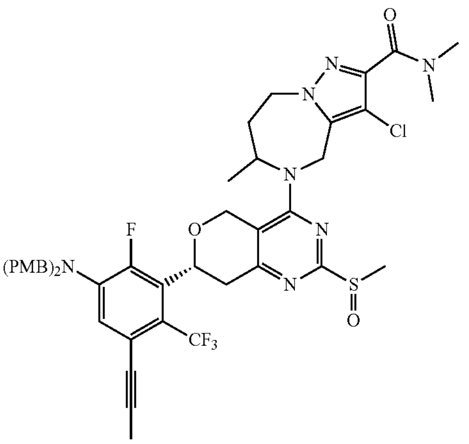
32-13
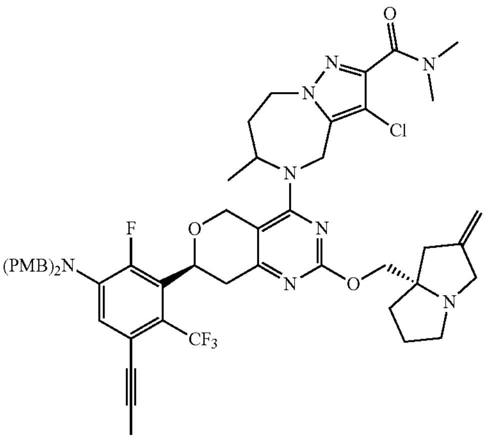
or
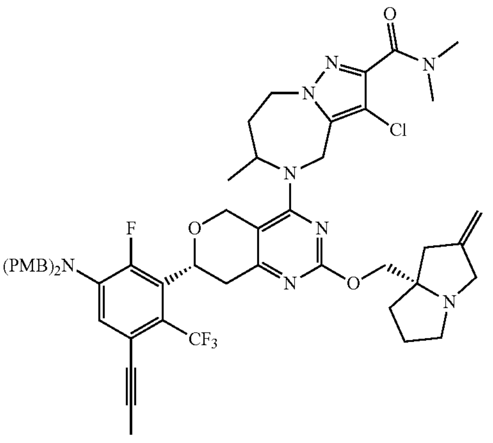
or -continued
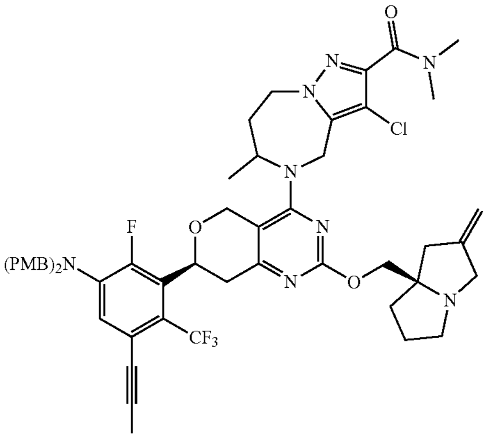
or
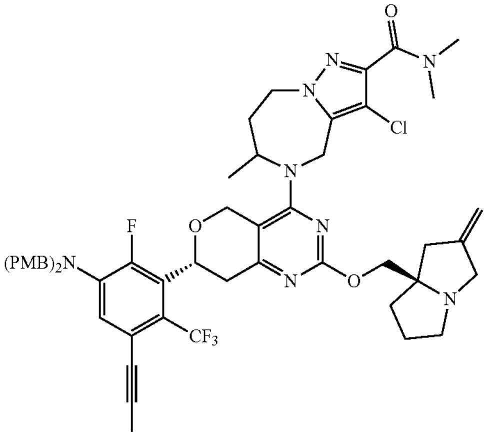
32-14
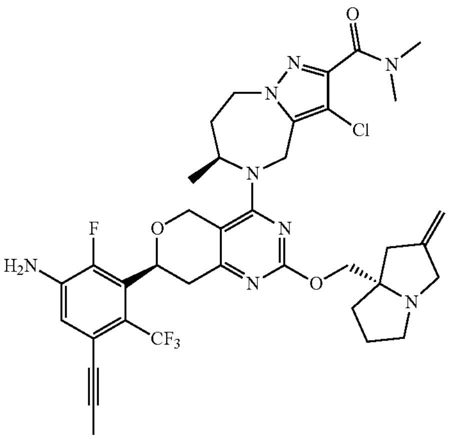
or
-continued
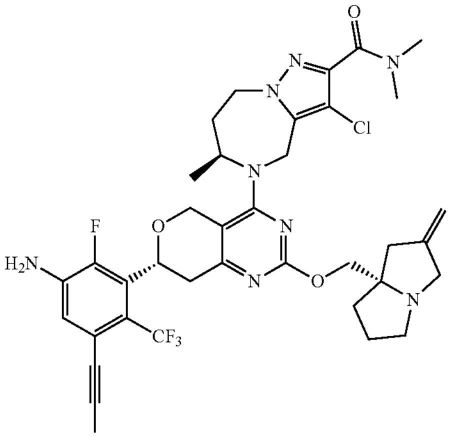
or
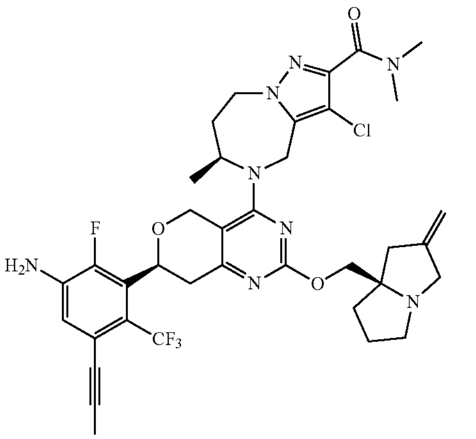
or
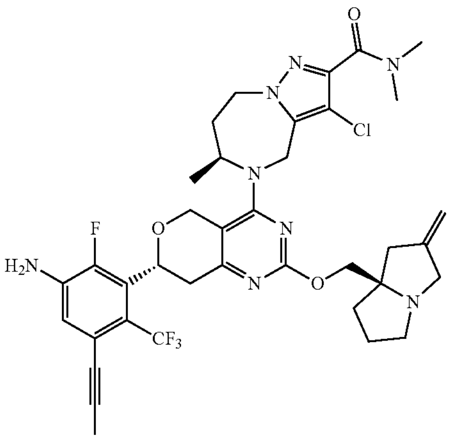
32A or 32B -continued

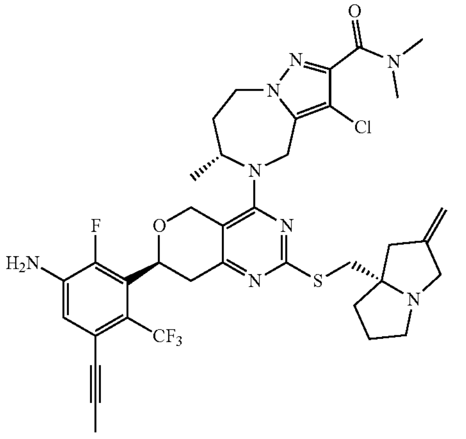

or

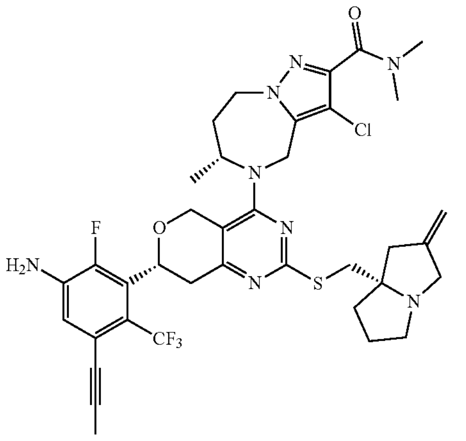

or

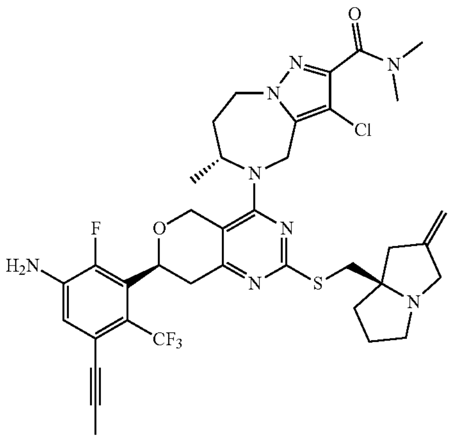

or

-continued

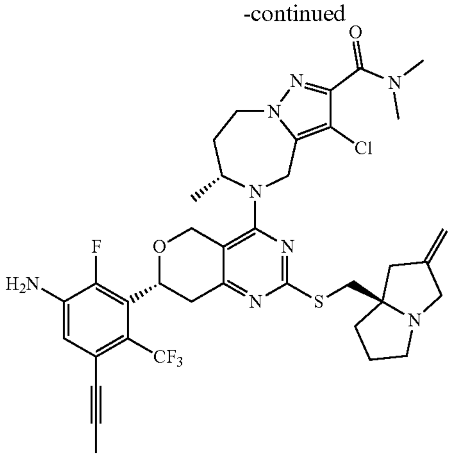

32B or 32A

Step 1: Synthesis of Intermediate 32-2

Compound 3,5-methyldicarboxylate pyrazole (6.5 g, 35.30 mmol) and compound 32-1 (10.56 g, 35.30 mmol) were added to N,N-dimethylformamide (60 mL). Then potassium carbonate (9.76 g, 70.59 mmol) was added. The reaction solution was heated to 100° C. and stirred to react for 2 h under nitrogen protection. The reaction solution was concentrated under reduced pressure to obtain the crude product. 500 mL of ethyl acetate was added to the crude product, stirred for 5 min, filtered, and concentrated under reduced pressure to obtain the crude product. The crude product was purified by column chromatography (petroleum ether:ethyl acetate=1:1) to obtain compound 32-2. HNMR: (400 MHz, $CDCl_3$) δ: 7.34 (m, 1H), 4.69 (t, J=6.8 Hz, 2H), 4.49 (br s, 1H), 3.94 (s, 3H), 3.90 (s, 3H), 3.83-3.64 (m, 1H), 2.12-2.05 (m, 1H), 1.99-1.83 (m, 1H), 1.44 (s, 9H), 1.17 (d, J=6.4 Hz, 3H).

Step 2: Synthesis of Intermediate 32-3

Compound 32-2 (11.5 g, 32.36 mmol) was dissolved with DCM (10 mL). Then hydrogen chloride/ethyl acetate (4 M, 40.45 mL) was added. The reaction solution was stirred to react at 15° C. for 4 h under nitrogen protection. The reaction solution was concentrated under reduced pressure to obtain the residue. Water (30 mL) and dichloromethane (50 mL) were added to the residue. Then the pH was adjusted to 9 with a 2 M sodium hydroxide solution. The organic phase was separated. The aqueous phase was extracted with dichloromethane (50 mL). The organic phases were mixed, dried with anhydrous sodium sulfate, filtered, and concentrated under reduced pressure to obtain compound 32-3.

Step 3: Synthesis of Intermediate 32-4

Compound 32-3 (8.3 g, 32.51 mmol) was dissolved with anhydrous methanol (50 mL). Then sodium methoxide (3.51 g, 65.03 mmol) was added and stirred to react at 60° C. for 15 h under nitrogen protection. The reaction solution was cooled to room temperature and filtered. Solids were collected and dried in vacuum for 0.5 h to obtain compound 32-4. HNMR: (400 MHz, $CDCl_3$) δ: 7.34 (s, 1H), 6.10 (br s, 1H), 4.65 (ddd, J=3.6, 6.8, 14.3 Hz, 1H), 4.49 (ddd, J=5.9, 10.3, 14.3 Hz, 1H), 3.95 (s, 3H), 3.68-3.52 (m, 1H), 2.46-2.33 (m, 1H), 2.09-1.95 (m, 1H), 1.37 (d, J=6.4 Hz, 3H).

Step 4: Synthesis of Intermediate 32-5

Compound 32-4 (4.05 g, 18.14 mmol) was dissolved with tetrahydrofuran (80 mL). Aluminum lithium hydrogen (2.75 g, 72.57 mmol) was added slowly in batches. After that, the reaction solution was stirred to react at 20° C. for 2 h, and then heated slowly to 60° C. and stirred to react for 15 h. The reaction solution was cooled to 0° C. Then 2.8 mL of water and 2.8 mL of a 15% sodium hydroxide solution were slowly added to quench the reaction. The reaction solution was stirred for 10 min, filtered with diatomite, and concentrated under reduced pressure to obtain compound 32-5. (400 MHz, $CDCl_3$) δ: 6.07 (s, 1H), 4.61 (s, 2H), 4.53-4.40 (m, 1H), 4.25-4.05 (m, 2H), 3.72 (d, J=15.6 Hz, 1H), 3.10-2.96 (m, 1H), 1.98-1.90 (m, 1H), 1.57-1.45 (m, 1H), 1.20 (d, J=6.5 Hz, 3H).

Step 5: Synthesis of Intermediate 32-6

Compound 32-5 (2.80 g, 15.45 mmol) was dissolved with dichloromethane (30 mL). Then tert-butoxycarbonyl anhydride (3.37 g, 15.45 mmol, 3.55 mL) was added. The reaction solution was stirred to react at 15° C. for 15 h under nitrogen protection. The reaction solution was concentrated under reduced pressure. Methanol (20 mL) and water (20 mL) were added to the residue. Then potassium carbonate (4.27 g, 30.90 mmol) was added. The resulting system was heated to 80° C. and stirred to react for 8 h. The reaction solution was concentrated under reduced pressure and then extracted with dichloromethane (30 mL×3). The organic phases were mixed, dried with anhydrous sodium sulfate, filtered, and concentrated under reduced pressure to obtain crude compound 32-6. 1H NMR: (400 MHz, $CDCl_3$) δ: 6.07 (br s, 1H), 5.12-4.67 (m, 1H), 4.60 (s, 2H), 4.46-4.34 (m, 1H), 4.17-3.89 (m, 2H), 2.45 (br s, 1H), 2.26-2.12 (m, 1H), 2.04-1.79 (m, 1H), 1.50-1.30 (m, 9H), 1.24 (d, J=5.8 Hz, 3H).

Step 6: Synthesis of Intermediate 32-7

Compound 32-6 (4.3 g, 15.28 mmol) was dissolved with dichloromethane (100 mL). The resulting solution was cooled to 0° C. Then Dess-Martin periodinane (6.48 g, 15.28 mmol) was slowly added. After that, the ice bath was removed. The reaction solution was heated to room temperature of 20° C. and stirred to react for 3 h. The reaction solution was quenched with 30 mL of a saturated sodium bicarbonate solution. The organic phase was separated. The aqueous phase was extracted with dichloromethane (30 mL×2). The organic phases were mixed and concentrated under reduced pressure to obtain the crude product. The crude product was purified by column chromatography (petroleum ether:ethyl acetate=2:1) to obtain compound 32-7. $^1H$ NMR: (400 MHz, $CDCl_3$) δ: 9.92-9.85 (m, 1H), 6.62 (br s, 1H), 5.17-4.33 (m, 3H), 4.24 (dd, J=10.1, 14.1 Hz, 1H), 4.02 (br d, J=16.6 Hz, 1H), 2.33-2.19 (m, 1H), 2.03-1.89 (m, 1H), 1.39 (br s, 9H), 1.30-1.26 (m, 3H).

Step 7: Synthesis of Intermediate 32-8

Compound 32-7 (2.0 g, 7.16 mmol) was dissolved with dimethyl sulfoxide (25 mL). Then a solution of potassium dihydrogen phosphate (2.53 g, 18.62 mmol) in water (5 mL) was added. Then a solution of sodium chlorite (1.36 g, 15.04 mmol) in water (5 mL) was added dropwise and stirred to react at 20° C. for 2 h. The reaction solution was diluted with 200 mL of ethyl acetate and then washed with water (40 mL×2) and 40 mL of a saturated table salt solution. The organic phase was dried with anhydrous sodium sulfate, filtered, and concentrated under reduced pressure to obtain compound 32-8. 1H NMR: (400 MHz, $CDCl_3$) δ: 6.69 (br s, 1H), 5.18-4.34 (m, 3H), 4.24 (br dd, J=10.3, 14.1 Hz, 1H), 4.03 (br d, J=16.6 Hz, 1H), 2.32-2.18 (m, 1H), 2.00 (br s, 1H), 1.40 (br s, 9H), 1.27 (d, J=6.8 Hz, 3H).

Step 8: Synthesis of Intermediate 32-9

Compound 32-8 (1.0 g, 3.39 mmol) were dissolved with tetrahydrofuran (15 mL). Then carbonyl diimidazole (823.56 mg, 5.08 mmol) was added and stirred to react at 10° C. for 1 h under nitrogen protection. Then, a dimethylamine/tetrahydrofuran solution (2 M, 5.08 mL) was added. The resulting reaction solution was stirred to continue to react for 1 h under nitrogen protection. The reaction solution was concentrated under reduced pressure to obtain the crude product. The crude product was dissolved with ethyl acetate (50 mL) and washed with water (10 mL×3). The organic phase was dried, filtered, and concentrated under reduced pressure to obtain crude compound 32-9. $^1H$ NMR: (400 MHz, CDCl3) δ: 6.46 (s, 1H), 5.18-4.30 (m, 3H), 4.22-4.10 (m, 1H), 4.00 (d, J=16.8 Hz, 1H), 3.32 (br s, 3H), 3.08 (s, 3H), 2.29-2.16 (m, 1H), 2.03-1.88 (m, 1H), 1.50-1.31 (m, 9H), 1.26 (d, J=6.8 Hz, 3H).

Step 9: Synthesis of Intermediate 32-10

Compound 32-9 (1.03 g, 3.19 mmol) was dissolved with N, N-dimethylformamide (10 mL). Then N-chlorosuccinimide (853.21 mg, 6.39 mmol) was added. The resulting reaction solution was stirred to react at 55° C. for 3 h under nitrogen protection. The reaction solution was concentrated under reduced pressure to obtain the crude product. The crude product was purified by column chromatography (petroleum ether:ethyl acetate=2:1) to obtain compound 32-10, MS m/z=357.0 $[M+H]^+$.

Step 10: Synthesis of Hydrochloride of Intermediates 32-11

Compound 32-10 (300 mg, 622.12 mol) was dissolved with dichloromethane (0.5 mL). Then a hydrogen chloride/ethyl acetate solution (4 M, 1.56 mL) was added. The resulting reaction solution was stirred to react at 20° C. for 0.5 h under nitrogen protection. The reaction solution was concentrated under reduced pressure to obtain the hydrochloride of crude compound 32-11. MS m/z=257.0 $[M+H]^+$.

Step 11: Synthesis of Intermediate 32-12

Compound 4-11B (200 mg, 254.53 mol) was weighed and dissolved with DMF (1.5 mL). The hydrochloride of compound 32-11 (217.00 mg) was added. Then DIPEA (164.48 mg, 1.27 mmol) was added to react at 100° C. for 1 h. The reaction solution was cooled to room temperature. Water (10 mL) was added. The reaction solution was extracted with ethyl acetate (5 mL×3) and separated. The organic phases were mixed, extracted with a saturated table salt solution (5 mL×2), separated, dried with anhydrous sodium sulfate, filtered, and concentrated under reduced pressure. The crude product was purified by column chromatography (petroleum ether:ethyl acetate=2:1) to obtain compound 32-12. MS m/z=892.4 $[M+H]^+$.

Step 12: Synthesis of Intermediate 32-13

Compound 32-12 (58 mg, 64.99 mol) was weighed and dissolved with DCM (1 mL). m-CPBA (13.19 mg, 64.99 mol, 85% purity) was added to react at room temperature of 18° C. for 1 h. The reaction solution was concentrated under reduced pressure to obtain compound 32-13, MS m/z=908.3 $[M+H]^+$.

Step 13: Synthesis of Intermediate 32-14

Compound 5-2 (39.13 mg, 255.39 mol) was dissolved with anhydrous tetrahydrofuran (2 mL). Sodium tert-butoxide (24.54 mg, 255.39 mol) was added at 0° C. The reaction system reacted at 0° C. for 1 h. Compound 32-13 (58 mg, 63.85 mol) was added to continue to react for 1 h. The reaction solution was quenched with 0.5 mL of water, dried with anhydrous sodium sulfate, filtered, concentrated under reduced pressure, and purified by column chromatography (dichloromethane:methanol=10:1), to obtain compound 32-14, MS m/z=997.4 $[M+H]^+$.

Step 14: Synthesis of Hydrochlorides of Compounds 32A and 32B

Compound 32-14 (36 mg, 36.09 mol) was dissolved with trifluoroacetic acid (0.5 mL) to react at 20° C. for 2 h. The reaction solution was concentrated under reduced pressure to obtain the crude product. The crude product was separated by HPLC (chromatographic column: Xtimate C18 150×40 mm×5 m; mobile phase: [water (0.05% HCl)-acetonitrile]; acetonitrile %: 30-60%), to obtain the hydrochlorides of compounds 32A and 32B. Analysis liquid phase: chromatographic column: ChromCore 120 C18 3 μm, 3.0×30 mm; mobile phase: [Water (0.04% trifluoroacetic acid)-acetonitrile (0.02% trifluoroacetic acid)]; acetonitrile (0.02% trifluoroacetic acid) %: 10%-80%, 7 min_220&254 nm), retention time: 32A (Rt=3.484 min), MS m/z=757.1 $[M+H]^+$, 32B (Rt=3.606 min), MS m/z=757.2 $[M+H]^+$.

Biological Test Data

Experimental Example 1. Antiproliferative Effects of Compounds in Tumor Cell Line AsPC-1

Research Objective

The experiment studies the antiproliferative effects of compounds by detecting the effects of the compounds on in vitro cell activity of the $KRAS^{G12D}$ mutant tumor cell line AsPC-1.

Experimental Materials

The cell line was AsPC-1. The tumor type was pancreatic cancer. The cell line was cultured by adherent growth using RPMI 1640+10% FBS.

Ultra Low Cluster-96-well plate (Corning-7007)

Greiner CELLSTAR 96-well plate (#655090)

Promega CellTiter-Glo 3D luminescence cell activity assay kit (Promega-G9683)

2104-10 EnVision reader, PerkinElmer

RPMI 1640, DMEM, PBS (phosphate buffer), FBS (fetal bovine serum), Antibiotic-antimycotic, L-glutamine, and DMSO (dimethyl sulfoxide)

Experimental Methods and Steps

Cell Culture

The tumor cell line was incubated in an incubator at 37° C., 5% $CO_2$ under the culture conditions shown by the culture method. Regular passage was conducted, and the cells in the logarithmic growth phase were taken for seeding.

Cell Seeding

The cells were stained with trypan blue and the number of living cells was counted.

The cell concentration was adjusted to a suitable concentration.

The cell line was AsPC-1, with a density of 7,000 cells (per well).

A cell suspension is added at a density of 135 μL per well to a ULA culture plate, and the same volume of cell-free medium is added to a blank control plate.

The ULA culture plate was centrifuged at room temperature for 10 min at 1,000 rpm immediately after seeding. Caution: Always handle follow-up actions with care after centrifuging to avoid unnecessary shaking.

The culture plate was incubated overnight in an incubator at 37° C., 5% $CO_2$, and 100% relative humidity.

Preparation of 10× Compound Working Fluid and Treatment of Cells with Compounds (Day 1)

After a 10× compound working fluid (DMSO 10× working fluid) was prepared, 15 μL of the 10× compound working fluid was added to a ULA culture plate, and 15 μL of a DMSO-cell medium mixture was added to a vehicle control and the blank control.

The 96-well cell plate was put back into the incubator and incubated for 120 h.

Sphere formation of the cells was observed daily until the end of the experiment.

CellTiter-Glo Luminescence Cell Viability Assay (Day 5)

The following steps were performed according to the instructions of the Promega CellTiter-Glo 3D luminescence cell activity assay kit (Promega #G9683).

A CellTiter-Glo 3D reagent is added at a density of 150 μL (equal to the volume of the cell medium per well) per well. The cell plate was wrapped in aluminum foil paper to avoid light.

The culture plate was shaken on an orbital shaker for 5 min.

The mixture was carefully blown up and down 10 times with a pipette to mix the mixture in the wells. It is necessary to ensure that cell spheres are sufficiently separated before proceeding to the next step.

The solution in the ULA plate was then transferred into a black plate (#655090) and placed at room temperature for 25 min to stabilize the luminous signals.

The luminous signals were detected on a 2104 EnVision reader.

Data Analysis

The inhibition rate (IR) of the detected compound was calculated using the following formula: IR (%)=(1−(RLU compound−RLU blank control)/(RLU vehicle control−RLU blank control))×100%. The inhibition rates of compounds with different concentrations were calculated in Excel, and then a diagram of inhibition curves was made and related parameters were calculated using GraphPad Prism software, including the minimum inhibition rate, maximum inhibition rate, and $IC_{50}$.

Experimental Results

The results are shown in Table 1.

TABLE 1

IC$_{50}$ values of compounds in inhibiting AsPC-1 cells

| Compound No. | KRAS$^{G12D}$ AsPC-1 IC$_{50}$ (nM) |
|---|---|
| Hydrochloride of compound 3 | 69.3 |
| Compound 4A | 6.9 |
| Compound 5A | 6.1 |
| Compound 6A | 2.99 |

The experimental conclusion is that the compounds of the present invention have excellent antiproliferative effects on KRAS$^{G12D}$ mutant AsPC-1 cells.

Experimental Example 2. AsPC-1 Cell Proliferation Assay

1. Objective

The compounds which can effectively inhibit the proliferation of KRAS$^{G12D}$ mutant AsPC-1 cells were screened out by a 3D-CTG method.

2. Experimental Materials

ASPC-1 cells from ATCC; RPMI-1640 medium from ATCC; fetal bovine serum from Ausgenex; CellTiter-Glo® 3D assay kit (3D-CTG) from Promega; and CellCarrier-96 Spheroid ULA/CS from PE.

3. Experimental Method

1) ASPC-1 cells were seeded in a transparent 96-well cell culture plate, at a density of 195 μL of cell suspension per well containing 2,000 cells.

2) The compound to be tested was diluted with 100% DMSO to 10 mM as the 1st concentration and then diluted 5 times by a pipette to the 8th concentration, i.e. from 10 mM to 0.13 M. 2 μL of the gradient-diluted compound was added to 48 μL of cell medium for secondary dilution. After mixed, 5 μL of the secondary-diluted compound was added to the corresponding wells of the cell plate containing 195 μL of cells. The cell plate was put into a carbon dioxide incubator and incubated for 7 days. The concentration of the compound at this time was 10 μM to 0.128 nM, with the DMSO concentration of 0.1%.

3) After incubation, 100 μL of cell supernatant was discarded and 3D-CTG was added at a density of 60 μL per well. The cells were shaken and incubated at room temperature and 200 rpm for 20 min, and incubated in an incubator at room temperature for 1 h.

4) 100 μL of supernatant was pipetted from the well plate and transferred to a 96-well black plate with a clear bottom, and the luminescence was read in the BMG.

4. Data Analysis

The original data was converted into the inhibition rate using equation Inhibition %=(Ave_H−Sample)/(Ave_H−Ave_L), and the IC$_{50}$ value was obtained by curve fitting through four parameters (log(inhibitor) vs. response—Variable slope mode in GraphPad Prism).

H well: Reading of DM well

L well: Reading of Medium

5. Experimental Results

The results are shown in Table 2.

TABLE 2

IC$_{50}$ values of compounds in inhibiting AsPC-1 cells

| Compound No. | KRAS$^{G12D}$ AsPC-1 IC$_{50}$ (nM) |
|---|---|
| Compound 5A | 11.84 |
| Hydrochloride of compound 11A | 18.5 |
| Compound 14 | 1.78 |
| Hydrochloride of compound 15 | 129.4 |
| Compound 16 | 113.2 |
| Compound 17 | 113 |
| Compound 19 | 3.99 |
| Compound 20 | 1.75 |
| Hydrochloride of compound 21 | 1.74 |
| Hydrochloride of compound 22 | 2.16 |
| Hydrochloride of compound 23 | 34.3 |
| Compound 25 | 10.78 |
| Compound 26 | 5.64 |
| Hydrochloride of compound 27 | 11.66 |
| Hydrochloride of compound 28 | 5.04 |
| Hydrochloride of compound 30 | 3.54 |
| Hydrochloride of compound 31 | 5.79 |

The experimental conclusion is that the compounds of the present invention have excellent antiproliferative effects on KRAS$^{G12D}$ mutant AsPC-1 cells.

Experimental Example 3. H727 Cell Proliferation Assay

1. Objective

The compounds which can effectively inhibit the proliferation of KRAS$^{G12V}$ mutant H727 cells were screened out by a 3D-CTG method.

2. Experimental Materials

H727 cells from ATCC; RPMI-1640 medium from ATCC; fetal bovine serum from Ausgenex; CellTiter-Glo® 3D assay kit (3D-CTG) from Promega; and CellCarrier-96 Spheroid ULA/CS from PE.

3. Experimental Method

5) The aforementioned cells were seeded in a transparent 96-well cell culture plate, at a density of 195 μL of cell suspension per well containing 2,000 cells.

6) The compound to be tested was diluted with 100% DMSO to 10 mM as the 1st concentration and then diluted 5 times by a pipette to the 8th concentration, i.e. from 10 mM to 0.13 μM. 2 μL of the gradient-diluted compound was added to 48 μL of cell medium for secondary dilution. After mixed, 5 μL of the secondary-diluted compound was added to the corresponding wells of the cell plate containing 195 μL of cells. The cell plate was put into a carbon dioxide incubator and incubated for 7 days. The concentration of the compound at this time was 10 M to 0.128 nM, with the DMSO concentration of 0.1%.

7) After incubation, 100 μL of cell supernatant was discarded and 3D-CTG was added at a density of 60 μL per well. The cells were shaken and incubated at room temperature and 200 rpm for 20 min, and incubated in an incubator at room temperature for 1 h. 8) 100 μL of supernatant was pipetted from the well plate and transferred to a 96-well black plate with a clear bottom, and the luminescence was read in the BMG.

4. Data Analysis

The original data was converted into the inhibition rate using equation Inhibition %=(Ave_H−Sample)/(Ave_H−Ave_L), and the IC50 value was obtained by curve fitting through four parameters (log(inhibitor) vs. response—Variable slope mode in GraphPad Prism).

H well: Reading of DMSO well

L well: Reading of Medium

5. Experimental Results

The results are shown in Table 3.

TABLE 3

| $IC_{50}$ values of compounds in inhibiting H727 cells | |
|---|---|
| Compound No. | $KRAS^{G12V}$ H727 $IC_{50}$ (nM) |
| Compound 5A | 45.9 |
| Compound 14 | 3.51 |

The experimental conclusion is that the compounds of the present invention have excellent antiproliferative effects on $KRAS^{G12V}$ mutant H727 cells.

Experimental Example 4. SW620 Cell In Vitro Proliferation Assay

Experimental Materials

RPMI1640 medium, penicillin/streptomycin antibiotics from Gibco, and fetal bovine serum from Hyclone. 3D CellTiter-Glo (cell viability chemiluminescent assay) reagent from Promega. SW620 (KRAS G12V mutant) cell line from ATCC, Envision Multilabel analyzer (PerkinElmer).

Experimental Method

The cells were seeded in a 96-well, ultra-low adsorption U-plate, at a density of 80 μL of cell suspension per well containing 1,000 cells. The cell plate was incubated overnight in a carbon dioxide incubator.

The compound to be tested was diluted using a multichannel pipette by 5 times for 8 concentrations, that was, from 2 mM to 25.6 nM, and double replicates were set up. 78 μL of medium was added to an intermediate plate. Then the gradient-diluted compound was transferred to the intermediate plate at a density of 2 μL per well according to the corresponding position, mixed and transferred at a density of 20 μL per well to a cell plate. The concentration of the compound transferred into the cell plate ranged from 10 μM to 0.128 nM. The cell plate was incubated in a carbon dioxide incubator for 10 days. Another cell plate was prepared, and the signal value read on the day of addition was taken as the maximum value (the Max value in the equation below) to be used in data analysis.

A cell viability chemiluminescent assay reagent was added to the cell plate at a density of 100 μL per well and incubated at room temperature for 30 min to stabilize luminous signals. The readings are taken using a multilabel analyzer.

Data Analysis:

The original data was converted into the inhibition rate using equation (Sample-Min)/(Max-Min)×100%, and the $IC_{50}$ value was obtained by curve fitting through four parameters (“log(inhibitor) vs. response—Variable slope” mode in GraphPad Prism). Table 4 provides the inhibitory activity of the compounds of the present invention on proliferation of SW620 cells.

TABLE 4

| Results of in vitro screen test of the compounds of the present invention | |
|---|---|
| Compound No. | SW620 $IC_{50}$ (nM) |
| Compound 5A | 27.5 |
| Compound 14 | 12.6 |
| Compound 25 | 42.9 |
| Compound 26 | 37.7 |
| Hydrochloride of compound 27 | 44.9 |
| Hydrochloride of compound 28 | 10.1 |
| Hydrochloride of compound 31 | 98.1 |
| Hydrochloride of compound 32A | 50.9 |

The experimental conclusion is that the compounds of the present invention have excellent antiproliferative effects on $KRAS^{G12V}$ mutant SW620 cells.

Experimental Example 5. LU99 Cell In Vitro Proliferation Assay

Experimental Materials

RPMI1640 medium, penicillin/streptomycin antibiotics from Gibco, and fetal bovine serum from Hyclone. 3D CellTiter-Glo (cell viability chemiluminescent assay) reagent from Promega. LU99 (KRAS G12C mutant) cells from JCRB, Envision Multilabel analyzer (PerkinElmer).

Experimental Method

The cells were seeded in a 96-well, ultra-low adsorption U-plate, at a density of 80 μL of cell suspension per well containing 1,000 cells. The cell plate was incubated overnight in a carbon dioxide incubator.

The compound to be tested was diluted using a multichannel pipette by 5 times for 8 concentrations, that was, from 2 mM to 25.6 nM, and double replicates were set up. 78 μL of medium was added to an intermediate plate. Then the gradient-diluted compound was transferred to the intermediate plate at a density of 2 μL per well according to the corresponding position, mixed and transferred at a density of 20 μL per well to a cell plate. The concentration of the compound transferred into the cell plate ranged from 10 M to 0.128 nM. The cell plate was incubated in a carbon dioxide incubator for 10 days. Another cell plate was prepared, and the signal value read on the day of addition was taken as the maximum value (the Max value in the equation below) to be used in data analysis.

A cell viability chemiluminescent assay reagent was added to the cell plate at a density of 100 μL per well and incubated at room temperature for 30 min to stabilize luminous signals. The readings were taken using a multilabel analyzer.

Data Analysis:

The original data was converted into the inhibition rate using equation (Sample−Min)/(Max−Min)×100%, and the $IC_{50}$ value was obtained by curve fitting through four parameters (“log(inhibitor) vs. response—Variable slope” mode in GraphPad Prism). Table 5 provides the inhibitory activity of the compounds of the present invention on proliferation of LU99 cells.

TABLE 5

| Results of in vitro screen test of the compounds of the present invention | |
|---|---|
| Compound No. | LU99 $IC_{50}$ (nM) |
| Compound 14 | 2.7 |

The experimental conclusion is that the compounds of the present invention have excellent antiproliferative effects on $KRAS^{G12C}$ mutant LU99 cells.

Experimental Example 6. MKN-1 Cell In Vitro Proliferation Assay

Experimental Materials

RPMI1640 medium, penicillin/streptomycin antibiotics from Gibco, and fetal bovine serum from Hyclone. 3D CellTiter-Glo (cell viability chemiluminescent assay) reagent from Promega. MKN-1 (KRAS WT amplified) cells from JCRB, Envision Multilabel analyzer (PerkinElmer).

Experimental Method

The cells were seeded in a 96-well, ultra-low adsorption U-plate, at a density of 80 μL of cell suspension per well containing 1,000 cells. The cell plate was incubated overnight in a carbon dioxide incubator.

The compound to be tested was diluted using a multichannel pipette by 5 times for 8 concentrations, that was, from 2 mM to 25.6 nM, and double replicates were set up. 78 μL of medium was added to an intermediate plate. Then the gradient-diluted compound was transferred to the intermediate plate at a density of 2 μL per well according to the corresponding position, mixed and transferred at a density of 20 μL per well to a cell plate. The concentration of the compound transferred into the cell plate ranged from 10 μM to 0.128 nM. The cell plate was incubated in a carbon dioxide incubator for 10 days. Another cell plate was prepared, and the signal value read on the day of addition was taken as the maximum value (the Max value in the equation below) to be used in data analysis.

A cell viability chemiluminescent assay reagent was added to the cell plate at a density of 100 μL per well and incubated at room temperature for 30 min to stabilize luminous signals. The readings were taken using a multilabel analyzer.

Data Analysis:

The original data was converted into the inhibition rate using equation (Sample-Min)/(Max-Min)×100%, and the $IC_{50}$ value was obtained by curve fitting through four parameters ("log(inhibitor) vs. response—Variable slope" mode in GraphPad Prism). Table 6 provides the inhibitory activity of the compounds of the present invention on proliferation of MKN-1 cells.

TABLE 6

Results of in vitro screen test of the compounds of the present invention

| Compound No. | MKN-1 $IC_{50}$ (nM) |
|---|---|
| Compound 14 | 3.6 |

NOTE:
"/" means not detected.

The experimental conclusion is that the compounds of the present invention have excellent antiproliferative effects on $KRAS^{WT}$ amplified MKN-1 cells.

Experimental Example 7. Study on Drug Efficacy In Vivo

Experimental Method

Establishment of human colon cancer GP2D cell subcutaneous xenograft Balb/c nude mouse models: Each mouse was subcutaneously inoculated with 0.2 mL of ($2\times10^6$) GP2D cells (with Matrigel added at a volume ratio of 1:1) on the right back. The mice were divided into groups (6 or 4 per group) and administered when the average tumor volume reached 270 $mm^3$. The mice were administered with the corresponding drugs according to the groups on the day of the experiment. The first group G1 was set as a vehicle group, and administered intragastrically with 5% DMSO+95% (10% HP-3-CD) alone. The second group G2 was administered with the hydrochloride of compound 14 (vehicle: 5% DMSO+95% (10% HP-β-CD)), and the dose and regimen are shown in Table 7.

TABLE 7

Study on effects of subjects on animal tumor size in human colon cancer GP2D xenograft mouse models

| Group | Number of animals | Subject | Dose (mg/kg) | Volume of administration (mL/kg) | Route and frequency of administration |
|---|---|---|---|---|---|
| G1 | 6 | Vehicle | (N/A) | (N/A) | PO, BID × 28 |
| G2 | 4 | Hydrochloride of compound 14 | 150 | 10 | PO, BID × 28 |

Note:
PO means oral, QD means once a day, and BID means once a day.

The animals' body weight and tumor size were measured twice a week during the experiment, and the clinical symptoms of the animals were observed and recorded daily. The most recently measured animal body weight was taken as a reference for each dose.

The length (a) and width (b) of tumor were measured using a digital caliper. The formula for calculating the tumor volume (TV) is $TV=a\times b^2/2$.

Experimental Results

The hydrochloride of compound 14 has significant inhibitory effects on human colon cancer GP2D mouse xenografts. After 28 days of administration, the tumor volume inhibitory rate TGI (%) of group G2 (150 mg/kg, PO, BID) was 97.2 on day 28, and the detailed results are shown in Table 8.

TABLE 8

Effects of subjects on animal tumor size in human colon cancer GP2D xenograft mouse models

| Group | Number of animals | Subject | Frequency of administration | Dose mg/kg | Tumor volume inhibition rate TGI (%) |
|---|---|---|---|---|---|
| G1 | 6 | Vehicle | PO, BID × 28 | NA | N/A |
| G2 | 4 | Hydrochloride of compound 14 | PO, BID × 28 | 150 | 97.2 |

Note:
N/A means not detected.

The experimental conclusion is that the compounds of the present invention have excellent tumor inhibiting effects in GP2D cell line in terms of drug efficacy in vivo.

Experimental Example 8. Study on Drug Efficacy In Vivo

Experimental Method

Establishment of human pancreatic cancer Panc0403 cell subcutaneous xenograft Balb/c nude mouse models: Each mouse was subcutaneously inoculated with 0.2 mL of ($5\times10^6$) Panc0403 cells on the right back. The mice were divided into groups (6 or 4 mice per group) and administered when the average tumor volume reached 190 $mm^3$. The mice were administered with the corresponding drugs according to the groups on the day of the experiment. The first group G1 was set as a vehicle group, and administered intragastrically with 5% DMSO+95% (10% HP-3-CD) alone. The second group G2 was administered with compound 4A (vehicle: 5% DMSO+95% (10% HP-β-CD)), and the dose and regimen are shown in Table 9.

TABLE 9

Study on effects of subjects on animal tumor size in human pancreatic cancer Panc0403 xenograft mouse models

| Group | Number of animals | Subject | Dose (mg/kg) | Volume of administration (mL/kg) | Route and frequency of administration |
|---|---|---|---|---|---|
| G1 | 6 | Vehicle | (N/A) | (N/A) | PO, BID × 28 |
| G2 | 4 | Compound 4A | 150 | 10 | PO, BID × 28 |

Note:
PO means oral, QD means once a day, and BID means once a day.

The animals' body weight and tumor size were measured twice a week during the experiment, and the clinical symptoms of the animals were observed and recorded daily. The most recently measured animal body weight was taken as a reference for each dose.

The length (a) and width (b) of tumor were measured using a digital caliper. The formula for calculating the tumor volume (TV) is $TV=a\times b^2/2$.

Experimental Results

The compound 4A has significant inhibitory effects on human pancreatic cancer Panc0403 mouse xenografts. After 28 days of administration, the tumor volume inhibitory rate TGI (%) of group G2 (150 mg/kg, PO, BID) was 113.7 on day 28, and the detailed results are shown in Table 10.

TABLE 10

Effects of subjects on animal tumor size in human pancreatic cancer Panc0403 xenograft mouse models

| Group | Number of animals | Subject | Frequency of administration | Dose mg/kg | Tumor volume inhibition rate TGI (%) |
|---|---|---|---|---|---|
| G1 | 6 | Vehicle | PO, BID × 28 | NA | N/A |
| G2 | 4 | Compound 4A | PO, BID × 28 | 150 | 113.7 |

Note:
N/A means not detected.

The experimental conclusion is that the compounds of the present invention have excellent tumor inhibiting effects in Panc0403 cell line in terms of drug efficacy in vivo.

The invention claimed is:

1. A compound selected from the group consisting of

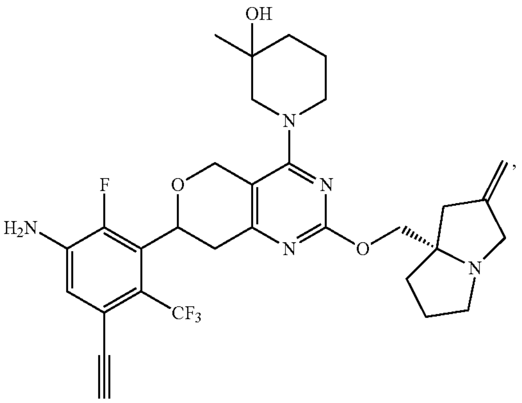

,

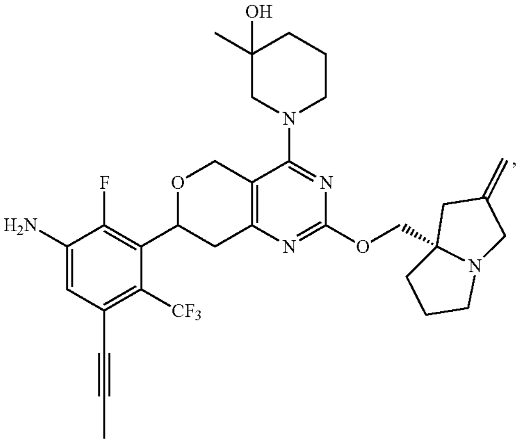

,

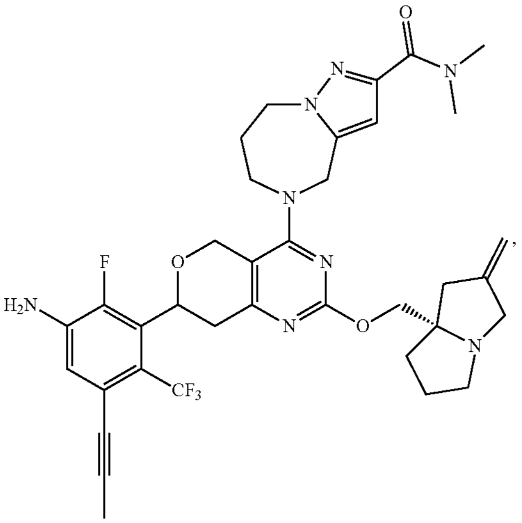

,

-continued
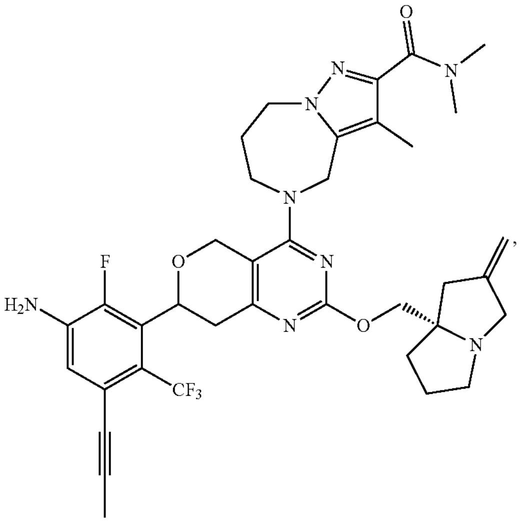
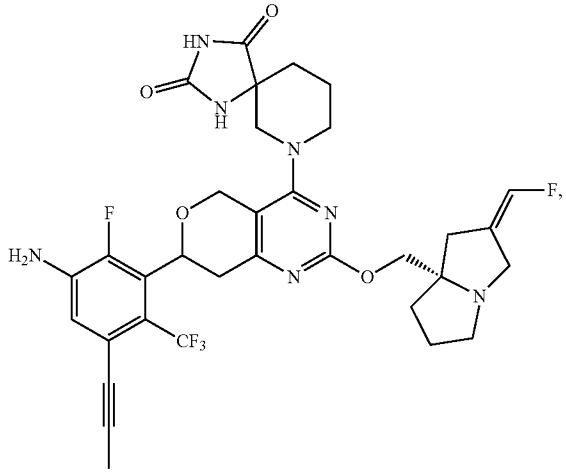
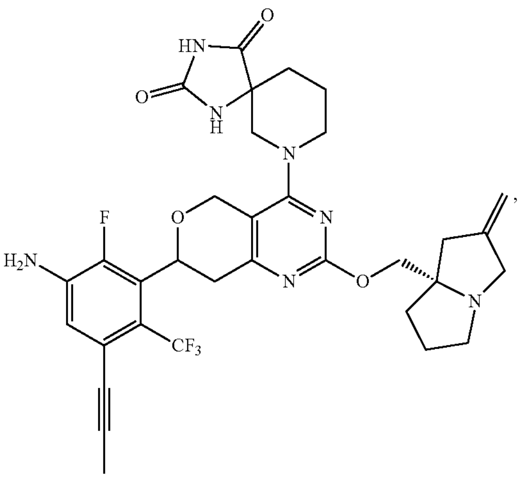
-continued
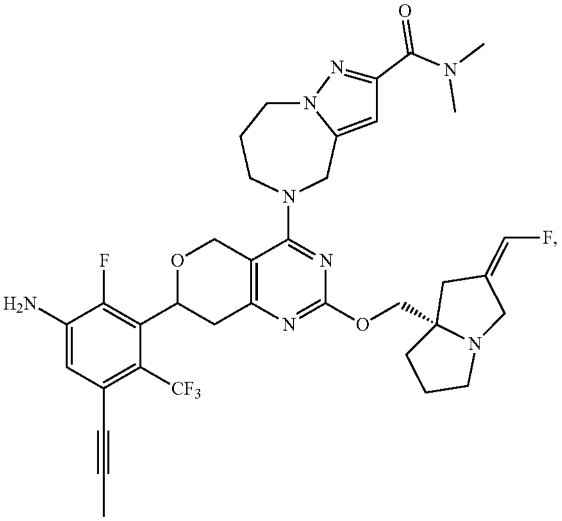
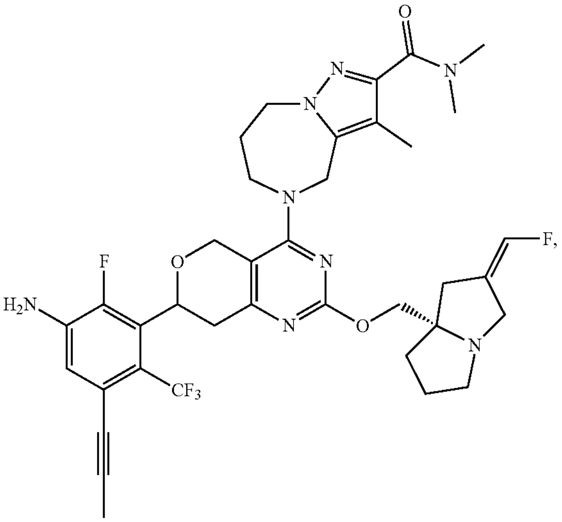
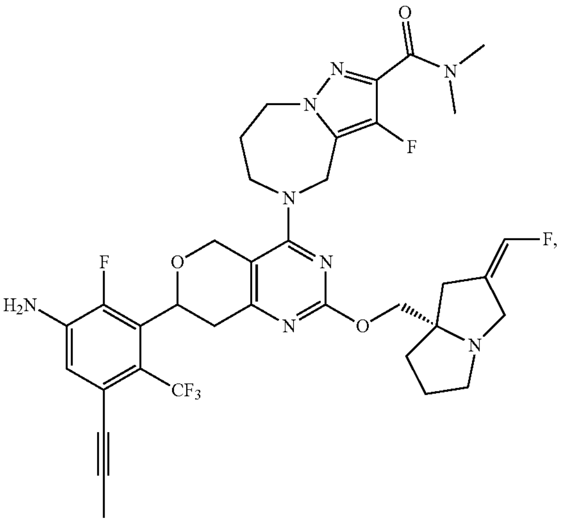

-continued
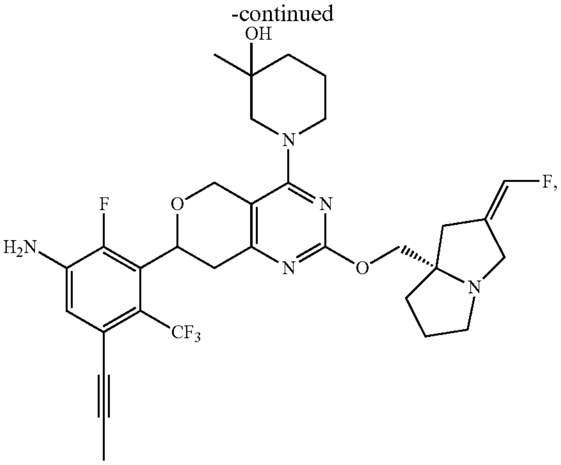
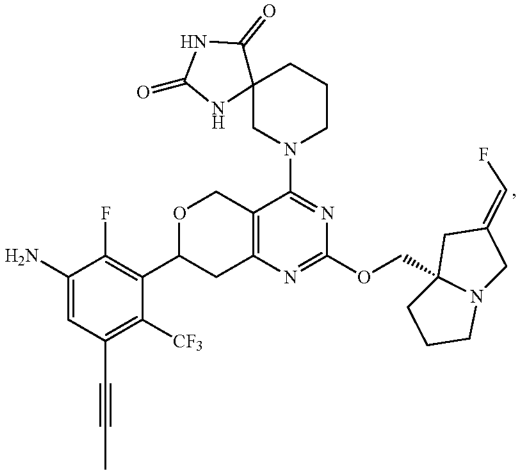
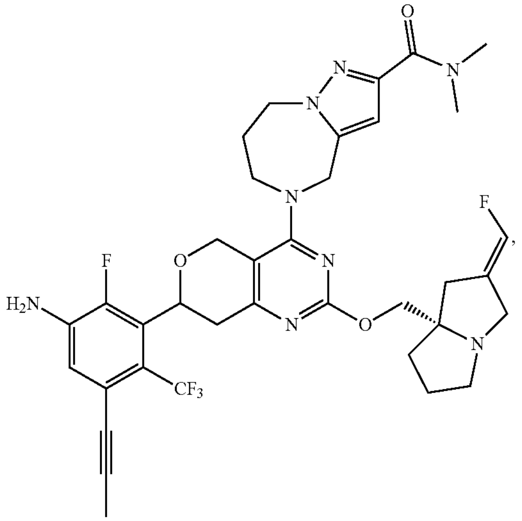
-continued
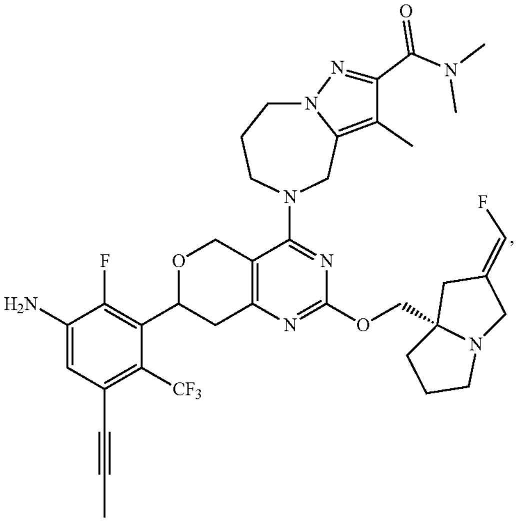
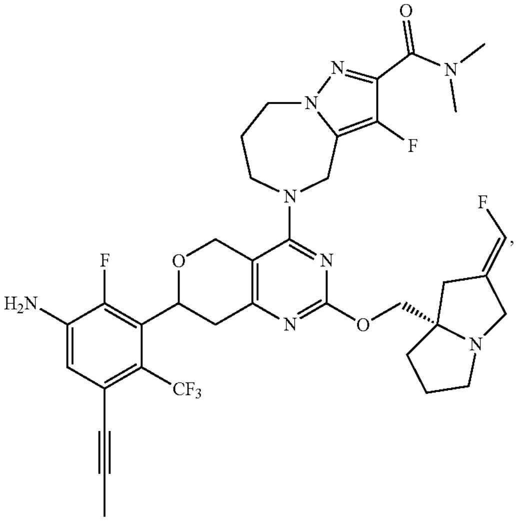
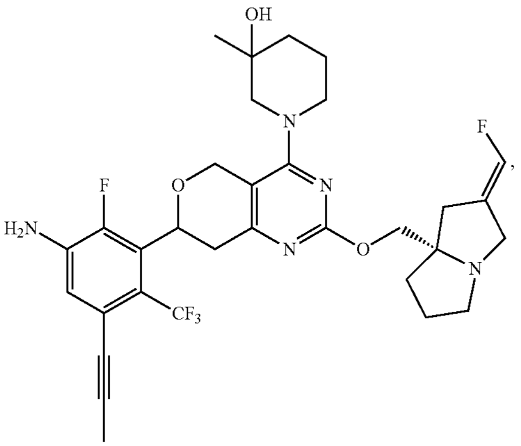

-continued
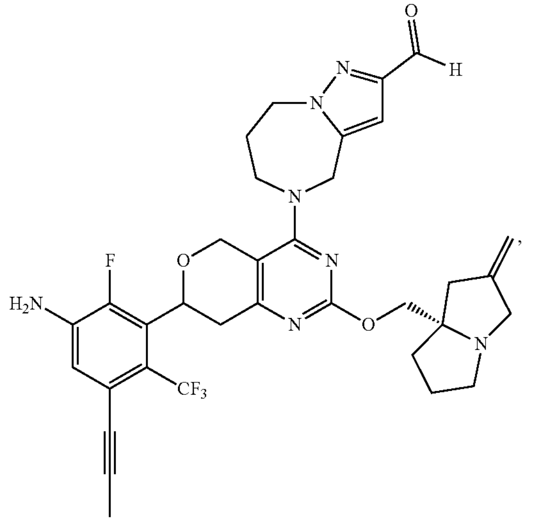
,
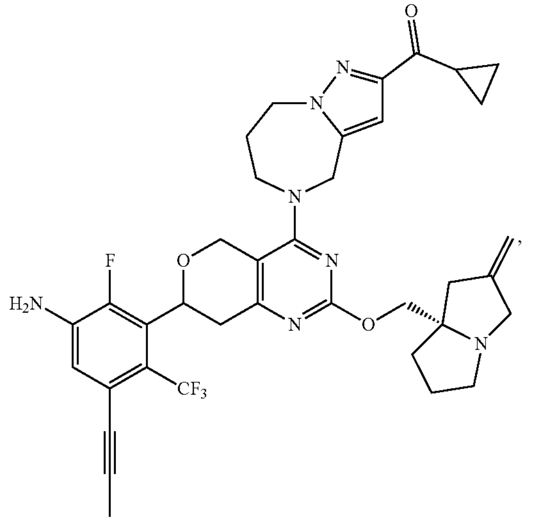
,
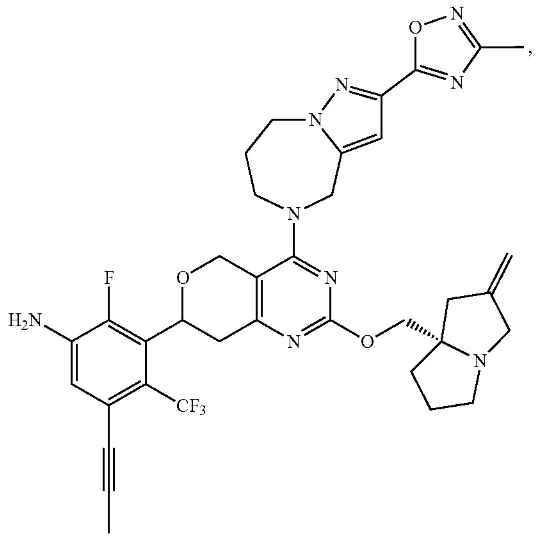
,
-continued
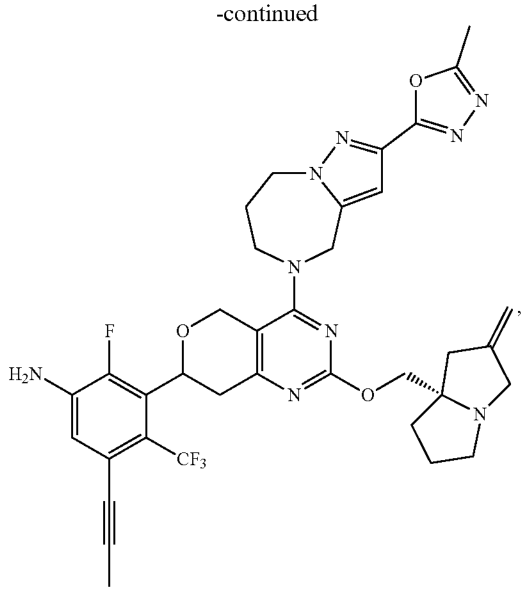
,
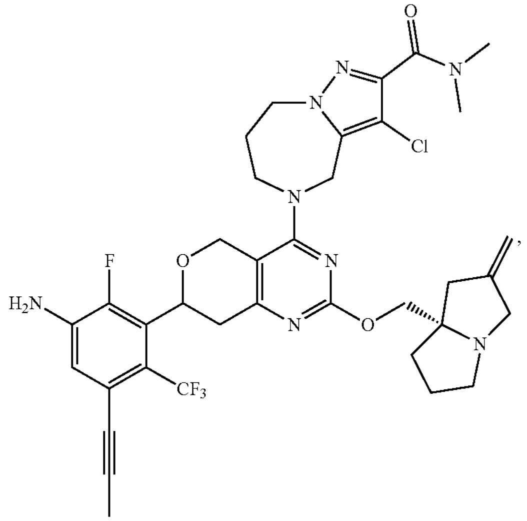
,
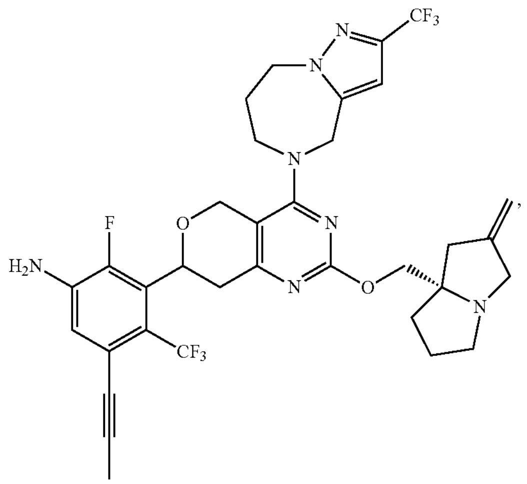
, -continued
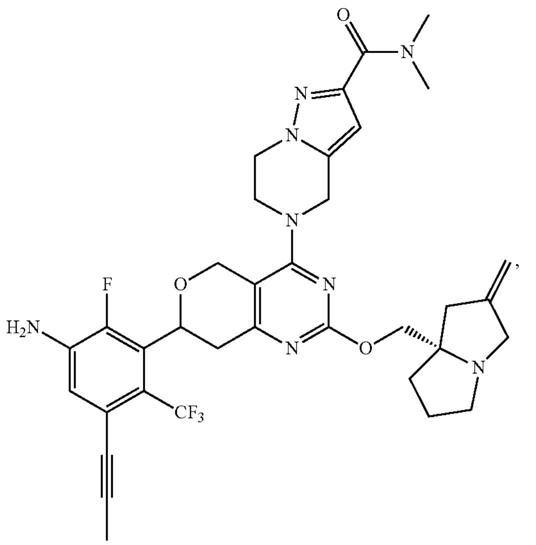
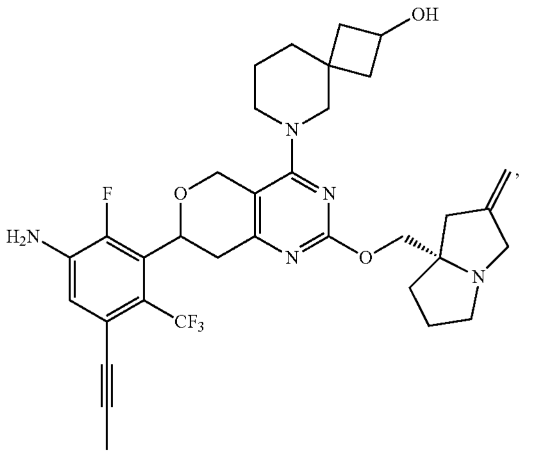
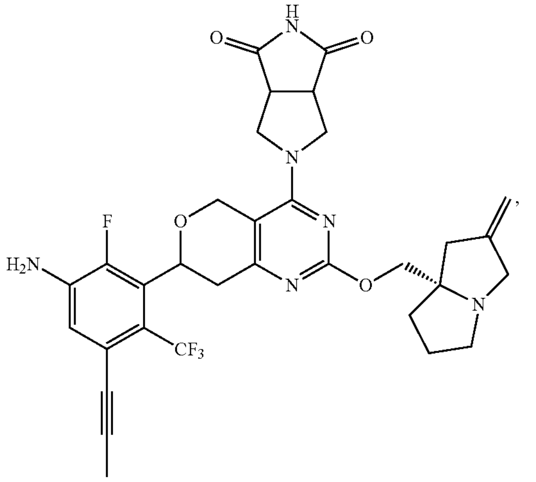
-continued
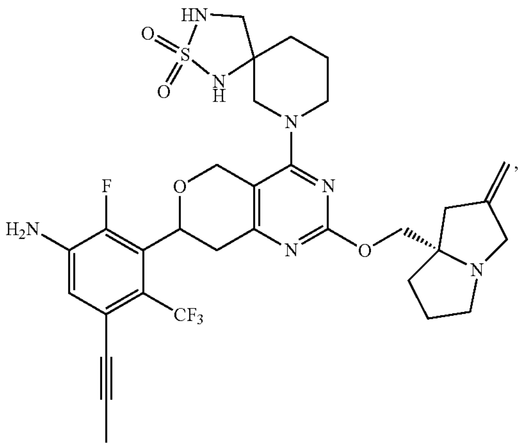
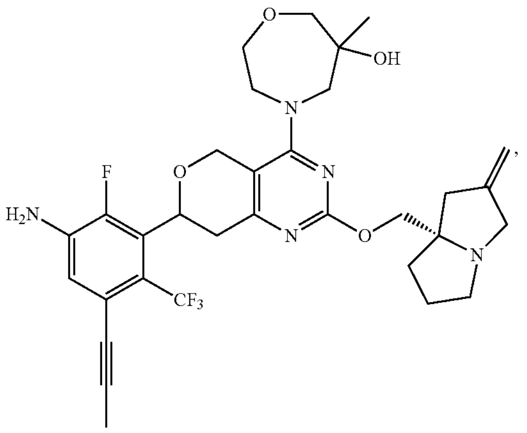
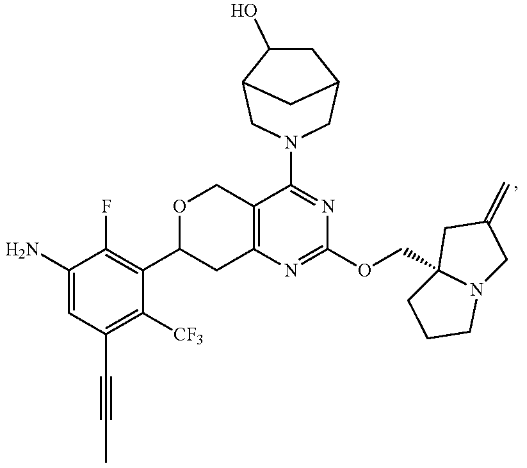

-continued
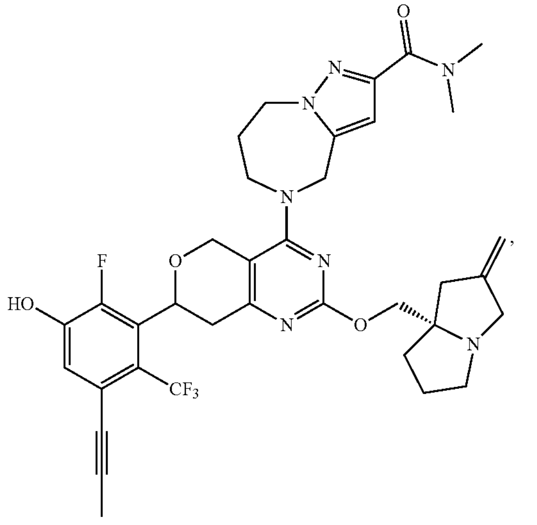
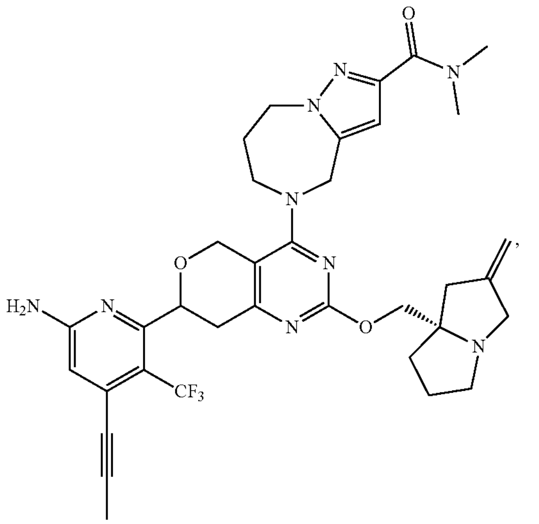
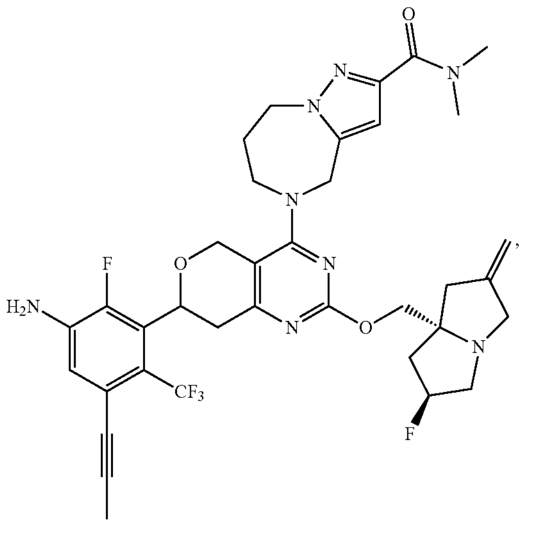
-continued
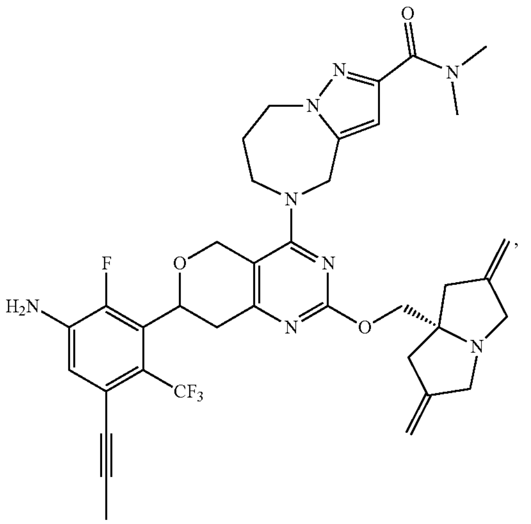
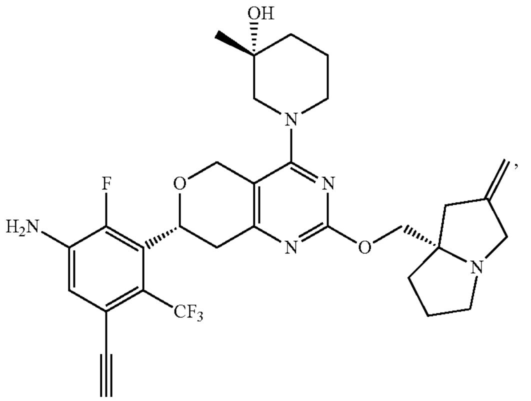
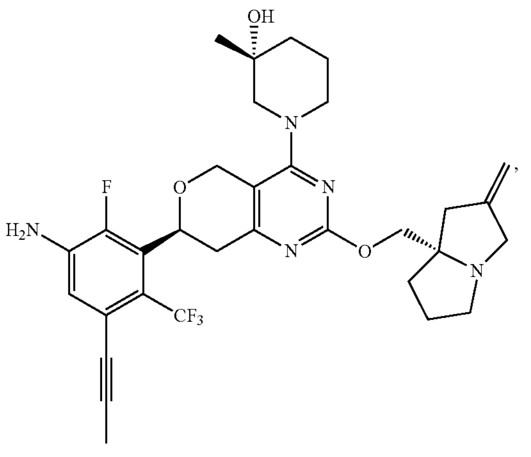

-continued
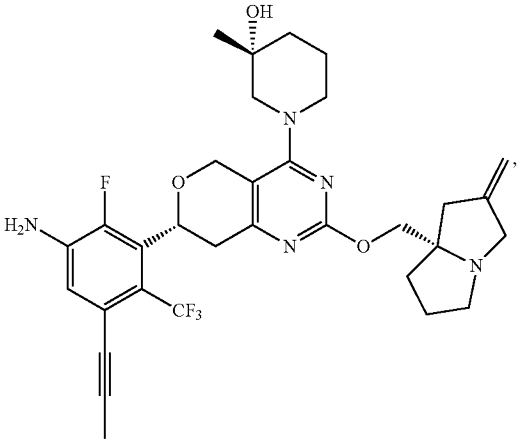
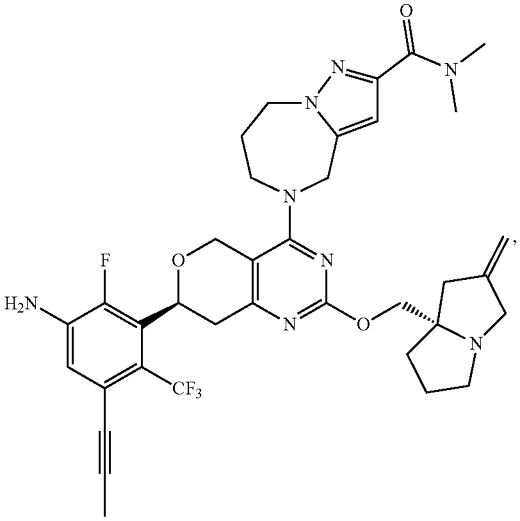
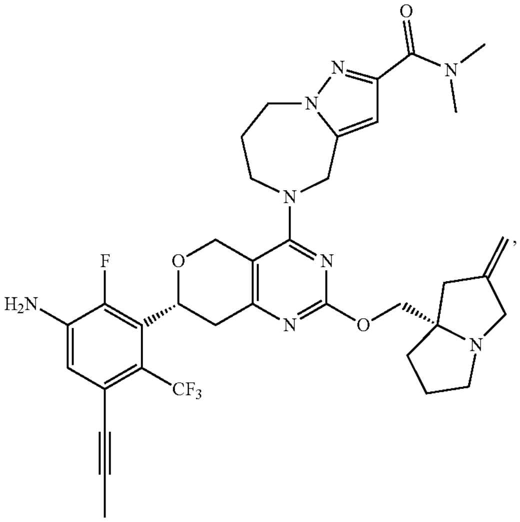
-continued
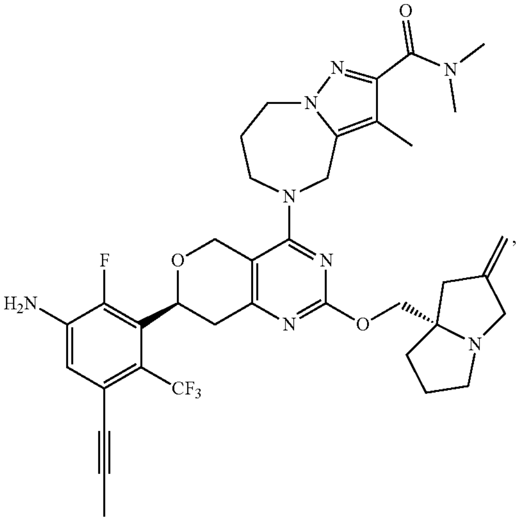
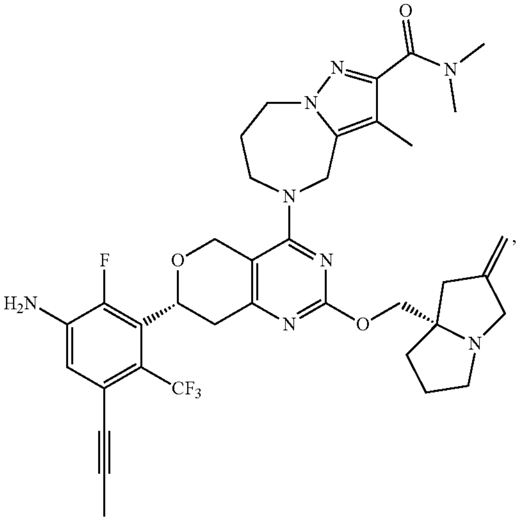
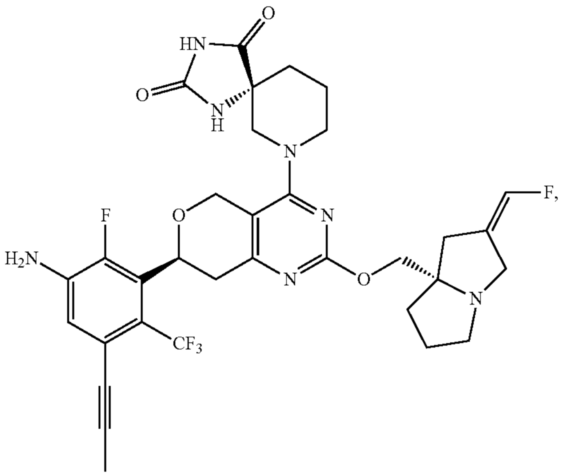

-continued
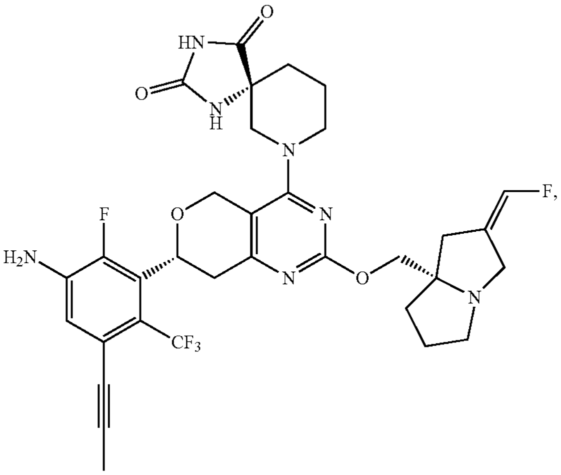
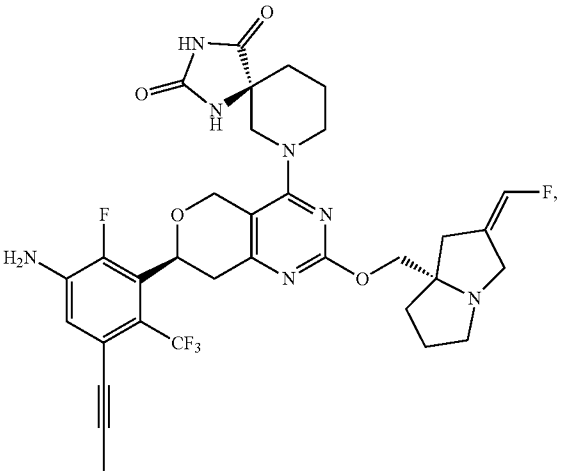
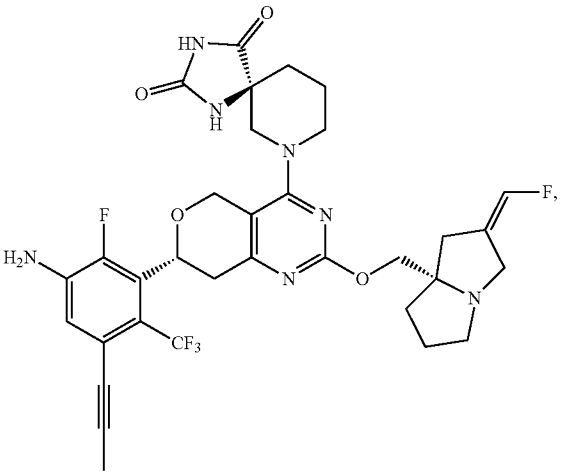
-continued
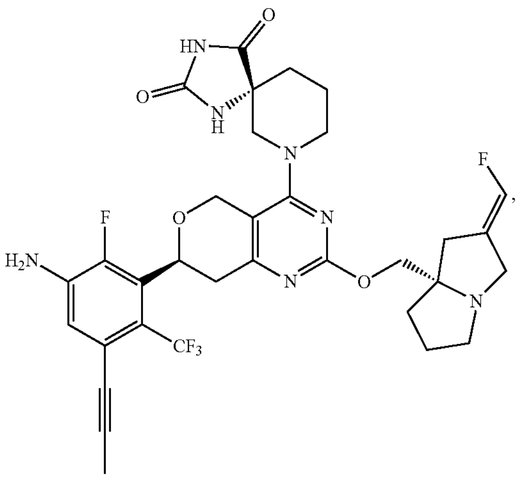
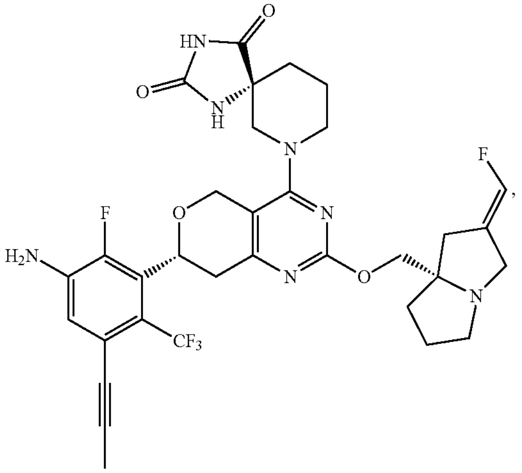
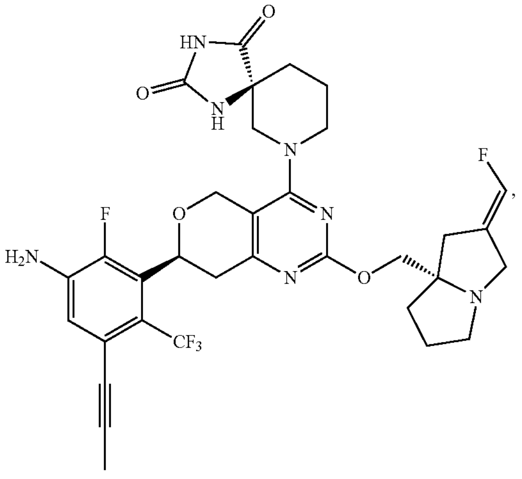

-continued
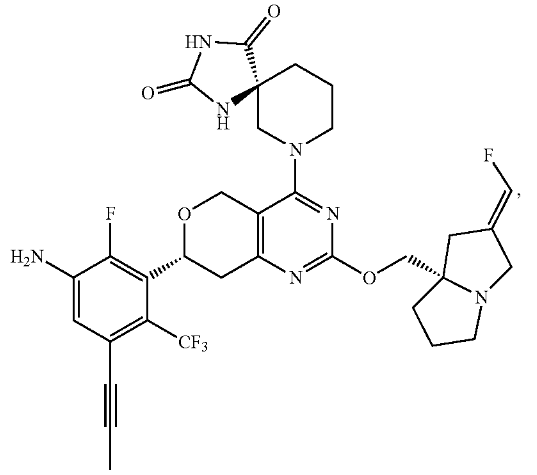
,
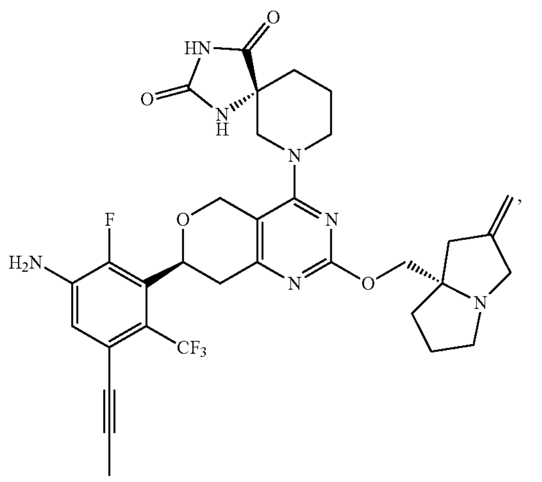
,
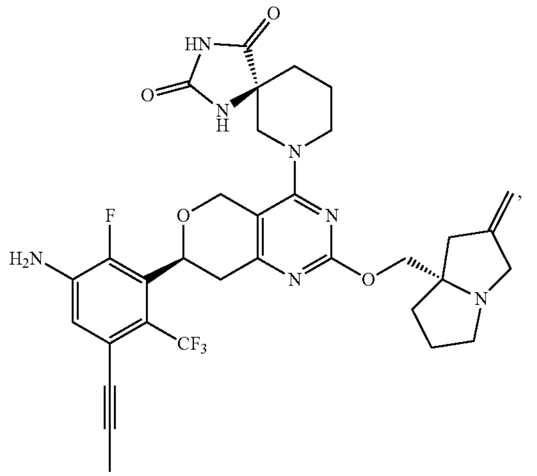
,
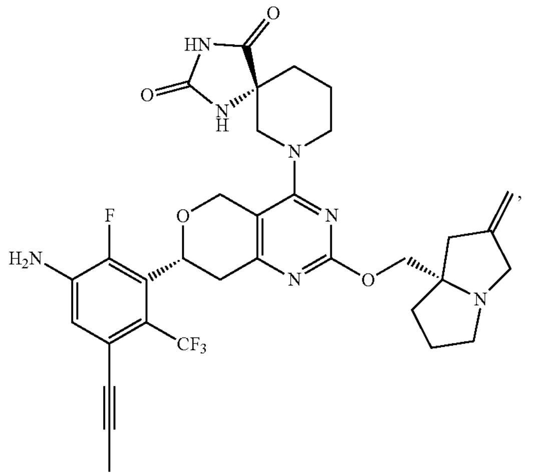
,
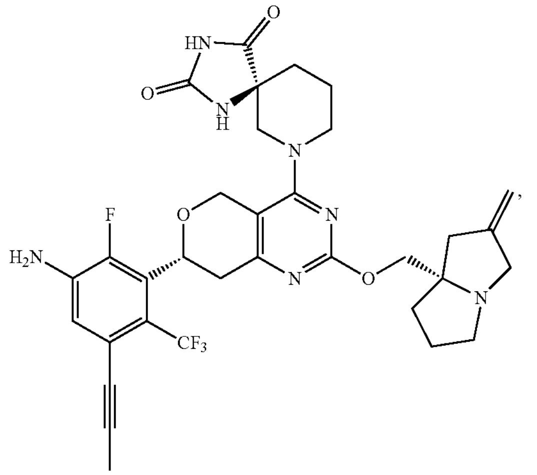
,
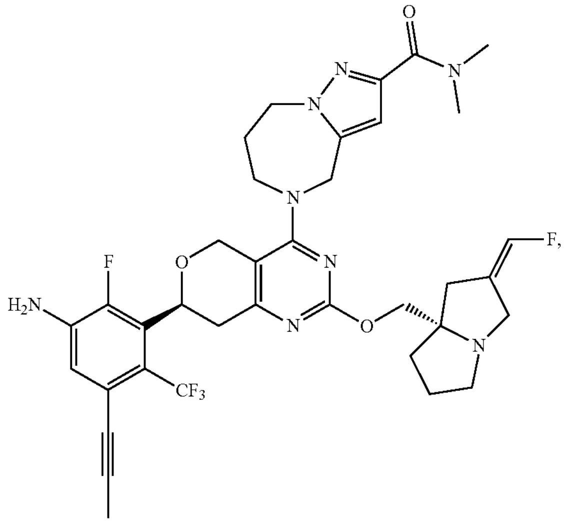
, -continued
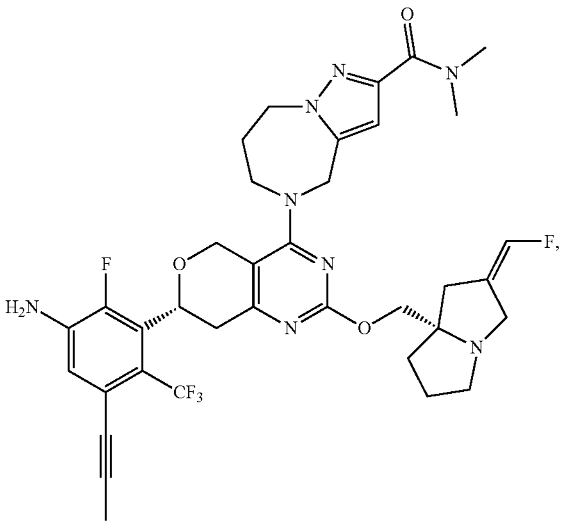
,
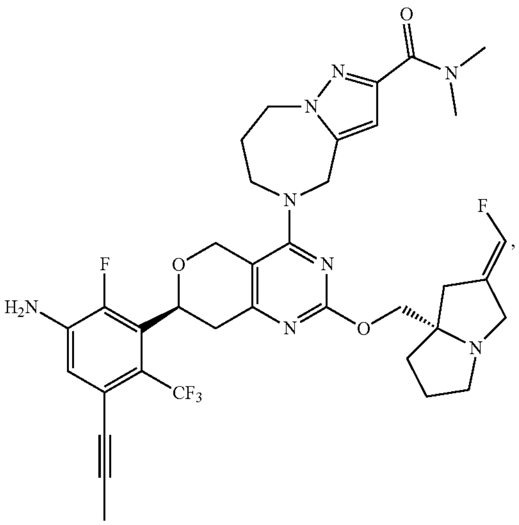
,
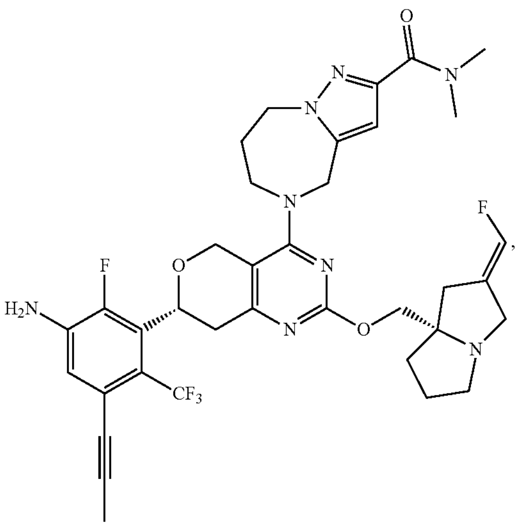
,
-continued
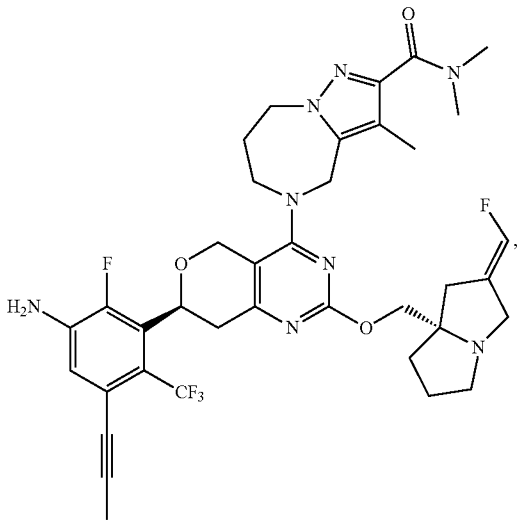
,
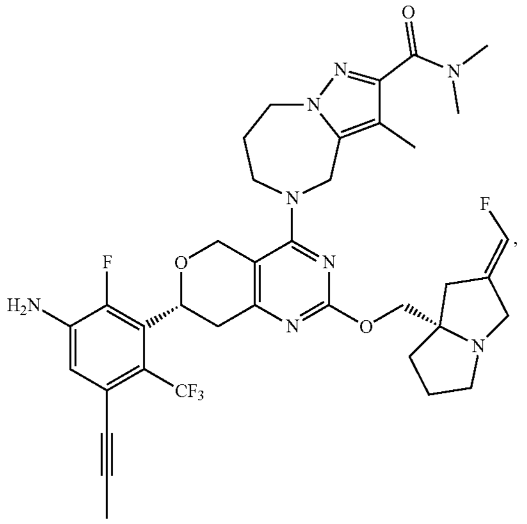
,
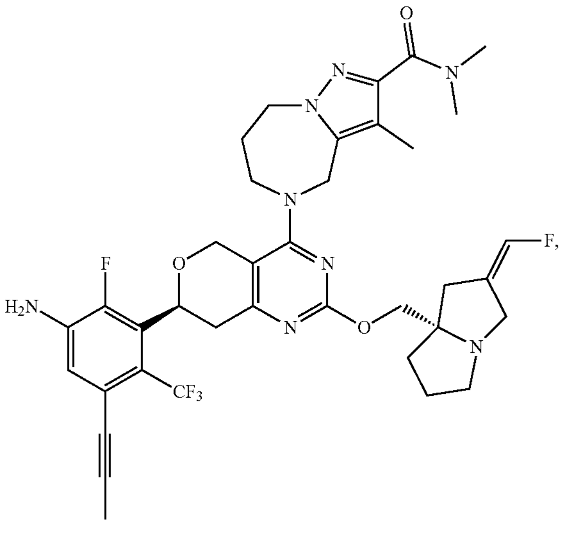
, -continued
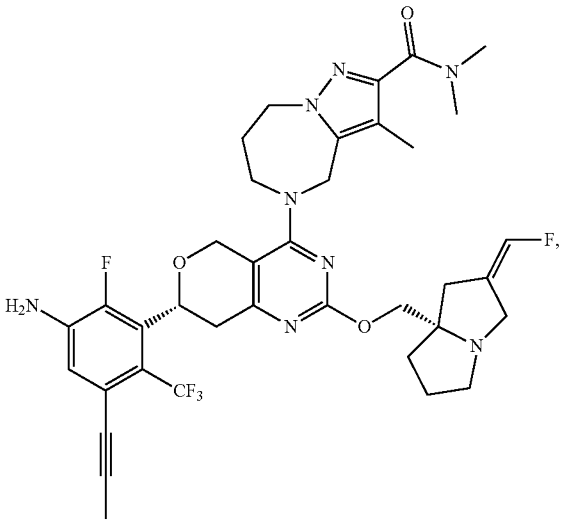
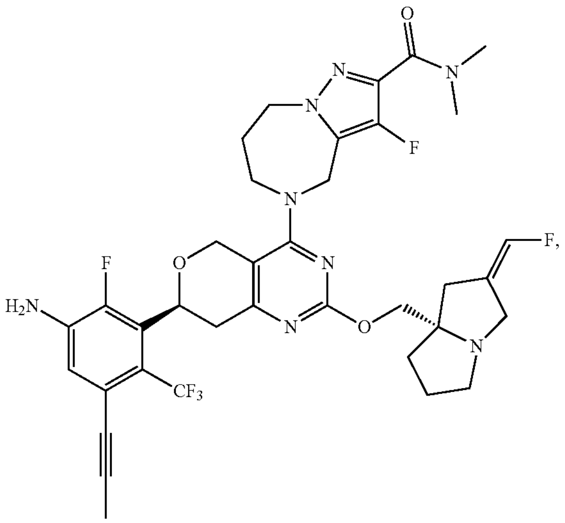
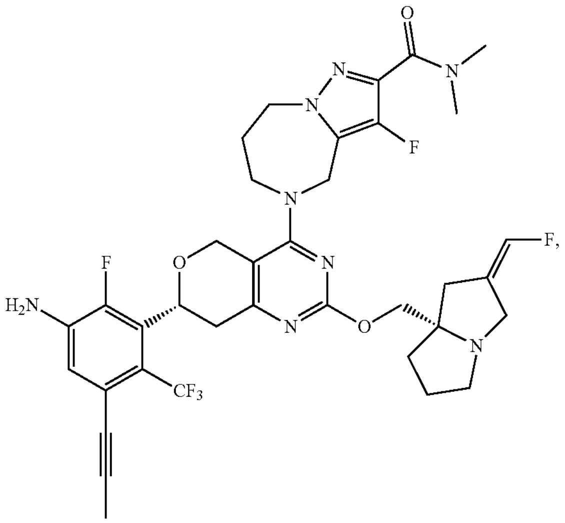
-continued
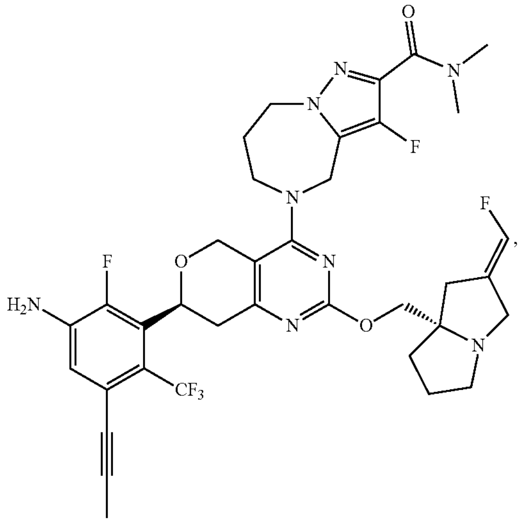
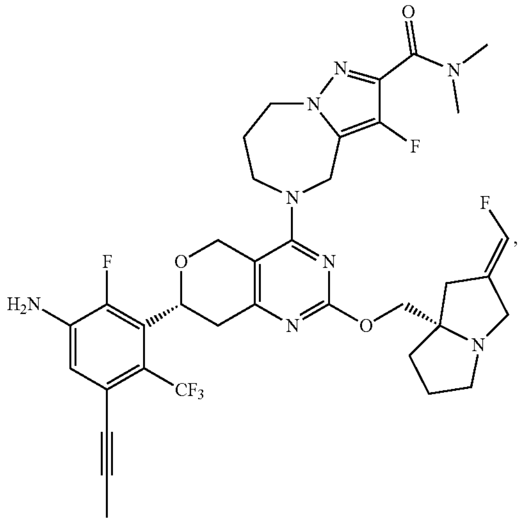
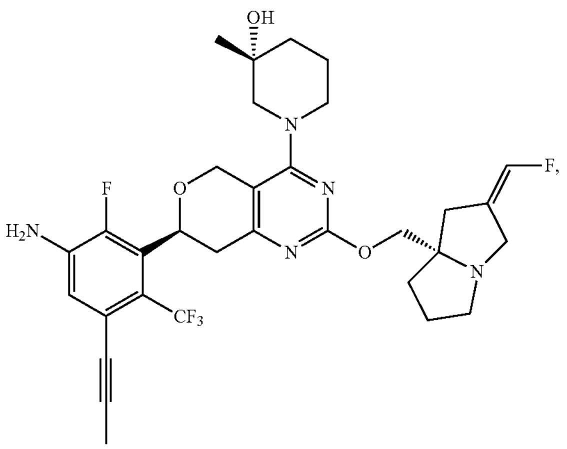

-continued
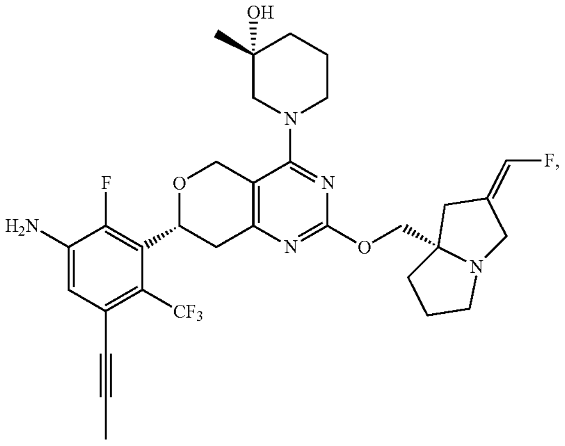
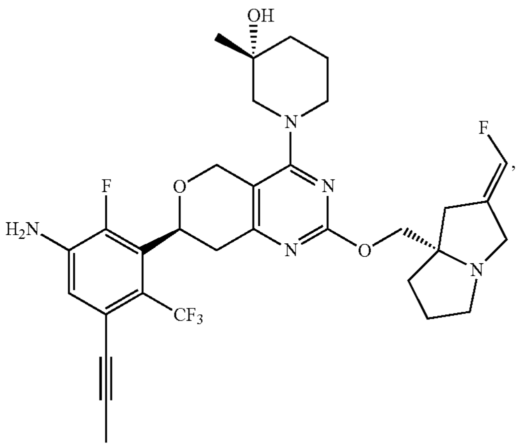
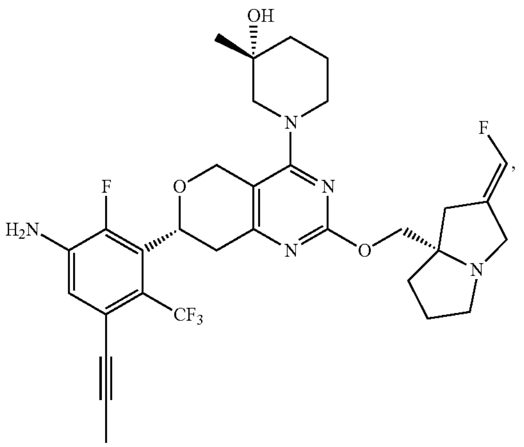
-continued
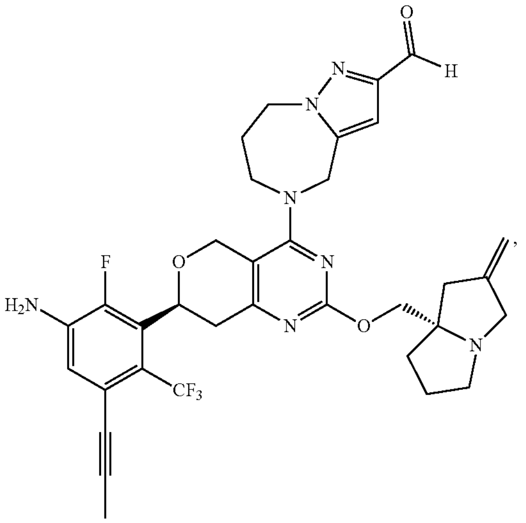
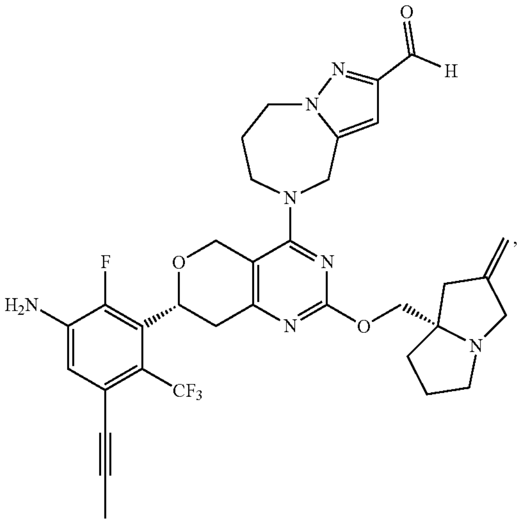
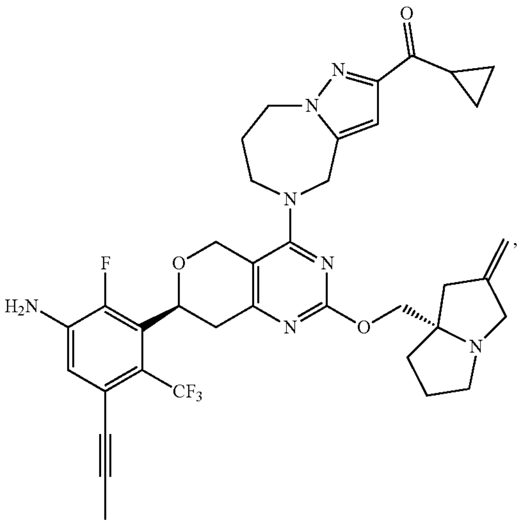

-continued
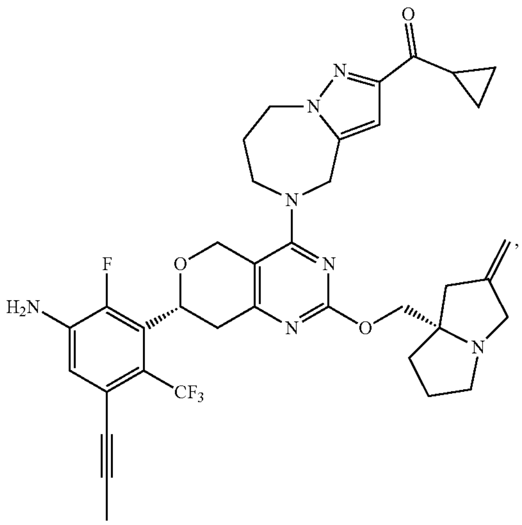
,
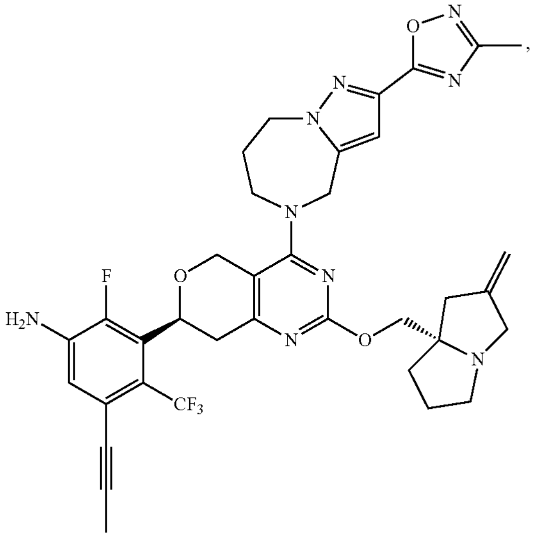
,
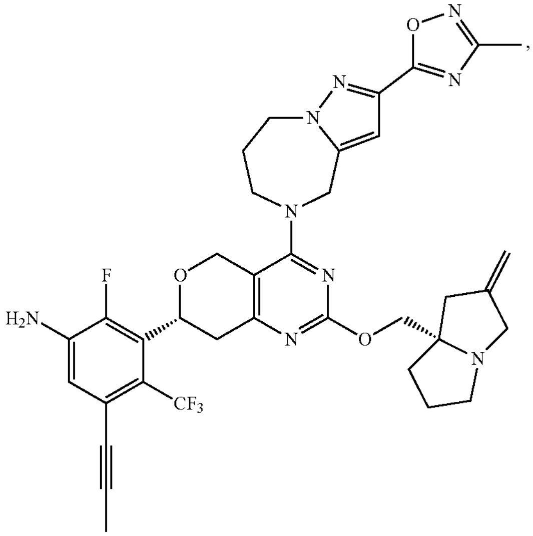
,
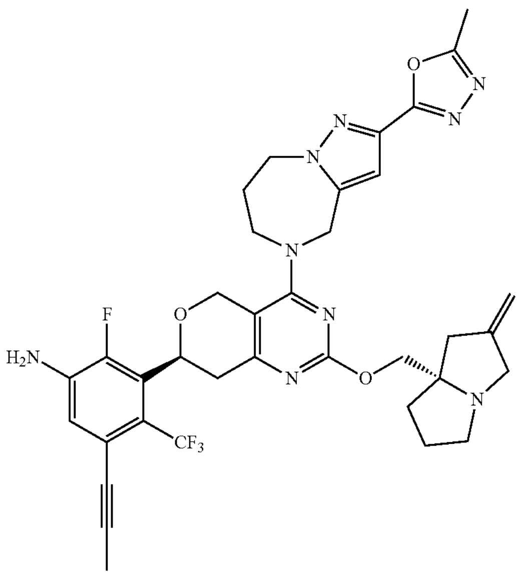
,
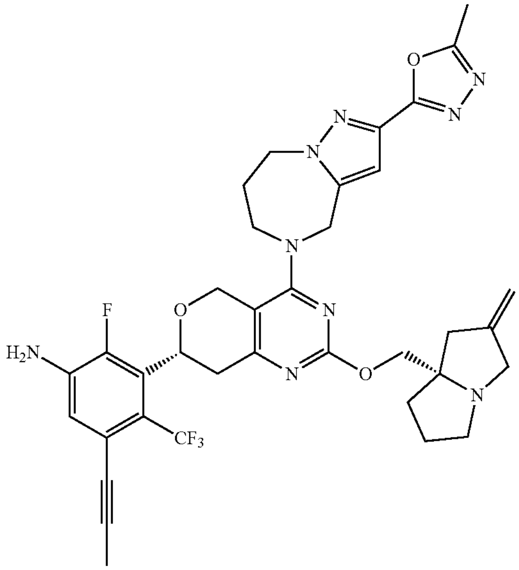
,
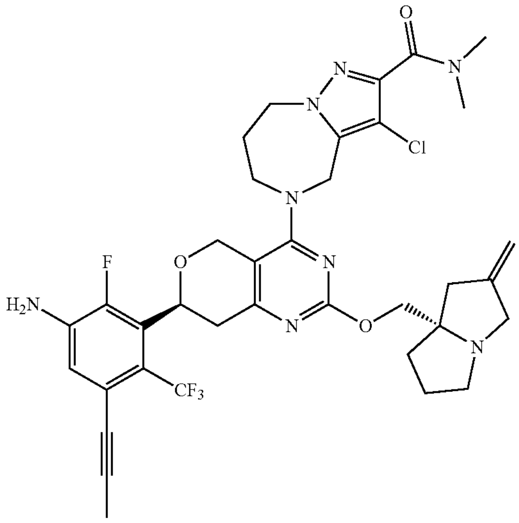
,

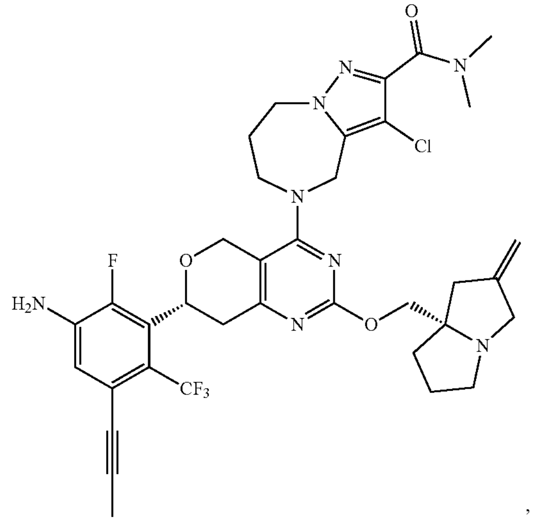
,
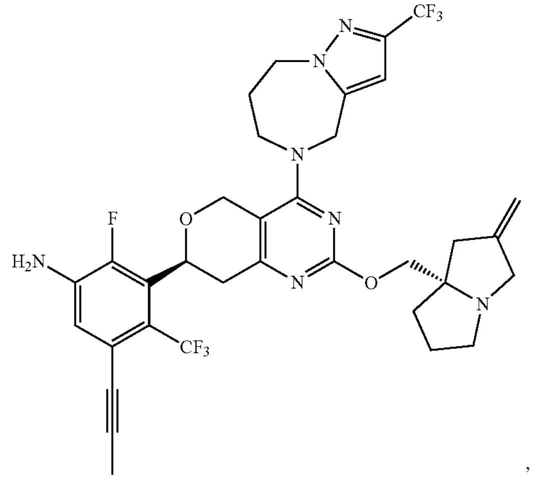
,
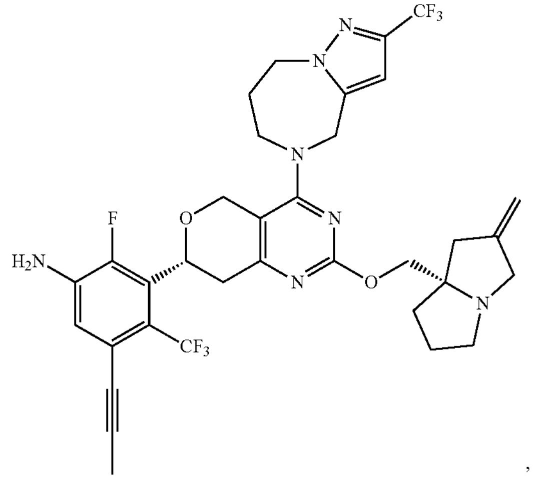
,
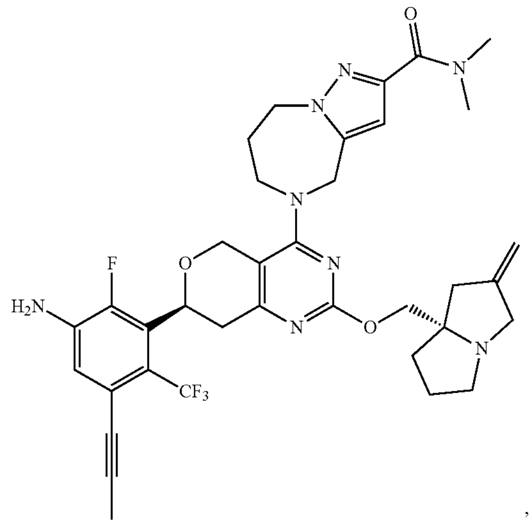
,
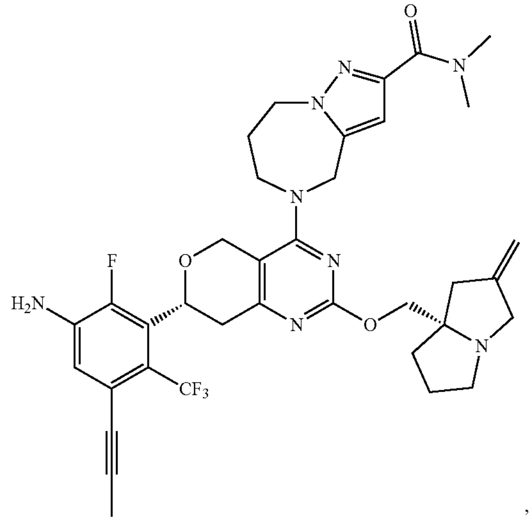
,
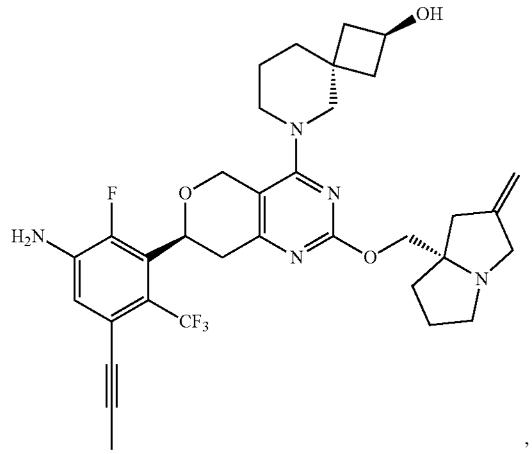
, -continued
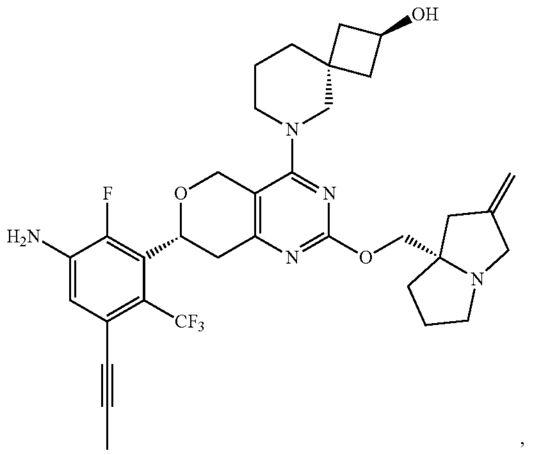
,
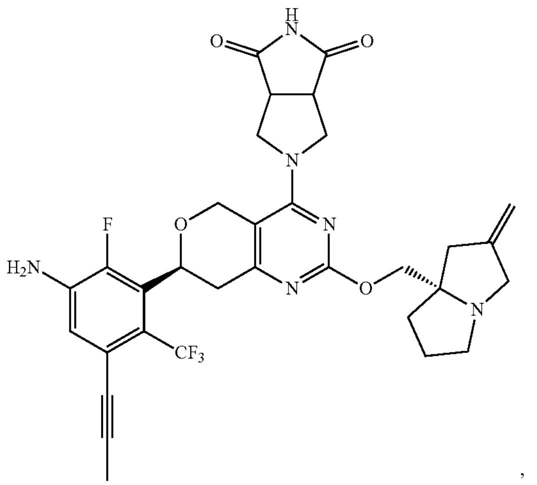
,
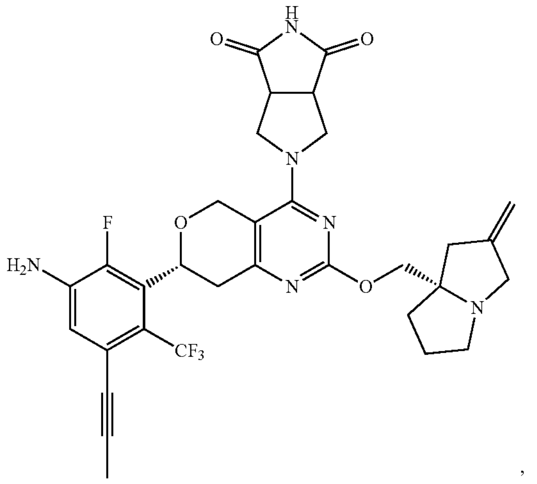
,
-continued
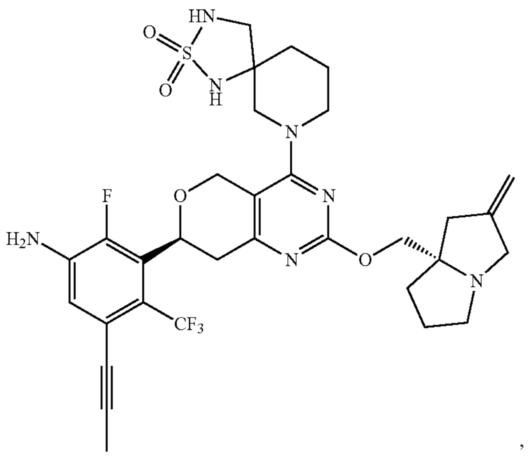
,
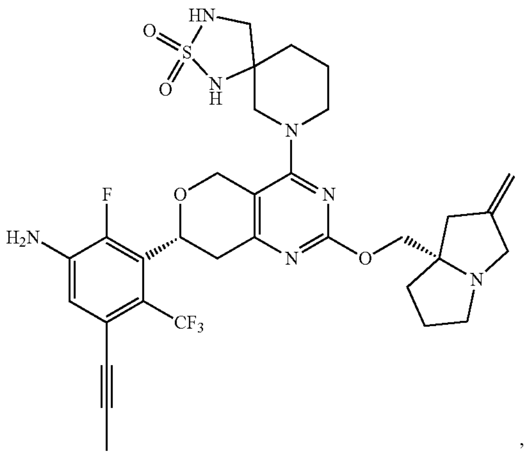
,
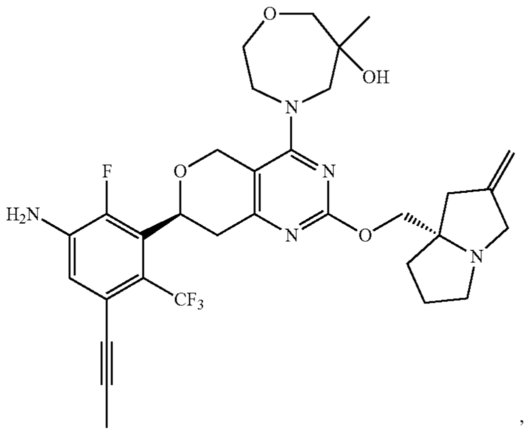
, -continued
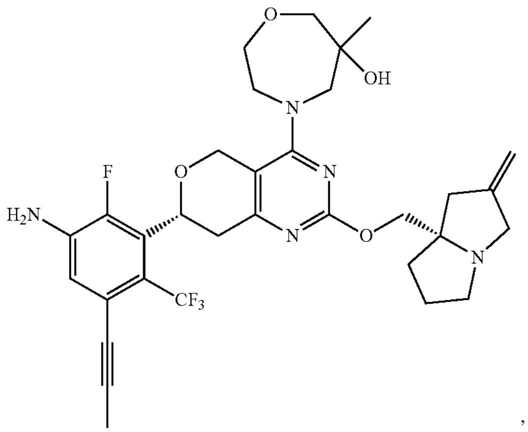
,
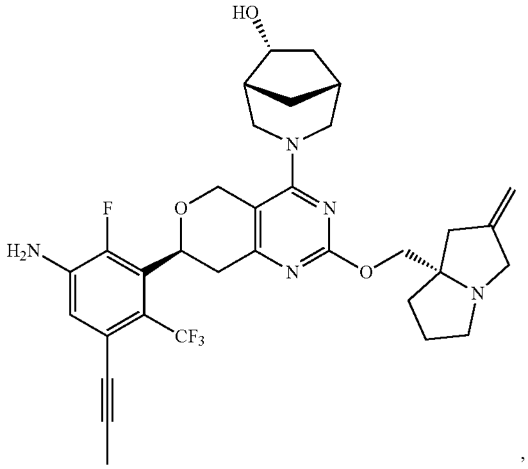
,
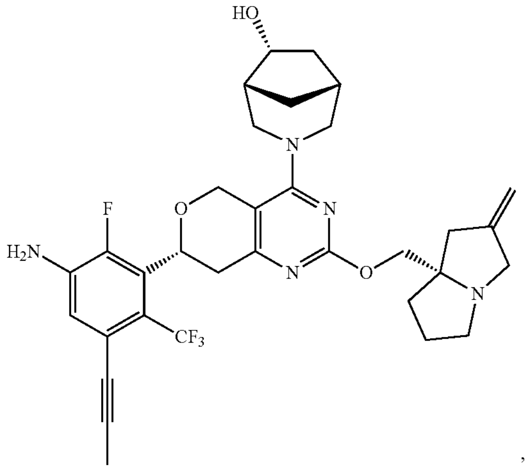
,
-continued
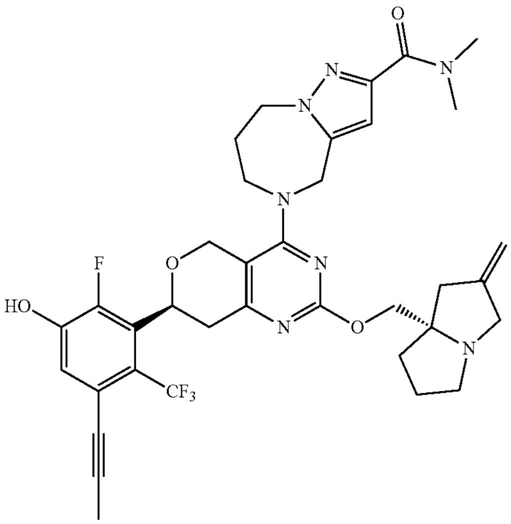
,
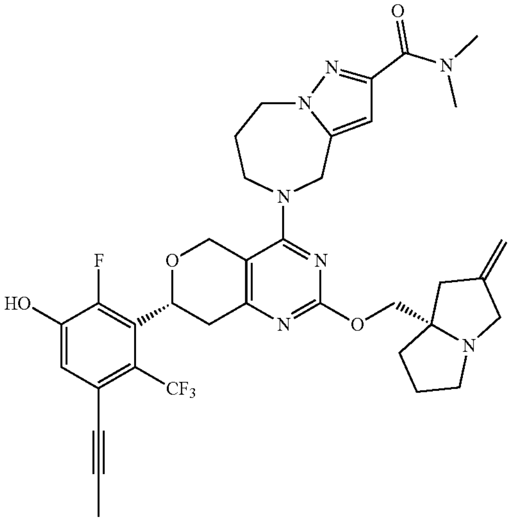
,
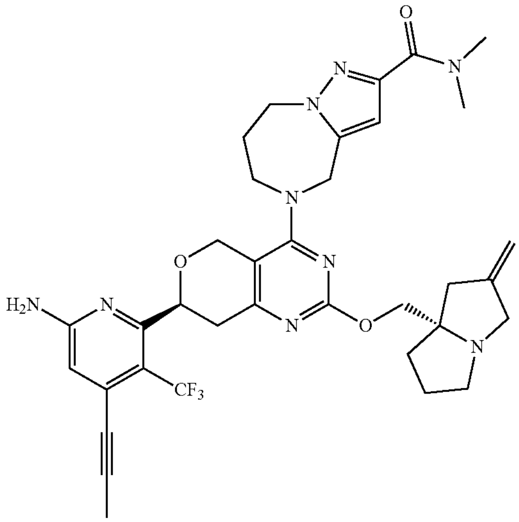
, -continued
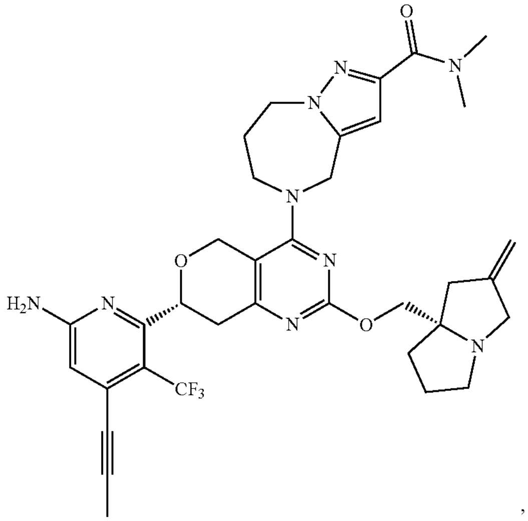
,
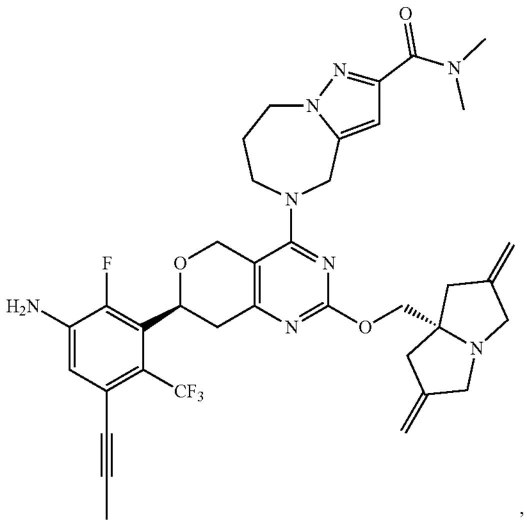
,
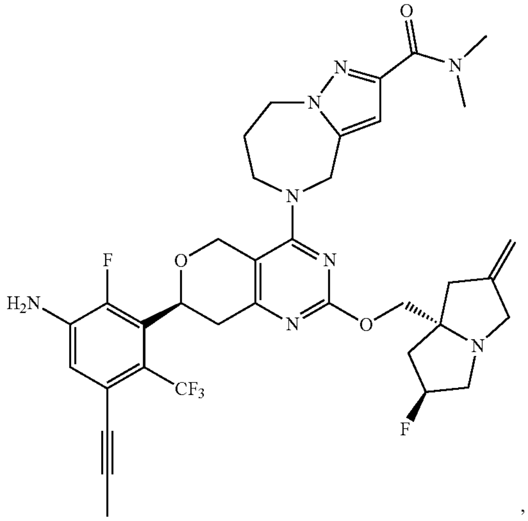
,
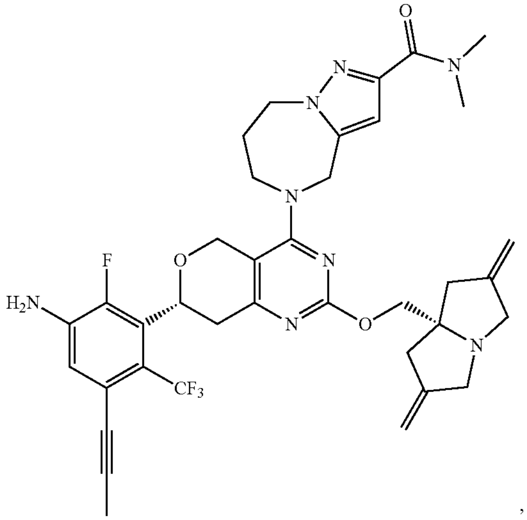
,
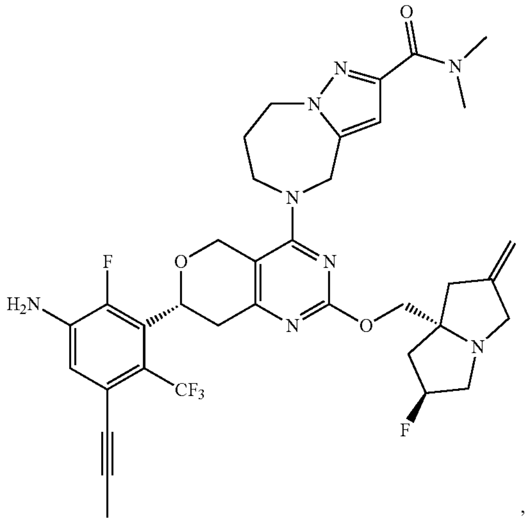
,
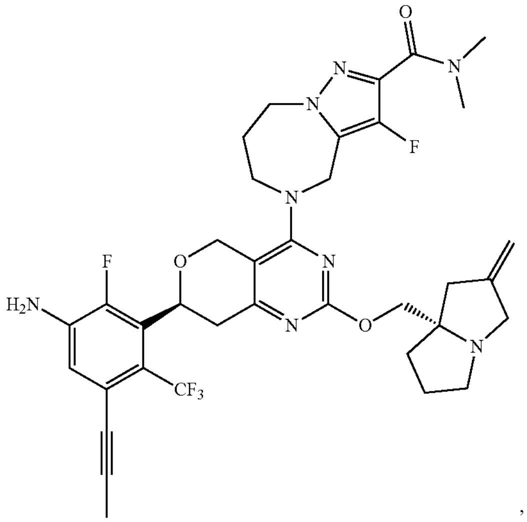
, -continued
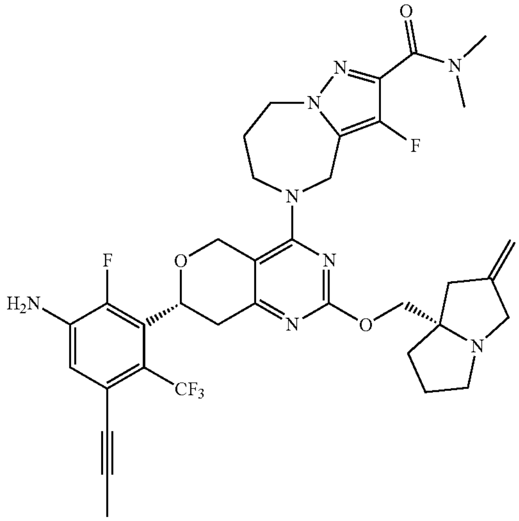
,
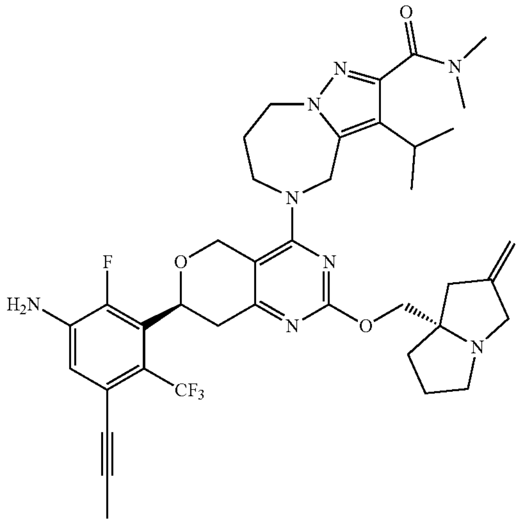
,
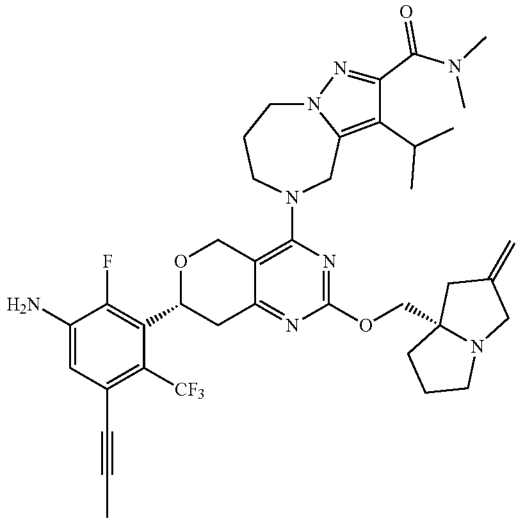
,
-continued
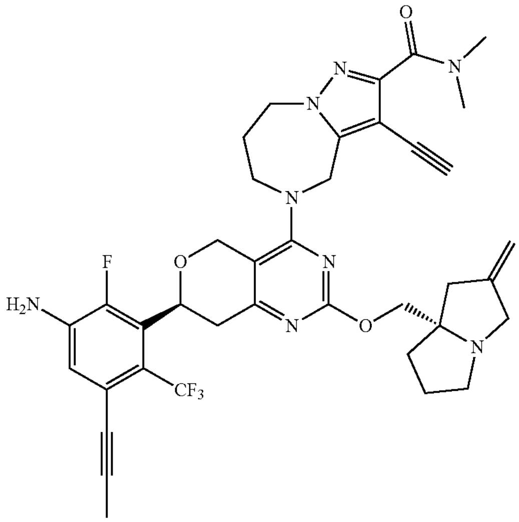
,
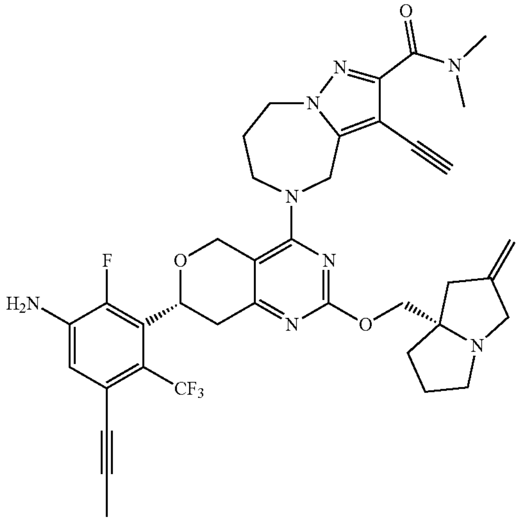
,
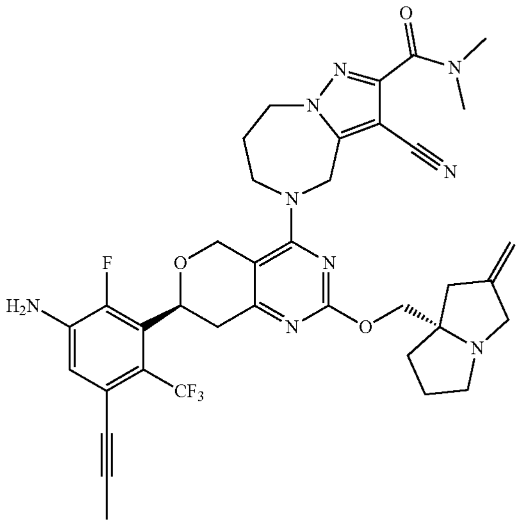
, -continued
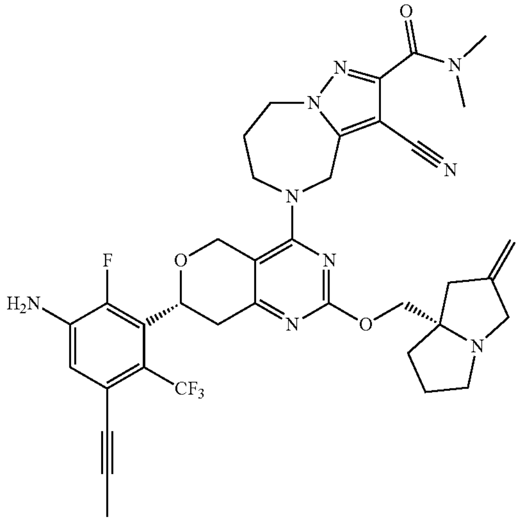
,
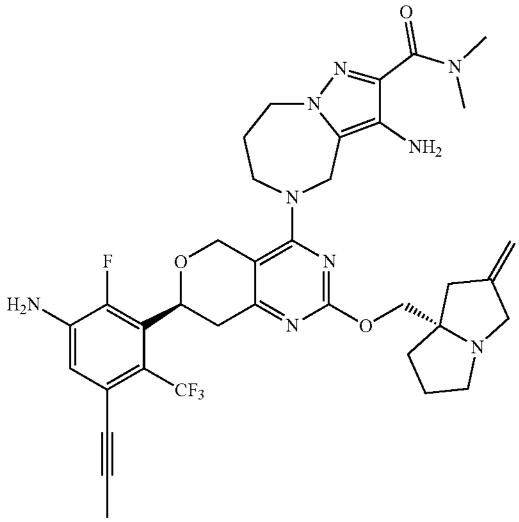
,
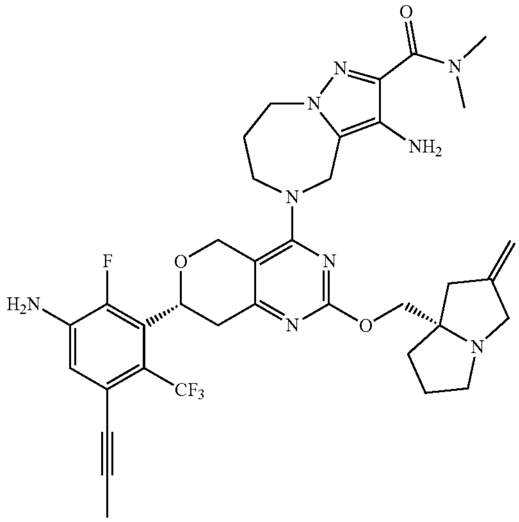
,
-continued
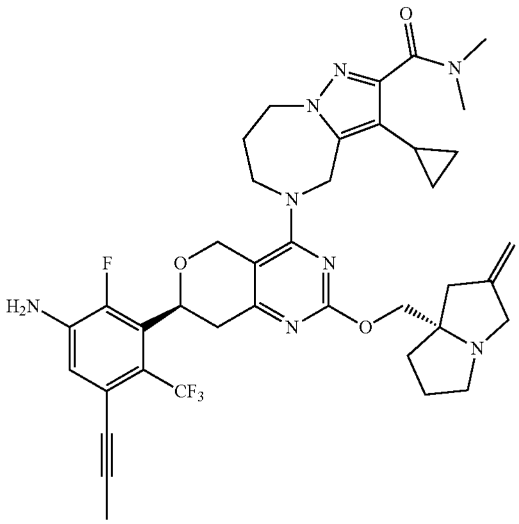
,
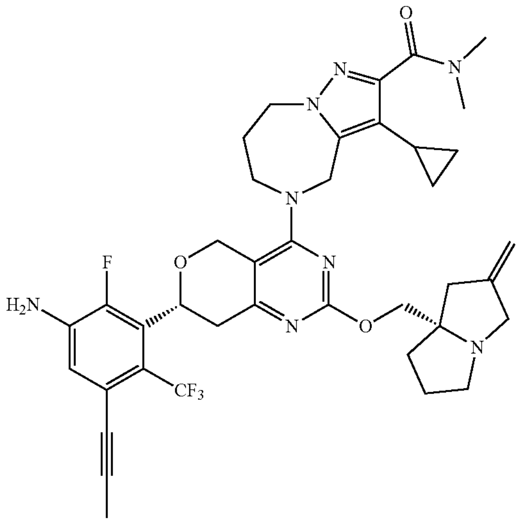
,
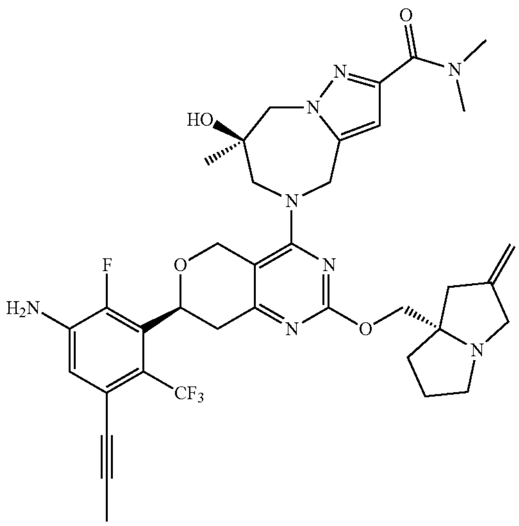
, -continued
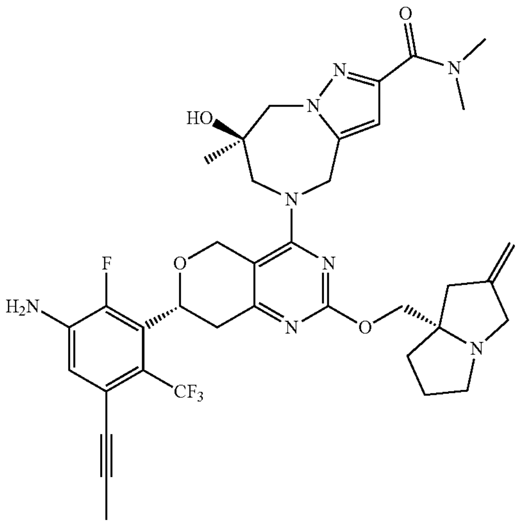
,
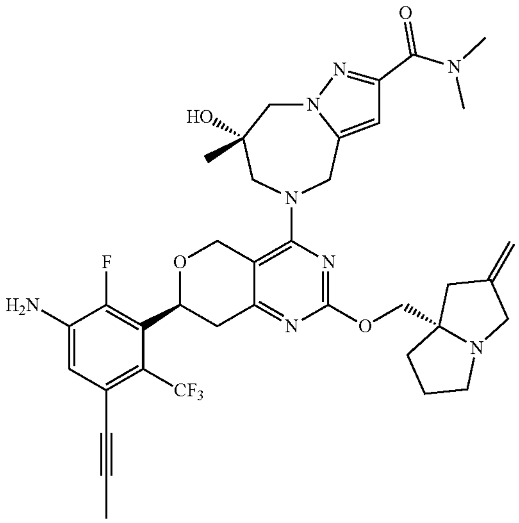
,
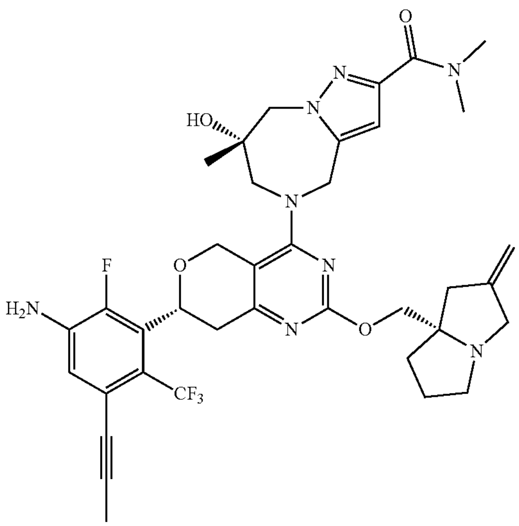
,
-continued
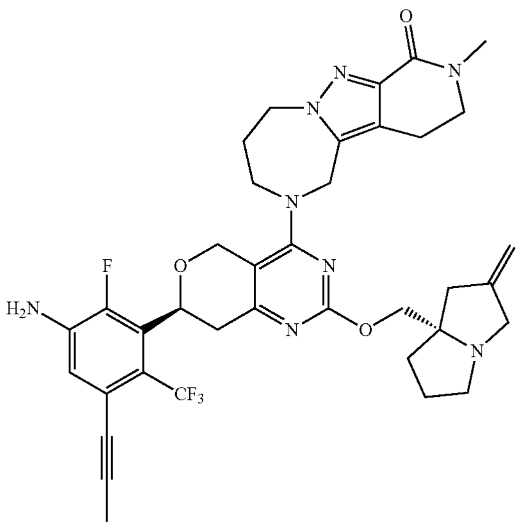
,
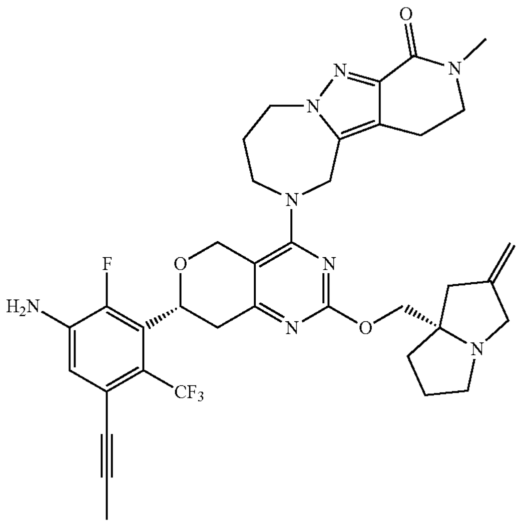
,
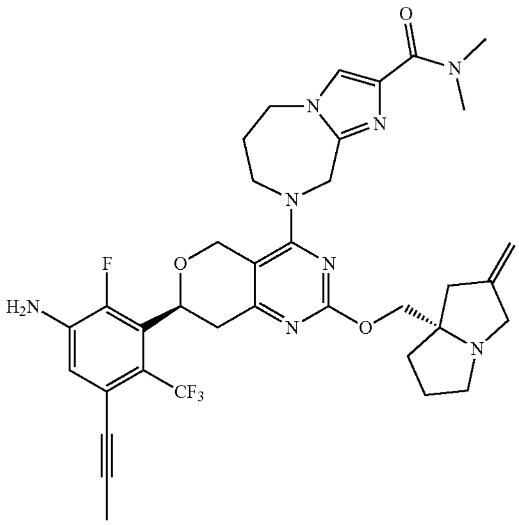
, -continued
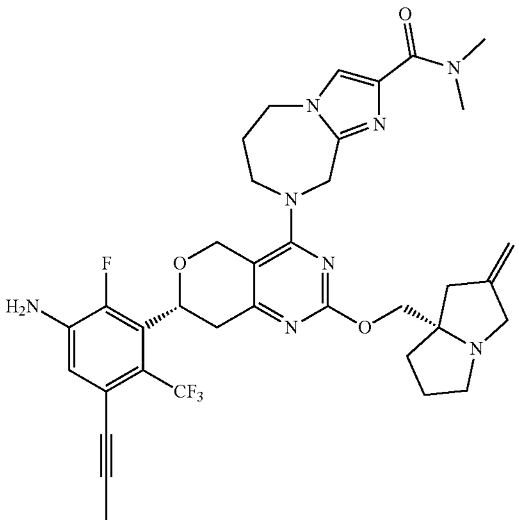
,
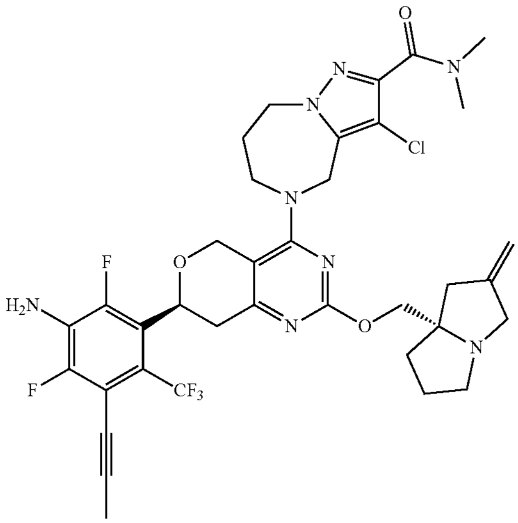
,
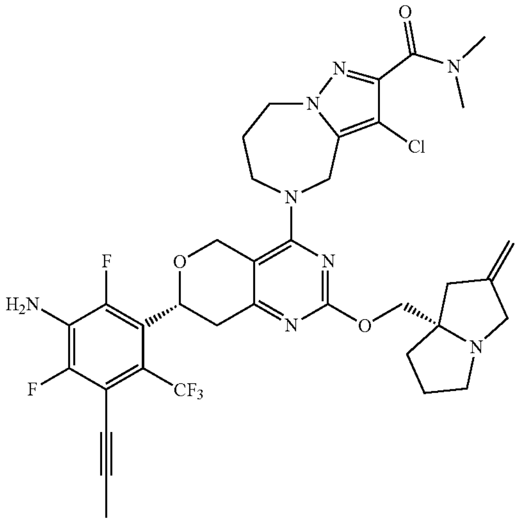
,
-continued
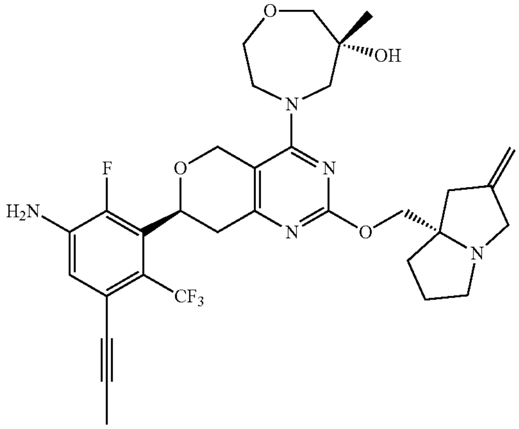
,
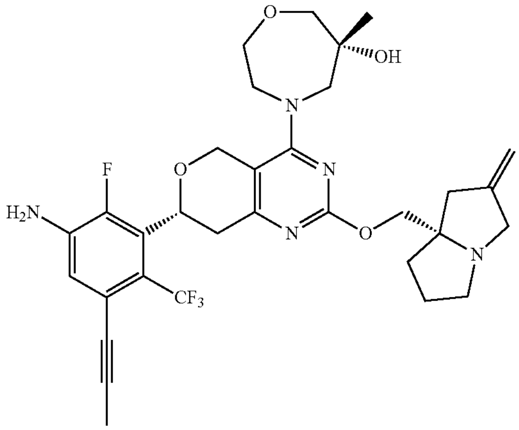
,
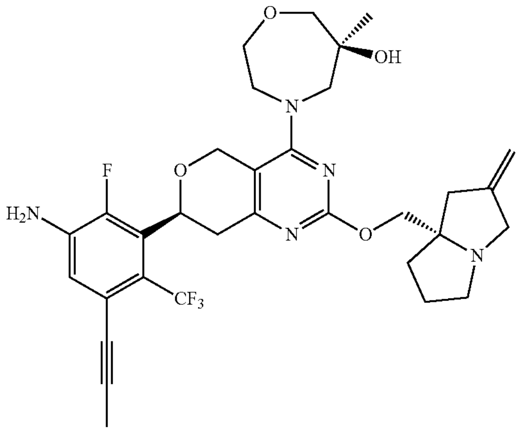
,
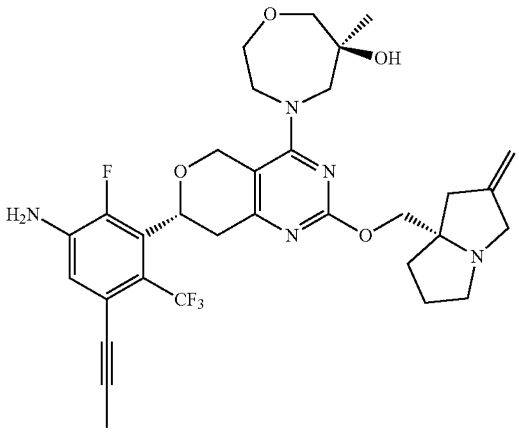
, -continued
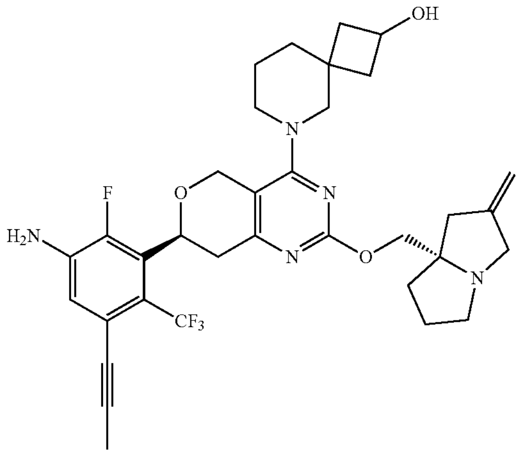
,
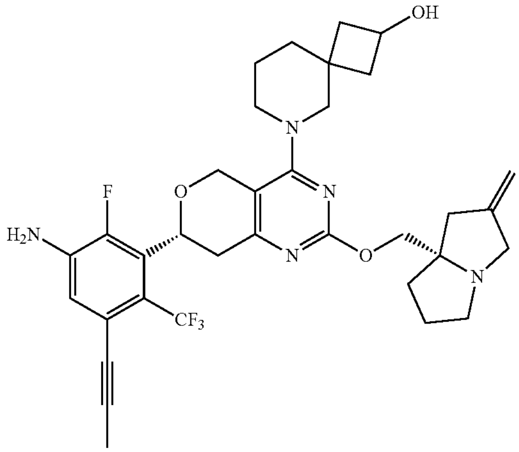
,
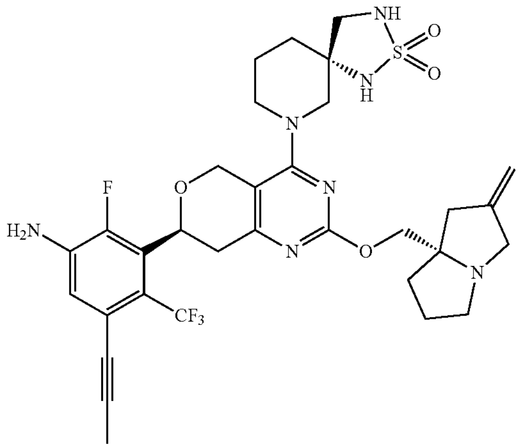
,
-continued
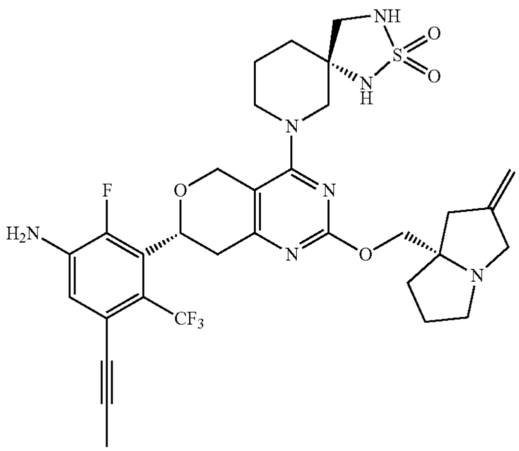
,
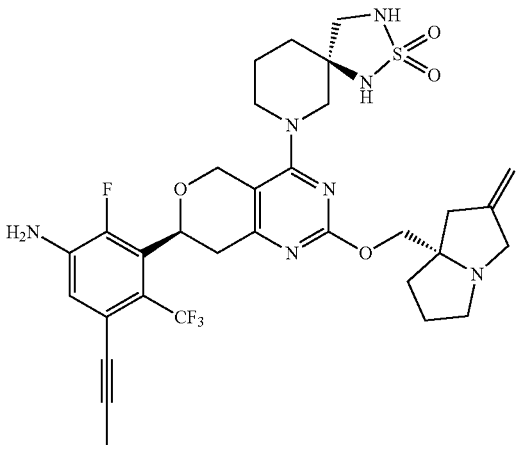
,
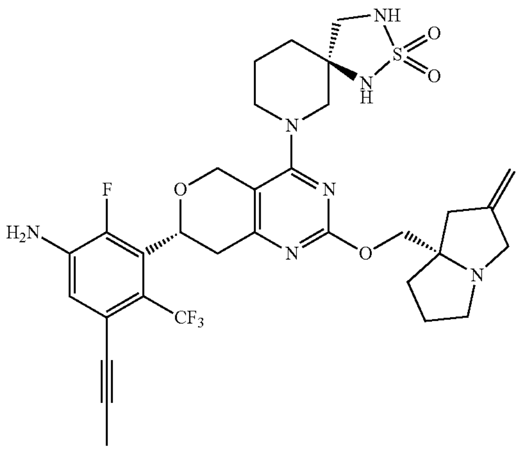
, -continued
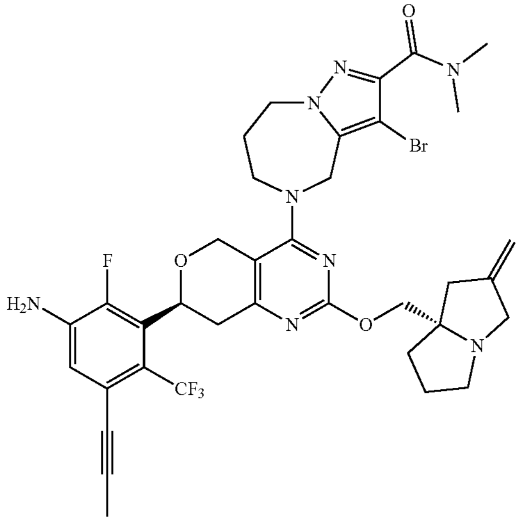
,
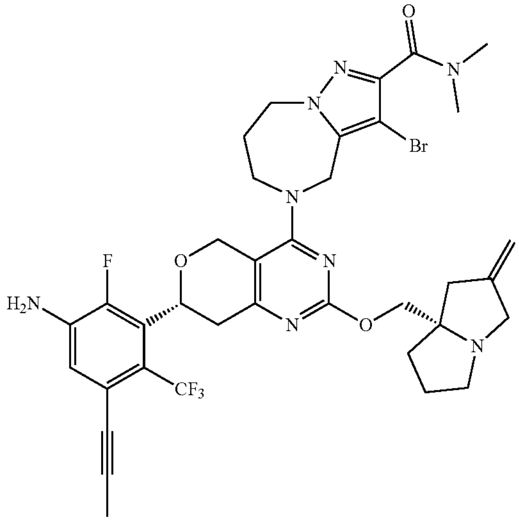
,
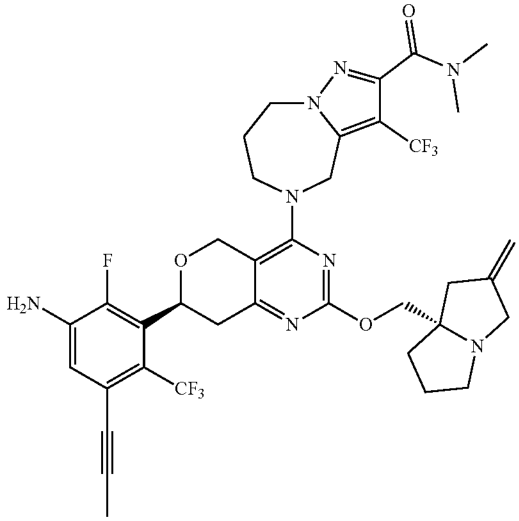
,
-continued
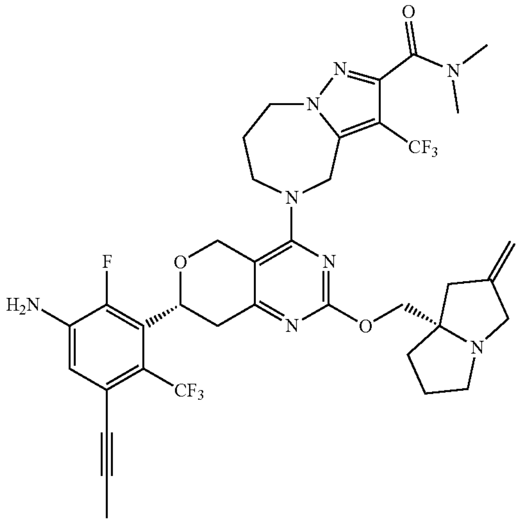
,
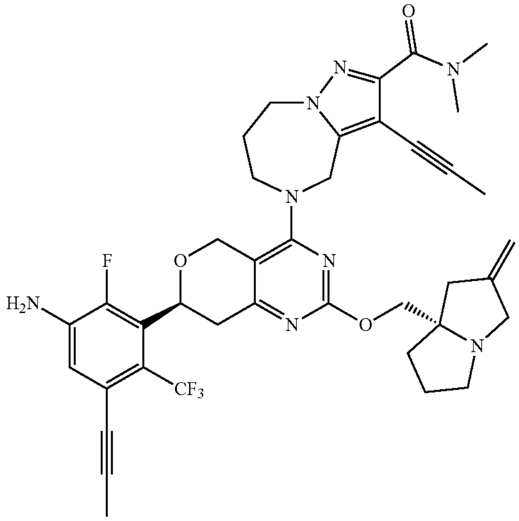
,
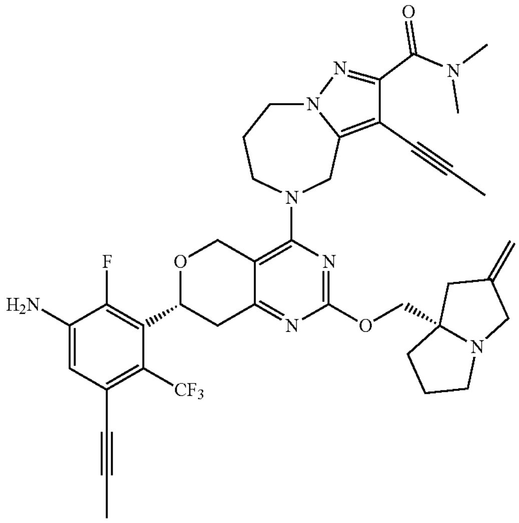
, -continued
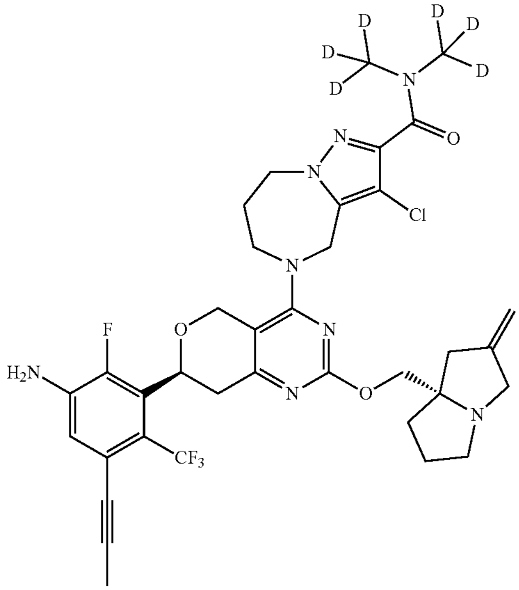
,
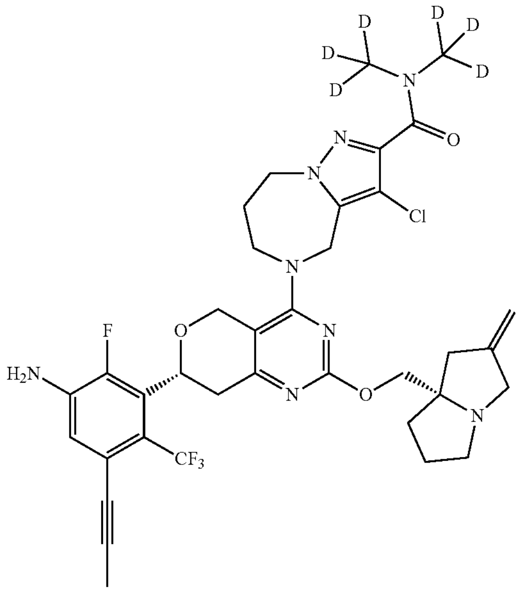
,
-continued
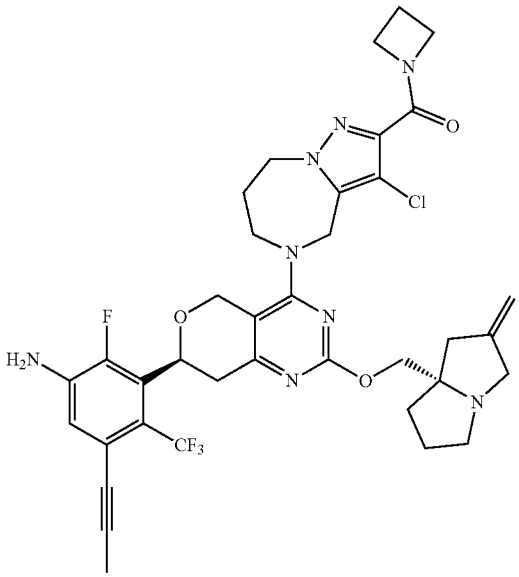
,
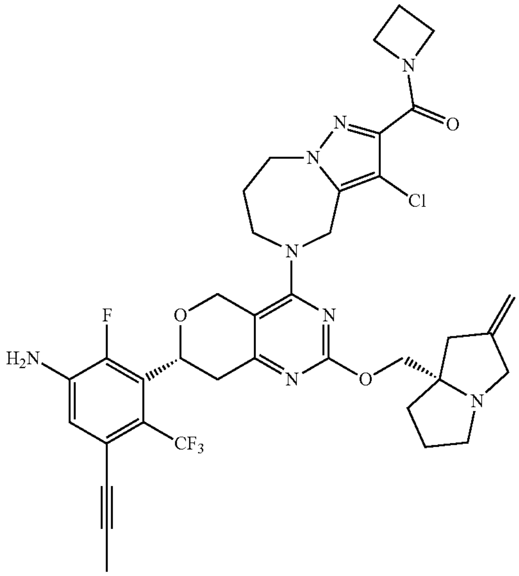
,
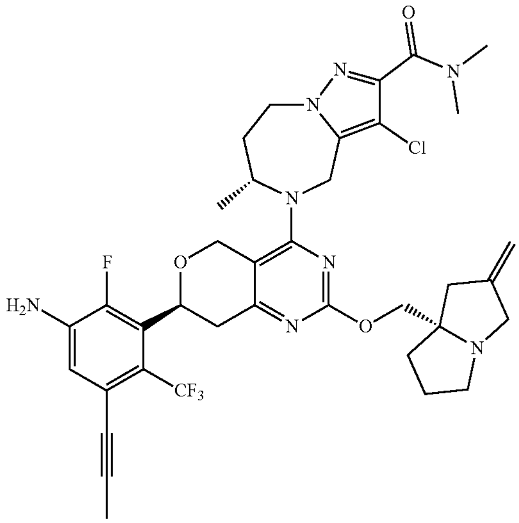
, -continued
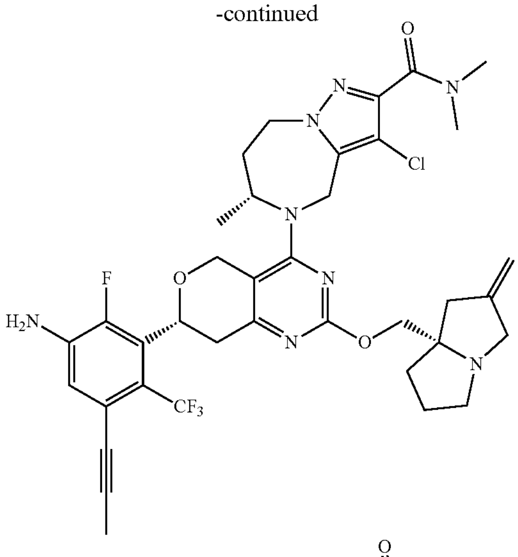
,
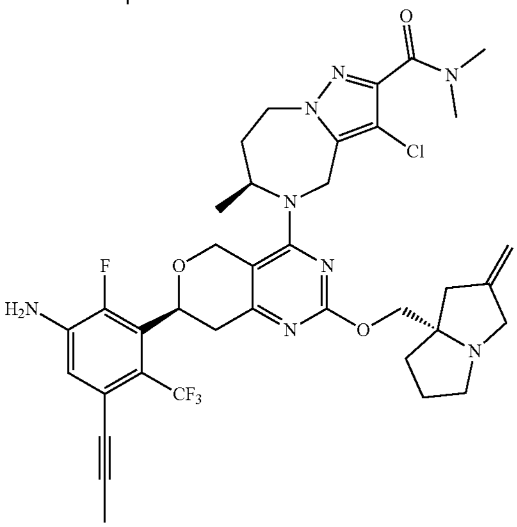
, and
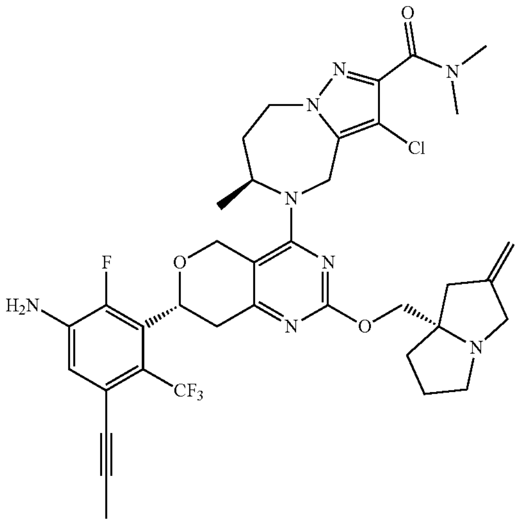
,
or a pharmaceutically acceptable salt or solvate thereof.
2. The compound of claim 1, wherein the compound is
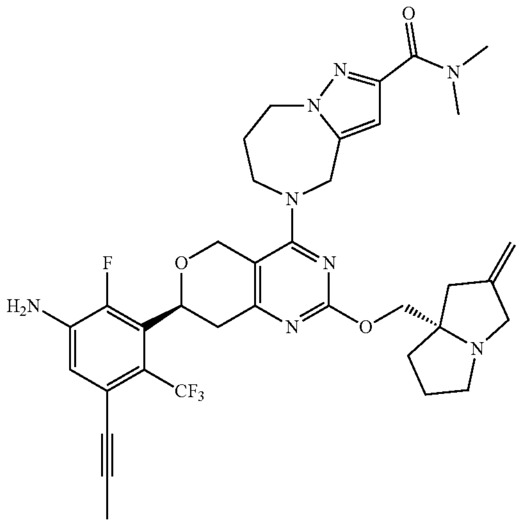 [SMILES: C=C1CN2CCC[C@@]2(COc2nc3c(c(N4CCCn5nc(C(=O)N(C)C)cc5C4)n2)CO[C@H](c2c(F)c(N)cc(C#CC)c2C(F)(F)F)C3)C1]
or a pharmaceutically acceptable salt or solvate thereof.
3. The compound of claim 1, wherein the compound is
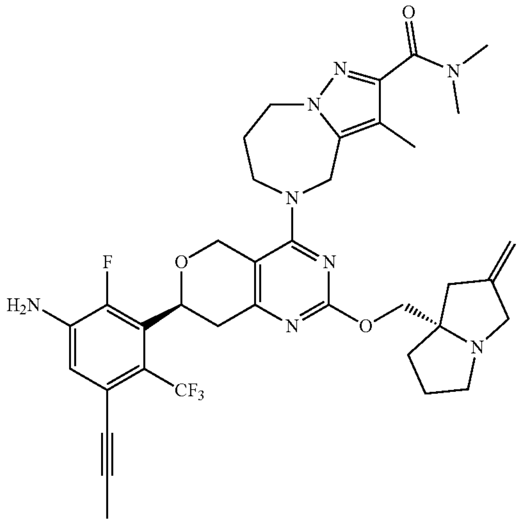 [SMILES: C=C1CN2CCC[C@@]2(COc2nc3c(c(N4CCCn5nc(C(=O)N(C)C)c(C)c5C4)n2)CO[C@H](c2c(F)c(N)cc(C#CC)c2C(F)(F)F)C3)C1]
or a pharmaceutically acceptable salt or solvate thereof.

4. The compound of claim 1, wherein the compound is

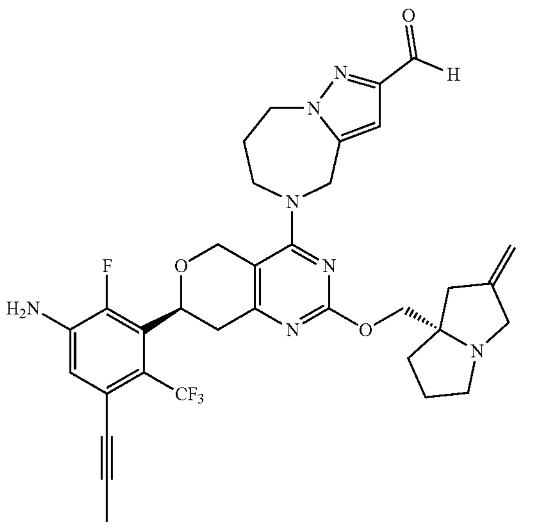 [SMILES: C=C1CN2CCC[C@@]2(COc2nc3c(c(N4CCCn5nc(C=O)cc5C4)n2)CO[C@H](c2c(F)c(N)cc(C#CC)c2C(F)(F)F)C3)C1]

or a pharmaceutically acceptable salt or solvate thereof.

5. The compound of claim 1, wherein the compound is

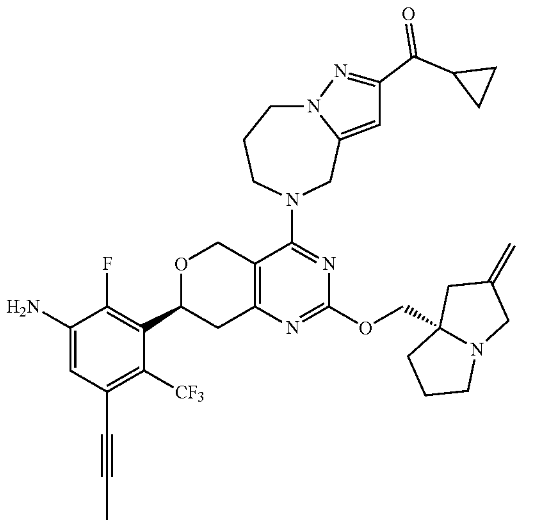 [SMILES: C=C1CN2CCC[C@@]2(COc2nc3c(c(N4CCCn5nc(C(=O)C6CC6)cc5C4)n2)CO[C@H](c2c(F)c(N)cc(C#CC)c2C(F)(F)F)C3)C1]

or a pharmaceutically acceptable salt or solvate thereof.

6. The compound of claim 1, wherein the compound is

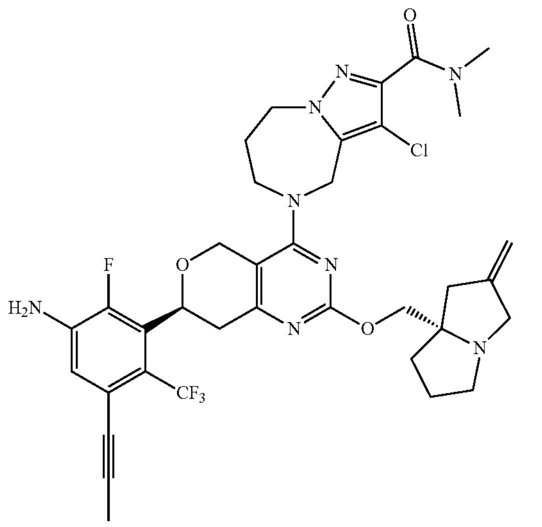 [SMILES: C=C1CN2CCC[C@@]2(COc2nc3c(c(N4CCCn5nc(C(=O)N(C)C)c(Cl)c5C4)n2)CO[C@H](c2c(F)c(N)cc(C#CC)c2C(F)(F)F)C3)C1]

or a pharmaceutically acceptable salt or solvate thereof.

7. The compound of claim 1, wherein the compound is

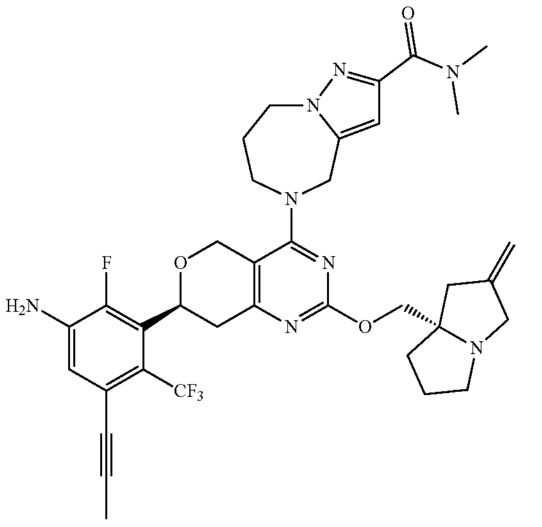 [SMILES: C=C1CN2CCC[C@@]2(COc2nc3c(c(N4CCCn5nc(C(=O)N(C)C)cc5C4)n2)CO[C@H](c2c(F)c(N)cc(C#CC)c2C(F)(F)F)C3)C1]

or a pharmaceutically acceptable salt or solvate thereof.

8. The compound of claim 1, wherein the compound is

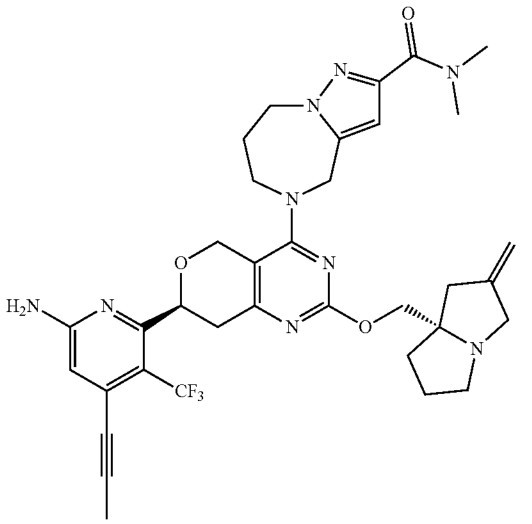 [SMILES: C=C1CN2CCC[C@@]2(COc2nc3c(c(N4CCCn5nc(C(=O)N(C)C)cc5C4)n2)CO[C@H](c2nc(N)cc(C#CC)c2C(F)(F)F)C3)C1]

or a pharmaceutically acceptable salt or solvate thereof.

9. The compound of claim 1, wherein the compound is

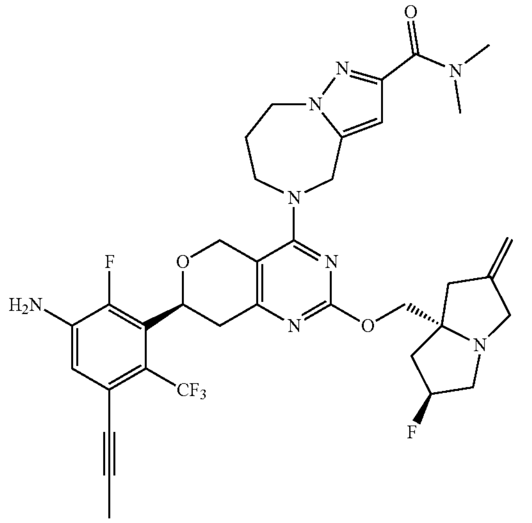 [SMILES: C=C1CN2C[C@@H](F)C[C@@]2(COc2nc3c(c(N4CCCn5nc(C(=O)N(C)C)cc5C4)n2)CO[C@H](c2c(F)c(N)cc(C#CC)c2C(F)(F)F)C3)C1]

or a pharmaceutically acceptable salt or solvate thereof.

10. The compound of claim 1, wherein the compound is

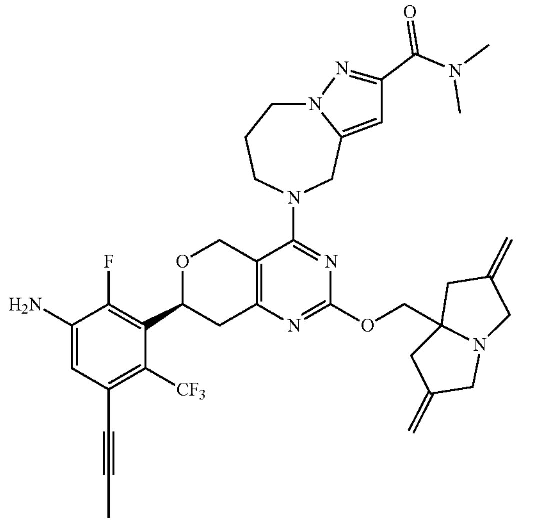 [SMILES: C=C1CN2CC(=C)CC2(COc2nc3c(c(N4CCCn5nc(C(=O)N(C)C)cc5C4)n2)CO[C@H](c2c(F)c(N)cc(C#CC)c2C(F)(F)F)C3)C1]

or a pharmaceutically acceptable salt or solvate thereof.

11. The compound of claim 1, wherein the compound is

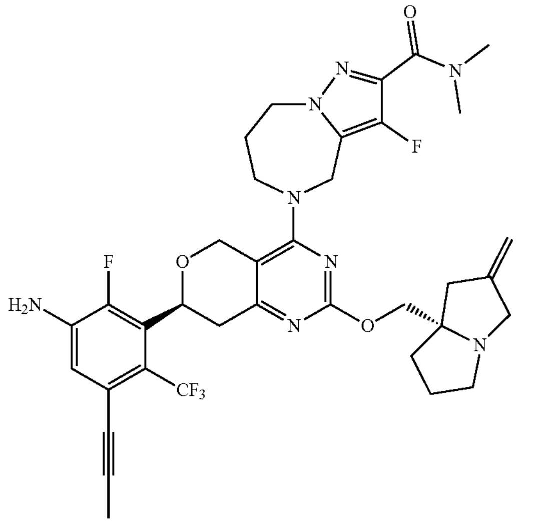 [SMILES: C=C1CN2CCC[C@@]2(COc2nc3c(c(N4CCCn5nc(C(=O)N(C)C)c(F)c5C4)n2)CO[C@H](c2c(F)c(N)cc(C#CC)c2C(F)(F)F)C3)C1]

or a pharmaceutically acceptable salt or solvate thereof.

12. The compound of claim 1, wherein the compound is

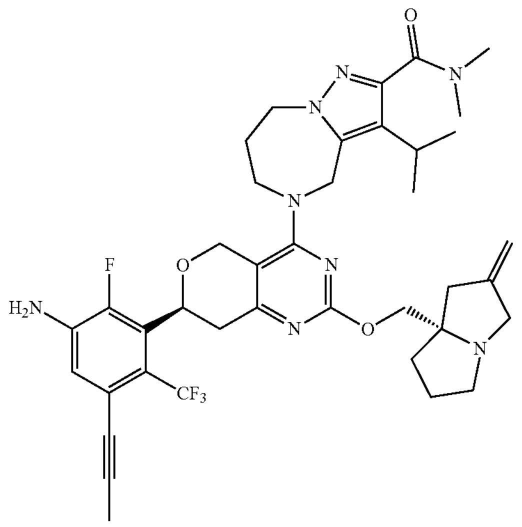 [SMILES: C=C1CN2CCC[C@@]2(COc2nc3c(c(N4CCCn5nc(C(=O)N(C)C)c(C(C)C)c5C4)n2)CO[C@H](c2c(F)c(N)cc(C#CC)c2C(F)(F)F)C3)C1]

or a pharmaceutically acceptable salt or solvate thereof.

13. The compound of claim 1, wherein the compound is

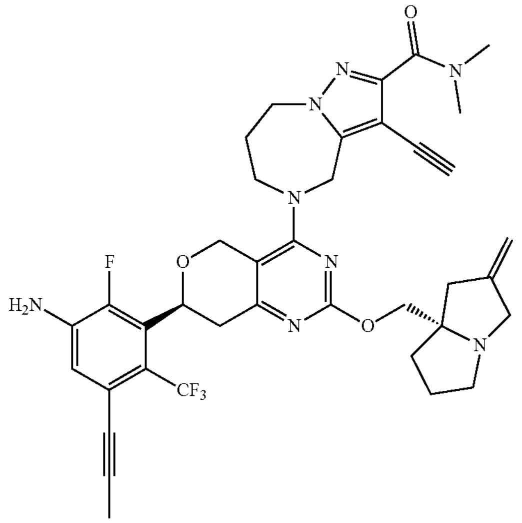 [SMILES: C#Cc1c(C(=O)N(C)C)nn2c1CN(c1nc(OC[C@@]34CCCN3CC(=C)C4)nc3c1CO[C@H](c1c(F)c(N)cc(C#CC)c1C(F)(F)F)C3)CCC2]

or a pharmaceutically acceptable salt or solvate thereof.

14. The compound of claim 1, wherein the compound is

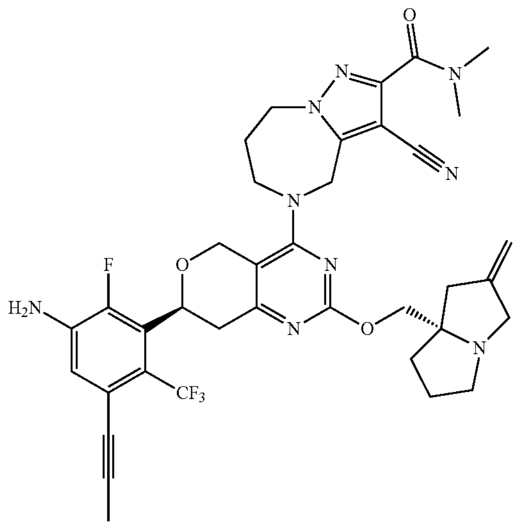 [SMILES: C=C1CN2CCC[C@@]2(COc2nc3c(c(N4CCCn5nc(C(=O)N(C)C)c(C#N)c5C4)n2)CO[C@H](c2c(F)c(N)cc(C#CC)c2C(F)(F)F)C3)C1]

or a pharmaceutically acceptable salt or solvate thereof.

15. The compound of claim 1, wherein the compound is

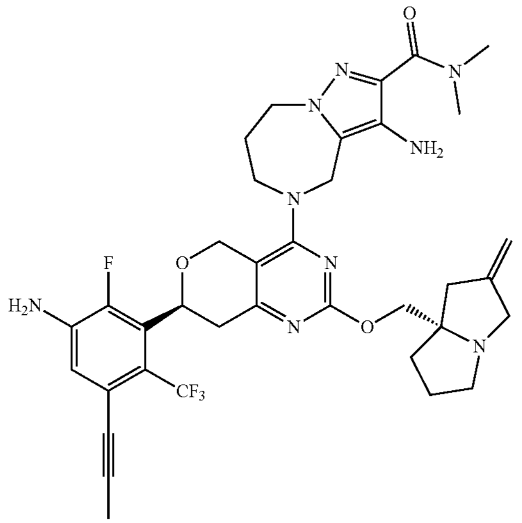

or a pharmaceutically acceptable salt or solvate thereof.

16. The compound of claim 1, wherein the compound is

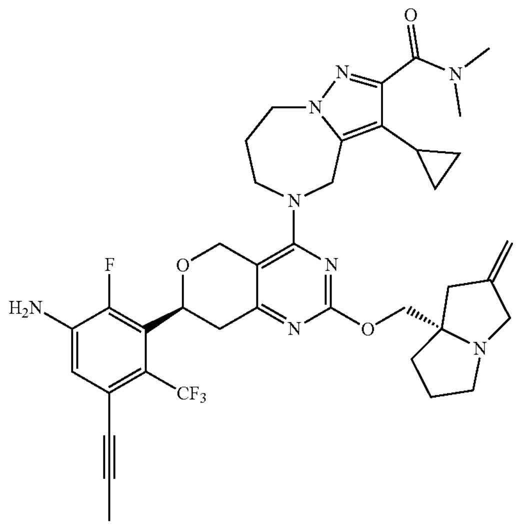 [SMILES: C=C1CN2CCC[C@@]2(COc2nc3c(c(N4CCCn5nc(C(=O)N(C)C)c(C6CC6)c5C4)n2)CO[C@H](c2c(F)c(N)cc(C#CC)c2C(F)(F)F)C3)C1]

or a pharmaceutically acceptable salt or solvate thereof.

17. The compound of claim 1, wherein the compound is

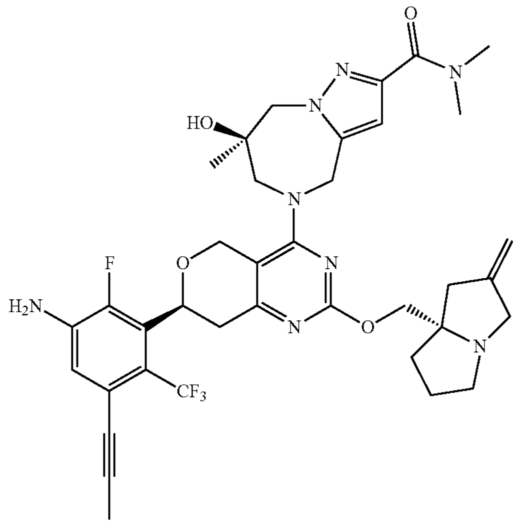 [SMILES: C=C1CN2CCC[C@@]2(COc2nc3c(c(N4Cc5cc(C(=O)N(C)C)nn5C[C@](C)(O)C4)n2)CO[C@H](c2c(F)c(N)cc(C#CC)c2C(F)(F)F)C3)C1]

or a pharmaceutically acceptable salt or solvate thereof.

18. The compound of claim 1, wherein the compound is

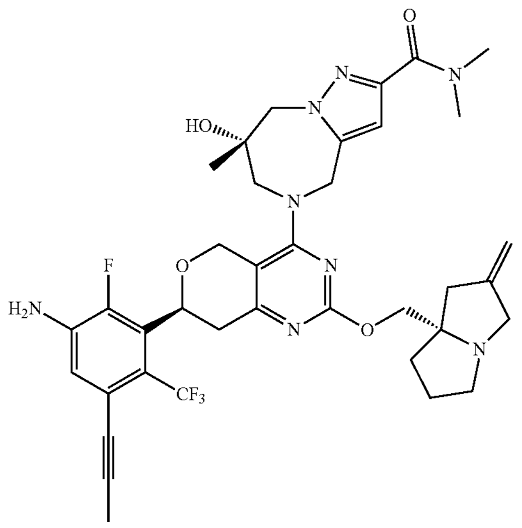 [SMILES: C=C1CN2CCC[C@@]2(COc2nc3c(c(N4Cc5cc(C(=O)N(C)C)nn5C[C@@](C)(O)C4)n2)CO[C@H](c2c(F)c(N)cc(C#CC)c2C(F)(F)F)C3)C1]

or a pharmaceutically acceptable salt or solvate thereof.

19. The compound of claim 1, wherein the compound is

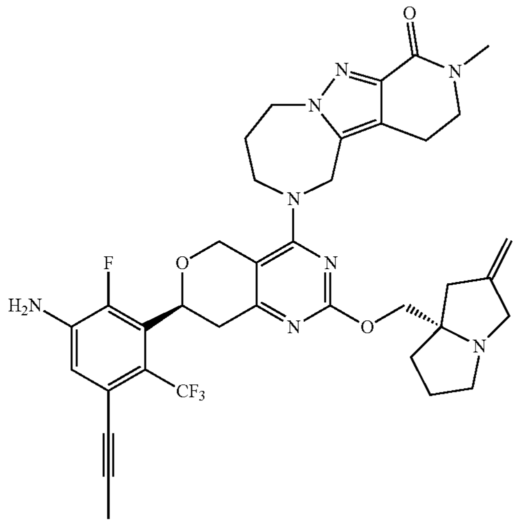 [SMILES: C=C1CN2CCC[C@@]2(COc2nc3c(c(N4CCCn5nc6c(c5C4)CCN(C)C6=O)n2)CO[C@H](c2c(F)c(N)cc(C#CC)c2C(F)(F)F)C3)C1]

or a pharmaceutically acceptable salt or solvate thereof.

20. The compound of claim 1, wherein the compound is

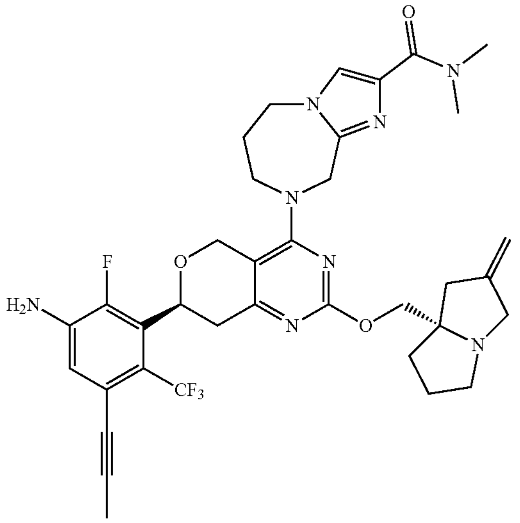 [SMILES: C=C1CN2CCC[C@@]2(COc2nc3c(c(N4CCCn5cc(C(=O)N(C)C)nc5C4)n2)CO[C@H](c2c(F)c(N)cc(C#CC)c2C(F)(F)F)C3)C1]

or a pharmaceutically acceptable salt or solvate thereof.

21. The compound of claim 1, wherein the compound is

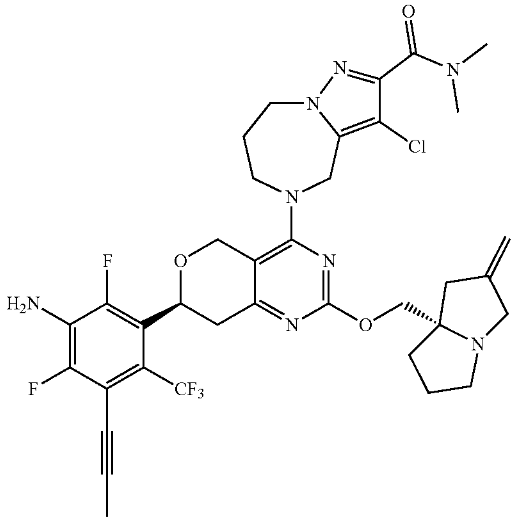 [SMILES: C=C1CN2CCC[C@@]2(COc2nc3c(c(N4CCCn5nc(C(=O)N(C)C)c(Cl)c5C4)n2)CO[C@H](c2c(F)c(N)c(F)c(C#CC)c2C(F)(F)F)C3)C1]

or a pharmaceutically acceptable salt or solvate thereof.

22. The compound of claim 1, wherein the compound is

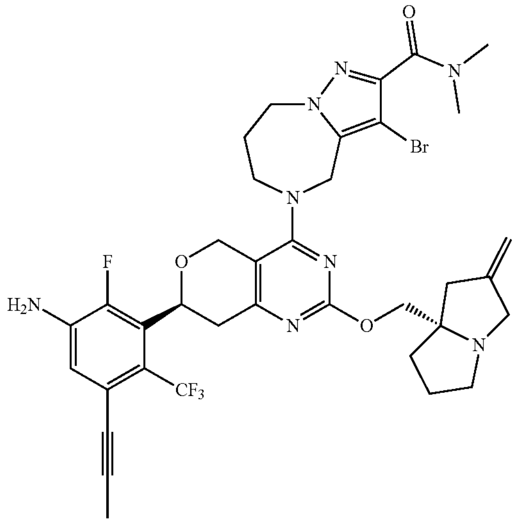

or a pharmaceutically acceptable salt or solvate thereof.

23. The compound of claim 1, wherein the compound is

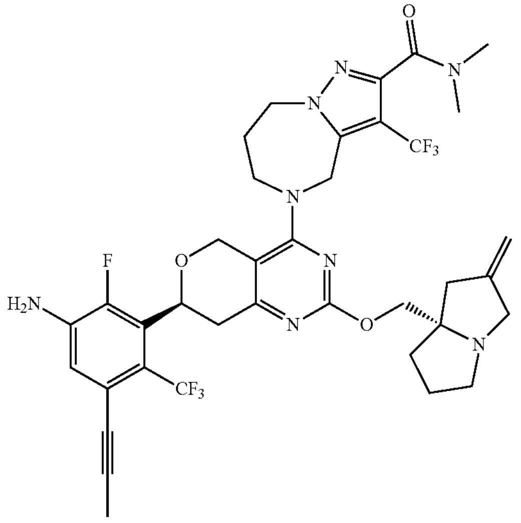 [SMILES: C=C1CN2CCC[C@@]2(COc2nc3c(c(N4CCCn5nc(C(=O)N(C)C)c(C(F)(F)F)c5C4)n2)CO[C@H](c2c(F)c(N)cc(C#CC)c2C(F)(F)F)C3)C1]

or a pharmaceutically acceptable salt or solvate thereof.

24. The compound of claim 1, wherein the compound is

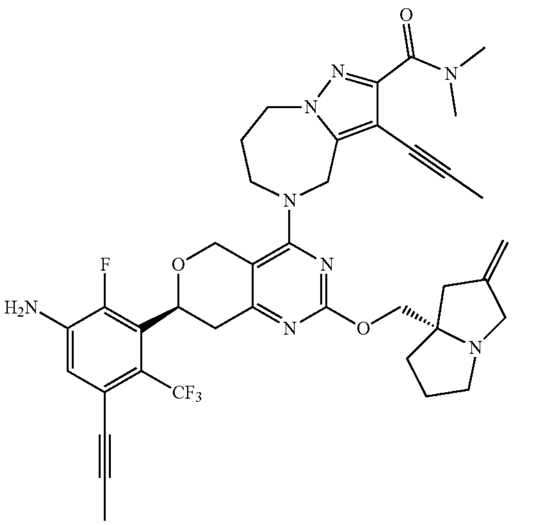 [SMILES: C=C1CN2CCC[C@@]2(COc2nc3c(c(N4CCCn5nc(C(=O)N(C)C)c(C#CC)c5C4)n2)CO[C@H](c2c(F)c(N)cc(C#CC)c2C(F)(F)F)C3)C1]

or a pharmaceutically acceptable salt or solvate thereof.

25. The compound of claim 1, wherein the compound is

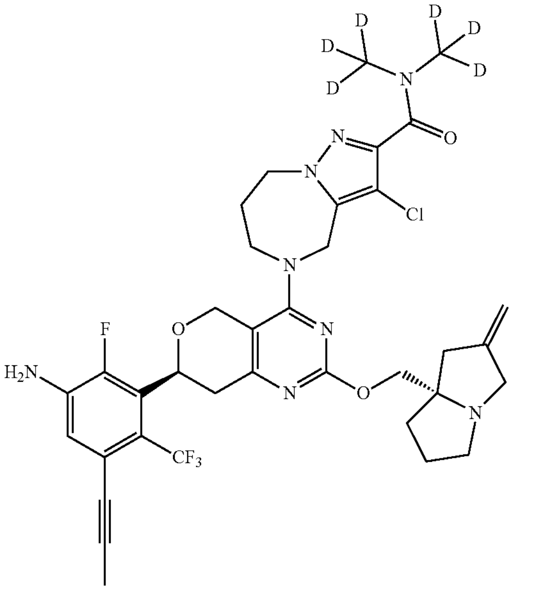 [SMILES: [2H]C([2H])([2H])N(C(=O)c1nn2c(c1Cl)CN(c1nc(OC[C@@]34CCCN3CC(=C)C4)nc3c1CO[C@H](c1c(F)c(N)cc(C#CC)c1C(F)(F)F)C3)CCC2)C([2H])([2H])[2H]]

or a pharmaceutically acceptable salt or solvate thereof.

26. The compound of claim 1, wherein the compound is

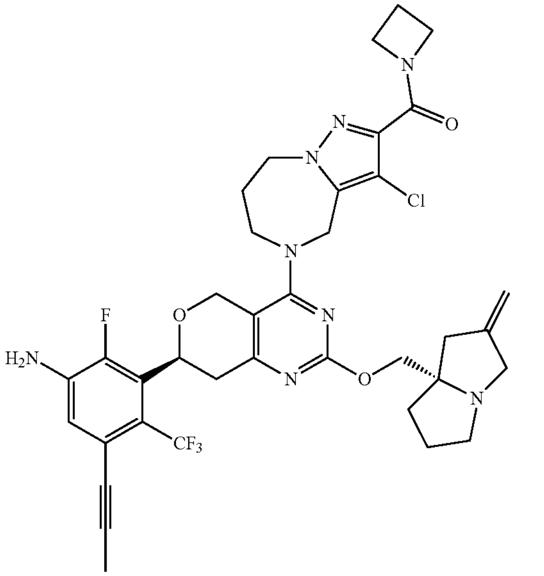 [SMILES: C=C1CN2CCC[C@@]2(COc2nc3c(c(N4CCCn5nc(C(=O)N6CCC6)c(Cl)c5C4)n2)CO[C@H](c2c(F)c(N)cc(C#CC)c2C(F)(F)F)C3)C1]

or a pharmaceutically acceptable salt or solvate thereof.

27. The compound of claim 1, wherein the compound is

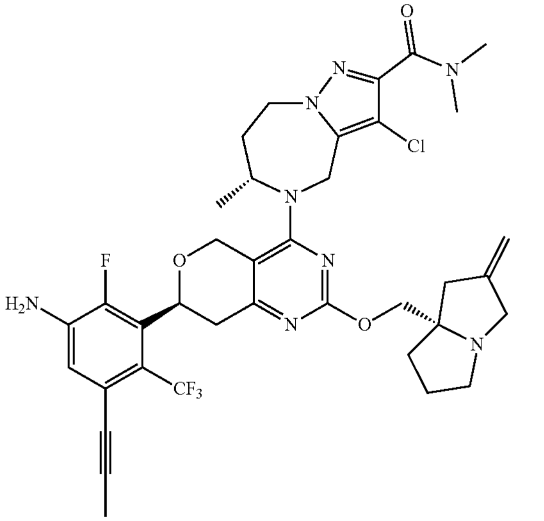 [SMILES: C=C1CN2CCC[C@@]2(COc2nc3c(c(N4Cc5c(Cl)c(C(=O)N(C)C)nn5CC[C@H]4C)n2)CO[C@H](c2c(F)c(N)cc(C#CC)c2C(F)(F)F)C3)C1]

or a pharmaceutically acceptable salt or solvate thereof.

28. The compound of claim 1, wherein the compound is

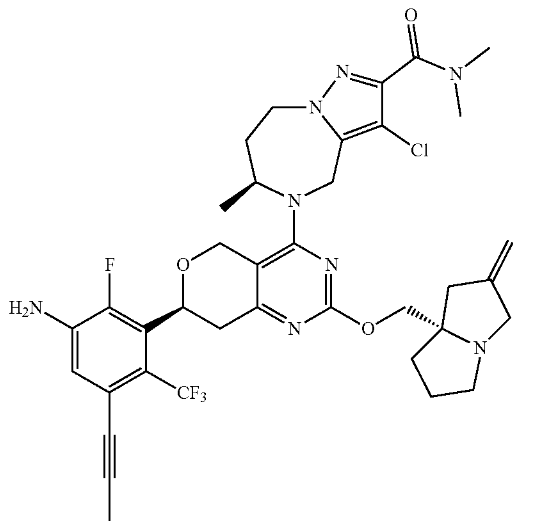 [SMILES: C=C1CN2CCC[C@@]2(COc2nc3c(c(N4Cc5c(Cl)c(C(=O)N(C)C)nn5CC[C@@H]4C)n2)CO[C@H](c2c(F)c(N)cc(C#CC)c2C(F)(F)F)C3)C1]

or a pharmaceutically acceptable salt or solvate thereof.

29. The compound of claim 1, wherein the compound is

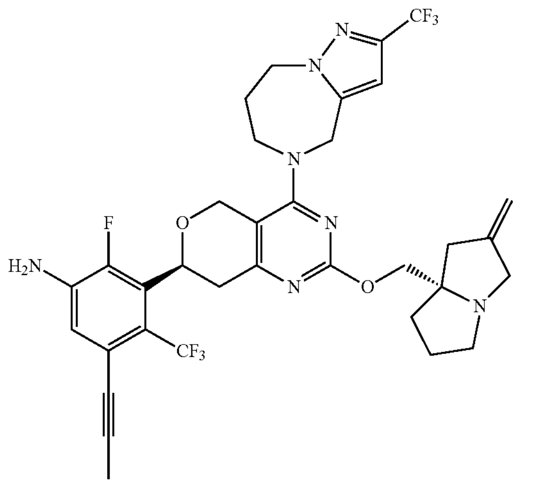 [SMILES: C=C1CN2CCC[C@@]2(COc2nc3c(c(N4CCCn5nc(C(F)(F)F)cc5C4)n2)CO[C@H](c2c(F)c(N)cc(C#CC)c2C(F)(F)F)C3)C1]

or a pharmaceutically acceptable salt or solvate thereof.

30. A pharmaceutical composition comprising a compound of claim 1 or a pharmaceutically acceptable salt or solvate thereof and a pharmaceutically acceptable excipient.

* * * * *